US009816096B2

(12) United States Patent
Heintz et al.

(10) Patent No.: US 9,816,096 B2
(45) Date of Patent: Nov. 14, 2017

(54) METHODS AND COMPOSITIONS FOR TRANSLATIONAL PROFILING AND MOLECULAR PHENOTYPING

(71) Applicant: THE ROCKEFELLER UNIVERSITY, New York, NY (US)

(72) Inventors: Nathaniel Heintz, Pelham Manor, NY (US); Paul Greengard, New York, NY (US); Myriam Heiman, New York, NY (US); Anne Schaefer, New York, NY (US); Joseph P. Doyle, New York, NY (US); Joseph D. Dougherty, St. Louis, MO (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 0 days.

(21) Appl. No.: 14/553,937

(22) Filed: Nov. 25, 2014

(65) Prior Publication Data
US 2015/0082470 A1 Mar. 19, 2015

Related U.S. Application Data

(63) Continuation of application No. 12/918,761, filed as application No. PCT/US2009/001614 on Mar. 12, 2009, now abandoned.

(60) Provisional application No. 61/070,327, filed on Mar. 21, 2008, provisional application No. 61/036,049, filed on Mar. 12, 2008, provisional application No. 61/199,108, filed on Nov. 12, 2008, provisional application No. 61/036,058, filed on Mar. 12, 2008.

(51) Int. Cl.
C12N 15/62 (2006.01)
C12N 15/11 (2006.01)
G01N 33/50 (2006.01)
A01K 67/027 (2006.01)

(52) U.S. Cl.
CPC .......... *C12N 15/62* (2013.01); *A01K 67/0278* (2013.01); *C12N 15/111* (2013.01); *G01N 33/5023* (2013.01); *G01N 33/5058* (2013.01); *A01K 2217/206* (2013.01); *A01K 2227/105* (2013.01); *A01K 2267/01* (2013.01); *C12N 2320/12* (2013.01); *G01N 2800/285* (2013.01)

(58) Field of Classification Search
None
See application file for complete search history.

(56) References Cited

U.S. PATENT DOCUMENTS

| 5,075,227 | A | 12/1991 | Hagen |
| 5,795,723 | A | 8/1998 | Tapscott et al. |
| 6,110,711 | A | 8/2000 | Serafini et al. |
| 6,130,090 | A | 10/2000 | Heintz et al. |
| 6,143,566 | A | 11/2000 | Heintz et al. |
| 6,156,574 | A | 12/2000 | Heintz et al. |
| 6,252,130 | B1 | 6/2001 | Federoff |
| 6,270,969 | B1 | 8/2001 | Hartley et al. |
| 6,403,374 | B1 | 6/2002 | Tsien et al. |
| 6,410,317 | B1 | 6/2002 | Farmer |
| 6,441,269 | B1 | 8/2002 | Serafini et al. |
| 6,485,912 | B1 | 11/2002 | Heintz et al. |
| 6,495,318 | B2 | 12/2002 | Harney |
| 6,635,422 | B2 | 10/2003 | Keene et al. |
| 6,821,759 | B1 | 11/2004 | Heintz et al. |
| 7,098,031 | B2 | 8/2006 | Choulika et al. |
| 7,297,482 | B2 | 11/2007 | Anderson et al. |
| 7,393,632 | B2 | 7/2008 | Cheo et al. |
| 2003/0119104 | A1 | 6/2003 | Perkins et al. |
| 2004/0023256 | A1 | 2/2004 | Puglisi et al. |
| 2005/0009028 | A1 | 1/2005 | Heintz et al. |
| 2006/0183147 | A1 | 8/2006 | Meyer-Franke |
| 2011/0314565 | A1 | 12/2011 | Heintz et al. |

FOREIGN PATENT DOCUMENTS

| EP | 1132479 A1 | 9/2001 |
| WO | WO-01/48480 A1 | 7/2001 |
| WO | WO-01/58954 A2 | 8/2001 |
| WO | WO-01/58954 A3 | 3/2002 |
| WO | WO-02/064749 A2 | 8/2002 |
| WO | WO-2002/064749 A3 | 3/2003 |
| WO | WO-03/064604 A2 | 8/2003 |
| WO | WO-03/064604 A3 | 11/2003 |

OTHER PUBLICATIONS

Agafonov, et al., Proteins on ribosome surface: measurements of protein exposure by hot tritium bombardment technique, Proceedings of the National Academy of Science U S A, 94(24):12892-12897 (1997).
Anthony, et al., Creating somatic cell genetic mosaics in the mouse, Cell, 121(3):322-323 (2005).
Antic, et al., ELAV tumor antigen, Hel-N1, increases translation of neurofilament MmRNA and induces formation of neurites in human teratocarcinoma cells, Genes Development, 13(4):449-461 (1999).
Ashiya, et al., A neuron-specific splicing switch mediated by an array of pre-mRNA repressor sites: evidence of a regulatory role for the polypyrimidine tract binding protein and a brain-specific PTB counterpart, RNA, 3(9):996-1015 (1997).
Brodersen, et al., The social life of ribosomal proteins, FEBS Journal, 272(9):2098-2108 (2005).
Broude, et al., Proteins of the 30-S subunit of *Escherichia coli* ribosomes which interact directly with natural mRNA, European Journal of Biochemistry, 132(1):139-45 (1983).
Buskila, et al., Serum monoclonal antibodies derived from patients with multiple myeloma react with mycobacterial phosphoinositides and nuclear antigens, Clin Exp Immunol, 76(3):378-83 (1989).

(Continued)

*Primary Examiner* — Channing S Mahatan
(74) *Attorney, Agent, or Firm* — Choate, Hall & Stewart LLP; Rober N. Sahr; David E. Shore

(57) ABSTRACT

Methods and compositions are provided for translational profiling and molecular phenotyping of specific tissues, cells and cell subtypes of interest. The methods provided herein facilitate the analysis of gene expression in the selected subset present within a heterogeneous sample.

18 Claims, 54 Drawing Sheets

(56) References Cited

OTHER PUBLICATIONS

Ceman, et al., Isolation of an FMRP-associated messenger ribonucleoprotein particle and identification of nucleolin and the fragile X-related proteins as components of the complex, Molecular Cell Biology, 19(12):7925-7932 (1999).
Chaible, et al., Genetically-modified animals for use in research and biotechnology, Genetic Molecular Research, 9(3):1469-1482 (2010).
Chambers, et al. Translational regulation of hepatic HMG-CoA reductase by dietary cholesterol, Biochem Biophys Res Commun, 232(2):278-281 (1997).
Christopher, et al. Implications of N and C-terminal proximity for protein folding, Journal of Molecular Biology, 257(1):175-87 (1996).
Chu, et al., Identification of a thymidylate synthase ribonucleoprotein complex in human colon cancer cells, Molecular Cell Biology, 14(1):207-213 (1994).
Chu, et al., Identification of in vivo target RNA sequences bound by thymidylate synthase, Nucleic Acids Research, 24(16):3222-3228 (1996).
Copeland, et al. A novel RNA binding protein, SBP2, is required for the translation of mammalian selenoprotein mRNAs, EMBO Journal, 19(2):306-314 (2000).
De Jonge et al., Transcriptional profile of the human peripheral nervous system by serial analysis of gene expression, Genomics, 82(2):97-108 (2003).
Doyle, et al., Application of a translational profiling approach for the comparative analysis of CNS cell types, Cell, (2008).
European Search Report and Opinion for EP Application No. 09719684.4 (dated Feb. 21, 2012).
Fisher, et al., Pulse labeling of small nuclear ribonucleoproteins in vivo reveals distinct patterns of antigen recognition by human autoimmune antibodies, The Proceedings of the National Academy of Science U S A., 81(10):3185-3189 (1984).
Gerfen, et al., D1 and D2 dopamine receptor-regulated gene expression of striatonigral and striatopallidal neurons, Science, 250(4986): 1429-1432 (1990).
Gimautdinova, et al., The proteins of the messenger RNA binding site of *Escherichia coli* ribosomes, Nucleic Acids Research, 9(14):3465-3481 (1981).
Gong, et al., A gene expression atlas of the central nervous system based on bacterial artificial chromosomes. Nature, 425(6961):917-925 (2003).
Gong, et al., Targeting Cre recombinase to specific neuron populations with bacterial artificial chromosome constructs, Journal of Neuroscience, 27(37):9817-23 (2007).
Gonzalo and Reboud, The puzzling lateral flexible stalk of the ribosome, Biology Cell, 95(3-4):179-93 (2003).
Hagen-Mann et al., RT-PCR and alternative methods to PCR for in vitro amplification of nucleic acids, Exp Clin Endocrinol Diabetes, 103(3):150-155 (1995).
Heiman, et al. A translational profiling approach for the molecular characterization of CNS cell types, Cell (2008).
Heintz, N., Analysis of mammalian central nervous system gene expression and function using bacterial artificial chromosome-mediated transgenesis, Human Molecular Genetics, 9(6):937-943 (2000).
Heintz, N., BAC to the future: the use of bac transgenic mice for neuroscience research, Nat Rev Neuroscience, 2(12):861-70 (2001).
Heintz, N., Gene expression nervous system atlas (GENSAT), Nature Neuroscience, 7(5):483 (2004).
International Search Report dated for PCT Application No. US2009/001614 (dated Nov. 21, 2009), 5 pages.
International Search Report for PCT Application No. US02/34645 (dated Jun. 18, 2004), 1 page.
Kalapos, et al. Identification of ribosomal protein Si as a poly(A) binding protein in *Escherichia coli*, Biochimie, 79(8):493-502 (1997).
Kubota, et al. Nuclear and nucleolar targeting of human ribosomal protein S25:; common features shared with HIV-1 regulatory proteins, Oncogene, 18(7):1503-1514 (1999).
Lalanne, et al. Complete sequence of mouse S6 ribosomal protein, Nucleic Acids Research, 15(12):4990 (1987).
Lee, et al., Cocaine-induced dendritic spine formation in D1 and D2 dopamine receptor-containing medium spiny neurons in nucleus accumbens, Proceedings of the National Academy of Science, USA, 103(9):3399-3404 (2006).
Lerner and Steitz, Antibodies to small nuclear RNAs complexed with proteins are produced by patients with systemic lupus erythematosus, Proceedings of the National Academy of Science USA, 76(11):5495-9 (1979).
Liang, et al., An estrogen-dependent polysomal protein binds to the 5' untranslated region of the chicken vitellogenin mRNA, Nucleic Acids Research, 19(9):2289-2294 (1991).
Lin, et al., The primary structure of rat liver ribosomal protein L37. Homology with yeast and bacterial ribosomal proteins, Journal of Biologic Chemistry, 258(17):10664-10671 (1983).
Misulovin, et al., A rapid method for targeted modification and screening of recombinant bacterial artificial chromosome, Journal of Immunology Methods, 257(1-2):99-105 (2001).
Nevskaya et al., Ribosomal protein LI recognizes the same specific structural motif in its target sites on the autoregulatory mRNA and 23S rRNA, Nucleic Acids Research, 33(2):478-485 (2005).
Noain et al., Identification of brain neurons expressing the dopamine D4 receptor gene using BAC transgenic mice, European Journal of Neuroscience, 24(9):2429-2438 (2006).
Office Action for U.S. Appl. No. 10/494,248, (dated Dec. 23, 2010), 14 pages.
Office Action for U.S. Appl. No. 10/494,248, (dated Feb. 19, 2010), 21 pages.
Office Action for U.S. Appl. No. 10/494,248, (dated Jul. 29, 2008), 27 pages.
Office Action for U.S. Appl. No. 10/494,248, (dated Jun. 5, 2009), 20 pages.
Office Action for U.S. Appl. No. 10/494,248 (dated Sep. 25, 2007), 13 pages.
Office Action for U.S. Appl. No. 12/918,761, 12 pages (dated Aug. 26, 2014), 10 pages.
Office Action for U.S. Appl. No. 13/104,316 (dated Jul. 26, 2012), 14 pages.
Peng, et al., RNA stabilization by the Au-rich element binding protein, HuR, an ELAV protein, The EMBO Journal, 17(12):3461-3470 (1998).
Remacha et al., Proteins PI, P2, and P0, components of the eukaryotic ribosome stalk. New structural and functional aspects, Biochem Cell Biology, 73(11-12):959-968 (1995).
Ristevski, S., Making better transgenic models: conditional, temporal, and spatial approaches, Mal Biatechnol, 29(2):153-63 (2005).
Roche, et al., SsrA-mediated peptide tagging caused by rare codons and tRNA scarcity, The EMBO Journal, 18(16):4579-4589 (1999).
Rusk, N., Targeted translational profiling, Nature Methods, 6(1):7 (2009).
Sano, et al., Streptavidin-containing chimeric proteins: design and production, Methods Enzymol, 326:305-311 (2000).
Sanz, et al., Cell-type-specific isolation of ribosome-associated mRNA from complex tissues, The Proceedings of the National Academy of Science USA, 106(33):13939-13944 (2009).
Schena, et al., Parallel human genome analysis: microarray-based expression monitoring of 1000 genes, The Proceedings of the National Academy of Science USA, 93(20):10614-10619 (1996).
Smith, K.R. Gene transfer in higher animals: theoretical considerations and key concepts, Journal of Biotechnology, 99(1):1-22 ( 2002).
Tallini et al., BAC transgenic mice express enhanced green fluorescent protein in central and peripheral cholinergic neurons, Physiol Genomics 27(3):391-7 (2006).
Tenenbaum, et al., Identifying mRNA subsets in messenger ribonucleoprotein complexes by using cDNA arrays, The Proceedings of the National Academy of Science USA, 4431W(26):14085-90 (2000).

(56) References Cited

OTHER PUBLICATIONS

Trifillis, et al., Finding the right RNA: identification of cellular mRNA substrates for RNA-binding proteins, RNA, 5(8):1071-82 (1999).

Uchiumi and Kominami, Binding of mammalian ribosomal protein complex PO.P1.P2 and protein L12 to the GTPase-associated domain of 28 S ribosomal RNA and effect on the accessibility to anti-28 S RNA autoantibody, Journal of Biol Chemistry, 272(6):3302-8 (1997).

Walles-Granberg, et al., Ribosomes with large synthetic N-terminal extensions of protein S15 are active in vivo, Biochim Byophys Acta, 1544(1-2):378-385 (2001).

Wilson, et al., Ribosomal proteins in the spotlight, Crit Rev Biochem Mol Biol, 40(5):243-67 (2005).

Yang, et al. BAC-mediated gene-dosage analysis reveals a role for Ziprol (Ru49/Zfp38) in progenitor cell proliferation in cerebellum and skin, Nat Genet, 22(4):327-35 (1999).

Yang, et al., Homologous recombination based modification in *Escherichia coli* and germline transmission in transgenic mice of a bacterial artificial chromosome, Nature Biotechnology, 15(9):859-65 (1997).

Zong, et al. Messenger RNA translation state: The second dimension of high-throughput expression screening, PNAS, 96(19):10632-10636 (1999).

Figure 2
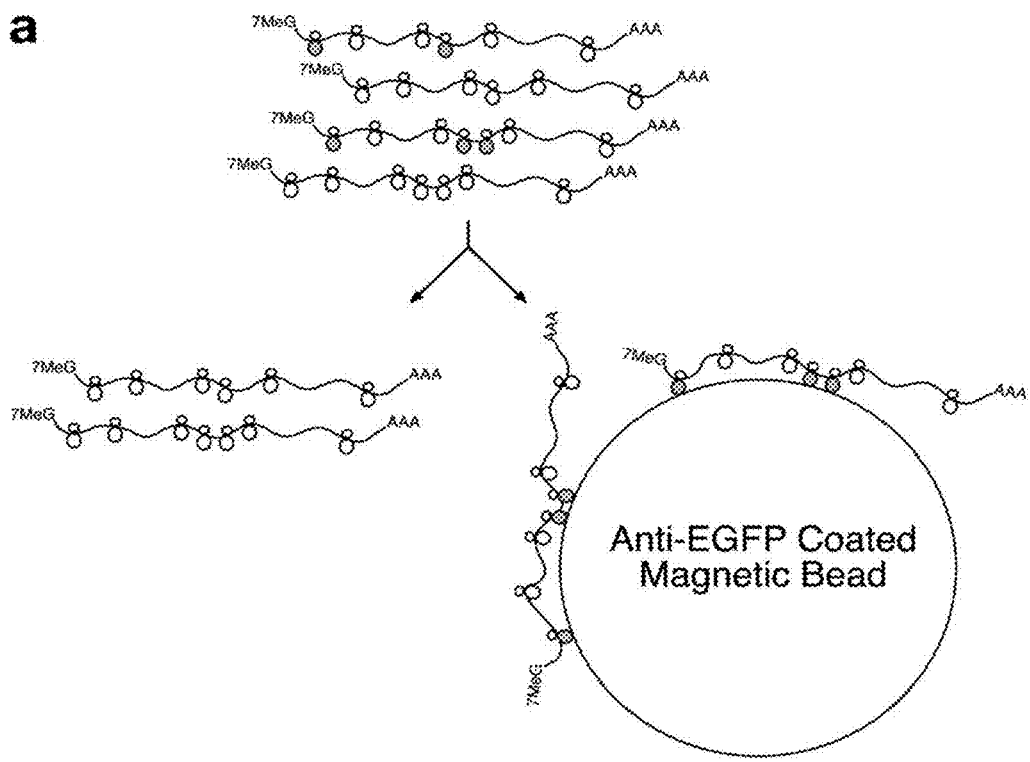
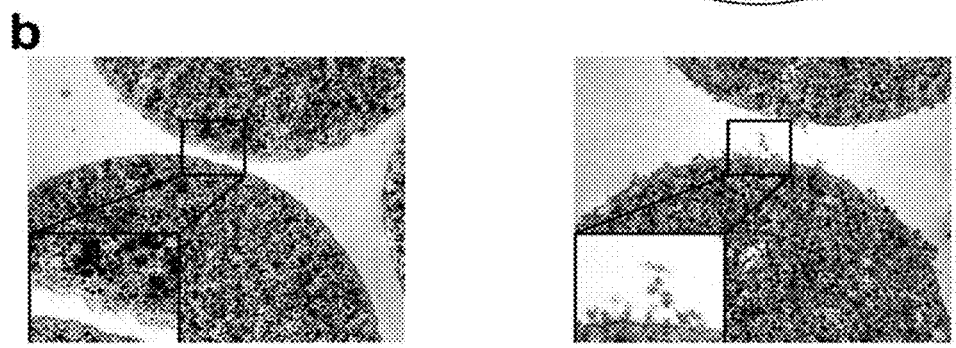

Translating Ribosome Affinity Purification Strategy

BAC engineering

BACarray Mouse Generation

Figure 11

Summary of Cell Types Studied

| | Region | BAC Driver | Line | Primary Cell Type Labeled | Confirmation of Cell Types | Minor Cell Type Labeled |
|---|---|---|---|---|---|---|
| 1 | Cerebellum | Pcp2 | DR166 | Purkinje Cells | Morphology, IF: PVALB+ and CALB1+ | None |
| | Cerebellum | Pcp2 | DR188 | Purkinje Cells | Morphology, IF: PVALB+ and CALB1+ | None |
| 2 | Cerebellum | Neurod1 | JP241 | Granule Cells, Deep Cerebellar Nuclei | Morphology, IF: NEUN+ | None |
| 3 | Cerebellum | Grm2 | JP77 | Granule Cell Layer Interneurons (Inner Golgi Cells) | Morphology, IF: GRM2/3+ | None |
| 4 | Cerebellum | Lypd6 | JP48 | Stellate and Basket Cells | Morphology, IF: PVALB+, NEUN-, CALB1- | None |
| 5 | Cerebellum | Grp | JP25 | Unipolar Brush Cells (mGluR1 subtypes) | Morphology, IF: CALB2-, GRM1+ or S100+ | Bergmann Glia |
| 6 | Cerebellum | Olig2 | JD97 | Mature Oligodendrocytes and Progenitors | Morphology, IF: OLIG2+, CSPG4+ or CNP+, GFAP- | None |
| 7 | Cerebellum | Cnlsm5 | JD307 | Mature Oligodendrocytes | Morphology, IF: CNP+, CSPG4- | Mature Oligodendrocytes |
| 8 | Cerebellum | Sept4 | DS153 | Bergmann Glia | Morphology, IF: S100+, ALDH1L1+, GFAP+ | None |
| 9 | Cerebellum | Aldh1L1 | JD130 | Astroglia (includes Bergmann Glia) | Morphology, IF: ALDH1L1+, GFAP+, CSPG4-, CNP- | None |
| 10 | Spinal Cord | Chat | DW167 | Motor Neurons, Cholinergic Interneurons | Morphology, IF: CHAT+, SLC18A3+ | None |
| 11 | Striatum | Drd1 | CP73 | Drd1 Positive Medium Spiny Neurons | Morphology, IF: PENK- | Cholinergic interneurons |
| 12 | Striatum | Drd2 | CP101 | Drd2 Positive Medium Spiny Neurons | Morphology, IF: PENK+ | None |
| 13 | Corpus Striatum | Chat | DW167 | Cholinergic Neurons | Morphology, IF: CHAT+, SLC18A3+ | None |
| 14 | Basal Forebrain | Chat | DW167 | Cholinergic Projection Neurons | Morphology, IF: CHAT+, SLC18A3+ | None |
| 15 | Brain Stem | Chat | DW167 | Motor Neurons, Midbrain Cholinergic Neurons | Morphology, IF: CHAT+, SLC18A3+ | None |
| 16 | Cortex | Ntsr1 | TS16 | Layer 6 Corticothalamic Pyramidal Neurons | Morphology, Morphometric comparison to eGFP lines | None |
| 17 | Cortex | Glt25d2 | DU9 | Layer 5a Corticospinal, Corticopontine Pyramidal Neurons, and Small Pyramidal Cells | Morphology, Morphometric comparison to eGFP lines | None |
| 18 | Cortex | Etv1 | TS58 | Layer 5a Corticostriatal Pyramidal Neurons | Morph, IF: some GABA+, some CALB2+, CALB1- | Few GFAP+ Astrocytes |
| 19 | Cortex | Prox | GM64 | Neurons | Morph, IF: some CALB1+, few PVALB+, CALB2- | None |
| 20 | Cortex | Cort | GM195 | Interneurons | Morph, IF: some CALB1+, few PVALB+, CALB2- | None |
| 21 | Cortex | Aldh1L1 | JD133 | Astroglia (reactive and non-reactive) | Morph, IF: ALDH1L1+, GLUL+, GFAP+, CSPG4-, CNP- | None |
| 22 | Cortex | Aldh1L1 | JD130 | Astroglia (reactive and non-reactive) | Morph, IF: ALDH1L1+, GLUL+, GFAP+, CSPG4-, CNP- | None |
| 23 | Cortex | Olig2 | JD97 | Mature Oligodendrocytes and Progenitors | Morphology, IF: OLIG2+, CSPG4+ or CNP+, GFAP- | None |
| 24 | Cortex | Cnlsm5 | JD307 | Mature Oligodendrocytes | Morphology, IF: CNP+, CSPG4- | None |
| 25 | Cortex | Cox | GM91 | Mixed Neurons | Morphology, IF: some CALB1+, all PVALB-, CALB2- | None |

Figure 12
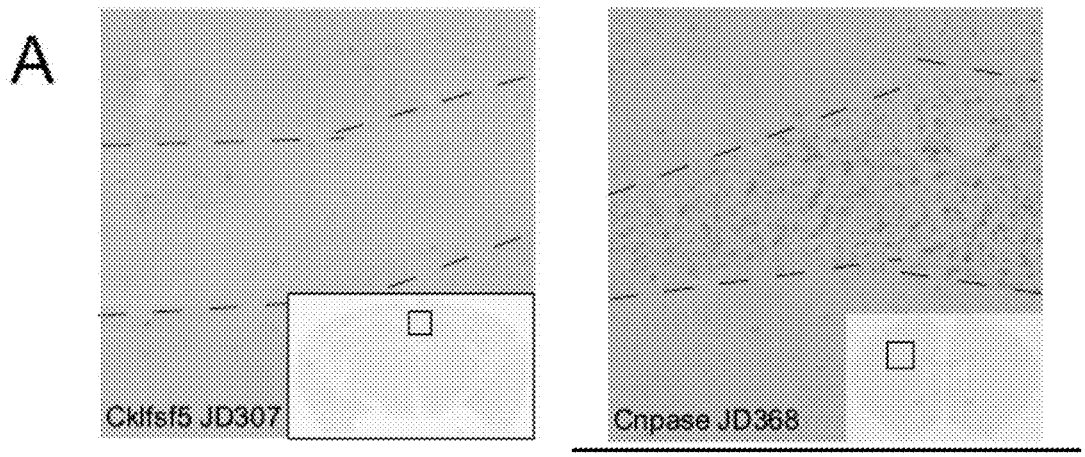
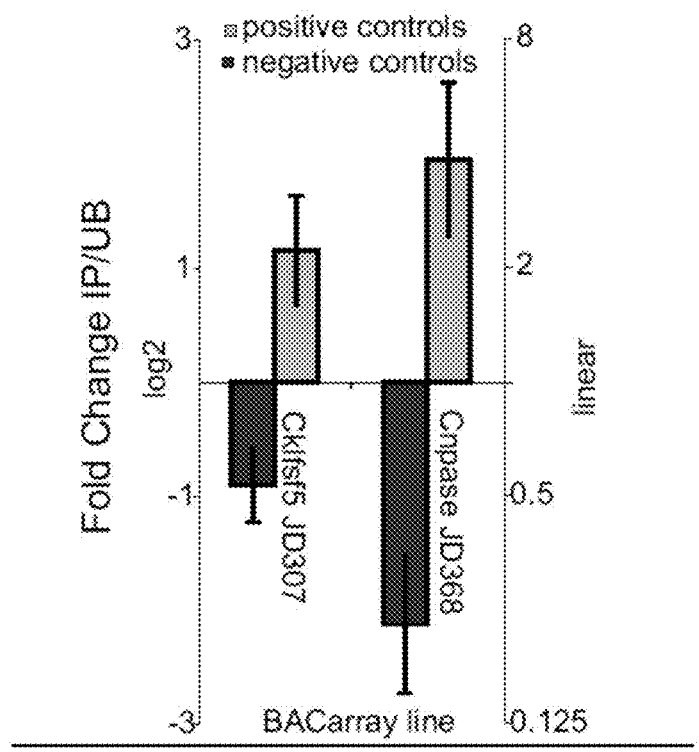

Purification of Tagged Polysomes

Control IP　　　　　　　　　　TRAP IP

Figure 15 continued

| Panel | Corr. | Cell Type | Panel | Corr. | Cell Type |
|---|---|---|---|---|---|
| A | -0.13 | Brain Stem Motor Neurons | P | -0.07 | Corticothalamic Neurons |
| B | -0.11 | Whole Tissue Brain Stem | Q | -0.07 | Cort+ Interneurons |
| C | -0.12 | Cerebellar Astrocyte | R | -0.11 | Pnoc+ Neurons |
| D | -0.12 | Bergmann Glia | S | -0.10 | Mature Oligodendrocytes from Cortex |
| E | -0.11 | Granule Cell Layer Interneurons | T | -0.11 | Mixed Oligodendrocytes from Cortex |
| F | -0.11 | Granule Cell | U | -0.11 | Cort+ Neurons |
| G | -0.12 | Mature Oligodendrocytes from Cerebellum | V | -0.08 | Whole Tissue Cortex |
| H | -0.12 | Mixed Oligodendrocytes from Cerebellum | W | -0.13 | Purkinje Ebf+ Oligodendrocyte Neurons |
| I | -0.11 | Purkinje Cells | X | -0.10 | Unbound RNA of the Basal Forebrain |
| J | -0.13 | Stellate and Basket Cells | Y | -0.09 | Motor Neurons of the Spinal Cord |
| K | -0.13 | Unipolar Brush Cell | Z | -0.09 | Whole Tissue Spinal Cord |
| L | -0.09 | Whole Tissue Cerebellum | AA | -0.13 | Corpus Striatum Cholinergic Neurons |
| M | -0.13 | Cortical Astrocytes | BB | -0.09 | Drd1 Positive Medium Spiny Neurons |
| N | -0.07 | Corticospinal, Corticopontine Neurons | CC | -0.07 | Drd2 Positive Medium Spiny Neurons |
| O | -0.09 | Corticostriatal Neurons | DD | -0.10 | Whole Tissue Basal Ganglia |

Figure 16
A)
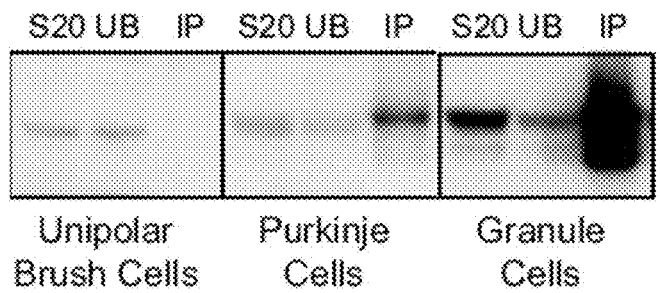
B)
| Line | IP # | ngs IP'd RNA | Amplified RNA |
|---|---|---|---|
| Unipolar Brush | IP1 | 61.6 | 6.8 ug/ul |
| Unipolar Brush | IP2 | 66.3 | 6.9 ug/ul |
| Unipolar Brush | IP3 | 62.1 | 6.2 ug/ul |
| Purkinje Cells | IP1 | 255.1 | 6.7 ug/ul |
| Purkinje Cells | IP2 | 358 | 7.2 ug/ul |
| Purkinje Cells | IP3 | 206 | 8.5 ug/ul |
| Granule Cells | IP1 | 4326.7 | 8.3 ug/ul |
| Granule Cells | IP2 | 4232.1 | 6.7 ug/ul |
| Granule Cells | IP3 | 6166 | 8.5 ug/ul |
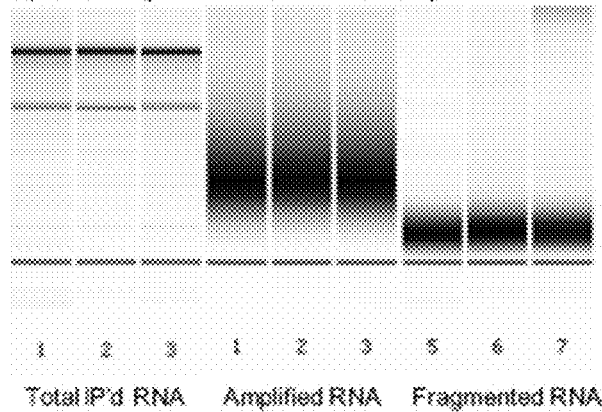

Figure 18
A
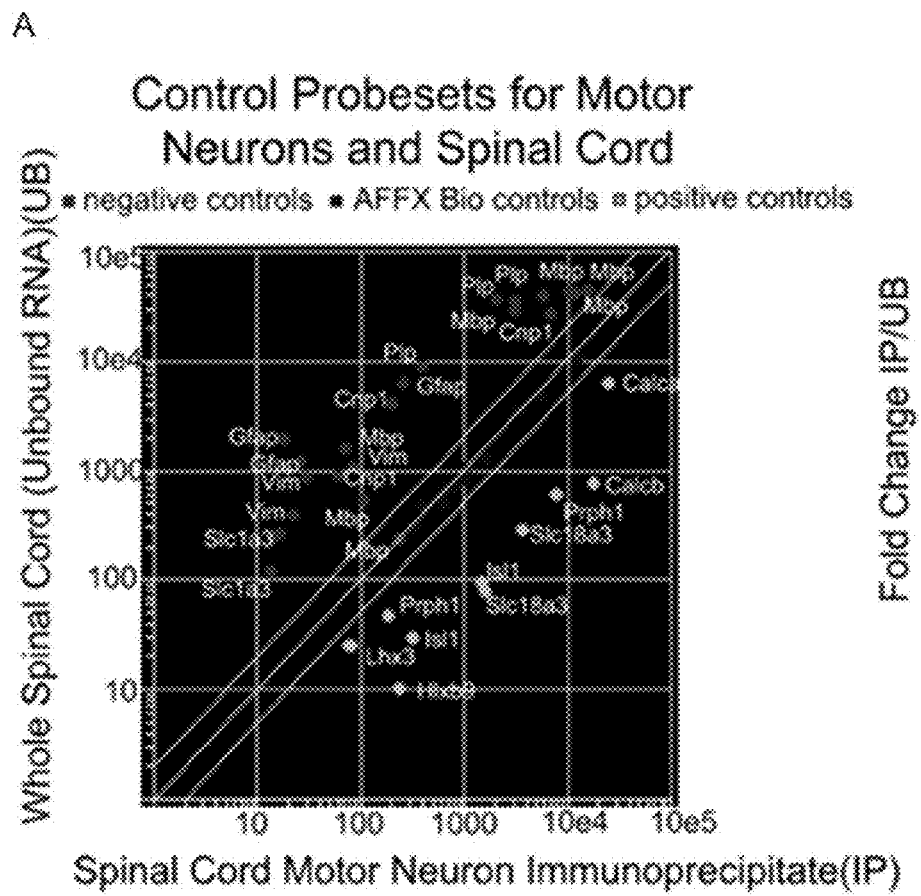
B
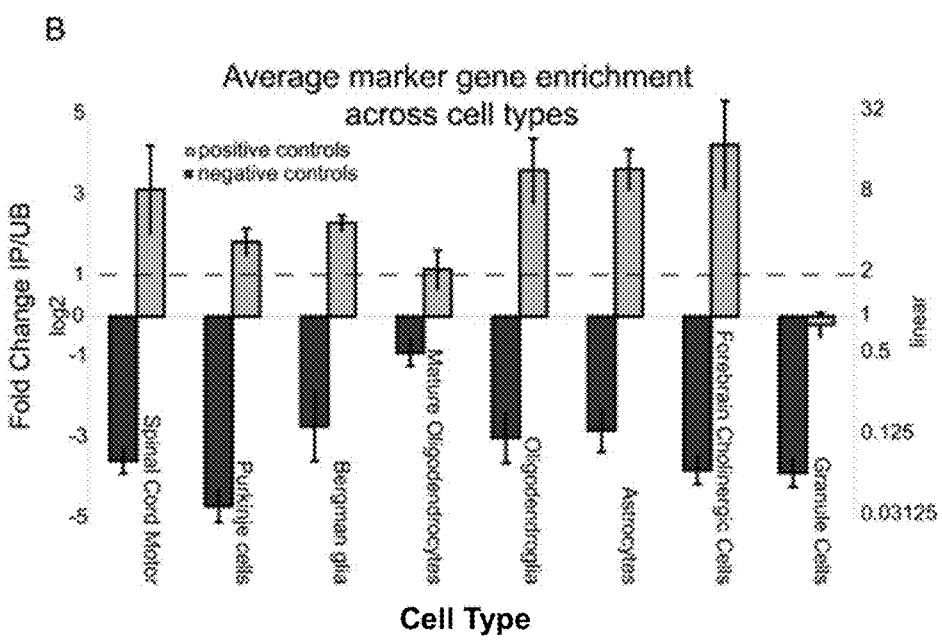

Figure 19
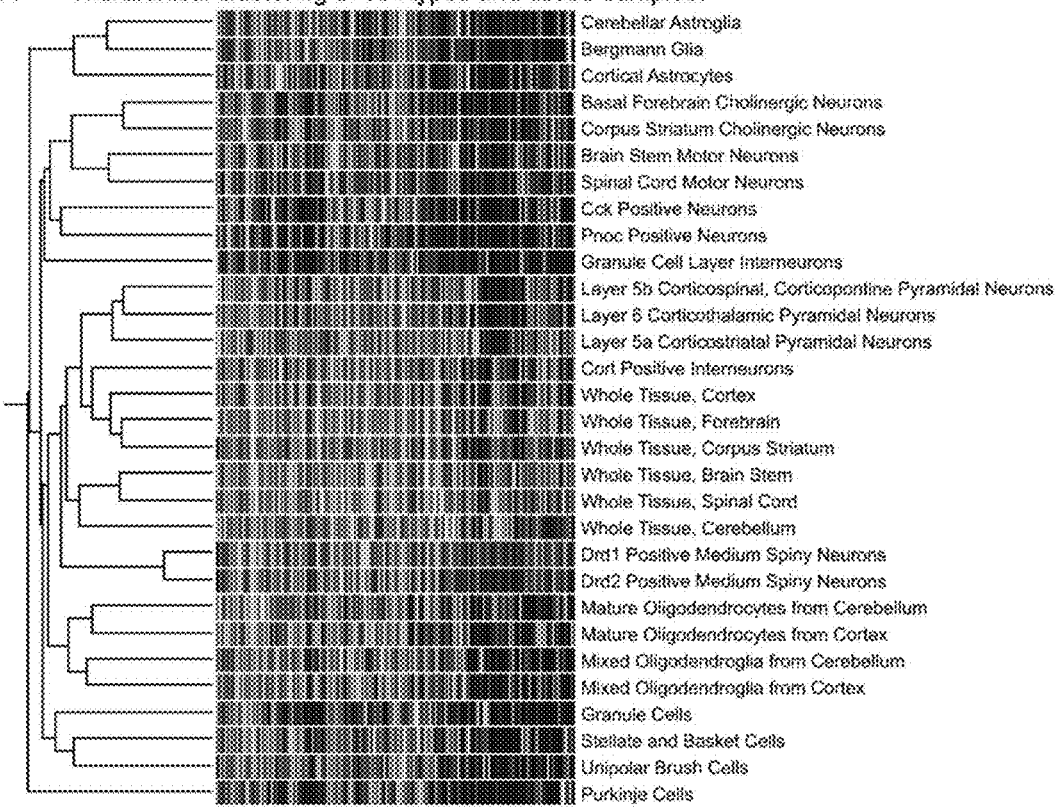
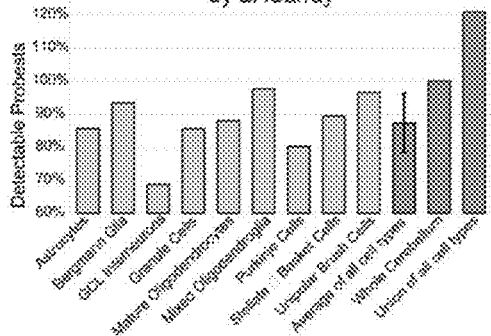
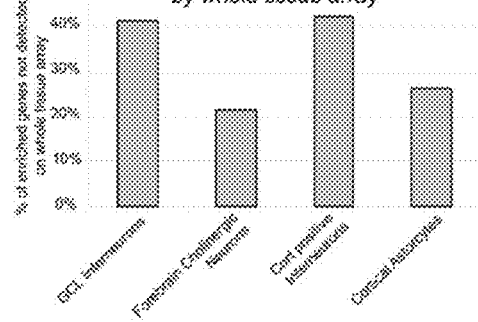

Figure 20
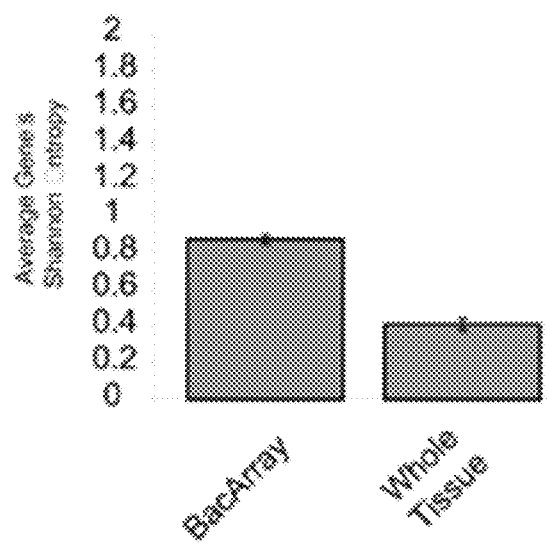
A  Average information of BACarray samples
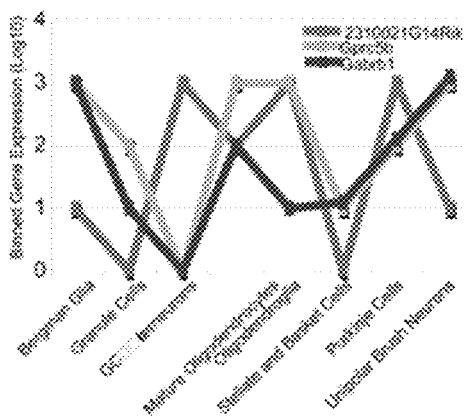
B  Examples of high entropy
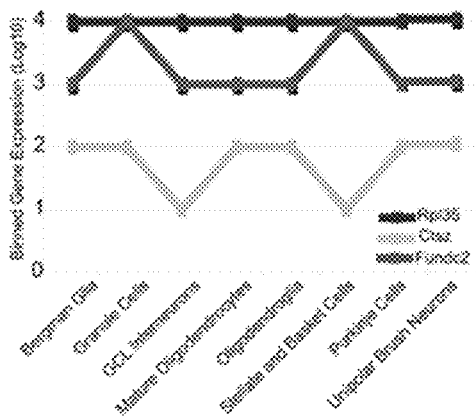
Examples of low entropy C      Cell type diversity is driven by channels and receptors C      Cell type diversity is driven by channels and receptors continued

| Str_drd2 | Str_drd1 | Cb_pcp2 | Ctx_aldh1l1 | Cb_grp | Cb_aldh1l1 |
|---|---|---|---|---|---|
| 1457132_at | 1457132_at | 1419880_x_at | 1442917_at | Acan5 | 1110017118Rik |
| Adora2a | 4930448N21Rik | 1460944_at | 1457215_at | Adcyap1 | 1447307_at |
| Ahnak | Adra2c | 1455870_at | 2010002N04Rik | AF529169 | 1459747_at |
| Arg2 | Ahnak | 1700023E05Rik | 2610034M16Rik | Ank1 | 1500015O10Rik |
| Bcl11b | Atp6v1c2 | 2410124H12Rik | Adora2b | Arg1 | 1810010K12Rik |
| Cd4 | Bcl2 | A730030A08 | Adora2b | Cd623a | Bbox1 |
| D430042O09Rik | C230078M08Rik | A730090H04Rik | Adora2b | Cxcl1 | BC029169 |
| Drd2 | Dmkn | Atp9a3 | AI449310 | Doc3a | Calml4 |
| Foxp1 | Drd1a | Cabl1 | AU067665 | Eomes | Cd38 |
| Fst | Drd1a | Car7 | AU067665 | Eomes | Chi3l |
| Fxt | Erc2 | Cep76 | Cyp4f15 | Grp | Cpe4l |
| Gng7 | Gyal1 | Ebf2 | Dmrta2 | Lef1 | Cxc5 |
| Gpr6 | Prcl1 | Eps8l2 | Fzd2 | Mao2l1 | Cyp4f14 |
| Gpr88 | Kcnip2 | Fgf7 | Idb3 | Nrb | Dap1 |
| Gprin3 | Myo5b | Fgf7 | Nr2e1 | Nnat | Dmp1 |
| Isl1 | Pde10a | Gchfr | Oaf | Nt3 | Dmp1 |
| Itch1 | Pdyn | Homer3 | Ppp1r3g | Otop2 | Dnahc8 |
| LOC665282 | Peg3 | Itk | Rpe65 | Otx2 | LOC433016 |
| Mn1 | Prkch | Mlf | Scara3 | Pttpne1 | Mdk |
| Pde10a | Prkch | Pep2 | Slc15a2 | Serpina1 | Mex2 |
| Rasgrp2 | Pum1 | Sec5a1 | Slc15a2 | Sln | Ramp1 |
| Rxrg | Rab40b | Smpx | Slc1a2 | Sln | Slco4a1 |
| Sec16a | Spata13 | Sox1 | Spp1 | Sln | Syn2 |
| Sec16a | Wnt2 | Sycp1 | T2bp | Tdo2 | Tnfsf7 |
| Tlc12 | Zfp281 | Tspan11 | Upp1 | Tmem182 | Tpa |

| Cb_sept4 | Cb_olig2 | Ctx_olig2 | Ctx_cntn5 | Cb_cntn5 | SC_chat |
|---|---|---|---|---|---|
| 8030451F13Rik | 1439734_at | 5730559C18Rik | 1435119_at | 1441721_at | 0610040B09Rik |
| A2m | 2310031A18Rik | Adm | 1445955_at | 1459882_at | Ahnak2 |
| Abi3 | 5730559C18Rik | Bmal | 2010001M06Rik | 1700063D05Rik | Amhr2 |
| Apg | 9630013A20Rik | Calcrl | 4933406E14Rik | 2210020M01Rik | Amhr2 |
| BC055107 | 9630013A20Rik | Ccng2 | Abca8a | 2700049A07Rik | Arhgap9 |
| C2 | 9630013A20Rik | Ccnb1 | Adamts1 | 2810003C17Rik | Arhgap9 |
| Cables1 | A030001D16Rik | Chst1 | Apod | 4833411O04Rik | Calca |
| Casp12 | A930009A15Rik | Cogg4 | Bfsp2 | A230001M10Rik | Calcb |
| Cox7b2 | Adam12 | Dmrta1 | C030030A07Rik | Apod | Cd24a |
| Gdf10 | Ascl1 | E2f8 | Cldn1 | Gfi1 | Cd24a |
| Gli | Bmp4 | Ect2 | Efnb3 | Gli1 | Chodl |
| Pax3 | C1ql1 | EG232599 | Eloxl1 | Gli1 | Dnahc2 |
| Plekho2 | Eya2 | Fgnl | Galnt6 | Gli3 | Enpep |
| Slc14a1 | Lmo1 | Gpr17 | Il33 | Hapln2 | Gna14 |
| Tbc1d30 | Lmo1 | Lad1 | Maas1 | Insc | Gna14 |
| Tmem30b | Lrrn2 | Pbk | Mobp | Mobp | Gna14 |
| Tmprss3 | Matn4 | Pdgfra | Ndrg1 | Nrg2 | Hoxb8 |
| Usp2 | Meox1 | Phip | Nrg2 | Nkx2-9 | Hoxc8 |
| Usp2 | Mmp2 | Prc1 | Nmral1 | Pcx18 | Hoxd8 |
| Usp2 | Mmp3 | Prkcs | Pcoloe2 | Serpinb1a | Hspb1 |
| Vim | Pcdh15 | Rasef10 | Plexhh1 | Slc34a3 | Hspb1 |
| Vim | Ppib | Rbp1 | Rasgrf1 | Slc34a3 | Lcn2 |
| Vim | Prlr5 | Rnf122 | Serpinb1a | Slc34a3 | Mrvi1 |
| Wif1 | Susd5 | Spel | Tmcc2 | Syt1 | Prph1 |
| Wnt8 | Traf4 | Top2a | Tnni1 | Tmem125 | Rtbdn | continued

| Brst_chat | Cb_neurod1 | Cb_grm2 | Cb_lypd6 | Ctx_pnoc | BFbr_chat |
|---|---|---|---|---|---|
| 1700001E04Rik | 1700021K02Rik | 1110002E22Rik | 1446785_at | Acaa1b | 2900001G08Rik |
| Calb | 1700021K02Rik | 1700048E17Rik | 1458324_x_at | Adam2 | AK006473 |
| Cgkar | 1700021K02Rik | 1810033B17Rik | 1459359_at | Cnr | Ccdc109b |
| Cks | 2310015B20Rik | 4930511J11Rik | 5830408C15Rik | Cnr1 | Cdkn3 |
| Gal | 5430421F17Rik | Akhp | 9030425E11Rik | Crh | Cox6a2 |
| Gppr1 | AI118078 | Acyp1 | Adamts15 | Crispld2 | Cox6a2 |
| Hoxc4 | Ankrd25 | Cd8a | Akr1b7 | Dlx1 | Crabp1 |
| Hspb1 | Calb2 | Chrd1 | Arg1 | Dlx1 | Dapl1 |
| Hspb1 | Calb2 | Fgf6 | Asgr1 | Hs3a | Edem3 |
| Hspb8 | Car4 | Gscr | Cdh1 | Igf1 | Edem3 |
| Kcnj14 | Cbln3 | Gdf3 | Cxcl12 | Igf1 | Gbx2 |
| Lpin | Cbln3 | Il2-13 | Grid2 | Lman1l | Gpr14 |
| Mbl2 | Comp | Igf2bp1 | Hrc | Mlf4 | Gpx2 |
| Nppb | Crtam | Klra3 | Kit | Necab1 | Grem1 |
| Nts | D16Ertd472e | Lbxcor1 | Lbx1h | Ngp | Hcrtr1 |
| Phox2b | Gprc5c | Pik3k1b | Lmc38 | Pnoc | Isl1 |
| Pde6H | Il6 | Serpinb1b | Lypd6 | Prox1 | Lhx8 |
| Pigs | Il6 | Sic14 | Lypd6 | Pth2 | LOC545261 |
| Rgs11 | Il17re | Slc3 | Plch1 | Ptn | Ngb |
| Shox2 | Negr1 | Tcfap2b | Prkcd | Rab3c | Plxnr2 |
| Slc18a3 | Neurod1 | Tpx2 | Scrn1a | Slc2 | Scn9a |
| Slc5a5 | Np220 | Tpx1 | Sla | Syt1 | Tacr3 |
| Tbx20 | Rad51l1 | Uchl3a | Sla | Tac2 | Tacr3 |
| Ucn | Rps6ka1 | Vav2 | Sla | Tent1 | Th |
| Ush1c | Uncx4.1 | Yif1 | Tcfap2b | Vip | Zar1 | continued

| CorpStr_chat | Ctx_cck | Ctx_cort | Ctx_etv1 | Ctx_ntsr1 | Ctx_glt25d2 |
|---|---|---|---|---|---|
| 2010007E15Rik | 1700101I19Rik | 1442650_at | C1qa | 1441808_at | 1459626_at |
| 8430704N06 | 9130024F11Rik | 1447819_x_at | C1qb | 1456371_at | Abcb1a |
| Ache | A430108G06Rik | 2900040J22Rik | C1qb | 8430418L06Rik | Acsl4 |
| Ager1 | Bnk | 4930529K06Rik | C1qg | Arhgap25 | Cacna2d1 |
| AI606473 | Bsn | 4930401H06Rik | Ctx2 | Cdh4 | Cdkr |
| BB086117 | Ccl21b | A330056F23Rik | Cd14 | Epha4 | Cldn5 |
| Bves | Ccl4 | Akr1c18 | Clec4f10 | Epha4 | Clan1 |
| Cd44 | Fgf | Ath4 | Csf1r | Gpx4 | Flt1 |
| Cpne4 | Fgf | Casp14 | Cxcl4 | Ifitrap | Gli25d2 |
| Crabp2 | Fmo2 | Cd4 | Egr4 | Lamc2 | Gpr103 |
| Ecel1 | Golf1a | Cort | F13a | Met | Lamc2 |
| Gad | Herc5 | Crhbp | Fcgr2b | Myh3 | Ly6a |
| Gm691 | Igfbp6 | Ddx5 | Fcgr2b | Nov | Ly6c |
| Mxra7 | Kn1-12 | Med1 | Fcgr2b | Nov | Mef2c |
| Nefr | Kn1-12 | Mexd1 | Gmfg | Nov | Mef2c |
| Nrk1 | Neurod6 | Neg2 | Hcgd1b | Pcdh21 | Pcdh19 |
| Ocep | Ppp1r11 | R3hdm | Lyz8 | Pde4dg | Pkp |
| Pcz1 | Rtn4r2 | Rbp4 | Lyz8 | Pthr2 | Slc28a10 |
| Pcpde3 | Slc22a16 | Scn1a | Lrp-6 | Scube1 | Slc7a4 |
| Slc7a14 | Slc5a9 | Slmc2 | Mrc1 | Tcrb-V13 | Slc7a4 |
| Spink12 | Slap2 | Slc5a9 | Ms4a7 | Tcrb-V13 | Slco1a4 |
| Tmsb10 | Tacstd1 | Srl81 | Msr2 | Tcrb-V13 | Smoc2 |
| Trag1a | Tcrb-V13 | Ssr | Vtn | Tcrb-V13 | Sox17 |
| Utap1 | Tcrb-V13 | Tacstd1 | Vtn | Tcrb-V13 | Sox18 |
| Zar1 | Tncc | Tcrb | Xlkd1 | vps11 | Wdr35 | continued

Figure 22

▪ Not Expressed in M.N.

▪ Expressed in M.N.

▪ Enriched in M.N. (IP/UB >2)

Glutamate/Aspartate Receptors

| Gene | ip/ub | rf | Title |
|---|---|---|---|
| Gria3 | 1.03 | 1 | ionotropic, AMPA3 |
| Gria4 | 0.57 | 1 | ionotropic, AMPA4 |
| Grid1 | 0.73 |  | ionotropic, delta 1 |
| Grik1 |  | 1 | ionotropic, kainate 1 |
| Grik2 | 1.35 |  | ionotropic, kainate 2 |
| Grik4 | 1.31 | 1 | ionotropic, kainate 4 |
| Grik5 |  |  | ionotropic, kainate 5 |
| Grin1 | 0.45 | 1 | ionotropic, NMDA1 |
| Grin3a | 0.48 |  | ionotropic, NMDA3A |
| Grin3b | 5.66 | 2 | ionotropic, NMDA3B |
| Grm4 | 1.85 | 3 | metabotropic 4 |

GABA Receptors

| Gene | ip/ub | rf | Title |
|---|---|---|---|
| Gabbr1 | 0.92 | 4 | GABA-B receptor 1 |
| Gabra2 | 1.2 | 1 | GABA-A subunit alpha 2 |
| Gabra5 | 0.6 | 1 | GABA-A subunit alpha 5 |
| Gabra6 |  | 1 | GABA-A subunit alpha 6 |
| Gabrb2 |  | 1 | GABA-A subunit beta 2 |
| Gabrb3 | 0.44 | 1 | GABA-A subunit beta 3 |
| Gabrd |  | 1 | GABA-A subunit delta |
| Gabrg1 |  | 1 | GABA-A subunit gamma 1 |
| Gabrg1 | 0.69 |  | GABA-A subunit gamma 2 |
| Gabrg2 | 0.79 | 1 | GABA-A subunit gamma 2 |

Glycine Receptors

| Gene | ip/ub | rf | Title |
|---|---|---|---|
| Glra2 | 0.48 | 5 | alpha 2 subunit |
| Glrb | 1.14 | 5 | beta subunit |

Figure 22 continued

| | | |
|---|---|---|
| Acetylcholine Receptors | | |
| Chrm1 | | muscarinic 1, CNS |
| Chrna3 | | nicotinic, a polypeptide 3 |
| Chrna4 | 0.74 | nicotinic, a polypeptide 4 |
| Chrna5 | | nicotinic, a polypeptide 5 |
| Chrna6 | | nicotinic, a polypeptide 6 |
| Chrna7 | 0.4 | nicotinic, a polypeptide 7 |
| Chrna9 | | nicotinic, a polypeptide 9 |
| Chrnb1 | | nicotinic, B polypeptide 1 |
| Chrnb2 | 0.74 | nicotinic, B polypeptide 2 |
| Chrnb3 | | nicotinic, B polypeptide 3 |
| Chrnb4 | | nicotinic, B polypeptide 4 |
| Serotonin Receptors | | |
| Htr1d | 2.56 | serotonin receptor 1D |
| Htr3a | | 1 serotonin receptor 3A |
| Htr7 | 1.23 | 1 serotonin receptor 7 |
| Adenosine Receptors | | |
| Adora1 | 0.88 | 1 A1 receptor |
| Adora2a | | 6 A2a receptor |
| Adora2b | | A2b receptor |
| Nucleoside (ATP) Receptors, P2X | | |
| P2rx4 | 0.88 | 1 ligand-gated ion channel, 4 |
| P2rx5 | 1.32 | 1 ligand-gated ion channel, 5 |
| P2rxl1 | 5.36 | P2X-like 1, orphan receptor |
| Nucleoside (ATP) Receptors, P2Y | | |
| P2ry12 | | P2Y, G-protein coupled 12 |
| P2ry14 | 0.38 | P2Y, G-protein coupled, 14 |
| P2ry5 | | P2Y, G-protein coupled, 5 |
| P2ry6 | | P2Y, G-protein coupled, 6 |
| Norepinephrine/Epinephrine Receptors | | |
| Adra1a | 0.64 | 1 Adrenergic alpha 1a |
| Adra2a | 0.43 | 1 Adrenergic alpha 2a |
| Adrb1 | | 1 Adrenergic beta 1 |
| Dopamine Receptors | | |
| Drd1 | | 1 Dopamine receptor 1 |
| Drd2 | | 1 Dopamine receptor 2 |
| Histamine Receptors | | |
| Hrh1 | 1.25 | Histamine receptor H 1 |
| Hrh3 | | Histamine receptor H 3 |
| Thyrotropin releasing hormone | | |
| Trhr | 2.05 | 1 TRH receptor |
| Trhr2 | | TRH receptor 2 |

Figure 22 continued

Selected novel and expressed receptors

| Gene | ip/ub | rf | Title |
|---|---|---|---|
| Acvr1 | 1.24 | | Activin A type 1 |
| Acvr1b | 0.74 | | Activin A type 1B |
| Acvr2 | 0.8 | | Activin A type 2 |
| Agtr2 | 0.85 | 1 | Angiotensin II type 2 |
| Amhr2 | 28 | 2 | Anti-Mullerian hormone, 2 |
| Cd151 | 5.45 | | CD151 antigen |
| Cd24a | 4.72 | | CD24a antigen |
| Gfra1 | 2.11 | 3 | GDNF family alpha 1 |
| Gfra4 | 1.03 | | GDNF family alpha 4 |
| Ghr | 0.82 | | Growth hormone |
| Gpr3 | 2.48 | | G-protein coupled 3 |
| Gpr22 | 1.3 | | G protein-coupled 19 |
| Gpr27 | 0.49 | | G protein-coupled 27 |
| Gpr45 | 1.3 | | G-protein coupled 45 |
| Gpr49 | 0.6 | | G-protein coupled 49 |
| Gpr54 | 1.39 | | G-protein coupled 54 |
| Gpr61 | 1.09 | | G-protein coupled 61 |
| Gpr68 | 1.67 | | G protein-coupled 68 |
| Gpr83 | 1.34 | | G-protein coupled 83 |
| Gpr85 | 0.85 | | G protein-coupled 85 |
| Gpr123 | 2.48 | | G protein-coupled 123 |
| Gpr135 | 0.47 | | G protein-coupled 135 |
| Gpr139 | 0.51 | | G protein-coupled 139 |
| Ifngr | 0.72 | | Interferon gamma |
| Ifngr2 | 2.8 | | Interferon gamma 2 |
| Oprs1 | 2.66 | | Opioid sigma 1 |
| Tnfrsf12a | 2.62 | | TNFR superfamily, 12a |
| Tnfrsf1a | 1.44 | | TNFR superfamily, 1a |
| Tnfrsf21 | 1.68 | | TNFR superfamily, 21 |
| Vdr | 8.54 | | Vitamin D |

Figure 22 continued

Acetylcholine neurotranmission genes

| Gene | ip/ub | rf | Title |
|---|---|---|---|
| Chat | 8.0 | 4 | choline acetyl-transferase |
| Ache | 2.1 | 5 | acetylcholinesterase |
| Slc18a3 | 16.8 | 6 | Vesicular ACH transporter |
| Slc5a7 | 26.4 | | Choline transporter |

Peptide Transmitters

| Calca | 3.83 | 7 | CGRP, alpha |
|---|---|---|---|
| Calcb | 21.7 | 7 | CGRP, beta |

Cytokines and others

| Ccl17 | 5.07 | | chemokine (cc) ligand 17 |
|---|---|---|---|
| Cfi | 30.8 | | complement component i |
| Cxcl12 | 6.63 | | chemokine (cxc) ligand 12 |
| Cxcl5 | 2.9 | | chemokine (cxc) ligand 5 |
| Egfl7 | 2.7 | | EGF-like domain 7 |
| Fgf1 | 2.54 | 8 | fibroblast growth factor 1 |
| Il7 | 5.44 | | interleukin 7 |
| Kitl | 1.7 | | kit ligand |

Homeobox transcription factors

| Hlxb9 | 46.7 | 9 | homeobox gene HB9 |
|---|---|---|---|
| Hod | 0.56 | | homeobox only domain |
| Hoxa5 | 0.43 | 10 | homeo box A5 |
| Hoxa7 | 0.53 | 10 | homeo box A7 |
| Hoxa9 | 0.54 | 10 | homeo box A9 |
| Hoxb5 | 0.31 | 10 | homeo box B5 |
| Hoxc5 | 3 | 10 | homeo box C5 |
| Hoxc8 | 0.97 | 10 | homeo box C8 |
| Hoxc9 | 0.67 | 10 | homeo box C9 |
| Hoxc10 | 0.46 | 10 | homeo box C10 |
| Hoxd9 | 0.88 | 10 | homeo box D9 |
| Irx1 | | | Iroquois rltd homeobox 1 |
| Irx3 | 8.12 | 11 | Iroquois rltd homeobox 3 |
| Irx5 | | | Iroquois rltd homeobox 5 |
| Isl1 | 20 | 9 | insulin rltd protein 1 |
| Isl2 | 5.67 | 9 | insulin rltd protein 2 |

Figure 34
BACarray Molecular Phenotyping of Cerebellar Cell Types in ATM KO Mice
Bergmann Glia
Purkinje Cells
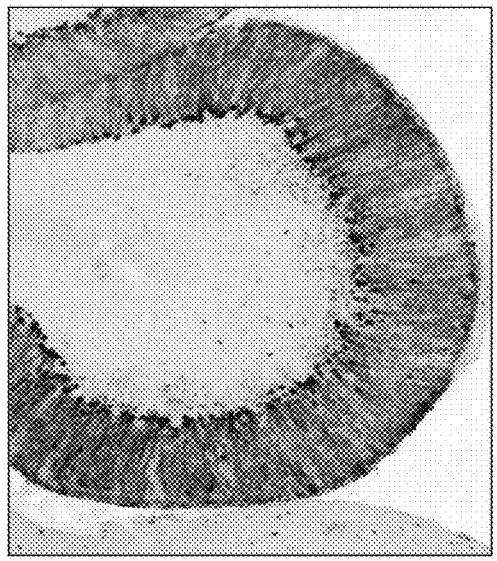 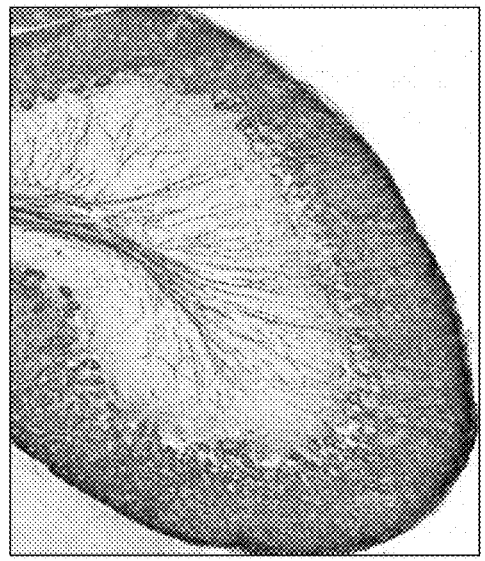
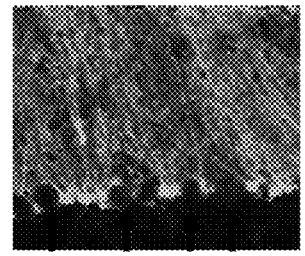 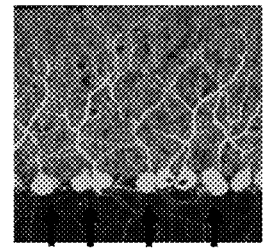
mitotic
post-mitotic Figure 38
Ventral Tegmental Area-Specific Markers
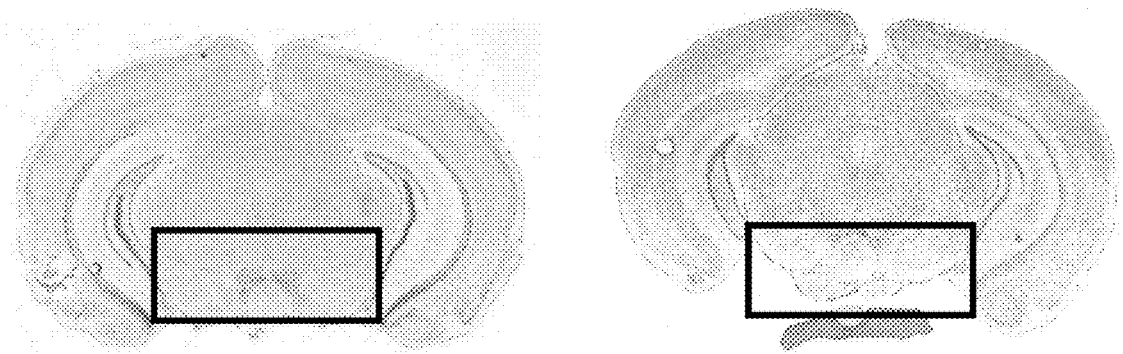
Substantia Nigra Pars
Compacta-Specific Markers
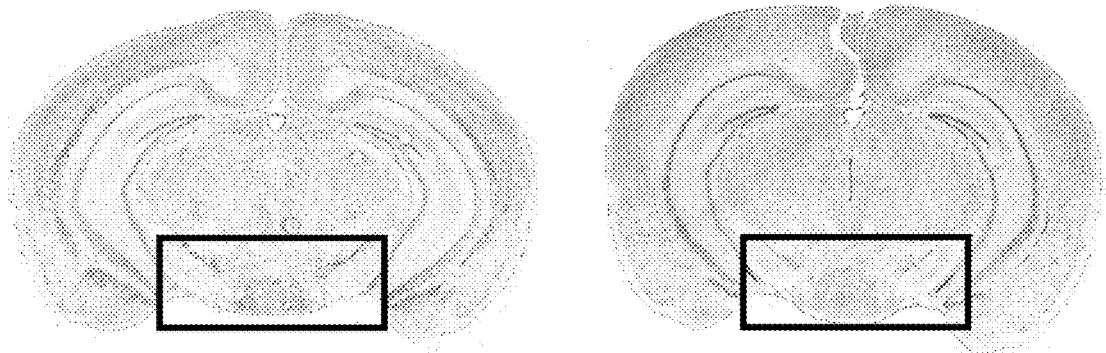

Figure 39

Dopaminergic cell loss in the Rodent Substantia Nigra:
Unilateral 6-OHDA lesion

Left Side  Right Side
Vehicle injected  6-OHDA injected

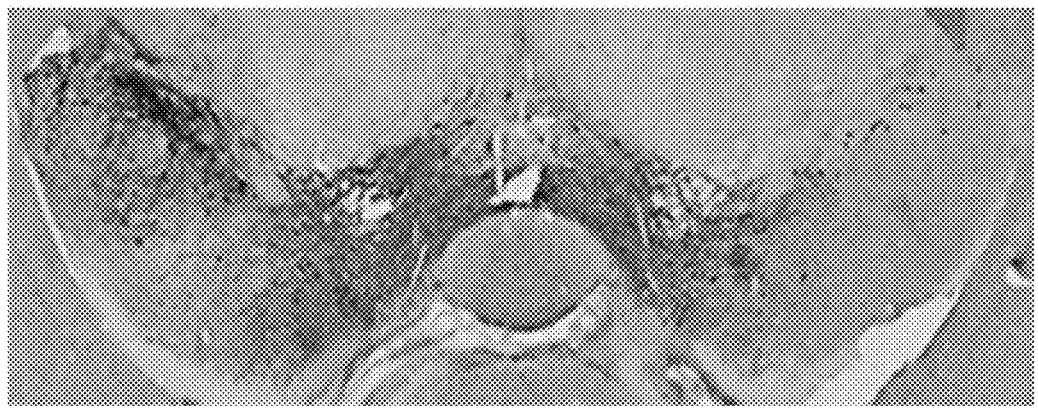

6-OHDA injected into the striatum, mice sacrificed 3 weeks post-injection,
and tissue stained with tyrosine hydroxylase antibody The BACarray strategy will be used to explore the
differential vulnerability of SN vs VTA
cells in animal models of PD Parkinson's Disease Therapeutic Opportunity:
Develop New Strategy for Stimulation of Sub-Thalamic Nucleus
Antagonists of Gpr6

METHODS AND COMPOSITIONS FOR TRANSLATIONAL PROFILING AND MOLECULAR PHENOTYPING

CROSS-REFERENCE

The present application is a continuation of U.S. patent application Ser. No. 12/918,761, filed Nov. 15, 2010, which was the National Stage of International Application No. PCT/US09/01614, filed Mar. 12, 2009, which claims the benefit of U.S. Provisional Application Nos. 61/036,049 filed Mar. 12, 2008, 61/036,058 filed Mar. 12, 2008, 61/070,327, filed Mar. 21, 2008, and 61/199,108 filed Nov. 12, 2008 which applications are incorporated herein by reference in their entirety.

SEQUENCE LISTING

In accordance with 37 CFR 1.52(e)(5), a Sequence Listing in the form of a text file (entitled "2011060-0010 ST25", created on Jan. 30, 2017, and having a size of 9,250 bytes) is hereby incorporated by reference in its entirety.

STATEMENT AS TO FEDERALLY SPONSORED RESEARCH

This invention was made with the support of the U.S. Government under Grant No: AG09464 awarded by the National Institute on Aging, MH074866 awarded by the National Institute of Mental Health, DA10044 and 5F32DA021487 awarded by the National Institute on Drug Abuse, 5UL1RR024143 awarded by the National Institutes of Health/National Center for Research Resources, and NS34696 awarded by the National Institute of Neurological Disorders and Stroke. The U.S. Government may have certain rights to the subject matter provided herein.

BACKGROUND OF THE INVENTION

A paradigm in the development of new diagnostics and therapies for human diseases and disorders is the characterization of the gene expression of defined cell types. The cellular complexity of many tissues poses a challenge for those seeking to characterize gene expression at this level. The enormous heterogeneity of a tissue such as the nervous system (thousands of neuronal cell types, with non-neuronal cells outnumbering neuronal cells by an order of magnitude) is a barrier to the identification and analysis of gene transcripts present in individual cell types. Cellular subtypes are highly heterogeneous and often intermixed. Gene expression studies on isolated cells have been limited by stresses introduced during cellular isolation procedures, the adaptations which occur upon the loss of tissue-intrinsic signals that control cellular physiology in vivo, and the technical challenges associated with reproducible mRNA purification from fixed tissue. A method to isolate translated mRNAs from defined cell types and subtypes without the need for cell isolation is needed in order to define previously undefined cell types, identify molecular targets for diseases and disorders, and provide a way in which to identify co-regulated gene sets for a particular biological function. The invention is described here.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

The invention described herein provides methods, compositions, and kits useful in elucidating the biological properties of distinct cellular populations. The embodiments described herein comprise a translating ribosome affinity purification (TRAP) methodology, which is a generalizable method useful for the identification of molecular changes in any genetically defined cell type in response to genetic alterations, disease, environmental, pharmacological, other perturbations.

In one aspect, the invention described herein provides a method of identifying a co-regulated gene set for a function, comprising determining translational profiles for a plurality of cell types that express a gene associated with that function, comparing the translational profiles to determine what additional genes are similarly regulated, thereby identifying a co-regulated gene set involved in that function specifically. In one embodiment, the method is provided to identify a co-regulated gene set involved in myelination, and in a further embodiment the gene associated with myelination is Mbp. In one embodiment, the co-regulated gene set comprises at least two genes listed in Table 9. In a related embodiment, the gene set comprises at least two genes selected from the group consisting of Pip1, Cnp, Mog, Mal and Mobp.

In another aspect, the invention described herein provides a method for detecting one or more cell type-enriched genes not detectable by the whole-tissue microarray technique comprising assessing a translational profile for a cell type, comparing the translational profile to the results of a whole-tissue microarray, and determining the presence of one or more genes in the translational profile that are not present in the results of a whole-tissue microarray, thereby detecting one or more cell type-enriched genes that are not detectable by the whole-tissue microarray technique. In particular embodiments, greater than 20%, 30% or 40% of the genes enriched in that cell type are not detectable by the whole-tissue microarray technique. These methods can be applied to any cell type of interest including neuronal and non-neuronal cell types. In exemplary embodiments, the cell type is selected from the group consisting of striatal cell, cerebellar cell, cortical cell, hypothalamic cell, hippocampal cell, brainstem cell, and a spinal cord cell.

In another aspect, the invention described herein provides a method of identifying medium spiny neuron-enriched mRNAs, the method comprising expressing a ribosomal protein regulated by a regulatory region specific to a gene expressed in medium spiny neurons in an organism, isolating complexes comprising the ribosomal protein associated with mRNAs, identifying the mRNAs in the complexes, and comparing the mRNAs to those identified from a reference sample. In one embodiment the regulatory region used for expression is specific to a gene expressed in striatonigral neurons or striatopallidal neurons. In some embodiments the medium spiny neuron is associated with a disease or disorder such as but not limited to Parkinson's disease, addiction, attention deficit hyperactivity disorder, or Huntington's disease. In an additional embodiment, the method can be used in guiding the selection of candidate targets for the treatment of the disease or disorder, and for further screening of potential modulators of the candidate targets.

In yet another aspect, the invention described herein provides a method of identifying motor neuron-enriched mRNAs, the method comprising expressing a ribosomal protein regulated by a regulatory region specific to a gene expressed in motor neurons, isolating complexes comprising the ribosomal protein associated with mRNAs, identifying the mRNAs in the complexes, and comparing the mRNAs to those identified from a reference sample. In a specific embodiment, the regulatory region comprises regulatory sequences from a choline acetyltransferase (Chat) locus. This method can be utilized to identify mRNAS from any motor neuron, such as but not limited to brain stem motor neurons, spinal cord motor neurons, upper motor neurons and others.

In another aspect, the invention described herein provides a method for assessing the translational profile of a cerebellar cell, comprising expressing a ribosomal protein regulated by a regulatory region specific to a cerebellar gene in the cell, isolating at least one complex comprising the ribosomal protein associated with a mRNA from the cell, and identifying the mRNA from the complex whereby generating a translational profile. In one embodiment, the cerebellar cell is associated with a disease or disorder, such as ataxia.

The present invention also provides for kits comprising a recombinant vector engineered to express a nucleic acid sequence encoding a ribosomal protein and a detectable tag operably linked to an endogenous regulatory region, useful for practicing the methods described herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 presents the translating ribosome affinity purification (TRAP) methodology. (a) Schematic of affinity purification of eGFP tagged polysomes (originating from the target cell population) using anti GFP antibody coated beads. (b) Transmission electron micrographs of anti GFP coated magnetic beads after incubation with extracts taken from HEK293T cells transfected with an empty vector (left panel) or the eGFP L10a construct (right panel); images acquired at 50,000× magnification, inserts enlarged by a factor of 2.3×.

FIG. 3 is comprised of Panels a, b, c, d, e, and f. Panel a of FIG. 3 shows that induction of the iron-storage protein Ferritin was seen after 36 hours of iron treatment. Panel b of FIG. 3 shows post-mitochondrial supernatants of untreated or iron-treated cells loaded onto linear sucrose gradients (20-50% w/w). After velocity sedimentation, fractions (direction of sedimentation noted by arrow) were collected while UV absorbance (254 nm) was being measured. A representative trace is shown, as profiles from non-treated and iron-treated lysates looked nearly identical. Non-polysome and polysome gradient fractions were generated as indicated. To avoid Ferritin mRNAs associated with mRNPs, only heavier polysomes (with greater than 4 ribosomes) were included in the polysome fraction. Panel c of FIG. 3 shows that after iron treatment, as expected, a shift of Ferritin heavy chain mRNA (Fth1) out of non-polysome fractions into polysome fractions was observed, as determined by reverse transcription followed by quantitative PCR of total RNA purified from non-polysome and polysome gradient fractions (range of fold-change in non-polysome fraction: 0.16-0.22; range of fold-change in polysome fraction: 1.83-2.15). Panel d of FIG. 3 shows immunoprecipitations performed from non-polysome or polysome gradient fractions and 0.2% of the Input (IN), 0.02% of the unbound (UB); 1% of the bound (IP) samples were loaded onto gels for immunoblot analysis with eGFP or Rpl7 antibodies; * indicates the presence of a weak Rpl7 band upon much longer exposure. Rpl7 was not present in the non-polysome fraction, presumably because, unlike the overexpressed eGFP-Rpl10a, it was all incorporated into polysomes. As expected from the lack of Rpl7 (and thus assembled ribosomes) in the non-polysome fraction, immunoprecipitations from non-polysome fractions did not pull down any RNA above background, indicating that the immunoprecipitation was specific to translated messages. Panel e of FIG. 3 shows a direct eGFP immunoprecipitation of post-mitochondrial supernatants (whole cell lysates, unfractionated) performed to determine if the translating ribosome affinity purification (TRAP) methodology could faithfully reflect the changes observed in Panel c of FIG. 3. 0.5% of input (IN), 0.5% of the unbound fraction (UB), and 1.0% of the bound (IP) samples were loaded onto gels for immunoblot analysis with eGFP (top pane of Panel e of FIG. 3), Rpl10a (middle pane of Panel e of FIG. 3), or Rpl7 (bottom pane of Panel e of FIG. 3) antibodies. * indicates the presence of a light eGFP-L10a band upon longer exposure. No endogenous Rpl10a or Rpl7 was recovered in the bound (IP) fraction of mock samples, while endogenous Rpl10a and Rpl7 were both recovered in the bound (IP) fraction of untreated and iron-treated samples. Panel f of FIG. 3 shows the iron-induced fold-change in Fth1 mRNA levels relative to Actb mRNA levels in samples immunoprecipitated (IP) from either polysomes or from whole cell lysates (range of fold-change in polysome IP samples: 2.01-2.43; range of fold-change in direct IP samples: 1.80-1.93) was similar to the change observed in the polysome gradient fraction before immunoprecipitation (c).

FIG. 12 illustrates that higher transgene expression yields better signal to noise. A) DAB immunohistochemistry for eGFP-L10a reveals differential intensity of transgene expression in two BACarray lines targeting the same cell population. B) Quality of BACarray data, as assessed by average IP/UB fold change for positive and negative controls, is better for the line with higher transgene expression.

FIG. 16 illustrates that BACarray can consistently purify RNA efficiently from rare and common cell types. A) Western blot for eGFP from S20 fraction, flow through (UB), and immunoprecipitate from rare (unipolar brush cells), common (Purkinje cells) and extremely common (granule cells) cell types of cerebellum. Note that even when protein is undetectable, there is sufficient good quality RNA for microarray amplification. B) Yield of RNA is consistent across replicates within each line. C) Total RNA is of good quality for all three cell types, with intact 18s and 28s bands, as well as mRNA which can be amplified and fragmented following standard protocols.

FIG. 17 is comprised of Panels A, B, C, and D. Panel A of FIG. 17 shows that replicates for the same cell type gave nearly identical genome wide translational profiles, confirming the results of Heiman et al, and extending this finding to many other cell types. The average Pearson's correlation between replicates for a given cell population from independently isolated samples was above 0.98 across all cell types. Panel B of FIG. 17 shows scatter plots for three representative cell types of the cerebellum. Panel C of FIG. 17 shows Venn diagrams constructed from the top 1000 most enriched probesets for each cell type. Panel D of FIG. 17 presents an examination of results obtained from independent BACarray founder lines prepared with the same engineered BAC to determine whether the position of integration of the BACarray construct would influence the data.

FIG. 18 is comprised of Panels A, B, C, and D. Panel A of FIG. 18 shows a scatter plot of IP vs. UB for spinal cord motor neurons. Probesets for known markers of motor neurons with measurable signal on the array are clearly enriched in the IP sample, whereas probesets for glial cell-specific RNAs, that should not be present in these cells, are enriched in the UB sample. To establish the generality of this finding, the enrichment in the IP or UB sample was quantified by calculating an average ratio of IP/UB for positive and negative controls for each cell type where at least three positive controls could be found in the literature. Panel B of FIG. 18 shows that all IPs showed a clear enrichment for appropriate known markers (plotted in log base 2). Even for cell types with only one known marker (Pnoc positive interneurons, and Grp expressing unipolar brush cells), probesets for these genes were consistently and highly enriched in the IP. In the IPs with the lowest relative yield of RNA, such as those for mature oligodendrocytes (Panel B of FIG. 18), and Cort expressing interneurons, background was proportionally higher, and enrichment was less robust. Panel C of FIG. 18 shows that in the case of cerebellar Golgi cells, there is a great deal of overlap between eGFP-L10a expression in the BACarray line and expression of the genes chosen for this analysis. Panel D of FIG. 18 shows results of quantitative real time PCR (qRT-PCR) measuring the enrichment of a variety of mRNAs isolated from the Chat (motor neuron) and Pcp2 (Purkinje cell) BACarray transgenic lines in order to further validate the BACarray datasets. For all of the control genes tested, this methodology confirmed the BACarray results. For genes not previously known to be expressed in a specific cell type, results from qRTPCR demonstrated that seven out of the eight mRNAs assayed were in fact cell type enriched (Panel D of FIG. 18). Moreover, despite a negative ISH result, qRT-PCR validated the expression of Ceacam10 in the cerebellum and its enrichment in Golgi cells (Panel D of FIG. 18). In some cases, therefore, the translating ribosome affinity purification (TRAP) methodology appears to be more sensitive than ISH.

FIG. 19 illustrates that BACarray clusters cells by type and provides greater sensitivity than whole tissue arrays. FIG. 19 is comprised of Panels A, B, and C. Panel A of FIG. 19 shows hierarchical clustering of cell types and tissue samples. Panel B of FIG. 19 shows relative number of probesets detected by Bacarray. Panel C of FIG. 19 shows enrichment of genes undetected by whole tissue array.

FIG. 20 is comprised of Panels A, B, and C. Panel A of FIG. 20 shows average Shannon entropy of BACarray samples.

Figure 20:
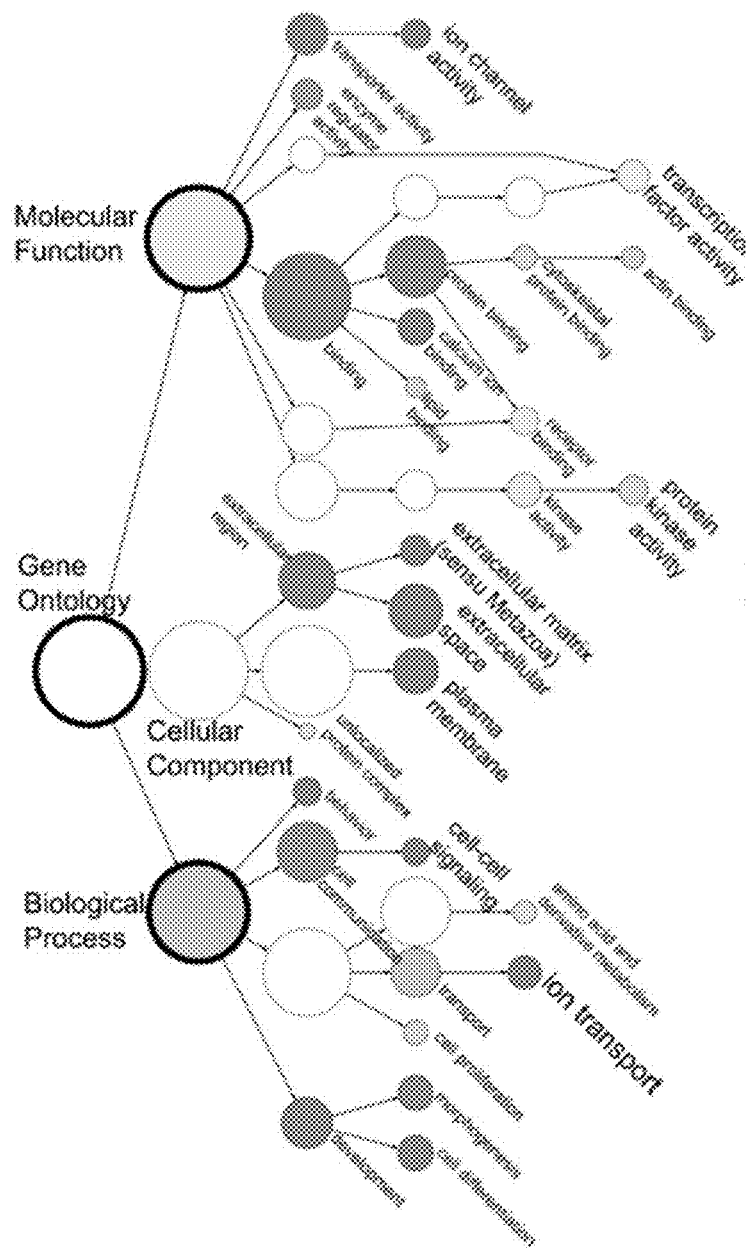
FIG. 20 illustrates cell type diversity is driven by proteins on the cell surface, such as receptors and ion channels.
Figure 20:
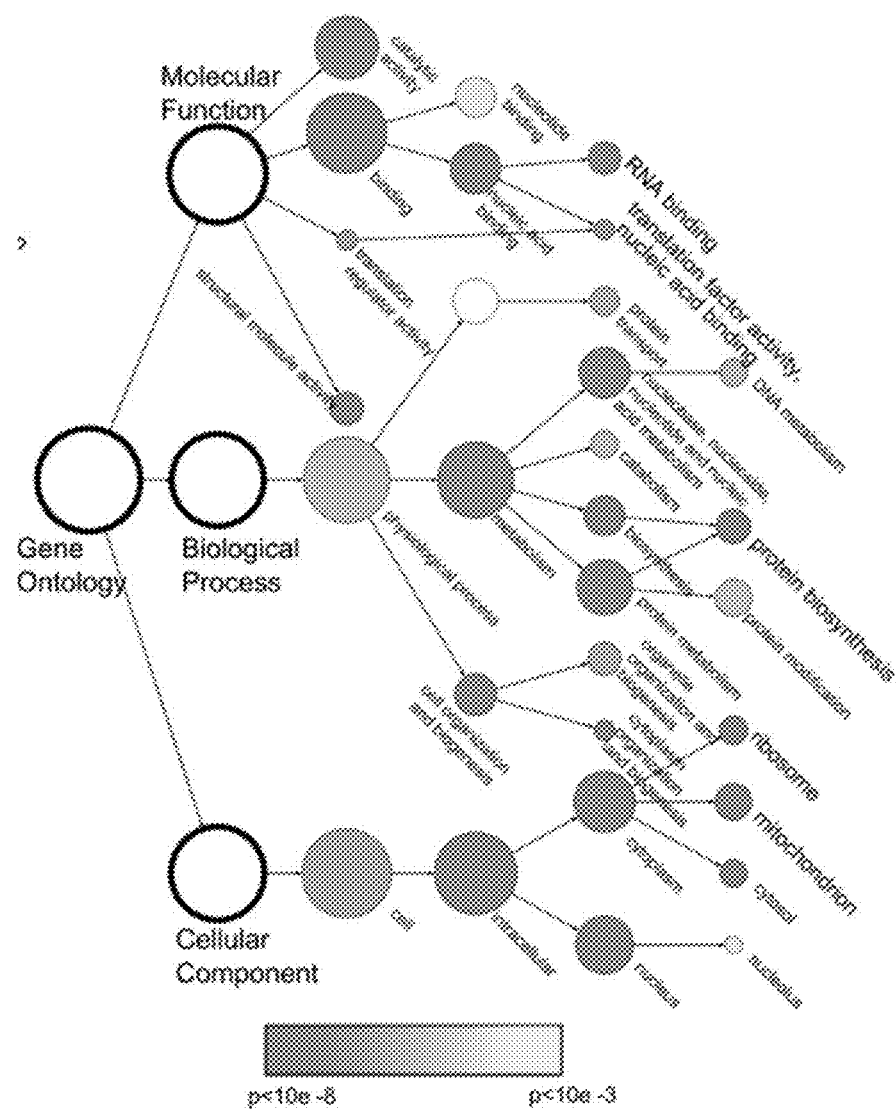

Panel B of FIG. 20 shows examples of probeset with low and high information. Panel C of FIG. 20 shows the ten percent of the probesets with highest entropy and those with the lowest entropy classified with Gene Ontologies and then searched for functional categories that were over-represented.

Figure 21:
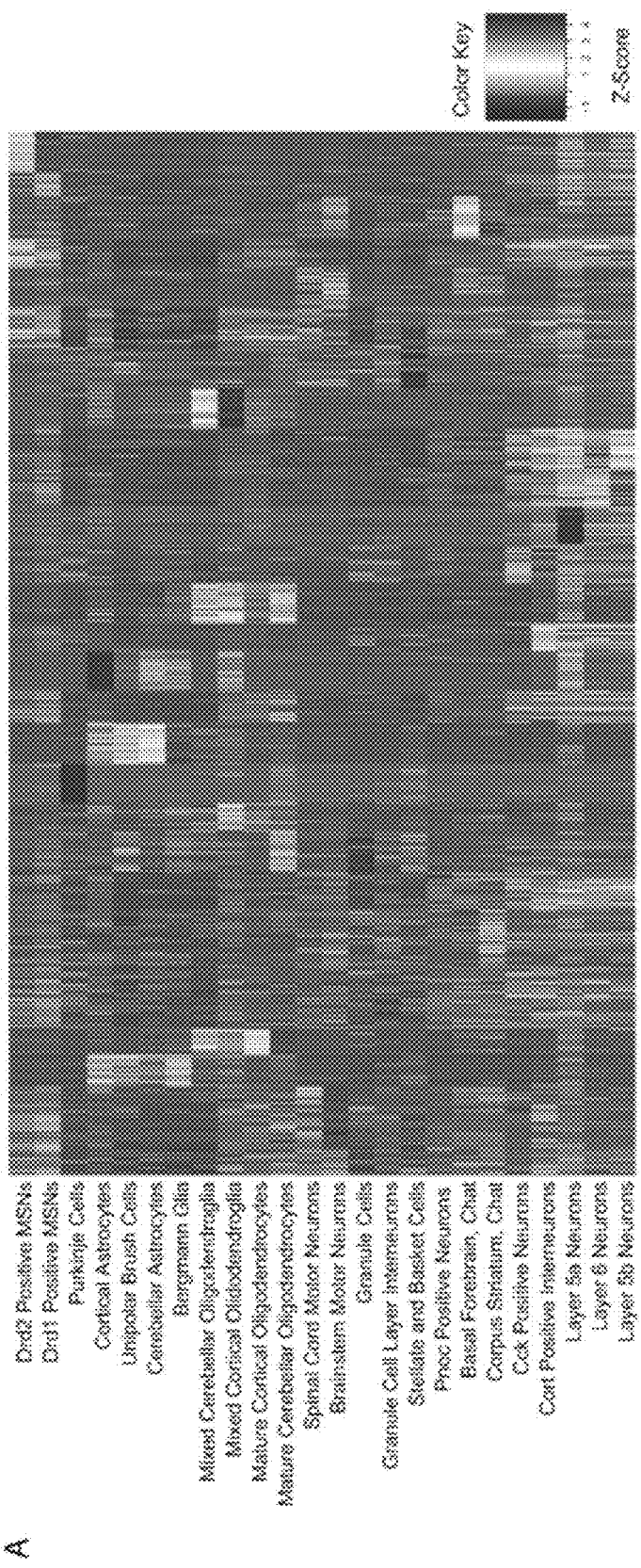

FIG. 21 illustrates that a comparative analysis reveals unique translational profiles for each cell type. An iterative comparison was performed: one-by-one, each sample was compared to each other sample in the dataset, and for each population, probesets were sorted by their average ranking across these comparisons. FIG. 21 is comprised of Panels A and B. Panel A of FIG. 21 shows data combined and clustered by expression the top one hundred ranked probesets for each population in a heatmap. This heat map readily illustrates the extent to which distinct cell types are characterized by specific cohorts of genes. Panel B of FIG. 21 shows the top twenty five most specific probesets in each cell type include probesets for both well-known cell-specific markers and novel, previously uncharacterized genes.

FIG. 22 illustrates the transcriptional sketch of a spinal motor neuron.

Figure 23:
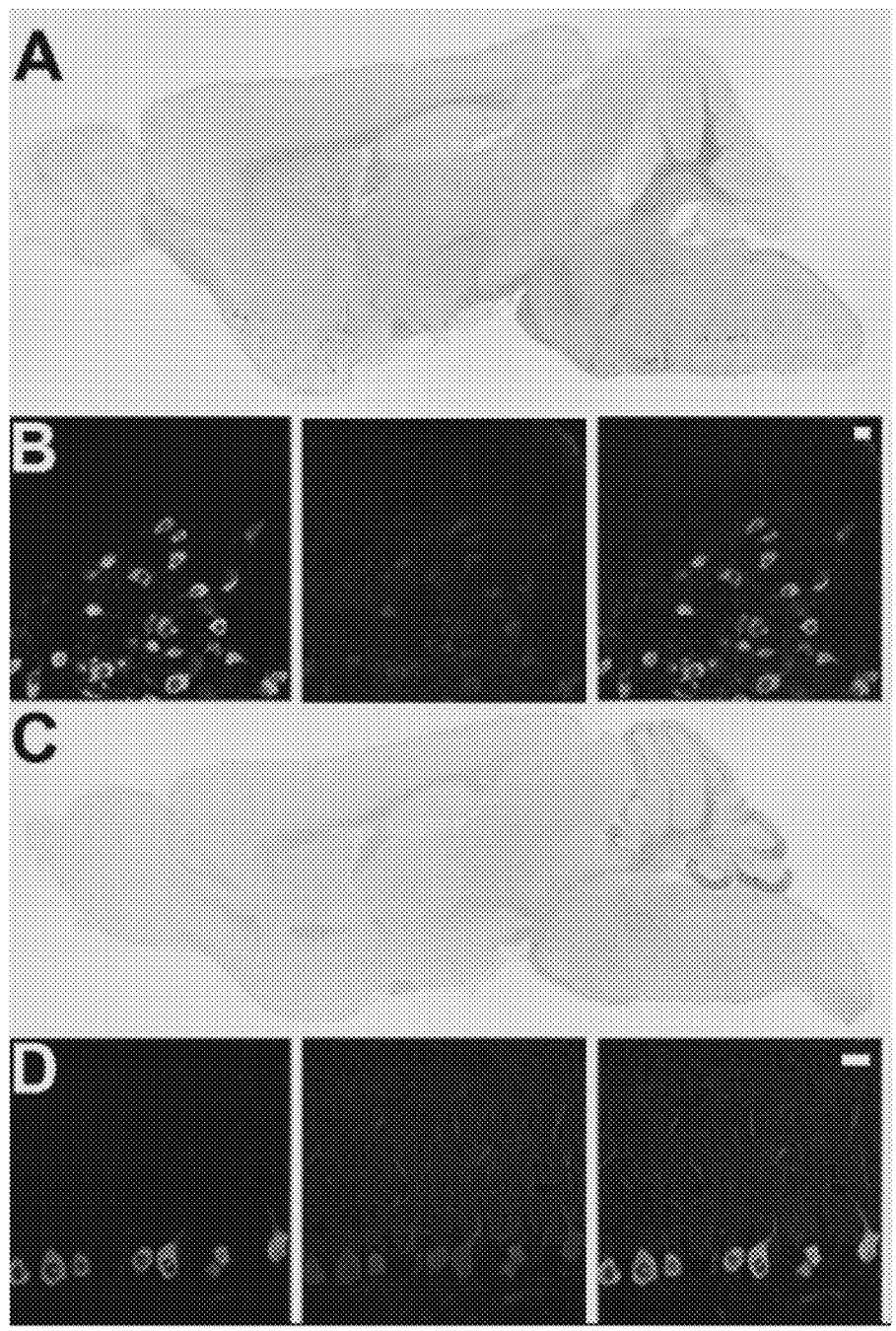

FIG. 23 illustrates expression of eGFP-L10a in the Chat and Purkinje cell BACarray lines. (A) Immunohistochemistry to eGFP in adult sagittal sections from the Chat BACarray line DW167. (B) Indirect immunofluorescent characterization of Chat BACarray line DW167 brain stem facial motor nucleus: eGFP staining (left panel); Chat staining (middle panel) and merge (right panel, with 20 um scale bar). (C) Immunohistochemistry to eGFP in adult sagittal sections from the Pcp2 BACarray line DR166. (D) Indirect immunofluorescent characterization of Pcp2 BACarray line DR 166 Purkinje cell neurons: eGFP staining (left panel); Calbindin-D28K staining (middle panel) and merge (right panel, with 20 um scale bar).

Figure 24:
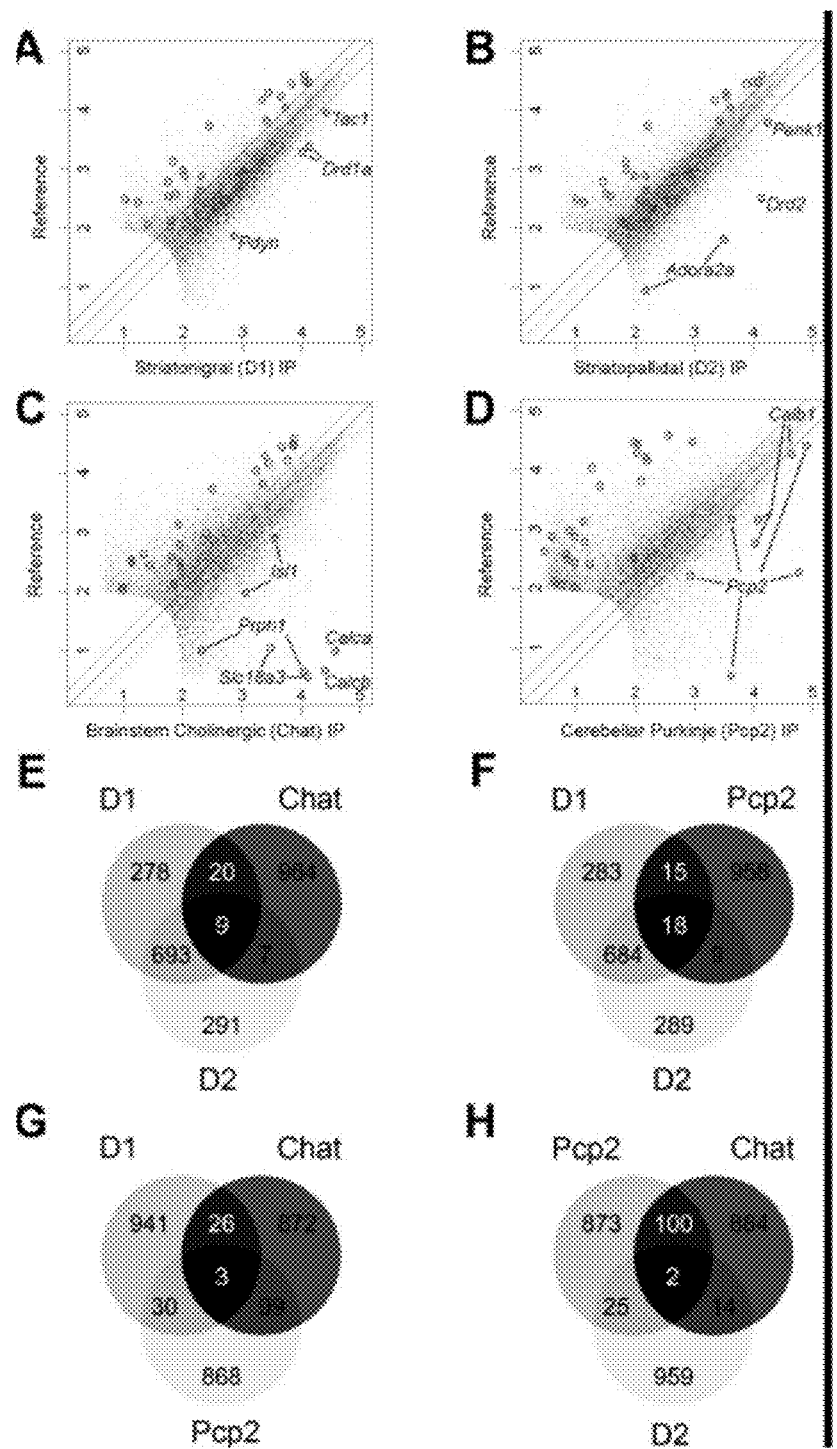

FIG. 24 illustrates that BACarray profiles recapitulate known cell-specific markers and reveal new ones for four distinct cell types. Scatterplots of D1, D2, Chat, and Pcp2 BACarray data compared to a reference mRNA sample reveal hundreds of genes enriched in each cell type (A-D). Lines on either side of the diagonal mark 2-fold enrichment. Axes are labeled for expression in powers of 10. Venn diagrams of the top 1,000 enriched probesets (Tables 17-20) (with expression value cut-off>100) for each cell type reveal that each cell type has a unique pattern of enriched genes (E-H).

Figure 25:
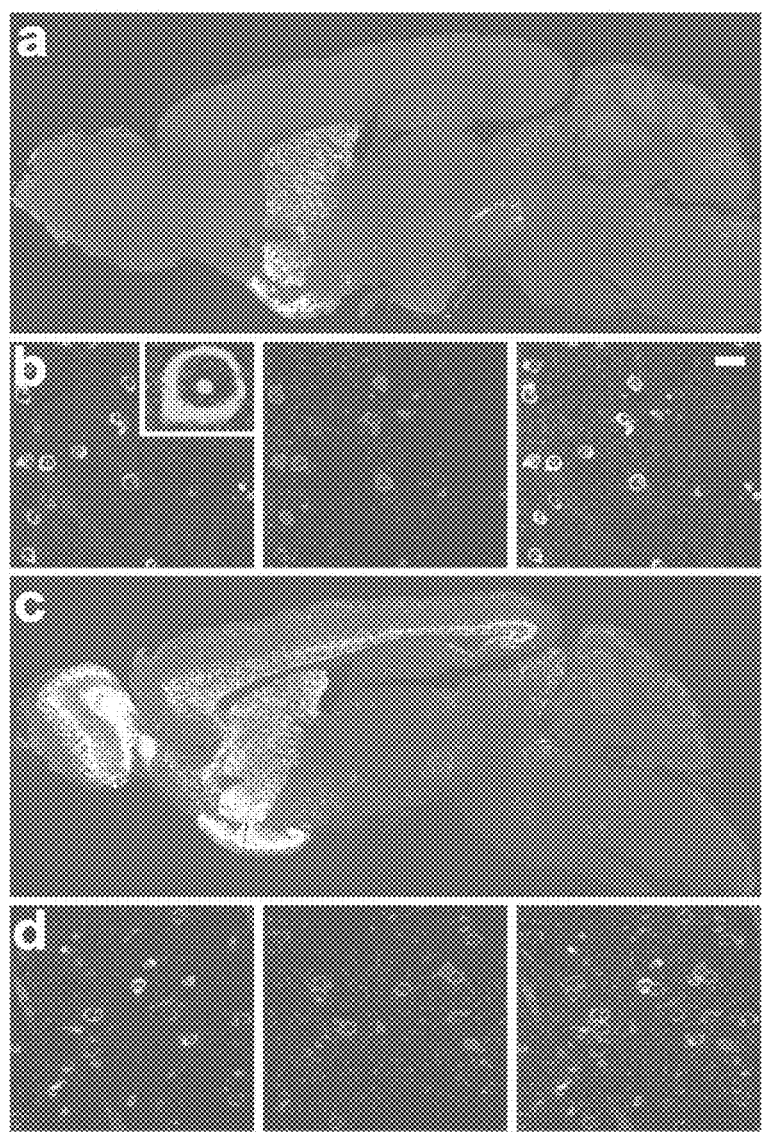

FIG. 25 illustrates expression of eGFP L10a in D1 and D2 BACarray lines. (a) Immunohistochemistry to eGFP in adult sagittal sections from the D2 BACarray line CP101. (b) Characterization of D2 BACarray line CP101 striatal MSN cells: direct eGFP fluorescence (left panel with high magnification image insert); enkephalin immunohistochemical staining (middle panel); merge (right panel, with 20 μm scale bar). (c) Immunohistochemistry to eGFP in adult sagittal sections from the D1 BACarray line CP73. (d) Characterization of D1 BACarray line CP73 striatal MSN cells: direct eGFP fluorescence (left panel); enkephalin immunohistochemical staining (middle panel); merge (right panel).

Figure 26:
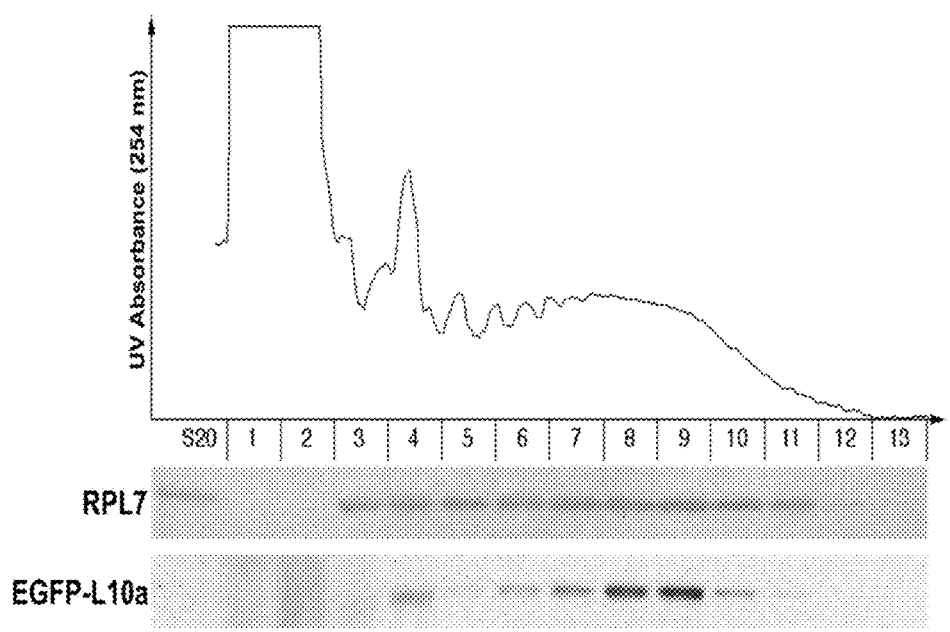

FIG. 26 illustrates the polysome profile from D2 BACarray mouse striatal extracts.

Figure 27:
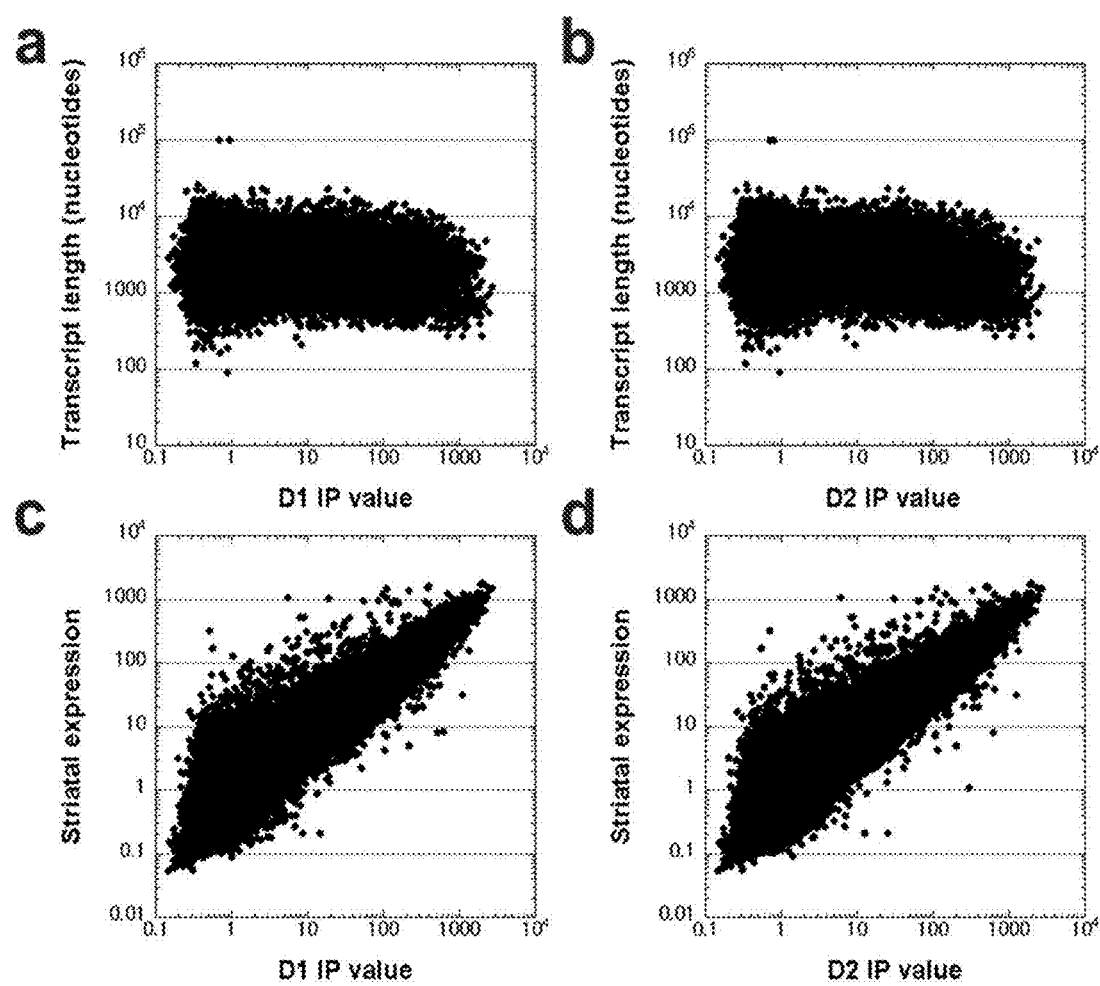

FIG. 27 illustrates an analysis of striatal MSN IP values relative to message abundance and length. Lengths of transcripts were based on all available mouse curated RefSeq RNA sequences (available using the file transfer protocol, ncbi.nih.gov/genomes/M_musculus/RNA). Where multiple transcript variants for a single gene were available, the longest one was chosen. RefSeq lengths were plotted against D1 (a) or D2 (b) BACarray IP normalized expression values. There was no correlation observed between transcript length and IP values. Striatal expression values for all Affymetrix Genechip probe sets were obtained by total RNA arrays from wild type striatal tissue (data not shown). These values were plotted against (c) D1 BACarray or (d) 02 BACarray IP normalized values. As expected, higher expression in total striatum (no IP, wild type mice) correlates with higher D1 or D2 BACarray IP values. The few genes that show modest expression in total striatum but have low IP values include known non neuronal genes.

Figure 28:
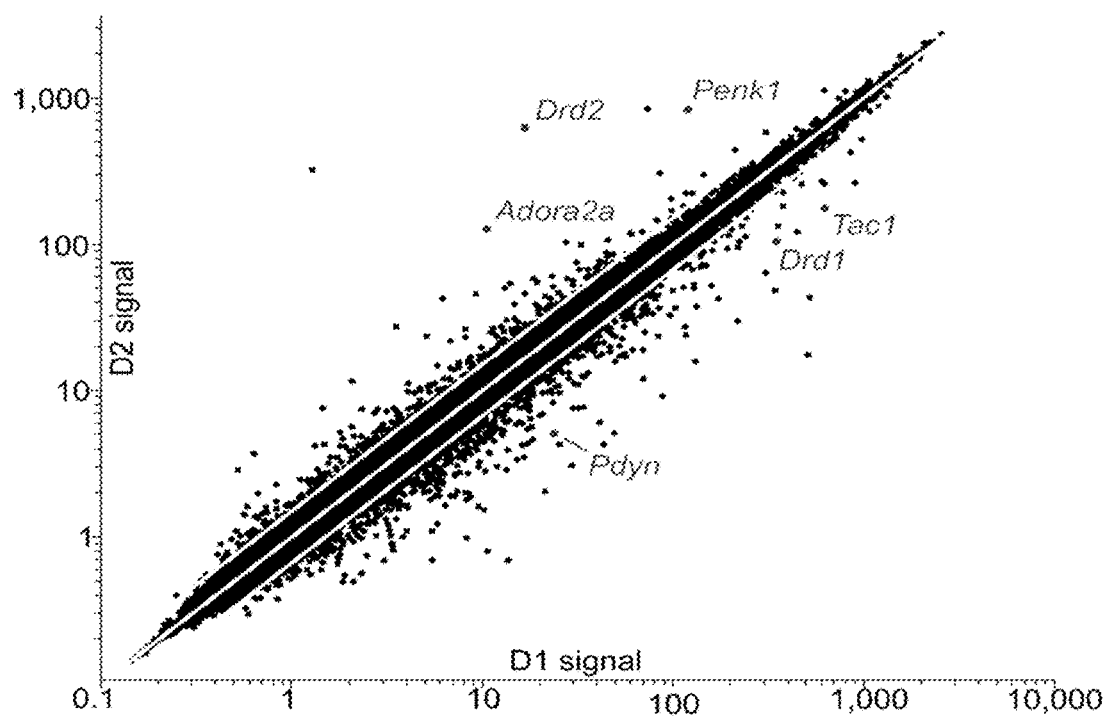

FIG. 28 illustrates gene expression analysis of BACarray purified mRNA. Normalized expression values from Affymetrix Mouse Genome 430 2.0 arrays are plotted for D1 and D2 BACarray samples. Middle diagonal line represents equal expression, and lines to each side represent 1.5 fold enrichment in either cell population.

Figure 29:
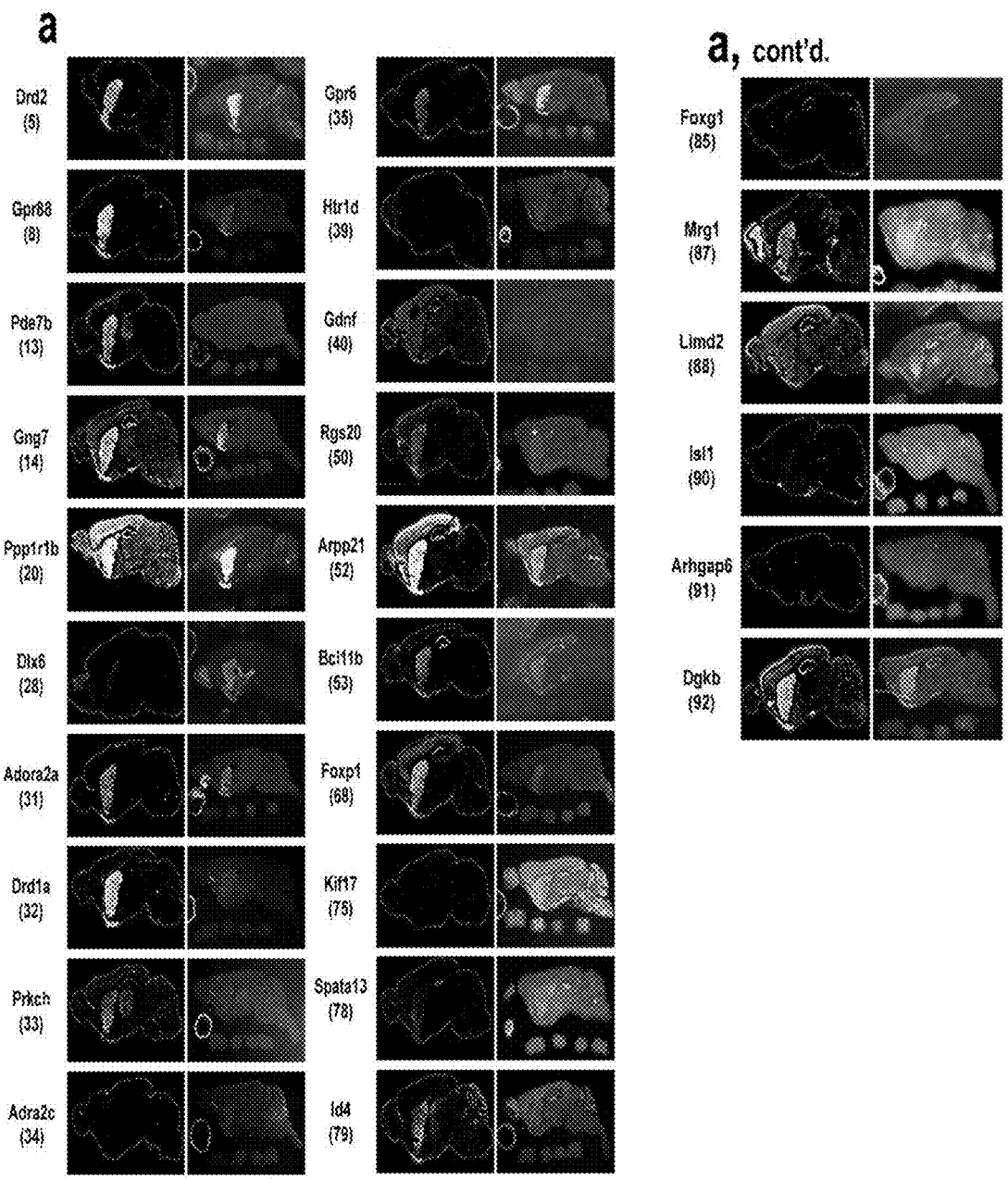
Figure 29:
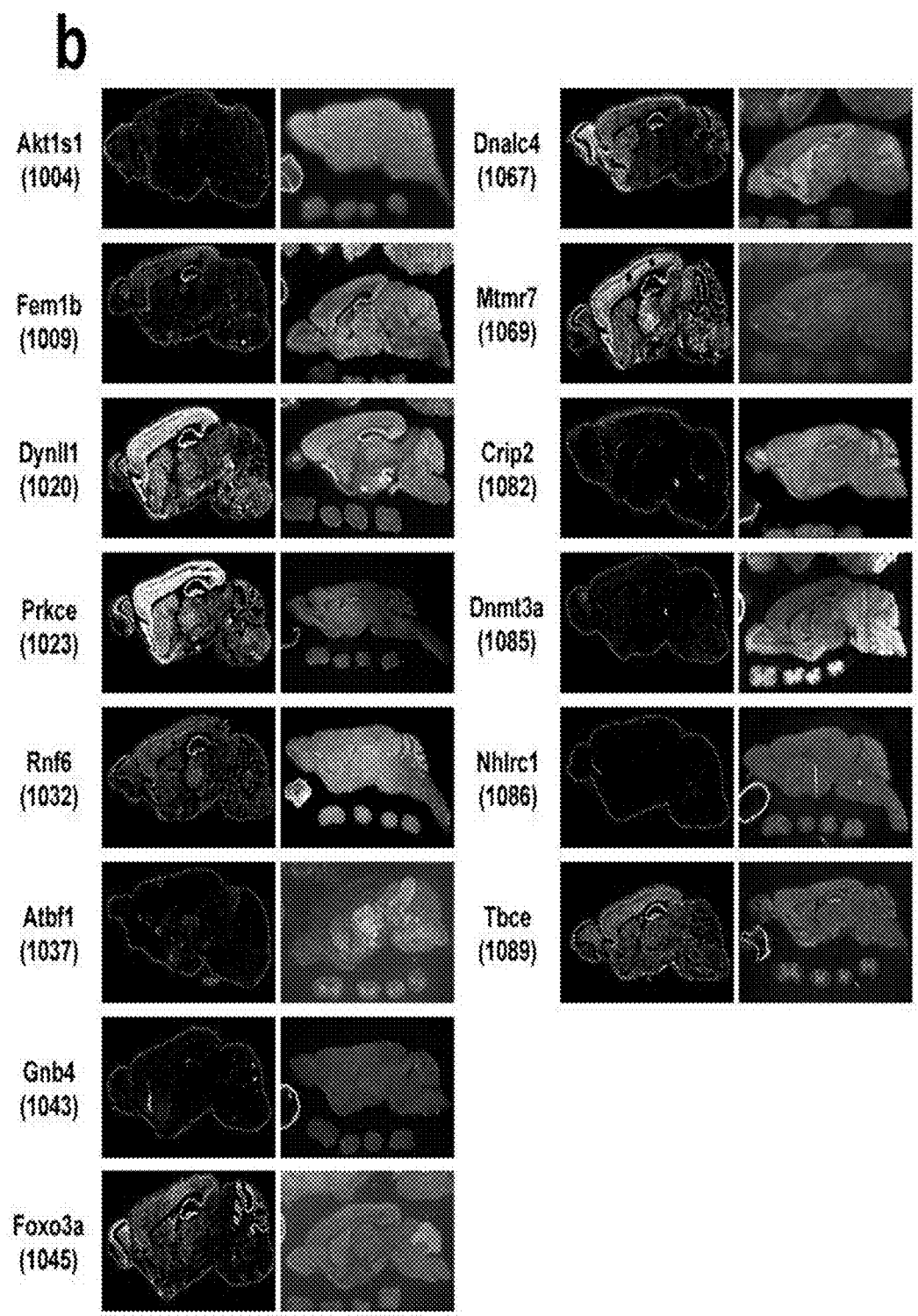

FIG. 29 illustrates expression analysis of medium spiny neuron (MSN) enriched genes. Expression analysis in sagittal sections of genes which were amongst the top 100 (a) or 1,000 1,100 (b) genes identified in the study as MSN enriched, with the rank order of each gene noted below the gene name. Non redundant gene ranking was calculated using the highest ranked probeset corresponding to each gene with redundant probesets eliminated. Left panel, in situ hybridization images taken from the Allen Brain Atlas (Allen Brain Atlas, [Internet]. Seattle (Wash): Allen Institute for Brain Science.© 2006. Available from the hypertext transfer protocol on the world wide web, brain-map.org.) (3); right panel, in situ hybridization images taken from the Brain Gene Expression Map (BGEM) database found using the hypertext transfer protocol and the world wide web at stjudebgem.org) (4). Allen Brain Atlas images all correspond to adult brain; BGEM images all correspond to adult brain except for the following, for which the oldest available data were postnatal day 7 (P7): Drd2, Ppp1r1b, D1x6, Gdnf, Bcl11b, Foxg1, Limd2, Fem1b, Dyn111, Atbf1, Foxo3a, Dna1c4, Mtmr7, Dnmt3a.

Figure 30:
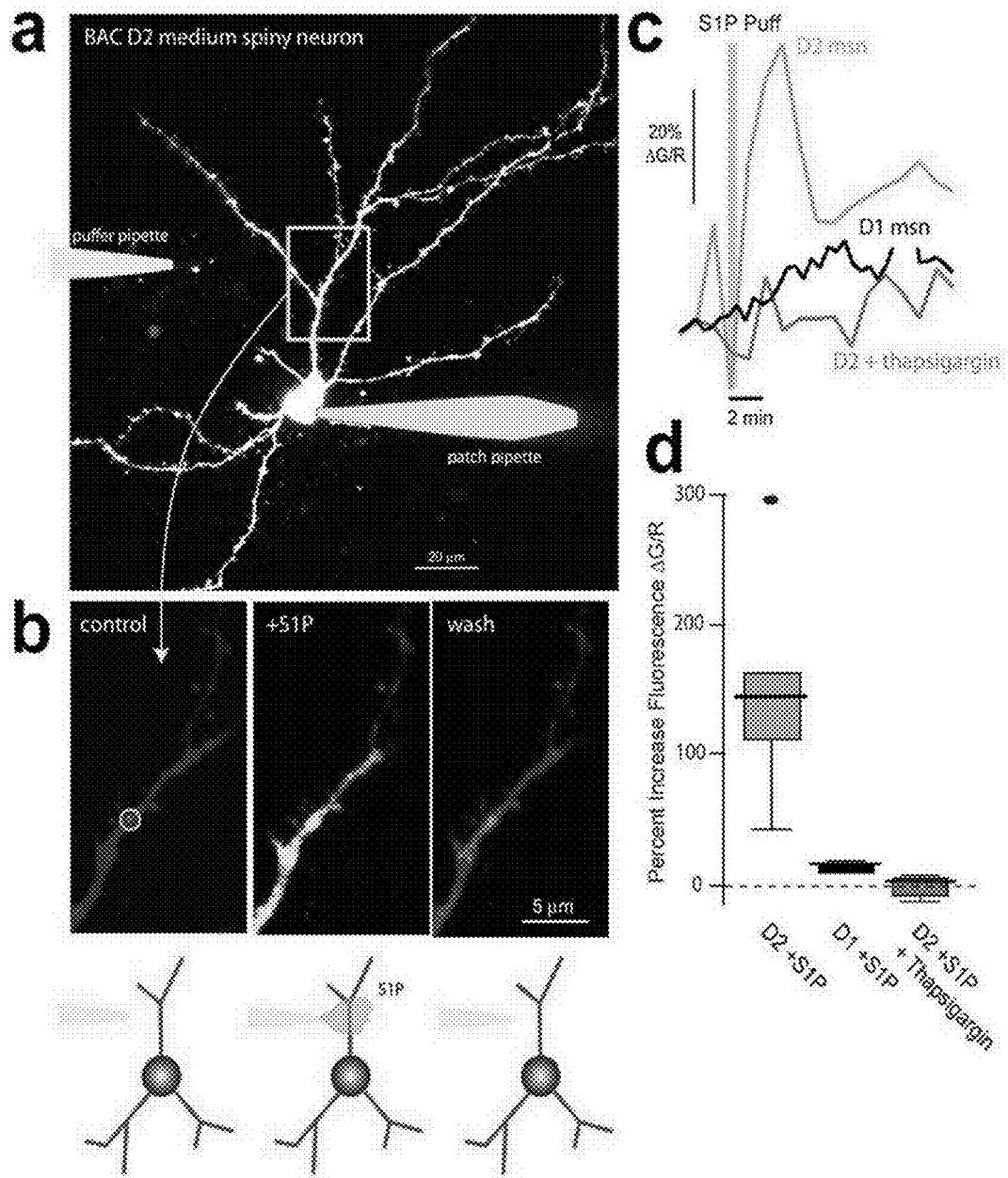

FIG. 30 illustrates that functional Gpr6 receptors are found in BAC D2 striatopallidal neurons but not BAC D1 striatonigral medium spiny neurons. (a) Projection of an eGFP labeled medium spiny neuron from a BAC D2 mouse. The cell was patched with a pipette containing Alexa 594 (50 μM) for visualization and Fluo 4 (200 μM) for measuring changes in intracellular Ca2+(right). Cells were voltage clamped at −70 mV. A puffer pipette containing sphingosine 1 phosphate (S1P, 10 μM) was positioned near a dendrite, 60 80 μm from the soma (left/cartoon). (b) High magnification images of a dendritic segment (control, left panel) show an increase in Ca2+ associated with SIP application (SIP puff, center panel) that reversed with washing (wash, right panel). The change in Ca2+ was determined by calculating the percent change in fluorescence of Fluo 4 relative to that of Alexa 594 (ΔG/R). (c) Time course showing the SIP induced increase in intracellular Ca2+ in the ROI from b (orange trace); similar recordings from BAC D1 medium spiny neurons (black trace) or thapsigargin loaded BAC D2 medium spiny neurons did not reveal any changes in dendritic Ca2+ levels with S1P application. (d) Box plot summarizing the S1P effects. Percent increase in fluorescence (ΔG/R) in BAC D2 medium spiny neurons (median=146%, range 44 to 294%, n=6); BAC D1 medium spiny neurons (median=17%, range 13 to 22%, n=4); and thapsigargin loaded BAC D2 medium spiny neurons (median=4%, range-9 to 10%, n=4).

Figure 31:
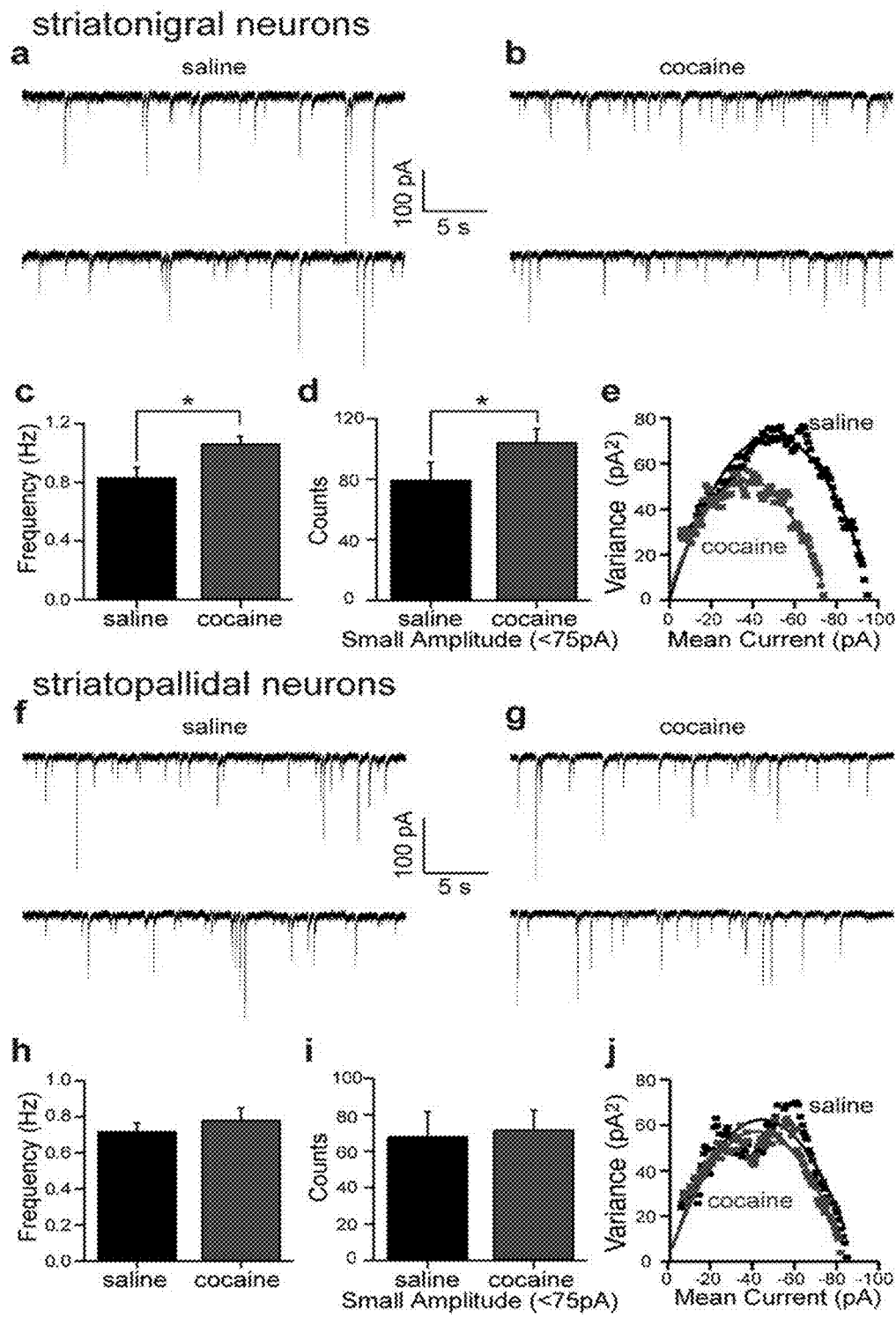

FIG. 31 illustrates that cocaine treatment increases the frequency of small amplitude GABAergic mIPSCs in BAC D1 striatonigral neurons. (a) Representative spontaneous mIPSCs traces from BAC D1 striatonigral neurons (expressing soluble eGFP under the D1 promoter) taken from mice treated for 15 days with saline or (b) cocaine (20 mg/kg/day). (c) Bar graph summary of mean mIPSC frequency showing a increase in BAC D1 striatonigral neuron mIPSCs frequency following cocaine treatment (Mann Whitney Rank Sum Test, $p<0.05$, saline median=0.82 Hz, n=22; cocaine median=1.03 Hz, n=26). (d) Bar graph summary showing that the number of small amplitude mIPSCs (<75 pA) in equal length records (7 min) increased in BAC D1 striatonigral neurons following cocaine treatment (t test, $p<0.05$, saline=79.4±18.2, n=22; cocaine=104.2±6.3, n=26). (e) Representative variance mean current plots from saline treated and cocaine treated BAC D1 neurons suggesting that the cocaine induced small amplitude events arise from synapses that have fewer GABAA receptors (N) per synapse but receptors with an unchanged unitary receptor conductance (g) (saline N=33, g=31 pS; cocaine N=27, g=30 pS; see FIG. S6c d for means). (f) Representative spontaneous mIPSCs traces from BAC D2 striatopallidal neurons following saline treatment for 15 days and (g) following cocaine treatment for 15 days. (h) Bar graph summary of mean mIPSC frequency in saline and cocaine treated neurons, showing no effect of treatment condition (t test, $p>0.05$, saline=0.72±0.05 Hz, n=12; cocaine=0.78±0.07 Hz, n=16). (i) Bar graph summary showing that the number of small amplitude mIPSCs (<75 pA) in equal length records (7 min) was not altered by treatment condition in BAC D2 neurons (t test, $p>0.05$, saline=68.1±9.7, n=12; cocaine=71.7±7.5, n=16). (j) Representative variance mean current plots showing that cocaine treatment did not change in the number of receptors per synapse or the unitary receptor conductance in BAC D2 neurons (saline N=29, g=33 pS; cocaine N=31, g=29 pS;).

Figure 32:
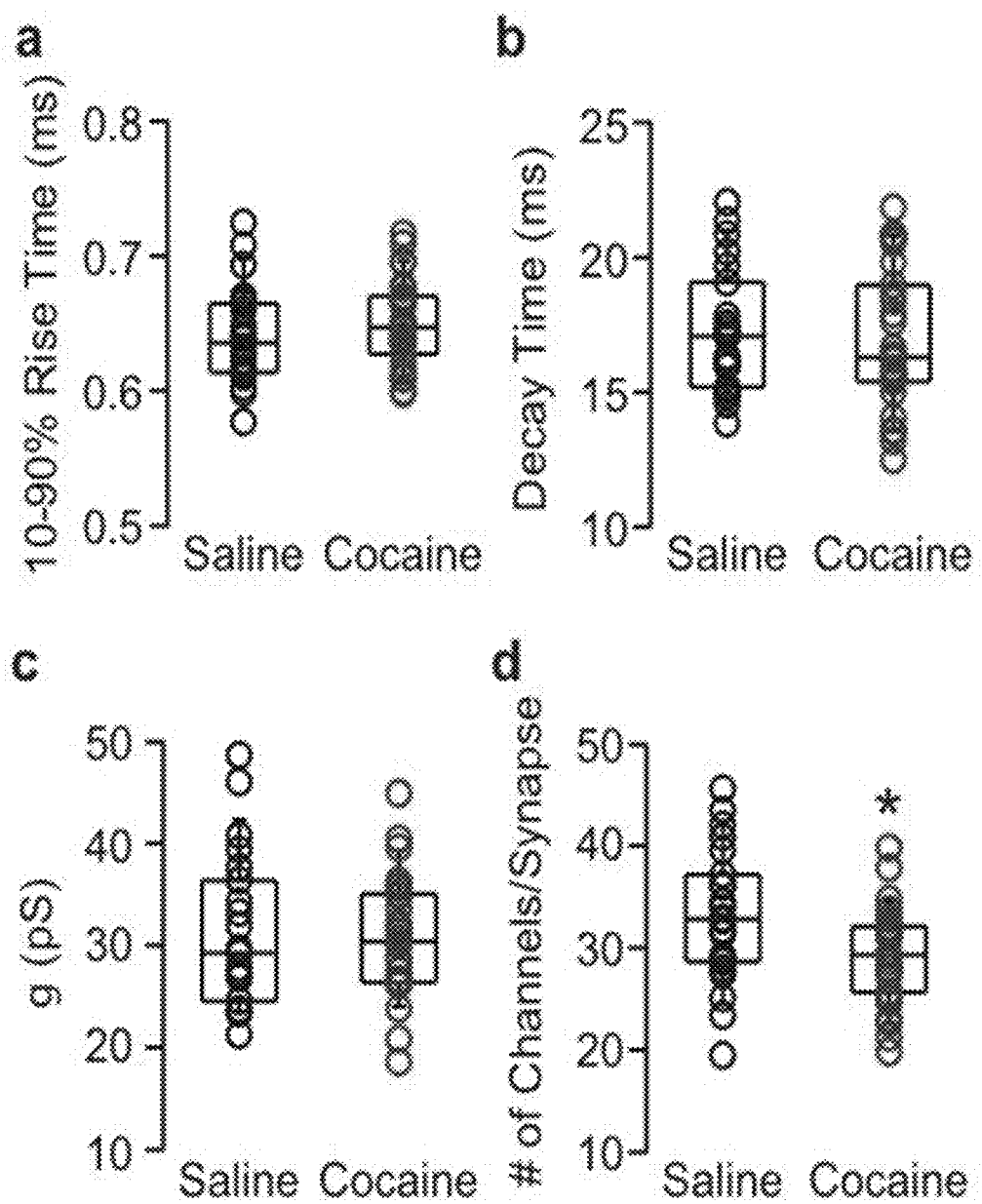

FIG. 32 illustrates that cocaine treatment decreases the number of GABAA channels per synapse in BAC D1 striatonigral neurons. Box plot summaries showing mean mIPSCs kinetics and non stationary noise analysis measures of individual striatonigral neurons taken from saline treated control and 15 day treated cocaine BAC D1 mice. (a) Neither mean 10 90% rise times (t test, $p>0.05$, Saline=0.64±0.008, n=22; Cocaine=0.65±0.006, n=26) nor (b) mean decay times (ttest, $p>0.05$, Saline=17.3±0.5, n=22; Cocaine=17.0±0.5, n=26) were different between groups. Non stationary noise analysis of mIPSCs demonstrated no change between groups in the (c) mean unitary conductance (g) of GABAA receptors of striatonigral neurons (t test, $p>0.05$, Saline g-=31.1±1.6, n=22; Cocaine g=30.8±1.2, n=26), and a decrease in the (d) mean number of channels per synapse in striatonigral neurons taken from cocaine treated BAC D1 mice (t test, $p<0.05$, Saline N=33.1±1.4, n=22; Cocaine N=29.3±1.0, n=26).

Figure 33:
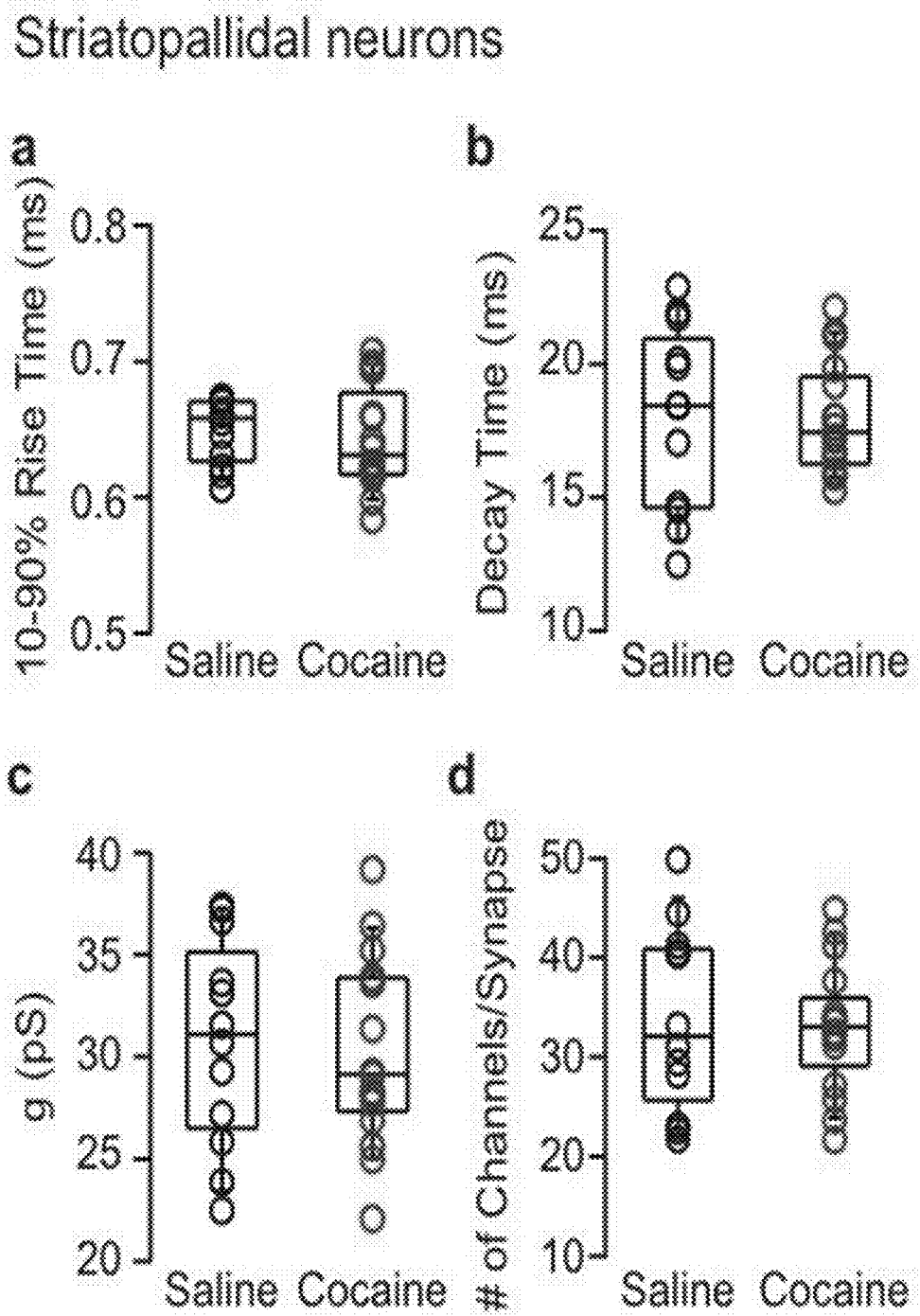

FIG. 33 illustrates that cocaine treatment does not alter GABAergic mIPSCs kinetics or GABAA receptor number per synapse or unitary receptor conductance in BAC D2 striatopallidal neurons. Box plot summaries showing mean mIPSCs kinetics and non stationary noise analysis measures of individual striatopallidal neurons taken from saline treated control and 15 day treated cocaine BAC D2. (a) Neither mean 10 90% rise times (t test, $p>0.05$, Saline=0.65±0.007, n=12; Cocaine=0.6410.010, n=16) nor (b) mean decay times (t test, $p>0.05$, Saline=18.0±1.0, n=12; Cocaine=18.0±0.5, n=16) were different between groups. Non stationary noise analysis of mIPSCs demonstrated no change between groups in the (c) mean unitary conductance (referred to as g in the y-axis) of GABAA receptors of striatopallidal neurons (t test, $p>0.05$, Saline g=30.7±1.5, n=12; Cocaine g=30.3±1.2, n=16) or in the (d) mean number of channels per synapse in striatopallidal neurons taken from cocaine treated BAC D2 mice (t test, $p>0.05$, Saline N=33.8±2.7, n=12; Cocaine N=33.0±1.6, n=16).

FIG. 34 illustrates BACarray molecular phenotyping of cerebellar cell types in ATM KO mice.

Figure 35:
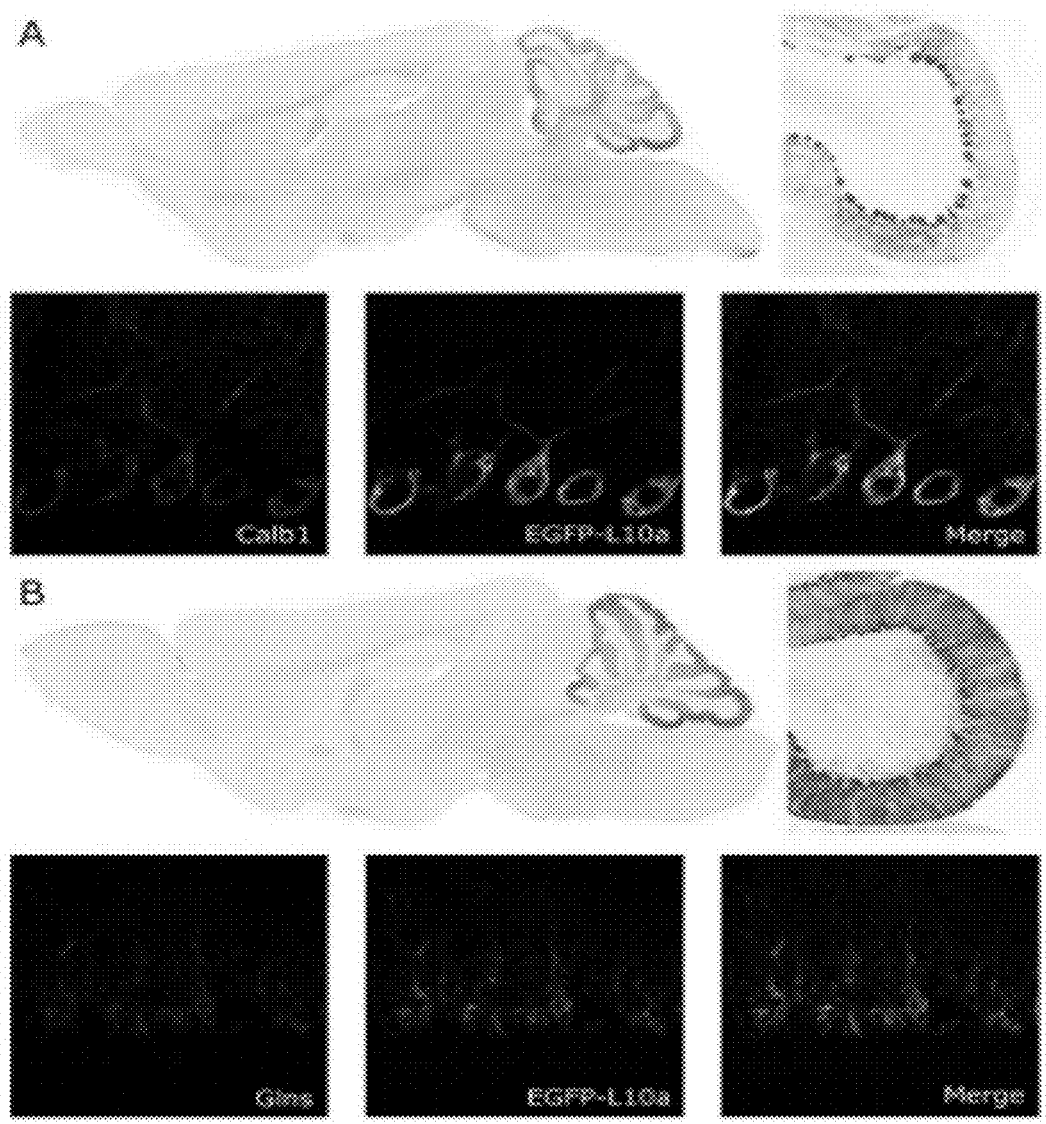

FIG. 35 illustrates the characterization of Pcp2 and Sept4 BACarray transgenic mouse lines. (A) Expression of the eGFP L10a fusion in Purkinje cells in the cerebellum of the Pcp2 BACarray line. Immunohistochemical stain of Pcp2 BACarray brain section using anti eGFP antiserum (top panel). Double immuno fluorescence analysis (bottom panels) of calbindin (Calb1) and eGFP L10a expression in Pcp2 BACarray mice showing co labeling of Purkinje cells (merge). (B) Expression of the eGFP L10a fusion in Bergmann glia in the cerebellum of the Sept4 BACarray line. Immunohistochemical stain of Sept4 BACarray brain section using anti eGFP antiserum (top panel). Double immuno fluorescence analysis of glutamine synthetase (Gins) and eGFP L10a expression in Sept4 BACarray mice showing co labeling of Bergmann glial cells (merge).

Figure 36:
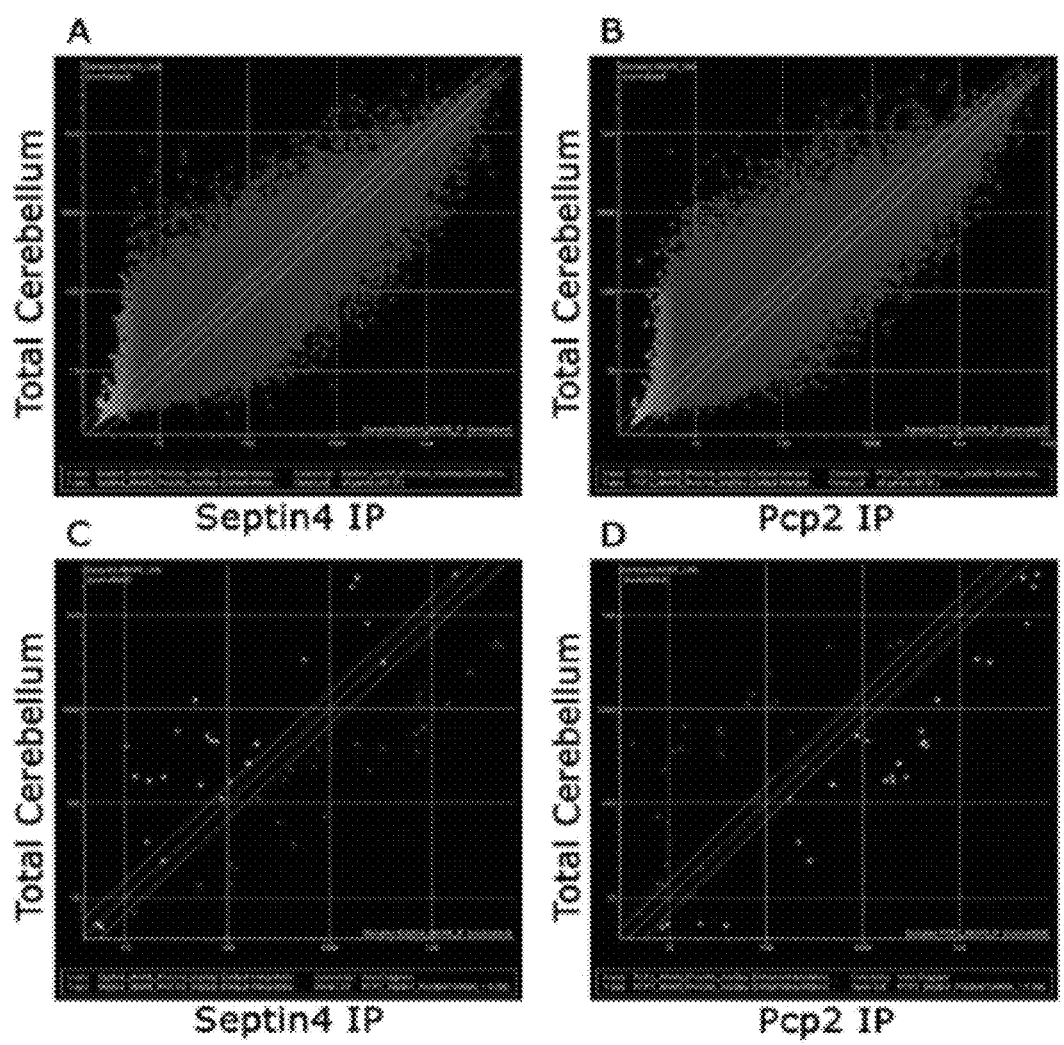

FIG. 36 illustrates a scatter Plot analysis of BACarray data for Septin4 and Pcp2 lines. Immunoprecipitated (IP) mRNA from Septin4 (A, C) and Pcp2 (B, D) BAC transgenic lines was directly compared in scatter plot analysis to mRNA samples from total cerebellum. The analysis clearly demonstrates that thousands of genes are enriched in the immunoprecipitated samples relative to total cerebellum. Scatter plots (C) and (D) show the same experiments with known positive control genes for Bergmann glial cells and Purkinje neurons. Bergmann glial positive controls are clearly enriched in the Septin4 IP samples (C) whereas Purkinje cell positive control genes are enriched in Pcp2 IP samples (D).

Figure 37:
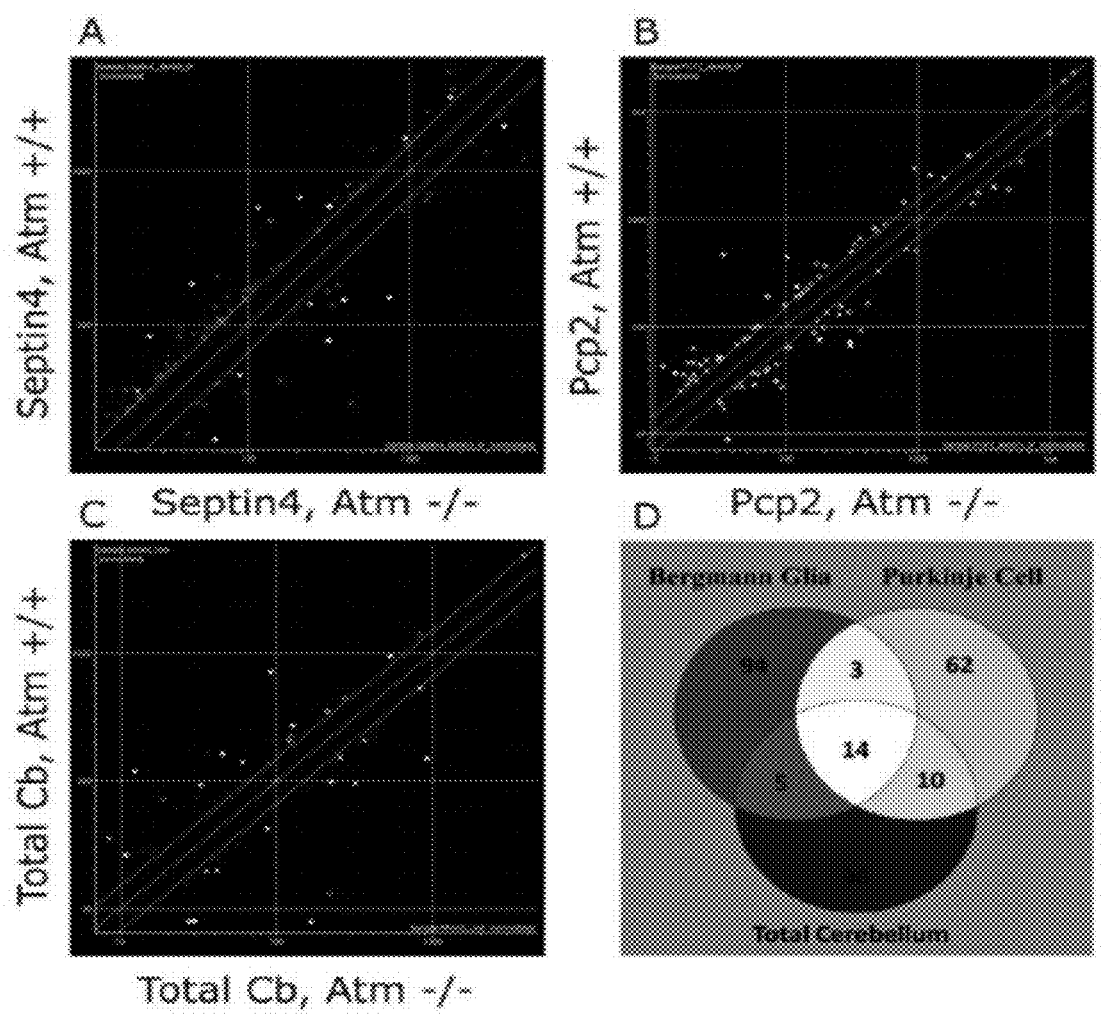

FIG. 37 illustrates cell type specific differential regulation of gene expression in Atm-/- cerebellum. (A-C) Atm -/- IP data were compared to Atm+/+IP data in scatter plot analyses for the Septin4 (A), the Pcp2 (B) and the total cerebellum (C) experiments. Gene lists of both upregulated and downregulated genes were generated by filtering on expression values greater than 25, on fold change values greater than 1.5, and performing one way ANOVA, $p=0.05$. Scatter plots display the distribution of regulated genes in each experiment. Colors refer to the Venn Diagram analysis (D). Genes shared by Bergmann glia and Purkinje cells are colored yellow, those shared by Purkinje cells and total cerebellum are turquoise, and those shared by Bergmann glia and total cerebellum are colored magenta. Genes identified in all three conditions are colored white. (D) Venn Diagram analysis of all regulated genes. In total cerebellum, 40/69 genes are found differentially regulated exclusively in total cerebellum, in the Septin4 experiment, 94/116 genes are specifically regulated in the Septin4 data, and in the Pcp2 experiment, 62/89 regulated genes which are specific to the Pcp2 data have been identified.

FIG. 38 illustrates ventral tegmental area and substantia nigra area specific markers, as revealed by BACarrays.

FIG. 39 illustrates dopaminergic cell loss in the rodent substantia nigra with the use of 6-OHDA.

Figure 40:
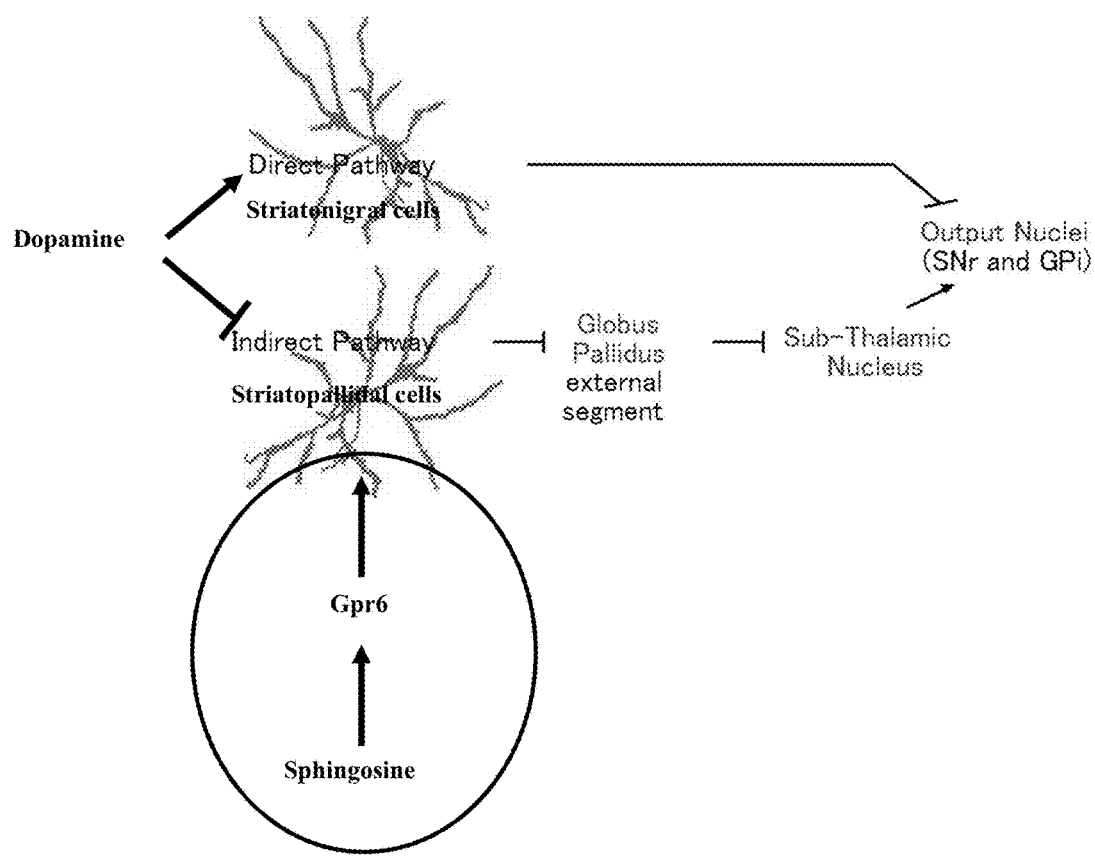

FIG. 40 illustrates a therapeutic opportunity for Parkinson's disease, by developing new strategies for stimulation of Sub-Thalamic Nucleus, by using antagonists of Gpr6.

DETAILED DESCRIPTION OF THE INVENTION

Translational Profiling and Molecular Phenotyping

The present disclosure provides for methods and compositions useful in translational profiling and molecular phenotyping of heterogeneous tissues and cell types. In one embodiment the methods can be used to define previously undefined cell types, identify molecular targets for diseases and disorders, and provide a way in which to identify co-regulated gene sets for particular biological and/or medically relevant functions.

Translational profiling is the profiling, identification, or isolation of translated mRNAs. In some embodiments such profiling is a measure of the nascent proteome. In other embodiments, this profiling allows for the identification of mRNAs being actively translated, or otherwise associated with the cellular translational machinery. Molecular phenotyping is the molecular and/or gene expression description of organs, tissues, and cell types.

The present disclosure provides for methods and compositions to practice translating ribosome affinity purification (TRAP) profiling methodology. In one embodiment these profiling methods are be utilized to further distinguish morphologically, anatomically, developmentally, or otherwise indistinguishable, cells into cellular subtypes, further defining cell populations and sub-populations. In some cases, these otherwise indistinguishable cells are intermixed. In other cases, these cells are spatially separated. In some cases, these cells are cells of the central or peripheral nervous system, for example neurons or glia, only distinguishable by their translational profiles and molecular phenotypes. In other cases these are cells outside the nervous system. In another embodiment these profiling methods are be utilized to identify translated mRNAs in single cell types with a sensitivity that is may not be achievable by techniques such as whole-tissue microarray. In yet other embodiments, these profiling methods are used to identify co-regulated gene sets for particular biological functions in cells that are spatially separated or intermixed, morphologically distinct or indistinct, in different developmental stages, associated with different tissues or regions of a tissue, or from different individuals with the same disease, disorder or state.

The methods provided herein allow for isolation of mRNAs associated with ribosomes or polysomes (clusters of ribosomes) from specific cell types, allowing for cell translational profiling and molecular phenotyping of the cell types and subtypes. In some cases, the cells are genetically targeted.

The methods described herein in allow for identifying translated mRNAs in any cell subtype of interest. The methodology involves expression of a tagged functional ribosomal protein, which enables tagging of polysomes for purification of mRNA, in specific cell populations. In some embodiments, the purification of polysomes is by affinity or immunoaffinity purification. In some embodiments, the cell subtypes are genetically targeted. In some embodiments the tagged ribosomes are expressed in transgenic animals.

The translating ribosome affinity purification methodology (TRAP) for translational profiling and molecular phenotyping involves expression of a tagged ribosomal protein, which enables tagging of polysomes for affinity-based, sometimes immunoaffinity-based, purification of mRNA, in specific cell populations. In some cases this is achieved with the use of animals or transgenic animals, allowing translation profiling and molecular phenotyping from whole animals. Methods provided herein allow for defining the distinguishing molecular characteristics of closely related or critical cell types. Methods also demonstrate that methods described herein can be employed to analyze physiological adaptations of specific cell types in vitro, in vivo, ex vivo, or in situ.

Molecular Tagging of Ribosomes

Embodiments of this invention provide methods for isolating cell type- or cell subtype-specific polysomal, mRNA. The methods include using molecularly tagged ribosomal proteins resulting in functional tagged ribosomes or ribosomal complexes, able to support translation, assemble into polysomal complexes. Ribosomes can be molecularly tagged and expressed in one or more cell types or cell subtypes of interest. Molecularly tagged ribosomal proteins for the purposes of this disclosure will interchangeably be referred to as a 'fusion proteins' or 'tagged proteins' or 'molecularly tagged fusion proteins' or 'molecularly tagged ribosomal proteins'. In various embodiments these fusion proteins contain all or a portion of a ribosomal proteins. In certain embodiments ribosome tagging causes no disruption of native function or distribution of the tagged protein, thus resulting in a functional ribosome, functional ribosomal complex, or functional polysome. That is, although molecularly tagged, the portion that has the biological activity of the native ribosomal protein is retained and can function in an intact ribosome to carry out translation or binding of mRNA. In some embodiments, the molecularly tagged ribosomal is expressed in a organ, tissue, cell type, or cell subtype of interest, by introducing into cells, culture, slices, or into an entire organism, a nucleic acid encoding the molecularly tagged ribosomal protein under the control of regulatory elements or transcriptional units that direct expression in the cell type or cell subtype of choice. In some embodiments the ribosomal protein to be tagged can be from the same or different species as the cell that expresses the molecularly tagged protein.

In certain embodiments, the ribosome or ribosomal protein is molecularly tagged by engineering the ribosomal protein to fuse to or bind a small molecule, a protein, or peptide that is not bound by the unengineered ribosome or the ribosomal protein. In certain embodiments the nucleic acid encoding the ribosomal protein fused to the tag can be generated by routine genetic engineering methods in which a nucleotide sequence encoding the amino acid sequence for the tag sequence is engineered in frame with the nucleotide sequence encoding a ribosomal protein. This can be accomplished by any method known in the art, for example, via oligonucleotide-mediated site-directed mutagenesis or polymerase chain reaction (PCR) and other routine protocols of molecular biology (see, e.g., Sambrook et al., 2001, Molecular Cloning, A Laboratory Manual, Third Edition, Cold Spring Harbor Laboratory Press, N.Y.; and Ausubel et al., 1989, Current Protocols in Molecular Biology, Green Publishing Associates and Wiley Interscience, N.Y., both of which are hereby incorporated by reference in their entireties).

In exemplary embodiments the ribosomal protein is L10a and the tag is eGFP.

1) Ribosomal Proteins

Nucleic acids encoding the tagged proteins can be produced using genetic engineering methods and cloning and expression vectors that are well known in the art. In some embodiments, a naturally occurring or synthetically produced nucleic acid or gene can be engineered to function as a ribosomal protein and support translation or bind (directly or indirectly) or associate with polysomal, translating ribosomal mRNA. Nucleic acids encoding the ribosomal protein to be molecularly tagged may be obtained using any method known in the art. Nucleic acids may be obtained, for example, by PCR using oligonucleotide primers based upon the published sequences. Other related ribosomal (for example from other species) may be obtained by low, medium or high stringency hybridization of appropriate nucleic acid libraries using the ribosomal in hand as a probe.

Exemplary ribosomal proteins for use in various embodiments of this invention are provided in Table 1, but not limited to those listed. In an exemplary embodiment, the ribosomal protein is L10a. In some embodiments the tagged ribosomal protein is incorporated into a ribosomal complex and is associated with one or more mRNAS, but does not bind mRNA directly.

In certain embodiments, the ribosomal protein is mouse ribosomal protein L10a having the amino acid sequence set forth in GenBank NM_011287.1 (SEQ ID NO: 30).

or interfere with function of the tagged protein. The tag may be an intact naturally occurring or synthetically produced protein, fragment, analog or derivative thereof of any length that permits binding to the corresponding binding reagent/method. In certain embodiments, the tag is about 8, 10, 12, 15, 18 or 20 amino acids, is less than 15, 20, 25, 30, 40 or 50 amino acids, but may be 100, 150, 200, 250, 300, 400, 500, 1000 or more amino acids in length. The tag may be bound specifically by a reagent that does not otherwise bind any component of: (1) the cell of interest; or (2) a polysomal preparation of interest; or (3) whatever cellular fraction of interest is being contacted by the reagent that binds the tag.

In certain embodiments, the nucleotide sequence encoding a tag is preferably inserted in frame such that the tag is placed at the N- or C-terminus of the ribosomal protein, since these portions of proteins are often accessible to detection, affinity, immunological, or purification reagents.

TABLE 1

Ribosomal Proteins

| | | | | | | | |
|---|---|---|---|---|---|---|---|
| A52 | L11 | L23a | L35a | LP2 (Large P2) | S11 | S24 | |
| Ke-3 | L12 | L24 | L36 | LP1 (Large P1) | S12 | S25 | |
| L3 | L13 | L26 | L36a | S2 | S13 | S26 | |
| L3L (L3-like) | L13a | L27 | L37 | S3 | S14 | S27 | |
| L4 | L14 | L27a | L37a | S3a | S15 | S27a | |
| L5 | L15 | L28 | L38 | S4 | S15a | S28 | |
| L6 | L17 | L29 | L39 | S5 | S16 | S29 | |
| L7 | L18 | L30 | L41 | S6 | S17 | S30 | |
| L7a | L18a | L31 | L44 | S7 | S18 | S23 | |
| L8 | L19 | L32 | LAMR1 | S8 | S19 | RPLP1 | |
| L9 | L21 | L32-3a (3a) | LLRep3 | S9 | S20 | | |
| L10 | L22 | L34 | LP0 (Large P0) | S10 | S21 | | |
| L10a | L23 | L35 | Region containing hypothetical protein FLJ23544 | | | | |

In certain embodiments, a nucleic acid encoding a molecularly tagged ribosomal protein is intended for a particular expression system, in which the codon frequencies reflect the tRNA frequencies of the host cell or organism in which the protein is expressed. Codon optimization can allow for maximum protein expression by increasing the translational efficiency of a gene of interest. In other embodiments the nucleic acid encoding a molecularly tagged ribosomal protein may be a synthetic nucleic acid in which the codons have been optimized for increased expression in the host cell in which it is produced.

2) Molecular Tags

Molecular tags can be any protein (or fragment, portion, analog or derivative thereof) that is not present or accessible in the cell of interest (or the cell fraction from which the tagged ribosomes are to be isolated, or other cells that will be contacted with the reagent that binds the tag) for which there exists a reagent (such as an antibody) or method (such as optical, fluorescence or magnetic sorting) that recognizes the tag and that is accessible to solution (and thereby, the tag).

Molecular tagging with tags that are traditionally utilized as reporter genes is well known in the art (Current Protocols in Molecular biology, Section 9.6.1, "Uses of Fusion Genes in mammalian Transfection" (2004)). Molecular tagging with epitopes are also well known in the art ("epitope tagging" reviewed in Fritze C E, Anderson T R. Epitope tagging: general method for tracking recombinant proteins. Methods Enzymol. 2000; 327:3-16; Jarvik J W, Telmer C A. Epitope tagging. Annu Rev Genet. 1998; 32:601-18).

Tags can include those for which methods/reagents/devices exist that allow facile identification and isolation of the tagged protein, but do not, minimally, or negligibly inhibit Alternatively, the tag can be inserted into any portion of the ribosomal protein such that when the fusion protein is incorporated into an intact ribosome, ribosomal function is not compromised and the tag is accessible to the reagent/method to be used in the detection, isolation or and/or purification. That is, tagging can still allow for a functional ribosome. In other embodiments, a ribosomal protein may be molecularly tagged with a plurality of tags.

In some embodiments, the tag is Green Fluorescent Protein (GFP). GFP can be utilized as an optical or immunoaffinity tag for a variety of applications, all well known in the art. GFP is a protein, composed of 238 amino acids (26.9 kDa), originally isolated from the jellyfish that fluoresces green when exposed to blue light (Prendergast F, Mann K (1978). "Chemical and physical properties of aequorin and the green fluorescent protein isolated from Aequorea forskilea". Biochemistry 17 (17):3448-53; Tsien R (1998). "The green fluorescent protein". Annu Rev Biochem 67: 509-44). The GFP from *A. victoria* has a major excitation peak at a wavelength of 395 nm and a minor one at 475 nm. Its emission peak is at 509 nm which is in the lower green portion of the visible spectrum. The GFP from the sea pansy (*Renilla reniformis*) has a single major excitation peak at 498 nm. In cell and molecular biology, the GFP gene is frequently used as a reporter of expression (Phillips G (2001). "Green fluorescent protein—a bright idea for the study of bacterial protein localization". FEMS Microbiol Lett 204 (1): 9-18.). In modified forms it has been used to make biosensors, and many animals have been created that express GFP. The GFP gene can be introduced into organisms and maintained in their genome through breeding, or local injection with a viral vector can be used to introduce the gene. To date, many bacteria, yeast and other fungal cells, plant, fly, and mammalian cells have been created using GFP as a marker.

In other embodiments, the tag is a GFP mutant, variant, analog, fragment, or derivative thereof. Different mutants of GFP have been engineered (Shaner N, Steinbach P, Tsien R (2005). "A guide to choosing fluorescent proteins". Nat Methods 2 (12): 905-9). One improvement was a single point mutation (S65T) reported in 1995 in Nature by Roger Tsien (Heim R, Cubitt A, Tsien R (1995). "Improved green fluorescence". Nature 373 (6516): 663-4.)). The addition of the 37° C. folding efficiency (F64L) point mutant to the scaffold yielded enhanced GFP (eGFP). eGFP has an extinction coefficient (denoted $\epsilon$), also known as its optical cross section of $9.13 \times 10^{-21}$ m$^2$/molecule, also quoted as 55,000 L/(mol·cm) (Shelley R. McRae, Christopher L. Brown and Gillian R. Bushell (May 2005)). "Rapid purification of eGFP, EYFP, and ECFP with high yield and purity". Protein Expression and Purification 41 (1): 121-127.). Superfolder GFP, a series of mutations that allow GFP to rapidly fold and mature even when fused to poorly folding peptides, was reported in 2006 (Pédelacq J, Cabantous S, Tran T, Terwilliger T, Waldo G (2006). "Engineering and characterization of a superfolder green fluorescent protein". Nat Biotechnol 24 (1): 79-88). In an exemplary embodiment the tag is enhanced GFP (eGFP).

Other mutations have been made, including color mutants; in particular blue fluorescent protein (EBFP, EBFP2, Azurite, mKalama1), cyan fluorescent protein (ECFP, Cerulean, CyPet) and yellow fluorescent protein derivatives (YFP, Citrine, Venus, YPet). BFP derivatives (except mKalama1) contain the Y66H substitution. The mutation in cyan derivatives is the Y66W substitution. The red-shifted wavelength of the YFP derivatives is accomplished by the T203Y mutation (Tsien R (1998). "The green fluorescent protein". Annu Rev Biochem 67: 509-44).

Molecular tags may include both fluorescent, magnetic, epitope, radioactive or otherwise detectable tags, by way of example, and not by limitation, those listed in Table 2.

TABLE 2

Molecular Tags

GFP, eGFP, mGFP, emerald GFP, derivatives and variants (Green Fluorescent protein)
BFP, eBFP, eBFP2, Azurite, mKalama1, sapphire GFP, derivatives and variants (Blue fluorescent proteins)
ECFP, Cerulean, CyPet, DFP, TFP, mTFP, derivatives and variants (cyan and teal fluorescent proteins)
YFP, Citrine, Venus, YPet, Topaz GFP, derivatives and variants (yellow fluorescent proteins)
RFP, mCherry, td-tomato, derivatives and variants (red fluorescent protein)
Bgal, derivatives and variants (Bgalactosdiase)
Luc, derivatives and variants (Luciferase)
CAT, derivatives and variants (Chloramphenicol acetyltransferase)
hGH, derivatives and variants (human growth hormone)
Protein A fragments;
Myc epitopes
Btag and polyhistidine tracts
Influenza virus hemagglutinin protein, fragments, derivatives, variants
C-myc gene, fragments, derivatives, variants
Bluetongue virus VP7 protein, fragments, derivatives, variants
FLAG peptide, fragments, derivatives, variants
Strep-tag peptide, fragments, derivatives, variants
pHlourins, fragment, derivatives, variants References for Table 2 are provided here, and incorporated by reference herein: Evan et al., Mol. Cell Biol. 5(12):3610-3616; Wang et al., 1996, Gene 169(1):53-58; Bornhorst et al., 2000, Purification of proteins using polyhistidine affinity tags, Methods Enzymol 326:245-54; Wilson I A, Niman H L, Houghten R A, Cherenson A R, Connolly M L, Lerner R A. The structure of an antigenic determinant in a protein. Cell. 1984 July; 37(3):767-78; Evan G I, Lewis G K, Ramsay G, Bishop J M. Isolation of monoclonal antibodies specific for human c-myc proto-oncogene product. Mol Cell Biol. 1985 December; 5(12): 3610-6; Wang L F, Yu M, White J R, Eaton B T. BTag: a novel six-residue epitope tag for surveillance and purification of recombinant proteins. Gene. 1996 Feb. 22; 169(1): 53-8; Hopp et al., U.S. Pat. No. 4,703,004, entitled "Synthesis of protein with an identification peptide" issued Oct. 27, 1987; Brizzard B L, Chubet R G, Vizard D L. Immunoaffinity purification of FLAG epitope-tagged bacterial alkaline phosphatase using a novel monoclonal antibody and peptide elution. Biotechniques. 1994 April; 16(4):730-5; Knappik A, Pluckthun A. An improved affinity tag based on the FLAG peptide for the detection and purification of recombinant antibody fragments. Biotechniques. 1994 October; 17(4):754-761; Skerra et al., U.S. Pat. No. 5,506,121, entitled Fusion peptides with binding activity for streptavidin, issued Apr. 9, 1996; Skerra A, Schmidt T G. Applications of a peptide ligand for streptavidin: the Strep-tag. Biomol Eng. 1999 Dec. 31; 16(1-4):79-86; Skerra A, Schnudt T G. Use of the Strep-Tag and streptavidin for detection and purification of recombinant proteins. Methods Enzymol. 2000; 326:271-304; Shaner N, Steinbach P, Tsien R (2005). "A guide to choosing fluorescent proteins". Nat Methods 2 (12): 905-9. doi:10.1038/nmeth819. PMID16299475.; Shaner N, Steinbach P, Tsien R (2005). "A guide to choosing fluorescent proteins". Nat Methods 2 (12): 905-9. PMID16299475; Heim R, Cubitt A, Tsien R (1995). "Improved green fluorescence". Nature 373 (6516): 663-4. PMID7854443; Shelley R. McRae, Christopher L. Brown and Gillian R. Bushell (May 2005). "Rapid purification of eGFP, EYFP, and ECFP with high yield and purity". Protein Expression and Purification 41 (1): 121-127; Pedelacq J, Cabantous S, Tran T, Terwilliger T, Waldo G (2006). "Engineering and characterization of a superfolder green fluorescent protein". Nat Biotechnol 24 (1): 79-88. PMID16369541; Miesenböck G, De Angelis D, Rothman J (1998). "Visualizing secretion and synaptic transmission with pH-sensitive green fluorescent proteins". Nature 394 (6689): 192-5. PMID9671304.

Isolation of Ribosomes, Polysomes, mRNA

1) Isolation of Ribosomes

Various methods exist to isolate ribosomes/tagged ribosomes, particularly polysomes (ribosomal clusters bound to mRNA)/tagged polysomes, from cells, cultured cells and tissues (see, e.g., Bommer et al., 1997, Isolation and characterization of eukaryotic polysomes, in Subcellular Fractionation, Graham and Rickwood (eds.), IRL Press, Oxford, pp. 280-285; incorporated herein by reference in its entirety). Polysomes are interchangeably referred to as polyribosomes, ribosomal complexes or ribosomal clusters. In preferred embodiments, the isolated polysomes (ribosomal-mRNA complexes) contain functional ribosomes, capable of supporting translation, association with mRNA, and/or association with translation factors.

In certain embodiments, the isolation method employed has one or more of the following aspects:
  a. Maintenance of ribosomal subunits on mRNA during isolation: translation arresting compounds, such as emetine or cycloheximide can be added to arrest translation, whereby reducing or preventing dissociation of mRNA from the ribosome. In preferred embodiments isolation is achieved without crosslinking and crosslinking reagents;

b. Inhibition of endogenous RNAase activity: RNAase inhibitors can be added to buffers to maintain the integrity of the mRNA;

c. Isolation of Polysomes: After tissue or cell homogenization, total polysomes are isolated by preparing a post-mitochondrial supernatant in the presence of at least a high concentration salt buffer, for example about 100-150 mM KCl; and d. Solubilization of rough ER-bound Polysomes under non-denaturing conditions: Detergent can also be added to release membrane-associated polysomes from endoplasmic reticulum membranes; total polysomes are usually collected by centrifugation through, for example, a sucrose cushion.

In other embodiments, variations of the above-described general method are used to isolate membrane-associated polysomes from a total pool of polysomes. This allows for further enrichment of mRNA encoding secreted or transmembrane proteins. Various methods may be used to isolate membrane-associated polysomes from cultured cells and tissue, e.g., methods that employ differential centrifugation (Hall C, Lim L. Developmental changes in the composition of polyadenylated RNA isolated from free and membrane-bound polyribosomes of the rat forebrain, analyzed by translation in vitro. Biochem J. 1981 Apr. 15; 196(1):327-36), rate-zonal centrifugation (Rademacher and Steele, 1986, Isolation of undegraded free and membrane-bound polysomal mRNA from rat brain, J. Neurochem. 47(3):953-957), isopycnic centrifugation (Mechler, 1987, Isolation of messenger RNA from membrane-bound polysomes, Methods Enzymol. 152: 241-248), and differential extraction (Bommer et al., 1997, Isolation and characterization of eukaryotic polysomes, in Subcellular Fractionation, Graham and Rickwood (eds.), IRL Press, Oxford, pp. 280-285; incorporated herein by reference in its entirety) to isolate the membrane-associated polysomes (Heintz US publication 20050009028 incorporated in its entirety).

In other embodiments, affinity methods are used to isolate or purify tagged proteins using methods well known in the art including but not limited to including chromatography, solid phase chromatography precipitation, matrices, co-immunoprecipitation, etc.

In specific embodiments, molecularly tagged functional ribosomes are provided, bound to mRNA, that can bind a reagent for the molecular tag. In other embodiments, the molecularly tagged ribosomes are bound to a specific reagent or affinity reagent that is bound, covalently or non-covalently, to a solid surface, such as a bead, a resin, or a chromatography resin, e.g., agarose, sepharose, and the like. In other embodiments, other methods are used with or in place of affinity purification. In other embodiments, specific polysomes can be isolated utilizing optical sorting, fluorescence-based sorting or magnetic-based sorting methods and devices.

In certain embodiments, polysomes are not isolated from the post-mitochondrial supernatant or even from a cell or tissue lysate before being subject to affinity purification.

FIG. 2a presents a schematic to illustrate affinity purification of eGFP-tagged polysomes using anti-GFP antibody-coated beads.

2) Isolation of mRNA from Ribosomes

Once the tagged ribosome has been isolated, the associated mRNA complexed with the protein may be isolated using chemical, mechanical or other methods well known in the art. For example, elution of mRNA is accomplished by addition of EDTA to buffers, which disrupts polysomes and allows isolation of bound mRNA for analysis (Schutz, et al. (1977), Nucl. Acids Res. 4:71-84; Kraus and Rosenberg (1982), Proc. Natl. Acad. Sci. USA 79:4015-4019). In addition, isolated polysomes (attached or detached from isolation matrix) can be directly inputted into RNA isolation procedures using reagents such as Tri-reagent (Sigma) or Triazol (Sigma). In particular embodiments, poly A$^+$ mRNA is preferentially isolated by virtue of its hybridization of oligodT cellulose. Methods of mRNA isolation are described, for example, in Sambrook et al., 2001, Molecular Cloning, A Laboratory Manual, Third Edition, Cold Spring Harbor Laboratory Press, N.Y.; and Ausubel et al., 1989, Current Protocols in Molecular Biology, Green Publishing Associates and Wiley Interscience, N.Y., both of which are hereby incorporated by reference in their entireties.

Nucleic Acid Sequences for Cloning, Expression and Regulation of Tagged Ribosomes 1) General Methods that are well known to those skilled in the art can be used to construct vectors containing tagged ribosomal protein coding sequences operatively associated with the appropriate transcriptional and translational control signals required for expression. These methods include, for example, in vitro recombinant DNA techniques and in vivo genetic recombination. See, for example, the techniques described in Sambrook et al., 2001, Molecular Cloning, A Laboratory Manual, Third Edition, Cold Spring Harbor Laboratory Press, N.Y.; and Ausubel et al., 1989, Current Protocols in Molecular Biology, Green Publishing Associates and Wiley Interscience, N.Y.

2) Regulatory Sequences

Certain embodiments of the invention provide vectors, cell lines, and lines of organisms that contain nucleic acid constructs that comprise the coding sequence for a tagged ribosomal protein under the control of regulatory sequences. According to the methods described herein, the tagged ribosomal proteins are selectively expressed in a particular chosen cell type, cell subtype, molecular pathway, or circuit using regulatory elements naturally occurring or engineered to recapitulate a desired expression pattern. Such expression is achieved by driving the expression of the tagged ribosomal protein using regulatory sequences or a transcriptional unit from a characterizing or endogenously regulated gene expressed in the chosen cell type, subtype, pathway, circuit and/or point in development. In certain embodiments a particular cell type is one that resides within a mixed population of cells, comprising a discernable group of cells sharing a common characteristic. This group may be morphologically, anatomically, genetically, or functionally discernible. In other embodiments, this group may be morphologically, genetically, and developmentally indistinguishable, but be genetically distinguishable. Because of its selective expression, the population of cells may be characterized or recognized based on its positive expression of an endogenously regulated characterizing gene. Some or all of the regulatory sequences/elements may be incorporated into nucleic acids (including transgenes) to regulate the expression of tagged ribosomal protein coding sequences. Examples of regulatory sequences or elements include but are not limited to enhancer sequences, insulator sequences, silencer sequences, or a combination of said sequences. In certain embodiments, a gene that is not constitutively expressed, (i.e., exhibits some spatial or temporal restriction in its expression pattern) is used as a source of a regulatory sequence. In other embodiments, a gene that is constitutively expressed is used as a source of a regulatory sequence. In other embodiments a regulatory sequence is engineered or modified to achieve desired expression characteristics and patterns.

Regulatory regions can be whole or parts or the regulatory sequences from the loci of the genes of interest. For example, to drive specific expression of a tagged ribosomal protein (for example eGFP tagged L10a) in medium spiny neurons, regulatory sequences from a medium spiny neuron-specific gene locus, for example a Drd1a or Drd2 locus, can be utilized. In another example, to drive specific expression of a tagged ribosomal protein (for example eGFP tagged L10a) in motor neurons, regulatory sequences from a motor-specific gene locus, for example choline acetyl transferase (Chat) locus, can be utilized. Similarly, to drive specific expression of a tagged ribosomal protein (for example eGFP tagged L10a) in cerebellar cells, regulatory sequences from a cerebellar cell-specific gene loci. For example loci from Pcp2, Neurod1, Grm2, Grp, Septin4, or Aldh1l1 can be utilized, to drive specific expression in Purkinje cells, granule cells, golgi neurons, unipolar brush cells, Bergmann glial cells, and astrocytes, respectively. An entire locus, an entire non-coding region of a locus, a portion of a locus, or a modified locus can be utilized as the regulatory sequences to drive expression of tagged ribosomal proteins in a genetically targeted, cell subtype specific manner.

The tagged ribosomal gene coding sequences may placed under the transcriptional control of some or all of the regulatory sequences from a particular locus such that the tagged ribosomal gene is expressed in substantially the same expression pattern as the endogenously regulated gene found in that locus in the transformed organism, or at least in an anatomical region or tissue of the organism (by way of example, in the brain, spinal cord, heart, skin, bones, head, limbs, blood, muscle, peripheral nervous system, etc. of an animal) containing the population of cells to be marked by expression of the tagged ribosomal protein gene coding sequences. By "substantially the same expression pattern" is meant that the tagged ribosomal protein gene coding sequences are expressed in at least 50%, 60%, 70% 80%, 85%, 90%, 95%, and about 100% of the cells shown to express the endogenous characterizing gene by in situ hybridization, PCR, other gene expression detection methods or functional methods familiar to those with skill in the art.

The regulatory sequence is, e.g., a promoter or enhancer, or any other cis or trans activating element or transcriptional unit of a characterizing gene. In some embodiments this characterizing gene is endogenous to a host cell or host organism (or is an ortholog of an endogenous gene) and is expressed in a particular select population of cells of the organism. The regulatory sequence can be derived from a human, rat, or mouse or any mammalian gene associated with specific neuronal, cellular, and metabolic pathways. In certain embodiments, a non mammalian regulatory sequence can be utilized. Cis and trans, 5' and 3' regulatory sequences and transcriptional units from several known pathways are amenable for cell-type specific, cell subtype-specific, developmental stage-specific, temporal-specific, tissue-specific, pathway-specific, or circuit-specific expression of transgenes. Examples of known pathways include but are not limited to the adrenergic or noradrenergic neurotransmitter pathway, the dopaminergic neurotransmitter pathway, the GABAergic neurotransmitter pathway, the glutamingergic neurotransmitter pathway, the glycinergic neurotransmitter pathway, the histaminergic neurotransmitter pathway, a neuropeptidergic neurotransmitter pathway, a serotonergic neurotransmitter pathway, a nucleotide receptor-specific pathway, ion channels, transcriptions factors, markers of undifferentiated or not fully differentiated cells, the sonic hedgehog signaling pathway, calcium binding, or a neurotrophic factor receptor (tables in US2005/0009028, herein incorporated by reference).

In certain embodiments regulatory sequences that may be used to control expression can be derived from, include but are not limited to, the following animal transcriptional control regions that exhibit tissue specificity and that have been utilized in cell culture and transgenic animals. Examples of transcriptional control regions are: elastase I gene control region, enolase promoter, insulin gene control region, immunoglobulin gene control region, mouse mammary tumor virus control region, albumin gene control region, alpha-fetoprotein gene control region, alpha 1-antitrypsin gene control region, beta.-globin gene control region, myelin basic protein gene control region, myosin light chain-2 gene control region, and gonadotropic releasing hormone gene control region. In other embodiments, the gene sequence from which the regulatory sequence derives can be protein kinase C, gamma, TH-elastin, Pax7, Eph receptors, islet-1 and Sonic hedgehog.

Nucleic acids to be used for regulating expression may include all or a portion of the upstream and/or downstream and 5' and/or 3' regulatory sequences from the naturally occurring or modified locus of a selected gene. The regulatory sequences preferably direct expression of the tagged ribosomal protein sequences in substantially the same pattern as the endogenous characterizing gene within transgenic organism, or tissue derived therefrom. This would provide of for any and all cis- and trans-acting regulatory sequences and transcriptional units that would direct expression of the tagged ribosomal protein in an endogenous regulatory fashion. A regulatory sequence can be 1 kb, 5 kb, 10 kb, 50 kb, 100 kb, 200 kb, 250 kb, 500 kb or even 1 Mb in length.

In certain embodiments, the nucleic acids encoding the molecularly tagged ribosomal proteins may be selectively expressed in random but distinct subsets of cells, as described in Feng et al. (2000, Imaging neuronal subsets in transgenic mice expressing multiple spectral variants of GFP, Neuron 28(1):41-51, which is hereby incorporated by reference in its entirety). Using such methods, independently generated transgenic lines may express the nucleic acids encoding the molecularly tagged ribosomal proteins in a unique pattern, perhaps pathway-specific, or circuit-specific, and although spatially separated, would all incorporate identical regulatory elements.

3) Placement and Construction of Regulatory Sequences and Transgenes

In certain embodiments the nucleotide sequences encoding the tagged ribosomal protein product may replace all or a portion of the characterizing gene coding sequences in a genomic clone/locus of the characterizing gene, leaving only all or part of the characterizing gene regulatory non-coding sequences.

In other embodiments, the tagged ribosomal gene coding sequences are inserted into or replace transcribed coding or non-coding sequences of the genomic characterizing gene sequences, for example, into or replacing a region of an exon or of the 3' UTR of the characterizing gene genomic sequence.

In one embodiment, the tagged ribosomal protein gene coding sequence is inserted into or replaces a portion of the 3' untranslated region (UTR) of the characterizing gene genomic sequence. In another embodiment, the coding sequence of the characterizing gene is mutated or disrupted to abolish characterizing gene expression from the nucleic acid construct without affecting the expression of the tagged fusion protein gene. In certain embodiments, the tagged ribosomal fusion protein gene coding sequence has its own internal ribosome entry site (IRES).

In some embodiments, the tagged ribosomal protein gene coding sequences are inserted using 5' direct fusion wherein the tagged ribosomal protein gene coding sequences are inserted in-frame adjacent to the initial ATG sequence (or adjacent the nucleotide sequence encoding the first two, three, four, five, six, seven or eight amino acids of the characterizing gene protein product) of the characterizing gene, so that translation of the inserted sequence produces a fusion protein of the first methionine (or first few amino acids) derived from the characterizing gene sequence fused to the tagged ribosomal fusion protein gene protein.

In other embodiments, a tagged ribosomal fusion protein gene is inserted into a separate cistron in the 5' region of the characterizing gene genomic sequence and has an independent IRES sequence. In certain embodiments, an IRES is operably linked to the tagged ribosomal fusion protein gene coding sequence to direct translation of the tagged fusion protein gene. The IRES permits the creation of polycistronic mRNAs from which several proteins can be synthesized under the control of an endogenous transcriptional regulatory sequence. Such a construct is advantageous because it allows marker proteins to be produced in the same cells that express the endogenous gene (Heintz, 2000, Hum. Mol. Genet. 9(6): 937-43; Heintz et al., WO 98/59060; Heintz et al., WO 01/05962; which are incorporated herein by reference in their entireties).

In certain embodiments, exogenous translational control signals, including, for example, the ATG initiation codon, can be provided by the characterizing gene or some other heterologous gene. The initiation codon is usually in phase with the reading frame of the desired coding sequence of the tagged ribosomal fusion protein gene to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153: 516-44).

The construct can also comprise one or more selectable markers that enable identification and/or selection of recombinant vectors. The selectable marker may be the tagged ribosomal fusion protein gene product itself or an additional selectable marker not necessarily tied to the expression of the characterizing gene.

In certain embodiments where a tagged ribosomal fusion protein gene is expressed conditionally, the tagged ribosomal fusion protein gene coding sequence is embedded in the genomic sequence of the characterizing gene and is inactive unless acted on by a transactivator or recombinase, whereby expression of the tagged ribosomal fusion protein gene can then be driven by the characterizing gene regulatory sequences. In such a system, expression of the transactivator gene, as regulated by the characterizing gene regulatory sequences, activates the expression of the tagged fusion protein gene.

In a specific embodiment, a nucleic acid of the invention is expressed conditionally, using any type of inducible or repressible system available for conditional expression of genes known in the art, e.g., a system inducible or repressible by tetracycline ("tet system"); interferon; estrogen, ecdysone, or other steroid inducible system; Lac operator, progesterone antagonist RU486, or rapamycin (FK506). For example, a conditionally expressible nucleic acid of the invention can be created in which the coding region for the tagged ribosomal fusion protein gene (and, optionally also the characterizing gene) is operably linked to a genetic switch, such that expression of the tagged ribosomal fusion protein gene can be further regulated. One example of this type of switch is a tetracycline-based switch.

In several embodiments, the nucleic acids of the invention comprise all or a significant portion of the genomic sequence of the characterizing gene locus, at least all or a portion of the 5' and/or 3' regulatory sequences of the characterizing endogenously regulated gene, at least sufficient sequence 5' and/or 3' of the characterizing gene coding sequence to direct expression of the tagged ribosomal fusion protein gene coding sequences in the same expression pattern (temporal and/or spatial) as the endogenous counterpart of the characterizing gene. In certain embodiments, the nucleic acid of the invention comprises at least one exon, at least two exons, at least three exons, all but one exon, or all but two exons, of the characterizing endogenously regulated gene.

4) Expression Using a Binary System

Since the level of expression of the tagged ribosomal protein within a cell may needed in the efficiency of the isolation procedure, in certain embodiments of the invention, a binary system can be used, in which the endogenous regulatory sequence such as a promoter drives expression of a protein that then activates a second expression construct. This second expression construct uses a strong regulatory sequence such as a promoter to drive expression of the tagged ribosomal fusion protein at higher levels than is possible using the endogenous regulatory region itself.

In certain embodiments, a particular population-specific gene drives expression of a molecular switch (e.g., a recombinase, a transactivator) in a population-specific manner. This switch then activates high-level expression though a second regulatory element regulating expression of the tagged ribosomal protein.

For example, the molecularly tagged ribosomal protein coding sequence may be expressed conditionally, through the activity of a molecular switch gene which is an activator or suppressor of gene expression. In this case, the second gene encodes a transactivator, e.g., tetR, a recombinase, or FLP, whose expression is regulated by the characterizing gene regulatory sequences. The gene encoding the molecularly tagged ribosomal protein is linked to a conditional element, e.g., the tet promoter, or is flanked by recombinase sites, e.g., FRT sites, and may be located any where within the genome. In such a system, expression of the molecular switch gene, as regulated by the characterizing gene regulatory sequences, activates the expression of the molecularly tagged ribosomal protein.

5) Transcriptional Regulation Systems

In certain embodiments, the tagged ribosomal fusion protein gene can be expressed conditionally by operably linking at least the coding region for the tagged ribosomal fusion protein gene to all or a portion of the regulatory sequences from the characterizing gene's genomic locus, and then operably linking the tagged ribosomal fusion protein gene coding sequences and characterizing gene sequences to an inducible or repressible transcriptional regulation system. Transactivators in these inducible or repressible transcriptional regulation systems are designed to interact specifically with sequences engineered into the vector. Such systems include those regulated by tetracycline ("tet systems"), interferon, estrogen, ecdysone, Lac operator, progesterone antagonist RU486, and rapamycin (FK506) with tet systems being particularly preferred (see, e.g., Gingrich and Roder, 1998, Annu. Rev. Neurosci. 21: 377-405; incorporated herein by reference in its entirety). These drugs or hormones (or their analogs) act on modular transactivators composed of natural or mutant ligand binding domains and intrinsic or extrinsic DNA binding and transcriptional activation domains. In certain embodiments, expression of the detectable or selectable marker can be regulated by varying the concentration of the drug or hormone in medium in vitro or in the diet of the transformed organism in vivo.

The inducible or repressible genetic system can restrict the expression of the detectable or selectable marker either temporally, spatially, or both temporally and spatially.

In other embodiments, expression of the tagged ribosomal fusion protein gene is regulated by using a recombinase system that is used to turn on or off tagged ribosomal fusion protein gene expression by recombination in the appropriate region of the genome in which the marker gene is inserted. Such a recombinase system, in which a gene that encodes a recombinase can be used to turn on or off expression of the tagged ribosomal fusion protein gene (for review of temporal genetic switches and "tissue scissors" using recombinases, see Hennighausen and Furth, 1999, Nature Biotechnol. 17: 1062-63). Exclusive recombination in a selected cell type may be mediated by use of a site-specific recombinase such as Cre, FLP-wild type (wt), FLP-L or FLPe. Recombination may be effected by any art-known method, e.g., the method of Doetschman et al. (1987, Nature 330: 576-78; incorporated herein by reference in its entirety); the method of Thomas et al., (1986, Cell 44: 419-28; incorporated herein by reference in its entirety); the Cre-loxP recombination system (Stemberg and Hamilton, 1981, J. Mol. Biol. 150: 467-86; Lakso et al., 1992, Proc. Natl. Acad. Sci. USA 89: 6232-36; which are incorporated herein by reference in their entireties); the FLP recombinase system of *Saccharomyces cerevisiae* (O'Gorman et al., 1991, Science 251: 1351-55); the Cre-loxP-tetracycline control switch (Gossen and Bujard, 1992, Proc. Natl. Acad. Sci. USA 89: 5547-51); and ligand-regulated recombinase system (Kellendonk et al., 1999, J. Mol. Biol. 285: 175-82; incorporated herein by reference in its entirety). Preferably, the recombinase is highly active, e.g., the Cre-loxP or the FLPe system, and has enhanced thermostability (Rodriguez et al, 2000, Nature Genetics 25: 139-40; incorporated herein by reference in its entirety).

In certain embodiments, a recombinase system can be linked to a second inducible or repressible transcriptional regulation system. For example, a cell-specific Cre-loxP mediated recombination system (Gossen and Bujard, 1992, Proc. Natl. Acad. Sci. USA 89: 5547-51) can be linked to a cell-specific tetracycline-dependent time switch detailed above (Ewald et al., 1996, Science 273: 1384-1386; Furth et al. Proc. Natl. Acad. Sci. U.S.A. 91: 9302-06 (1994); St-Onge et al, 1996, Nucleic Acids Research 24(19): 3875-77; which are incorporated herein by reference in their entireties).

In one embodiment, an altered cre gene with enhanced expression in mammalian cells is used (Gorski and Jones, 1999, Nucleic Acids Research 27(9): 2059-61; incorporated herein by reference in its entirety).

In a specific embodiment, the ligand-regulated recombinase system of Kellendonk et al. (1999, J. Mol. Biol. 285: 175-82; incorporated herein by reference in its entirety) can be used. In this system, the ligand-binding domain (LBD) of a receptor, e.g., the progesterone or estrogen receptor, is fused to the Cre recombinase to increase specificity of the recombinase.

6) Sources of Nucleic Acids

Nucleic acids comprising the characterizing gene sequences and tagged ribosomal fusion protein gene coding sequences can be obtained from any available source. In most cases, all or a portion of the characterizing gene sequences and/or the tagged ribosomal fusion protein gene coding sequences are known, for example, in publicly available databases such as GenBank, UniGene and the Mouse Genome Informatic (MGI) Database to name just a few, or in private subscription databases. With a portion of the sequence in hand, hybridization probes can be designed using highly routine methods in the art (for example filter hybridization or PCR amplification) to identify clones containing the appropriate sequences for example in a library or other source of nucleic acid. If the sequence of the gene of interest from one species is known and the counterpart gene from another species is desired, it is routine in the art to design probes based upon the known sequence. The probes hybridize to nucleic acids from the species from which the sequence is desired, for example, hybridization to nucleic acids from genomic or DNA libraries from the species of interest. By way of example and not limitation, genomic clones can be identified by probing a genomic DNA library under appropriate hybridization conditions, e.g., high stringency conditions, low stringency conditions or moderate stringency conditions, depending on the relatedness of the probe to the genomic DNA being probed.

7) Vectors

Briefly, the characterizing gene genomic sequences are preferably in a vector that can accommodate lengths of sequence (for example, 10 kb's of sequence), such as cosmids, yeast artificial chromosomes (YACs) and bacterial artificial chromosomes (BACs), and encompass at least 50, 70, 80, 100, 120, 150, 200, 250, 300, 400, 500 or 1000 kb of sequence that comprises all or a portion of the characterizing gene sequence. The larger the vector insert, the more likely it is to identify a vector that contains the characterizing gene cis and trans sequences of interest. In some embodiments the vector containing the entire genomic sequence (i.e. genomic locus) for the characterizing endogenously regulated gene is present. In other embodiments the entire genomic sequence cannot be accommodated by a single vector or such a clone is not available. In these instances (or when it is not known whether the clone contains the entire genomic sequence), the vector contains at least the characterizing gene sequence with the start, i.e., the most 5' end, of the coding sequence in the approximate middle of the vector insert containing the genomic sequences and/or has at least 20 kb, 30 kb, 40 kb, 50 kb, 60 kb, 80 kb, 100 kb or 200 kb of genomic sequence on either side of the start of the characterizing gene coding sequence. This can be determined by any method known in the art, for example, but not by way of limitation, by sequencing, restriction mapping, PCR amplification assays, etc.

Once the appropriate vector containing the regulatory region/regulatory gene sequences has been created, the tagged ribosomal fusion protein gene can be incorporated into the characterizing gene sequence by any method known in the art for manipulating DNA. In one embodiment, homologous recombination in bacteria is used for target-directed insertion of the tagged ribosomal fusion protein gene sequence into the genomic DNA encoding the characterizing endogenously regulated gene and sufficient regulatory sequences to promote expression of the gene in its endogenous expression pattern, which characterizing gene sequences have been inserted into a vector. The vector comprising the tagged ribosomal fusion protein gene and regulatory gene sequences is then introduced into the genome of a potential founder organism for generating a line of transformed organisms, using methods well known in the art, e.g., those methods described herein. Such transformed organisms are then screened for expression of the tagged ribosomal fusion protein gene coding sequences that mimics the expression of the endogenous characterizing gene. Several different constructs containing nucleic acids of the invention may be introduced into several potential founder organisms and the resulting transformed organisms are then screened for the best, (e.g., highest level) and most accurate (best mimicking expression of the endogenous characterizing gene) expression of the tagged ribosomal fusion protein gene coding sequences.

The nucleic acid construct can be used to transform a host or recipient cell or organism using well known methods, e.g., those described herein. Transformation can be either a permanent or transient genetic change. In one aspect of the invention, a vector is used for stable integration of the nucleic acid construct into the genome of the cell. In another aspect, the vector is maintained episomally.

8) Bacterial Artificial Chromosomes (BACs) and Other Vectors

The methods described herein provide transformed organisms, e.g., transgenic mice that express a tagged ribosomal protein within a chosen cell type. In some embodiments, BAC-mediated recombination (Yang, et al., 1997, Nat. Biotechnol. 15(9):859-865) is used to create the transformed organism. Such expression is achieved by using the endogenous regulatory sequences and transcriptional units of a particular gene, wherein the expression of gene is a defining characteristic of the chosen cell type (as also described in PCT/US02/04765, entitled "Collections of Transgenic Animal Lines (Living Library)" by Serafini, published as WO 02/064749 on Aug. 22, 2002, which is incorporated by reference herein in its entirety). A collection of transgenic animals expressing tagged ribosomal proteins within a set of chosen cell types is assembled, and this is often referred to as a BACarray collection.

In another embodiment, a nucleic acid of the invention is inserted into a yeast artificial chromosome (YAC) (Burke et al., 1987 Science 236: 806-12; and Peterson et al., 1997, Trends Genet. 13: 61). A collection of transgenic animals expressing tagged ribosomal proteins within a set of chosen cell types or subtypes is assembled, and this is often referred to as a YACarray collection.

In other embodiments, the nucleic acid of the invention is inserted into another vector developed for the cloning of large segments of mammalian DNA, such as a cosmid or bacteriophage P1 (Sternberg et al., 1990, Proc. Natl. Acad. Sci. USA 87: 103-07). The approximate insert size is about 30-35 kb for cosmids and 100 kb for bacteriophage P1.

In another embodiment, the nucleic acid of the invention is inserted into a P-1 derived artificial chromosome (PAC) (Mejia et al., 1997, Retrofitting vectors for Escherichia coli-based artificial chromosomes (PACs and BACs) with markers for transfection studies, Genome Res. 7(2):179-86). The maximum insert size is about 300 kb.

BACs and other vectors used in the methods described here often can accommodate, and in certain embodiments comprise, large pieces of heterologous DNA such as genomic sequences. Such vectors can contain an entire genomic locus, or at least sufficient sequences to confer endogenous regulatory expression pattern and to insulate the expression of coding sequences from the effect of regulatory sequences surrounding the site of integration of the nucleic acid in the genome to mimic better wild type expression.

When entire genomic loci or portions thereof are used, few, if any, site-specific expression problems are encountered, unlike insertions of nucleic acids into smaller sequences. When insertions of nucleic acids are too large, other problems can be encountered. In some embodiments, the vector is a BAC containing genomic sequences into which a selected sequence encoding a molecular tag that has been inserted by directed homologous recombination in bacteria, e.g., by the methods of Heintz WO 98/59060; Heintz et al., WO 01/05962; Yang et al., 1997, Nature Biotechnol. 15: 859-865; Yang et al., 1999, Nature Genetics 22: 327-35; which are incorporated herein by reference in their entireties.

Using such methods, a BAC can be modified directly in a recombination-deficient E. coli host strain by homologous recombination. i.e., a cell that cannot independently support homologous recombination, e.g., Rec A.sup.-. In one embodiment, homologous recombination in bacteria is used for target-directed insertion of a sequence encoding a molecularly tagged ribosomal protein into the genomic DNA encoding sufficient regulatory sequences (termed "characterizing gene sequences") to promote expression of the tagged ribosomal protein in the endogenous expression pattern of the characterizing gene, which sequences have been inserted into the BAC. The BAC comprising the tagged fusion protein sequence under the control/regulation of a regulatory region comprising sequences from a genomic locus of the desired characterizing gene is then recovered and introduced into the genome of a potential founder organism for a line of transformed organisms. In one aspect, the particular nucleotide sequence that has been selected to undergo homologous recombination is contained in an independent origin based cloning vector introduced into or contained within the host cell, and neither the independent origin based cloning vector alone, nor the independent origin based cloning vector in combination with the host cell, can independently support homologous recombination (e.g., is RecA). The exact method used to introduce the tagged ribosomal protein encoding sequence and to remove (or not) the RecA (or other appropriate recombination enzyme) will depend upon the nature of the BAC library used (for example, the selectable markers present on the BAC vectors) and such modifications are within the skill in the art.

Once the BAC containing the characterizing gene regulatory sequences and molecularly tagged ribosomal protein coding sequences in the desired configuration is identified, it can be isolated from the host E. coli cells using routine methods and used to make transformed organisms as described within.

Alternatively, the BAC can also be engineered or modified by "E-T cloning," as described by Muyrers et al (1999, Nucleic Acids Res. 27(6): 1555-57, incorporated herein by reference in its entirety). Using these methods, specific DNA may be engineered into a BAC independently of the presence of suitable restriction sites. This method is based on homologous recombination mediated by the recE and recT proteins ("ET-cloning") (Zhang et al., 1998, Nat. Genet. 20(2): 123-28; incorporated herein by reference in its entirety).

Host Cells and Organisms Engineered to Express Molecularly Tagged Ribosomes

1) Introduction of Vectors into Host Cells

In one aspect, a vector containing the nucleic acid encoding the regulatory sequences and the molecularly tagged fusion protein can be introduced transiently or stably into the genome of a host cell. In another aspect, the vector can be transiently transfected wherein it is not integrated, but is maintained as an episome. The terms "host cell" and "recombinant host cell" are used interchangeably herein.

It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., bacterium such as *E. coli*) or eukaryotic cell (e.g., a cell from a yeast, plant, insect (e.g., *Drosophila*), amphibian, amniote, or mammal, to name but a few. In certain embodiments the host cell is a human cell, a rodent cell, a mouse cell, a rat cell, a mammalian cell, an immortalized cultured cell or primary human or rodent cell. In specific embodiments, the host cells are human or rodent embryonic stem cells, neuronal stem cells, hippocampal stem cells, hippocampal progenitor cells, or partially differentiated pluripotent cells, or tumor cells or cancer cells (particularly circulating cancer cells such as those resulting from leukemias and other blood system cancers). Methods can utilize genetically engineered host cells that contain any of the foregoing tagged ribosomal protein coding sequences, optionally operatively associated with a regulatory element (preferably from a characterizing gene, as described above) that directs the expression of the coding sequences in the host cell. Both cDNA and genomic sequences can be cloned and expressed.

In one aspect, the host cell is recombination deficient, i.e., Rec.sup.-, and used for BAC recombination. In specific embodiments the host cell may contain more than one type of ribosomal fusion, where the fusion of the different ribosomal is to the same or different tags. Alternatively, a single ribosomal may be fused to more than one tag, for example, at both is N-terminal and C-terminal ends.

A vector containing a nucleotide sequence can be introduced into the desired host cell by methods known in the art, e.g., transfection, transformation, transduction, electroporation, infection, microinjection, cell fusion, DEAE dextran, calcium phosphate precipitation, liposomes, LIPOFECTIN™, lysosome fusion, synthetic cationic lipids, use of a gene gun or a DNA vector transporter, such that the nucleotide sequence is transmitted to offspring in the line. For various techniques for transformation or transfection of mammalian cells, see Keown et al., 1990, Methods Enzymol. 185: 527-37; Sambrook et al., 2001, Molecular Cloning, A Laboratory Manual, Third Edition, Cold Spring Harbor Laboratory Press, N.Y.

In certain embodiments, the vector is introduced into a cultured cell. In other embodiments, the vector is introduced into a proliferating cell (or population of cells), e.g., a tumor cell, a stem cell, a blood cell, a bone marrow cell, a cell derived from a tissue biopsy, etc.

2) Introduction of Vectors to Create Transgenic Animals

Particular embodiments encompass methods of introduction of the vector containing the nucleic acid, using pronuclear microinjection into the mononucleus of a mouse embryo or infection with a viral vector comprising the construct. Methods of pronuclear injection into mouse embryos are well-known in the art and described in Hogan et al. 1986, Manipulating the Mouse Embryo, Cold Spring Harbor Laboratory Press, New York, N.Y. and Wagner et al., U.S. Pat. No. 4,873,191, issued Oct. 10, 1989, herein incorporated by reference in their entireties. Viral methods of inserting nucleic acids are known in the art. Targeted delivery can utilize lentivirus, retrovirus, adenovirus, herpes simplex virus, adeno associated virus, or any other virus amenable to gene delivery.

3) Transgenic Organisms

Any model organism can be engineered to express a molecularly tagged ribosome using methods well known in the art. These can include but are not limited to non-human primates, mice, rats, sheep, dogs, cows, goats, chickens, amphibians, fish, zebrafish, (Danio rerio), flies (*Drosophila melanogaster*), worms (*Caenorhabditis elegans*), or yeast (or other fungi). A transgenic animal is a non-human animal in which one or more of the cells of the animal includes a nucleic acid that is non-endogenous (i.e., heterologous) and is present as an extrachromosomal element in a portion of its cell or stably integrated into its germ line DNA (i.e., in the genomic sequence of most or all of its cells). In certain embodiments a transgenic animal comprises stable changes to the germline sequence. Heterologous nucleic acid is introduced into the germ line of such a transgenic animal by genetic manipulation of, for example, embryos or embryonic stem cells of the host animal.

The heterologous nucleic acid may integrate into the genome of the founder organism by random integration. If random, the integration preferably does not knock out, e.g., insert into, an endogenous gene(s) such that the endogenous gene is not expressed or is mis-expressed.

In other embodiments, the nucleic acid of the may integrate by a directed method, e.g., by directed homologous recombination ("knock-in"), Chappel, U.S. Pat. No. 5,272,071; and PCT publication No. WO 91/06667, published May 16, 1991; U.S. Pat. No. 5,464,764; Capecchi et al., issued Nov. 7, 1995; U.S. Pat. No. 5,627,059, Capecchi et al issued, May 6, 1997; U.S. Pat. No. 5,487,992, Capecchi et al., issued Jan. 30, 1996).

Transformed organisms, e.g., transgenic animals, can be generated by random integration of a vector into the genome of the organism, for example, by pronuclear injection in an animal zygote as described above. Other methods involve introducing the vector into cultured embryonic cells, for example ES cells using methods of injection or electroporation well known in the art, and then introducing the transformed cells into animal blastocysts, thereby generating a "chimeras" or "chimeric animals", in which only a subset of cells have the altered genome. Chimeras are often used for breeding purposes in order to generate the desired transgenic animal. Animals having a heterozygous alteration are generated by breeding of chimeras. Male and female heterozygotes are typically bred to generate homozygous animals.

Methods for generating transgenic animals via embryo manipulation and microinjection, particularly animals such as mice, have become conventional in the art and are described, for example, in U.S. Pat. Nos. 4,736,866 and 4,870,009, 4,873,191, in Hogan, Manipulating the Mouse Embryo, (Cold Spring Harbor Laboratory Press, Cold Spring Harbor, N.Y., 1986) and in Wakayama et al., 1999, Proc. Natl. Acad. Sci. USA, 96:14984-89. Similar methods are used for production of other transgenic animals.

A transgenic founder animal can be identified based upon the presence of the nucleic acid introduced in its genome and/or expression of mRNA in tissues or cells of the animals. A transgenic founder animal can then be used to breed additional animals carrying the nucleic acid of. These transgenic animals can further be bred to other transgenic animals carrying other heterologous nucleic acids. Progeny harboring homologously recombined or integrated DNA in their germline cells can be used to breed animals in which all cells of the animal contain the homologously recombined DNA by germline transmission of the nucleic acid of interest.

Clones of the non-human transgenic animals described herein can also be produced according to the methods described in Wilmut et al., 1997, Nature 385: 810-13 and PCT Publication NOS. WO 97/07668 and WO 97/07669.

Once the transgenic mice are generated they may be bred and maintained using methods well known in the art. By way of example, the mice may be housed in an environmentally controlled facility maintained on a 10 hour dark: 14 hour light cycle. Mice are mated when they are sexually mature (6 to 8 weeks old). In certain embodiments, the transgenic founders or chimeras are mated to an unmodified animal. In one embodiment, the transgenic founder or chimera is mated to C57BL/6 mice (Jackson Laboratories). In a specific embodiment where the nucleic acid is introduced into ES cells and a chimeric mouse is generated, the chimera is mated to 129/Sv mice, which have the same genotype as the embryonic stem cells. Protocols for successful creation and breeding of transgenic mice are known in the art (Manipulating the Mouse Embryo. A Laboratory Manual, 2nd edition. B. Hogan, Beddington, R., Costantini, F. and Lacy, E., eds. 1994. Cold Spring Harbor Laboratory Press: Plainview, N.Y.).

Methods to establish heterozygousity or homozygousity are well known in the art and utilize PCR and Southern blotting.

In some embodiments, the transgenic mice are so highly inbred to be genetically identical except for sexual differences. The homozygotes are tested using backcross and intercross analysis to ensure homozygosity. Homozygous lines for each integration site in founders with multiple integrations are also established. Brother/sister matings for 20 or more generations define an inbred strain. In another preferred embodiment, the transgenic lines are maintained as hemizygotes.

In an alternative embodiment, individual genetically altered mouse strains are also cryopreserved rather than propagated. Methods for freezing embryos for maintenance of founder animals and transgenic lines are known in the art. Methods for reconstituting frozen embryos and bringing the embryos to term are known in the art.

The nucleic acid encoding the molecularly tagged ribosomal protein may be introduced into the genome of a founder plant (or embryo that gives rise to the founder plant) using methods well known in the art (Newell, 2000, Plant transformation technology. Developments and applications, Mol. Biotechnol. 16(1):53-65; Kumar and Fladung, 2001, Controlling transgene integration in plants, Trends in Plant Science 6 (4): 155-159). The nucleic acid encoding the molecularly tagged ribosomal protein may be introduced into the genome of bacteria and yeast using methods described in Ausubel et al., 1989, Current Protocols in Molecular Biology, Green Publishing Associates and Wiley Interscience, N.Y., Chapters 1 and 13, respectively).

4) Screening for Expression of Tagged Ribosomal Proteins in Transgenic Organisms Potential founder organisms for a line of transformed organisms can be screened for expression of the molecularly tagged fusion protein coding sequence by ribosomes in the population of cells characterized by expression of the endogenous characterizing gene.

In one embodiment, immunohistochemistry using an antibody specific for the molecular tag or a marker activated or repressed thereby is used to detect expression of the molecular tag. In another embodiment, other methods and devices are used to detect the tag, such as with the use of optics-based sorting or magnetics-based sorting.

Transformed organisms that exhibit appropriate expression (e.g., detectable expression having substantially the same expression pattern as the endogenous characterizing gene in a corresponding non-transgenic organism or anatomical region thereof, i.e., detectable expression in at least 50%, 60%, 70%, 80%, 90% or, preferably, 95% of the cells shown to express the endogenous gene by in situ hybridization) are selected as lines of transformed organisms.

BACarray Lines

In some embodiments, a collection of lines of transformed organisms that contain a selected subset of cells or a cell population expressing molecularly-tagged ribosomes is provided. In some aspects, when the transformed organism has been created utilizing BAC-related methods, this is referred to as a BACarray collection. The collection comprises at least 2 individual lines, preferably at least 5, 10, 25, 50, 100, 500, 1000, 1500, 2000, 2500, 5000, 10,000, 15,000, or 30,000 individual lines. Each individual line is selected for the collection based on the identity of the subset of cells in which the molecularly tagged ribosomes are expressed.

In one embodiment, a BACarray line related to neuronal diseases (neurodegenerative, neuropsychiatric, behavioral, etc) can be created. These include, but are not limited to BACarray lines specific for expression for cells involved in disease processes such as depression, obesity, anxiety, epilepsy, sleep, Parkinson's disease, ADHD, Huntington's disease, addiction, dementia, Alzheimer's disease, ALS, and the like. For example, see FIG. 1 for a representative BACarray collection specific to central nervous system diseases.

In one embodiment, a BACarray collection relating to sub-regions of a tissue, for example regions of the central nervous system can be created. These include, but are not limited to BACarray lines specific for expression in only striatal cells (for example expression in medium spiny neurons, striatonigral and/or striatopallidal neurons), in only cerebellar cells (for example expression in Purkinje neurons, astrocytes, Bergmann glia, granule cells, etc), in only hippocampal cells (for example, expression in CA1 neurons, CA2 neurons, CA3/4 neurons, glia, astrocytes, DG neurons), in only hypothalamic cells, in only spinal cord cells, in only pineal gland cells, and the like.

In another related embodiment, a BACarray collection relating to a particular biological function can be created. These include but are not limited to BACarray lines specific for functions related to myelination, excitatory neural transmission, motor function, migration, adhesion, infiltration, processing of noxious stimuli, processing of sensory stimuli, visual processing, auditory processing, olfactory processing, vestibular control, regulation of feeding and satiety, regulation of wakefulness and sleep, regulation of reward behavior (for example as how it relates to addictive behavior), and the like.

Analyses of mRNA Species

The embodiments described herein provide for translation profiling and molecular phenotyping of particular cells and/or tissues. mRNA complexed in polysomes with tagged ribosomal proteins are isolated and can be analyzed by any method known in the art. In one aspect, the translational profile of cells expressing the tagged ribosomal proteins can be analyzed by isolating the mRNA and constructing cDNA libraries or by labeling the RNA for gene expression analysis, for example by disposing the mRNA on a microarray.

Embodiments of this invention utilize techniques described in US 2005/0009028, which is herein incorporated in its entirety.

In one aspect, mRNA bound by the tagged ribosomal proteins may be used to produce a cDNA library and, in fact, a collection of such cell type-specific, cell-subtype specific, tissue-specific, organism-specific, disease-specific, function-specific, cDNA libraries may be generated from different populations of isolated cells. Such cDNA libraries are useful to analyze gene expression, isolate and identify cell type-specific genes, splice variants and non-coding RNAs, as well as identify co-regulated gene sets for a particular cell related to a function or a disease state. In another aspect, such cell-type specific libraries prepared from mRNA bound by, and isolated from, the tagged ribosomal proteins from treated and untreated or transgenic or otherwise manipulated cells/animals having can be used, for example in subtractive hybridization procedures, to identify genes expressed at higher or lower levels in response to a particular treatment or in a disease state as compared to untreated animals. The mRNA isolated from the tagged ribosomal proteins may also be analyzed using particular microarrays generated and analyzed by methods well known in the art. Gene expression analysis using microarray technology is well known in the art. Methods for making microarrays are taught, for example, in U.S. Pat. No. 5,700,637 by Southern, U.S. Pat. No. 5,510,270 by Fodor et al. and PCT publication WO 99/35293 by Albrecht et al., which are incorporated by reference in their entireties. By probing a microarray with various populations of mRNAs, transcribed genes in certain cell populations can be identified. Moreover, the pattern of gene expression in different cell types of cell states may be readily compared.

The mRNA bound by the tagged ribosomal proteins may be analyzed, for example by northern blot analysis, PCR, RNase protection, etc., for the presence of mRNAs encoding certain protein products and for changes in the presence or levels of these mRNAs depending on manipulation.

In yet another embodiment, specific cells or cell populations that express a potential a molecularly tagged ribosomal protein are isolated from the collection and analyzed for specific protein-protein interactions or an entire protein profile using proteomics methods known in the art, for example, chromatography, mass spectroscopy, 2D gel analysis, etc.

Other types of assays may be used to analyze the cell population expressing the molecularly tagged ribosomal protein either in vivo, in explanted or sectioned tissue or in the isolated cells, for example, to monitor the response of the cells to a certain manipulation/treatment or candidate agent (for example, a small molecule, an antibody, a hybrid antibody, an antibody fragment, a siRNA, an antisense RNA, an aptamer, a protein, or a peptide) or to compare the response of the animals, tissue or cells to expression of the target or inhibitor thereof, with animals, tissue or cells from animals not expressing the target or inhibitor thereof. The cells may be monitored, for example, but not by way of limitation, for changes in electrophysiology, physiology (for example, changes in physiological parameters of cells, such as intracellular or extracellular calcium or other ion concentration, change in pH, change in the presence or amount of second messengers, cell morphology, cell viability, indicators of apoptosis, secretion of secreted factors, cell replication, contact inhibition, etc.), morphology, etc.

In particular embodiments, the isolated mRNA is used to probe a comprehensive expression library (see, e.g., Serafini et al., U.S. Pat. No. 6,110,711, issued Aug. 29, 2000, which is incorporated by reference herein). The library may be normalized and presented in a high density array, such as a microarray.

In a particular embodiment, a subpopulation of cells expressing a molecularly tagged ribosomal protein is identified and/or gene expression analyzed using the methods of Serafini et al., WO 99/29877 entitled "Methods for defining cell types," which is hereby incorporated by reference in its entirety.

Data from such analyses may be used to generate a database of gene expression analysis for different populations of cells in the animal or in particular tissues or anatomical regions, for example, in the brain. Using such a database together with bioinformatics tools, such as hierarchical and non-hierarchical clustering analysis and principal components analysis, cells are "fingerprinted" for particular indications from healthy and disease-model animals or tissues, co-regulated gene sets for a particular function, and the like.

Applications and Considerations

1) Sensitivity

The methods provided herein are applicable to any cell, tissue, or organism as well as any disease or disorder. The sensitivity afforded by the ability to interrogate an individual cell subtype in a complex heterogeneous tissue or organ system provides a resolution than can be greater than with other techniques such as whole-tissue microarrays and in situ hybridization. In some embodiments the TRAP method of detecting one or more cell subtype-specific mRNAs/genes allows for identification of greater than 5%, 10%, 15%, 20%, 25%, 30%, 35%, 40%, 45% and even 50% of the mRNAs/genes enriched in that cell type which are not detectable by other means such as whole-tissue microarrays or in situ hybridization.

2) Diseases and Disorders

The methods provided herein are applicable to any cell, tissue, or organism as well as any disease or disorder. Several disease are cited in, but not limited to those found in the 'The Merck Manual of Diagnosis and Therapy', often called simply 'The Merck Manual' (2006). The diseases and disorders can be central nervous system disorders, peripheral nervous system disorders, and non nervous system disorders.

Examples of neurodegenerative diseases/disorders include, but are not limited to: alcoholism, Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Huntington's disease, HIV-associated dementia, Kennedy's disease, Krabbe's disease, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, and Tables *dorsalis*.

Examples of neuropsychiatric diseases/disorders include, but are not limited to: depression, bipolar disorder, mania, obsessive compulsive disease, addiction, ADHD, schizophrenia, auditory hallucinations, eating disorders, hysteria, autism spectrum disorders and personality disorders.

Examples of neurodevelopmental diseases/disorders include, but are not limited to: attention deficit hyperactivity disorder (ADHD), attention deficit disorder (ADD), schizophrenia, obsessive-compulsive disorder (OCD), mental retardation, autistic spectrum disorders (ASD), cerebral palsy, Fragile-X Syndrome, Downs Syndrome, Rett's Syndrome, Asperger's syndrome, Williams-Beuren Syndrome, childhood disintegrative disorder, articulation disorder, learning disabilities (i.e., reading or arithmetic), dyslexia, expressive language disorder and mixed receptive-expressive language disorder, verbal or performance aptitude. Diseases that can result from aberrant neurodevelopmental processes can also include, but are not limited to bi-polar disorders, anorexia, general depression, seizures, obsessive compulsive disorder (OCD), anxiety, bruixism, Angleman's syndrome, aggression, explosive outburst, self injury, post traumatic stress, conduct disorders, Tourette's disorder, stereotypic movement disorder, mood disorder, sleep apnea, restless legs syndrome, dysomnias, paranoid personality disorder, schizoid personality disorder, schizotypal personality disorder, antisocial personality disorder, borderline personality disorder, histrionic personality disorder, narcissistic personality disorder, avoidant personality disorder, dependent personality disorder, reactive attachment disorder; separation anxiety disorder; oppositional defiant disorder; dyspareunia, pyromania, kleptomania, trichotillomania, gambling, pica, neurotic disorders, alcohol-related disorders, amphetamine-related disorders, cocaine-related disorders, marijuana abuse, opioid-related disorders, phencyclidine abuse, tobacco use disorder, bulimia nervosa, delusional disorder, sexual disorders, phobias, somatization disorder, enuresis, encopresis, disorder of written expression, expressive language disorder, mental retardation, mathematics disorder, transient tic disorder, stuttering, selective mutism, Crohn's disease, ulcerative colitis, bacterial overgrowth syndrome, carbohydrate intolerance, celiac sprue, infection and infestation, intestinal lymphangiectasia, short bowel syndrome, tropical sprue, Whipple's disease, Alzheimer's disease, Parkinson's Disease, ALS, spinal muscular atrophies, and Huntington's Disease. Further examples, discussion, and information on neurodevelopmental disorders can be found, for example, through the Neurodevelopmental Disorders Branch of the National Institute of Mental Health (worldwide website address at nihm-.nih.gov/dptr/b2-nd.cfm).

3) Profiling of mRNA Species

In one embodiment, the invention provides for a method to obtain a translational profile of a cell type of interest. The method comprises expressing a tagged ribosomal protein under the control of a regulatory sequence specific to a gene expressed in the cell type of interest, isolating mRNAs complexed with the ribosomal protein from the cell, and identifying the mRNAs, thereby obtaining a translational profile for the cell type of interest.

In one exemplary embodiment the cell types of interest are striatonigral and striatopallidal cells. L10a fused to eGFP under the control of a Drd1a or a Drd2 specific regulatory sequence is expressed and translational profiles are obtained. Tables 10, 13, 17, and 18 identify genes that are translationally profiled in striatonigral and striatopallidal cells.

In another exemplary embodiment the cell type of interest are cholinergic motor neurons. Ribosomal protein L10a fused to eGFP under the control of a choline acetyl transferase (chat)-specific regulatory sequence is expressed and translational profiles are obtained. Table 19 identifies genes that are translationally profiled in cholinergic motor neurons. In this embodiment, the cholinergic motor neurons are spatially separated.

In another exemplary embodiment the cell type of interest are cerebellar neurons and glia, specifically Purkinje neurons and Bergmann glia. Ribosomal protein L10a fused to eGFP under the control of either a Pcp2 or Septin4-specific regulatory sequence is expressed and translational profiles are obtained. Table 20 identifies genes that are translationally profiled in cerebellar Purkinje neurons and Bergmann glia.

In another embodiment a gene translational profile following the manipulation of a cell, tissue or organism is obtained. The method comprises manipulating a cell, tissue or organism, using the TRAP methodology to obtain a translational profile, and comparing the profiled to a reference profile from an non-manipulated cell, tissue or organism. Manipulations include but are not limited to:
 a. Pharmacological: for example administration of a candidate agent such as a small molecule antagonist or an agonist; administration of a pharmacological agent to recapitulate a disease such as the administration of MPTP or OHDA to an animal model or cell culture to induce a Parkinson's disease-like state; or administration of a drug or substance of abuse, for example cocaine or alcohol;
 b. Genetic: for example introduction of a germline or non-germline mutation or transgene to recapitulate an animal or cellular model of a disease or disorder such as ataxia, Parkinson's disease, Alzheimer's disease, autism spectrum disorders and the like;
 c. Mechanical: for example surgical treatment; and/or
 d. Environmental: for example change of habitat, climatic change, reversal of day-nite cycles; for example induction of a chronic-mild-stress protocol, art-recognized, to recapitulate a depression-like phenotype perturbations. Examples of candidate agents are but not limited to a small molecule, an antibody, a hybrid antibody, an antibody fragment, a siRNA, an antisense RNA, an aptamer, a protein, or a peptide. In exemplary embodiments, the cell is a cell of a nervous system, such as a neuronal or glial cell, a striatal cell, a cerebellar cell, a hippocampal cell, a hypothalamic cell, a cortical cell, a dopaminergic cell, a spinal cord cell. In other embodiments the cell is a neuron such as a dopaminergic neuron or a medium spiny neuron.

In an exemplary embodiment, the effect of cocaine on the translational profile of dopaminergic striatonigral and striatopallidal cells is obtained. In related embodiments the effects of acute cocaine administration and the effects of chronic cocaine administration is obtained. In specific embodiments, the gene translation changes following acute cocaine treatment comprise those identified in Table 15. In related specific embodiments, the gene translation changes following chronic cocaine treatment comprise those identified in Table 16.

4) Disease Screening, Diagnostics, Prognostics, and Theranostics

One embodiment of this invention is to establish a translational profile and molecular phenotype for a tissue or cell type taken from a subject to be screened for, suspected of having, or presenting with a particular disease or disorder, using the methods described herein. In this aspect, markers associated with and/or indicative of a particular disease or disorder are identified. In one embodiment, in a manner similar to a biopsy, a subject's tissue can be removed for sampling. In another embodiment, a sampling of cerebrospinal fluid (CSF) will be obtained from the subject. In other embodiments, any bodily fluid can be obtained from the subject. Following the isolation of desired tissue or fluid, a molecularly tagged ribosomal protein is introduced with the regulatory elements required for a cell-type specific expression. The translational profile and molecular phenotype is established using the methods described herein. The resulting profile and phenotype is then be compared to a profile and phenotype obtained using said methods from a subject or subjects not having or presenting with the particular disease or disorder, i.e. a reference cell, tissue or subject. The results can be used for diagnostics, prognostic, or theranostic purposes in relation to a disease or disorder. The disease or disorder to be detected, diagnosed, prognosed or theranosed, can be any disease named herein, or previously undescribed diseases and disorders.

Figure 1:
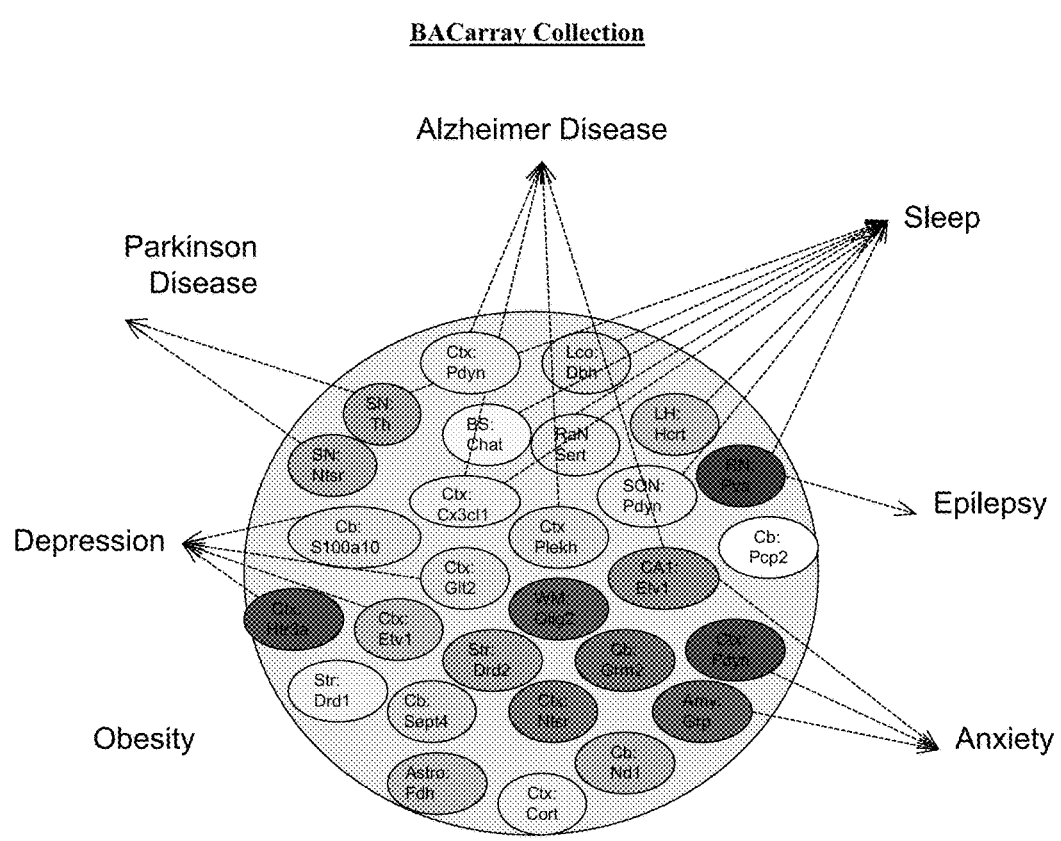
FIG. 1 illustrates a CNS disease-related BACarray collection.

In certain embodiments, BAC-mediated expression can be utilized to drive expression of a molecularly tagged ribosomal protein in a particular cell type. Several BACarrays have been created and collected that, based on expression of the endogenously regulated gene, have restricted patterns of expression that are directly relevant to several diseases or disorders (FIG. 1)

5) Screening for Modulatory Agents

Another embodiment of this invention is to screen for candidate agents for modulation of a desired modulatory (antagonistic, agonistic, synergistic modulation) activity. In certain embodiments a vehicle or candidate agent is administered in a single or repeated dose to either a cell type or a subject. Following administration a translational profile is established for the cell type of interest based on the methods disclosed herein. The profile and phenotypes from those dosed with candidate agent are compared and related to the profile and phenotype from those dosed with a vehicle (i.e. reference sample). A determination is made whether a candidate agent modulates translation and phenotype of one or more mRNA isolated from the cell type of interest, thereby screening said candidate agent for translational modulation. In some embodiments the candidate agent may be a candidate therapeutic agent or drug. In other embodiments, the candidate agent may be a toxin. In some embodiments the candidate agent may be but is not limited to a small molecule, an antibody, hybrid antibody or antibody fragment, a siRNA, an antisense RNA, an aptamer, a protein therapeutic, or a peptide.

6) Therapeutic Target Screening and Selection

Another aspect of this invention is to identify candidate therapeutic targets for a disease or disorder. In certain embodiments this would entail transforming a cell or creating an organism expressing a molecularly tagged ribosomal protein and exposing the cell or organism to a perturbation or stimulus, mRNA transcripts selectively down regulated or up regulated would be potential targets for ameliorating the perturbation. In other embodiments, a translational profile from a cell from a subject with a disease or disorder, a cell that has been perturbed, etc will be compared to an otherwise normal or unperturbed cell. The differential translational profile will allow for identification of potential therapeutic targets, In one embodiment, any mRNA found to be upregulated in a cell type of interest associated with a disease or disorder, for example in but not limited to a striatal, hippocampal, cortical, cerebellar, spinal cord, hypothalamic, pineal, retinal, auditory, olfactory, vestibular, or brain stem cell may represent a target for antagonism. That is, the protein encoded by the identified mRNA would be a therapeutic target for which antagonists could be developed. In one exemplary embodiment, the target of interest is Gpr6. Gpr6 represents a target for which antagonists can be screened for and developed as a therapeutic for Parkinson's disease, due to its overexpression.

In a similar manner, an mRNA found to be downregulated in a cell type of interest associated with a disease or disorder, as above, could represent a target for agonism. That is, the protein encoded by the identified mRNA would be a therapeutic target for which agonists could be developed.

7) Personalized Medicine

In one embodiment, a method is provided for assessing whether a subject in need thereof is amenable to a therapeutic agent, comprising determining a translational profile for a cell type, cell sub-type or tissue from the subject, determining if the translational profile is predictive of treatment with one or more therapeutic agents, and identifying the one or more therapeutic agents to administer to the subject.

In another embodiment, a method is provided for screening one or more therapeutic agents in a subject in need thereof comprising, administering one or more therapeutic agents to a subject, determining a translational profile for a cell type, cell sub-type or tissue from the subject, comparing the translational profile obtained to one or more reference profiles that indicate a positive or negative prognosis, and determining the treatment should continue or be modified based on the comparison. In a further embodiment, it is determined that a different treatment modality (e.g., different therapeutic agent should be administered, such as for example, a second line drug, that is shown to be amenable to the translational profile observed for a first line drug).

8) Co-regulated Gene Sets

In one embodiment, a method to identify a co-regulated gene set for a known function or a candidate function for a novel gene is provided. The method comprises determining the translational profiles for a plurality of cell types that express a gene associated with a specific function, comparing the translational profiles to determine what additional genes are similarly regulated thereby identifying a co-regulated gene set involved in the function.

In further embodiments the function can be a cellular function or a cellular process. In other related embodiments the method is applied to determine a co-regulated gene set involved in myelination, excitatory neural transmission, motor function, cellular migration, cellular adhesion, cellular infiltration, processing of noxious stimuli, processing of sensory stimuli, visual processing, auditory processing, olfactory processing, vestibular control, regulation of feeding and satiety, regulation of wakefulness and sleep, or the regulation of reward behavior.

In one exemplary embodiment, the method is applied to determine a co-regulated gene set involved in myelination comprising determining the translation profiles for a plurality of cells that express the myelin basic protein (Mbp). In a related embodiment the gene set comprises one or more of the genes listed in Table 9.

This method can be useful in identifying gene sets for known functions or candidate functions for novel gene products, since in many cases the cohorts of co-regulated genes can include genes with well known functions Kits In a further aspect, the present invention provides kits. In certain embodiments the kit contains reagents for determining the presence, absence, and/or differential presence, of one or more markers indicative of a disease, disorder, and/or pharmacologic, genetic, or environmental manipulation. The disease could be, but is not limited to a neurodegenerative, neuropsychiatric, neurodevelopmental disorder in a sample from an individual suspected of having a susceptibility to such a disease or disorder. In another embodiment, the disease or disorder is a proliferative disease such as a cancer. In other embodiments the kit is utilized to identify co-regulated gene sets for a particular biological function. Biological functions are described herein.

In one embodiment, the kit contains a customized set of clones, vectors, molecular tags from which to choose, for molecular labeling and materials such as CDs, instructions for use, and other reference guides that would allow the individual to choose the correct clone/vector for the cell type, tissue, molecular pathway, or circuit of choice. In another embodiment the kit contains a recombinant vector encoding a nucleic acid sequence which encodes a ribosomal protein and a detectable tag operably linked to a regulatory region. In particular embodiments, the kit can contain a customized BACarray clone collection relevant for a particular disease or disorder.

In one embodiment a kit includes a recombinant vector engineered to express a nucleic acid sequence encoding a ribosomal protein and a detectable tag operably linked to a regulatory region containing sequences endogenous to a genomic locus of a gene of interest. In a related embodiment the ribosomal protein is fused in-frame to a detectable tag. In certain embodiments, the recombinant vector is a BAC. The gene of interested can be selected from but is not limited to one that expresses in a striatal cell, cerebellar cell, cortical cell, hypothalamic cell, hippocampal cell, brainstem cell, and a spinal cord cell. In exemplary embodiments the tag is eGFP and the ribosomal protein is L10a.

EXAMPLES

The methodology reported here provides an enabling technology for translational profiling and molecular phenotyping. Examples allow for defining the distinguishing molecular characteristics of closely related or critical cell types. Examples also demonstrate that methods described herein can be employed to analyze physiological adaptations of specific cell types in vitro, in vivo, ex vivo, or in situ.

In various embodiments, compositions and methods feature methodology, which readily and reproducibly identify translated mRNAs in any cell type or tissue of interest. This methodology involves expression of a molecularly tagged ribosomal transgene, which enables tagging of polysomes for isolation, purification and identification of mRNA, in specific populations. In some embodiments, this can be achieved using Bacterial Artificial Chromosome (BAC) transgenic mice, allowing translational profiling and molecular phenotyping from whole animals.

The following examples are offered to illustrate, but not to limit the claimed invention. Some embodiments of the present invention have been shown and described herein, but it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Example 1

Molecular Tagging of a Ribosomal Proteins mRNAs translated into protein are at one point usually attached to a ribosome or a polyribosome complex (polysomes). Any tag, not limited to those named herein, fused to a ribosomal protein allows for isolation of bound mRNAS. eGFP fused to the N-terminus of the large subunit ribosomal protein L10a, hereafter eGFP-L10a, was utilized in this and ensuing examples, but is by no ways limiting to the tens, hundreds, thousands, or even more tag-protein combinations that can be utilized.

FIG. 2: (a) A schematic is presented to illustrate affinity purification of eGFP-tagged Polysomes (originating from the target cell population) using anti-GFP antibody-coated beads (Schematic in a). Fusions of Enhanced Green Fluorescent Protein (eGFP) with ribosomal proteins were screened for efficient incorporation into polysomes to provide a tag for all translated cellular mRNAs. (b): A BAC carrying the eGFP-L10a fusion protein was transfected into HEK293T cells. The eGFP-L10a fusion protein's nucleolar and cytoplasmic localization was consistent with incorporation into intact ribosomes and immuno-electron microscopy data demonstrated its presence on polysome complexes. The figure displays transmission electron micrographs of anti-GFP coated magnetic beads after incubation with extracts taken from HEK293T cells transfected with an empty vector (left panel) or the eGFP-L1010a construct (right panel); images acquired at 50,000× magnification, inserts enlarged by a factor of 2.3×.

There was no gross alteration in cell physiology or growth rate was evident in eGFP-L10a transfected cells, as seen by fluorescence microscopy of eGFP-L10a expression in cells. HEK293T cells grown on coverslips were transiently transfected, grown for two days, fixed with paraformaldehyde, and mounted with media containing 4',6-diamidino-2phenylindo (DAPI) to stain DNA.

Example 2

Isolation, Purification and Analysis of Ribosome-mRNA Complexes In Vitro

Rapid immunoaffinity purification of polysomes was achieved from HEK293T cells transiently transfected with the eGFP-L10a transgene but not mock transfected cells. HEK293T cells transfected with eGFP-L1010a were homogenized in lysis buffer. The solubilized and clarified lysate was loaded onto a linear density (20-50% w/w) gradient of sucrose and centrifuged for 2 hours at 4° C. using a Beckman SW41 rotor at 40,000 r. p. m. (200, 000×g). 750 µl fractions were collected as absorbance at 254 nm was monitored with an ISCO UA-6 UV detector.

Immunoaffinity purification of polysomes from transfected cell cultures (in which approximately 30% of cells expressed eGFP-L10a) gave an approximate 10% overall co-purification of untagged ribosomal proteins and ribosomal RNA, and led to the recovery of only translated mRNAs (Table 3).

TABLE 3

Total RNA yields from cultured cell BACarray purifications. HEK293T cells were transiently transfected with eGFP (mock transfection) or eGFP-L10a constructs. Transfection efficiency was approximately 30%. Plates of different sizes were used to grow mock or eGFP-L10a-transfected cells, which is reflected in different input RNA amounts. Input and immunoprecipitated (bound) RNA were purified and the quantity and purity of RNA were determined using a Bioanalyzer 2100 (Agilent Technologies).

| Transfection | Total RNA Bound (ng) | Total RNA Input (ng) | Yield (%) |
|---|---|---|---|
| eGFP (Mock) | 61 | 33,320 | 0.2 |
| eGFP-L10a | 6,117 | 56,630 | 10.8 |

Figure 3:
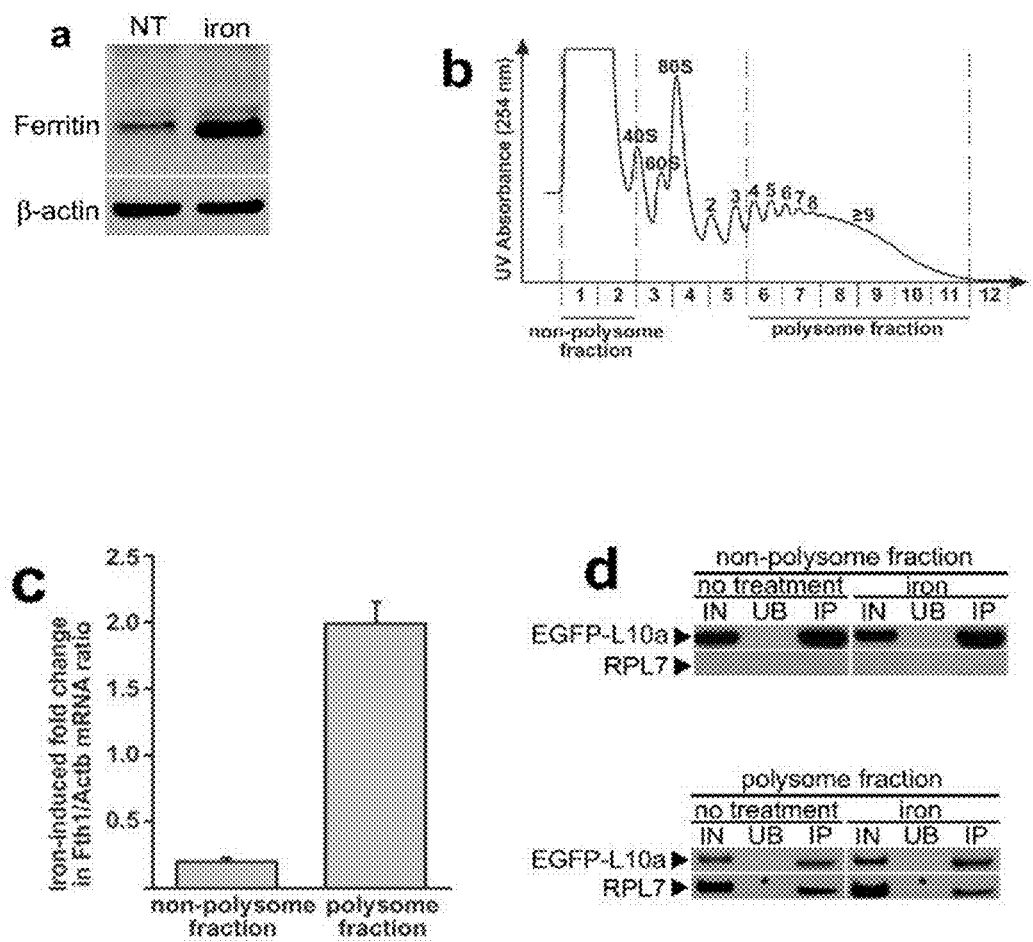
FIG. 3 illustrates immunoprecipitation of translated mRNAs from transfected cells.
Figure 3:
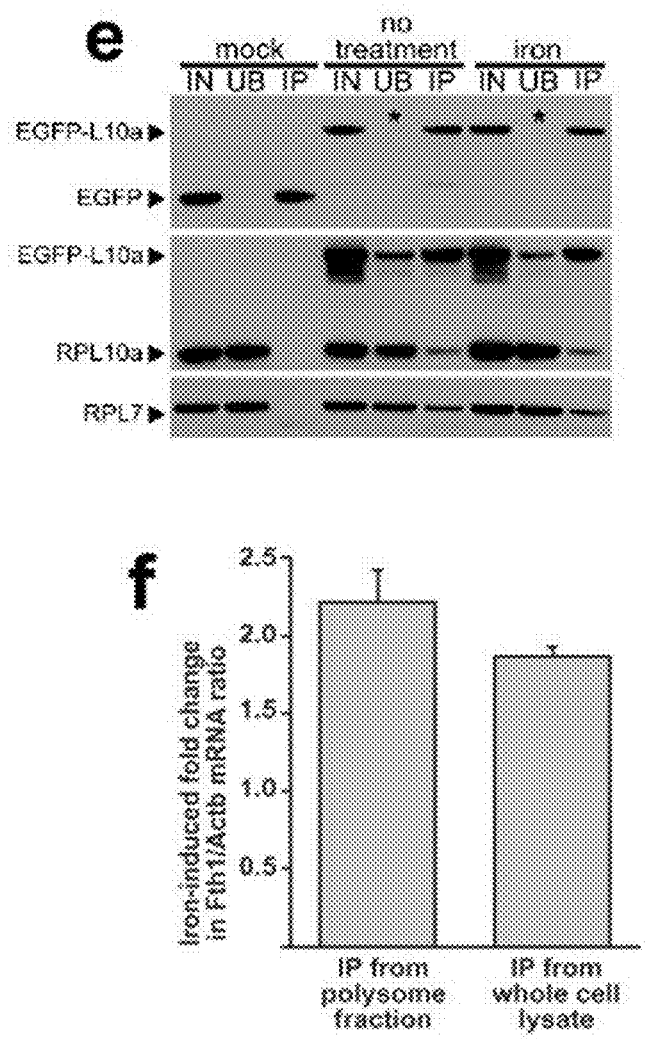

FIG. 3 displays immunoprecipitation of translated mRNAs from transfected cells. HEK293T cells were transiently transfected (~30% efficiency) with eGFP (mock) or eGFP-L10a constructs and grown in medium alone (no treatment, NT) or in medium supplemented with 100 μg/ml ferric ammonium citrate [pH 7.0](iron) for 36 hours. (a) Induction of the iron-storage protein Ferritin was seen after 36 hours of iron treatment. (b) The post-mitochondrial supernatants of untreated or iron-treated cells were loaded onto linear sucrose gradients (20-50% w/w). After velocity sedimentation, fractions (direction of sedimentation noted by arrow) were collected while UV absorbance (254 nm) was being measured. A representative trace is shown, as profiles from non-treated and iron-treated lysates looked nearly identical. Non-polysome and polysome gradient fractions were generated as indicated. To avoid Ferritin mRNAs associated with mRNPs, only heavier polysomes (with greater than 4 ribosomes) were included in the polysome fraction. (c) After iron treatment, as expected, a shift of Ferritin heavy chain mRNA (Fth1) out of non-polysome fractions into polysome fractions was observed, as determined by reverse transcription followed by quantitative PCR of total RNA purified from non-polysome and polysome gradient fractions (range of fold-change in non-polysome fraction: 0.16-0.22; range of fold-change in polysome fraction: 1.83-2.15). (d) Immunoprecipitations were performed from non-polysome or polysome gradient fractions and 0.2% of the Input (IN), 0.02% of the unbound (UB), and 1% of the bound (IP) samples were loaded onto gels for immunoblot analysis with eGFP or Rpl7 antibodies; * indicates the presence of a weak Rpl7 band upon much longer exposure. eGFP-L10a was recovered equally well from non-polysome and polysome fractions with or without iron treatment. Rpl7 was recovered equally well from untreated or iron-treated polysome fractions. Rpl7 was not present in the non-polysome fraction, presumably because, unlike the overexpressed eGFP-Rpl10a, it was all incorporated into polysomes. As expected from the lack of Rpl7 (and thus assembled ribosomes) in the non-polysome fraction, immunoprecipitations from non-polysome fractions did not pull down any RNA above background, indicating that the immunoprecipitation was specific to translated messages. (e) To determine if the translating ribosome affinity purification (TRAP) methodology could faithfully reflect the changes observed in c, a direct eGFP immunoprecipitation of post-mitochondrial supernatants (whole cell lysates, unfractionated) was performed. 0.5% of input (IN), 0.5% of the unbound fraction (UB), and 1.0% of the bound (IP) samples were loaded onto gels for immunoblot analysis with eGFP (top), Rpl10a (middle), or Rpl7 (bottom) antibodies. eGFP-L10a was recovered equally well from untreated and iron-treated samples, as was all eGFP from mock samples; * indicates the presence of a light eGFP-L10a band upon longer exposure. No endogenous Rpl10a or Rpl7 was recovered in the bound (IP) fraction of mock samples, while endogenous Rpl10a and Rpl7 were both recovered in the bound (IP) fraction of untreated and iron-treated samples. The reduced recovery of endogenous Rpl10a versus endogenous Rpl7 in the immunoprecipitation likely reflects competition between endogenous Rpl10a and eGFP-L10a for incorporation into ribosomes. (f) The iron-induced fold-change in Fth1 mRNA levels relative to Actb mRNA levels in samples immunoprecipitated (IP) from either polysomes or from whole cell lysates (range of fold-change in polysome IP samples: 2.01-2.43; range of fold-change in direct IP samples: 1.80-1.93) was similar to the change observed in the polysome gradient fraction before immunoprecipitation (c).

Methods

Standard methods for immunoblotting were used. Antibodies were used as follows: GFP detection: JL-8, Clontech (Mountain View, Calif.), 1:2,000 in 5% non-fat milk/PBST (phosphate buffered saline-0.05% Tween-20; Rpl7 detection: NB200-308, Novus Biologicals (Littleton, Colo.), 1:2,000 in 5% IgG-free bovine serum albumin/PBS-T; Rpl10a detection: H00004736-M01, Abnova Corporation (Taipei City, Taiwan), 1:2,000 in 5% IgG-free bovine serum albumin/PBS-T; Ferritin detection: 65077, MP Biomedicals (Solon, Ohio), 1:1,500 in 0.2% I-block (Applied Biosystems, Foster City, Calif.)/PBS-T; β-Actin detection: Ab8224, Abcam (Cambridge, Mass.), 1:2,500 in 5% nonfat milk/PBS-T.

Example 3

Characterization and Analysis of BACarray Transgenic Mice

1) Overview

Comparative analysis of BACarray data can provide important mechanistic insights into complex biological systems. BACarray translational profiling permits comprehensive studies of translated mRNAs in genetically defined cell populations, and their responses to physiological perturbations. To establish the generality of this approach, BACarray translational profiles for twenty four distinct and diverse CNS cell populations are presented here. Identification of cell-specific and enriched transcripts, previously not identified in whole tissue microarray studies are provided as examples to illustrate the added value of comparative analysis of these large datasets. The BAC transgenic strategy has been applied (Heintz, 2004; Yang et al., 1997) to provide high resolution anatomical data and BAC vectors for the design of genetic studies of specific, morphologically defined cells in the CNS (Gong et al., 2003) (www.gensat.org). Heiman et al. have reported the development of the BACarray translational profiling methodology for use in discovery of the complement of proteins synthesized in any genetically defined cell population. Here, the methodology is used to generate BACarray transgenic mice for a wide variety of anatomically and genetically defined cell types in the mammalian brain. In some embodiments, such a collection can provide a resource that will allow detailed molecular phenotyping of CNS cell types at specified developmental stages, and in response to a wide variety of pharmacological, genetic or behavioral alterations. The mice and data presented confirm the generality of the BACarray approach and provide a resource for studies of the molecular bases for cellular diversity in the mammalian brain.

The generation of BACarray translational profiles of specific CNS cell types requires targeting of the eGFP-L10a ribosomal protein fusion to desired CNS cell types, affinity purification of polysomal RNAs from these cell types, and interrogation of the resultant mRNA populations using massively parallel analytical techniques. To provide a resource for comparative analysis of diverse CNS cell types, described in this examples is: the application of this strategy to generate and characterize further BACarray transgenic lines, to isolate and characterize mRNA populations from twenty four cell types targeted in these lines, to analyze these data relative to one another, and to archive and present the BACarray transgenic lines and their associated anatomic and microarray data.

2) Selection of Drivers to Target Specific CNS Cell Types

To confirm the general applicability of the translating ribosome affinity purification (TRAP) methodology, and to obtain initial data concerning the depth of information one can obtain with this approach across multiple cell types, BACs reported by the Gene Expression Nervous System Atlas (GENSAT) Project (Gong et al, 2003; S. Falcon, R. Gentleman, Bioinformatics 23, 257-8 (2007); both incorporated in their entirety) were chosen to specifically target a wide range of neurons and glia from different structures throughout the CNS.

3) BACarray Mice

Figure 4:
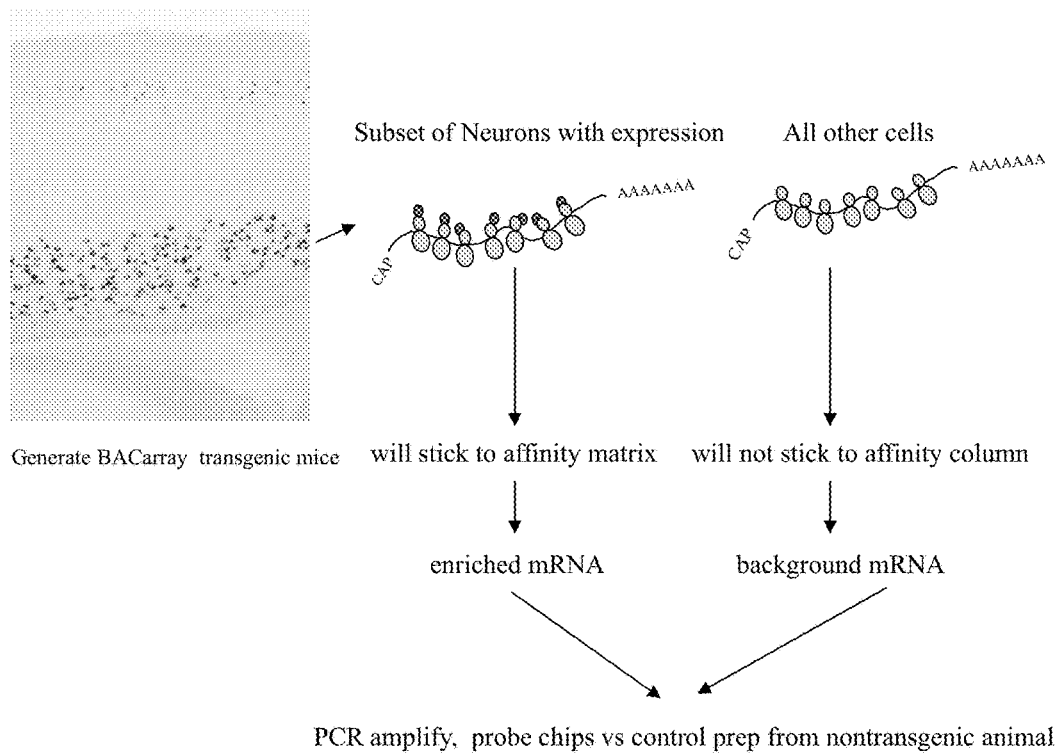
FIG. 4 illustrates the in vivo BACarray strategy.
Figure 5:
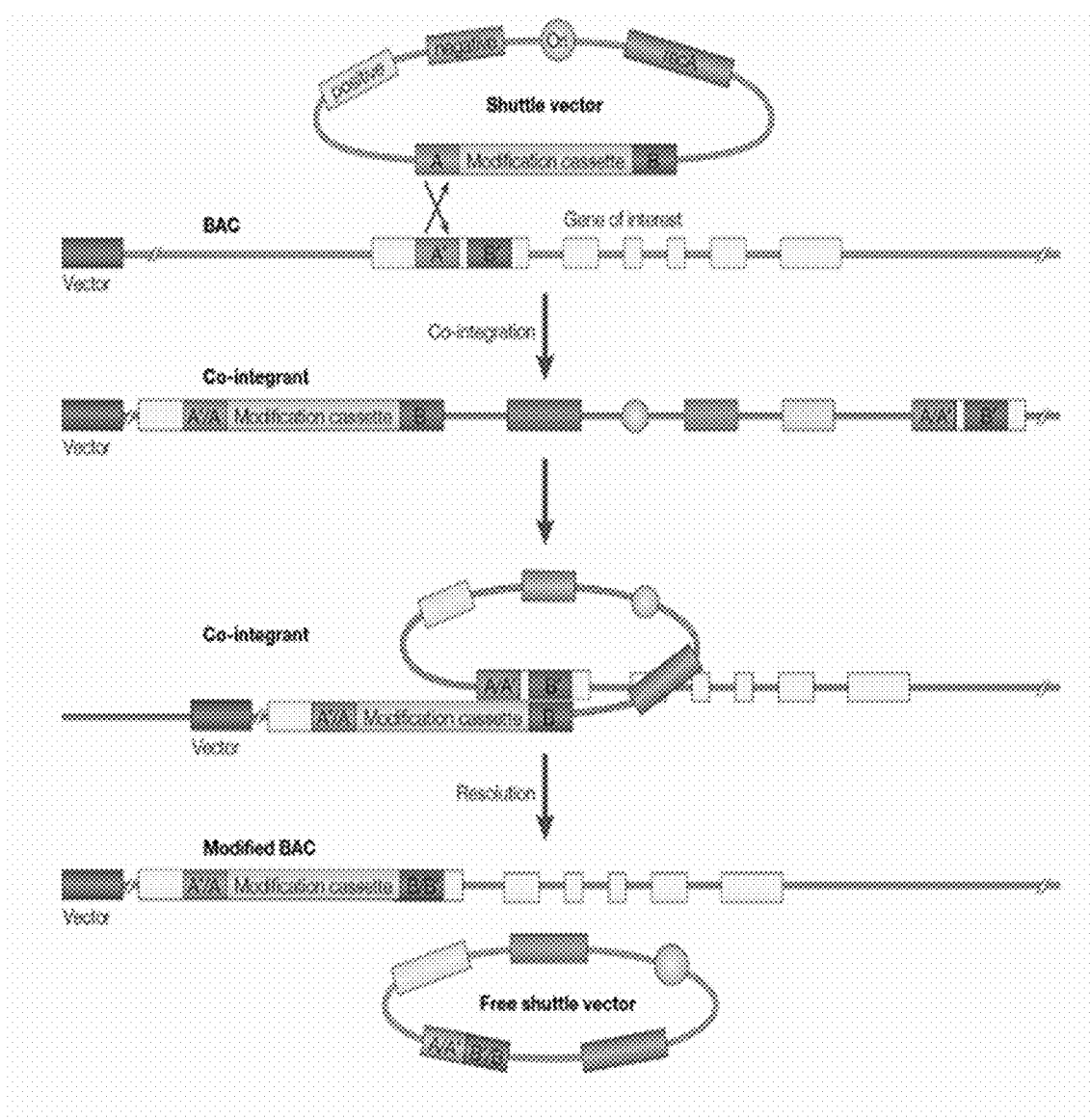
FIG. 5 illustrates BAC vector engineering.
Figure 6:
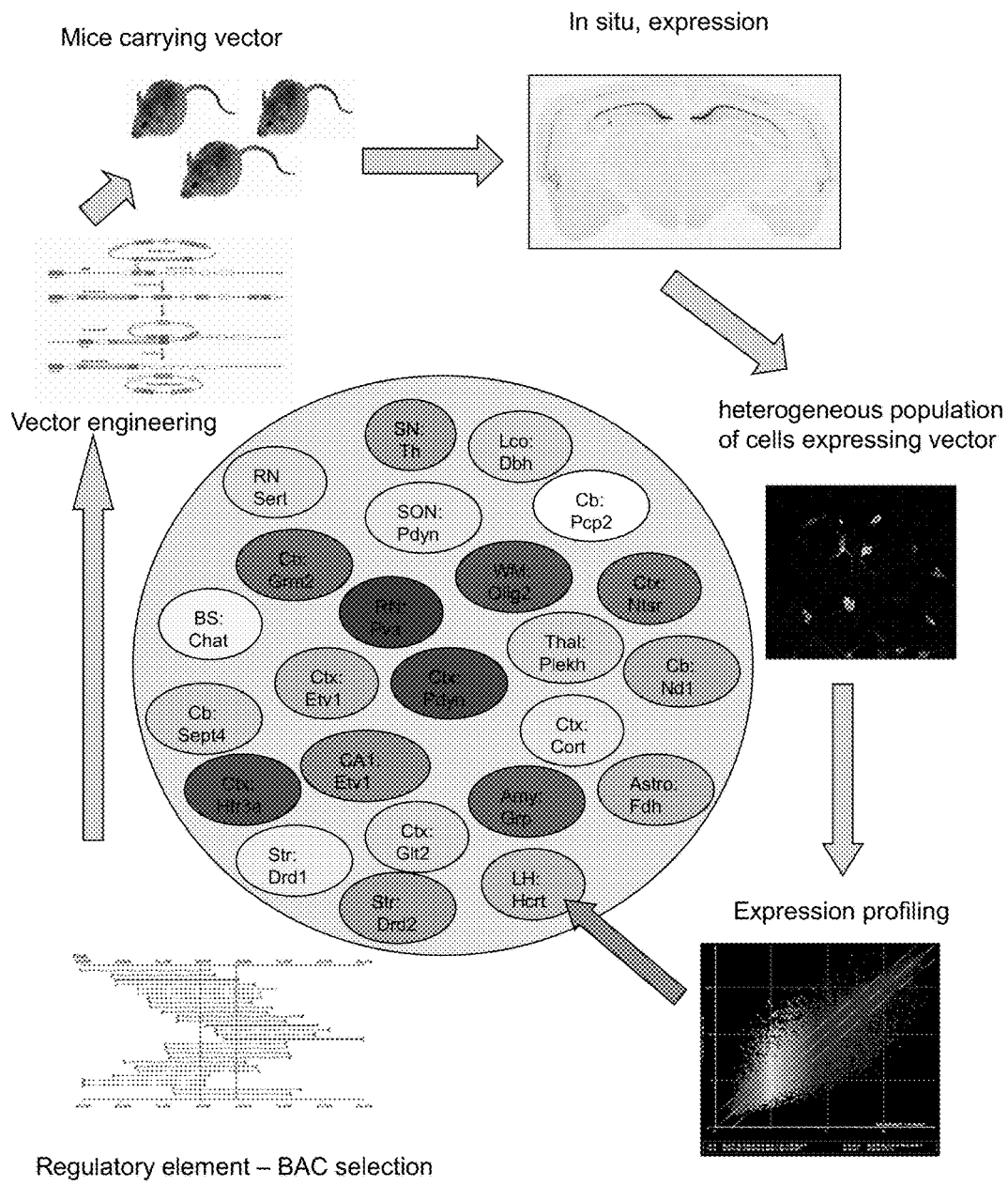
FIG. 6 illustrates BACarray mouse generation.
Figure 7:
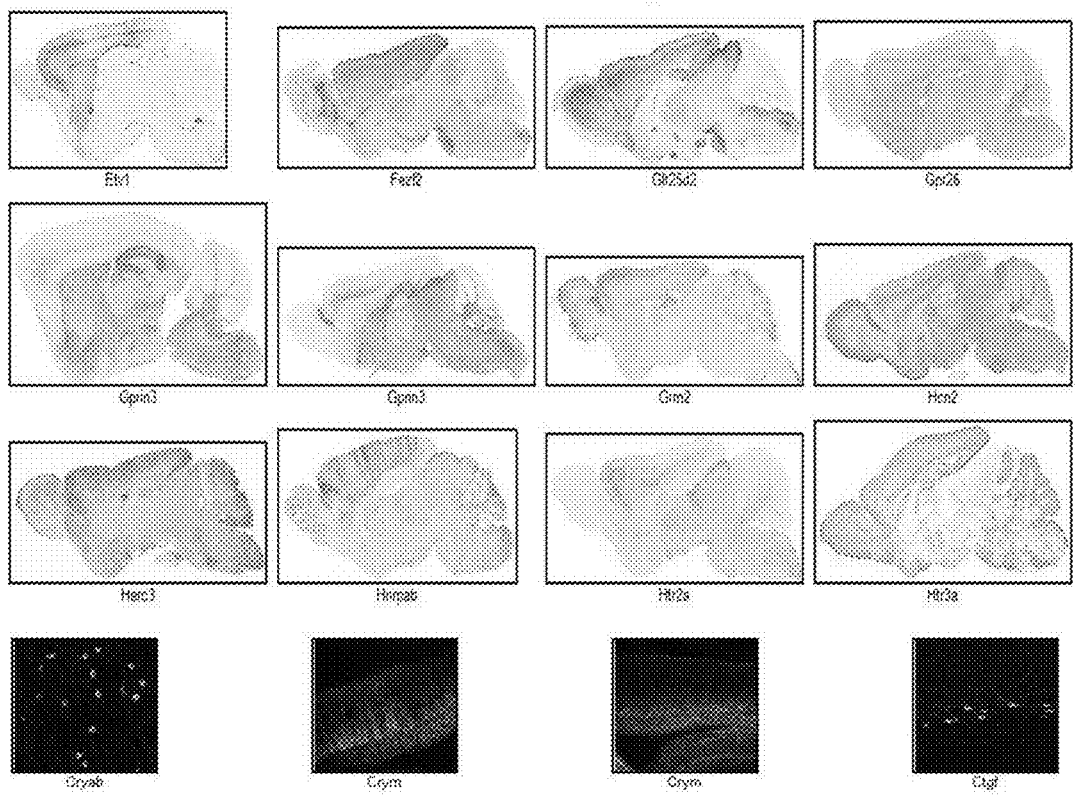
FIG. 7 illustrates examples of drivers used to produce BACarray mice with specific expression in the cerebral cortex.
Figure 8:
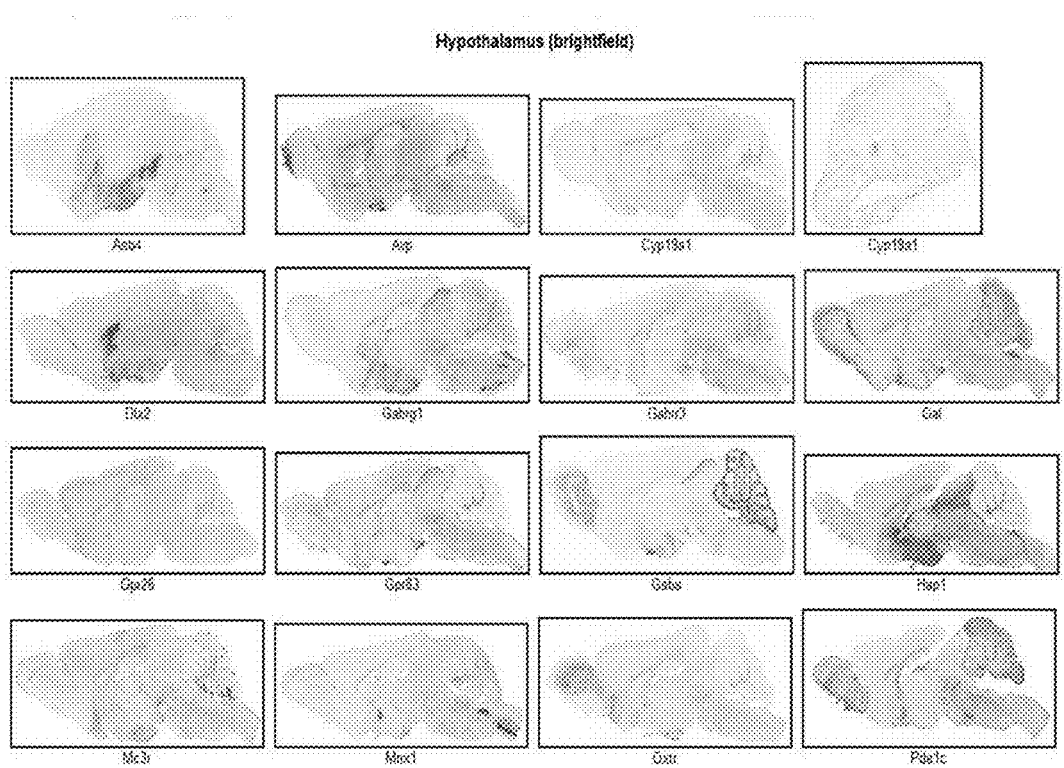
FIG. 8 illustrates examples of drivers used to produce BACarray mice with specific expression in the hypothalamus.

To genetically target expression of the eGFP-L10a fusion protein to defined CNS cell populations in vivo, BAC transgenic mice were created (FIG. 4 represents the BACarray strategy; FIGS. 5 and 6 represent engineering of BAC vectors and the creation of mice carrying BACs). To tag mRNAs in specific cell types of the mouse, cell specific cis and trans regulatory elements and known transcriptional units were utilized as described herein and in (Gong et al. Nature Vol 425, 2003). Mouse lines with specific expression in different subsets of cells in the cerebral cortex (FIG. 7) or hypothalamus (FIG. 8) from BAC array lines are presented by way of example. Detailed anatomic characterization of selected BACarray transgenic mouse lines is presented below.

4) Anatomic Characterization of BACarray Transgenic Mouse Lines

Figure 9:
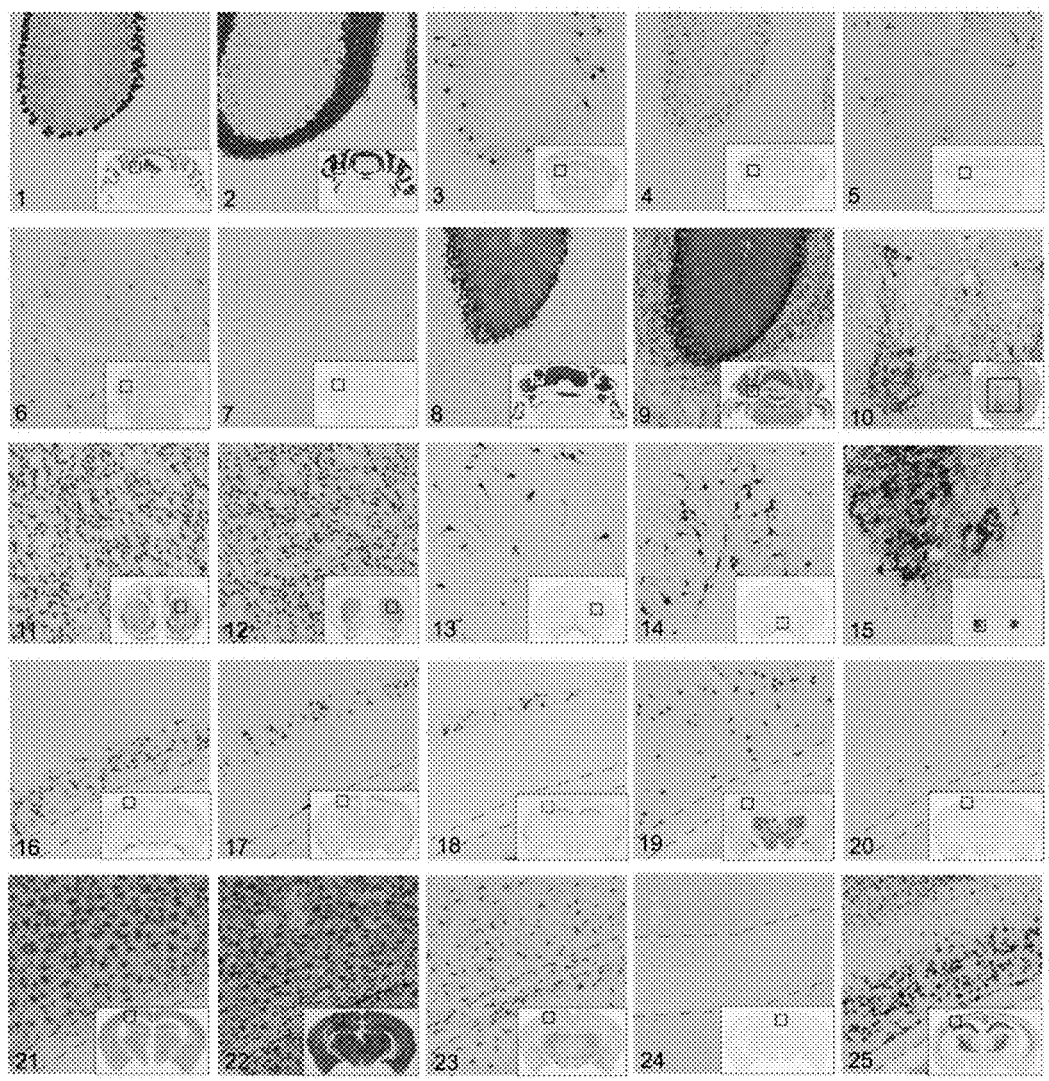
FIG. 9 Panels 1-25 illustrates that BAC transgenesis targets eGFP-L10a to specific CNS cell populations. DAB immunohistochemistry with anti-eGFP antibody on each mouse line reveals a unique and specific pattern of expression for the eGFP-L10a transgene. Panels (10×) show the morphology and localization of cell types expressing the transgene, while inset shows location of panel, for cerebellar (1-9), spinal cord (10), striatal/basal forebrain (11-14) brainstem (15), and cortical (16-25) cell types. Dashed lines (panels 16-25) indicate corpus callosum. A key for all cell types is in FIG. 11A.

Detailed anatomic studies were conducted for BACarray transgenic mouse lines as displayed in FIG. 9. For each line, transgene expression was assayed by immunohistochemistry (IHC) using an antibody against eGFP. IHC data from serial coronal sections of the whole brain were collected, scanned at high resolution and mounted for inspection. All sections were processed equivalently (Neuroscience Associates) so that apparent differences in staining intensity accurately reflect differences in transgene expression level. The figure shows thumbnail images for each of the 24 cell populations selected for microarray analysis, and high resolution data to illustrate the morphology evident from IHC analysis of eGFPL10a expression. The regions covered in this characterization include the cerebellum (panels 1-9), the spinal cord (10), the basal forebrain and corpus striatum (11-14), the brainstem (15), and cerebral cortex (16-25).

For well characterized cell types, anatomic confirmation of the cells targeted for BACarray analysis was facilitated. For example, given the well described cytoarchitecture of the cerebellum, BACarray lines for Purkinje cells (Pcp2, panel 1), granule cells (Neurod1, panel 2), Golgi neurons (Grm2, panel 3), unipolar brush cells (Grp, panel 5), Bergmann glia (Sept4, panel 8), and astrocytes (Aldh1l1, panel 9) were easily identified from the IHC data presented. Purkinje cells can be recognized in the eGFP-L10a IHC data by their large cell bodies and molecular layer dendrites, granule cells by their small size, dense packing, and location in the granule layer, and Bergmann glial cells by their morphology, radial projections, and close proximity to Purkinje cells. IHC analysis of eGFP-L10a fusion proteins in these well known cell types using these regulatory regions allow for identification of well known and previously unknown cell types. The expression of the eGFP-L10a transgene from each BAC driver is regionally correct, conforming both to the literature and to the expectation given the anatomic data presented in GENSTAT and for these cell types the distribution of the eGFPL10a fusion protein, while more limited than that of soluble eGFP, is sufficient to provide enough anatomic detail to unambiguously identify these well described CNS cell types.

Many BACarray lines, the eGFP-L10a fusion protein is detected in multiple structures within the brain. An example is the characterization of fusion protein IHC in cholinergic cell populations targeted in the Chat BACarray lines. In this case expression is clear in brainstem motor neurons, spinal cord motor neurons, neurons of the corpus striatum, basal forebrain projection neurons, and neurons of the medial habenula. As detailed below, BACarray translational profiles for four of these cholinergic cell populations were collected by separately dissecting the spinal cord, brainstem, corpus striatum and basal forebrain prior to affinity purification of the eGFPL10a tagged polysome populations. Since specifically expressed genes are often found in distinct cell types in physically separable brain structures, several lines offer opportunities for analysis of many cell types not included in this example. Thus, the eGFP-L10a fusion protein is abundant in hippocampal CA1 cells in the Cck BACarray line, allowing translational profiling of mRNAs expressed in this cell type (panel 25). Creation of a BACarray anatomic database allows the user to browse through serial brain sections for each of the lines presented here to determine whether a cell type of interest can be analyzed in one of the BACarray lines presented in this example.

Figure 10:
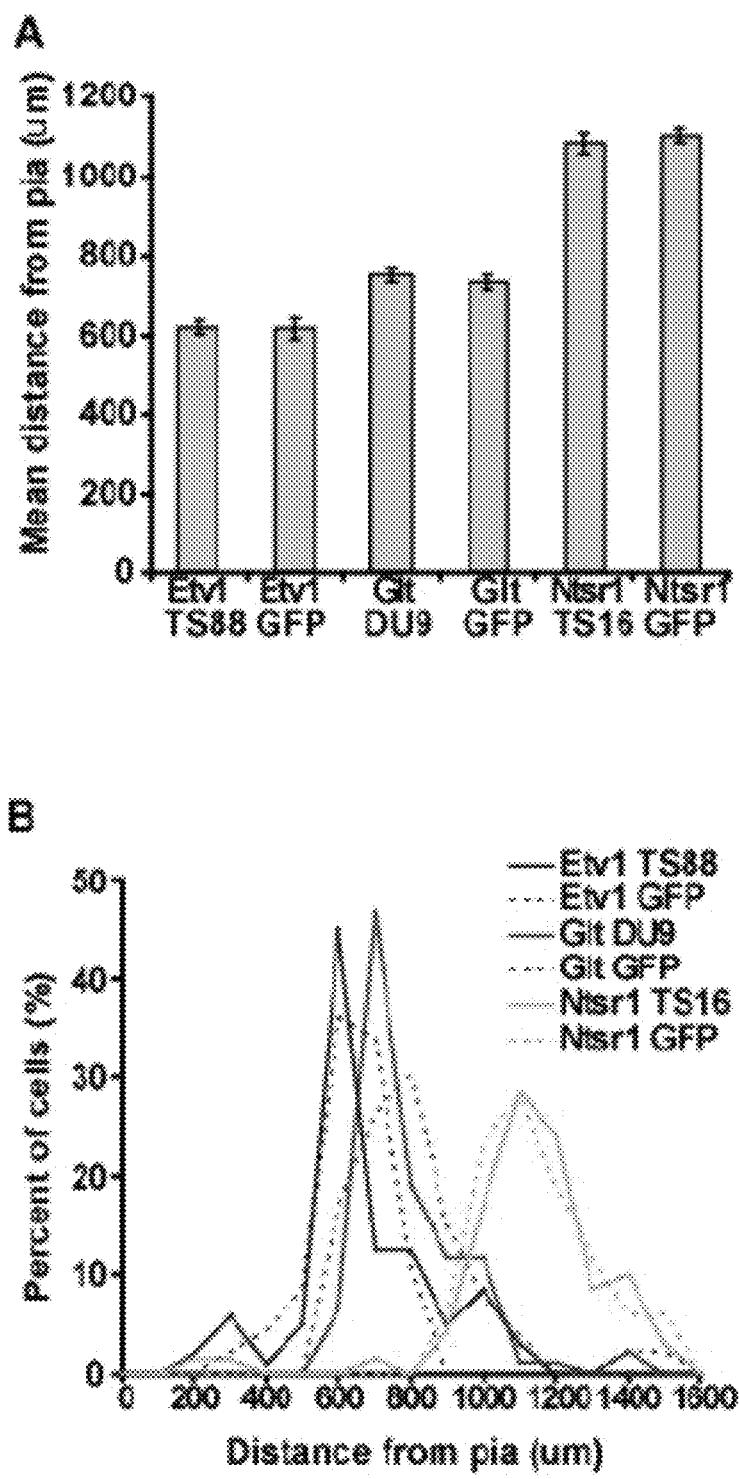
FIG. 10 illustrates that GENSTAT eGFP and BACarray cortical pyramidal cell lines have same laminar distribution. A) Graph (mean+/−SE) of the distance of eGFP+ cell somas from the pial surface for the BACarray and GENSAT eGFP lines for each pyramidal cell BAC driver. The depth of the cells was consistent between both lines for each driver. B) The percentage of cells in 100 micron bins is shown as a histogram of the distribution of cell depths for each line in A. The BACarray line and eGFP line for each driver had overlapping distributions of cell depths.

The figure also shows that projection neurons in the cerebrum can be identified by their pyramidal shape, and broadly classified by their laminar specificity, dendritic arbor, and axonal targets. Lines which clearly label the large pyramidal cells of layers 6 (Ntsr1, panel 16), 5b (Glt25d2, panel 17), and 5a (Etv1, panel 18) have also been reproduced. Morphometric studies provide additional data indicating that the GENSAT eGFP lines and eGFP-L10a BACarray lines target similar cortical pyramidal cell populations FIG. 10 shows that BACarray cortical pyramidal cells have the same laminar distribution as eGFP GENSAT lines. The figure shows: A) Graph (mean+/−SE) of the distance of eGFP+ cell somas from the pial surface for the BACarray and GENSAT eGFP lines for each pyramidal cell BAC driver. The depth of the cells was consistent between both lines for each driver. B) The percentage of cells in 100 micron bins is shown as a histogram of the distribution of cell depths for each line in A. The BACarray line and eGFP line for each driver had overlapping distributions of cell depths.

Figure 11:
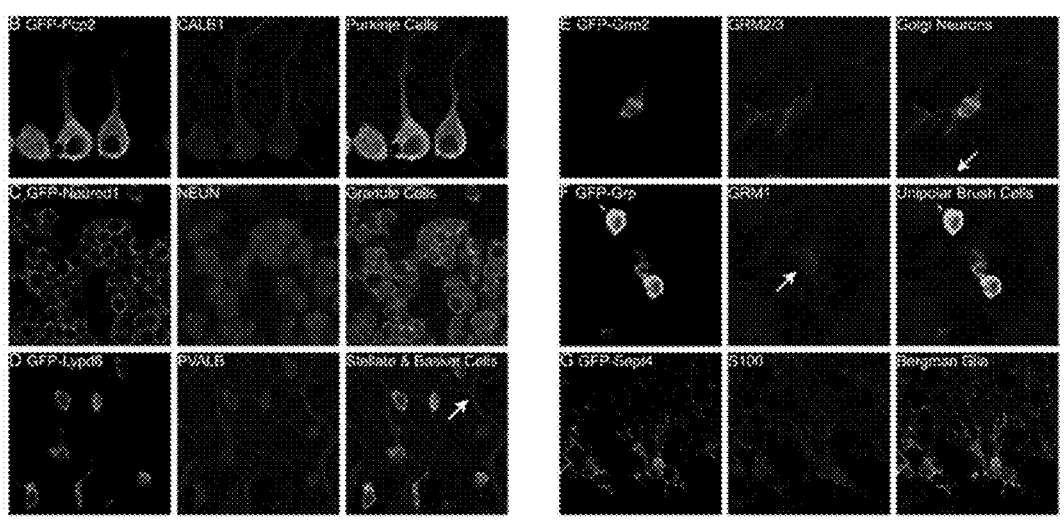
FIG. 11 illustrates a summary of cell types studied and characterization of lines. A) Table of all cell populations studied with BACarray, corresponding to FIG. 9. B) Detection of eGFP-L10a under the control of a Pcp2 BAC in Calbindin positive Purkinje cells. C) Detection of eGFP-L10a under the control of a Neurod1 BAC in granule cells with NeuN positive nuclei. D) Detection of eGFPL10a under the control of a Lypd6 BAC in Parvalbumin positive outer stellate and deep stellate (basket) neurons of the molecular layer, but not in Parvalbumin positive Purkinje cell fibers (arrow). E) Detection of eGFP-L10a under the control of a Grm2 BAC in Grm2/3 positive interneurons (Golgi cells) of the granule cell layer, but not in Grm2/3 positive glomeruli (arrow). F) eGFP-L10a detected under the control of a Grp BAC in unipolar brush cells with Grm1 positive brushes (arrow). G) eGFP-L10a detected under the control of a Sept4 BAC in s100 positive Bergman glia.

FIG. 11 shows that in many BACarray lines, the presumed cellular identity of the targeted lines was confirmed using double immunofluorescence for the eGFP-L10a fusion protein and well characterized cell type specific markers. In some cases, the cell type specific markers corresponded with the BAC drivers chosen for modification (Olig2, Aldh1l1, Grm2, Chat). In other cases, commonly used markers which have been well characterized for specific cell types were used, as seen in panel B. In most cases, these studies established that BAC drivers limited expression to well-defined cell populations. There were also several BACarray lines in which the transgene is expressed in two or more cell types. For example, the immunofluorescence (IF) analysis of the Lypd6 BACarray line revealed that eGFP-L10a is found in all Pvalb positive and NeuN negative interneurons of the cerebellar molecular layer, suggesting that this line is valuable for analyses of both stellate and basket cells. Finally, in certain lines it is apparent that the eGFP-L10a transgene is expressed in a only a subset of a particular cell type. For instance, as seen in panel B, in the Grp BACarray line the eGFP-L10a fusion protein is restricted to the subpopulation of unipolar brush cells (Nunzi et al., 2002) which are immunoreactive for Grm1 but not Calb2 (calretinin).

BACarray lines whose expression did not conform to readily identified cell types, were also analyzed by IF analysis to provide data concerning the broad classification of cell populations targeted. For example, in the cerebral cortex of the Cort BACarray line, Calb1 was detected in nearly 50% of eGFP-L10a positive cells, Pvalb was found in less than 5% of these cells, and Calb2 was not detected. Characterization of the fusion protein in the cortex of Pnoc BACarray mice revealed that the majority of eGFP-L10a positive cells in the superficial layers of the cerebral cortex are multipolar and are GABA positive, although some cells in deeper layers of cortex are GABA negative and appear to have a single apical dendrite. The multipolar cells in this case are often positive for Calb2, but not Calb1 or Pvalb. Both IHC and IF studies of the cortex of the Cck BACarray line clearly demonstrate that eGFP-L10a is detected in small neurons positive for Calb1 but not Pvalb or Calb2, as well as in pyramidal cells (data not shown), consistent with previous ISH data (found on: the world wide web at stjudegem.org; world wide web at brain-map.org) (Lein et al., 2007; Magdaleno et al., 2006).

In addition to neuronal cell types, three BACarray lines for glial cell types were generated which were analyzed in both cerebellar and cortical tissue. These glial cell types included astrocytes, mature oligodendrocytes, and a mixed oligodendroglial line that included mature oligodendrocytes and oligodendrocyte progenitors (also called synantocytes or polydendrocytes) (Butt et al., 2005). Astrocytes were targeted using a BAC for the gene Aldh1l1 that has previously been described as astrocyte specific (Anthony and Heintz, 2007; Cahoy et al., 2008). This BAC drove transgene expression in both Gfap+ (reactive) and Gfap− astrocytes, as well as Bergmann glia. It did not express in Ng2+ oligodendrocyte progenitors, nor in Cnp+ myelinating oligodendrocytes. In contrast, a BAC for the Olig2 transcription factor directed expression specifically into both the Ng2+ and Cnp+ oligodendrocyte lineage cells. Finally, a BACarray line for Cmtm5 expressed specifically, albeit weakly, in mature (Cnp+) oligodendrocytes. With these three lines, the translational profile of the three major classes of glia across the CNS can be examined.

In cases of relatively weakly expressing lines, such as Cmtm5, new drivers can be selected to more effectively target the same cell type. Studies with a mature oligodendrocyte line (Cnp JD368) have demonstrated improved RNA yield and data quality from a more strongly expressing transgene (FIG. 12).

5) Methods

BAC Modification, Transgenesis, and Animal Husbandry: BACs from Table 4 were modified as described to insert an eGFP-L10a fusion protein into the translation start site of the driver gene (Gong et al., 2002; Gong et al., 2003). Founders and subsequent generations were bred to either Swiss-Webster or c57bl/6 wildtype mice. Lines were maintained as trans-heterozygotes.

TABLE 4

List of BACs utilized for transgenesis
Included are the list of abbreviations used throughout for
each gene, and the ID for the BAC clone that was modified.

| Abbreviation | Full Gene Name | BAC |
| --- | --- | --- |
| Sept4 | Septin 4 | RP23-21 N23 |
| Aldh1l1 | Aldehyde Dehydrogenase 1 family, member L1 | RP23-7N19 |
| Cmbm5 | CKLF-like MARVEL transmembrane domain containing 5 | RP24-317F19 |
| C ck | Cholecystokinin | RP23-234l17 |
| C hat | Choline Acetyltransferase | RP23-431D9 |
| C ort | Cortistatin | RP23-281A14 |
| Drd2 | Dopamine receptor 2 | RP23-161H15 |
| Drd1 | Dopamine receptor D1A | RP23-47M2 |
| Grp | Gastrin-Releasing Peptide | RP23-179M10 |
| Grm 2 | Glutamate Receptor, Metabotropic 2 | RP23-335E12 |
| Glt25d2 | Glycosyltransferase 25 Domain-containing 2 | RP23-160M1 |
| Lypd6 | LY6/PLAUR domain containing 6 | RP23-14O24 |
| NeuroD1 | Neurogenic Differentiation 1 | RP24-151C22 |
| Ntsr1 | Neurotensin Receptor 1 | RP23-314D14 |
| Olig2 | Oligodendrocyte Transcription Factor 2 | RP23-356P18 |
| Pnoc | Prepronociceptin | RP23-264L8 |
| Pcp2 | Purkinje Cell Protein-2 | RP24-186D18 |
| Etv1 | Ets1 Variant Gene 1 | RP23-250K4 |

Immunohistochemistry: Six to twelve week old mice were euthanized with CO2 and perfused transcardially with phosphate buffered saline (PBS) pH 7.4 followed by 4% paraformaldehyde in PBS. For diaminobenzidine tetrahydrochloride (DAB) immunohistochemistry, fixed brains were treated overnight with 20% glycerol and 2% dimethylsulfoxide to prevent freeze-artifacts. Multiple brains (up to 25 per block) were embedded in a gelatin matrix using MultiBrain™ Technology (NeuroScience Associates, Knoxville, Tenn.). After curing, the block was rapidly frozen to −70° C. by immersion in a mixture of isopentane and crushed dry ice, and mounted on a freezing stage of an AO 860 sliding microtome. The MultiBrain™ block was sectioned coronally at 40 microns. All sections were collected sequentially into the wells of a 4×6 plate filled with Antigen Preserve solution (50% PBS pH 7.0, 50% Ethylene glycol, 1% Polyvinyl Pyrrolidone).

After blocking with hydrogen peroxide and serum, the sections were incubated with a 1:75,000 solution of Goat anti-eGFP serum (Heiman et al) overnight at room temperature. Following extensive washing, the sections were incubated with biotinylated secondary antibody (Anti Goat IgG, Vector Labs, Burlingame, Calif.), washed again, and incubated with avidin-biotin-HRP (Vectastain elite ABC kit, Vector Labs, Burlingame, Ca) according to the manufacturer's instructions. Sections were again washed and incubated with DAB and hydrogen peroxide until fully developed. Finally, developed sections were mounted on gelatinized (subbed) glass slides, air dried, dehydrated in alcohols, cleared in xylene and coverslipped. Images were acquired with a Zeiss Axioskop2 microscope with a 10×(1.5 NA) objective using an automated x,y stage (Marzhauser scan8) controlled by a PC with Zeiss KS400 software running custom macros. Wildtype brains showed no labeling.

For fluorescence immunohistochemistry, fixed brains were cryoprotected in 30% sucrose in phosphate buffered saline (PBS), frozen, cut to 40 micron serial floating sections by cryostat, and stored in PBS 0.1% Sodium Azide at 4° C.

until use. Sections were blocked in PBS with 5% normal donkey serum, 0.25% triton for 30 minutes, then incubated overnight with primary antibodies (Table 5). Sections were washed in PBS, exposed to appropriate Alexa dye conjugated secondary antibodies (Molecular Probes/Invitrogen, Carlsbad, Calif.) for 90 minutes, washed, then mounted. All images were acquired with a Zeiss Inverted LSM 510 laser scanning confocal microscope, with a Z thickness of 2 microns. Z-stacks through the sections were acquired to confirm colocalization.

rogen Corporation, Carlsbad, Calif.) for 1 h at room temperature. Sections were washed with PBS/0.05% Tween-20 and a fluorescent HRP substrate, Tyramide-AlexaFluor 546 conjugate (from TSA kit #13, Invitrogen Corporation, Carlsbad, Calif.), was deposited on the slides. Slides were washed again with PBS/0.05% Tween-20, mounted with Prolong Gold Antifade (Invitrogen Corporation, Carlsbad, Calif.), dried overnight, and fluorescence was visualized on a Zeiss LSM510 confocal microscope (Carl Zeiss, Thornwood, N.Y.).

TABLE 5

Antibodies, product numbers, and sources used for immunohistochemistry.

| Symbol | Antibody Name | Product Number | Source |
|---|---|---|---|
| EGFP | Goat Anti-EGFP | NA | (Heiman et al.) |
| EGFP | Chicken Anti-EGFP | AB19370 | Abcam, Cambridge Ma. |
| NEUN | Neuronal Nuclei | MAB377 | Chemicon, Temecula, Ca. |
| OLIG2 | Oligodendrocyte transcription factor 2 | AB9610 | Chemicon, Temecula, Ca. |
| CSPG4 | Ng2 Proteoglycan | AB53420 | Chemicon, Temecula, Ca. |
| CHAT | Choline Acetyl-Transferase | AB143 | Chemicon, Temecula, Ca. |
| GRM2/GRM3 | metabotropic glutamate receptor 2&3 | AB1553 | Chemicon, Temecula, Ca. |
| GRM1 | metabotropic glutamate receptor 1 | AB1551 | Chemicon, Temecula, Ca. |
| CNP1 | Cnpase | MAB326R | Chemicon, Temecula, Ca. |
| CALB1 | Calbindin | 300 | Swant, Bellinzona, CH |
| CALB2 | Calretinin | 6B3 | Swant, Bellinzona, CH |
| PVALB | Parvalbumin | Pv28 | Swant, Bellinzona, CH |
| GFAP | Glial Fibrillary acidic protein | Z0334 | Dako, Denmark |
| S100 | S100 | Z0311 | Dako, Denmark |
| GLUL | Glutamine Synthetase | G2781 | Sigma-Aldrich, St Louis, Mo. |
| SLC18a3 | Vesicular Acetylcholine Transporter | sc-7717 | Santa Cruz Biotech, Santa Cruz, Ca. |
| ALDH1L1 | 10-Formyltetrahydrofolate Dehydrogenase | NA | a gift from Dr. Robert Cook |
| — | GABA | A2052 | Sigma-Aldrich, St Louis, Mo. |

Fixed Sections: For fixed sections, BACarray transgenic mice were deeply anesthetized with pentobarbital or 50 mg/ml Nembutal and transcardially perfused with 10 ml of phosphate buffered saline (PBS) followed by 40 ml of 4% paraformaldehyde (PFA) in PBS. Brains were dissected and post-fixed at room temperature for exactly 1 h with 4% PFA in PBS. After fixation, brains were washed 3 times in PBS and incubated in 5% weight/volume (w/v) sucrose in PBS at 4° C. for 1 hour with gentle agitation. Brains were then incubated for 24 h in 15% w/v sucrose in PBS at 4° C. with gentle agitation and for 24 h in 30% w/v sucrose in PBS at 4° C. with gentle agitation. Brains were placed in an embedding mold filled with Neg-50 embedding medium (Richard Allan Scientific, Kalamazoo, Mich.) for 1 hour at room temperature, and were subsequently incubated on dry ice for 1 hour to freeze the embedding medium. Brains were then transferred to and stored at −80° C. until sectioned. 12 µm sagittal sections were cut, mounted on glass slides, and kept overnight at −20° C., then transferred to −80° C. until used for immunohistochemistry.

Before use sections were thawed and dried at room temperature for 20 min, washed with PBS, and incubated in 0.2% H2O2/PBS at room temperature for 30 min to quench endogenous peroxidase activity. Sections were washed with PBS, permeabilized with PBS/0.05% Tween-20, and blocked with Image-it FX signal enhancer (Invitrogen Corporation, Carlsbad, Calif.) for 30 min at room temperature. Sections were washed with PBS/0.05% Tween-20 and blocked again with 2% donkey serum/0.1% fish gelatin/PBS/0.05% Tween-20. Sections were then incubated overnight at 4° C. with primary antibodies. The next day, sections were washed with PBS/0.05% Tween-20 and incubated with anti-rabbit Superpicture HRP Polymer Detection Kit (Invit- Fresh Frozen Sections: For all nuclear immunohistochemistry (Anti-Atrx, Anti-PML, Anti-γH2A.X), fresh frozen brain sections were used. For fresh frozen brain sections, BACarray mice were euthanized with CO2, decapitated, and their brains removed into ice-cold PBS. Brains were then embedded in Neg50, placed on dry ice for an hour, and stored until needed at −80° C. Before sectioning, frozen blocks of tissue were equilibrated at −20° C., and 16 um sections were cut on a Leica cryostat. Slides with fresh frozen brain sections were stored at −80° C. or −20° C. until further use.

Prior to use, sections were allowed to air-dry at room temperature for 15 minutes, then fixed with 1% freshly made PFA in 1×PBS for 10 minutes at room temperature. Next, slides were washed three times with 1x PBS, and permeabilized for 10 minutes at room temperature with 0.05% Triton X-100 in PBS. After permeabilization, tissue sections were blocked using either 5% horse serum or 5% goat serum in PBS for at least one hour. Sections were incubated with primary antibodies overnight in a humidified chamber at 4° C., washed three times with PBS, and incubated at room temperature for one hour with appropriate secondary antibodies. After incubation with secondary antibodies, sections were incubated for 10 minutes with the nuclear stain TO-PRO-3 (Invitrogen Corp., Carlsbad, Calif.), washed three times with PBS, and coverslipped with Aquamount mounting medium (Lerner Laboratories, Pittsburgh, Pa.). Images were collected on an upright Zeiss Axioplan LSM 510 laser scanning confocal microscope (Carl Zeiss MicroImaging, Inc., Thornwood, N.Y.) using 40×/1.2, water immersion objective, 63×/1.4 oil immersion, and 100×/1.4 oil immersion lenses.

Quantification of Laminar Position of Cortical Pyramidal Cells: Anti-eGFP immunohistochemistry with DAB was performed on 20 micron sagittal sections from the Etv1 TS88, Glt25d2 DU9, and Ntsr1 TS16 BACarray lines as described (Gong et al), and images were acquired as above. Corresponding digital images of the adult sagittal sections were downloaded from gensat.org for lines expressing eGFP from the same BACs. Sections containing motor cortex (corresponding to Paxinos section 111) (Paxinos and Franklin, 2001) were imported into ImageJ (rsb.info.nih.gov/ij). The distance from the apical tip of the soma to the pial surface was measured using the 'straight line selection' tool. The apical tip was defined as the site at which the apical dendrite and the cell body converge. Only cells with a clearly visible apical dendrite and a uniformly stained soma were measured. At least 50 cells were measured from each image. All measurements were then converted from pixels to microns using the following scale: 1 pixel=1.33 microns.

In Situ Hybridization: IMAGE consortium clones containing sequences from genes of interest were purchased from Open Biosystems (Table 6). Probes were synthesized by linearization of plasmid with appropriate restriction enzyme, template purification with Qiagen PCR purification kit, followed by in vitro transcription with appropriate enzyme (T3 or T7) using DIG RNA labeling kit (Roche, Basel, CH). Labeled RNA was purified with ProbeQuant G-50 microcolumns (GE Healthcare), and assayed for quality and quantity with a Bioanalyzer, following manufacturer's instructions (Agilent Technologies, Santa Clara Calif.).

Adult mice were processed as above, and brains were cut on cryostat into 20 micron sections and mounted onto Fisher Superfrost Plus slides. Tissue was washed, then post fixed for 20 minutes in 4% paraformaldehyde PBS, permeabilized with 0.05% Triton X100, digested with 50 ug/ml Proteinase K in TE for 10 minutes, and acetylated for 10 minutes in 0.1M TEA with 0.25% acetic anhydride. Sections were prehybridized in Atlas hybridization chambers (Clontech, Mountain View, Ca) in 5×SSC, 2.5×Denhardt's solution, with 500 ug/ml sheared denatured salmon sperm for 30 minutes, then hybridized overnight with labeled riboprobe. Slides were washed for 5 minutes at 65 C with 5×SSC, then for 1 hour with 0.2×SSC at 68° C., and for 5 minutes at room temperature. Slides were washed in TBS (100 mM Tris HCl, 150 nM NaCl, pH 7.5) twice for five minutes, blocked with 10% Roche blocking solution in TBS for one hour, incubated with primary antibodies for 1 hour in the same solution (Sheep anti-Dig, alkaline phosphatase conjugated, Roche 11 093 274 910) and Goat anti-eGFP where appropriate, washed with TBS, and developed with NBT/BCIP or HNPP/Fast Red following manufacturers protocols (Roche). For eGFP/ISH double fluorescence, sections were then incubated with alexa-488 donkey anti-goat antibody (Invitrogen) for one hour before counterstaining with DAPI, washing and coverslipping. Images were acquired with Zeiss Inverted LSM 510 laser scanning confocal microscope.

Example 4

Isolation and Purification of Ribosome-mRNA Complexes In Vivo

Improved procedures for rapid extraction and immunoaffinity purification of the eGFP-tagged functional polyribosome complexes from in vivo intact brain tissue were developed and optimized (A. Alexa, J. Rahnenfuhrer, T. Lengauer, Bioinformatics 22, 1600-7 (2006)). Highly purified RNA and protein was consistently obtained from BAC-array mice. Key steps of the purification protocol included rapid manual dissection and homogenization of the tissue in question, inclusion of magnesium and cycloheximide in the lysis buffer to maintain ribosomal subunits on mRNA during purification, inhibition of endogenous RNase activity, solu-

TABLE 6

List of plasmids of in situ hybridization studies:
ISH was conducted on 11 genes enriched in either Grm2 positive granule cell layer interneurons, or Pnoc positive neurons of cortex, using plasmids ordered from Open Biosystems. Plasmids were sequenced to confirm the accuracy and orientation of the ESTs. Plasmids were linearized with either Sal I or Eco RI and Dig labeled RNA was transcribed with either T3 or T7 polymerase to create anti-sense cRNA probe.

Figure 13:
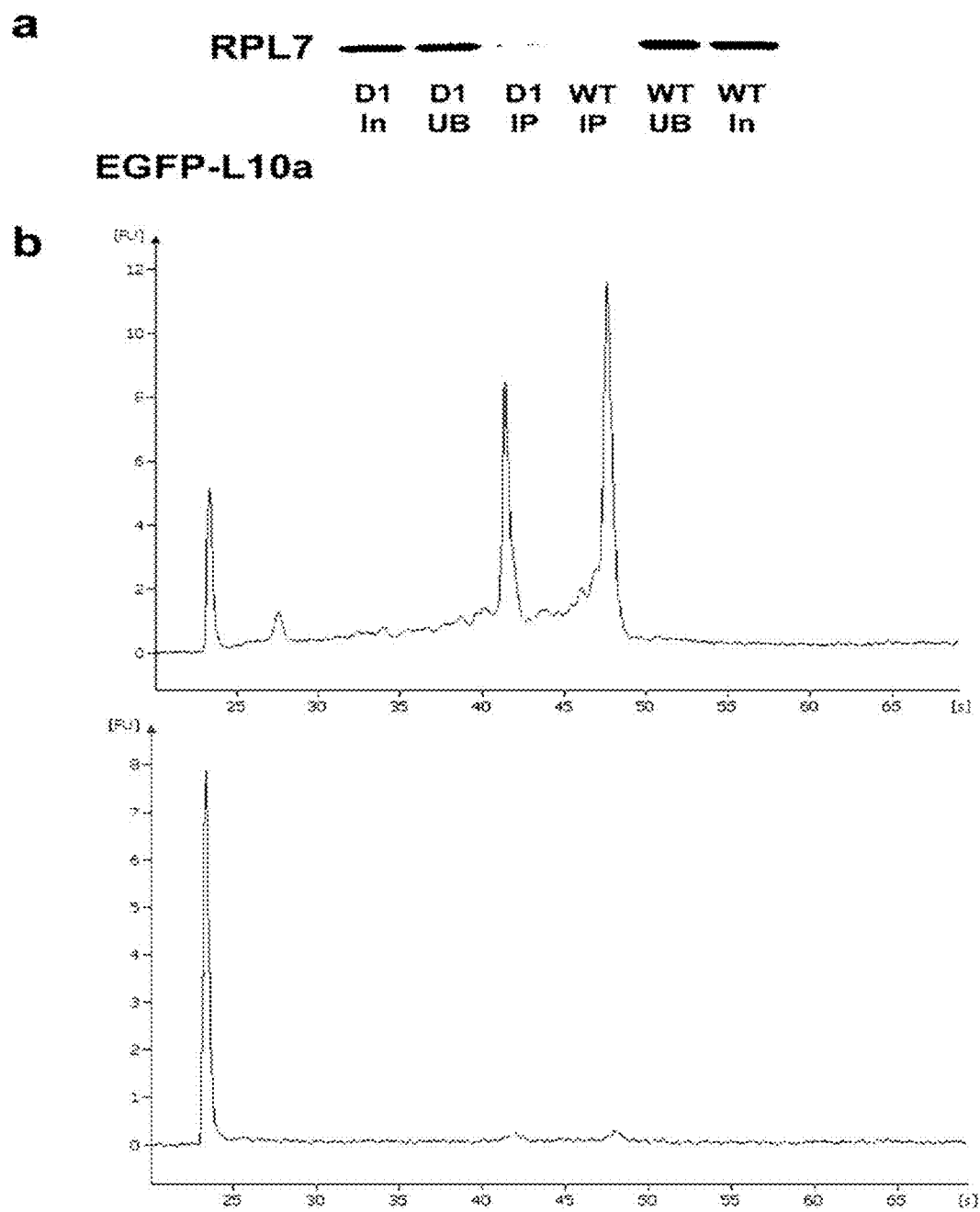
FIG. 13 illustrates protein and mRNA purification from BACarray lines. (a) Purification of eGFP tagged L10a and co purification of untagged ribosomal protein L7 from D1 BACarray animals but not wild type littermates (D1, samples from D1 BACarray mice; WT, samples from wild type littermates; In, 1% Input; UB, 1% Unbound; IP, 6.5% Immunoaffinity purified sample). eGFP L10a signal is only present in the D1 IP lane because the IP samples were more concentrated relative to In and UB. (b) Purification of 18S and 28S rRNA from D1 BACarray transgenic animals (top panel) but not wild type littermates (bottom panel) as detected by Bioanalyzer PicoChips (Agilent Technologies). 28S rRNA runs at ~47 sec, 18S rRNA runs at ~43 sec, and the marker peak runs at ~23 sec.

|  | Genbank | Open Biosystems # | Gene Name | Enzymes |
|---|---|---|---|---|
| PNOC Gene ID | | | | |
| B230118H07Rik | BC025075 | MMM1013-7513748 | RIKEN cDNA B230118H07 gene | Sal I cut, T7 polymerase |
| Chd4 | BC058578 | MMM1013-9201124 | chromodomain helicase DNA binding protein 4 | Sal I cut, T7 polymerase |
| Cidea | AA061879 | EMM1002-1115733 | cell death-inducing DNA fragmentation factor, alpha subunit-like effector A | Eco RI cut, T3 polymerase |
| Crabp1 | BC065787 | MMM1013-9202137 | cellular retinoic acid binding protein I | Eco RI cut, T3 polymerase |
| Ddef1 | BC094581 | MMM1013-98479313 | development and differentiation enhancing | Eco RI cut, T3 polymerase |
| Igf1 | BC012409 | MMM1013-65370 | insulin-like growth factor 1 | Sal I cut, T7 polymerase |
| GRM2 Gene ID | | | | |
| Lypd1 | CA328245 | EMM1002-6960067 | RIKEN cDNA 2700050C12 gene | Eco RI cut, T3 polymerase |
| Slc6a5, GlyT2 | BM941867 | EMM1032-584726 | solute carrier family 6 (neurotransmitter transporter, glycine), member 5 | Eco RI cut, T3 polymerase |
| Amn | AA023455 | EMM1002-1077429 | amnionless | Eco RI cut, T3 polymerase |
| Penk1 | AA098193 | EMM1002-1183311 | preproenkephalin 1 | Eco RI cut, T7 polymerase |
| Gcqr | BC031885 | MMM1013-7511930 | glucagon receptor | Sal I cut, T7 polymerase |
| Ceacam 10 | BC003346 | MMM1013-62963 | CEA-related cell adhesion molecule 10 | Sal I cut, T7 polymerase | bilization of rough endoplasmic reticulum-bound polysomes under nondenaturing conditions, use of high-affinity anti-eGFP antibodies, and the addition of high-salt washes after immunoaffinity purification to reduce background. FIG. 13 displays purification of eGFP-tagged L10a and co-purification of untagged ribosomal protein L7 from D1 BACarray animals but not wild-type littermates in (a) (D1, samples from D1 BACarray mice; WT, samples from wild-type littermates; In, 1% Input; UB, 1% Unbound; IP, 6.5% Immunoaffinity purified sample). eGFP-L10a signal is only present in the D1 IP lane because the IP samples were more concentrated relative to In and UB. In (b) purification of 18S and 28S rRNA from D1 BACarray transgenic animals (top panel) but not wild type littermates (bottom panel) as detected by Bioanalyzer PicoChips (Agilent Technologies) is shown. 28S rRNA runs at ~47 sec, 18S rRNA runs at ~43 sec, and the marker peak runs at ~23 sec.

Figure 14:
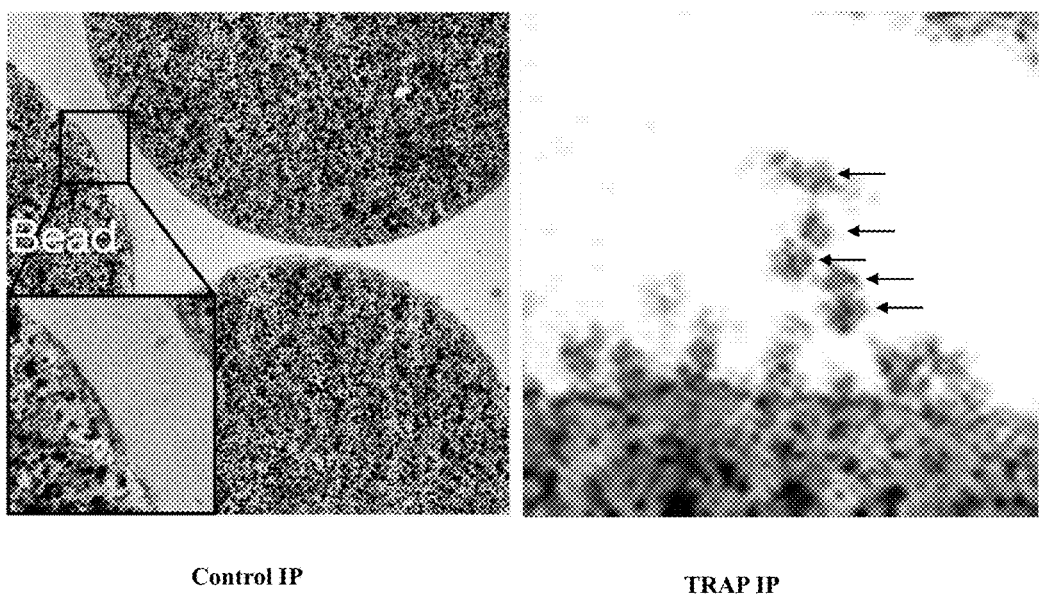
FIG. 14 illustrates electron microscopy of immunoprecipitated ribosome complexes.

Following immunoprecipitation of ribosomal complexes, electron microscopy was utilized to visualize the ribosomes. Aliquots of anti-GFP coated magnetic beads were fixed in 2.5% glutaraldehyde/0.1M cacodylate [pH 7.4] on ice. The bead pellet was post-fixed with 1% osmium tetroxide in the same buffer on ice. After treatment with 0.5% aqueous uranyl acetate at room temperature, the specimen was dehydrated with graded alcohol (70, 90, 100%) and treated with propylene oxide before embedding in Embed 812 resin. The resin was polymerized in a 60° C. oven for 2-3 days. Silver sections were cut with a Dupont diamond knife on a Reichert-Jung UltraCut E ultramicrotome. The sections were collected on copper grids, doubly stained with saturated, aqueous uranyl acetate and lead citrate before examination with a Jeol 100cx electron microscope (JEOL, Peabody, Mass.) operated at 80 kV (FIG. 14).

1) Generation of Monoclonal Antibodies

All immunoprecipitations except for the Drd1 and Drd2 lines, which used the Goat Anti-eGFP described in later examples, were done using two monoclonal anti-eGFP antibodies (clones 19C8 and 19F7) specifically generated for this purpose at the Monoclonal Antibody Core Facility at Memorial Sloan-Kettering cancer center. Mice were immunized with purified GST-eGFP fusion protein and several rounds of screening were performed to identify clones which functioned well in immunoprecipitation assays. Initially, monoclonal supernatants were tested by ELISA using 96 well plates coated with eGFP purified from transiently transfected 293T cells. Next, positive clones were screened in immunoprecipitation assays, again using the eGFP purified from transfected 293T cells. Finally, positive clones which strongly immunoprecipitated eGFP from lysates from a transgenic mouse line expressing eGFP under the BAC driver of interest were identified.

2) Immunoprecipitation of Polyribosomes

Immunoprecipitation of polyribosomes and isolation of mRNA was done as described in detail below, except goat anti-eGFP antibody was substituted with a mix of two monoclonal eGFP antibodies (19C8, 19F7). Three to six mice for each replicated sample were euthanized with CO2 and distinct brain regions (cerebellum, cortex, corpus striatum, basal forebrain, brainstem, or spinal cord) were dissected Each cell population was assayed in triplicate. RNA quality control, amplification and hybridization were done as described by Heiman et al. For consistency across cell types, 15 ngs of total RNA were amplified for each sample.

Example 5

Analysis of mRNA from BACarray Mice

1) Preparation of mRNA

For mRNA purification, mice were decapitated and the specific tissue of interest was quickly dissected from mice brains. Pooled tissue was immediately collected in ice-cold dissection buffer and homogenized in ice-cold polysome extraction buffer (10 mM HEPES [pH 7.4], 150 mM KCl, 5 mM MgCl2, 0.5 mM dithiothreitol, 100 µg/ml cycloheximide, protease inhibitors, and recombinant RNase inhibitors) using a motor-driven Teflon-glass homogenizer. Homogenates were centrifuged for 10 minutes at 2,000×g, 4° C., to pellet large cell debris, and NP-40 or IGEPAL (EMD Biosciences, San Diego, Calif.; Sigma, St. Louis, Mo.) and DHPC (Avanti Polar Lipids, Alabaster, Ala.) were added to the supernatant at a final concentration of 1% and 30 mM, respectively. After incubation on ice for 5 minutes, the clarified lysate is centrifuged for 10 minutes at 13,000×g to pellet unsolubilized material. Goat anti-GFP (custom made) coated protein G Dynal magnetic beads (Invitrogen Corporation, Carlsbad, Calif.) are added to the supernatant and the mixture was incubated at 4° C. with end-over-end rotation for 30 minutes. Beads were subsequently collected on a magnetic rack, washed three times with high-salt polysome wash buffer (10 mM HEPES [pH 7.4], 350 mM KCl, 5 mM MgCl2, 1% NP-40, 0.5 mM dithiothreitol, 100 µg/ml cycloheximide) and immediately placed in TriZol-LS reagent (Invitrogen Corporation, Carlsbad Calif.) and chloroform to extract the bound rRNA and mRNA from polysomes. After extraction, RNA was precipitated with sodium acetate and Glycoblue (Ambion, Austin, Tex.) in isopropanol overnight at −80° C., washed twice with 70% ethanol, resuspended in water, and further purified using an Rneasy Micro Kit (Qiagen, Valencia, Calif.) with in-column DNase digestion. Purified samples were analyzed using a Bioanalyzer (Agilent Technologies, Santa Clara, Calif.) in order to assess mRNA quantity and quality, as reflected by rRNA levels and integrity.

After purification of RNA samples, 1.5 ul was used for quantification using a Nanodrop spectrophotometer (NanoDrop Technologies, Wilmington, Del.). Each sample was further analyzed with a Bioanalyzer (Agilent Technologies, Santa Clara, Calif.) to ensure that the quality of each RNA sample met standard criteria and that they were comparable to each other. Specifically, all RNA samples had a 260/280 ratio (Nanodrop) of at least 1.8, and a RNA Integrity Number (Bioanalyzer) of at least 7. Moreover, the quality of the samples was visually estimated using the Bioanalyzer readout to estimate the level of potential degradation or contamination for each sample.

2) Microarray Analysis of mRNA

Once these criteria were met, a total of 15 ng of RNA from each sample was amplified, biotinylated, and fragmented with the Affymetrix two-cycle amplification kit (Affymetrix, Santa Clara, Calif.). After amplification, samples were again quantified with a Nanodrop spectrophotometer, and 20 ug of amplified RNA was fragmented following the Affymetrix protocol. Amplified and fragmented samples were analyzed with a Bioanalyzer before hybridization to Affymetrix mouse 430 2.0 microarrays. All hybridizations were done according to standard Affymetrix protocols at the Rockefeller University Genome Array Center.

Tissue handling and RNA purification for all samples was as described. Purified RNA was converted to double-stranded cDNA using the SuperScript GeneChip Expression 3'Amplification Reagents Two-Cycle cDNA Synthesis Kit (Affymetrix, Santa Clara, Calif.) and the GeneChip T7-Oligo(dT) Primer (Affymetrix, Santa Clara, Calif.). cDNA was used for the in vitro synthesis of cRNA using the MEGAscriptT7 Kit (Ambion, Austin, Tex.). cRNA was purified using the GeneChip Sample Cleanup Module (Affymetrix, Santa Clara, Calif.). 600 ng or less of clean cRNA was used in the second-cycle cDNA synthesis reaction using the SuperScript GeneChip Expression 3'-Amplification Reagents Two-Cycle cDNA Synthesis Kit (Affymetrix, Santa Clara, Calif.) and random primers (Affymetrix, Santa Clara, Calif.). The cDNA was purified using the GeneChip Sample Cleanup Module (Affymetrix, Santa Clara, Calif.). Purified cDNA was used for the in vitro synthesis of biotin-labeled cRNA using the GeneChip IVT Labeling Kit (Affymetrix, Santa Clara, Calif.). cRNA was purified using the GeneChip Sample Cleanup Module (Affymetrix, Santa Clara, Calif.) and fragmented into 35-200 base pair fragments using a magnesium acetate buffer (Affymetrix, Santa Clara, Calif.).

As controls, Affymetrix standard spike-in controls (eukaryotic hybridization kit) were used.

For hybridization procedures and parameters, 10 micrograms of labeled cRNA were hybridized to Affymetrix GeneChip Mouse Genome 430 2.0 arrays (available using the hypertext transfer protocol on the world wide web at affymetrix.com/products/arrays/specific/mouse430_2.affx) for 16 h at 45° C. The GeneChips were washed and stained according to the manufacturer's recommendations (Affymetrix, Santa Clara, Calif.) using the GeneChips Fluidics Station 450 (Affymetrix, Santa Clara, Calif.). This procedure included staining the chips with phycoerythrin-streptavidin, signal amplification by a second staining with biotinylated anti-streptavidin, and a third staining with phycoerythrin-streptavidin.

For array design, Affymetrix Mouse Genome 430 2.0 arrays were used in all experiments. Information regarding the array design and features can be found at the hypertext transfer protocol on the world wide web at affymetrix.com.

For measurement data and specifications, Mouse Genome 430 2.0 arrays were scanned using the GeneChip Scanner 3000 (Affymetrix, Santa Clara, Calif.). Three biological replicates were performed for each experiment. GeneChip CEL files were subjected to Harshlight analysis to detect if any blemishes were present on the GeneChips (available using the hypertext transfer protocol at asterion.rockefeller.edu/Harshlight/index2.html) (M. Suarez-Farinas, M. Pellegrino, K. M. Wittkowski, M. O. Magnasco, BMC Bioinformatics 6, 294 (2005)). Only GeneChips without major blemishes were used. GeneChip CEL files were imported into Genespring GX 7.3.1 (Agilent Technologies, Santa Clara, Calif.), processed with the GC-RMA algorithm, and expression values on each chip were normalized to that chip's $50^{th}$ percentile. Data were filtered to eliminate genes with intensities in the lower range. Only genes where more than one sample had a normalized intensity larger than 16 (4 in log2 scale) were kept in the analysis. Statistical analysis to determine which genes are differentially expressed in the different conditions was carried out using the Limma package from Bioconductor project (available using the hypertext transfer protocol on the world wide web at bioconductor.org).

MIAME compliant raw data are available from the APNRR server and GEO. Replicate array samples were normalized with quantile normalization (GCRMA). Data were filtered to remove those probesets with low signal (<50) from analysis, as well as those probesets identified as monoclonal background (Table 7), and replicate samples were averaged.

TABLE 7

List of Probesets excluded from analysis
To identify mRNAs which interact with monoclonal antibodies or protein G dynabeads in the absence of eGFP, BACarray was performed on a wildtype mouse brain and compared to unbound whole brain RNA. The excluded probesets listed here are those for genes found to be highly enriched (>6 fold) in the wildtype IP/UB as well as enriched in multiple IPs from diverse regions and cell types.

| Probeset | IP/UB WT | Symbol | Name |
| --- | --- | --- | --- |
| 1428909_at | 374.4 | 1200015M12Rik | novel |
| 1428720_s_at | 41.55 | 2010309G21Rik | novel |
| 1453238_s_at | 57.87 | 3930401B19Rik | novel |
| 1435640_x_at | 159 | C8506T | novel |
| 1425247_a_at | 37.25 | Igh-4 | immunoglobulin heavy chain 4 iserum IgG') |
| 1425324_x_at | 11.34 | Igh-4 | immunoglobulin heavy chain 4 iserum IgG') |
| 1424305_at | 14.27 | Igj | immunoglobulin joining chain |
| 1452417_x_at | 68.89 | Igk-V28 | immunoglobulin kappa chain variable 8 (VE) |
| 1427455_x_at | 60.27 | Igk-V28 | immunoglobulin kappa chain variable 8 (VE) |
| 1427660_x_at | 58.46 | Igk-V28 | immunoglobulin kappa chain variable 8 (VE) |
| 1456162_x_at | 861.2 | Lmna | lamin AC |
| 1455892_x_at | 6.874 | Lmna | lamin AC |
| 1450009_at | 12.58 | Ltf | lactotransferrin |
| 1456456_x_at | 122.6 | Mela | melanoma antigen |
| 1427797_s_at | 42.54 | Mnda | myeloid cell nuclear differentiation antigen |
| 1427798_x_at | 313.97 | Mnda | myeloid cell nuclear differentiation antigen |
| 1452556_at | 14.87 | Mnda | myeloid cell nuclear differentiation antigen |
| 1416957 | 57.24 | Pou2af1 | Pou domain, class 2, associating factor 1 |
| 1435697_a_at | 9.079 | Pscdbp | pleckstrin homology, Sec7 and coiled-coil domains, binding protein |
| 1436727_x_at | 23.84 | Sptlc1 | serine palmitoyltransferase, long chain base subunit 1 |
| 1435137_s_at | 53.47 | | novel |
| 1427932_s_at | 26.78 | | novel |

Each IP was then compared to the unbound samples from the same tissue to calculate a ratio of IP/UB as a measure of 'enrichment'. UB samples generally show little or no depletion of cell-specific RNA following IP, and UB samples from several different IPs from the same tissue were averaged for each comparison. UB samples from corpus striatum (Chat line) and neostriatum (Drd1 and Drd2 lines) were normalized together. IPs were globally normalized to UBs using the Affymetrix biotinylated spike in controls, to correct for any broad biases in scanning and hybridization. For each cell type, Table 9 contains the IP/UB values for all genes with fold change >2 and p<0.05 by Welch's t-Test, with Benjamini and Hochberg FDR multiple testing correction, as calculated by Genespring GX version 7.3 (Agilent).

For three cell populations, a further 'corrected enrichment' was calculated. For the Bergmann glial line, Sept4, which also shows low level expression in mature oligodendrocytes, the corrected enrichment is the intersection of the IP/UB analysis described above with a comparison of the Bergman Glial line with the mature oligodendrocyte line, Cmtm5, using the same fold change and statistical criteria applied above. For unipolar brush cell line Grp, which also shows expression in some Bergmann glia, the corrected enrichment is the intersection of the IP/UB enrichment described above with a comparison of Grp with the Bergman glial line, using the same criteria. Finally, a substantial proportion of the RNA in the cerebellum is generated by granule cells, and thus the UB samples are highly enriched in granule cell RNA. Therefore, to identify granule cell genes, the 'corrected enrichment' was calculated by comparing granule cell IP to the average of all other cerebellar cell type IPs, using the same criteria as above.

Hierarchical clustering was performed in Genespring using the 'condition tree' function with a smoothed correlation metric on the GCRMA normalized data for the 20% of probesets with the highest coefficient of variation.

Shannon entropy was calculated in excel from GCRMA normalized values with the following procedure: After excluding probesets with no signal>100 in at least one sample, normalized expression measurements for each data set were categorized into 5 bins by log base 10 values (1-9, 10-99, 100-999, 1000-9999, 10000-99999), and Shannon entropy was calculated for each gene across 1) just the IP samples, 2) just the UB samples, and 3) across all samples using the following formula (Schneider, 2007).

$$H = -\sum_{i=1}^{M} P_i \log 2 P_i$$

The 10% of probesets with the highest and lowest entropy across all samples were analyzed using the BINGO plugin for the cytoscape software, using the full mouse Gene Ontologies, a p threshold of 0.01 on hypergemetic tests with Benjamin Hochberg FDR correction for multiple testing (Ashburner et al., 2000; Maere et al., 2005). Results from this analysis are substantially similar to those obtained using the EASE online implementation of Gene Ontologies and EASE statistic (Dennis et al., 2003).

Pearson's correlation with MBP was calculated in Genespring.

Comparative analysis of all cell types, and heat maps were generated with the R statistical software. Data were normalized as above. Then, for each cell type the total probeset list was filtered to remove those probesets with signal less than 50, or IP/UB values less than the average plus two standard deviations of the IP/UB values of the relevant negative control genes, or 1, whichever was lesser. Then, with this filtered list of genes, a fold change was calculated for this cell type versus all other samples, iteratively. For each comparison, the fold changes were ranked from highest to lowest, and these ranks were averaged across comparisons for a cell type. The top one hundred probesets from this average ranking were selected for further analysis.

Figure 15:
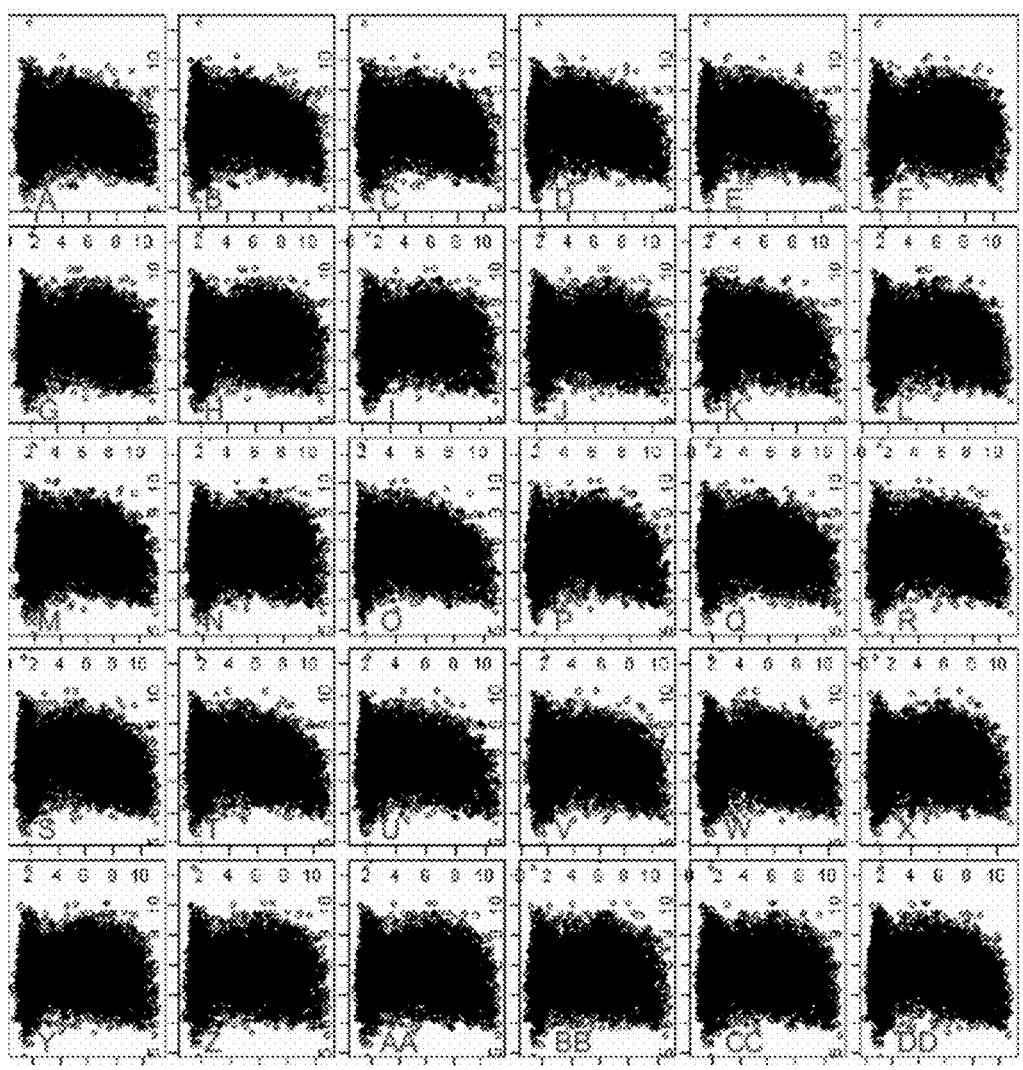
FIG. 15 illustrates that microarray signal intensity does not increase with transcript length. A-DD: To assess whether longer mRNA's were more efficiently immunoprecipitated than shorter transcripts, transcript length (Y-axis, log base 2), was plotted versus GCRMA normalized signal intensity (X-axis, log base 2) for all 30 samples. None of the immunoprecipitated nor the unbound (whole tissue RNA) samples show positive correlations between length and signal.

To assess if the ribosomal immunoprecipitation is biased towards longer transcripts, the signal intensity versus transcript length for all probesets was plotted. No positive correlation between signal intensity and length was detected for any sample (FIG. 15).

Example 6

BACarray Polysome Purification, RNA Extraction and Control Microarray Experiments 1) Overview In total, twenty four cell populations in five regions were chosen to assay with immunoprecipitation (IP) and genome wide translational profile via microarray, using the translating ribosome affinity purification (TRAP) methodology of Heiman et al (2008). For each cell type, pooled microdissected tissue from three to six transgenic mice was used. As shown in FIG. 16, this procedure yielded the purification of eGFP-ribosomal fusion protein along with cell specific mRNAs. The yield of total RNA from the initial IP is dependent on the number of labeled cells in the tissue and the intensity of the transgene expression within each cell, with RNA recoveries ranging from tens to thousands of nanograms per IP. RNA from the unbound (UB) fraction of the immunoprecipitation was harvested to measure the genes expressed in the dissected region as a whole. IP and UB mRNA were then amplified into labeled cRNA using standard protocols.

Figure 17:
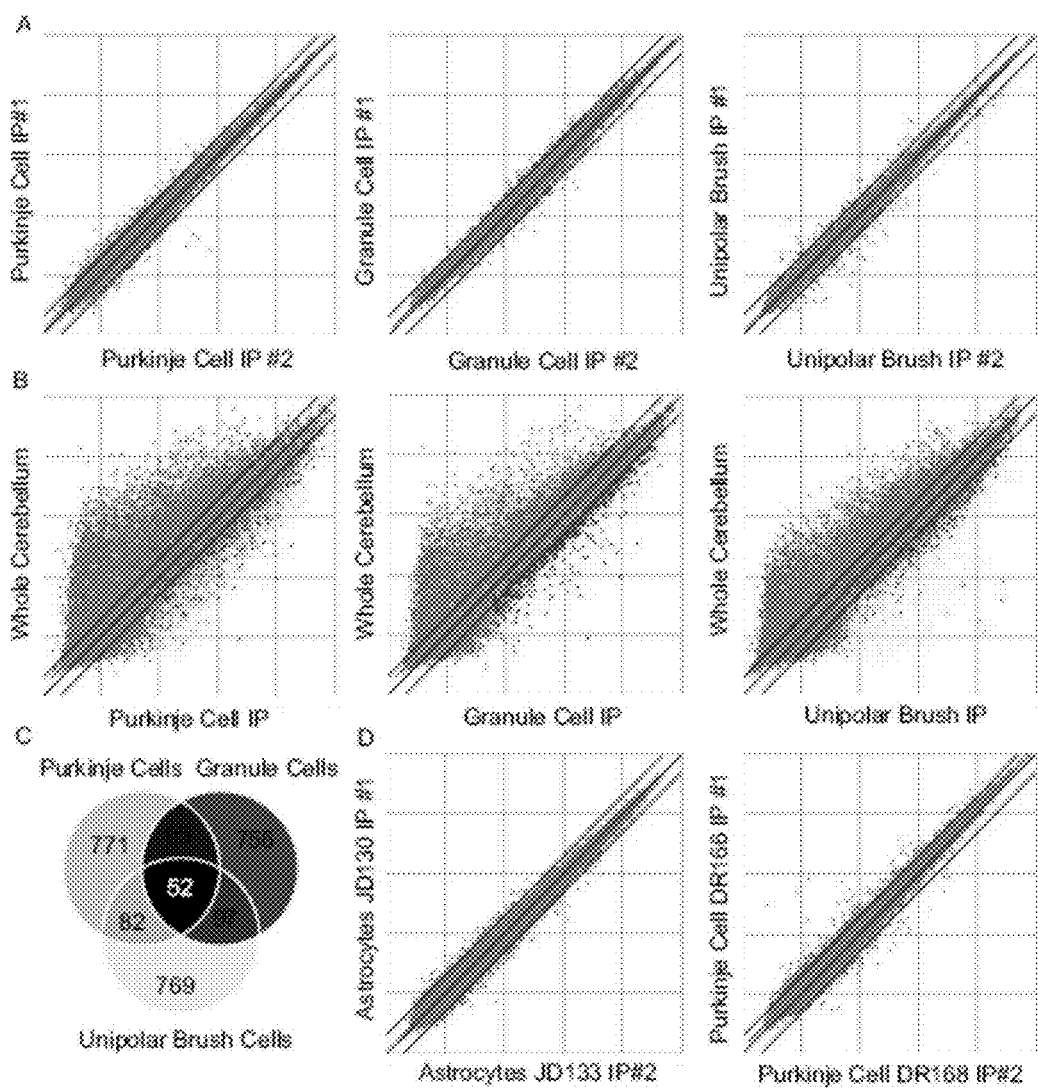
FIG. 17 illustrates that BACarray data are reproducible and cell-type specific.

Labeled cRNAs from the IP and UB fractions were then hybridized onto Affymetrix mouse 430 2.0 microarrays. Samples derived from multiple independent pools of mice (replicates) were assayed for each cell type. FIG. 17 presents these data and illustrates that BACarray data are highly reproducible and cell-type specific As shown in Panel A, replicates for the same cell type gave nearly identical genome wide translational profiles, confirming the results of Heiman et al, and extending this finding to many other cell types. The average Pearson's correlation between replicates for a given cell population from independently isolated samples was above 0.98 across all cell types. To determine whether the position of integration of the BACarray construct would influence the data, results obtained from independent BACarray founder lines prepared with the same engineered BAC were also examined, as presented in D. This analysis revealed that for independent founder lines targeting identical cell populations, the variation in translational profiles between lines was low, and no more extensive than that seen for replicate samples isolated from the same BACarray founder line (Panel D). Thus, the location of the transgene insertion into the genome had little global impact on the data obtained from the translating ribosome affinity purification (TRAP) methodology. Finally, four different monoclonal antibodies and one goat polyclonal against eGFP were tested. Each antibody immunoprecipitated comparable levels of mRNA for the BACarray lines tested; similar global gene translational profiles were obtained from each antibody tested in IPs from specific BACarray lines. A small number of probesets were consistently enriched in every BACarray dataset analyzed. Since these same probesets are also enriched in immunoprecipitates from control mice with no transgene expression, it was concluded that they represent background which have systematically eliminated from further analysis.

The enrichment for each mRNA immunoprecipitated from the targeted cell type (IP) versus its expression in the tissue sample dissected for the analysis (UB) was measured. The ratio of IP/UB was calculated, thereby identifying those genes which are highly enriched in each cell type. Panel B shows scatter plots for three representative cell types of the cerebellum. Differences are evident between the genome-wide translational profiles of IP samples compared to whole tissue (UB), with each cell population displaying a unique profile of thousands of specifically enriched genes on the microarray. As in Panel C, Venn diagrams constructed from the top 1000 most enriched probesets for each cell type can be used to illustrate this point. Thus, approximately 75% of these enriched probesets are not shared between cerebellar Purkinje cells, granule cells and unipolar brush cells, and only 52 of the probesets enriched in these three cell types versus whole cerebellum are shared between them. Furthermore, the primary data collected from these experiments has been deposited in the Gene Expression Omnibus (Edgar et al., 2002).

Figure 18:
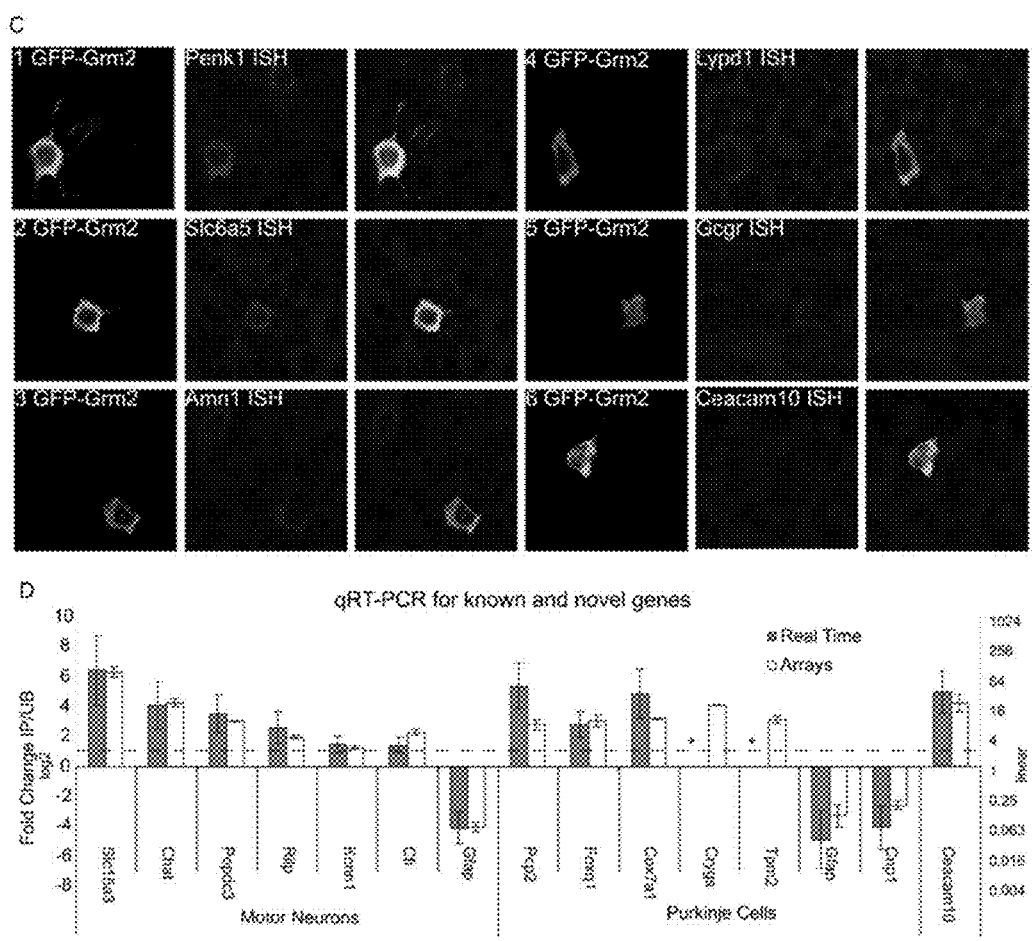
FIG. 18 illustrates that BACarrays can identify known markers, and discover new ones for a variety of cell types.

FIG. 18 presents the accuracy of this methodology to enrich for cell-specific genes. The BACarray data for known cell-specific markers (positive controls) for each cell type and the BACarray data for genes known to be expressed exclusively in other cell types (negative controls) were examined. Panel A shows a scatter plot of IP vs. UB for spinal cord motor neurons. Probesets for known markers of motor neurons with measurable signal on the array are clearly enriched in the IP sample, whereas probesets for glial cell-specific RNAs, that should not be present in these cells, are enriched in the UB sample. To establish the generality of this finding, the enrichment in the IP or UB sample was quantified by calculating an average ratio of IP/UB for positive and negative controls for each cell type where at least three positive controls could be found in the literature. As shown in Panel B, all IPs showed a clear enrichment for appropriate known markers, (Panel B, plotted in log base 2). Even for cell types with only one known marker (Pnoc positive interneurons, and Grp expressing unipolar brush cells), probesets for these genes were consistently and highly enriched in the IP. In the IPs with the lowest relative yield of RNA, such as those for mature oligodendrocytes (Panel B), and Cort expressing interneurons, background was proportionally higher, and enrichment was less robust.

Novel cell-specific markers for rare cell types using the BACarray approach were identified. Eleven genes predicted by BACarray to be enriched in either the Grm2 expressing interneurons of the granule cell layer (Golgi cells), or the Pnoc expressing cells of the cerebral cortex were screened. Using confocal microscopy, double immunofluorescence for both eGFP-L10a fusion protein and the ISH probes were evaluated. For the nine genes where ISH gave clear results, all were clearly overlapping with eGFP-L10a.

Panel C shows that in the case of cerebellar Golgi cells, there is a great deal of overlap between eGFP-L10a expression in the BACarray line and expression of the genes chosen for this analysis. This overlap confirms the specificity of the results obtained for this and other cell types. Nonetheless, the enrichment of a particular mRNA in the IP sample cannot be used to conclude that it is exclusively expressed in the cell type labeled in the BACarray transgenic line, or that it is expressed in all cells of that type. For example, the ISH databases (available on the world wide web at stjudebgem.org and the world wide web at brain-map.org) clearly indicate that Penkl is expressed in scattered cells in both the granular and molecular layers of the adult cerebellum. Furthermore, as shown in panel 1, Penkl mRNA does not appear to be expressed exclusively in those expressing Grm2. Finally, some mRNAs enriched in the BACarray data collected from Golgi cells were not detected using the fluorescence ISH technique, perhaps reflecting limited sensitivity of ISH for low expressed genes or the need for more rigorous probe design. Thus, although a clear result for Ceacam10 expression in granule layer interneurons is not evident in either of the ISH databases (available on the world wide web at stjudebgem.org and the world wide web at brain-map.org), in both cases one can see scattered signal in this area that may indicate expression of this mRNA in cerebellar Golgi neurons.

In order to further validate the BACarray datasets, the enrichment of a variety of mRNAs isolated from the Chat (motor neuron) and Pcp2 (Purkinje cell) BACarray transgenic lines were measured with quantitative real time PCR (qRT-PCR) (Panel D). For all of the control genes tested, this methodology confirmed the BACarray results. For genes not previously known to be expressed in a specific cell type, results from qRTPCR demonstrated that seven out of the eight mRNAs assayed were in fact cell type enriched (Panel D). Moreover, despite a negative ISH result, qRT-PCR validated the expression of Ceacam10 in the cerebellum and its enrichment in Golgi cells (Panel D). In some cases, therefore, the translating ribosome affinity purification (TRAP) methodology appears to be more sensitive than ISH.

2) Quantitative PCR (qPCR) of Purified mRNA

In some experiments, 20 ng of purified RNA was used to produce cDNA with a NuGEN WT Ovation kit (NuGEN Technologies, San Carlos, Calif.) and the resulting cDNA was purified and quantified. 10 ng of cDNA was used for each real-time gene expression assay. Applied Biosystems (Foster City, Calif.) TaqMan pre-designed gene expression assays were used, following the manufacturer's instructions and using an Applied Biosystems 7900 Sequence Detection System.

Alternatively, in some experiments, cDNA was synthesized from 20 ng of total RNA from the three replicate IP and UB samples using M-MulV reverse transcriptase (M0253L), from New England Biolabs (Ipswich, Ma), using oligo dT23VN (SEQ ID NO: 1) as a primer, then purified with the Qiagen Quick PCR cleanup, following manufacturer's instructions (Qiagen, Valencia, Calif.).

Most primer sequences (Table 8) for qRT-PCR were obtained from Primer Bank (Wang and Seed, 2003). PCR was performed using Bio-Rad iQ syber green supermix following manufacturer's protocols (Biorad, Hercules, Ca), with 500 nm final concentration of each primer. Cycling and quantitation were performed using Biorad iQ5 multiplex real-time detection hardware. PCR was carried out for 45 cycles (94°, 30 seconds, 63°, 30 seconds, 72°, 30 seconds), followed by a melt curve. Each replicate was assayed in triplicate. Conditions yielding dimers, as demonstrated by melt curve and/or gel electrophoresis were excluded from further analysis. Primers that did not yield product in at least 2 of 3 replicates prior to 35 cycles were excluded from further analysis. Data were normalized to B-actin (Overbergh et al., 1999) with the ddCT method, via iQ5's optical system software version 2, and averaged across replicates. All qPCR products were subcloned and sequenced to confirm accuracy of PCR. Microarray data were also normalized to B-actin for comparison purposes.

TABLE 8

List of qRT-PCR primers
qRT-PCR primer sequences were mostly from PrimerBank (Wang and Seed, 2003)
or literature. All are listed in 5' to 3' direction.
Table 8 discloses the "Forward Primer" sequences as SEQ ID NOS
16-29, all respectively, in order of appearance.

| Gene | Forward Primer | Reverse Primer | Primerbank ID or Ref |
|---|---|---|---|
| B-Actin | agagggaaatcgtgcgtgac | caatagtgatgacctggccgt | (Overbergh et al., 1999) |
| Gfap | gtaaagactgtggagatgcgggatggtg | gtgctggtgtgggtgggaactga | |
| Chat | ccattgtgaagcggtttggg | gccaggcggttgtttagataca | 26338049a1 |
| Slc18a3 | gtgaagataggcgtgctatttgc | gactgtggaggcgaacatgac | 11096330a2 |
| Cnp1 | tgcttgatgataccaaccacg | gctgggcacagtctagtcg | 6753476a3 |
| Pcp2 | tgcagggcgatcggatggaggag | tgaggggtgagcaggggttgagg | |
| Rilp | ctgatgcggcaacctcagat | ttgagcaagaacacgttggct | 30185833a1 |
| Popdc3 | tgactgaacacccactctgc | actgccacccataaaacctact | 31745187a1 |
| Kcnn1 | ttgaaaagcgtaaacggctca | cagagcaaaagagcagagtga | 14161696a1 |
| Foxq1 | aaattggaggtgttcgtccca | tccccgtctgagcctaagg | 31560693a1 |
| Cox7a1 | gctctggtccggtcttttagc | gtactgggaggtcattgtcgg | 6753504a1 |
| Tpm2 | aagtcgctgatagcctcagag | ggtctggtgtatctccacgttc | 50190a1 |
| Crygs | cagacttccgctcgtacctaa | tcgccctggggtaagatgt | 6753532a1 |
| Cfi | cttggctctccacttgagttc | ggagcgatgcgtgtatttctg | 6671744a1 |

Example 7

Comparative Analysis Of BACarray Data Collected From Many Cell Types

Previous examples show that the BACarray data accurately reflect expression of known positive and negative controls for each cell type and that these results can be confirmed by independent experimental analysis (Heiman et al.). This example illustrates the broad properties of these cells that could be inferred from comparative analysis of this large set of microarray data. The results of this analysis are presented in FIG. 19. A hierarchical clustering of the GCRMA normalized data from all 24 IP and 6 UB samples using the 20% of probesets with the highest coefficient of variation was performed, as presented in Panel A. This unsupervised clustering essentially recapitulates the known biology of CNS cell types. Thus, the three populations of cortical projection neurons are more similar to one another than they are to cortical interneurons, Purkinje cells, or motor neurons. Astroglial BACarray data collected from different regions of the brain are, as expected, more similar to one another and to Bergmann glia than they are to oligodendrocytes. Oligodendroglia are more similar to each other than they are to any neuronal population, etc. These findings support the concept that cells with similar gene expression patterns share similar functions, and suggest that analysis of BACarray data will allow for the identification of those gene products responsible for the distinguishing characteristics of each cell type.

The diversity of translational profiles across neuronal types nearly rivals the diversity between neurons and glia. Although related cell subtypes, such as different motor neurons or the Drd1 and Drd2 medium spiny neurons, are clearly tightly clustered, many neuronal types (e.g. Purkinje cells) are not strongly clustered with any other cell type. This suggests that comparative analysis of BACarray translational profiles obtained from highly specialized cell types may yield insights into their biochemical properties. Finally, individual cell types did not generally cluster tightly with the UB samples from their tissue of origin. In fact, profiles from UB samples derived from different brain regions were loosely clustered together relative to the data obtained from specific CNS cell types, suggesting that microarray data produced from dissected whole brain regions are less informative than BACarray analysis of individual cell types.

To examine this point in more detail, the microarray data from total cerebellum to that of the cerebellar cell types analyzed in this study were compared. As can be seen in Panel B, any single cell type has fewer probesets detectable than the whole cerebellar sample, since the whole cerebellar sample represents an aggregate of different cell types. However, comparative analysis of the sum of the probesets detectable in each of the six individual cerebellar cell types and the results obtained from whole cerebellar tissue reveals over 4000 probesets that are undetectable in the microarray from whole cerebellum. These undetectable probesets tend to represent cell-type enriched genes. In fact, for rare cell types, up to 42% of the genes enriched in that cell may not be detectable at all in whole-tissue microarray studies. For detection of genes expressed in specific cell types within complex brain regions, therefore, the translating ribosome affinity purification (TRAP) methodology can be more sensitive than microarray analysis of dissected brain regions.

The increased sensitivity of the translating ribosome affinity purification (TRAP) methodology results in identification of more mRNAs in each cell type, yielding a more complete picture of the translational profile for each cell type, more information. To assess if this increased sensitivity in fact does gives better information, the Shannon entropy was calculated for each probeset across the six whole tissue samples, and across the twenty four individual cell populations (Fuhrman et al., 2000; Shannon and Weaver, 1969). Shannon entropy is a measure of information content that describes the complexity of a signal across samples, with values ranging from 0 (low information) to 2 (high information). Data are presented in FIG. 20. Examples of probeset with low and high information are shown in Panel B. Shannon entropy measures of the information content in these samples reveals that the average Shannon entropy in cell type specific experiments (IP's) is over twice as high as that calculated from microarray data of whole tissue samples (t-Test, $p<0.0001$, average entropy across all IPs: 0.88+/−0.002, whole tissue: 0.41+/−0.003). This analysis demonstrates that microarray data collected from specific cell types using the BACarray strategy can provide better information than traditional microarray studies of dissected brain tissues.

As those genes with high entropy measures across all samples are those that vary in the most complex manner between cell types, this entropy measure was applied to assess what fundamentally determines the differences between cell types in the nervous system. As seen in Panel C, the ten percent of the probesets with highest entropy and those with the lowest entropy were classified with Gene Ontologies and then searched for functional categories that were over-represented (Ashburner et al., 2000; Maere et al., 2005). According to this analysis, cell type diversity in the nervous system is driven primarily by the expression of cell surface proteins, such as channels and receptors, and also to some extent by the specific expression of transcription factors and calcium binding proteins. Genes with less information content tend to be those that that are more ubiquitously expressed, such as ribosomal and mitochondrial proteins. This is not to say that they do not vary—their expression can range often from two to five fold across cell types—but they vary less dramatically than the tens to thousands fold changes of many receptors and channels.

Table 9 is a comparative analysis of translational profiling to identify co-regulated genes that could encode the highly specialized properties of individual cell types. This analysis is can be useful in trying to identify gene sets for known functions or candidate functions for novel gene products, since in many cases these cohorts of co-regulated genes will include genes with well known functions. To test whether the BACarray data provided can yield productive results in this sort of query, a probeset for a gene known to be involved in myelination was selected—the myelin basic protein (Mbp). Its highest correlates were examined across all IP and UB samples. In the top 35 genes correlating with Mbp expression (min correlation, 0.86), 6 genes also known to be involved in myelination were identified, including Plp1, Cnp, Mog, Mal and Mobp, and another three genes previously identified in a proteomic screen of myelin components (Table 9).

TABLE 9

Genes correlating with myelin basic protein.
Correlation of genes with a Mbp probeset (1419646_a_at) identifies known and putative novel myelination genes. Four of the first eleven genes correlated with Mbp represent genes for the known myelin components Mal, Plp, Mobp, and Mog. This coexpression suggests that novel genes highly correlated with Mbp (C11orf9, A330104H05Rik, Bcas1) may also be involved in myelination. Pearson's correlation. Only the first probeset for each gene is shown for those genes with multiple probesets on the array. In bold are genes identified in an independent proteomic screen of myelin components (Vanrobaeys et al., 2005).

| Probeset | Correlation | Symbol | Name |
|---|---|---|---|
| 1419646_a_at | 1 | Mbp | myelin basic protein |
| 1417275_at | 0.968 | Mal | myelin and lymphocyte protein, T-cell differentiation protein |
| 1451718_at | 0.964 | Plp | proteolipid protein (myelin) |
| 1440902_at | 0.958 | Galnt5 | UDP-N-acetyl-alpha-D-galactosamine:polypeptide N-acetylgalactosaminyltransferase 5 |
| 1433785_at | 0.958 | Mobp | myelin-associated oligodendrocytic basic protein |
| 1436578_at | 0.955 | A330104H05Rik | novel |
| 1428792_at | 0.946 | Bcas1 | breast carcinoma amplified sequence 1 |
| 1439506_at | 0.934 | C11ORF9 homolog | novel |
| 1426960_a_at | 0.931 | Fa2h | fatty acid 2-hydroxylase |
| 1433543_at | 0.926 | Anln | anillin, actin binding protein (scraps homolog, Drosophila) |
| 1448768_at | 0.921 | Mog | myelin oligodendrocyte glycoprotein |
| 1418086_at | 0.917 | Ppp1r14a | protein phosphatase 1, regulatory (inhibitor) subunit 14A |
| 1434094_at | 0.914 | 6330530A05Rik | novel |
| 1420760_s_at | 0.911 | Ndrg1 | N-myc downstream regulated 1 |
| 1447807_s_at | 0.905 | Plekhh1 | pleckstrin homology domain containing, family H (with MyTH4 domain) member 1 |
| 1425546_a_at | 0.905 | Trf | transferrin |
| 1436974_at | 0.904 | A230069A22Rik | novel |
| 1450241_a_at | 0.904 | Evi2a | ecotropic viral integration site 2a |
| 1418472_at | 0.903 | Aspa | aspartoacylase (aminoacylase) 2 |
| 1452834_at | 0.9 | 2600010E01Rik | novel |
| 1429909_at | 0.894 | 4833411O04Rik | novel |
| 1453009_at | 0.893 | 1110060I01Rik | novel |
| 1440813_s_at | 0.89 | Plxnb3 | plexin B3 |
| 1437171_x_at | 0.888 | Gsn | gelsolin |
| 1423871_at | 0.887 | BC014795 | novel |

TABLE 9-continued

Genes correlating with myelin basic protein.
Correlation of genes with a Mbp probeset (1419646_a_at) identifies known and putative novel myelination genes. Four of the first eleven genes correlated with Mbp represent genes for the known myelin components Mal, Plp, Mobp, and Mog. This coexpression suggests that novel genes highly correlated with Mbp (C11orf9, A330104H05Rik, Bcas1) may also be involved in myelination. Pearson's correlation. Only the first probeset for each gene is shown for those genes with multiple probesets on the array. In bold are genes identified in an independent proteomic screen of myelin components (Vanrobaeys et al., 2005).

| Probeset | Correlation | Symbol | Name |
| --- | --- | --- | --- |
| 1434399_at | 0.887 | Galnt6 | UDP-N-acetyl-alpha-D-galactosamine:polypeptide N-acetylgalactosaminyltransferase 6 |
| 1435854_at | 0.885 | Tmem10 | transmembrane protein 10 |
| 1416371_at | 0.878 | Apod | apolipoprotein D |
| 1418406_at | 0.877 | Pde8a | cAMP-specific cyclic nucleotide phosphodiesterase PDE8 |
| 1416003_at | 0.875 | Cldn11 | claudin 11 |
| 1434606_at | 0.872 | Erbb3 | v-erb-b2 erythroblastic leukemia viral oncogene homolog 3 (avian) |
| 1451932_a_at | 0.872 | Tsrc1 | thrombospondin repeat containing 1 |
| 1418980_a_at | 0.871 | Cnp1 | cyclic nucleotide phosphodiesterase 1 |
| 1416318_at | 0.87 | Serpinb1a | serine (or cysteine) proteinase inhibitor, clade B, member 1a |
| 1424468_s_at | 0.868 | D330037A14Rik | novel |

FIG. 21 shows a comparative analysis of the individual cell samples to identify only those genes most highly specific for each population. An iterative comparison was performed: one-by-one, each sample was compared to each other sample in the dataset, and for each population, probesets were sorted by their average ranking across these comparisons. Data were then combined and clustered by expression the top one hundred ranked probesets for each population in a heatmap (Panel A). This heat map readily illustrates the extent to which distinct cell types are characterized by specific cohorts of genes. For example, cerebellar Purkinje cells are clearly distinguished by a group of genes that are not seen in any other cell types (Panel A). Thus none of the top twenty five most specific probesets observed in the Purkinje cell sample are found in any of the top twenty five most specific probesets for any of the other cell types. In contrast, Drd1 and Drd2 medium spiny neurons, two closely related cell types, co-express many genes that are not found in the other cell populations analyzed, yet they also express distinct subsets of genes that differentiate them (Heiman et al). Thus, comparative analysis of BACarray data can be used to characterize CNS cell populations with unique biochemical and physiological properties, and to distinguish between closely related cell types at the molecular and biochemical level.

As shown in the tables in Panel B, the top twenty five most specific probesets in each cell type include probesets for both well known cell-specific markers and novel, previously uncharacterized genes. For example, Pcp2, the calcium binding protein Calb1, the scaffolding/synaptic protein Homer3, and the transcription factor Ebf2, all of which are known to be specifically expressed in Purkinje cells (Malgaretti et al., 1997; Shiraishi et al., 2004; Wang et al., 1997), are among the most highly ranked probesets in the Pcp2 BACarray list. Mobp, one of the most abundant components of the CNS myelin sheath (Montague et al., 2006), is prominent in the Cmtm5 myelinating oligodendrocytes' list. The expression of Tcrb in deep layer cortical neurons (Nishiyori et al., 2004) is confirmed in the Ntsr1 BACarray data. The large number of uncharacterized genes with cell specific translation identified here provide an important resource for discovery of novel biochemical pathways operating in these cell types, or for the identification of new proteins operating in well known pathways. Finally, comparative analysis can reveal discrepancies that are not apparent from anatomical studies. For example, the most specific probesets for the Etv1 line identify several genes well-known to be expressed in lymphoid cells, suggesting that in this line the eGFP-L10a transgene may also be expressed in circulating cells in the CNS vasculature. Taken together, the data shown above demonstrate two important strengths of large-scale comparative analyses of BACarray data. First, molecular relationships between cell types can be easily established with hierarchical clustering; second, groups of genes that encode the biochemical functions of specific cell types can be identified using this sort of systematic comparative approach.

Example 8

Analysis of BACarray Data Collected from Spinal Motor Neurons

Due to their involvement in a variety of serious neurological disorders and severe, acute injuries, spinal cord motor neurons (MN) are among the most well studied cell types of the CNS. As such, they provide an opportunity to evaluate the BACarray data with the depth of the knowledge available for this cell type. In particular, a wealth of anatomical and physiological data available for MN, and the comprehensive studies of transcription factors involved in their development, allowing comparison of the BACarray data presented here with the published literature. As shown in FIG. 22, in a single BACarray experiment, most of the MN expressed molecules that have been documented in prior studies are rediscovered. To perform this analysis, BACarray results were color coded as 'expressed,' 'enriched,' or 'not expressed,' as described in the methods. This classification was then compared to results reported in the adult rodent literature, color coded simply as either 'expressed' or 'not expressed' or left uncolored in cases where there were no studies or conflicting data. In most cases, where microarray probesets were present and informative, BACarray results agree well with the literature.

Thus, it has been reported that MNs express glutamate receptors sensitive to AMPA, kainate, and NMDA (Rekling et al., 2000). These results suggest that the specific receptor subunits mediating these responses include Gria3 and 4, Grik2 and 4, and Grin1, 3a and 3b. Inhibition in MNs should be due the actions of the Glrα2 and GlrB glycine receptor subunits and both metabotropic (Gabbr1) and ionotropic GABAergic receptors, potentially composed of Gabrα2, α5, and β3 subunits. These data predict that MNs should respond to all classic neurotransmitters, including acetylcholine, via Chrnα4/β2 and/or Chrnα7 receptors, and serotonin, via the Htr1d receptor. In disagreement with prior immunohistochemical findings (Rekling et al., 2000), expression of Drd1 and or Drd2 in MNs was not detected. Moreover, transgenic mice for Drd1 and Drd2 do not show transgene expression in MNs, nor does the Allen Brain Atlas ISH show expression in brain stem MN, supporting the BACarray results.

MNs also express a variety of newly characterized receptors and orphan receptors. For example, BACarray data has successfully identified Grin3b as a MN specific gene encoding an NMDA subunit. This receptor was recently characterized as creating a unique glycine gated channel in MNs (Chatterton et al., 2002; Nishi et al., 2001). Several other genes enriched in MNs have also been identified which potentially encode for MN specific receptors that either have not been previously characterized in MNs or are entirely unstudied. Two that are particularly interesting are the vitamin D receptor and the orphan receptor P2rx11. Future studies investigating the role of these receptors in MN behavior may explain cases of reversible muscle weakness in patients with vitamin D deficiency (Whitaker et al., 2000; Ziambaras and Dagogo-Jack, 1997), or suggest new pathways important to MN function.

Example 9

Molecular Phenotyping and Translational Profiling of Cholinergic Motor Neurons and Purkinje Neurons To determine whether the BACarray technique could be used for the characterization of other types of neurons, cholinergic and Purkinje cell-specific BACarray lines were produced, as presented in FIG. 23. The cholinergic cell BACarray line was produced by placement of the eGFP-L O10a transgene under the control of the choline acetyltransferase (Chat) locus, which is specifically expressed in cholinergic cells in the CNS. As expected from the published Chat expression pattern in the rat CNS (Oh et al., 1992), the Chat BACarray line DW167 showed highest eGFP-L10a expression in cholinergic cells of the dorsal striatum and ventral striatum (nucleus accumbens, olfactory tubercle, and islands of Calleja), basal forebrain, brain stem, spinal cord, and medial habenula (Panel a). eGFP expression was shown to be restricted to cholinergic cells in all of these structures, including motor neurons of the brain stem (Panel b), by indirect immunofluorescence staining for Chat. One exception to this colocalization was in the pedunculopontine and laterodorsal tegmental nuclei, where only a minority of cholinergic cells were labeled with eGFP.

The Purkinje cell BACarray line DR166 was produced by placement of the eGFP-L10a transgene under the control of the Purkinje cell protein 2 (Pcp2) locus, which is specifically expressed in cerebellar Purkinje cells of the CNS (Oberdick et al., 1988). The Pcp2 BACarray line showed eGFP-L10a expression that was restricted to cells that possessed a characteristic Purkinje cell morphology (Panel c). Restriction of eGFP-L10a expression to cerebellar Purkinje cells was confirmed by indirect immunofluorescent staining of Calbindin-D28K (Panel D), which in the cerebellum is specifically expressed in Purkinje cells (Nordquist et al., 1988). Array data were collected from brain stem cholinergic motor neurons using the Chat BACarray line and from Purkinje cells using the Pcp2 BACarray line. Replicate Chat BACarray samples gave nearly identical genome-wide translational profiles (average Pearson correlation=0.982), as was the case for replicate Pcp2

BACarray samples (average Pearson correlation=0.997). To provide a measure of the enrichment of each mRNA immunoprecipitated from the targeted cell type (IP) versus its expression in a reference sample (unbounds in immunoprecipitations), the ratio of the expression in each IP sample versus the reference sample was calculated. This comparison identified those genes which were highly enriched in each cell type versus a common reference sample. As expected from the analysis of D1 and D2 combined BACarray data versus whole brain minus, differences are evident between the genome-wide translational profiles of IP samples compared to the reference sample for all the individual samples analyzed: striatonigral (D1), striatopallidal (D2), brain stem cholinergic (Chat), and Purkinje cells (Pcp2). FIG. 24 shows that enrichment of cell-specific positive-control genes and exclusion of known negative-control genes (glial genes), were evident for each comparison (panels a-d). Venn diagrams constructed from the top 1,000 enriched probesets from this analysis (Tables 17-20) confirmed that the translational profiles of striatonigral and striatopallidal cells show greater similar to each other than they do to the translational profiles of either brain stem cholinergic cells or Purkinje cells (panels e-h).

Example 10

Molecular Phenotyping and Translational Profiling of the Striatum

1) Overview

This example presents a study of the specific properties of the striatum. This example illustrates one embodiment that can uncover unexpected molecular and physiological complexity in closely related and spatially adjacent CNS cell populations. The striatum is a subcortical part of the telencephalon. It is the major input station of the basal ganglia system. In this example, transgenic mice containing molecularly tagged ribosomal proteins in the striatonigral and striatopallidal cells of the striatum were created using standard BACarray techniques. Striatonigral and striatopallidal medium spiny neurons (MSNs), are intermixed, indistinguishable in somato-dendritic morphology, and of major interest due to their role in the etiology of various neurological diseases, including Parkinson's disease, schizophrenia, attention deficit hyperactivity disorder, drug addiction, and Huntington's disease. Striatonigral MSNs send projection axons directly to the output nuclei of the basal ganglia, i.e. the substantia nigra and the internal segment of the globus pallidus (the entopeduncular nucleus in rodents), while striatopallidal MSNs send projection axons to the external segment of the globus pallidus. Striatonigral MSNs are known to preferentially express the dopamine D1 receptor (Drd1; Drd1a) and the neuropeptides substance P (Tac1) and dynorphin (Pdyn), while striatopallidal MSNs preferentially express the dopamine D2 receptor (Drd2), the adenosine A2a receptor (Adora2a) and the neuropeptide enkephalin (Penk) (S. Gong et al., Nature 425, 917-25 (2003)).

2) Production of BACarray Striatal Mice

Mice containing molecularly tagged ribosomal proteins in the striatonigral and striatopallidal cells of the striatum were created. Homologous recombination in bacteria was used to place eGFP-L10a under the control of either the D2 receptor (striatopallidal) or D1 receptor (striatonigral) loci in the appropriate BACs. Mouse lines were generated by pronuclear injection of engineered BACarray DNA constructs into fertilized oocytes.

Mouse lines were screened by immunohistochemistry for appropriate expression of the transgene, as judged by known D1 and D2 receptor expression patterns. In the Drd2 line, 75.8% colocalization of pro-enkephalin with eGFP-L10a (n=204/269) was observed and in the Drd1a line 0% colocalization was observed (n=0/325). For the Drd2 line, this number is likely an underestimate, as heat-induced epitope retrieval in citrate buffer is needed for optimal staining using pro-enkephalin antibodies. Heat-induced epitope retrieval in the colocalization experiments was not utilized, however, because both eGFP fluorescence and the ability of various GFP antibodies to recognize eGFP are substantially diminished upon use of these epitope retrieval methods. Colocalization data for eGFP-L10a (direct eGFP fluorescence) and pro-enkephalin expression (immunohistochemical staining) is presented (FIG. 25): (a) Immunohistochemistry to eGFP in adult sagittal sections from the D2 BACarray line CP101. (b) Characterization of D2 BACarray line CP101 striatal MSN cells: direct eGFP fluorescence (left panel with high-magnification image insert); enkephalin immunohistochemical staining (middle panel); merge (right panel, with 20 m scale bar). (c) Immunohistochemistry to eGFP in adult sagittal sections from the D1 BACarray line CP73. (d) Characterization of D1 BACarray line CP73 striatal MSN cells: direct eGFP fluorescence (left panel); enkephalin immunohistochemical staining (middle panel); merge (right panel).

The D2 BACarray line showed highest transgenic eGFP-L10a expression in the dorsal and ventral striatum, olfactory tubercle, and hippocampus. In addition, expression of eGFP was seen in the substantia nigra pars compacta and ventral tegmental area of this line, as expected due to D2 autoreceptor expression in dopaminergic cells (panel a). The D1 BACarray line showed highest transgenic eGFP-L10a expression in the dorsal and ventral striatum, olfactory bulb, olfactory tubercle, and cortical layers 5 and 6 (panel c). As expected for a ribosomal protein fusion, direct visualization of eGFP fluorescence revealed localization of transgenic eGFP-L10a to the nucleoli and cytoplasm (panel b). eGFP co-localization with enkephalin expression (striatopallidal cell marker) was observed in striatal cells from the D2 BACarray line but not the D1 BACarray line (panels b and d), verifying correct BAC-mediated cell-type expression.

The polysome profile from D2 BACarray mouse striatal extract is presented in FIG. 26 as follows: Top: Post-mitochondrial striatal extract (S20) was loaded onto a linear sucrose gradient (20-50% w/w). After velocity sedimentation, fractions (direction of sedimentation noted by arrow) were collected as UV absorbance (254 nm) was measured. Bottom: gradient fractions were ethanol precipitated, resuspended in SDS-PAGE loading buffer, and Rpl7 and eGFP-L10a content were assayed by Western blotting. Velocity sedimentation analysis of polysome complexes isolated from striatal extracts for both lines of BACarray mice confirmed incorporation of the eGFP-L10a fusion protein into functional polysomes in vivo.

3) BACarray Profiling of Striatonigral and Striatopallidan MSNs

A plurality of differentially expressed genes can be identified which characterize striatonigral and striatopallidal MSNs, including all previously known markers. Translation profiling and molecular Phenotyping was performed with immunoaffinity-purified mRNA from adult striatonigral or striatopallidal BACarray mice. Following two rounds of in vitro transcription, biotin-labeled antisense RNA (cRNA) was used to interrogate Affymetrix GeneChip Mouse Genome 430 2.0 arrays. For each cell type, data were collected from three independent biological replicates, each prepared from a cohort of 7 animals. Analysis of immunoaffinity-purified samples revealed no bias for mRNA length or abundance (FIG. 27). Lengths of transcripts were based on all available mouse curated RefSeq RNA sequences (available using the file transfer protocol ncbi.nih.gov/genomes/M_musculus/RNA). Where multiple transcript variants for a single gene were available, the longest one was chosen. RefSeq lengths were plotted against D1 (a) or D2 (b) BACarray IP normalized expression values. There was no correlation observed between transcript length and IP values. Striatal expression values for all Affymetrix Genechip probe sets were obtained by total RNA arrays from wild-type striatal tissue (data not shown). These values were plotted against (c) D1 BACarray or (d) D2 BACarray IP normalized values. As expected, higher expression in total striatum (no IP, wild type mice) correlates with higher D1 or D2 BACarray IP values. The few genes that showed modest expression in total striatum but had low IP values include known non-neuronal genes.

Comparative analysis of these data revealed that all 8 of the well-characterized, differentially expressed MSN markers were enriched using the BACarray approach: D2 (Drd2) (36.6×), adenosine 2a receptor (Adora2a) (13.2×), and enkephalin (Penk) (7.5×) were enriched in the striatopallidal BACarray sample, while D1 (Drd1a) (3.9×), substance P (Tac1) (3.6×), and dynorphin (Pdyn) (5.6×) were enriched in the striatonigral BACarray sample (FIG. 28 and Table 10). Four striatopallidal-enriched mRNAs (Adk, Plxdc1, BC004044, and Hist1h2bc) and six striatonigral-enriched mRNAs (Slc35d3, Zfp521, Ebf1, Stmn2, Gnb4, and Nrxn1) were confirmed as reported in a microarray study of FACS sorted MSNs (S. Magdaleno et al., PLoS Biol 4, e86 (2006)). However, the data identified approximately 70 additional striatopallidal enriched transcripts and over 150 additional striatonigral-enriched transcripts ( Table 10). To provide an initial test of the data, quantitative PCR studies were carried out using independent biological BACarray D1 and D2 samples and a different cDNA amplification procedure (A. Alexa, J. Rahnenfuhrer, T. Lengauer, Bioinformatics 22, 1600-7 (2006)). Differential expression of Eya1, Isl1, Gng2, and Crym in striatonigral MSNs, and Gpr6, Lhx8, Gpr88, Trpc4, and Tpm2 in striatopallidal MSNs was confirmed (Table 11 and Table 12). qPCR assays used were Gapdh: Mm99999915_g1, Drd2: Mm00438541_m1, Gpr6: Mm01701705_s1, Lhx8: Mm00802919_m1, Gpr88: Mm02620353_s1, Trpc4: Mm00444284_m1, Tpm2: Mm00437172_g1, Eya1: Mm00438796_m1, Tac1: Mm00436880_m1, Isl1: Mm00627860_m1, Gng2: Mm00726459_s1, Chrm4: Mm00432514_s1, Drd1a: Mm02620146_s1, Crym: Mm01281258_m1, Actb: Hs99999903_m1, and Fth1: Hs01694011_s1. Each assay was performed in quadruplicate and fold enrichment values were derived from the comparative Ct method (following Applied Biosystems recommendations), with each target amplification compared to a Gapdh or Actb reference amplification.

TABLE 10

Genes differentially translated between striatonigral and striatopallidal cells.

| Probe | Symbol | GenBank | FCH |
|---|---|---|---|
| 1457424_at | Eya1 | BB760085 | 32.49 |
| 1424606_at | Cplx3 | BC024854 | 19.56 |
| 1418047_at | Neurod6 | NM_009717 | 13.05 |
| 1428393_at | Nrn1 | AK003046 | 12.21 |
| 1417560_at | Sfxn1 | BB478992 | 11.99 |
| 1422720_at | Isl1 | BQ176915 | 10.10 |
| 1450723_at | Isl1 | BQ176915 | 9.44 |
| 1420388_at | Prss12 | NM_008939 | 9.25 |
| 1419473_a_at | Cck | NM_031161 | 9.11 |
| 1447863_s_at | Nr4a2 | BB322941 | 9.00 |
| 1419200_at | Fxyd7 | NM_022007 | 7.90 |
| 1455034_at | Nr4a2 | BB703394 | 7.52 |
| 1417559_at | Sfxn1 | BB478992 | 7.42 |
| 1428642_at | Slc35d3 | AK018094 | 7.32 |
| 1451499_at | Cadps2 | AF000969 | 6.87 |
| 1450750_a_at | Nr4a2 | NM_013613 | 6.44 |
| 1426852_x_at | Nov | X96585 | 6.44 |
| 1431339_a_at | Efhd2 | AK007560 | 6.00 |
| 1428184_at | 3110035E14Rik | BB348639 | 5.61 |
| 1416266_at | Pdyn | AF026537 | 5.59 |
| 1428157_at | Gng2 | AV021455 | 5.08 |
| 1441388_at |  | BB428710 | 5.05 |
| 1437478_s_at | Efhd2 | AA409309 | 5.04 |
| 1423280_at | Stmn2 | BM115022 | 4.89 |
| 1428156_at | Gng2 | AV021455 | 4.85 |
| 1421727_at | Eya1 | NM_010164 | 4.84 |
| 1451322_at | Cmbl | BC024580 | 4.82 |
| 1423281_at | Stmn2 | BM115022 | 4.73 |
| 1448293_at | Ebf1 | BB125261 | 4.72 |
| 1416711_at | Tbr1 | NM_009322 | 4.70 |
| 1422256_at | Sstr2 | NM_009217 | 4.68 |
| 1416302_at | Ebf1 | BB125261 | 4.55 |
| 1440361_at |  | BB272510 | 4.48 |
| 1455893_at | Rspo2 | BG067392 | 4.35 |
| 1428664_at | Vip | AK018599 | 4.35 |
| 1419470_at | Gnb4 | BI713933 | 4.32 |
| 1452779_at | 3110006E14Rik | AK014009 | 4.26 |
| 1416301_a_at | Ebf1 | BB125261 | 4.25 |
| 1436312_at | Ikzf1 | AV317621 | 4.20 |
| 1424737_at | Thrsp | BC009165 | 4.16 |
| 1448366_at | Stx1a | NM_016801 | 4.14 |
| 1451620_at | C1ql3 | BB768838 | 4.11 |
| 1448889_at | Slc38a4 | NM_027052 | 4.08 |
| 1426851_a_at | Nov | X96585 | 4.07 |
| 1426318_at | Serpinb1b | AF426025 | 4.03 |
| 1423287_at | Cbln1 | AA016422 | 4.01 |
| 1417343_at | Fxyd6 | AB032010 | 3.99 |
| 1427017_at | Satb2 | BB104560 | 3.92 |
| 1419469_at | Gnb4 | BI713933 | 3.89 |
| 1455629_at | Drd1a | BE957273 | 3.87 |
| 1417400_at | Rai14 | NM_030690 | 3.74 |
| 1423286_at | Cbln1 | AA016422 | 3.71 |
| 1456051_at | Drd1a | BB282271 | 3.69 |
| 1419184_a_at | Fhl2 | NM_010212 | 3.64 |
| 1434440_at | Gnai1 | BQ174580 | 3.64 |
| 1418789_at | Sntg2 | NM_133742 | 3.61 |
| 1416783_at | Tac1 | NM_009311 | 3.61 |
| 1457440_at | Sstr4 | BB451927 | 3.59 |
| 1418451_at | Gng2 | BB522409 | 3.57 |
| 1442724_at | AW060763 | AW120464 | 3.55 |
| 1455758_at | Prkcc | BM215011 | 3.52 |
| 1430306_a_at | Atp6v1c2 | AK004157 | 3.48 |
| 1456515_s_at | Tcfl5 | AV044715 | 3.43 |
| 1416953_at | Ctgf | NM_010217 | 3.40 |
| 1441917_s_at | Tmem40 | BB468188 | 3.35 |
| 1437091_at | Accn4 | AV323885 | 3.30 |
| 1436786_at | Sec14l3 | AV024133 | 3.29 |
| 1429274_at | 2310010M24Rik | AK009282 | 3.23 |
| 1421017_at | Nrg3 | NM_008734 | 3.23 |
| 1416503_at | Lxn | NM_016753 | 3.22 |
| 1417933_at | Igfbp6 | NM_008344 | 3.18 |

TABLE 10-continued

Genes differentially translated between striatonigral and striatopallidal cells.

| Probe | Symbol | GenBank | FCH |
|---|---|---|---|
| 1427510_at | Gnai1 | U38501 | 3.16 |
| 1436862_at | Doc2a | BB543070 | 3.13 |
| 1452065_at | Vstm2 | BB085570 | 3.11 |
| 1448546_at | Rassf3 | BB703307 | 3.08 |
| 1429175_at | Tmem178 | AK014196 | 3.08 |
| 1418417_at | Msc | NM_010827 | 3.08 |
| 1448812_at | Hpcal1 | NM_016677 | 3.07 |
| 1454691_at | Nrxn1 | BB336165 | 3.04 |
| 1450042_at | Arx | BB322201 | 3.04 |
| 1446498_at | Il20ra | BB551879 | 3.03 |
| 1457984_at | Crh | BM933756 | 3.03 |
| 1438729_at |  | BB176347 | BB331017 | 3.03 |
| 1440108_at | Foxp2 | BM964154 | 2.99 |
| 1434695_at | Dtl | AV270035 | 2.97 |
| 1439632_at |  | BQ174397 | 2.96 |
| 1417288_at | Plekha2 | NM_031257 | 2.93 |
| 1426937_at | 6330406I15Rik | AK018128 | 2.92 |
| 1438624_x_at | Hs3st2 | BB494451 | 2.85 |
| 1440849_at | 6330417G04Rik | AV327187 | 2.85 |
| 1426738_at | Dgkz | BC014860 | 2.84 |
| 1428781_at | Dmkn | BI452905 | 2.83 |
| 1439789_at | Ebf1 | BQ177189 | 2.83 |
| 1450055_at | Vsnl1 | NM_012038 | 2.83 |
| 1417569_at | Ncald | BG071381 | 2.80 |
| 1437671_x_at | Prss23 | BB378796 | 2.79 |
| 1444661_at | Gpr26 | BB247791 | 2.79 |
| 1427975_at | Rasl10a | AK008807 | 2.77 |
| 1438112_at | 9430021M05Rik | AA546727 | 2.76 |
| 1436787_x_at | Sec14l3 | AV024133 | 2.73 |
| 1417579_x_at | Gmppa | NM_133708 | 2.72 |
| 1456146_at | 2210411A11Rik | BI735554 | 2.72 |
| 1436503_at | BC048546 | BF302511 | 2.71 |
| 1420720_at | Nptx2 | NM_016789 | 2.70 |
| 1455925_at | Prdm8 | AV349236 | 2.68 |
| 1448632_at | Psmb10 | NM_013640 | 2.67 |
| 1426329_s_at | Baalc | AF371320 | 2.65 |
| 1448669_at | Dkk3 | AK004853 | 2.65 |
| 1425090_s_at | Kcnc4 | BC024837 | 2.64 |
| 1454959_s_at | Gnai1 | BQ174580 | 2.63 |
| 1453558_at | 4930504H06Rik | AK015697 | 2.63 |
| 1423757_x_at | Igfbp4 | BC019836 | 2.62 |
| 1437405_a_at | Igfbp4 | BB787243 | 2.59 |
| 1450059_at | Fancg | BG072083 | 2.54 |
| 1450708_at | Scg2 | NM_009129 | 2.52 |
| 1429269_at | BC068157 | BE992549 | 2.51 |
| 1422537_a_at | Id2 | NM_010496 | 2.51 |
| 1417568_at | Ncald | BG071381 | 2.49 |
| 1435411_at |  | BE950834 | 2.49 |
| 1424966_at | Tmem40 | BC019416 | 2.48 |
| 1438796_at | Nr4a3 | BE692107 | 2.48 |
| 1416776_at | Crym | NM_016669 | 2.47 |
| 1437406_x_at | Igfbp4 | BB787243 | 2.45 |
| 1423202_a_at | Ncor1 | U22016 | 2.45 |
| 1444307_at |  | AW491448 | 2.44 |
| 1439573_at | Rtn4rl2 | BE992565 | 2.43 |
| 1417605_s_at | Camk1 | NM_133926 | 2.42 |
| 1425784_a_at | Olfm1 | D78264 | 2.39 |
| 1455074_at | Efcab1 | AV307860 | 2.39 |
| 1451342_at | Spon1 | BC020531 | 2.38 |
| 1420955_at | Vsnl1 | NM_012038 | 2.38 |
| 1417192_at | Tomm70a | NM_138599 | 2.38 |
| 1452169_a_at | Dgkz | BC014860 | 2.37 |
| 1418304_at | Pcdh21 | NM_130878 | 2.37 |
| 1454770_at | Cckbr | AV221910 | 2.37 |
| 1440918_at |  | AW495511 | 2.37 |
| 1448754_at | Rbp1 | NM_011254 | 2.37 |
| 1428240_at | Nrxn1 | AK017578 | 2.36 |
| 1453245_at | 9130024F11Rik | BB329046 | 2.36 |
| 1438231_at | Foxp2 | AV322952 | 2.36 |
| 1438232_at | Foxp2 | AV322952 | 2.35 |
| 1417578_a_at | Gmppa | NM_133708 | 2.34 |
| 1428077_at | Tmem163 | AK011522 | 2.32 |
| 1453317_a_at | Khdrbs3 | AK014353 | 2.32 |
| 1419551_s_at | Stk39 | BG919998 | 2.32 |
| 1421144_at | Rpgrip1 | NM_023879 | 2.32 |

TABLE 10-continued

Genes differentially translated between striatonigral and striatopallidal cells.

| Probe | Symbol | GenBank | FCH |
|---|---|---|---|
| 1421926_at | Mapk11 | AV329330 | 2.30 |
| 1415849_s_at | Stmn1 | BC010581 | 2.30 |
| 1424763_at | 1700027N10Rik | BC019423 | 2.27 |
| 1459847_x_at | Gfra2 | AV354240 | 2.27 |
| 1449314_at | Zfpm2 | NM_011766 | 2.26 |
| 1430634_a_at | Pfkp | BB076574 | 2.26 |
| 1457032_at | Ak5 | BB546359 | 2.25 |
| 1453129_a_at | Rgs12 | AK004813 | 2.24 |
| 1447669_s_at | Gng4 | AV347903 | 2.24 |
| 1433909_at |  | AW048713 | 2.22 |
| 1424701_at | Pcdh20 | BB528056 | 2.21 |
| 1435959_at | Arhgap15 | BM246535 | 2.21 |
| 1417988_at | Resp18 | NM_009049 | 2.21 |
| 1455885_at | Gna12 | AV238106 | 2.21 |
| 1427054_s_at | Abi3bp | BC026627 | 2.20 |
| 1458112_at | Adarb2 | BB527550 | 2.20 |
| 1427115_at | Myh3 | M74753 | 2.19 |
| 1449556_at | H2-T23 | NM_010398 | 2.18 |
| 1435176_a_at | Id2 | BF019883 | 2.16 |
| 1422552_at | Rprm | NM_023396 | 2.15 |
| 1416131_s_at | C920006C10Rik | BB188557 | 2.15 |
| 1436609_a_at | Lrpap1 | AV309553 | 2.14 |
| 1451332_at | Zfp521 | BC021376 | 2.13 |
| 1452444_at | Napb | AU067119 | 2.13 |
| 1457277_at | BC038925 | AI314927 | 2.13 |
| 1434243_s_at | Tomm70a | AV233564 | 2.12 |
| 1436592_at |  | BB453760 | 2.12 |
| 1448249_at | Gpd1 | BC019391 | 2.11 |
| 1417604_at | Camk1 | NM_133926 | 2.09 |
| 1443129_at |  | BB363699 | 2.09 |
| 1452741_s_at | Gpd2 | BQ175968 | 2.08 |
| 1417960_at | Cpeb1 | NM_007755 | 2.08 |
| 1418726_a_at | Tnnt2 | NM_011619 | 2.08 |
| 1442887_at | Gpr39 | BQ175060 | 2.07 |
| 1421176_at | Rasgrp1 | BB354696 | 2.06 |
| 1428650_at | Tns1 | AK003780 | 2.06 |
| 1428323_at | Gpd2 | BQ175968 | 2.06 |
| 1425287_at | Zfp189 | BC021326 | 2.06 |
| 1452974_at | Nol8 | AK017551 | 2.05 |
| 1417038_at | 8-Sep | NM_017380 | 2.03 |
| 1417943_at | Gng4 | NM_010317 | 2.03 |
| 1448326_a_at | Crabp1 | NM_013496 | 2.03 |
| 1416407_at | Pea15 | AI323543 | 2.03 |
| 1436821_at | Plcxd3 | BB293136 | 2.02 |
| 1426606_at | Crtac1 | BB426194 | 2.01 |
| 1449429_at | Fkbp1b | NM_016863 | 2.01 |
| 1452731_x_at | LOC554327 | BM195235 | 2.00 |
| 1425854_x_at | Tcrb-V13 | U07661 | 2.00 |
| 1452936_at | Crtac1 | AV341285 | 1.99 |
| 1448660_at | Arhgdig | NM_008113 | 1.98 |
| 1415897_a_at | Mgst1 | BI150149 | 1.98 |
| 1431429_a_at | Arl4a | AK006286 | 1.98 |
| 1416004_at | Ywhah | NM_011738 | 1.97 |
| 1418982_at | Cebpa | BC011118 | 1.97 |
| 1418271_at | Bhlhb5 | NM_021560 | 1.96 |
| 1449403_at | Pde9a | NM_008804 | 1.95 |
| 1449799_s_at | Pkp2 | AA516617 | 1.94 |
| 1454745_at | Arhgap29 | BG074320 | 1.94 |
| 1425051_at | Isoc1 | AK010892 | 1.94 |
| 1455324_at | Plcxd2 | BQ176176 | 1.94 |
| 1418792_at | Sh3gl2 | AF326561 | 1.93 |
| 1437390_x_at | Stx1a | AV339210 | 1.93 |
| 1416133_at | C920006C10Rik | BB188557 | 1.93 |
| 1455443_at | Gdap1l1 | BB733286 | 1.93 |
| 1433664_at | Ube2q2 | BM202586 | 1.92 |
| 1431749_a_at | Rasgrp1 | AK013548 | 1.91 |
| 1455374_at |  | BB332873 | 1.91 |
| 1426766_at | 6330403K07Rik | AK018106 | 1.91 |
| 1445081_at | A930041I02Rik | BB335888 | 1.90 |
| 1455458_x_at | Gmppa | AU044197 | 1.89 |
| 1436182_at |  | BG092481 | 1.88 |
| 1425484_at | Tox | BB547854 | 1.87 |
| 1456954_at | Kcna6 | BM119753 | 1.84 |
| 1417434_at | Gpd2 | NM_010274 | 1.83 |
| 1454708_at | Ablim1 | BG065289 | 1.83 |
| 1416008_at | Satb1 | AV172776 | 1.81 |
| 1449839_at | Casp3 | BG070529 | 1.80 |
| 1420858_at | Pkia | AK010212 | 1.79 |
| 1425006_a_at | Vrk1 | BC016676 | 0.57 |
| 1437573_at |  | BF018351 | 0.57 |
| 1456434_x_at | Hspb8 | BB764222 | 0.56 |
| 1452879_at | Synpo2 | AI848603 | 0.55 |
| 1436238_at | Lgi3 | AI841179 | 0.54 |
| 1431320_a_at | Myo5a | AK002362 | 0.54 |
| 1448845_at | Rpp25 | NM_133982 | 0.53 |
| 1428574_a_at | Chn2 | AK006398 | 0.53 |
| 1416967_at | Sox2 | U31967 | 0.53 |
| 1445461_at |  | BB096245 | 0.53 |
| 1426572_at | Me2 | BM235734 | 0.53 |
| 1423171_at | Gpr88 | BE947345 | 0.53 |
| 1423424_at | Zic3 | BB732077 | 0.52 |
| 1451236_at | Rerg | BC026463 | 0.52 |
| 1420533_at | Gucy1a3 | AK004815 | 0.52 |
| 1419754_at | Myo5a | NM_010864 | 0.52 |
| 1455265_a_at | Rgs16 | BB100249 | 0.52 |
| 1419717_at | Sema3e | NM_011348 | 0.52 |
| 1436946_s_at | Gng5 | AV216608 | 0.51 |
| 1419738_a_at | Tpm2 | AK003186 | 0.51 |
| 1439526_at | Me2 | AV375160 | 0.51 |
| 1458951_at | Vrk1 | AV341598 | 0.51 |
| 1441368_at |  | BB102769 | 0.50 |
| 1455753_at | C630035N08Rik | BQ176181 | 0.50 |
| 1436994_a_at | Hist1h1c | BB533903 | 0.49 |
| 1428283_at | Cyp2s1 | AK004699 | 0.49 |
| 1420694_a_at | Dach1 | BB522228 | 0.49 |
| 1454821_at | B3gat1 | BB424673 | 0.49 |
| 1452540_a_at | Hist1h2bp | M25487 | 0.48 |
| 1456093_at | AI606473 | AI606473 | 0.48 |
| 1419879_s_at | Trim25 | AA960166 | 0.48 |
| 1426215_at | Ddc | AF071068 | 0.48 |
| 1420534_at | Gucy1a3 | AK004815 | 0.48 |
| 1418072_at | Hist1h2bc | NM_023422 | 0.47 |
| 1426573_at | Me2 | BM235734 | 0.47 |
| 1437231_at | Slitrk6 | AV246497 | 0.47 |
| 1456858_at | Gpr149 | BB075339 | 0.47 |
| 1442226_at | Sema3e | AV348197 | 0.47 |
| 1448839_at | Ankrd47 | NM_030697 | 0.46 |
| 1422673_at | Prkcm | NM_008858 | 0.46 |
| 1443365_at | Htr4 | BB431008 | 0.46 |
| 1438841_s_at | Arg2 | AV002218 | 0.46 |
| 1434141_at | Gucy1a3 | BG072799 | 0.46 |
| 1448415_a_at | Sema3b | NM_009153 | 0.45 |
| 1439614_at | Htr4 | BB308379 | 0.45 |
| 1436913_at | Cdc14a | BB479310 | 0.45 |
| 1451033_a_at | Trpc4 | BB271442 | 0.45 |
| 1449241_at | Klhl1 | NM_053105 | 0.45 |
| 1460327_at | Gpr88 | BE947345 | 0.45 |
| 1448162_at | Vcam1 | BB250384 | 0.44 |
| 1446681_at |  | BB086117 AV327329 | 0.44 |
| 1450992_a_at | Meis1 | AW547821 | 0.44 |
| 1449577_x_at | Tpm2 | AK003186 | 0.44 |
| 1417688_at | BC004044 | NM_030565 | 0.44 |
| 1435138_at | Tmem28 | AV016797 | 0.43 |
| 1457648_x_at | BC004044 | BB084182 | 0.42 |
| 1417306_at | Tyk2 | NM_018793 | 0.42 |
| 1424854_at | Hist1h4i | BC019757 | 0.41 |
| 1443827_x_at | BC004044 | BB375974 | 0.41 |
| 1418895_at | Skap2 | NM_018773 | 0.41 |
| 1443372_at |  | BB417900 | 0.41 |
| 1440484_at | Unc5d | BB525782 | 0.41 |
| 1448276_at | Tspan4 | NM_053082 | 0.40 |
| 1425028_a_at | Tpm2 | BC024358 | 0.39 |
| 1447623_s_at | Prkcm | AV297026 | 0.39 |
| 1455739_at | EG245190 | BB279146 | 0.39 |
| 1418355_at | Nucb2 | NM_016773 | 0.38 |
| 1419517_at | Cnih3 | NM_028408 | 0.38 |
| 1423477_at | Zic1 | BB361162 | 0.38 |
| 1422860_at | Nts | NM_024435 | 0.38 |
| 1423367_at | Wnt7a | AK004683 | 0.37 |
| 1435479_at |  | BM055476 | 0.36 |

TABLE 10-continued

Genes differentially translated between
striatonigral and striatopallidal cells.

| Probe | Symbol | GenBank | FCH |
|---|---|---|---|
| 1437156_at | Efcbp1 | BB392041 | 0.36 |
| 1452135_at | Gpx6 | AV001252 | 0.34 |
| 1460623_at | Skap2 | BB753881 | 0.34 |
| 1417577_at | Trpc3 | NM_019510 | 0.33 |
| 1439566_at | Gprin3 | BB245373 | 0.33 |
| 1418639_at | Sftpc | NM_011359 | 0.33 |
| 1457142_at | Efcbp1 | BB667731 | 0.32 |
| 1439627_at | Zic1 | AV031691 | 0.31 |
| 1454659_at | Dctd | BG069699 | 0.30 |
| 1427300_at | Lhx8 | D49658 | 0.30 |
| 1416319_at | Adk | NM_134079 | 0.29 |
| 1438292_x_at | Adk | BB559878 | 0.28 |
| 1451191_at | Crabp2 | BC018397 | 0.26 |
| 1419577_at | A530089I17Rik | NM_133999 | 0.26 |
| 1440177_at | 9.63E+17 | BM899529 | 0.26 |
| 1422586_at | Ecel1 | NM_021306 | 0.25 |
| 1433787_at | Nell1 | AI841091 | 0.23 |
| 1422541_at | Ptprm | NM_008984 | 0.22 |
| 1434458_at | Fst | BB444134 | 0.21 |
| 1427519_at | Adora2a | BG311385 | 0.18 |
| 1433578_at | Slc10a4 | BE824538 | 0.17 |
| 1421365_at | Fst | NM_008046 | 0.15 |
| 1424902_at | Plxdc1 | AF378760 | 0.13 |
| 1427038_at | Penk1 | M13227 | 0.13 |
| 1428547_at | Nt5e | AV273591 | 0.13 |
| 1460244_at | Upb1 | NM_133995 | 0.11 |
| 1440148_at | Gpr6 | AI852874 | 0.08 |
| 1460710_at | Adora2a | BB748999 | 0.08 |
| 1418950_at | Drd2 | NM_010077 | 0.03 |
| 1435211_at | Ttc12 | BB554351 | 0.00 |

Fold-change values (FCH) are given relative to D1 (striatonigral) cells.
Probe = Affymetrix probe identification; Symbol = official gene symbol.

TABLE 11

Real time PCR analysis of D1 enriched
messages: range from replicates.

| Gene | Fold enrichment in D1 versus D2 cell type |
|---|---|
| Eya1 | 19.85-21.51 |
| Tac1 (known) | 10.97-11.87 |
| Isl1 | 10.06-10.87 |
| Gng2 | 5.91-6.43 |
| Chrm4 (known) | 5.02-5.57 |
| Drd1a (known) | 2.96-3.4 |
| Crym | 1.57-1.88 |

TABLE 12

Real time PCR analysis of D2-enriched
messages: range from replicates.

| Gene | Fold enrichment in D2 versus D1 cell type |
|---|---|
| Drd2 (known) | 49.79-51.55 |
| Gpr6 | 12.30-12.81 |
| Lhx8 | 3.57-4.06 |
| Gpr88 | 1.94-2.13 |
| Trpc4 | 1.93-2.25 |
| Tpm2 | 1.84-1.96 |

4) Large Scale Validation of BACarray Profiling of Striatonigral and Striatopallidan MSNs Large-scale validation of the data using publicly available gene expression databases was carried out. Data were pooled from D1 and D2 BACarray experiments to represent MSN-enriched subtypes and compared to data collected from the total RNA of one whole brain (minus striatum) (Table 13).

The analysis resulted in detection of several thousand translated mRNAs enriched in striatum relative to whole brain, including all previously-known striatal-enriched genes: Ppp1r1b/Darpp-32 (S. I. Walaas, P. Greengard, JNeurosci 4, 84-98 (January, 1984),) Ptpn5/Step (P. J. Lombroso, J. R. Naegele, E. Sharma, M. Lerner, J Neurosci 13, 3064-74 (July, 1993),) Arpp-19 (J. A. Girault, A. Horiuchi, E. L. Gustafson, N. L. Rosen, P. Greengard, J Neurosci 10, 1124-33 (Apr, 1990),) Arpp-21/RCS (C. C. Ouimet, H. C. Hemmings, Jr., P. Greengard, J Neurosci 9, 865-75 (March, 1989),) Goal/Golf (D. Herve eta!., J Neurosci 13, 2237-48 (May, 1993),) Rhes/Rasd2 (J. D. Falk et al., J Neurosci Res 57, 782-8 6(Sep. 15, 1999),) Rgs9 (S. J. Gold, Y. G. Ni, H. G. Dohlman, E. J. Nestler, J Neurosci 17, 8024-37 (Oct. 15, 1997),) Adcy5 (C. E. Glatt, S. H. Snyder, Nature 361, 536-8 (Feb. 11, 1993),) Gng7 (J. B. Watson et al., J Neurosci Res 39, 108-16 (Sep. 1, 1994),) Rasgrp2 (H. Kawasaki et al., Proc Natl Acad Sci USA 95, 13278-83 (Oct. 27, 1998),) Pdelb (J. W. Polli, R. L. Kincaid, Proc Natl Acad Sci USA 89, 11079-83 (Nov. 15, 1992),) Pde10a (K. Fujishige, J. Kotera, K. Omori, Eur J Biochem 266, 1118-27 (Dec., 1999),) Gpr88 (K. Mizushima et al., Genornics 69,314-21 (Nov. 1, 2000),) Rarb (W. Krezel, P. Kastner, P. Chambon, Neuroscience 89, 1291-300 (1999),) and Strn4 (F. Castets et al., J Cell Biol 134, 1051-62 (Aug., 1996)) as well as the transcription factors Foxpl, Foxp2 (R. J. Ferland, T. J. Cherry, P. O. Preware, E. E. Morrisey, C. A. Walsh, J Comp Neuro1460, 266-79 (May. 26, 2003),) Ebfl (S. Magdaleno et al., PLoS Bio14, e86 (2006)), and ZJP503/Nolz (C. W. Chang et al., Proc Natl Acad Sci USA 101, 2613-8 (Feb. 24, 2004).) (Table 13).

As independent confirmation of these data, mRNA expression patterns were examined for a subset of the candidate MSN-expressed genes in the GENSAT/Brain Gene Expression Map (BGEM) and Allen Brain Atlas (ABA) in situ hybridization (ISH) databasee(available using the hypertext transfer protocol and world wide web at ncbi.nlm.nih.gov/projects/gensat/; available using the hypertext transfer protocol and world wide web at stjudebgem.org). Only those genes for which expression data were available in both gene expression atlases were chosen. The data are presented in FIG. 29. Of the first 100 genes appearing in the MSN-enriched dataset, 26 were present in both the BGEM and ABA public ISH atlases. Enriched striatal expression is evident for 22 of these genes (Table 13); panel a).

ISH data were available in the GENSAT/BGEM and ABA for 16 genes appearing between numbers 1,000 to 1,100 on the MSN enriched list. In this case, striatally-enriched expression is apparent for 7 of these genes ((Table 13); panel b).

Expression analysis in sagittal sections of genes which were amongst the top 100 (a) or 1,000-1,100 (b) genes identified in the study as MSN-enriched, with the rank order of each gene noted below the gene name. Non-redundant gene ranking was calculated using the highest-ranked probeset corresponding to each gene, with redundant probesets eliminated. Left panel, in situ hybridization images taken from the Allen Brain Atlas (Allen Brain Atlas, Internet. Seattle (WA): Allen Institute for Brain Science.© 2006.; Available using the hypertext transfer protocol on the world wide web at brain-map.org; E. S. Lein et al., Nature 445, 168-76 (Jan. 11, 2007)); right panel, in situ hybridization images taken from the Brain Gene Expression Map (BGEM) database (available using the hypertext transfer protocol on the world wide web at stjudebgem.org/) (S. Magdaleno et al., *PLoS Biol* 4, e86 (Apr., 2006). Allen Brain Atlas images all correspond to adult brain; BGEM images all correspond to adult brain except for the following, for which the oldest available data were postnatal day 7 (P7): Drd2, Ppp1r1b, Dlx6, Gdnf, Bcl11b, Foxg1, Limd2, Femlb, Dynl11, Atbf1, Foxo3a, Dnalc4, Mtmr7, Dnmt3a.

TABLE 13

Genes differentially translated between medium spiny neurons (MSNs) and the rest of the brain.

| Probe | Symbol | GenBank | FCH |
|---|---|---|---|
| 1420437_at | Indo | NM_008324 | 198.43 |
| 1427343_at | Rasd2 | BC026377 | 149.45 |
| 1457132_at | | BF456117 | 133.95 |
| 1458342_at | Tmem90a | BB313069 | 108.01 |
| 1418950_at | Drd2 | NM_010077 | 85.64 |
| 1438355_at | Tmem90a | AI414870 | 79.94 |
| 1441368_at | | BB102769 | 71.65 |
| 1426814_at | AU024582 | BM248309 | 57.27 |
| 1418782_at | Rxrg | NM_009107 | 56.75 |
| 1423171_at | Gpr88 | BE947345 | 52.53 |
| 1457143_at | LOC665139 | BB322292 | 50.59 |
| 1426438_at | Ddx3y | AA210261 | 49.33 |
| 1419696_at | Cd4 | NM_013488 | 45.51 |
| 1458499_at | Pde10a | AW123977 | 41.50 |
| 1427344_s_at | Rasd2 | BC026377 | 34.92 |
| 1450213_at | Pde7b | NM_013875 | 33.08 |
| 1455190_at | Gng7 | BM114283 | 31.37 |
| 1429285_at | Serpina9 | AK009343 | 29.48 |
| 1454906_at | Rarb | BB266455 | 28.73 |
| 1443287_at | Gm1337 | BB555669 | 28.56 |
| 1428642_at | Slc35d3 | AK018094 | 28.48 |
| 1417680_at | Kcna5 | NM_008419 | 28.33 |
| 1451331_at | Ppp1r1b | BC026568 | 28.25 |
| 1442558_at | Ptprn2 | BB180191 | 27.93 |
| 1454867_at | Mn1 | BB234631 | 27.26 |
| 1437750_at | Tmem158 | BI133257 | 26.54 |
| 1457919_at | D030054H15Rik | BB446049 | 25.08 |
| 1427807_at | ENSMUSG00000060559 | BC017159 | 24.97 |
| 1436566_at | Rab40b | AV364488 | 24.65 |
| 1456818_at | Stk32a | BB279083 | 24.52 |
| 1452507_at | Dlx6 | AF022078 | 24.32 |
| 1457651_x_at | Rem2 | BB270375 | 24.03 |
| 1428781_at | Dmkn | BI452905 | 23.79 |
| 1460710_at | Adora2a | BB748999 | 23.75 |
| 1455629_at | Drd1a | BE957273 | 23.51 |
| 1422079_at | Prkch | NM_008856 | 22.36 |
| 1435296_at | Adra2c | AV349563 | 21.79 |
| 1440148_at | Gpr6 | AI852874 | 20.60 |
| 1437935_at | 4930486G11Rik | BB821151 | 19.59 |
| 1427523_at | Six3 | AI509029 | 19.13 |
| 1419389_at | Pde10a | BQ180352 | 19.09 |
| 1454581_at | 5330425B07Rik | AK019908 | 19.03 |
| 1440166_x_at | Htr1d | BB378627 | 18.87 |
| 1426815_s_at | AU024582 | BM248309 | 18.68 |
| 1419080_at | Gdnf | NM_010275 | 17.98 |
| 1435211_at | Ttc12 | BB554351 | 17.93 |
| 1438022_at | Rab11fip3 | BQ266518 | 17.69 |
| 1445539_at | | BE687857 | 17.64 |
| 1449420_at | Pde1b | NM_008800 | 17.44 |
| 1427683_at | Egr2 | X06746 | 16.79 |
| 1456640_at | Sh3rf2 | AW910872 | 16.61 |
| 1456280_at | Clspn | BG067086 | 16.53 |
| 1451236_at | Rerg | BC026463 | 16.46 |
| 1460262_a_at | 1700037H04Rik | NM_026091 | 16.39 |
| 1460038_at | Pou3f1 | BG065255 | 16.23 |
| 1443694_at | Rgs20 | BB794177 | 16.06 |
| 1417804_at | Rasgrp2 | NM_011242 | 16.01 |
| 1451280_at | Arpp21 | BB159263 | 15.99 |
| 1450339_a_at | Bcl11b | NM_021399 | 15.73 |
| 1449977_at | Egr4 | NM_020596 | 15.61 |
| 1457424_at | Eya1 | BB760085 | 15.60 |
| 1441000_at | EG237749 | BB076832 | 15.52 |
| 1454043_a_at | Kcnab1 | AK015412 | 15.48 |
| 1438841_s_at | Arg2 | AV002218 | 15.44 |
| 1417210_at | Eif2s3y | NM_012011 | 15.28 |
| 1429229_s_at | 4930534B04Rik | BE980134 | 15.28 |
| 1454762_at | Nox1 | BM932447 | 15.26 |
| 1419390_at | Pde10a | BQ180352 | 15.22 |
| 1435366_at | D430042O09Rik | BB486367 | 15.19 |
| 1425756_at | Rab40b | AF425643 | 15.18 |
| 1418744_s_at | Tesc | NM_021344 | 14.99 |
| 1416627_at | Spint1 | NM_016907 | 14.90 |
| 1436650_at | Filip1 | AV241894 | 14.84 |
| 1460136_at | AW047481 | AI462839 | 14.68 |
| 1435808_at | A230051G13Rik | BB174377 | 14.53 |
| 1421140_a_at | Foxp1 | BG962849 | 14.38 |
| 1437698_at | Myo5b | AV370579 | 14.36 |
| 1416456_a_at | Chia | BC011134 | 14.31 |
| 1442166_at | Cpne5 | BB273427 | 14.21 |
| 1456051_at | Drd1a | BB282271 | 13.84 |
| 1421365_at | Fst | NM_008046 | 13.82 |
| 1420496_at | F12 | NM_021489 | 13.79 |
| 1436092_at | | BB336256 | 13.75 |
| 1448327_at | Actn2 | NM_033268 | 13.69 |
| 1429228_at | 4930534B04Rik | BE980134 | 13.65 |
| 1419826_at | Kif17 | AW492270 | 13.61 |
| 1436734_at | E130309F12Rik | BB523550 | 13.60 |
| 1421353_at | Pde7b | NM_013875 | 13.54 |
| 1425833_a_at | Hpca | AF326551 | 13.53 |
| 1454656_at | Spata13 | AV271736 | 13.50 |
| 1455298_at | Id4 | BB306828 | 13.39 |
| 1425363_at | B4galnt1 | BC022180 | 13.23 |
| 1439854_at | Hrk | BQ175572 | 13.22 |
| 1434008_at | Scn4b | BE993937 | 13.11 |
| 1417812_a_at | Lamb3 | NM_008484 | 13.10 |
| 1435221_at | Foxp1 | BM220880 | 13.06 |
| 1429617_at | Cyld | BM119209 | 12.96 |
| 1418357_at | Foxg1 | NM_008241 | 12.81 |
| 1436532_at | Dcamkl3 | BB326709 | 12.78 |
| 1441468_at | | BB326028 | 12.77 |
| 1447861_x_at | Mrg1 | AV329643 | 12.66 |
| 1447766_x_at | Limd2 | AV003249 | 12.63 |
| 1454877_at | Sertad4 | BQ174721 | 12.63 |
| 1418847_at | Arg2 | NM_009705 | 12.57 |
| 1422720_at | Isl1 | BQ176915 | 12.56 |
| 1417704_a_at | Arhgap6 | NM_009707 | 12.45 |
| 1455361_at | Dgkb | AW493391 | 12.28 |
| 1432073_at | 1700113I22Rik | AK007198 | 12.27 |
| 1418743_a_at | Tesc | NM_021344 | 12.18 |
| 1444734_at | A330001L22Rik | BB183877 | 12.17 |
| 1433815_at | Jakmip1 | AV290082 | 12.08 |
| 1452217_at | Ahnak | BE570050 | 12.02 |
| 1452135_at | Gpx6 | AV001252 | 11.98 |
| 1460325_at | Pum1 | BB837171 | 11.96 |
| 1439618_at | Pde10a | AI448308 | 11.94 |
| 1434521_at | Rfxdc2 | BB148972 | 11.92 |
| 1435285_at | Mpped2 | BB731805 | 11.92 |
| 1416266_at | Pdyn | AF026537 | 11.84 |
| 1422230_s_at | Cyp2a5 | NM_007812 | 11.82 |
| 1422706_at | Tmepai | AV370981 | 11.81 |
| 1448468_a_at | Kcnab1 | AF033003 | 11.74 |
| 1434917_at | Cobl | BQ173923 | 11.68 |
| 1418881_at | Efcbp2 | NM_054095 | 11.68 |
| 1433743_at | Dach1 | BG075820 | 11.67 |
| 1441733_s_at | Nup153 | C88147 | 11.66 |
| 1442077_at | Htr1b | BB197581 | 11.66 |
| 1433566_at | Rasl10b | BB381618 | 11.54 |
| 1423117_at | Pum1 | BB837171 | 11.50 |
| 1426439_at | Ddx3y | AA210261 | 11.48 |
| 1436216_s_at | 2610204M08Rik | BM234799 | 11.46 |
| 1431751_a_at | Mpped2 | AK012553 | 11.40 |
| 1437865_at | Spata13 | AW546433 | 11.40 |
| 1418691_at | Rgs9 | NM_011268 | 11.39 |
| 1442058_s_at | Psmc3ip | BE687992 | 11.38 |
| 1419033_at | 2610018G03Rik | AW556821 | 11.36 |
| 1455564_at | Bcr | BQ176236 | 11.36 |
| 1455156_at | Strn | BG519214 | 11.35 |
| 1434664_at | 2410129H14Rik | BI153133 | 11.33 |
| 1415953_s_at | Mark2 | BI686265 | 11.31 |
| 1417129_a_at | Mrg1 | U68384 | 11.26 |

TABLE 13-continued

Genes differentially translated between medium spiny neurons (MSNs) and the rest of the brain.

| Probe | Symbol | GenBank | FCH |
|---|---|---|---|
| 1436275_at | Kcnip2 | AW490636 | 11.23 |
| 1456515_s_at | Tcfl5 | AV044715 | 11.15 |
| 1453222_at | 4833427B12Rik | BE863648 | 11.04 |
| 1425870_a_at | Kcnip2 | AF439339 | 10.91 |
| 1420666_at | Doc2b | BM117900 | 10.75 |
| 1459941_at | Asph | BB096900 | 10.73 |
| 1448913_at | Smarcd1 | NM_031842 | 10.71 |
| 1440741_at | Htr1d | BB829587 | 10.68 |
| 1457038_at | Frem2 | BM201912 | 10.66 |
| 1458406_at | AI429294 | BG144063 | 10.63 |
| 1430686_at | 4833418N02Rik | AK014719 | 10.62 |
| 1446877_at | C230014O12Rik | BB381622 | 10.52 |
| 1441928_x_at | Ell | BB139475 | 10.44 |
| 1416350_at | Klf16 | NM_078477 | 10.40 |
| 1444978_at |  | BM223267 | 10.36 |
| 1417356_at | Peg3 | AB003040 | 10.34 |
| 1431386_s_at | Mbtps1 | AK002809 | 10.32 |
| 1421943_at | Tgfa | M92420 | 10.27 |
| 1435553_at | Pdzd2 | AV376136 | 10.17 |
| 1427931_s_at | Pdxk | BG063905 | 10.16 |
| 1427682_a_at | Egr2 | X06746 | 10.09 |
| 1444681_at | Erc2 | BB749686 | 10.07 |
| 1422153_a_at | Asb11 | NM_026853 | 10.00 |
| 1439566_at | Gprin3 | BB245373 | 9.99 |
| 1420146_at | Tfb1m | AI429207 | 9.98 |
| 1449957_at | Ptprv | NM_007955 | 9.95 |
| 1426241_a_at | Scmh1 | AB030906 | 9.94 |
| 1424208_at | Ptger4 | BC011193 | 9.86 |
| 1450026_a_at | B3gnt2 | AV306734 | 9.85 |
| 1436738_at | Pif1 | AV094878 | 9.75 |
| 1434248_at | Prkch | BM243756 | 9.75 |
| 1422068_at | Pou3f1 | NM_011141 | 9.75 |
| 1448374_at | Med28 | AK005130 | 9.72 |
| 1456760_at | Centg3 | BB342676 | 9.70 |
| 1422813_at | Cacng1 | NM_007582 | 9.69 |
| 1449425_at | Wnt2 | BC026373 | 9.64 |
| 1438799_at | Dlx6os1 | AV338180 | 9.63 |
| 1456283_at | Neto1 | AV346211 | 9.57 |
| 1425351_at | Srxn1 | BC011325 | 9.57 |
| 1424576_s_at | Cyp2c44 | BC025819 | 9.56 |
| 1423544_at | Ptpn5 | BB188812 | 9.53 |
| 1433923_at | Krt77 | AV230775 | 9.53 |
| 1430640_a_at | Prkar2b | BI695530 | 9.52 |
| 1427779_a_at | Cd4 | U75219 | 9.51 |
| 1452966_at | 9130430L19Rik | AK020296 | 9.46 |
| 1425130_a_at | Ptpn5 | U28216 | 9.41 |
| 1440711_at | C630001G18Rik | BB426320 | 9.37 |
| 1431936_a_at | Neu2 | AK009828 | 9.36 |
| 1434025_at | Klf5 | BG069607 | 9.33 |
| 1441867_x_at | 4930534B04Rik | AI480494 | 9.30 |
| 1427912_at | Cbr3 | AK003232 | 9.27 |
| 1436002_at |  | BB484128 | 9.23 |
| 1449502_at | Dazl | NM_010021 | 9.21 |
| 1430612_at | 1810033B17Rik | BB533148 | 9.19 |
| 1455242_at | Foxp1 | BM220880 | 9.18 |
| 1441105_at |  | BE980314 | 9.16 |
| 1447017_at |  | BE956696 | 9.03 |
| 1435334_at | Ttc7 | BG866904 | 8.97 |
| 1436998_at | Ankrd43 | BB428991 | 8.96 |
| 1454086_a_at | Lmo2 | AK013416 | 8.87 |
| 1419542_at | Dazl | NM_010021 | 8.82 |
| 1442234_at | Chst2 | BB770422 | 8.72 |
| 1449331_a_at | Rapsn | NM_009023 | 8.68 |
| 1442021_at | Mppe1 | BB502545 | 8.65 |
| 1429201_at | Cyld | AK013508 | 8.55 |
| 1440435_at | Ky | BB126077 | 8.55 |
| 1441350_at | Fgf3 | AV302620 | 8.53 |
| 1434519_at | Ddah1 | AW556888 | 8.53 |
| 1452298_a_at | Myo5b | AW546331 | 8.51 |
| 1422407_s_at | Hras1 | NM_008284 | 8.45 |
| 1416996_at | Tbc1d8 | BC005421 | 8.43 |
| 1428873_a_at | 4121402D02Rik | AW495537 | 8.37 |
| 1422448_at | Tff2 | NM_009363 | 8.36 |
| 1443036_at | Zfp804a | BG073535 | 8.35 |
| 1417522_at | Fbxo32 | AF441120 | 8.32 |
| 1453799_at | 9430038I01Rik | AK020460 | 8.31 |
| 1438224_at | Zswim5 | BE572265 | 8.28 |
| 1430864_at | Ttll9 | AK015740 | 8.25 |
| 1451008_at | St8sia3 | BB360510 | 8.25 |
| 1453330_at | 0610010D24Rik | AK002458 | 8.24 |
| 1420872_at | Gucy1b3 | BF472806 | 8.22 |
| 1444383_at | 1110014J01Rik | AV347845 | 8.21 |
| 1424132_at | Hras1 | BC011083 | 8.20 |
| 1420695_at | Dach1 | BB522228 | 8.13 |
| 1438266_at | Adamtsl5 | BB764453 | 8.09 |
| 1456054_a_at | Pum1 | BB314559 | 8.08 |
| 1422157_a_at | Itgb1bp1 | NM_008403 | 8.06 |
| 1420961_a_at | Ivns1abp | NM_028582 | 8.05 |
| 1424899_at | Nmnat3 | BC005737 | 7.97 |
| 1424409_at | Cldn23 | BC019534 | 7.94 |
| 1435071_at | Zfyve1 | AV327165 | 7.93 |
| 1437353_at | Setd1b | BB494182 | 7.87 |
| 1456830_at | Ppp1r2 | BB542221 | 7.87 |
| 1445606_a_at | 2900009J06Rik | BB663189 | 7.87 |
| 1435227_at |  | BM117007 | 7.85 |
| 1446455_at |  | BB520649 | 7.85 |
| 1443676_at | Slc4a4 | AV339935 | 7.83 |
| 1429316_at | Rasgef1a | AK018120 | 7.82 |
| 1438247_at | Pwwp2 | BB809239 | 7.82 |
| 1434996_at | Slc25a16 | AV316233 | 7.79 |
| 1422621_at | Ranbp2 | BM507707 | 7.79 |
| 1452176_at | Nup153 | BB292874 | 7.78 |
| 1437460_x_at | Rin1 | BB264363 | 7.78 |
| 1447642_x_at | Dmwd | AV354897 | 7.70 |
| 1417341_a_at | Ppp1r2 | NM_025800 | 7.69 |
| 1431349_at | Hnrpab | AK013709 | 7.65 |
| 1438441_at | Id4 | AI323288 | 7.64 |
| 1416242_at | Klhl13 | NM_026167 | 7.64 |
| 1441963_at | Ubox5 | BB427703 | 7.64 |
| 1422678_at | Dgat2 | AK002443 | 7.60 |
| 1447359_at | Zfp575 | AI326876 | 7.58 |
| 1450183_a_at | Sh2b3 | NM_008507 | 7.58 |
| 1451517_at | Rhobtb2 | AF420001 | 7.55 |
| 1437017_at | AI480653 | BB046727 | 7.54 |
| 1455296_at | Adcy5 | BE952286 | 7.52 |
| 1422779_at | Smpd3 | NM_021491 | 7.49 |
| 1434531_at | Mgat5b | BB400317 | 7.46 |
| 1450072_at | Ash1l | BG694892 | 7.45 |
| 1422335_at | Adra2c | NM_007418 | 7.45 |
| 1417062_at | Armc10 | NM_026034 | 7.45 |
| 1426454_at | Arhgdib | AK002516 | 7.38 |
| 1443073_at | LOC545681 | BB355954 | 7.38 |
| 1458407_s_at | AI429294 | BG144063 | 7.36 |
| 1453323_at | 2900079G21Rik | AK013806 | 7.34 |
| 1438664_at | Prkar2b | BB216074 | 7.27 |
| 1428839_at | Wdr53 | AK005105 | 7.27 |
| 1442708_at |  | BB504418 | 7.26 |
| 1418467_at | Smarcd3 | NM_025891 | 7.25 |
| 1455401_at | Camkk2 | AW061083 | 7.24 |
| 1434732_x_at | Tomm7 | AV044898 | 7.24 |
| 1429618_at | Cyld | BM_119209 | 7.23 |
| 1428860_at | 4930572J05Rik | AK019809 | 7.22 |
| 1453264_at | Marveld3 | AK007346 | 7.22 |
| 1421142_s_at | Foxp1 | BG962849 | 7.22 |
| 1418714_at | Dusp8 | NM_008748 | 7.20 |
| 1452077_at | Ddx3y | AA210261 | 7.19 |
| 1441124_at | 1500011B03Rik | AK018264 | 7.19 |
| 1454832_at | Phactr1 | BG228702 | 7.19 |
| 1434153_at | Shb | BI408715 | 7.18 |
| 1456475_s_at | Prkar2b | BB216074 | 7.15 |
| 1422722_at | 1700001K19Rik | NM_025488 | 7.14 |
| 1434495_at | Patz1 | BM208058 | 7.14 |
| 1423532_at | Rnf44 | AI850285 | 7.12 |
| 1437091_at | Accn4 | AV323885 | 7.11 |
| 1418017_at | Pum2 | BI689507 | 7.10 |
| 1423049_a_at | Tpm1 | AK002271 | 7.10 |
| 1455080_at | Ppp1r16b | BB375209 | 7.10 |
| 1416239_at | Ass1 | NM_007494 | 7.10 |
| 1428338_at | Spata2L | AK019166 | 7.07 |
| 1425104_at | Kctd1 | BC022615 | 7.06 |

TABLE 13-continued

Genes differentially translated between medium spiny neurons (MSNs) and the rest of the brain.

| Probe | Symbol | GenBank | FCH |
|---|---|---|---|
| 1433627_at | Sec23ip | AW546839 | 7.02 |
| 1455085_at | 1700086L19Rik | BI526033 | 7.02 |
| 1416804_at | Ehbp1l1 | NM_053252 | 7.00 |
| 1452729_at | Dpm3 | BE446919 | 7.00 |
| 1419234_at | Helb | BG070273 | 7.00 |
| 1449261_at | Pbx2 | NM_017463 | 6.99 |
| 1456336_at | A330102K23Rik | BB182912 | 6.99 |
| 1416983_s_at | Foxo1 | AI462296 | 6.99 |
| 1442220_at |  | BB313387 | 6.97 |
| 1455961_at |  | AV174022 | 6.96 |
| 1460567_at | Rfxdc2 | BB148972 | 6.94 |
| 1437579_at | Nek2 | C77054 | 6.94 |
| 1452913_at | Pcp4l1 | AV337888 | 6.93 |
| 1441223_at | 3-Mar | BB260801 | 6.93 |
| 1435504_at | Clip4 | BM217861 | 6.93 |
| 1434077_at | Wdr37 | AV222037 | 6.91 |
| 1452879_at | Synpo2 | AI848603 | 6.90 |
| 1460285_at | Itga9 | NM_133721 | 6.90 |
| 1424796_at | 1700054N08Rik | BC024705 | 6.89 |
| 1435125_at | BB120497 | BB303627 | 6.87 |
| 1433962_at | 6720458F09Rik | BB131965 | 6.86 |
| 1429098_s_at | Nhej1 | AK006481 | 6.85 |
| 1452411_at | Lrrc1 | BG966295 | 6.85 |
| 1422159_at | Ppef2 | BC027049 | 6.83 |
| 1452166_a_at | Krt10 | AK014360 | 6.83 |
| 1416981_at | Foxo1 | AI462296 | 6.82 |
| 1437092_at | Clip4 | AV042829 | 6.81 |
| 1430306_a_at | Atp6v1c2 | AK006481 | 6.80 |
| 1421442_at | Flt4 | NM_008029 | 6.77 |
| 1435649_at | Nexn | BM225804 | 6.75 |
| 1455683_a_at | Tbc1d8 | BB451404 | 6.73 |
| 1434649_at | Ccm2 | BI903794 | 6.72 |
| 1455804_x_at | Oxct1 | AV213379 | 6.71 |
| 1423344_at | Epor | AK010968 | 6.69 |
| 1460555_at | 6330500D04Rik | BM242294 | 6.68 |
| 1436799_at | Rpl23a | BB386177 | 6.67 |
| 1426687_at | Map3k3 | BG175594 | 6.66 |
| 1434032_at | Centg3 | BQ175381 | 6.65 |
| 1423530_at | Stk32c | BB320288 | 6.63 |
| 1443543_at |  | BE980616 | 6.63 |
| 1447100_s_at |  | C80506 | 6.62 |
| 1437842_at | Plcxd1 | BB311508 | 6.59 |
| 1420534_at | Gucy1a3 | AK004815 | 6.59 |
| 1455301_at | Wipf3 | BG064092 | 6.59 |
| 1429637_at | 2210419I08Rik | AK006987 | 6.57 |
| 1442051_at | Hist2h3c1 | BE691662 | 6.54 |
| 1434458_at | Fst | BB444134 | 6.54 |
| 1435605_at | Actr3b | BB125424 | 6.53 |
| 1422034_a_at | Palm | NM_023128 | 6.53 |
| 1419742_at | 1700037H04Rik | NM_026091 | 6.52 |
| 1438171_x_at | Mettl9 | BB056666 | 6.52 |
| 1448807_at | Hrh3 | NM_133849 | 6.50 |
| 1437097_at | Zbed3 | BB703866 | 6.49 |
| 1424759_at | Arrdc4 | BC017528 | 6.49 |
| 1438210_at | Gpr149 | BB126999 | 6.48 |
| 1441340_at | Cep68 | BF018298 | 6.47 |
| 1443887_at | Ankrd13c | BE132758 | 6.47 |
| 1422608_at | Arpp19 | BE648432 | 6.45 |
| 1452917_at | Rfc5 | AK011489 | 6.43 |
| 1416982_at | Foxo1 | AI462296 | 6.43 |
| 1418894_s_at | Pbx2 | NM_017463 | 6.42 |
| 1449158_at | Kcnk2 | NM_010607 | 6.42 |
| 1448978_at | Ngef | NM_019867 | 6.41 |
| 1427196_at | Wnk4 | BG074348 | 6.41 |
| 1424507_at | Rin1 | BC011277 | 6.40 |
| 1441089_at | Eif2c1 | BB205493 | 6.40 |
| 1427293_a_at | Auts2 | AK012475 | 6.39 |
| 1457195_at | Plekhm1 | BB206527 | 6.38 |
| 1436930_x_at | Hmbs | BB000512 | 6.37 |
| 1434359_at | 6330500D04Rik | AV329091 | 6.37 |
| 1420444_at | Slc22a3 | NM_011395 | 6.37 |
| 1417440_at | LOC675933 | NM_033566 | 6.37 |
| 1425503_at | Gcnt2 | AB037596 | 6.36 |
| 1438784_at | Bcl11b | BB329234 | 6.34 |
| 1460044_at | Onecut2 | BB389395 | 6.34 |
| 1439576_at |  | BB325333 | 6.34 |
| 1428777_at | Spred1 | AK017680 | 6.34 |
| 1430413_at | Tmem29 | AK018228 | 6.34 |
| 1422293_a_at | Kctd1 | NM_134112 | 6.33 |
| 1423488_at | Mmd | BC021914 | 6.33 |
| 1436645_a_at | Cnot4 | BB066603 | 6.32 |
| 1445404_at | Kif27 | BB054454 | 6.32 |
| 1428547_at | Nt5e | AV273591 | 6.32 |
| 1454752_at | Rbm24 | AV307961 | 6.29 |
| 1452092_at | 4631426J05Rik | AK019474 | 6.28 |
| 1447830_s_at | Rgs2 | BB034265 | 6.27 |
| 1455447_at | D430019H16Rik | BM116882 | 6.26 |
| 1452904_at | 1700026L06Rik | BQ175881 | 6.26 |
| 1444363_at |  | BB269445 | 6.26 |
| 1437839_x_at | Mrpl11 | AV209741 | 6.25 |
| 1445385_at |  | BB551855 | 6.25 |
| 1419247_at | Rgs2 | AF215668 | 6.24 |
| 1416886_at | C1d | NM_020558 | 6.21 |
| 1419378_a_at | Fxyd2 | NM_052823 | 6.20 |
| 1450366_at | Hrk | NM_007545 | 6.19 |
| 1428495_at | 2410003K15Rik | BF300229 | 6.19 |
| 1439844_at | 8430426J06Rik | BE628126 | 6.18 |
| 1455345_at | Phf15 | BI663145 | 6.16 |
| 1449304_at | 2310061J03Rik | NM_133677 | 6.16 |
| 1435564_at | C230078M08Rik | BB547893 | 6.16 |
| 1451819_at | Zswim6 | BC021311 | 6.16 |
| 1449141_at | Fblim1 | BG070068 | 6.15 |
| 1448860_at | Rem2 | NM_080726 | 6.15 |
| 1450835_a_at | Gfra4 | NM_020014 | 6.15 |
| 1435096_at | Ric8b | BB667093 | 6.15 |
| 1454901_at | Ypel2 | BG069663 | 6.15 |
| 1423270_at | Nedd4l | BB663717 | 6.14 |
| 1452202_at | Pde2a | BG069616 | 6.12 |
| 1442754_at | C030013G03Rik | BE692283 | 6.10 |
| 1449863_a_at | Dlx5 | NM_010056 | 6.09 |
| 1422134_at | Fosb | NM_008036 | 6.09 |
| 1430222_at | 9130007G19Rik | BB538672 | 6.09 |
| 1434648_a_at | Ccm2 | BI903794 | 6.09 |
| 1428139_at | Tmem180 | AK015988 | 6.08 |
| 1439947_at | Cyp11a1 | C87524 | 6.08 |
| 1421141_a_at | Foxp1 | BG962849 | 6.08 |
| 1415976_a_at | Carhsp1 | AU080787 | 6.07 |
| 1433988_s_at | C230098O21Rik | BG075755 | 6.06 |
| 1422705_at | Tmepai | AV370981 | 6.06 |
| 1443334_at | D430042O09Rik | BB487579 | 6.06 |
| 1434909_at | Rragd | BF462770 | 6.04 |
| 1456930_at | Camsap1 | BE989461 | 6.03 |
| 1416605_at | Nola2 | BC024944 | 6.03 |
| 1417090_at | Rcn1 | NM_009037 | 6.02 |
| 1460686_at | Cntd1 | BC006866 | 6.02 |
| 1430190_at | 1700041C02Rik | AK006668 | 6.02 |
| 1430616_at | 4930528A17Rik | BB185833 | 6.01 |
| 1419248_at | Rgs2 | AF215668 | 5.99 |
| 1417524_at | Cnih2 | NM_009920 | 5.97 |
| 1453260_a_at | Ppp2r2a | AK010380 | 5.95 |
| 1443612_at | Tmem16c | AW123199 | 5.95 |
| 1424248_at | Arpp21 | BB159263 | 5.93 |
| 1449843_at | St8sia2 | BG071333 | 5.93 |
| 1420391_at | Pard3 | NM_033620 | 5.93 |
| 1434115_at | Cdh13 | BQ176681 | 5.92 |
| 1457052_at | AW536275 | BG064867 | 5.92 |
| 1456838_at |  | BC072620 | 5.92 |
| 1436538_at | Ankrd37 | AV084342 | 5.91 |
| 1438226_at | AU022252 | AV349089 | 5.90 |
| 1422208_a_at | Gnb5 | BC016135 | 5.89 |
| 1452368_at | Bcr | AI853148 | 5.88 |
| 1416488_at | Ccng2 | U95826 | 5.87 |
| 1435222_at | Foxp1 | BM220880 | 5.87 |
| 1432579_at | Rshl2b | AA544511 | 5.85 |
| 1417658_at | Tbrg4 | NM_134011 | 5.85 |
| 1422923_at | Fgf3 | NM_008007 | 5.85 |
| 1421037_at | Npas2 | BG070037 | 5.85 |
| 1431711_a_at | 9030409G11Rik | AK018497 | 5.85 |
| 1431242_at | 6330575P09Rik | BE995561 | 5.85 |
| 1452911_at | Spred1 | AK017680 | 5.84 |

TABLE 13-continued

Genes differentially translated between medium spiny neurons (MSNs) and the rest of the brain.

| Probe | Symbol | GenBank | FCH |
|---|---|---|---|
| 1458133_at | | BB360008 | 5.81 |
| 1438019_at | Ippk | BM196347 | 5.81 |
| 1417003_at | 0610012G03Rik | BC021536 | 5.80 |
| 1448231_at | Fkbp5 | U16959 | 5.80 |
| 1428074_at | Tmem158 | BE981853 | 5.80 |
| 1456401_at | Cacnb2 | BB078175 | 5.79 |
| 1423376_a_at | Dok4 | AV341904 | 5.77 |
| 1443365_at | Htr4 | BB431008 | 5.76 |
| 1416087_at | Ap1s1 | NM_007457 | 5.76 |
| 1429104_at | Limd2 | AK012581 | 5.76 |
| 1435218_at | Rasgef1a | BI134758 | 5.75 |
| 1454742_at | Rasgef1b | BB003229 | 5.75 |
| 1437948_x_at | Eif3s6ip | BB443362 | 5.75 |
| 1447640_s_at | Pbx3 | BB554874 | 5.75 |
| 1460718_s_at | Mtch1 | AF192558 | 5.74 |
| 1453972_x_at | Pparbp | AK005207 | 5.74 |
| 1430520_at | Cpne8 | AW548480 | 5.71 |
| 1418015_at | Pum2 | BI689507 | 5.70 |
| 1455701_at | Snx26 | BI965517 | 5.67 |
| 1436160_at | Krt26 | BB150142 | 5.67 |
| 1458025_at | Ttc7 | BB519333 | 5.66 |
| 1427005_at | Plk2 | BM234765 | 5.66 |
| 1434682_at | Zfp770 | AV347367 | 5.64 |
| 1439291_at | | BB354792 | 5.64 |
| 1438680_at | Auts2 | BB429147 | 5.63 |
| 1443552_at | E230008N13Rik | BM932485 | 5.63 |
| 1453089_at | 3110079O15Rik | AA259365 | 5.62 |
| 1440501_at | AU041480 | BG072095 | 5.62 |
| 1440940_at | Cacnb1 | BE949510 | 5.62 |
| 1446840_at | Thrap1 | BQ032894 | 5.62 |
| 1460327_at | Gpr88 | BE947345 | 5.57 |
| 1426230_at | Sphk2 | AK016616 | 5.55 |
| 1419130_at | Deadc1 | NM_025748 | 5.54 |
| 1434967_at | Zswim6 | BM938007 | 5.53 |
| 1432782_at | 4933435C09Rik | AK017064 | 5.52 |
| 1441967_at | Pddc1 | BB467791 | 5.51 |
| 1433468_at | 6430527G18Rik | BB770958 | 5.51 |
| 1435741_at | Pde8b | BB312125 | 5.49 |
| 1437400_at | Nedd41 | BB309512 | 5.48 |
| 1460206_at | Grasp | NM_019518 | 5.47 |
| 1433767_at | 1110018G07Rik | AV257687 | 5.45 |
| 1420918_at | Sgk3 | BB768208 | 5.45 |
| 1438189_s_at | Rai16 | BB492312 | 5.44 |
| 1433507_a_at | Hmgn2 | BE553881 | 5.42 |
| 1450930_at | Hpca | AK002992 | 5.42 |
| 1418373_at | Pgam2 | NM_018870 | 5.40 |
| 1427278_at | Clip4 | AK017914 | 5.40 |
| 1430013_at | Git1 | BE993118 | 5.39 |
| 1437586_at | Cnot4 | BB756908 | 5.38 |
| 1439821_at | Lrp2bp | BB075157 | 5.38 |
| 1453268_at | Thg11 | AV224102 | 5.37 |
| 1451483_s_at | 1700054N08Rik | BC024705 | 5.35 |
| 1436725_at | E130306D19Rik | BM226118 | 5.34 |
| 1425123_at | BC025816 | BC025816 | 5.34 |
| 1442434_at | D8Ertd82e | BM195829 | 5.32 |
| 1444379_at | Pwwp2 | BB318408 | 5.31 |
| 1416558_at | Melk | NM_010790 | 5.30 |
| 1439855_at | Tmtc1 | AV341449 | 5.30 |
| 1427045_at | Synpo | AI849322 | 5.30 |
| 1450480_a_at | Gprk6 | AF040749 | 5.30 |
| 1427015_at | C230021P08Rik | BI732921 | 5.30 |
| 1417829_a_at | Rab15 | NM_134050 | 5.29 |
| 1457632_s_at | Mrg1 | BB207647 | 5.29 |
| 1453040_at | 2810402A17Rik | AK013345 | 5.28 |
| 1445459_at | Sstr5 | BB023293 | 5.27 |
| 1455670_at | | BQ175884 | 5.27 |
| 1424475_at | Camkk2 | BI157430 | 5.26 |
| 1424020_at | Arl6ip6 | BB837198 | 5.26 |
| 1444522_at | | BM942961 | 5.26 |
| 1434124_x_at | 2400001E08Rik | AV100071 | 5.26 |
| 1436100_at | Sh2d5 | AV347995 | 5.25 |
| 1437453_s_at | Pcsk9 | AV010795 | 5.24 |
| 1431665_a_at | Timm8b | AK004190 | 5.23 |
| 1420752_at | Dtx3 | NM_030714 | 5.23 |
| 1453165_at | Mettl4 | BB701076 | 5.22 |
| 1454256_s_at | 1700113I22Rik | AK004415 | 5.22 |
| 1427954_at | BC048403 | BC028785 | 5.21 |
| 1450227_at | Ankrd6 | BM199504 | 5.21 |
| 1454309_at | 2810002N01Rik | BB646622 | 5.20 |
| 1435941_at | Rhbdl3 | BM118307 | 5.20 |
| 1450723_at | Isl1 | BQ176915 | 5.19 |
| 1419006_s_at | Peli2 | NM_033602 | 5.18 |
| 1434301_at | D330050I23Rik | BE303700 | 5.18 |
| 1423442_a_at | Fbxw2 | BE854125 | 5.18 |
| 1434828_at | B430201A12Rik | BM200103 | 5.18 |
| 1431717_at | 3526401B18Rik | AK014386 | 5.18 |
| 1439028_at | Ufm1 | AI415161 | 5.17 |
| 1444615_x_at | Runx1t1 | AV327778 | 5.17 |
| 1434775_at | Pard3 | AW543460 | 5.17 |
| 1437980_at | 9130230N09Rik | BB814947 | 5.16 |
| 1455923_at | Kctd8 | BB352927 | 5.16 |
| 1455200_at | Pak6 | BB818370 | 5.15 |
| 1416479_a_at | Tmem14c | NM_025387 | 5.15 |
| 1452964_at | Ttll11 | AK016577 | 5.15 |
| 1422440_at | Cdk4 | NM_009870 | 5.15 |
| 1420694_a_at | Dach1 | BB522228 | 5.15 |
| 1456197_x_at | | BB342782 | 5.14 |
| 1418592_at | Dnaja4 | NM_021422 | 5.14 |
| 1421234_at | Tcf1 | NM_009327 | 5.13 |
| 1425753_a_at | Ung | BC004037 | 5.13 |
| 1426964_at | 3110003A17Rik | AK013984 | 5.13 |
| 1420778_at | Tas1r3 | NM_031872 | 5.12 |
| 1433610_at | AA986860 | BB522283 | 5.12 |
| 1422807_at | Arf5 | NM_007480 | 5.11 |
| 1447559_at | AI834762 | AI834762 | 5.10 |
| 1434014_at | Atg4c | BB291836 | 5.10 |
| 1433642_at | Arl15 | BB384173 | 5.09 |
| 1426573_at | Me2 | BM235734 | 5.08 |
| 1422165_at | Pou3f4 | X66603 | 5.08 |
| 1431186_at | Dlg5 | BF140264 | 5.08 |
| 1429422_at | 4933412E12Rik | AK016788 | 5.08 |
| 1453309_at | 9330179D12Rik | BB749938 | 5.08 |
| 1457512_at | | BB167650 | 5.08 |
| 1435615_at | Zfp365 | BB277790 | 5.08 |
| 1437378_x_at | Scarb1 | BB224405 | 5.07 |
| 1429124_s_at | Rexo1 | BQ178367 | 5.07 |
| 1455153_at | Zfp236 | BQ177220 | 5.07 |
| 1430617_at | Oip5 | BB238604 | 5.06 |
| 1427519_at | Adora2a | BG311385 | 5.06 |
| 1436142_at | 3526401B18Rik | BM218877 | 5.06 |
| 1438068_at | | BB251859 | 5.04 |
| 1429678_at | 5730508B09Rik | AK017758 | 5.04 |
| 1455022_at | Strn | BG070684 | 5.03 |
| 1448684_at | Ppp1r2 | NM_025800 | 5.03 |
| 1423639_at | Hrh2 | AK020259 | 5.02 |
| 1451998_at | Tasp1 | BC024597 | 5.02 |
| 1460166_at | Rit2 | BB271919 | 5.02 |
| 1451604_a_at | Acvrl1 | BC014291 | 5.02 |
| 1450418_a_at | Yipf4 | NM_026417 | 5.01 |
| 1453000_at | Camsap1l1 | AK005444 | 5.01 |
| 1438665_at | Smpd3 | BF456582 | 5.01 |
| 1432184_a_at | 2610204M08Rik | AK011884 | 5.01 |
| 1428020_a_at | Tmem24 | AK004920 | 5.01 |
| 1427745_x_at | Prpmp5 | X63005 | 5.01 |
| 1423802_at | Camkv | BC017634 | 5.00 |
| 1417897_at | Brms1 | NM_134155 | 5.00 |
| 1438967_at | | BM939341 | 5.00 |
| 1420950_at | Znrf1 | BB026596 | 4.99 |
| 1418783_at | Trpm5 | AF228681 | 4.99 |
| 1438613_at | Kcna4 | BB131475 | 4.98 |
| 1433996_at | Suv39h2 | BB296443 | 4.97 |
| 1435423_x_at | 4933433P14Rik | AV281088 | 4.96 |
| 1417082_at | Anp32b | NM_130889 | 4.96 |
| 1441883_at | 0610010O12Rik | AV092359 | 4.95 |
| 1456225_x_at | Trib3 | BB508622 | 4.95 |
| 1434154_at | Kctd13 | BQ177107 | 4.95 |
| 1423489_at | Mmd | BC021914 | 4.94 |
| 1452476_at | Cacnb2 | W41214 | 4.94 |
| 1447844_at | | AV077281 | 4.93 |
| 1433668_at | Pnrc1 | BI410130 | 4.93 |

TABLE 13-continued

Genes differentially translated between medium spiny neurons (MSNs) and the rest of the brain.

| Probe | Symbol | GenBank | FCH |
|---|---|---|---|
| 1416398_at | Mesdc1 | BB474887 | 4.93 |
| 1423260_at | Id4 | BB121406 | 4.92 |
| 1440108_at | Foxp2 | BM964154 | 4.92 |
| 1430439_at | Mctp1 | AK013379 | 4.91 |
| 1440426_at | Nfatc2 | BB427970 | 4.91 |
| 1437181_at | Peli2 | BM121149 | 4.89 |
| 1422474_at | Pde4b | BM246564 | 4.89 |
| 1455033_at | B430201A12Rik | BB325849 | 4.88 |
| 1430519_a_at | Cnot7 | AK007767 | 4.88 |
| 1433451_at | Cdk5r1 | BB177836 | 4.88 |
| 1423202_a_at | Ncor1 | U22016 | 4.88 |
| 1455754_at | Lmo3 | BQ043839 | 4.87 |
| 1425400_a_at | Cited4 | BC025116 | 4.87 |
| 1422737_at | Ncoa3 | NM_008679 | 4.87 |
| 1442363_at | 1110012J17Rik | BB461471 | 4.86 |
| 1428698_at | Dpp8 | BM939621 | 4.86 |
| 1450071_at | Ash1l | BG694892 | 4.86 |
| 1447711_x_at | 4933412E12Rik | BB265147 | 4.85 |
| 1450975_at | Cacng4 | BB333636 | 4.84 |
| 1451898_a_at | Sema6c | AF363972 | 4.84 |
| 1426644_at | Tbc1d20 | BC002196 | 4.83 |
| 1428872_at | 4121402D02Rik | AW495537 | 4.82 |
| 1417393_a_at | C1qdc2 | NM_026125 | 4.82 |
| 1453314_x_at | 2610039C10Rik | AK012533 | 4.80 |
| 1450700_at | Cdc42ep3 | BB012489 | 4.80 |
| 1455178_at | Rutbc1 | BB496468 | 4.80 |
| 1424611_x_at | Trub2 | BG064045 | 4.79 |
| 1435083_at | Ctxn1 | BI155559 | 4.78 |
| 1439422_a_at | C1qdc2 | AV048291 | 4.78 |
| 1437707_at | Slmo1 | BB835597 | 4.77 |
| 1452533_at | Ryr3 | X83934 | 4.77 |
| 1455114_at | Ccnu | BB547482 | 4.77 |
| 1439031_at | Jph4 | BB376821 | 4.76 |
| 1451696_at | Zfp64 | BC004695 | 4.76 |
| 1424201_a_at | Seh1l | AW537349 | 4.76 |
| 1436733_at | E130309F12Rik | BB523550 | 4.75 |
| 1449241_at | Klhl1 | NM_053105 | 4.75 |
| 1435435_at | Cttnbp2 | BB357580 | 4.74 |
| 1451867_x_at | Arhgap6 | AF177664 | 4.73 |
| 1453551_at | Polq | AK020790 | 4.73 |
| 1436563_at | 4932441J04Rik | AV277283 | 4.73 |
| 1417530_a_at | Srp9 | BI661964 | 4.72 |
| 1428357_at | 2610019F03Rik | AK011462 | 4.72 |
| 1424117_at | BC056474 | BC024937 | 4.72 |
| 1452063_at | 2410081M15Rik | AK010736 | 4.72 |
| 1430729_at | Myg1 | AK017955 | 4.71 |
| 1435763_at | Tbc1d16 | BI218684 | 4.71 |
| 1417893_at | Sfxn3 | NM_053197 | 4.70 |
| 1460610_at | 9430057O19Rik | BG134491 | 4.70 |
| 1420094_at | Hnrpdl | AU015266 | 4.69 |
| 1426676_s_at | Tomm70a | BB225670 | 4.69 |
| 1431520_at | 4933406J09Rik | AK016696 | 4.69 |
| 1425080_at | Zfp286 | BE651907 | 4.68 |
| 1428279_a_at | Atxn7l4 | AK013145 | 4.68 |
| 1453781_at | | AK009527 | 4.68 |
| 1436013_at | Gsg1l | AI852434 | 4.67 |
| 1441879_x_at | Mkrn1 | AV218897 | 4.67 |
| 1454572_at | 2810414N06Rik | AK013093 | 4.67 |
| 1435585_at | Tceal7 | BB378019 | 4.67 |
| 1441051_at | Trim27 | BB401251 | 4.67 |
| 1420580_at | 4930429B21Rik | NM_026249 | 4.66 |
| 1420446_at | Odf3 | NM_027019 | 4.66 |
| 1450306_at | Zp1 | NM_009580 | 4.66 |
| 1437069_at | Osbpl8 | BG969333 | 4.66 |
| 1423835_at | Zfp503 | BB447914 | 4.66 |
| 1416397_at | Mesdc1 | BB474887 | 4.65 |
| 1425154_a_at | Csf1 | M21149 | 4.65 |
| 1426893_at | C230093N12Rik | BC023470 | 4.64 |
| 1426032_at | Nfatc2 | AF289078 | 4.63 |
| 1453577_at | 2610018I03Rik | BB399635 | 4.63 |
| 1439888_at | | BB271581 | 4.63 |
| 1436421_s_at | Arpc5l | BB403233 | 4.63 |
| 1432312_a_at | 4931440B09Rik | AK016509 | 4.62 |
| 1423831_at | Prkag2 | BB756794 | 4.62 |
| 1439246_x_at | Tnrc6a | BB822587 | 4.62 |
| 1420533_at | Gucy1a3 | AK004815 | 4.61 |
| 1418169_at | Zcchc14 | BB223737 | 4.61 |
| 1443542_at | | BB767151 | 4.60 |
| 1428676_at | Tmprss6 | AK004939 | 4.60 |
| 1437146_x_at | Coro7 | AV025980 | 4.60 |
| 1428535_at | 9430020K01Rik | AK004276 | 4.59 |
| 1418173_at | Krt25 | NM_133730 | 4.59 |
| 1443888_at | AU023762 | BB426608 | 4.59 |
| 1438327_at | Zfp533 | BE981788 | 4.59 |
| 1433937_at | Trp53bp2 | BB814564 | 4.58 |
| 1454958_at | Gsk3b | BQ175580 | 4.58 |
| 1420667_at | Doc2b | BM117900 | 4.58 |
| 1448922_at | Dusp19 | NM_024438 | 4.57 |
| 1453008_at | 2300002D11Rik | AK009004 | 4.57 |
| 1418375_at | Mbd6 | NM_033072 | 4.56 |
| 1417443_at | Acot11 | NM_025590 | 4.56 |
| 1425328_at | BC008163 | AU067643 | 4.56 |
| 1456601_x_at | Fxyd2 | AV002675 | 4.54 |
| 1454845_x_at | Mchr1 | AW049955 | 4.54 |
| 1425327_at | BC008163 | AU067643 | 4.54 |
| 1455772_at | Pgr | BB428874 | 4.54 |
| 1450649_at | Gng10 | NM_025277 | 4.54 |
| 1435966_x_at | Mrpl13 | BE953095 | 4.54 |
| 1457088_at | Pldn | BB780781 | 4.54 |
| 1432541_at | 4930408O17Rik | AK015114 | 4.53 |
| 1422642_at | Cdc42ep3 | BB012489 | 4.53 |
| 1416606_s_at | Nola2 | BC024944 | 4.53 |
| 1423438_at | Kptn | AK009746 | 4.53 |
| 1420871_at | Gucy1b3 | BF472806 | 4.52 |
| 1417372_a_at | Peli1 | BC016515 | 4.52 |
| 1455170_at | 2810001G20Rik | BB250227 | 4.51 |
| 1438889_at | | BB183456 | 4.51 |
| 1460058_at | | BE648595 | 4.51 |
| 1427674_a_at | Sez6 | D29763 | 4.51 |
| 1440204_at | Foxg1 | AW494150 | 4.50 |
| 1423699_at | Ncaph2 | BC003900 | 4.50 |
| 1443372_at | | BB417900 | 4.50 |
| 1456858_at | Gpr149 | BB075339 | 4.49 |
| 1445605_s_at | 4921533L14Rik | AI835491 | 4.49 |
| 1441048_at | 5930430L01Rik | BB037822 | 4.49 |
| 1460343_at | Neurl | AF401228 | 4.49 |
| 1421364_at | Lrfn1 | NM_030562 | 4.49 |
| 1435666_at | Mast3 | AW553439 | 4.48 |
| 1434295_at | Rasgrp1 | BE691356 | 4.48 |
| 1442562_at | | BB346556 | 4.48 |
| 1418016_at | Pum2 | BI689507 | 4.48 |
| 1426585_s_at | Mapk1 | BM209765 | 4.47 |
| 1426450_at | Plcl2 | BM207017 | 4.47 |
| 1425558_at | Klc3 | BC017147 | 4.47 |
| 1419838_s_at | Plk4 | AI385771 | 4.46 |
| 1417178_at | Gipc2 | NM_016867 | 4.46 |
| 1454069_at | 9030409C19Rik | AK018495 | 4.46 |
| 1438955_x_at | Ppif | AV209130 | 4.46 |
| 1458399_at | Lrrc3 | AI413999 | 4.45 |
| 1448553_at | Myh7 | NM_080728 | 4.45 |
| 1453782_at | 3021401C12Rik | BI737125 | 4.45 |
| 1439552_at | Trio | BE985618 | 4.44 |
| 1450748_at | Smpd3 | NM_021491 | 4.44 |
| 1422799_at | Bat2 | AK019427 | 4.44 |
| 1436827_at | Gm944 | BB053232 | 4.44 |
| 1440359_at | 1700012H17Rik | BB427277 | 4.44 |
| 1427138_at | 0610010D24Rik | AW556861 | 4.44 |
| 1454772_at | Ascc3l1 | AI327392 | 4.43 |
| 1435624_at | 9030409G11Rik | AV345336 | 4.42 |
| 1423186_at | Tiam2 | BM228957 | 4.42 |
| 1455548_at | Dlgap4 | BB314358 | 4.41 |
| 1423973_a_at | Arf3 | BC024935 | 4.41 |
| 1421979_at | Phex | U73910 | 4.40 |
| 1452609_at | Cox4nb | BI133691 | 4.40 |
| 1419757_at | Pitpnm2 | NM_011256 | 4.40 |
| 1455024_at | Tlk1 | AV269836 | 4.40 |
| 1439548_at | Rap2b | BB390705 | 4.40 |
| 1460244_at | Upb1 | NM_133995 | 4.40 |
| 1435319_at | Ihpk2 | BB777667 | 4.39 |
| 1451630_at | Ttl | BC018513 | 4.39 |

TABLE 13-continued

Genes differentially translated between medium spiny neurons (MSNs) and the rest of the brain.

| Probe | Symbol | GenBank | FCH |
|---|---|---|---|
| 1440901_at | Dgkb | BB279524 | 4.38 |
| 1423563_at | Prrt1 | AA739053 | 4.38 |
| 1426097_a_at | Ccdc106 | BC018462 | 4.38 |
| 1456755_at | Trak1 | AI467545 | 4.38 |
| 1423641_s_at | Cnot7 | BC006021 | 4.38 |
| 1424439_at | 1810065E05Rik | BC026941 | 4.38 |
| 1429557_at | Mcm8 | AK010365 | 4.37 |
| 1415999_at | Hey1 | NM_010423 | 4.37 |
| 1439632_at |  | BQ174397 | 4.37 |
| 1457149_at | Ttc22 | BB005679 | 4.36 |
| 1423836_at | Zfp503 | BB447914 | 4.36 |
| 1448378_at | Fscn1 | NM_007984 | 4.35 |
| 1421897_at | Elk1 | AI385733 | 4.35 |
| 1437001_at | Gsk3b | BQ173949 | 4.35 |
| 1435441_at | Ablim2 | BB336053 | 4.34 |
| 1449110_at | Rhob | BC018275 | 4.34 |
| 1429122_a_at | 1700040I03Rik | AK006658 | 4.34 |
| 1450623_at | Gnb2 | NM_010312 | 4.33 |
| 1427607_at | Cacna1h | AB041801 | 4.33 |
| 1419924_at | Fnip1 | AW557298 | 4.33 |
| 1426978_at | Klhl2 | AW682368 | 4.32 |
| 1421193_a_at | Pbx3 | NM_016768 | 4.32 |
| 1438722_at | 2610014I16Rik | AI854368 | 4.31 |
| 1420834_at | Vamp2 | BG571810 | 4.31 |
| 1425680_a_at | Btrc | AF110396 | 4.31 |
| 1427930_at | Pdxk | BG063905 | 4.31 |
| 1418161_at | Jph3 | NM_020605 | 4.30 |
| 1450863_a_at | Dcamkl1 | BQ174703 | 4.30 |
| 1439957_at | Gnal | BF457720 | 4.29 |
| 1447530_at | F8a | BB274927 | 4.29 |
| 1421260_a_at | Srm | NM_009272 | 4.29 |
| 1441783_at | Ccni | BB749856 | 4.28 |
| 1428812_at | 1700040L02Rik | AK006661 | 4.28 |
| 1452019_at | Cyyr1 | AF442733 | 4.28 |
| 1454939_at | Phf20l1 | BB268102 | 4.28 |
| 1420427_a_at | Dhx32 | NM_133941 | 4.27 |
| 1455632_at | Gnb5 | BE446953 | 4.27 |
| 1448718_at | 2400001E08Rik | NM_025605 | 4.26 |
| 1432813_at | 2900064F13Rik | AK013749 | 4.26 |
| 1430135_at | Dnase2a | AK018651 | 4.26 |
| 1435845_at |  | BB764479 | 4.26 |
| 1416508_at | Med28 | AK005130 | 4.26 |
| 1421199_at | Dlg2 | BB622767 | 4.26 |
| 1420887_a_at | Bcl2l1 | NM_009743 | 4.25 |
| 1439133_at | 4930524O07Rik | AV267216 | 4.25 |
| 1417216_at | Pim2 | NM_138606 | 4.25 |
| 1424037_at | Itpka | BC027291 | 4.25 |
| 1422683_at | Irak1bp1 | NM_022986 | 4.24 |
| 1454902_at | Prkcz | BB430502 | 4.24 |
| 1417233_at | Chchd4 | NM_133928 | 4.24 |
| 1418181_at | pPtp4a3 | AK014601 | 4.24 |
| 1424384_a_at | Znrf1 | BC006765 | 4.24 |
| 1437306_at | C130092O11Rik | BG071013 | 4.24 |
| 1417890_at | Pdxp | NM_020271 | 4.24 |
| 1434943_at | BC023055 | BF464669 | 4.24 |
| 1430358_at | Becn1 | AV338072 | 4.23 |
| 1438211_s_at | Dbp | BB550183 | 4.23 |
| 1437780_at | Fancb | AV222467 | 4.23 |
| 1455865_at | Insm1 | BB468410 | 4.22 |
| 1456377_x_at | LOC632329 | AV010467 | 4.22 |
| 1418893_at | Pbx2 | NM_017463 | 4.22 |
| 1453324_at | Nip7 | BF459399 | 4.21 |
| 1449063_at | Sec22b | BC009024 | 4.21 |
| 1428951_at | Nol8 | AK017551 | 4.21 |
| 1422627_a_at | Mkks | BF581250 | 4.21 |
| 1433816_at | Mcart1 | BQ031264 | 4.21 |
| 1439508_at | Rab11b | BI663913 | 4.21 |
| 1433955_at | Brwd1 | BB467195 | 4.20 |
| 1436128_at | Plekha8 | AI324154 | 4.20 |
| 1458457_at |  | BB750877 | 4.20 |
| 1448150_at | Nup62 | NM_053074 | 4.20 |
| 1460395_at | Nudcd3 | BB139222 | 4.19 |
| 1434830_at | Mxd1 | AV228517 | 4.19 |
| 1451884_a_at | Lsm2 | AF204156 | 4.19 |
| 1447696_x_at | Adcy5 | BB091427 | 4.18 |
| 1452984_at | Ccny | AK014507 | 4.18 |
| 1451020_at | Gsk3b | BB831420 | 4.18 |
| 1448877_at | Dlx2 | NM_010054 | 4.17 |
| 1455365_at | Cdh8 | BB426483 | 4.17 |
| 1448498_at | Rps6ka4 | NM_019924 | 4.17 |
| 1427261_at | Wwc1 | BQ176786 | 4.17 |
| 1423330_at | Ensa | AK006149 | 4.17 |
| 1453278_a_at | Clip4 | AV273445 | 4.16 |
| 1432103_a_at | Sh3gl3 | AK012114 | 4.16 |
| 1455102_at | D330037H05Rik | BB213860 | 4.16 |
| 1451917_a_at | Dcamkl1 | AF155820 | 4.16 |
| 1433657_at | A130092J06Rik | BI111848 | 4.15 |
| 1442927_at | Ptk2b | BB548690 | 4.15 |
| 1430037_at | Snx27 | AK017836 | 4.15 |
| 1449552_at | Zfr | NM_011767 | 4.15 |
| 1435367_at | Mapk4 | BQ177154 | 4.14 |
| 1458711_at |  | BB762344 | 4.14 |
| 1428214_at | Tomm7 | BB609428 | 4.14 |
| 1427673_a_at | Sema3e | Z93948 | 4.14 |
| 1427450_x_at | Myo1b | BI080370 | 4.14 |
| 1456290_x_at | Ccm2 | BB813044 | 4.13 |
| 1432574_at | 4930548F15Rik | BF466430 | 4.13 |
| 1423897_at | Rnf187 | AW488376 | 4.13 |
| 1450570_a_at | Cd19 | NM_009844 | 4.13 |
| 1422977_at | Gp1bb | NM_010327 | 4.12 |
| 1454844_at | Mchr1 | AW049955 | 4.12 |
| 1423785_at | Egln1 | BE995700 | 4.11 |
| 1423012_at | Syt7 | NM_018801 | 4.11 |
| 1457116_at | Rexo1 | BI555624 | 4.10 |
| 1416391_at | Ptcd1 | NM_133735 | 4.10 |
| 1456471_x_at | Phgdh | BB204486 | 4.10 |
| 1450142_a_at | Card14 | NM_130886 | 4.09 |
| 1442113_at | 5330417C22Rik | BB183350 | 4.09 |
| 1439986_at | Dgki | BE647270 | 4.09 |
| 1448709_at | LOC669477 | NM_033566 | 4.09 |
| 1423640_at | Synpr | BC026512 | 4.08 |
| 1458443_at | Crtc1 | BE986758 | 4.08 |
| 1441894_s_at | Grasp | BB071890 | 4.08 |
| 1426065_a_at | Trib3 | BC012955 | 4.08 |
| 1417326_a_at | Anapc11 | NM_025389 | 4.08 |
| 1434569_at |  | AA474455 | 4.08 |
| 1460392_a_at | Eny2 | BB610210 | 4.07 |
| 1426354_at | Bap1 | AK009033 | 4.07 |
| 1457704_at | Zfp533 | BE982894 | 4.07 |
| 1458660_at | AI414330 | AI414330 | 4.06 |
| 1454721_at | 1110018G07Rik | AV257687 | 4.06 |
| 1434403_at | Spred2 | AV229054 | 4.06 |
| 1455271_at | LOC620695 | BB560177 | 4.05 |
| 1420853_at | Sdc3 | BB528350 | 4.05 |
| 1431394_a_at | Lrrk2 | AK014938 | 4.05 |
| 1459983_at | Impa2 | AI115397 | 4.05 |
| 1455620_at | 4930551E15Rik | BQ177219 | 4.04 |
| 1454943_a_at | Paxip1 | BM935413 | 4.04 |
| 1434964_at | X83328 | BM952039 | 4.04 |
| 1438662_at | Ajap1 | AW123234 | 4.03 |
| 1452974_at | Nol8 | AK017551 | 4.03 |
| 1435169_at | A930001N09Rik | BB431047 | 4.03 |
| 1425271_at | Psmc3ip | AB000121 | 4.03 |
| 1437642_at | Hrbl | BB243375 | 4.03 |
| 1419137_at | Shank3 | NM_021423 | 4.03 |
| 1423673_at | Ldoc11 | BC023053 | 4.03 |
| 1448360_s_at | Angel2 | NM_021421 | 4.03 |
| 1424523_at | Elmo1 | BC024727 | 4.02 |
| 1455206_at | C130006E23 | BQ175276 | 4.02 |
| 1422527_at | H2-DMa | NM_010386 | 4.02 |
| 1450928_at | Id4 | BB121406 | 4.02 |
| 1458351_s_at | Klhl2 | BB428573 | 4.01 |
| 1422902_s_at | Mgea5 | NM_023799 | 4.01 |
| 1435942_at | Kcnq2 | BE993301 | 4.01 |
| 1454960_at | Smad3 | BI646741 | 4.00 |
| 1433854_at | Tmem164 | BG064061 | 4.00 |
| 1445653_at | BC031361 | BB825492 | 4.00 |
| 1442695_at | C030007I01Rik | AW494399 | 4.00 |
| 1417192_at | Tomm70a | NM_138599 | 4.00 |
| 1447301_at | Akap5 | BG228875 | 4.00 |

TABLE 13-continued

Genes differentially translated between medium spiny neurons (MSNs) and the rest of the brain.

| Probe | Symbol | GenBank | FCH |
|---|---|---|---|
| 1426416_a_at | Yipf4 | AV216410 | 4.00 |
| 1438381_x_at | Ddx47 | BB305306 | 4.00 |
| 1425354_a_at | Aggf1 | BC027286 | 4.00 |
| 1420192_at | D16Bwg1494e | N28171 | 4.00 |
| 1458074_at | EG328280 | BB179240 | 3.99 |
| 1421355_at | Tgm3 | NM_009374 | 3.99 |
| 1426031_a_at | Nfatc2 | AF289078 | 3.99 |
| 1446498_at | Il20ra | BB551879 | 3.99 |
| 1434920_a_at | Evl | AW553781 | 3.99 |
| 1452531_at | Runx1 | X97306 | 3.99 |
| 1452541_at | Epb4.1l2 | AJ245854 | 3.98 |
| 1417375_at | Tuba4a | AW491660 | 3.98 |
| 1439932_at | 3110003A22Rik | BQ174624 | 3.98 |
| 1459299_at | Myo3b | AV381193 | 3.98 |
| 1420590_at | Has1 | NM_008215 | 3.98 |
| 1448990_a_at | Myo1b | AI255256 | 3.98 |
| 1454092_a_at | Gtf2h3 | AK017176 | 3.97 |
| 1435638_at | 9130221H12Rik | BG808297 | 3.97 |
| 1426580_at | Plk4 | BB706079 | 3.97 |
| 1423174_a_at | Pard6b | BE953582 | 3.97 |
| 1450655_at | Pten | AA214868 | 3.97 |
| 1460214_at | Pcp4 | NM_008791 | 3.97 |
| 1452281_at | Sos2 | Z11664 | 3.97 |
| 1429393_at | Wdr40a | BI558553 | 3.97 |
| 1422897_at | Slc22a12 | NM_009203 | 3.96 |
| 1416125_at | Fkbp5 | U16959 | 3.95 |
| 1440213_a_at | 2010001M06Rik | BE200030 | 3.95 |
| 1420767_at | 1700019G17Rik | NM_029331 | 3.95 |
| 1423175_s_at | Pard6b | BE953582 | 3.95 |
| 1435674_at | Rhobtb2 | BB351953 | 3.94 |
| 1434736_at | Hlf | BB744589 | 3.94 |
| 1460205_at | Dcakd | NM_026551 | 3.94 |
| 1422255_at | Kcna4 | NM_021275 | 3.94 |
| 1433777_at | L3mbtl2 | BB152370 | 3.94 |
| 1439659_at | Usp49 | BB014981 | 3.94 |
| 1427161_at | Cenpf | BE848253 | 3.94 |
| 1448141_at | 1110014J01Rik | NM_029101 | 3.94 |
| 1418657_at | Znhit4 | BC019383 | 3.93 |
| 1425006_a_at | Vrk1 | BC016676 | 3.93 |
| 1436408_at | Rprml | BE946298 | 3.93 |
| 1453113_at | Wdsub1 | BB820363 | 3.93 |
| 1415904_at | Lpl | BC003305 | 3.92 |
| 1426266_s_at | Zbtb8os | BB417508 | 3.92 |
| 1433860_at | 6030458C11Rik | BB126127 | 3.92 |
| 1427409_at | 8-Mar | BB366341 | 3.92 |
| 1436280_at | Zfp31 | BB757838 | 3.92 |
| 1450853_at | Tle4 | AU045006 | 3.91 |
| 1460436_at | Ndst1 | BI652065 | 3.91 |
| 1424434_at | BC024814 | BC024814 | 3.91 |
| 1435043_at | Plcb1 | BB794831 | 3.90 |
| 1458413_at | Fbxw8 | BB357976 | 3.90 |
| 1454675_at | Thra | BI076689 | 3.90 |
| 1434795_at | Disp1 | BB174877 | 3.90 |
| 1445854_at | C230004F18Rik | BB380166 | 3.90 |
| 1420985_at | Ash1l | BG694892 | 3.90 |
| 1426383_at | Cry2 | BF303057 | 3.90 |
| 1448467_a_at | Ehbp1l1 | NM_053252 | 3.90 |
| 1437520_a_at | Nup85 | BB320388 | 3.89 |
| 1421477_at | Cplx2 | NM_009946 | 3.89 |
| 1417331_a_at | Arl6 | NM_019665 | 3.88 |
| 1460738_at | Limd2 | AK012581 | 3.88 |
| 1417456_at | Gnpat | NM_010322 | 3.88 |
| 1454789_x_at | Prpf6 | BB085604 | 3.88 |
| 1452628_at | Bag5 | AK005534 | 3.87 |
| 1417075_at | 2010309E21Rik | NM_025591 | 3.87 |
| 1443225_at | Acvr1c | BB396526 | 3.87 |
| 1438309_at |  | BB432539 | 3.87 |
| 1416744_at | Uap1 | NM_133806 | 3.87 |
| 1419166_at | Slc5a2 | BC022226 | 3.87 |
| 1436795_at | 9630058J23Rik | BM247060 | 3.86 |
| 1448364_at | Ccng2 | U95826 | 3.86 |
| 1427358_a_at | Dapk1 | BC026671 | 3.85 |
| 1440505_at | Plcxd1 | BB187908 | 3.85 |
| 1433847_at | D330017J20Rik | BB098407 | 3.85 |
| 1417114_at | Gmcl1 | AF163665 | 3.85 |
| 1419352_at | l7Rn6 | BC003916 | 3.84 |
| 1428443_a_at | Rap1gap | AK005063 | 3.84 |
| 1428723_at | 2310047M10Rik | AK009886 | 3.84 |
| 1426887_at | Nudt11 | BQ174833 | 3.84 |
| 1422439_a_at | Cdk4 | NM_009870 | 3.84 |
| 1442039_at | Tox | BF020502 | 3.84 |
| 1419669_at | Prtn3 | U97073 | 3.83 |
| 1456970_at | Cdh7 | BF472513 | 3.83 |
| 1452295_at | Tmepai | AV291712 | 3.82 |
| 1448511_at | Ptprcap | NM_016933 | 3.82 |
| 1431646_a_at | Stx6 | AK009690 | 3.82 |
| 1448414_at | Rad1 | NM_011232 | 3.82 |
| 1417355_at | Peg3 | AB003040 | 3.82 |
| 1456441_at | Rbm4b | BB667164 | 3.81 |
| 1417214_at | Rab27b | BB121269 | 3.81 |
| 1448554_s_at | Myh7 | NM_080728 | 3.81 |
| 1453266_at | Zbtb4 | BB767069 | 3.81 |
| 1419611_at | 4632415L05Rik | BC023403 | 3.81 |
| 1448919_at | Cd302 | NM_025422 | 3.80 |
| 1429670_a_at | Lrriq2 | BB321286 | 3.80 |
| 1421975_a_at | Add2 | AF189769 | 3.79 |
| 1459054_at | BC035954 | BB496939 | 3.79 |
| 1458339_at | Cdadc1 | BB231078 | 3.79 |
| 1427038_at | Penk1 | M13227 | 3.79 |
| 1417844_at | Med4 | NM_026119 | 3.79 |
| 1434306_at | Rab3ip | BF319015 | 3.78 |
| 1439764_s_at | Igf2bp2 | BB098431 | 3.78 |
| 1435431_at | 2310047M15Rik | AW558989 | 3.78 |
| 1420397_a_at | Spen | NM_019763 | 3.78 |
| 1433558_at | Dab2ip | BM231046 | 3.78 |
| 1420052_x_at | Psmb1 | C81484 | 3.78 |
| 1439882_at | Sec23ip | BE685845 | 3.78 |
| 1443952_at | Thra | BI525006 | 3.77 |
| 1432378_at | C030004G16Rik | AK021043 | 3.77 |
| 1457897_at | Iqce | AV245518 | 3.77 |
| 1460671_at | Gpx1 | BI219063 | 3.77 |
| 1431771_a_at | Irak1bp1 | AK014712 | 3.77 |
| 1422609_at | Arpp19 | BE648432 | 3.77 |
| 1427522_at | Arhgap20 | BB623455 | 3.76 |
| 1426452_a_at | Rab30 | BG070713 | 3.76 |
| 1452932_at | Zbtb7a | AK010379 | 3.76 |
| 1441495_at | Kctd8 | BB183090 | 3.75 |
| 1419225_at | Cacna2d3 | NM_009785 | 3.75 |
| 1434141_at | Gucy1a3 | BG072799 | 3.75 |
| 1450662_at | Tesk1 | NM_011571 | 3.75 |
| 1423217_a_at | 2510049I19Rik | AV109006 | 3.75 |
| 1434277_a_at | Ypel2 | BG069663 | 3.75 |
| 1430630_at |  | BB236218 | 3.74 |
| 1436986_at | Sntb2 | BB219478 | 3.74 |
| 1437006_x_at | Becn1 | C86082 | 3.74 |
| 1416603_at | Rpl22 | NM_009079 | 3.74 |
| 1435525_at | Kctd17 | BI408602 | 3.74 |
| 1437131_x_at | Mrpl11 | AV045020 | 3.74 |
| 1453428_at | 2700045P11Rik | AK012380 | 3.74 |
| 1444808_at | Pawr | BG070555 | 3.73 |
| 1453083_at | 6430701C03Rik | AK018294 | 3.73 |
| 1435430_at | Tmem1 | BM200437 | 3.73 |
| 1457310_x_at | Scrt2 | BG807042 | 3.73 |
| 1434082_at | Pctk2 | BM243464 | 3.73 |
| 1425920_at | Cuedc1 | BC025434 | 3.73 |
| 1456106_x_at | Sdccag3 | BB343189 | 3.73 |
| 1434805_at | Mllt1 | BG063049 | 3.73 |
| 1422457_s_at | Sumo3 | NM_019929 | 3.72 |
| 1416113_at | Fkbp8 | NM_010223 | 3.72 |
| 1417462_at | Cap1 | NM_007598 | 3.72 |
| 1435825_at | Acvrl1 | BG969012 | 3.72 |
| 1437703_at | EG382156 | BM229128 | 3.71 |
| 1428222_at | Dcamkl2 | AK018179 | 3.71 |
| 1451746_a_at | Atg12 | AK016474 | 3.71 |
| 1419224_at | Cecr6 | NM_033567 | 3.70 |
| 1457341_at |  | BE991676 | 3.70 |
| 1428914_at | 2310014D11Rik | AK009333 | 3.70 |
| 1418081_at | Wbscr18 | NM_025362 | 3.70 |
| 1426521_at | D230025D16Rik | BG065702 | 3.70 |
| 1436887_x_at | Grwd1 | BB251524 | 3.70 |

TABLE 13-continued

Genes differentially translated between medium spiny neurons (MSNs) and the rest of the brain.

| Probe | Symbol | GenBank | FCH |
|---|---|---|---|
| 1445970_at | Ablim2 | BG068300 | 3.70 |
| 1438213_at | A830018L16Rik | BB128962 | 3.70 |
| 1429591_at | Tacc1 | BE862546 | 3.70 |
| 1440407_at |  | BE956823 | 3.69 |
| 1426367_at | Cab39l | AK013205 | 3.69 |
| 1436787_x_at | Sec14l3 | AV024133 | 3.69 |
| 1448959_at | Ndufs4 | NM_010887 | 3.69 |
| 1418789_at | Sntg2 | NM_133742 | 3.69 |
| 1447157_at | 4930480K23Rik | BB751612 | 3.68 |
| 1444107_at | 9430029N19Rik | BB091357 | 3.68 |
| 1454815_at | Sertad2 | BI219769 | 3.68 |
| 1434663_at | 2410129H14Rik | BI153133 | 3.68 |
| 1434997_at | Cdc2l6 | BB510904 | 3.68 |
| 1455820_x_at | Scarb1 | BB138434 | 3.68 |
| 1458027_at | Mrpl17 | BB343967 | 3.68 |
| 1422787_at | Fkbpl | NM_019873 | 3.68 |
| 1455562_at | Sox12 | BF468186 | 3.68 |
| 1421000_at | Cnot4 | AI448404 | 3.68 |
| 1422495_a_at | Hmgn1 | NM_008251 | 3.67 |
| 1424731_at | Nle1 | BC018399 | 3.67 |
| 1451723_at | Cnot6l | BC018506 | 3.67 |
| 1449353_at | Zmat3 | NM_009517 | 3.67 |
| 1434825_at | Zfp469 | BQ175287 | 3.67 |
| 1451291_at | Obfc2b | BC026942 | 3.67 |
| 1422121_at | Oprd1 | L06322 | 3.67 |
| 1423116_at | Dom3z | BG071924 | 3.67 |
| 1429174_at | Wdr34 | AK014304 | 3.67 |
| 1427286_at | D11Bwg0517e | BB130195 | 3.67 |
| 1443250_at | Rgs2 | AV246932 | 3.66 |
| 1440368_at | Jmjd2b | BG075393 | 3.66 |
| 1435204_at | Prmt8 | BG065273 | 3.66 |
| 1435270_x_at | N6amt2 | BF730076 | 3.66 |
| 1427300_at | Lhx8 | D49658 | 3.66 |
| 1452506_a_at | Ilkap | BC011427 | 3.66 |
| 1428582_at | 2010208K18Rik | AK008476 | 3.66 |
| 1430735_at | 4930424G05Rik | AK015195 | 3.66 |
| 1433907_at | Pknox2 | BQ175824 | 3.66 |
| 1453485_s_at | 1110005A03Rik | AK016897 | 3.65 |
| 1437989_at | Pde8b | BB357157 | 3.65 |
| 1448687_at | C1qdc2 | NM_026125 | 3.65 |
| 1455703_at | Akt2 | BG074736 | 3.65 |
| 1426009_a_at | Pip5k1b | BC003763 | 3.65 |
| 1426701_at | 4632419K20Rik | BM055600 | 3.65 |
| 1440823_x_at | D130058I21Rik | BB005209 | 3.65 |
| 1435544_at | Exosc6 | BB446614 | 3.65 |
| 1455313_at | Ablim2 | BB336053 | 3.64 |
| 1419216_at | Azi1 | NM_009734 | 3.64 |
| 1453025_at | 2900006F19Rik | AK011824 | 3.64 |
| 1423583_at | Fem1a | AK005041 | 3.64 |
| 1426328_a_at | Scn3b | AY049036 | 3.64 |
| 1422594_at | 5730470L24Rik | BC004090 | 3.64 |
| 1426457_at | Slmap | BB473571 | 3.64 |
| 1437392_at | AW123113 | AW123113 | 3.64 |
| 1424851_at | Chchd5 | BE991735 | 3.63 |
| 1445202_at |  | BB526676 | 3.63 |
| 1434653_at | Ptk2b | AV026976 | 3.63 |
| 1457246_at | Rai16 | AU040322 | 3.63 |
| 1457864_at | Rab11fip3 | BB206151 | 3.63 |
| 1419443_at | Sap18 | NM_009119 | 3.63 |
| 1415761_at | Mrpl52 | AV021593 | 3.63 |
| 1422710_a_at | Cacna1h | NM_021415 | 3.63 |
| 1424082_at | Tbc1d13 | BC025586 | 3.63 |
| 1435128_at | Baiap2 | BB429313 | 3.63 |
| 1452861_at | 2010300C02Rik | AK008485 | 3.62 |
| 1449128_at | Ccdc43 | NM_025918 | 3.62 |
| 1436810_x_at | 2900010M23Rik | AV046927 | 3.62 |
| 1460261_at | Dlg4 | AI646416 | 3.62 |
| 1416533_at | Egln2 | NM_053208 | 3.62 |
| 1433151_at | 4933415B22Rik | AK016815 | 3.62 |
| 1435921_at | D8Ertd587e | BM223036 | 3.61 |
| 1421107_at | Stk4 | NM_021420 | 3.61 |
| 1439569_at | Gpr83 | AV291031 | 3.61 |
| 1449072_a_at | N6amt2 | NM_026526 | 3.61 |
| 1439731_at | E130309F12Rik | BB546288 | 3.61 |
| 1424777_at | Wdr21 | BC003284 | 3.61 |
| 1438128_at | Gnat2 | BB427907 | 3.61 |
| 1426894_s_at | C230093N12Rik | BC023470 | 3.61 |
| 1421739_a_at | Matk | NM_010768 | 3.61 |
| 1436639_at | Bola2 | BE951004 | 3.60 |
| 1420059_at | 2410166I05Rik | AI480750 | 3.60 |
| 1457702_at | Gpr12 | BB284435 | 3.60 |
| 1451665_a_at | Ap4s1 | BC001985 | 3.60 |
| 1431056_a_at | Lpl | AK017272 | 3.60 |
| 1455064_at | Rab36 | BB313586 | 3.60 |
| 1455958_s_at | Pptc7 | AI881989 | 3.60 |
| 1438751_at | Slc30a10 | BB736474 | 3.60 |
| 1429392_at | Wdr40a | BI558553 | 3.60 |
| 1434216_a_at | Nudt19 | BG070689 | 3.59 |
| 1439645_at | Adra2b | BQ031032 | 3.58 |
| 1439557_s_at | Ldb2 | BB097063 | 3.58 |
| 1429197_s_at | Rabgap1l | BB431654 | 3.58 |
| 1454219_at | Dnajc2 | AK013295 | 3.58 |
| 1434704_at | Srpk2 | BB529352 | 3.58 |
| 1416783_at | Tac1 | NM_009311 | 3.58 |
| 1429752_x_at | Clip4 | AV273445 | 3.58 |
| 1422713_a_at | Ube2i | U31934 | 3.58 |
| 1415762_x_at | Mrpl52 | AV021593 | 3.58 |
| 1433471_at | Tcf7 | AI323642 | 3.58 |
| 1416990_at | Rxrb | BC019432 | 3.57 |
| 1437559_at | Rgs7bp | BB130891 | 3.57 |
| 1423522_at | Npm3 | BB811478 | 3.57 |
| 1452452_at |  | M73818 | 3.57 |
| 1435265_at |  | BF466929 | 3.57 |
| 1419285_s_at | Cyhr1 | NM_019396 | 3.57 |
| 1416285_at | Ndufc1 | NM_025523 | 3.57 |
| 1452789_at | Snn | AK012171 | 3.57 |
| 1425211_at | 2010003O18Rik | BC021775 | 3.57 |
| 1454720_at | Hs3st5 | AV328620 | 3.57 |
| 1428892_at | Ppil1 | AK004331 | 3.57 |
| 1439662_at | Homer1 | BM124609 | 3.57 |
| 1435233_at | Ncoa2 | BM234716 | 3.56 |
| 1423916_s_at | Mlf2 | BC003975 | 3.56 |
| 1450560_a_at | Ppp2r5d | NM_009358 | 3.56 |
| 1430070_at | 1500035N22Rik | AK005363 | 3.56 |
| 1435472_at | Kremen1 | BG069617 | 3.56 |
| 1419564_at | Zfp467 | NM_020589 | 3.55 |
| 1426822_at | Rhot2 | BM201133 | 3.55 |
| 1436085_at | Zbtb34 | BB361974 | 3.55 |
| 1442019_at | Rcvrn | BB627097 | 3.55 |
| 1418135_at | Afl1 | NM_133919 | 3.55 |
| 1425956_a_at | Cdadc1 | BC004588 | 3.55 |
| 1416600_a_at | Dscr1 | AF282255 | 3.54 |
| 1425455_a_at | Churc1 | BC019472 | 3.54 |
| 1437214_at | Lrrtm4 | BB667279 | 3.54 |
| 1457097_at | Skap2 | BB212597 | 3.54 |
| 1433583_at | Zfp365 | AV327248 | 3.54 |
| 1434567_at | 4732496O08Rik | BE952228 | 3.54 |
| 1438231_at | Foxp2 | AV322952 | 3.54 |
| 1456697_x_at | Dmtf1 | BB248138 | 3.54 |
| 1419173_at | Acy1 | NM_025371 | 3.54 |
| 1435200_at | 6330419J24Rik | AV327542 | 3.53 |
| 1447470_at | Hdhd2 | BF451327 | 3.53 |
| 1440212_at | Slc12a1 | AI788571 | 3.53 |
| 1436387_at | Homer1 | BB398124 | 3.53 |
| 1429738_at | Myt1l | AK013847 | 3.53 |
| 1438379_x_at | 2310007F21Rik | AV330311 | 3.53 |
| 1436483_at | Myt1l | BM116113 | 3.53 |
| 1460701_a_at | Mrpl52 | AV021593 | 3.53 |
| 1425510_at | Mark1 | BM213279 | 3.52 |
| 1447538_at | Crtc1 | AW124625 | 3.52 |
| 1415888_at | Hdgf | NM_008231 | 3.52 |
| 1423161_s_at | Spred1 | BQ044290 | 3.52 |
| 1448691_at | Ubqln4 | BB764994 | 3.52 |
| 1424810_at | Tasp1 | BC005776 | 3.52 |
| 1451751_at | Ddit4l | AF335325 | 3.52 |
| 1421101_a_at | Ldb2 | NM_010698 | 3.52 |
| 1460652_at | Esrra | NM_007953 | 3.52 |
| 1423081_a_at | Tomm20 | AK002902 | 3.51 |
| 1424191_a_at | Tmem41a | BC019770 | 3.51 |
| 1425059_at | Prmt6 | BC022899 | 3.51 |

TABLE 13-continued

Genes differentially translated between medium spiny neurons (MSNs) and the rest of the brain.

| Probe | Symbol | GenBank | FCH |
|---|---|---|---|
| 1419754_at | Myo5a | NM_010864 | 3.51 |
| 1429218_at | Det1 | BE457100 | 3.51 |
| 1422569_at | Yy1 | BI665246 | 3.50 |
| 1450844_at | Stx6 | BQ174465 | 3.50 |
| 1451908_a_at | Sec14l1 | BC005766 | 3.50 |
| 1448224_at | Tfam | NM_009360 | 3.50 |
| 1448170_at | Siah2 | AA414485 | 3.50 |
| 1455885_at | Gna12 | AV238106 | 3.50 |
| 1455058_at | Mtmr9 | BM118290 | 3.50 |
| 1460702_at | Triap1 | AK007514 | 3.50 |
| 1449633_s_at | Nt5c3l | AI841843 | 3.50 |
| 1420708_at | Traip | AK012948 | 3.50 |
| 1449472_at | Gpr12 | NM_008151 | 3.50 |
| 1448889_at | Slc38a4 | NM_027052 | 3.49 |
| 1420530_at | Neud4 | AW553317 | 3.49 |
| 1418168_at | Zcchc14 | BB223737 | 3.49 |
| 1447856_x_at | Slc25a25 | BB186319 | 3.49 |
| 1449877_s_at | Kifc1 | NM_016761 | 3.49 |
| 1448947_at | 2810004N23Rik | NM_025615 | 3.49 |
| 1459372_at | Npas4 | AV348246 | 3.48 |
| 1422463_a_at | Mrpl3 | AB049633 | 3.48 |
| 1434693_at |  | BE952823 | 3.48 |
| 1437929_at | Dact2 | AV306847 | 3.48 |
| 1423461_a_at | Ubl3 | AV328436 | 3.48 |
| 1454773_at | Rxra | BQ175050 | 3.48 |
| 1442153_at | Uty | BB206087 | 3.48 |
| 1419683_at | Trp53rk | BB400773 | 3.48 |
| 1435141_at | Sft2d2 | AV238378 | 3.48 |
| 1422487_at | Smad4 | AK004804 | 3.48 |
| 1421493_a_at | Rgs20 | NM_021374 | 3.48 |
| 1449392_at | Hsd17b1 | NM_010475 | 3.48 |
| 1437524_x_at | Coro7 | BB534801 | 3.47 |
| 1420545_a_at | Chn1 | NM_029716 | 3.47 |
| 1419445_s_at | Sap18 | NM_009119 | 3.47 |
| 1426984_at | 2310067B10Rik | BC007157 | 3.47 |
| 1455609_at | C030025P15Rik | BB525143 | 3.46 |
| 1418172_at | Hebp1 | AF117613 | 3.46 |
| 1447959_at | Zfp398 | AI506402 | 3.46 |
| 1435063_at | RP23-25C1.8 | AV326964 | 3.46 |
| 1449140_at | Nudcd2 | BC005646 | 3.46 |
| 1419816_s_at | Errfi1 | AI788763 | 3.46 |
| 1443129_at |  | BB363699 | 3.46 |
| 1453433_at | Wdr89 | AK011125 | 3.46 |
| 1418412_at | Tpd52l1 | NM_009413 | 3.46 |
| 1429417_at | 4833446K15Rik | AK009528 | 3.45 |
| 1434755_at | Coro2b | BB538661 | 3.45 |
| 1420374_at | Foxj2 | BI249549 | 3.45 |
| 1424575_at | Rabl5 | BC009150 | 3.45 |
| 1433703_s_at | Bahd1 | BM115038 | 3.45 |
| 1442268_a_at |  | BB749041 | 3.45 |
| 1429573_at | Dmrtc1a | AK014934 | 3.45 |
| 1448520_at | Dclre1b | NM_133865 | 3.45 |
| 1455230_at | Cacng4 | BQ176350 | 3.45 |
| 1451717_s_at | Senp2 | AV317107 | 3.44 |
| 1436690_at | Lrba | BB494139 | 3.44 |
| 1415950_a_at | Pebp1 | NM_018858 | 3.44 |
| 1422486_a_at | Smad4 | AK004804 | 3.44 |
| 1428526_at | Lsm d1 | AK018782 | 3.43 |
| 1423038_at | Stx6 | BQ174465 | 3.43 |
| 1435547_at |  | BQ175722 | 3.43 |
| 1443172_at | Orc1l | BB210535 | 3.43 |
| 1453262_at | 2810032G03Rik | AK012851 | 3.43 |
| 1434969_at | Brunol5 | BB381558 | 3.43 |
| 1450326_at | Shc3 | NM_009167 | 3.43 |
| 1456786_at | Ldb2 | BB097063 | 3.43 |
| 1424416_at | Nkiras2 | BC024398 | 3.43 |
| 1455708_at | Tmod3 | BB749726 | 3.43 |
| 1425846_a_at | Caln1 | AF282251 | 3.42 |
| 1418082_at | Nmt1 | BC016526 | 3.42 |
| 1434183_at | LOC666704 | BI415031 | 3.42 |
| 1451592_at | P42pop | AF364868 | 3.42 |
| 1434255_at | Pacs2 | AV145060 | 3.42 |
| 1424175_at | Tef | BC017689 | 3.42 |
| 1417626_at | Pde4dip | NM_031401 | 3.42 |
| 1425479_at | Smyd5 | BF160651 | 3.41 |
| 1460592_at | Epb4.1l1 | BI684958 | 3.41 |
| 1424005_at | B230219D22Rik | BC006718 | 3.41 |
| 1456579_x_at | Telo2 | BB462079 | 3.41 |
| 1434928_at | Gas2l1 | BB769886 | 3.41 |
| 1416050_a_at | Scarb1 | NM_016741 | 3.40 |
| 1420158_s_at | Abcf1 | AA408356 | 3.40 |
| 1452684_at | Akt1s1 | BM068933 | 3.40 |
| 1441264_x_at | A930005H10Rik | AV009179 | 3.40 |
| 1460428_at | Ankrd13a | BC003286 | 3.40 |
| 1456682_at | Lonrf2 | AV221843 | 3.40 |
| 1416730_at | Rcl1 | BC004574 | 3.40 |
| 1418323_at | Fem1b | BM232562 | 3.39 |
| 1436786_at | Sec14l3 | AV024133 | 3.39 |
| 1451971_at | Cul4a | BC024113 | 3.39 |
| 1434085_at | Zfp523 | AV136654 | 3.39 |
| 1429394_at | A130010J15Rik | BB025778 | 3.39 |
| 1433526_at | Klhl8 | BM942651 | 3.39 |
| 1429745_at | LOC574405 | AK005439 | 3.39 |
| 1436285_at | Ccdc113 | AV279772 | 3.39 |
| 1433522_at | Pskh1 | BG073986 | 3.39 |
| 1440286_at | Fbxl16 | BM232403 | 3.38 |
| 1416977_at | Stam2 | BB125321 | 3.38 |
| 1447868_x_at | Txnl2 | BB030680 | 3.38 |
| 1440278_at | Dynll1 | BM939312 | 3.38 |
| 1448757_at | Pml | NM_008884 | 3.38 |
| 1434546_at | Smg5 | BI106637 | 3.38 |
| 1448785_at | Runx1t1 | BG072085 | 3.38 |
| 1449956_at | Prkce | NM_011104 | 3.38 |
| 1437037_x_at | Snd1 | BB240087 | 3.37 |
| 1456606_a_at | Phactr1 | AV259240 | 3.37 |
| 1457703_at | Cacna2d4 | BE952838 | 3.37 |
| 1460676_at | Josd1 | BC006928 | 3.37 |
| 1451046_at | Zfpm1 | AA014267 | 3.37 |
| 1436525_at | Ap3s2 | AV225391 | 3.37 |
| 1417710_at | Mettl9 | NM_021554 | 3.37 |
| 1418250_at | Arfl4 | NM_025404 | 3.37 |
| 1433680_x_at | Siva1 | AV216351 | 3.37 |
| 1434922_at | Phf12 | BB483595 | 3.37 |
| 1424480_s_at | Akt2 | BC026151 | 3.37 |
| 1427899_at | Rnf6 | BI738010 | 3.37 |
| 1445685_at | Gas7 | AI837851 | 3.36 |
| 1454612_at | Rkhd2 | BI656279 | 3.36 |
| 1452323_at | Spryd3 | BQ176406 | 3.36 |
| 1421498_a_at | 2010204K13Rik | NM_023450 | 3.36 |
| 1456427_at | Gp1bb | BE988990 | 3.36 |
| 1420650_at | Atbf1 | NM_007496 | 3.36 |
| 1459621_at | Itsn1 | BB713496 | 3.36 |
| 1453412_a_at | Sec14l1 | BI652727 | 3.35 |
| 1424195_a_at | Inpp5d | AF125996 | 3.35 |
| 1450710_at | Jarid2 | NM_021878 | 3.35 |
| 1430614_at | 4632415K11Rik | BG962576 | 3.35 |
| 1452015_at | 6330416G13Rik | AV326978 | 3.35 |
| 1436764_at | Pard3 | BE199556 | 3.35 |
| 1419470_at | Gnb4 | BI713933 | 3.35 |
| 1429774_a_at | Ccdc98 | AK014420 | 3.35 |
| 1434831_a_at | Foxo3a | BB364488 | 3.35 |
| 1415975_at | Carhsp1 | AU080787 | 3.35 |
| 1418924_at | Rassf7 | NM_025886 | 3.35 |
| 1437300_at | Mef2d | BG067616 | 3.34 |
| 1421175_at | Myt1l | NM_008666 | 3.34 |
| 1428712_at | Mon1b | AK017167 | 3.34 |
| 1418080_at | B4galt2 | AW125856 | 3.34 |
| 1438941_x_at | Ampd2 | AV330806 | 3.34 |
| 1426679_at | Zfp706 | AK004076 | 3.34 |
| 1418462_at | Exosc9 | NM_019393 | 3.34 |
| 1416027_at | Pdcd6 | NM_011051 | 3.34 |
| 1438313_at |  | BB233366 | 3.34 |
| 1456236_s_at | Commd10 | AU019438 | 3.34 |
| 1425465_a_at | Senp2 | AV317107 | 3.34 |
| 1428148_s_at | Coro7 | BB203098 | 3.34 |
| 1418235_at | Atg5 | AV168389 | 3.34 |
| 1415749_a_at | Rragc | NM_017475 | 3.34 |
| 1450539_at | Krtap5-1 | NM_015808 | 3.34 |
| 1431320_a_at | Myo5a | AK002362 | 3.34 |
| 1439452_x_at | Dnpep | BB407163 | 3.33 |

TABLE 13-continued

Genes differentially translated between medium spiny neurons (MSNs) and the rest of the brain.

| Probe | Symbol | GenBank | FCH |
|---|---|---|---|
| 1418255_s_at | Srf | BI662291 | 3.33 |
| 1442093_at | Adc | AU040368 | 3.33 |
| 1455056_at | Lmo7 | BM231903 | 3.33 |
| 1427579_at | Rhbdl3 | BE653576 | 3.33 |
| 1435170_at | Tsr2 | BQ177187 | 3.33 |
| 1422751_at | Tle1 | NM_011599 | 3.32 |
| 1459679_s_at | Myo1b | AA406997 | 3.32 |
| 1447449_at | | BE983114 | 3.32 |
| 1453183_at | 1110034A24Rik | BB815668 | 3.32 |
| 1423228_at | B4galt6 | BG066773 | 3.32 |
| 1423660_at | Ctdsp2 | BB294133 | 3.32 |
| 1416870_at | Dnalc4 | NM_017470 | 3.32 |
| 1437597_at | | BB182944 | 3.32 |
| 1415710_at | Cox18 | BM123013 | 3.32 |
| 1447831_s_at | Mtmr7 | BB431693 | 3.32 |
| 1422901_at | Mgea5 | NM_023799 | 3.31 |
| 1423269_a_at | Nedd4l | BB663717 | 3.31 |
| 1423350_at | Socs5 | AA510713 | 3.31 |
| 1451938_a_at | Sntb1 | BC003748 | 3.31 |
| 1427878_at | 0610010O12Rik | AK002512 | 3.31 |
| 1436617_at | Cetn4 | AV211098 | 3.31 |
| 1457790_at | Asb3 | BB002295 | 3.31 |
| 1441998_at | | BB369709 | 3.31 |
| 1434706_at | Vcpip1 | AV175609 | 3.31 |
| 1428950_s_at | Nol8 | AK017551 | 3.31 |
| 1435974_at | Arhgef9 | BB271482 | 3.31 |
| 1419650_at | Zfr | NM_011767 | 3.30 |
| 1443827_x_at | BC004044 | BB375974 | 3.30 |
| 1460418_x_at | H2-T18 | X03052 | 3.30 |
| 1426108_s_at | Cacnb1 | AY094172 | 3.30 |
| 1460021_at | EG626231 | BB825323 | 3.30 |
| 1432972_at | 4921518B13Rik | AK014916 | 3.29 |
| 1438727_at | Wdr32 | BB317629 | 3.29 |
| 1419351_a_at | l7Rn6 | BC003916 | 3.29 |
| 1429730_at | 1810009N02Rik | AK007409 | 3.28 |
| 1417311_at | Crip2 | NM_024223 | 3.28 |
| 1424315_at | 1110004E09Rik | BC019533 | 3.28 |
| 1448057_at | | BI320076 | 3.28 |
| 1438932_at | Rasgrp2 | BE688720 | 3.28 |
| 1455947_at | AK162044 | BB667208 | 3.28 |
| 1423064_at | Dnmt3a | BB795491 | 3.27 |
| 1435213_at | Nhlrc1 | BB309133 | 3.27 |
| 1420377_at | St8sia2 | BG071333 | 3.27 |
| 1433960_at | Isg20l2 | BB546077 | 3.27 |
| 1454642_a_at | Commd3 | BB230296 | 3.27 |
| 1450143_at | Rasgrp1 | BB354696 | 3.27 |
| 1445668_at | Tbce | BE993759 | 3.27 |
| 1450106_a_at | Evl | NM_007965 | 3.27 |
| 1428903_at | 3110037I16Rik | AK014134 | 3.27 |
| 1437730_at | Ppp2r2a | C78402 | 3.27 |
| 1417349_at | Pldn | NM_019788 | 3.26 |
| 1418038_s_at | Dusp19 | NM_024438 | 3.26 |
| 1424389_at | Nupl1 | BC026743 | 3.26 |
| 1420870_at | Mllt10 | BB353133 | 3.26 |
| 1441856_x_at | Tysnd1 | AV259286 | 3.26 |
| 1448747_at | Fbxo32 | AF441120 | 3.26 |
| 1424640_at | Arl8a | BC018479 | 3.26 |
| 1455775_at | B230315N10Rik | AW988196 | 3.26 |
| 1451106_at | Tut1 | BC025499 | 3.26 |
| 1435505_at | Dmwd | BB698273 | 3.26 |
| 1438480_a_at | Vps26b | AV301675 | 3.26 |
| 1428165_at | Vps24 | AK009414 | 3.25 |
| 1416126_at | Rpo1-2 | NM_009086 | 3.25 |
| 1451178_at | Mrpl53 | BC022162 | 3.25 |
| 1417919_at | Ppp1r7 | NM_023200 | 3.25 |
| 1446477_at | Zfp622 | BB038030 | 3.25 |
| 1425081_at | Zfp286 | BE651907 | 3.25 |
| 1427564_at | Diap2 | Y15910 | 3.25 |
| 1420643_at | Lfng | NM_008494 | 3.25 |
| 1425396_a_at | Lck | BC011474 | 3.25 |
| 1432096_at | Snrpn | AK010671 | 3.24 |
| 1442524_at | | AI836848 | 3.24 |
| 1446556_at | Kcnd1 | BB073575 | 3.24 |
| 1420034_at | Ppp2r2d | AU019644 | 3.24 |
| 1422083_at | Tlr9 | AF348140 | 3.23 |
| 1437262_x_at | Bcas2 | AA940256 | 3.23 |
| 1437861_s_at | Prkce | BB335101 | 3.23 |
| 1424332_at | Rab40c | AF422144 | 3.23 |
| 1435604_at | Trim37 | BM941778 | 3.23 |
| 1435527_at | Nfic | BB533448 | 3.23 |
| 1454871_at | Rbm15b | BB776868 | 3.23 |
| 1436138_at | Ttc19 | BB078627 | 3.23 |
| 1423923_a_at | Wdr8 | BC016120 | 3.23 |
| 1447249_at | | BF149076 | 3.23 |
| 1426675_at | Tomm70a | BB225670 | 3.23 |
| 1435225_s_at | Brpf3 | BB728354 | 3.23 |
| 1428554_a_at | 1810035L17Rik | BQ126239 | 3.22 |
| 1437481_at | 1110039F03Rik | AV032349 | 3.22 |
| 1426398_at | Ube2w | BB796558 | 3.22 |
| 1440829_x_at | Ttll11 | AV266869 | 3.22 |
| 1460191_at | Ykt6 | NM_019661 | 3.22 |
| 1436383_at | Cplx2 | BE946238 | 3.22 |
| 1421817_at | Gsr | AK019177 | 3.22 |
| 1438423_at | Ssbp2 | BB085949 | 3.21 |
| 1452214_at | Skil | AK018608 | 3.21 |
| 1428672_at | Snrpf | BI080799 | 3.21 |
| 1440997_at | Tnrc6c | AV236734 | 3.21 |
| 1454873_at | Zfp775 | BB667577 | 3.21 |
| 1418986_a_at | Uxt | NM_013840 | 3.21 |
| 1434058_at | Mtmr12 | BB667459 | 3.21 |
| 1417044_at | Lcmt1 | NM_025304 | 3.21 |
| 1435961_at | Nat14 | BB702376 | 3.21 |
| 1428189_at | 5730494M16Rik | BQ174627 | 3.21 |
| 1442883_s_at | D10Bwg1364e | BI413749 | 3.20 |
| 1432478_a_at | Ibrdc3 | AK015966 | 3.20 |
| 1421968_a_at | Nipa2 | NM_023647 | 3.20 |
| 1434476_at | Crtc1 | BM119896 | 3.20 |
| 1433922_at | Rab35 | BG074549 | 3.19 |
| 1428520_at | 1110032A13Rik | AK004019 | 3.19 |
| 1419221_a_at | Rgs14 | NM_016758 | 3.19 |
| 1423317_at | 3110001D03Rik | BE915283 | 3.19 |
| 1450746_at | Keap1 | AW764104 | 3.19 |
| 1415792_at | Rbck1 | NM_019705 | 3.19 |
| 1452958_at | Asphd2 | AK013495 | 3.19 |
| 1418763_at | Nit2 | BC020153 | 3.19 |
| 1419081_at | Atg10 | NM_025770 | 3.18 |
| 1449688_at | D10Ertd610e | AU014694 | 3.18 |
| 1423873_at | Lsm1 | BC021460 | 3.18 |
| 1431049_at | Ica1l | BM964047 | 3.18 |
| 1416501_at | Pdpk1 | NM_011062 | 3.18 |
| 1438506_s_at | Abi1 | AV330821 | 3.18 |
| 1434564_at | E2f3 | BQ176318 | 3.18 |
| 1416432_at | Pfkfb3 | NM_133232 | 3.17 |
| 1445475_at | Pak6 | BB003750 | 3.17 |
| 1417461_at | Cap1 | NM_007598 | 3.17 |
| 1428924_at | Mocs3 | AU016306 | 3.17 |
| 1422605_at | Ppp1r1a | NM_021391 | 3.17 |
| 1451680_at | Srxn1 | BC011325 | 3.17 |
| 1427468_at | Ppp3cb | M81483 | 3.17 |
| 1455172_at | AU020094 | BG069639 | 3.17 |
| 1417368_s_at | Ndufa2 | NM_010885 | 3.17 |
| 1444774_at | Det1 | BM123155 | 3.17 |
| 1447707_s_at | Pde2a | BB367174 | 3.17 |
| 1429095_at | Cenpp | AK006234 | 3.16 |
| 1455289_at | Ankrd13b | BQ174304 | 3.16 |
| 1431179_at | Entpd7 | BB873170 | 3.16 |
| 1437715_x_at | Apex1 | AV100480 | 3.16 |
| 1434243_s_at | Tomm70a | AV233564 | 3.15 |
| 1424062_at | Ube2d1 | BC019464 | 3.15 |
| 1435780_at | Psd | BG966595 | 3.15 |
| 1437363_at | Homer1 | BQ043238 | 3.15 |
| 1442799_x_at | Nudcd3 | BB048987 | 3.15 |
| 1455881_at | Ier5l | BB078200 | 3.15 |
| 1449116_a_at | Dtymk | NM_023136 | 3.15 |
| 1438217_at | A2bp1 | AW494804 | 3.15 |
| 1421845_at | Golph3 | AV174110 | 3.15 |
| 1429929_at | Mei1 | AK016514 | 3.15 |
| 1429072_at | 1110001D15Rik | AK003211 | 3.14 |
| 1429715_at | Ppp2r2a | AK010380 | 3.14 |
| 1421176_at | Rasgrp1 | BB354696 | 3.14 |

TABLE 13-continued

Genes differentially translated between medium spiny neurons (MSNs) and the rest of the brain.

| Probe | Symbol | GenBank | FCH |
|---|---|---|---|
| 1420449_at | Heatr5b | NM_028084 | 3.14 |
| 1455542_at | C630043F03Rik | BB226174 | 3.14 |
| 1422441_x_at | Cdk4 | NM_009870 | 3.14 |
| 1437921_x_at | Zfp516 | AW744723 | 3.14 |
| 1429108_at | Msl211 | BB745314 | 3.14 |
| 1423216_a_at | 2510049I19Rik | AV109006 | 3.14 |
| 1417065_at | Egr1 | NM_007913 | 3.14 |
| 1449007_at | Btg3 | NM_009770 | 3.14 |
| 1460352_s_at | Pik3r4 | BC017537 | 3.13 |
| 1437010_a_at | Oaz3 | BF319714 | 3.13 |
| 1425599_a_at | Gatad1 | BC019449 | 3.13 |
| 1424047_at | Dera | BC016218 | 3.13 |
| 1426861_at | Aftph | BC004630 | 3.13 |
| 1455771_at | Bzrap1 | BB467799 | 3.13 |
| 1428824_at | 2310003C23Rik | AK009106 | 3.13 |
| 1441890_x_at | Tmeff1 | BB366425 | 3.13 |
| 1436648_at | Nanos1 | BB251623 | 3.13 |
| 1428267_at | Dhx40 | AK010512 | 3.13 |
| 1433720_s_at | Ndg2 | AI647775 | 3.13 |
| 1422526_at | Acsl1 | BI413218 | 3.13 |
| 1450992_a_at | Meis1 | AW547821 | 3.13 |
| 1432271_a_at | Dcun1d5 | AK012764 | 3.13 |
| 1448989_a_at | Myo1b | AI255256 | 3.13 |
| 1424264_at | Med6 | BC013096 | 3.13 |
| 1454978_at | Ttyh3 | BQ180649 | 3.12 |
| 1421500_at | Sts | NM_009293 | 3.12 |
| 1438416_at | Thrap5 | BM238407 | 3.12 |
| 1434304_s_at | D10Ertd438e | BE949414 | 3.12 |
| 1437141_x_at | Dym | BB549381 | 3.12 |
| 1416622_at | Wbscr16 | NM_033572 | 3.12 |
| 1452175_at | 1810026J23Rik | BB027373 | 3.12 |
| 1428926_at | 1110003O08Rik | AK003388 | 3.12 |
| 1456946_at | Sh3md4 | BE949337 | 3.12 |
| 1449413_at | Mpv17l | NM_033564 | 3.12 |
| 1428081_at | Klhl21 | AK007786 | 3.12 |
| 1447934_at | 9630033F20Rik | BB128741 | 3.12 |
| 1459998_at | Zfp407 | AW547438 | 3.12 |
| 1416299_at | Shcbp1 | NM_011369 | 3.12 |
| 1426247_at | Stk24 | BG060677 | 3.12 |
| 1422485_at | Smad4 | AK004804 | 3.11 |
| 1433419_at | 4930405A07Rik | AK015090 | 3.11 |
| 1459751_s_at | Ppp1r16a | R75527 | 3.11 |
| 1418575_at | Shfm1 | NM_009169 | 3.11 |
| 1428327_at | Trak1 | BB010301 | 3.11 |
| 1428358_at | 1810010M01Rik | BF581690 | 3.11 |
| 1416743_at | Uap1 | NM_133806 | 3.11 |
| 1445691_at | Chn1 | AW121426 | 3.11 |
| 1452593_a_at | Tceb1 | AI019214 | 3.11 |
| 1439024_at | Bag4 | BB082119 | 3.11 |
| 1418574_a_at | Shfm1 | NM_009169 | 3.11 |
| 1451288_s_at | 1810043G02Rik | BC010330 | 3.11 |
| 1419773_at | 2010301N04Rik | BB080387 | 3.11 |
| 1416324_s_at | Kctd20 | AV281062 | 3.11 |
| 1427309_at | Pars2 | BF583012 | 3.11 |
| 1449634_a_at | Anks1b | AW046296 | 3.11 |
| 1454032_at | Neto2 | AK017458 | 3.11 |
| 1419568_at | Mapk1 | NM_011949 | 3.10 |
| 1418416_x_at | Psg23 | NM_020261 | 3.10 |
| 1428658_at | Pin4 | AW012413 | 3.10 |
| 1437743_at | Aebp2 | BM242614 | 3.10 |
| 1428533_at | D1Bwg0212e | BG918881 | 3.10 |
| 1455407_at | Zfp236 | BB282741 | 3.10 |
| 1425781_a_at | Plcb1 | U85714 | 3.10 |
| 1419984_s_at | Zfp644 | AU015726 | 3.10 |
| 1435728_at | Tyw3 | AW457809 | 3.10 |
| 1428474_at | Ppp3cb | AK004360 | 3.10 |
| 1419995_at | D10Ertd641e | AU015124 | 3.10 |
| 1435476_a_at | Fcgr2b | BM224327 | 3.10 |
| 1429382_at | Tomm401 | AV253376 | 3.09 |
| 1417084_at | Eif4ebp2 | NM_010124 | 3.09 |
| 1417176_at | Csnk1e | BE952001 | 3.09 |
| 1457661_at | B930036G03Rik | BB405928 | 3.09 |
| 1445677_x_at | Slc35f2 | BB401264 | 3.09 |
| 1439408_a_at | Pparbp | AV100992 | 3.09 |
| 1427212_at | Mapkap1 | BC027377 | 3.09 |
| 1455204_at | Pitpnc1 | BB305507 | 3.09 |
| 1459906_at | Dgkh | BB655998 | 3.09 |
| 1438306_at | Rnf180 | AV340072 | 3.09 |
| 1418144_a_at | Pip5k1b | NM_008847 | 3.09 |
| 1416767_a_at | 1110003E01Rik | NM_133697 | 3.09 |
| 1428630_x_at | Haghl | AK021220 | 3.09 |
| 1450685_at | Arpp19 | BE648432 | 3.08 |
| 1436731_at | Zfp533 | BB333374 | 3.08 |
| 1438561_x_at | Tmem180 | BB400326 | 3.08 |
| 1416545_at | Zdhhc7 | NM_133967 | 3.08 |
| 1436122_at | Zfp667 | BF467246 | 3.08 |
| 1424317_at | Slc25a19 | BC018167 | 3.08 |
| 1432447_a_at | 2310005N01Rik | AK009177 | 3.08 |
| 1458322_x_at | E230008N13Rik | BB139156 | 3.08 |
| 1416281_at | Wdr45l | BC004595 | 3.08 |
| 1452026_a_at | Pla2g12a | AY007382 | 3.08 |
| 1444388_at |  | BB020727 | 3.08 |
| 1428665_at | Pfn4 | BQ174081 | 3.08 |
| 1416292_at | Prdx3 | NM_007452 | 3.08 |
| 1416394_at | Bag1 | NM_009736 | 3.07 |
| 1448611_at | Wwc2 | NM_133791 | 3.07 |
| 1454996_at | Hsdl1 | BE985436 | 3.07 |
| 1441356_at | Shc2 | BB053802 | 3.07 |
| 1437573_at |  | BF018351 | 3.07 |
| 1428593_at | 1700029F09Rik | BG095162 | 3.07 |
| 1424527_at | Ppp2r2d | AF366393 | 3.07 |
| 1423519_at | 2210412D01Rik | BE457744 | 3.07 |
| 1424163_at | Rmnd5b | BC016075 | 3.07 |
| 1454797_at | Tmem55b | AW556098 | 3.06 |
| 1448724_at | Cish | NM_009895 | 3.06 |
| 1437452_x_at | Vdac1 | AV008054 | 3.06 |
| 1443821_at | Lect2 | AW122758 | 3.06 |
| 1428585_at | Actn1 | BE853286 | 3.06 |
| 1426915_at | Dapk1 | BC021490 | 3.06 |
| 1439611_at | Chrm1 | BE947522 | 3.06 |
| 1452933_at | Ankrd39 | AK018681 | 3.06 |
| 1428215_x_at | Tomm7 | BB609428 | 3.06 |
| 1418656_at | Lsm5 | NM_025520 | 3.06 |
| 1420390_s_at | Zfp354a | NM_009329 | 3.05 |
| 1432295_a_at | 2310035K24Rik | AK009634 | 3.05 |
| 1421123_at | Cdk5r1 | NM_009871 | 3.05 |
| 1443688_at | BC050092 | BB710844 | 3.05 |
| 1460372_at | Duoxa1 | BC019755 | 3.05 |
| 1423967_at | Palm | BC015297 | 3.05 |
| 1436329_at | Egr3 | AV346607 | 3.05 |
| 1440343_at | Rps6ka5 | BQ174267 | 3.05 |
| 1427236_a_at | Mll5 | BB295149 | 3.05 |
| 1447882_x_at | Ddx54 | AV318690 | 3.05 |
| 1420219_at | 4930461P20Rik | BB192718 | 3.05 |
| 1426572_at | Me2 | BM235734 | 3.05 |
| 1460116_s_at | Spred1 | AI450584 | 3.05 |
| 1425718_a_at | Ivns1abp | BC004092 | 3.04 |
| 1447762_x_at | Car12 | BB503164 | 3.04 |
| 1416664_at | Cdc20 | NM_023223 | 3.04 |
| 1437679_at | Glrx2 | BB172698 | 3.04 |
| 1459994_x_at | Trfr2 | AV027486 | 3.04 |
| 1452287_at |  | BB414973 | 3.04 |
| 1435900_at | Zbtb43 | BF466570 | 3.04 |
| 1415945_at | Mcm5 | NM_008566 | 3.04 |
| 1424330_at | Senp1 | BC023129 | 3.03 |
| 1418300_a_at | Mknk2 | NM_021462 | 3.03 |
| 1418174_at | Dbp | BC018323 | 3.03 |
| 1420833_at | Vamp2 | BG871810 | 3.03 |
| 1452046_a_at | Ppp1cc | BG071790 | 3.03 |
| 1452438_s_at | Taf4a | BE632382 | 3.03 |
| 1422493_at | Cpox | BG067254 | 3.03 |
| 1429094_at | Ddi2 | BI110088 | 3.03 |
| 1427067_at | 4933439F18Rik | AJ404329 | 3.03 |
| 1426752_at | Phf17 | BG065238 | 3.03 |
| 1419377_at | Med9 | BC019367 | 3.02 |
| 1435067_at | B230208H17Rik | BG075288 | 3.02 |
| 1430305_at | 2500004C02Rik | AK010870 | 3.02 |
| 1443796_at | Il16 | BB206877 | 3.02 |
| 1435226_at | Ibrdc3 | BG064140 | 3.02 |
| 1431352_s_at | Pvt1 | BI453402 | 3.02 |

TABLE 13-continued

Genes differentially translated between medium spiny neurons (MSNs) and the rest of the brain.

| Probe | Symbol | GenBank | FCH |
|---|---|---|---|
| 1428192_at | Kbtbd7 | AK003597 | 3.02 |
| 1434033_at | Tle1 | AI325112 | 3.02 |
| 1417840_at | 1500031L02Rik | NM_025892 | 3.02 |
| 1452275_at | Zfand3 | BG976649 | 3.02 |
| 1424200_s_at | Seh1l | AW537349 | 3.02 |
| 1428763_at | Smug1 | AK004735 | 3.02 |
| 1421395_at | Zik1 | NM_009577 | 3.02 |
| 1419827_s_at | Kif17 | AW492270 | 3.02 |
| 1433603_at | Ndufs6 | C88200 | 3.02 |
| 1431875_a_at | E2f1 | AK017841 | 3.02 |
| 1453837_at | 6330500D04Rik | BB867666 | 3.02 |
| 1435714_x_at | Il17d | BB809808 | 3.01 |
| 1417360_at | Mlh1 | NM_026810 | 3.01 |
| 1416614_at | Eid1 | BC010712 | 3.01 |
| 1453348_at | 1700085D22Rik | AK007007 | 3.01 |
| 1453199_at | Acbd6 | AK011781 | 3.01 |
| 1431581_at | 4922502B01Rik | AK013705 | 3.01 |
| 1456183_at | Oog4 | BB555196 | 3.01 |
| 1421768_a_at | Homer1 | NM_011982 | 3.01 |
| 1433946_at | Zik1 | BE824681 | 3.01 |
| 1420849_at | Crnkl1 | AV143435 | 3.01 |
| 1453274_at | Ccdc103 | AK006639 | 3.01 |
| 1440005_at | Onecut2 | BB667396 | 3.01 |
| 1439434_x_at | Pcmt1 | BB317673 | 3.01 |
| 1460692_at | Ehmt2 | BI412952 | 3.01 |
| 1422763_at | Gipc1 | NM_018771 | 3.01 |
| 1455174_at | Rps19bp1 | AV107461 | 3.00 |
| 1436381_at | Dlgap3 | BQ175774 | 3.00 |
| 1416991_at | Mto1 | NM_026658 | 3.00 |
| 1423358_at | 1810009K13Rik | AK007407 | 3.00 |
| 1430129_a_at | Commd8 | AK017777 | 3.00 |
| 1448956_at | Stard10 | NM_019990 | 3.00 |
| 1416439_at | 2410015N17Rik | NM_023203 | 3.00 |
| 1439869_at | 2900054J07Rik | BB326106 | 3.00 |
| 1428550_at | 1810015A11Rik | AK007503 | 3.00 |
| 1439493_at | D630040G17Rik | BB111712 | 3.00 |
| 1441960_x_at | 5730494M16Rik | AV267590 | 2.99 |
| 1449147_at | Dlgap4 | BG066219 | 2.99 |
| 1426465_at | Bcor | AV318805 | 2.99 |
| 1429438_at | | BB259283 | 2.99 |
| 1434848_at | Rpl27a | BG141806 | 2.99 |
| 1437729_at | Tor1b | BB475906 | 2.99 |
| 1457114_at | Zmynd11 | BB832996 | 2.99 |
| 1426532_at | Dtnb | AW537479 | 2.99 |
| 1437651_a_at | Spock3 | NM_023689 | 2.99 |
| 1449979_a_at | Slc25a42 | BC025937 | 2.99 |
| 1424790_at | Dusp26 | BC018204 | 2.99 |
| 1425848_a_at | 4-Mar | AK009364 | 2.99 |
| 1452925_a_at | Tln2 | AV270892 | 2.99 |
| 1429111_at | Coch | BB731671 | 2.98 |
| 1423285_at | BC038822 | BB457436 | 2.98 |
| 1436608_at | Kif17 | AB008867 | 2.98 |
| 1422762_at | A830021K08Rik | AI851680 | 2.98 |
| 1443979_at | Ndufs4 | AV219958 | 2.98 |
| 1438166_x_at | Ubox5 | BB079377 | 2.98 |
| 1439867_at | Sez6 | NM_021286 | 2.98 |
| 1420885_a_at | Uqcrb | NM_026219 | 2.98 |
| 1416337_at | Senp2 | AV357107 | 2.98 |
| 1425466_at | Lrrc15 | AI506528 | 2.98 |
| 1436055_at | Lyrm2 | AA250510 | 2.98 |
| 1427934_at | C030027K23Rik | BC025847 | 2.97 |
| 1452351_at | Ascc1 | AK007519 | 2.97 |
| 1460703_at | Mrps9 | BC022587 | 2.97 |
| 1418034_at | Mrpl40 | NM_010922 | 2.97 |
| 1448849_at | Strn | NM_011500 | 2.97 |
| 1422036_at | | BF462648 | 2.97 |
| 1442881_at | Speg | NM_007463 | 2.97 |
| 1417305_at | Ppp1ca | NM_031868 | 2.97 |
| 1460165_at | BB086117 | AV327329 | 2.97 |
| 1446681_at | Tmie | BE957021 | 2.97 |
| 1439838_a_at | Atp5f1 | AK019459 | 2.97 |
| 1426742_at | Dnmt3a | BB795491 | 2.97 |
| 1423063_at | Gabarapl1 | AF180518 | 2.97 |
| 1416418_at | Tmem183a | AU080745 | 2.97 |
| 1431304_a_at | Cdo1 | NM_033037 | 2.97 |
| 1448842_at | Iah1 | AU016407 | 2.97 |
| 1454898_s_at | Ptpn12 | AV117227 | 2.96 |
| 1455105_at | Runx1 | X97306 | 2.96 |
| 1452530_a_at | Trib2 | BB354684 | 2.96 |
| 1426640_s_at | Pde4dip | AV374669 | 2.96 |
| 1433761_at | Tm2d1 | AF353993 | 2.96 |
| 1451996_at | Cox7a1 | BB284638 | 2.96 |
| 1428494_a_at | 1700015F17Rik | BB833901 | 2.96 |
| 1456366_at | | AA589431 | 2.96 |
| 1420103_at | Prkce | AK017901 | 2.96 |
| 1452878_at | Taf4a | BE632382 | 2.96 |
| 1427460_at | 2010305B15Rik | BE981170 | 2.96 |
| 1442408_at | Hdac11 | BB183559 | 2.96 |
| 1454803_a_at | Hist3h2a | AV297651 | 2.96 |
| 1435865_at | Arhgap20 | AK018317 | 2.96 |
| 1429918_at | 2610030H06Rik | BB410125 | 2.96 |
| 1452607_at | Ccrk | NM_053180 | 2.96 |
| 1422494_s_at | Akt3 | BG695418 | 2.95 |
| 1435260_at | Otud5 | BB158937 | 2.95 |
| 1438985_x_at | Mef2d | AV334508 | 2.95 |
| 1434487_at | Fhit | AF055573 | 2.95 |
| 1425893_a_at | Bmper | AK014221 | 2.95 |
| 1429273_at | Usp45 | BM249286 | 2.95 |
| 1427990_at | Sh3bgrl3 | NM_080559 | 2.95 |
| 1416376_at | 2010305B15Rik | AI428254 | 2.95 |
| 1448027_at | Sephs2 | NM_009266 | 2.95 |
| 1418325_at | Ttl | AV127581 | 2.95 |
| 1427112_at | Nova2 | BB524078 | 2.94 |
| 1439192_at | Mkrn1 | BQ176661 | 2.94 |
| 1418434_at | Ccdc122 | AW554226 | 2.94 |
| 1458438_at | Mras | AB004879 | 2.94 |
| 1449590_a_at | Anxa11 | AU019881 | 2.94 |
| 1419190_at | Preb | BB225012 | 2.94 |
| 1456037_x_at | Ctdsp2 | BB294133 | 2.94 |
| 1423661_s_at | Trio | BB080177 | 2.94 |
| 1454711_at | Ceacam16 | BB268577 | 2.94 |
| 1441120_at | Chst1 | NM_023850 | 2.94 |
| 1449147_at | | AV230618 | 2.94 |
| 1457719_at | Tnfrsf1b | M60469 | 2.94 |
| 1448951_at | Fundc2 | AI510221 | 2.94 |
| 1460434_at | 2610039C10Rik | AK012762 | 2.94 |
| 1428483_a_at | 6330569M22Rik | BB525203 | 2.94 |
| 1457513_at | Cap2 | AV261931 | 2.94 |
| 1423222_at | Rnf126 | BC016543 | 2.94 |
| 1424514_at | Rgs4 | NM_009062 | 2.93 |
| 1416286_at | 5530400B01Rik | AK017419 | 2.93 |
| 1428864_at | Esrrb | BB386239 | 2.93 |
| 1441921_x_at | Prr3 | BC016636 | 2.93 |
| 1424145_at | 9330180L21Rik | BG064966 | 2.93 |
| 1455412_at | Hmbs | AI325144 | 2.93 |
| 1426475_at | Akt1 | NM_009652 | 2.93 |
| 1416657_at | D10Ertd641e | BE692118 | 2.93 |
| 1449338_at | Ywhaz | AV027921 | 2.93 |
| 1448218_s_at | BC055324 | BB093351 | 2.93 |
| 1434365_a_at | Git1 | AV230461 | 2.92 |
| 1454759_at | Ndufa7 | NM_023202 | 2.92 |
| 1422976_x_at | Rragd | BB354941 | 2.92 |
| 1440555_at | Cdh13 | BB776961 | 2.92 |
| 1423551_at | Baiap2 | AA796998 | 2.92 |
| 1451028_at | Zfp319 | BE949045 | 2.92 |
| 1436284_s_at | Snapc3 | AK016168 | 2.92 |
| 1453077_a_at | Spin1 | BM228780 | 2.92 |
| 1415794_at | Clrn3 | BB496366 | 2.92 |
| 1434345_at | Gabpb1 | BQ177003 | 2.92 |
| 1436232_a_at | BC004044 | BB084182 | 2.92 |
| 1457648_x_at | 9430057O19Rik | AV277339 | 2.92 |
| 1439465_x_at | Ptpn9 | BB224063 | 2.92 |
| 1451037_at | Ube2g2 | AF296657 | 2.92 |
| 1417032_at | Zfp644 | AV261187 | 2.92 |
| 1429623_at | Cyp4b1 | NM_007823 | 2.92 |
| 1416194_at | | BB096245 | 2.91 |
| 1445461_at | Calm2 | NM_007589 | 2.91 |
| 1422414_a_at | Stc1 | BQ032752 | 2.91 |
| 1450448_at | Otud3 | AK014098 | 2.91 |
| 1430046_at | Sip1 | AK013414 | 2.91 |
| 1451044_at | | | |

TABLE 13-continued

Genes differentially translated between medium spiny neurons (MSNs) and the rest of the brain.

| Probe | Symbol | GenBank | FCH |
|---|---|---|---|
| 1426234_s_at | BC002199 | BC002199 | 2.91 |
| 1450084_s_at | Ivns1abp | NM_054102 | 2.91 |
| 1420340_at | Cspp1 | NM_026493 | 2.90 |
| 1456079_x_at | Apex1 | AV263745 | 2.90 |
| 1424423_at | Lenep | BC006806 | 2.90 |
| 1427467_a_at | Rpgr | AJ238396 | 2.90 |
| 1435422_at | 4933433P14Rik | AV281088 | 2.90 |
| 1450690_at | Ranbp2 | BM507707 | 2.90 |
| 1416345_at | Timm8a1 | W82151 | 2.90 |
| 1429306_at | Lzic | AK007657 | 2.90 |
| 1428979_at | Mtf1 | AV316320 | 2.90 |
| 1420107_at | Bbs4 | C86773 | 2.90 |
| 1437680_x_at | Glrx2 | BB172698 | 2.90 |
| 1448705_at | Zbtb22 | BC026964 | 2.90 |
| 1456072_at | Ppp1r9a | AU067663 | 2.90 |
| 1425600_a_at | Plcb1 | AW049748 | 2.90 |
| 1455755_at | Gm88 | BB026554 | 2.89 |
| 1433931_at | C030046I01Rik | AW553381 | 2.89 |
| 1434169_at | 9030409G11Rik | BQ175107 | 2.89 |
| 1425777_at | Cacnb1 | AY094173 | 2.89 |
| 1430803_at | Lin28b | BB074761 | 2.89 |
| 1421170_a_at | Plcb1 | BB215274 | 2.89 |
| 1423200_at | Ncor1 | U22016 | 2.89 |
| 1451409_at | 2210021J22Rik | BC025858 | 2.89 |
| 1426518_at | Tubgcp5 | AV333951 | 2.89 |
| 1446768_at | | BE653578 | 2.89 |
| 1438632_x_at | Tnp1 | AV206780 | 2.89 |
| 1456582_x_at | LOC637796 | BB024498 | 2.89 |
| 1425224_at | Slmo1 | BC019561 | 2.89 |
| 1453380_a_at | Xrcc6bp1 | AK010471 | 2.88 |
| 1455281_at | Wdr33 | BB520667 | 2.88 |
| 1415748_a_at | Dctn5 | NM_021608 | 2.88 |
| 1419690_at | 2610002M06Rik | NM_025921 | 2.88 |
| 1424785_at | Angptl6 | BC025904 | 2.88 |
| 1457695_at | Ap1gbp1 | C76297 | 2.88 |
| 1452051_at | Actr3 | BE372352 | 2.88 |
| 1425452_s_at | AW125753 | BC002154 | 2.88 |
| 1449476_at | Rage | NM_011973 | 2.88 |
| 1426404_a_at | Rnf11 | BI150320 | 2.88 |
| 1432332_a_at | Nudt19 | AK008430 | 2.88 |
| 1457378_at | Mrpl54 | AW123022 | 2.88 |
| 1419144_at | Cd163 | NM_053094 | 2.87 |
| 1435549_at | Trpm4 | BI685685 | 2.87 |
| 1449746_s_at | Krr1 | AU020154 | 2.87 |
| 1441947_x_at | BC033915 | BB327032 | 2.87 |
| 1451036_at | Spg21 | BB095517 | 2.87 |
| 1424884_at | Fbxw2 | BC003834 | 2.87 |
| 1428293_at | 2310022M17Rik | AK009485 | 2.87 |
| 1460020_at | AA930108 | W14742 | 2.87 |
| 1419937_at | AA536749 | C76423 | 2.87 |
| 1426780_at | D14Ertd436e | AV247381 | 2.87 |
| 1415743_at | Hdac5 | NM_010412 | 2.87 |
| 1457743_at | Rgs7bp | BQ175190 | 2.87 |
| 1423399_a_at | Yaf2 | BG143658 | 2.87 |
| 1440127_a_at | | AW123182 | 2.87 |
| 1426901_s_at | Camta2 | BB657856 | 2.87 |
| 1425050_at | Isoc1 | AK010892 | 2.87 |
| 1417854_at | Map2k5 | NM_011840 | 2.86 |
| 1451450_at | 2010011I20Rik | AK008190 | 2.86 |
| 1426850_a_at | Map2k6 | BB261602 | 2.86 |
| 1420774_a_at | 4930583H14Rik | NM_026358 | 2.86 |
| 1416574_at | 5730589K01Rik | NM_023434 | 2.86 |
| 1451722_s_at | Smyd5 | BF160651 | 2.86 |
| 1447897_x_at | Anapc11 | AV019615 | 2.86 |
| 1452121_at | Fbxo22 | BB756840 | 2.86 |
| 1434870_at | 2810004N23Rik | BB121003 | 2.86 |
| 1441693_at | Adamts3 | BB193360 | 2.86 |
| 1419763_at | 2610020O08Rik | NM_025937 | 2.86 |
| 1430208_at | Krt42 | AK019115 | 2.86 |
| 1456565_s_at | Map3k12 | BB370469 | 2.86 |
| 1460364_at | Gtf2ird1 | AI550317 | 2.86 |
| 1458386_at | C030009J22Rik | BB283503 | 2.86 |
| 1428321_at | Eml1 | AK003593 | 2.86 |
| 1427449_a_at | Adprhl2 | BC023177 | 2.86 |
| 1453204_at | 4933431K14Rik | BB762387 | 2.86 |
| 1419955_at | Zfand3 | AW539211 | 2.86 |
| 1456964_at | Rbm12 | BB104271 | 2.86 |
| 1441937_s_at | Pink1 | AV371921 | 2.86 |
| 1448184_at | Fkbp1a | AF483488 | 2.85 |
| 1416773_at | Wee1 | NM_009516 | 2.85 |
| 1416824_at | B230118H07Rik | NM_026592 | 2.85 |
| 1433762_at | C630043F03Rik | BB182501 | 2.85 |
| 1433917_x_at | D2Bwg1423e | BB359828 | 2.85 |
| 1457270_at | Rcvrn | AI506234 | 2.85 |
| 1429561_at | Brf2 | AK012680 | 2.85 |
| 1426669_at | C530044N13Rik | BC025476 | 2.85 |
| 1457610_at | Rbck1 | BB281404 | 2.85 |
| 1428248_at | Nfx1 | AK005038 | 2.85 |
| 1432543_a_at | Klf13 | AK002926 | 2.85 |
| 1429162_at | 1500015A07Rik | AK005240 | 2.85 |
| 1441892_x_at | 4933440H19Rik | BB341238 | 2.85 |
| 1416106_at | Kti12 | NM_029571 | 2.84 |
| 1446937_at | Bptf | AI450357 | 2.84 |
| 1416928_at | Rbm12 | NM_029397 | 2.84 |
| 1457061_at | Glcci1 | BB246045 | 2.84 |
| 1455942_at | Fbxl11 | BB448023 | 2.84 |
| 1416562_at | Gad1 | AF326547 | 2.84 |
| 1416128_at | Tuba1c | NM_009448 | 2.84 |
| 1416586_at | Zfp239 | NM_008616 | 2.84 |
| 1458107_at | | BB310489 | 2.84 |
| 1426912_at | Rfwd2 | BB296692 | 2.84 |
| 1438557_x_at | Dnpep | BB553721 | 2.84 |
| 1418217_at | Nme7 | NM_138314 | 2.84 |
| 1453564_a_at | Vps24 | AK014818 | 2.84 |
| 1441305_at | | BB360028 | 2.84 |
| 1435523_s_at | 2700089E24Rik | BB779140 | 2.84 |
| 1439382_x_at | Ddr1 | BB378700 | 2.83 |
| 1426209_at | Strn4 | AF414080 | 2.83 |
| 1453064_at | Etaa1 | AK018594 | 2.83 |
| 1439563_at | Zfp3 | BB309203 | 2.83 |
| 1418463_at | Pik3r2 | NM_008841 | 2.83 |
| 1426227_s_at | Vps37c | BC025865 | 2.83 |
| 1419583_at | Cbx4 | NM_007625 | 2.83 |
| 1455897_x_at | Hmgn1 | BF464696 | 2.83 |
| 1448897_at | Mkrn2 | BI134671 | 2.83 |
| 1439770_at | 6430598A04Rik | BB387298 | 2.83 |
| 1427296_at | BC010304 | BB553912 | 2.83 |
| 1451177_at | Dnajb4 | BC017161 | 2.83 |
| 1440242_at | C030014K22Rik | BB356428 | 2.83 |
| 1448227_at | Grb7 | NM_010346 | 2.83 |
| 1438473_at | Arl15 | BB445175 | 2.83 |
| 1428655_at | Ccdc128 | AK003781 | 2.82 |
| 1455712_at | Hist3h2a | AI848909 | 2.82 |
| 1416924_at | Bri3 | NM_018772 | 2.82 |
| 1440858_at | Crkrs | BB830220 | 2.82 |
| 1423486_at | Cript | BB775592 | 2.82 |
| 1427187_at | B3gntl1 | AV319801 | 2.82 |
| 1417510_at | Vps4a | NM_126165 | 2.82 |
| 1427909_at | 2410015M20Rik | BQ031065 | 2.82 |
| 1439106_at | Zfp462 | AV320128 | 2.82 |
| 1451479_a_at | Tmem53 | BC019937 | 2.82 |
| 1417448_at | 1810008A18Rik | NM_133998 | 2.82 |
| 1434326_x_at | Coro2b | BB317923 | 2.81 |
| 1453846_at | Chd2 | AK012891 | 2.81 |
| 1434820_s_at | Pkig | AV209892 | 2.81 |
| 1451073_at | Sppl3 | BC023131 | 2.81 |
| 1453632_at | 4930538K18Rik | BB548441 | 2.81 |
| 1460740_at | Cltb | AK009844 | 2.81 |
| 1426552_a_at | Bcl11a | BB772866 | 2.81 |
| 1455614_at | Tomm40l | AV225789 | 2.81 |
| 1434603_at | Thrap2 | BG074645 | 2.80 |
| 1444106_at | D330012F22Rik | BB522739 | 2.80 |
| 1435156_at | BC046331 | BF730275 | 2.80 |
| 1438469_at | Bcorl1 | BG071122 | 2.80 |
| 1416036_at | Fkbp1a | AF483488 | 2.80 |
| 1458753_at | Gm941 | BB548169 | 2.80 |
| 1449125_at | Tnfaip8l1 | NM_025566 | 2.80 |
| 1453374_at | Zfand5 | AW744618 | 2.80 |
| 1433450_at | Cdk5r1 | BB177836 | 2.80 |
| 1447630_x_at | Gnb5 | BB450318 | 2.80 |

TABLE 13-continued

Genes differentially translated between medium spiny neurons (MSNs) and the rest of the brain.

| Probe | Symbol | GenBank | FCH |
|---|---|---|---|
| 1428852_at | Dock3 | AK018140 | 2.80 |
| 1450557_at | Scn4a | NM_133199 | 2.80 |
| 1449040_a_at | Sephs2 | NM_009266 | 2.80 |
| 1454781_x_at | Commd9 | BB506415 | 2.80 |
| 1417363_at | Zfp61 | NM_009561 | 2.80 |
| 1451403_at | BC024868 | BC024868 | 2.80 |
| 1431270_a_at | Aste1 | AK006153 | 2.79 |
| 1435589_at | Ccdc85b | AV308222 | 2.79 |
| 1424488_a_at | Ppa2 | BC011417 | 2.79 |
| 1451098_at | Pcoln3 | BC010524 | 2.79 |
| 1417918_at | Mrpl11 | NM_025553 | 2.79 |
| 1450382_at | Nf2 | L28176 | 2.79 |
| 1448874_a_at | Sh2b1 | NM_011363 | 2.79 |
| 1458466_at | Ctsa | AV338634 | 2.79 |
| 1443859_at | Rsbn1 | AI551821 | 2.79 |
| 1428150_at | Coro7 | BB203098 | 2.79 |
| 1417265_s_at | Coq5 | AK014348 | 2.79 |
| 1448845_at | Rpp25 | NM_133982 | 2.79 |
| 1417657_s_at | Dnajc2 | BG067003 | 2.79 |
| 1435625_at | Entpd7 | BG064768 | 2.79 |
| 1427589_at | 8430419L09Rik | BE283366 | 2.78 |
| 1422770_at | Rad51l3 | AB052834 | 2.78 |
| 1453821_at | N6amt1 | BQ033064 | 2.78 |
| 1422510_at | Ctdspl | NM_133710 | 2.78 |
| 1417207_at | Dvl2 | BF466091 | 2.78 |
| 1424320_a_at | Traf7 | BC008598 | 2.78 |
| 1451260_at | Aldh1b1 | BC020001 | 2.78 |
| 1420199_at | Slc35a4 | AV144937 | 2.78 |
| 1423304_a_at | Rnf111 | BB366842 | 2.78 |
| 1451533_at | BC022687 | BC022687 | 2.78 |
| 1445482_at | Gle11 | BB375481 | 2.78 |
| 1451518_at | Zfp709 | BC021921 | 2.78 |
| 1416229_at | Rfk | NM_019437 | 2.78 |
| 1436086_at | 4921526F01Rik | AV256234 | 2.78 |
| 1437150_at | 1700012H17Rik | BB496291 | 2.78 |
| 1459981_s_at | Rsbn1 | AV240926 | 2.78 |
| 1434481_at | 4121402D02Rik | BI695596 | 2.78 |
| 1454885_at | BC063263 | BM211194 | 2.77 |
| 1441534_at | C86753 | BG067565 | 2.77 |
| 1437267_x_at | Hnrph1 | BB164501 | 2.77 |
| 1418497_at | Fgf13 | AF020737 | 2.77 |
| 1438898_at | | BB309301 | 2.77 |
| 1433858_at | Lrrc28 | BB667092 | 2.77 |
| 1416093_a_at | Mrpl20 | NM_025570 | 2.77 |
| 1455185_s_at | Phf16 | BG064477 | 2.77 |
| 1429053_at | 1110012J17Rik | BB795266 | 2.77 |
| 1431164_at | Rragd | AK017818 | 2.77 |
| 1423512_at | AW209491 | BF715189 | 2.77 |
| 1441317_x_at | Jakmip1 | BB316060 | 2.77 |
| 1434217_at | C330019G07Rik | BB400635 | 2.77 |
| 1452119_at | 2600005C20Rik | BG293527 | 2.77 |
| 1443724_at | Jph3 | AI849712 | 2.77 |
| 1449947_s_at | Atbf1 | NM_007496 | 2.77 |
| 1455774_at | Jund1 | BB049005 | 2.77 |
| 1426818_at | Arrdc4 | BC025091 | 2.77 |
| 1425053_at | Isoc1 | AK010892 | 2.77 |
| 1418982_at | Cebpa | BC011118 | 2.77 |
| 1416448_at | Itpa | NM_025922 | 2.77 |
| 1415926_at | Nup62 | NM_053074 | 2.77 |
| 1436808_x_at | Mcm5 | AI324988 | 2.76 |
| 1420981_a_at | Lmo4 | NM_010723 | 2.76 |
| 1436902_x_at | Tmsb10 | BB096368 | 2.76 |
| 1454014_a_at | Mkks | AK004987 | 2.76 |
| 1417535_at | Fbxo25 | NM_025785 | 2.76 |
| 1460665_a_at | Cnot7 | NM_011135 | 2.76 |
| 1455272_at | Grm5 | BB429439 | 2.76 |
| 1443822_s_at | Zcd1 | AV347904 | 2.76 |
| 1429779_at | Eif2c4 | AI481660 | 2.76 |
| 1425114_at | Rbbp6 | BC025874 | 2.76 |
| 1435097_at | Mmab | BB772640 | 2.76 |
| 1449511_a_at | Ssbp4 | NM_133772 | 2.75 |
| 1453305_at | Iqcd | AK017032 | 2.75 |
| 1420999_at | Cnot4 | AI448404 | 2.75 |
| 1433780_at | Ubn1 | BB463209 | 2.75 |
| 1451448_a_at | 1110005A03Rik | BC026936 | 2.75 |
| 1459920_at | 4933415E08Rik | AA163908 | 2.75 |
| 1426180_a_at | Smr2 | U82380 | 2.75 |
| 1436845_at | Axin2 | BB398993 | 2.75 |
| 1427970_at | Zfp689 | AV226931 | 2.75 |
| 1427935_at | Lyrm2 | AA250510 | 2.75 |
| 1453284_at | 4930405M20Rik | AK015100 | 2.75 |
| 1443890_at | | BE851943 | 2.75 |
| 1453010_at | Iws1 | AK006925 | 2.75 |
| 1455673_at | Alkbh2 | BG070741 | 2.75 |
| 1455169_at | Rab11fip2 | BG076094 | 2.75 |
| 1419994_s_at | D10Ertd641e | AU015124 | 2.75 |
| 1452153_at | Fbxo18 | AF184275 | 2.75 |
| 1415705_at | 9130011J15Rik | AK018610 | 2.75 |
| 1440205_at | Zmynd19 | BM195344 | 2.75 |
| 1451223_a_at | Btf3l4 | AK011367 | 2.75 |
| 1420626_at | 2410016F19Rik | BF782285 | 2.74 |
| 1459579_at | Cacng8 | BQ266161 | 2.74 |
| 1426673_at | Cdh3 | X06340 | 2.74 |
| 1415782_at | Sumo2 | NM_133354 | 2.74 |
| 1421065_at | Jak2 | NM_008413 | 2.74 |
| 1421191_s_at | Gopc | NM_053187 | 2.74 |
| 1439135_at | | BB129618 | 2.74 |
| 1452271_at | Xpr1 | AV337591 | 2.74 |
| 1420529_at | Neud4 | AW553317 | 2.74 |
| 1416768_at | 1110003E01Rik | NM_133697 | 2.74 |
| 1427879_at | 1810031K17Rik | AK007667 | 2.74 |
| 1421147_at | Terf2 | NM_009353 | 2.74 |
| 1452149_at | Ube3b | AU067784 | 2.74 |
| 1431753_x_at | Urm1 | AK012124 | 2.74 |
| 1428775_at | 1110008L16Rik | AK003589 | 2.73 |
| 1433673_at | E130309D14Rik | BG069691 | 2.73 |
| 1460568_at | Trim46 | BI156583 | 2.73 |
| 1449109_at | Socs2 | NM_007706 | 2.73 |
| 1426028_a_at | Cit | AF086823 | 2.73 |
| 1416805_at | 1110032E23Rik | NM_133187 | 2.73 |
| 1433710_at | Edc3 | BM208114 | 2.73 |
| 1420967_at | Slc25a15 | AW541300 | 2.73 |
| 1459875_x_at | 5730494M16Rik | AV333371 | 2.73 |
| 1420645_at | Pcgf2 | NM_009545 | 2.73 |
| 1431939_a_at | Mina | AK014426 | 2.73 |
| 1453848_s_at | Zbed3 | AK002774 | 2.73 |
| 1416224_at | Zbtb17 | NM_009541 | 2.73 |
| 1443719_x_at | Ddx42 | AW763628 | 2.73 |
| 1453387_at | 4833432E10Rik | BB095161 | 2.73 |
| 1433992_at | Synpo | BQ176992 | 2.73 |
| 1434745_at | Ccnd2 | BQ175880 | 2.73 |
| 1422800_at | Bat2 | AK019427 | 2.73 |
| 1425478_x_at | Ube2i | U76416 | 2.72 |
| 1451254_at | Ikbkap | AF367244 | 2.72 |
| 1419174_at | 2410004B18Rik | NM_025555 | 2.72 |
| 1443722_at | 6030419C18Rik | BE945915 | 2.72 |
| 1456098_a_at | Elmo2 | BG076364 | 2.72 |
| 1425557_x_at | Tsc22d3 | AF201288 | 2.72 |
| 1419235_s_at | Helb | BG070273 | 2.72 |
| 1422758_at | Chst2 | NM_018763 | 2.72 |
| 1448518_at | Timm22 | AK012130 | 2.72 |
| 1453886_a_at | Slc25a26 | AK017037 | 2.72 |
| 1426192_at | Smarcd2 | M60510 | 2.72 |
| 1434630_at | Ankrd28 | AV261293 | 2.72 |
| 1429908_at | 6530403A03Rik | AK004216 | 2.72 |
| 1423750_a_at | Sf1 | BC009091 | 2.72 |
| 1433939_at | Aff3 | BQ177036 | 2.72 |
| 1426373_at | Ski | AK019148 | 2.72 |
| 1427071_at | Fbxo42 | BC003960 | 2.71 |
| 1436561_at | Suv39h2 | BB440055 | 2.71 |
| 1452179_at | Phf17 | BG065238 | 2.71 |
| 1440029_at | St8sia3 | BB379120 | 2.71 |
| 1454800_at | Morn2 | BF319573 | 2.71 |
| 1421842_a_at | Scamp4 | AF295102 | 2.71 |
| 1457472_at | Tnrc15 | BB782031 | 2.71 |
| 1416351_at | Map2k1 | NM_008927 | 2.71 |
| 1435375_at | BC052328 | BM224662 | 2.71 |
| 1454650_at | Trim35 | BQ175280 | 2.71 |
| 1455437_at | 9030204A07Rik | AV369969 | 2.71 |
| 1427390_at | Bloc1s3 | BC025913 | 2.71 |

TABLE 13-continued

Genes differentially translated between medium spiny neurons (MSNs) and the rest of the brain.

| Probe | Symbol | GenBank | FCH |
|---|---|---|---|
| 1422595_s_at | 5730470L24Rik | BC004090 | 2.70 |
| 1437801_at | Morf4l1 | BM115860 | 2.70 |
| 1417088_at | Zfp346 | AW493043 | 2.70 |
| 1426316_at | 6330416G13Rik | AV326978 | 2.70 |
| 1448223_at | Fto | NM_011936 | 2.70 |
| 1432158_a_at | Trappc2 | AK007951 | 2.70 |
| 1429238_a_at | Ogfod2 | AK004916 | 2.70 |
| 1418236_s_at | Atg5 | AV168389 | 2.70 |
| 1450742_at | Bysl | BG079188 | 2.70 |
| 1433756_at | S100pbp | BI452674 | 2.70 |
| 1428609_at | Mylc2b | AW494458 | 2.70 |
| 1454605_a_at | Pi4k2a | BB208212 | 2.70 |
| 1448530_at | Gmpr | NM_025508 | 2.70 |
| 1457635_s_at | Nr3c1 | BB096079 | 2.70 |
| 1447326_s_at | Zmym3 | AW122925 | 2.70 |
| 1422725_at | Mak | BG069426 | 2.70 |
| 1451914_a_at | Add2 | AF100423 | 2.70 |
| 1419169_at | Mapk6 | BC024684 | 2.70 |
| 1420634_a_at | Smad2 | NM_010754 | 2.69 |
| 1423090_x_at | Slc37a2 | AV216331 | 2.69 |
| 1418865_at | Zfp385 | NM_013866 | 2.69 |
| 1448195_at | Taf5l | NM_133966 | 2.69 |
| 1442829_at | Rin2 | BB128602 | 2.69 |
| 1428695_at | 9130227C08Rik | BB424872 | 2.69 |
| 1416101_a_at | Hist1h1c | NM_015786 | 2.69 |
| 1449089_at | Nrip1 | NM_008735 | 2.69 |
| 1432329_a_at | Matk | AK018182 | 2.69 |
| 1427299_at | Rps6ka3 | BE376079 | 2.69 |
| 1433914_at | AI747699 | BM246193 | 2.69 |
| 1417506_at | Gmnn | NM_020567 | 2.69 |
| 1426577_a_at | 1810054G18Rik | BM570079 | 2.69 |
| 1435425_at | Pisd | AV212090 | 2.69 |
| 1417463_at | 2400001E08Rik | NM_025605 | 2.69 |
| 1440914_s_at | Aftph | BG071681 | 2.69 |
| 1451379_at | Rab22a | BC006596 | 2.69 |
| 1418417_at | Msc | NM_010827 | 2.69 |
| 1424503_at | Rab22a | BC006596 | 2.69 |
| 1424073_at | 5430437P03Rik | BC005692 | 2.68 |
| 1448144_at | Hnrpab | NM_010448 | 2.68 |
| 1434646_s_at | Sap18 | AV023865 | 2.68 |
| 1447865_x_at | Pdzd11 | BB037788 | 2.68 |
| 1417959_at | Pdlim7 | NM_026131 | 2.68 |
| 1441758_at | Rhot1 | BB830916 | 2.68 |
| 1429931_at | 4930553P18Rik | AK016112 | 2.68 |
| 1448320_at | Stim1 | NM_009287 | 2.68 |
| 1418386_at | N6amt2 | NM_026526 | 2.68 |
| 1459051_at | 6530418L21Rik | BB781615 | 2.68 |
| 1438765_at | Dhx33 | BB667230 | 2.68 |
| 1417196_s_at | Wwc2 | NM_133791 | 2.68 |
| 1420841_at | Ptprf | BF235516 | 2.68 |
| 1457242_at | Ubox5 | BB824671 | 2.68 |
| 1447682_x_at | Traf5 | BB108799 | 2.68 |
| 1436300_at | Ripk5 | BB435342 | 2.68 |
| 1428354_at | Foxk2 | BM206907 | 2.68 |
| 1423799_at | Eif1 | BI693609 | 2.68 |
| 1448637_at | Med25 | NM_029365 | 2.68 |
| 1460447_at | Pus7l | AK019372 | 2.67 |
| 1434429_at | Syt16 | AV348245 | 2.67 |
| 1457717_at | Anxa11 | AI875033 | 2.67 |
| 1452742_at | Trak1 | BB010301 | 2.67 |
| 1454767_at | D2Bwg1423e | BB359828 | 2.67 |
| 1422078_at | Akt3 | AF124142 | 2.67 |
| 1436758_at | Hdac4 | AI661423 | 2.67 |
| 1434744_at | Yrdc | BB230053 | 2.67 |
| 1434624_x_at | Rps9 | AA762498 | 2.67 |
| 1447302_at |  | BE956835 | 2.67 |
| 1427732_s_at | Abcg4 | BC026477 | 2.67 |
| 1417778_at | Zfp35 | NM_011755 | 2.67 |
| 1437539_at | Prkaa1 | BM236715 | 2.67 |
| 1460572_a_at | Zfp511 | BQ178976 | 2.67 |
| 1451276_at | E030041M21Rik | BG066858 | 2.67 |
| 1416781_at | Praf2 | NM_138602 | 2.67 |
| 1427271_at | Zbtb44 | BC027138 | 2.67 |
| 1453631_at | Stx8 | AK011376 | 2.67 |
| 1435618_at | Pnma2 | BB473446 | 2.67 |
| 1446486_at | Dtwd2 | BB068132 | 2.66 |
| 1428627_at | Zfp509 | AK015819 | 2.66 |
| 1457426_at | 1700048O20Rik | BE980678 | 2.66 |
| 1454835_at | Epm2aip1 | AV340515 | 2.66 |
| 1428886_at | Rbbp5 | AK016773 | 2.66 |
| 1460223_a_at | Epb4.9 | NM_013514 | 2.66 |
| 1436633_at | LOC667668 | BB323723 | 2.66 |
| 1417215_at | Rab27b | BB121269 | 2.66 |
| 1418895_at | Skap2 | NM_018773 | 2.66 |
| 1426972_at | Sec24d | AK009425 | 2.66 |
| 1459806_x_at | Mrps23 | BB110309 | 2.66 |
| 1449108_at | Fdx1 | D43690 | 2.66 |
| 1431076_at | Add2 | BG976853 | 2.66 |
| 1452846_at | Ppfia4 | AK003571 | 2.65 |
| 1449913_at | Zfp2 | NM_009550 | 2.65 |
| 1450184_s_at | Tef | NM_017376 | 2.65 |
| 1417479_at | Ppp2r3c | AV367559 | 2.65 |
| 1415952_at | Mark2 | BI686265 | 2.65 |
| 1450668_s_at | Hspe1 | NM_008303 | 2.65 |
| 1450436_s_at | Dnajb5 | AI664344 | 2.65 |
| 1429832_at | Ppih | AK014665 | 2.65 |
| 1423294_at | Mest | AW555393 | 2.65 |
| 1442441_at | D11Bwg0434e | AV008016 | 2.65 |
| 1423302_a_at | Paxip1 | AW742928 | 2.65 |
| 1434415_at | Dact3 | BB797871 | 2.65 |
| 1425850_a_at | Nek6 | BC019524 | 2.65 |
| 1455215_at | C530028O21Rik | AU067746 | 2.65 |
| 1427870_x_at | Igh-6 | K00686 | 2.65 |
| 1439776_at | Ogfod1 | BE956398 | 2.65 |
| 1424474_a_at | Camkk2 | BI157430 | 2.65 |
| 1423160_at | Spred1 | BQ044290 | 2.65 |
| 1444502_at | Pet112l | BG068580 | 2.64 |
| 1460634_at | Ralgds | NM_009058 | 2.64 |
| 1437927_at | Dlg2 | AV343743 | 2.64 |
| 1453125_at | Sox11 | BM508495 | 2.64 |
| 1421619_at | Kcnh3 | NM_010601 | 2.64 |
| 1451273_x_at | BC025546 | BC025546 | 2.64 |
| 1427113_s_at | Ttl | AV127581 | 2.64 |
| 1438201_at | Ppm2c | AV290622 | 2.64 |
| 1453069_at | Pik3cb | BF018155 | 2.64 |
| 1455463_at | Phyhip | BB427286 | 2.64 |
| 1448171_at | Siah2 | AA414485 | 2.64 |
| 1441727_s_at | Zfp467 | BE628275 | 2.64 |
| 1428800_a_at | Pus7l | AK019372 | 2.64 |
| 1423415_at | Gpr83 | BB110067 | 2.64 |
| 1416514_a_at | Fscn1 | NM_007984 | 2.64 |
| 1460576_at | Exoc6 | AV248277 | 2.64 |
| 1426897_at | Rcc2 | AV122997 | 2.64 |
| 1426307_at | Cyb5r4 | BC025438 | 2.63 |
| 1450972_at | 3110040N11Rik | AK019261 | 2.63 |
| 1429278_at | Nubpl | AK010827 | 2.63 |
| 1435669_at | Zfp532 | BB404446 | 2.63 |
| 1426548_a_at | Atpbd4 | BG070516 | 2.63 |
| 1451334_at | 1810009O10Rik | BC027022 | 2.63 |
| 1457080_at |  | BB046159 | 2.63 |
| 1456329_at | Prtg | BB130087 | 2.63 |
| 1417602_at | Per2 | AF035783 | 2.63 |
| 1447403_a_at | Zmynd19 | AW125726 | 2.63 |
| 1438922_x_at | Slc25a5 | AV110784 | 2.63 |
| 1452025_a_at | Zfp2 | AF483521 | 2.63 |
| 1448080_a_at | Sdhc | NM_025321 | 2.63 |
| 1456645_at | Wdr25 | BB352668 | 2.63 |
| 1421820_a_at | Nf2 | L28176 | 2.63 |
| 1420142_s_at | Pa2g4 | AA672939 | 2.63 |
| 1455700_at | Mterfd3 | BB359043 | 2.63 |
| 1434602_at | Thrap2 | BG074645 | 2.63 |
| 1417016_at | Mapkapk5 | NM_010765 | 2.63 |
| 1432489_a_at | 2410187C16Rik | AK010831 | 2.62 |
| 1460498_a_at | Dnajc5 | BI685030 | 2.62 |
| 1450847_at | Ncbp2 | BE285362 | 2.62 |
| 1415753_at | D10Bwg1364e | BC005632 | 2.62 |
| 1437035_x_at | Rnf14 | BB504639 | 2.62 |
| 1434762_at | Tmem142b | BF457736 | 2.62 |
| 1451745_a_at | Znhit1 | BC026751 | 2.62 |

TABLE 13-continued

Genes differentially translated between medium spiny neurons (MSNs) and the rest of the brain.

| Probe | Symbol | GenBank | FCH |
|---|---|---|---|
| 1457977_at | 2310005N01Rik | AI594274 | 2.62 |
| 1440479_at | Cbx4 | BB821623 | 2.62 |
| 1431836_x_at | 5430432N15Rik | AK017382 | 2.62 |
| 1441387_at | E130309D02Rik | BB182811 | 2.62 |
| 1423756_s_at | Igfbp4 | BC019836 | 2.62 |
| 1427901_at | Mrps18c | AK004139 | 2.62 |
| 1425656_a_at | Baiap2 | AF390178 | 2.62 |
| 1435210_s_at | Snph | BQ174936 | 2.62 |
| 1425304_s_at | Prima1 | AY043275 | 2.62 |
| 1430127_a_at | Ccnd2 | AK007904 | 2.62 |
| 1433833_at | Fndc3b | BG064539 | 2.62 |
| 1452748_at | Xrcc3 | AW537713 | 2.62 |
| 1419522_at | Zmynd19 | NM_026021 | 2.62 |
| 1451080_at | Usp1 | BC018179 | 2.62 |
| 1439405_x_at | Becn1 | AV296285 | 2.62 |
| 1416247_at | Dctn3 | NM_016890 | 2.62 |
| 1419987_at |  | C80388 | 2.62 |
| 1416938_at | Chchd1 | NM_025366 | 2.62 |
| 1426403_at | Actr1b | BG801851 | 2.62 |
| 1433733_a_at | Cry1 | BG069864 | 2.61 |
| 1455282_x_at | Alas1 | AI255644 | 2.61 |
| 1418591_at | Dnaja4 | NM_021422 | 2.61 |
| 1456785_at | Crsp2 | BQ175889 | 2.61 |
| 1435844_at | A330009N23Rik | BB164247 | 2.61 |
| 1441815_at | AI851453 | AI851453 | 2.61 |
| 1427910_at | Cst6 | AK003744 | 2.61 |
| 1417507_at | Cyb561 | BC006732 | 2.61 |
| 1455944_at | Zfp516 | BB467812 | 2.61 |
| 1451444_s_at | 2700008B19Rik | BF150550 | 2.61 |
| 1451141_at | Mettl8 | BC004636 | 2.61 |
| 1427590_at | Zfp39 | BC011182 | 2.61 |
| 1415925_a_at | Nup62 | NM_053074 | 2.61 |
| 1433747_at | Lnpep | BQ176475 | 2.61 |
| 1427966_at | BC087945 | AW551849 | 2.61 |
| 1448269_a_at | Klhl13 | NM_026167 | 2.61 |
| 1433593_at | Ypel5 | BB316456 | 2.61 |
| 1423733_a_at | Fiz1 | AF126746 | 2.61 |
| 1449339_at | D10Ertd641e | BE692118 | 2.60 |
| 1452979_at | 2610110G12Rik | AK014265 | 2.60 |
| 1436102_at | Sec22c | BB425408 | 2.60 |
| 1428259_at | Pxdn | AK010185 | 2.60 |
| 1456764_at | Slc35f3 | BB427860 | 2.60 |
| 1418820_s_at | Zcchc10 | BC025078 | 2.60 |
| 1448822_at | Psmb6 | BC013897 | 2.60 |
| 1438481_at | AW047464 | AI854375 | 2.60 |
| 1435843_x_at | Mrps9 | AI666552 | 2.60 |
| 1433616_a_at | 2310028O11Rik | BG793007 | 2.60 |
| 1430128_a_at | Reep6 | AK002562 | 2.60 |
| 1427898_at | Rnf6 | BI738010 | 2.60 |
| 1451294_s_at | Snrpe | BC008262 | 2.60 |
| 1448179_at | Usmg5 | BC024355 | 2.60 |
| 1460444_at | Arrb1 | AK004614 | 2.60 |
| 1424358_at | Ube2e2 | BC016265 | 2.60 |
| 1442060_at | Prep1 | BB224442 | 2.60 |
| 1439630_x_at | Sbsn | AI844734 | 2.60 |
| 1441610_at | N28178 | BB306826 | 2.60 |
| 1432232_at | Rcor3 | AK016486 | 2.60 |
| 1455356_at | Camsap1 | BG064669 | 2.59 |
| 1429837_at | 1700016D18Rik | AV278908 | 2.59 |
| 1422616_s_at | Wdr54 | NM_023790 | 2.59 |
| 1442793_s_at | Tbrg4 | BB139935 | 2.59 |
| 1456737_x_at | Acaa1a | BB314154 | 2.59 |
| 1420612_s_at | Ptp4a2 | BE134116 | 2.59 |
| 1452357_at | 4-Sep | AF033350 | 2.59 |
| 1460462_at | Med18 | AK012903 | 2.59 |
| 1429590_at | Tacc1 | BE862546 | 2.59 |
| 1416796_at | Nck2 | NM_010879 | 2.59 |
| 1448682_at | Dynll1 | NM_019682 | 2.59 |
| 1449194_at | Mrps25 | AK004037 | 2.59 |
| 1429170_a_at | Mtf1 | AK012676 | 2.59 |
| 1435602_at |  | BE200310 | 2.59 |
| 1422264_s_at | Klf9 | NM_010638 | 2.59 |
| 1450535_at | Krtap12-1 | NM_010670 | 2.59 |
| 1455672_s_at | Cplx2 | BE946238 | 2.59 |
| 1416301_a_at | Ebf1 | BB125261 | 2.59 |
| 1427173_a_at | Mrps33 | Y17852 | 2.59 |
| 1456765_at | 6430511F03 | AV339861 | 2.59 |
| 1449258_at | D11Wsu99e | AV225714 | 2.59 |
| 1444441_at | Rapgef1 | AW490909 | 2.59 |
| 1425147_at | 2410075B13Rik | BC024536 | 2.58 |
| 1420858_at | Pkia | AK010212 | 2.58 |
| 1437959_at | Zfp324 | BB277175 | 2.58 |
| 1443782_x_at | Cyp20a1 | AV214523 | 2.58 |
| 1451217_a_at | Immp1l | BC008259 | 2.58 |
| 1443427_at |  | C76966 | 2.58 |
| 1439834_at | 2400009B08Rik | AA261399 | 2.58 |
| 1460377_a_at | Tmem8 | BC005722 | 2.58 |
| 1455104_at | Mxd1 | AV228517 | 2.58 |
| 1452604_at | Stard13 | BB667840 | 2.58 |
| 1441786_at |  | AW048005 | 2.58 |
| 1436876_at | Rgs7bp | AV337421 | 2.58 |
| 1449188_at | Midn | NM_021565 | 2.58 |
| 1435289_at | D230014K01Rik | BB379430 | 2.58 |
| 1417628_at | Supt6h | NM_009297 | 2.58 |
| 1417300_at | Smpdl3b | NM_133888 | 2.58 |
| 1428289_at | 2310051E17Rik | AW488885 | 2.58 |
| 1428049_a_at | Nudt16l1 | BC028494 | 2.58 |
| 1422297_at | Pfdn5 | NM_027044 | 2.58 |
| 1460315_s_at | Tbk1 | NM_019786 | 2.58 |
| 1420866_at | Zfp161 | NM_009547 | 2.57 |
| 1449770_x_at | D16Bwg1494e | N28171 | 2.57 |
| 1455877_a_at | Nanos1 | BG075296 | 2.57 |
| 1449666_at | Atrnl1 | AW555641 | 2.57 |
| 1452101_at | Blmh | BB215260 | 2.57 |
| 1416323_at | Kctd20 | AV281062 | 2.57 |
| 1435392_at | Wdr17 | BB277182 | 2.57 |
| 1426487_a_at | Rbbp6 | BB092954 | 2.57 |
| 1423652_at | Isca1 | AV209097 | 2.57 |
| 1421557_x_at | Txn2 | NM_019913 | 2.57 |
| 1453834_at | Ssu72 | BB857377 | 2.57 |
| 1452988_at | 2610306M01Rik | AK011997 | 2.57 |
| 1416699_at | 1110008F13Rik | NM_026124 | 2.57 |
| 1423102_a_at | Rnf10 | AI746548 | 2.57 |
| 1440478_at | D10Ertd438e | BM941145 | 2.57 |
| 1427914_a_at | Tceb1 | AI019214 | 2.57 |
| 1454985_at | D030051N19Rik | BI872009 | 2.57 |
| 1452516_at | Smok3a | AJ245454 | 2.57 |
| 1427956_at | Pcgf1 | BG068910 | 2.57 |
| 1423651_at | Isca1 | AV209097 | 2.56 |
| 1416155_at | Hmgb3 | NM_008253 | 2.56 |
| 1460563_at | D10Ertd438e | BE949414 | 2.56 |
| 1448262_at | Psmb2 | NM_011970 | 2.56 |
| 1431838_at | 1700128E19Rik | AK007309 | 2.56 |
| 1437185_s_at | Tmsb10 | AV148480 | 2.56 |
| 1438422_at | Lrrc20 | BB143476 | 2.56 |
| 1423456_at | Bzw2 | BM932775 | 2.56 |
| 1424095_at | Rtcd1 | BC016519 | 2.56 |
| 1453175_at | Zbtb25 | AK013374 | 2.56 |
| 1423568_at | Psma7 | BG297088 | 2.56 |
| 1448505_at | C1d | NM_020558 | 2.56 |
| 1428619_at | 2310005N03Rik | BB783243 | 2.56 |
| 1423588_at | Arpc4 | BG145444 | 2.55 |
| 1421630_at | Zfy1 | NM_009570 | 2.55 |
| 1427124_at | 4932416H05Rik | AB041802 | 2.55 |
| 1426810_at | Jmjd1a | BC026605 | 2.55 |
| 1449076_x_at | Adi1 | NM_134052 | 2.55 |
| 1427060_at | Mapk3 | BI414398 | 2.55 |
| 1448882_at | Tmem93 | NM_025318 | 2.55 |
| 1438689_at | 4632433K11Rik | BB430846 | 2.55 |
| 1421910_at | Tcf20 | AW552808 | 2.55 |
| 1426966_at | Axin1 | BB004060 | 2.55 |
| 1453689_at | Fance | AK013325 | 2.55 |
| 1452002_at | Zfp508 | BC024969 | 2.55 |
| 1418121_at | Vrk3 | NM_133945 | 2.55 |
| 1451595_a_at | Kcnq2 | AB000497 | 2.55 |
| 1440376_at | Fbxo41 | AI747062 | 2.55 |
| 1422998_a_at | Glrx2 | NM_023505 | 2.55 |
| 1426313_at | Bre | BE984258 | 2.55 |
| 1421342_at | Kcns2 | NM_008436 | 2.55 |
| 1418732_s_at | 1500041N16Rik | NM_026399 | 2.54 |

TABLE 13-continued

Genes differentially translated between medium spiny neurons (MSNs) and the rest of the brain.

| Probe | Symbol | GenBank | FCH |
|---|---|---|---|
| 1428913_at | D2Bwg1335e | AK004089 | 2.54 |
| 1428413_at | Ccny | AK017493 | 2.54 |
| 1422451_at | Mrps21 | NM_078479 | 2.54 |
| 1436955_at | Tssc1 | BG065248 | 2.54 |
| 1424240_at | Arfip2 | BC022942 | 2.54 |
| 1422320_x_at | Phxr5 | NM_008836 | 2.54 |
| 1454846_at | Utp15 | AV227804 | 2.54 |
| 1449303_at | Sesn3 | NM_030261 | 2.54 |
| 1424044_at | Jmjd2b | BC007145 | 2.54 |
| 1416127_a_at | Dnpep | NM_016878 | 2.54 |
| 1418112_at | Mrpl10 | BC016219 | 2.54 |
| 1435019_at | Atxn713 | BB532141 | 2.54 |
| 1417279_at | Itpr1 | NM_010585 | 2.54 |
| 1452724_at | Ppp1r16a | AK013817 | 2.54 |
| 1434228_at | Ppm2c | AV255921 | 2.54 |
| 1424289_at | Osgin2 | BB817847 | 2.54 |
| 1416123_at | Ccnd2 | NM_009829 | 2.54 |
| 1434420_x_at | Tomm22 | AV102576 | 2.54 |
| 1437148_at | Arpc2 | BG967632 | 2.54 |
| 1436134_at | Scn2b | BQ175340 | 2.54 |
| 1439022_at | Phactr1 | AV259240 | 2.54 |
| 1428603_at | Glcci1 | AK009885 | 2.54 |
| 1436567_a_at | Ndufa7 | C88880 | 2.53 |
| 1450484_a_at | Tyki | AK004595 | 2.53 |
| 1432509_at | 5033430I15Rik | AK017206 | 2.53 |
| 1431020_a_at | Fgfr1op2 | AK008983 | 2.53 |
| 1423834_s_at | Gga1 | BC026802 | 2.53 |
| 1435960_at | EG434128 | BI733057 | 2.53 |
| 1416507_at | Tmem4 | NM_019953 | 2.53 |
| 1454987_a_at | H2-Ke6 | AI323545 | 2.53 |
| 1417774_at | Nans | BI151886 | 2.53 |
| 1454829_at | Rundc1 | BB796494 | 2.53 |
| 1452201_at | 2310047B19Rik | BC019749 | 2.53 |
| 1427006_at | Rapgef1 | BB339051 | 2.53 |
| 1428528_at | 1110007L15Rik | BM124553 | 2.53 |
| 1426586_at | Slc25a11 | AI647500 | 2.53 |
| 1452669_at | 2810012G03Rik | AK012724 | 2.53 |
| 1452024_a_at | Ldb1 | AF030333 | 2.53 |
| 1449326_x_at | Saa2 | NM_011314 | 2.53 |
| 1434381_at | BC060631 | AV287602 | 2.53 |
| 1428972_at | 0610012D17Rik | AK007178 | 2.53 |
| 1428515_at | 2410012H22Rik | AK010472 | 2.53 |
| 1432415_at | Rab3c | AK014050 | 2.53 |
| 1433460_at | Ttc7b | BB329157 | 2.53 |
| 1460617_s_at | Rab6b | AV220161 | 2.52 |
| 1424236_at | Tbc1d10b | AF285112 | 2.52 |
| 1453737_at | Wipf2 | BI157060 | 2.52 |
| 1449003_a_at | Vti1b | NM_016800 | 2.52 |
| 1421992_a_at | Igfbp4 | NM_010517 | 2.52 |
| 1433682_at | Arhgef17 | BE287052 | 2.52 |
| 1426716_at | Tdrd7 | BC025099 | 2.52 |
| 1425650_at | Tle4 | AF229633 | 2.52 |
| 1455982_at | Jmjd4 | BF466891 | 2.52 |
| 1449281_at | Nrtn | NM_008738 | 2.52 |
| 1444531_at | Sod2 | AI847438 | 2.52 |
| 1426514_at | 4631426J05Rik | AK019474 | 2.52 |
| 1418827_at | Thex1 | BF320755 | 2.52 |
| 1422693_a_at | Sub1 | BE989104 | 2.52 |
| 1457675_at | 2510002D24Rik | B0063089 | 2.52 |
| 1453030_at | Msl2l1 | BB745314 | 2.52 |
| 1435912_at | Ubxd7 | BM220232 | 2.52 |
| 1428447_at | Tmem14a | AK017734 | 2.52 |
| 1429290_at | Cbx6 | BE951971 | 2.52 |
| 1451321_a_at | Rbm43 | BC003333 | 2.52 |
| 1416535_at | Mcrs1 | BC003746 | 2.52 |
| 1449122_at | 3110003A22Rik | NM_026534 | 2.52 |
| 1447683_x_at | Mettl1 | AV118676 | 2.52 |
| 1452048_at | Mrpl12 | AK002757 | 2.51 |
| 1423502_at | Brd2 | BI155271 | 2.51 |
| 1428141_at | Gga2 | AK004632 | 2.51 |
| 1428508_at | Tbc1d2b | AK004526 | 2.51 |
| 1434832_at | Foxo3a | BB364488 | 2.51 |
| 1422164_at | Pou3f4 | X66603 | 2.51 |
| 1451672_at | Gprk6 | AF040748 | 2.51 |
| 1458979_at | | BB332816 | 2.51 |
| 1429043_at | Smndc1 | BG071121 | 2.51 |
| 1428519_at | 2610528E23Rik | AK019979 | 2.51 |
| 1416850_s_at | Zcd1 | NM_134007 | 2.51 |
| 1434834_at | Socs7 | BG067098 | 2.51 |
| 1452380_at | Epha7 | BB075797 | 2.51 |
| 1420860_at | Itga9 | NM_133721 | 2.51 |
| 1457250_x_at | Nr1d2 | BB147330 | 2.51 |
| 1419180_at | Bcl9l | NM_030256 | 2.51 |
| 1426997_at | Thra | AW208371 | 2.51 |
| 1431378_at | Nr3c1 | BB600983 | 2.51 |
| 1451872_a_at | Neurl | AF400063 | 2.50 |
| 1418915_at | Mmachc | NM_025962 | 2.50 |
| 1416110_at | Slc35a4 | NM_026404 | 2.50 |
| 1450061_at | Enc1 | BM120053 | 2.50 |
| 1448411_at | Wfs1 | NM_011716 | 2.50 |
| 1422558_at | Gamt | AF015887 | 2.50 |
| 1441178_at | Dtwd2 | BB818617 | 2.50 |
| 1424136_a_at | Ppih | BC016565 | 2.50 |
| 1443133_at | Nefm | BB394014 | 2.50 |
| 1420472_at | Mtpn | NM_008098 | 2.50 |
| 1430979_a_at | Prdx2 | AK011963 | 2.50 |
| 1428531_at | Ints7 | BB457797 | 2.50 |
| 1427063_at | 5330417C22Rik | AK017241 | 2.50 |
| 1435902_at | Nudt18 | BM120193 | 2.50 |
| 1424049_at | Lrrc42 | BC027203 | 2.50 |
| 1439541_at | Mat2a | BQ176011 | 2.50 |
| 1455640_a_at | Txn2 | AV053127 | 2.50 |
| 1444981_at | Punc | BG067286 | 2.50 |
| 1452921_at | B130050I23Rik | AK006992 | 2.50 |
| 1437571_at | Hic2 | BB292220 | 2.50 |
| 1452972_at | Ttc32 | AK005950 | 2.50 |
| 1415793_at | Pnpo | NM_134021 | 2.50 |
| 1438387_x_at | Top3b | BB107606 | 2.50 |
| 1424538_at | Ubl4 | BI650739 | 2.50 |
| 1426381_at | Pprc1 | BM199989 | 2.50 |
| 1460307_at | Akt3 | AF124142 | 2.50 |
| 1416327_at | Ufc1 | NM_025388 | 2.49 |
| 1423636_at | Wdr31 | AK017259 | 2.49 |
| 1451140_s_at | Prkag2 | BB756794 | 2.49 |
| 1426582_at | Atf2 | BM119623 | 2.49 |
| 1439837_at | Tnrc15 | BE136147 | 2.49 |
| 1423448_at | Rab11b | BE986863 | 2.49 |
| 1453020_at | 1810048J11Rik | AK007829 | 2.49 |
| 1455328_at | Accn2 | BQ176072 | 2.49 |
| 1452328_s_at | Pja2 | BF160731 | 2.49 |
| 1419671_a_at | Il17rc | NM_134159 | 2.49 |
| 1454669_at | Tmem11 | BG075225 | 2.49 |
| 1438274_at | Ikzf4 | BG071647 | 2.49 |
| 1420579_s_at | Cftr | NM_021050 | 2.49 |
| 1448326_a_at | Crabp1 | NM_013496 | 2.48 |
| 1436994_a_at | Hist1h1c | BB533903 | 2.48 |
| 1416863_at | Abhd8 | NM_022419 | 2.48 |
| 1448703_at | Lsm8 | NM_133939 | 2.48 |
| 1448784_at | Taf10 | NM_020024 | 2.48 |
| 1434900_at | Mkl1 | BM196656 | 2.48 |
| 1434843_at | A430041B07Rik | BG070968 | 2.48 |
| 1419766_at | Snf1lk | NM_010831 | 2.48 |
| 1416882_at | Rgs10 | NM_026418 | 2.48 |
| 1436059_at | Rfx1 | BB151173 | 2.48 |
| 1431387_at | | AK015329 | 2.48 |
| 1425511_at | Mark1 | BM213279 | 2.48 |
| 1427496_at | Cep152 | BC026366 | 2.48 |
| 1455969_at | Nudt15 | BB198496 | 2.48 |
| 1454018_at | Tlk2 | AK014829 | 2.48 |
| 1455039_a_at | Sin3b | BF017589 | 2.48 |
| 1423371_at | Pole4 | BF577544 | 2.48 |
| 1425884_at | Bxdc1 | BC025093 | 2.48 |
| 1454874_at | Btbd7 | BG076293 | 2.48 |
| 1453561_x_at | Prkg1 | BB809910 | 2.48 |
| 1455489_at | Lrrtm2 | BB281991 | 2.48 |
| 1430679_at | 4933404O12Rik | AK016656 | 2.48 |
| 1431334_a_at | 4933433P14Rik | AK017049 | 2.48 |
| 1434410_at | Mina | AV276428 | 2.47 |
| 1452343_at | D18Ertd653e | BQ032363 | 2.47 |
| 1455211_a_at | Timm13 | BF021416 | 2.47 |

TABLE 13-continued

Genes differentially translated between medium spiny neurons (MSNs) and the rest of the brain.

| Probe | Symbol | GenBank | FCH |
|---|---|---|---|
| 1432411_a_at | Fbxw2 | AK009893 | 2.47 |
| 1437424_at | Syde2 | BG069296 | 2.47 |
| 1422568_at | Ndel1 | AF323918 | 2.47 |
| 1428235_at | Sdhd | AK013962 | 2.47 |
| 1428473_at | Ppp3cb | AK004360 | 2.47 |
| 1452989_at | 2900009J20Rik | BB315961 | 2.47 |
| 1419834_x_at | Mark1 | AW491150 | 2.47 |
| 1442180_at | Dleu7 | BB382040 | 2.47 |
| 1434029_at | 2410025L10Rik | AW545676 | 2.47 |
| 1433744_at | Lrtm2 | BB180412 | 2.47 |
| 1416948_at | Mrpl23 | NM_011288 | 2.47 |
| 1435636_at | 2310051F07Rik | AI415636 | 2.47 |
| 1454807_a_at | Snx12 | BB414983 | 2.47 |
| 1423478_at | Prkcb1 | BF660388 | 2.47 |
| 1437606_at | | BB829614 | 2.46 |
| 1434637_x_at | Sin3b | BF017589 | 2.46 |
| 1435253_at | Rab11b | BM250605 | 2.46 |
| 1423715_a_at | Nedd8 | BC004625 | 2.46 |
| 1452467_at | Mmab | BQ042988 | 2.46 |
| 1436402_at | Dohh | BG292769 | 2.46 |
| 1427233_at | Tshz1 | AV291373 | 2.46 |
| 1454851_at | Nr2c2 | AV162817 | 2.46 |
| 1432091_a_at | Rutbc3 | AK007455 | 2.46 |
| 1433523_at | D930005D10Rik | BB521978 | 2.46 |
| 1417230_at | Ralgps2 | NM_023884 | 2.46 |
| 1440177_at | 9.63E+17 | BM899529 | 2.46 |
| 1428216_s_at | Tomm7 | BB609428 | 2.46 |
| 1435675_at | Tbc1d12 | BF228251 | 2.46 |
| 1416706_at | Rpe | BG916066 | 2.46 |
| 1439515_at | Setd5 | BM207556 | 2.46 |
| 1434556_at | | BI437942 | 2.46 |
| 1448219_a_at | Ywhaz | AV027921 | 2.46 |
| 1431712_a_at | 2310022A10Rik | AK009941 | 2.46 |
| 1452039_a_at | Bap1 | AK009033 | 2.46 |
| 1439371_x_at | Timm44 | AV102008 | 2.45 |
| 1429033_at | Gcc1 | AV339946 | 2.45 |
| 1422714_at | Ube2i | U31934 | 2.45 |
| 1424380_at | Vps37b | BC026744 | 2.45 |
| 1426888_at | Ehmt2 | BI412952 | 2.45 |
| 1422418_s_at | Supt4h2 | NM_011509 | 2.45 |
| 1449080_at | Hdac2 | NM_008229 | 2.45 |
| 1424940_s_at | BC022687 | BC022687 | 2.45 |
| 1428457_at | 5830472M02Rik | AK014262 | 2.45 |
| 1455191_x_at | Pip5k1b | BB822856 | 2.45 |
| 1424624_at | 2900011O08Rik | BC022741 | 2.45 |
| 1451187_at | 0610037P05Rik | BC011300 | 2.45 |
| 1438917_x_at | Nup62 | AW240611 | 2.45 |
| 1440384_at | Nfkbiz | AI506779 | 2.45 |
| 1453007_at | 3110082I17Rik | AK014271 | 2.45 |
| 1423625_a_at | Dnajc19 | AV053772 | 2.45 |
| 1452791_at | Coq2 | AK009092 | 2.45 |
| 1422480_at | Snx3 | NM_017472 | 2.45 |
| 1433924_at | Peg3 | BM200248 | 2.45 |
| 1417239_at | Cetn3 | BC002162 | 2.45 |
| 1426112_a_at | Cd72 | BC003824 | 2.44 |
| 1447540_at | Tigd3 | AV167924 | 2.44 |
| 1417241_at | X83328 | NM_025275 | 2.44 |
| 1415686_at | Rab14 | AV339290 | 2.44 |
| 1448382_at | Ehhadh | NM_023737 | 2.44 |
| 1422473_at | Pde4b | BM246564 | 2.44 |
| 1421529_a_at | Txnrd1 | NM_015762 | 2.44 |
| 1441738_at | | BE824623 | 2.44 |
| 1424379_at | Car11 | BC019393 | 2.44 |
| 1434908_at | AI480556 | BB212188 | 2.44 |
| 1420707_a_at | Traip | AK012948 | 2.44 |
| 1455279_at | Gm1060 | BG070552 | 2.44 |
| 1452226_at | Rcc2 | AV122997 | 2.44 |
| 1428316_a_at | Fundc2 | AI510221 | 2.44 |
| 1441974_at | Camk4 | BB209139 | 2.44 |
| 1447653_x_at | Rpl24 | AV153119 | 2.44 |
| 1452313_at | 5930416I19Rik | AK011167 | 2.44 |
| 1426769_s_at | Maml1 | BB522516 | 2.44 |
| 1445479_at | Ttbk1 | AI839084 | 2.44 |
| 1439180_at | A430093A21Rik | BE197105 | 2.44 |
| 1431420_s_at | Nsd1 | BI082843 | 2.44 |
| 1455665_at | Lonrf1 | BB705689 | 2.44 |
| 1419406_a_at | Bcl11a | NM_016707 | 2.44 |
| 1420488_at | Mrps14 | BI246587 | 2.43 |
| 1435747_at | Fgf14 | AV141013 | 2.43 |
| 1449935_a_at | Dnaja3 | AK004575 | 2.43 |
| 1451808_at | Kcnj4 | U11075 | 2.43 |
| 1456767_at | Lrfn3 | AV062156 | 2.43 |
| 1428797_at | Setd6 | AK010304 | 2.43 |
| 1437049_at | | BE627361 | 2.43 |
| 1452860_at | Fbxl17 | AK004419 | 2.43 |
| 1454805_at | Wtap | AV141160 | 2.43 |
| 1435039_a_at | Pip5k1b | BB822856 | 2.43 |
| 1425132_at | Neto1 | AF448840 | 2.43 |
| 1448543_at | Slmo2 | NM_025531 | 2.43 |
| 1418234_s_at | Bcas2 | NM_026602 | 2.43 |
| 1423910_at | Centg3 | AF459091 | 2.43 |
| 1428097_at | 2510009E07Rik | AK010940 | 2.43 |
| 1434439_at | Gsk3b | BQ175580 | 2.43 |
| 1438199_at | AI316807 | AW228053 | 2.43 |
| 1436763_a_at | Klf9 | AI267126 | 2.43 |
| 1452833_at | Rapgef2 | AK018008 | 2.43 |
| 1426012_a_at | 2610301G19Rik | BC010499 | 2.43 |
| 1429792_at | 9530048O09Rik | BB398793 | 2.43 |
| 1423843_at | Lrrc61 | BC027309 | 2.43 |
| 1416853_at | Ncdn | BC017126 | 2.43 |
| 1438300_at | Cdkn2aip | BB371618 | 2.42 |
| 1444914_at | | AW121574 | 2.42 |
| 1429239_a_at | Stard4 | AK014587 | 2.42 |
| 1440386_at | Glce | BB272589 | 2.42 |
| 1454640_at | Chchd7 | BI692256 | 2.42 |
| 1460623_at | Skap2 | BB753881 | 2.42 |
| 1450942_at | Ccdc16 | AI530149 | 2.42 |
| 1425052_at | Isoc1 | AK010892 | 2.42 |
| 1431538_at | 4931415C17Rik | AV271801 | 2.42 |
| 1428522_at | Ttf2 | BB283807 | 2.42 |
| 1422938_at | Bcl2 | NM_009741 | 2.42 |
| 1427039_at | Epn1 | AF057285 | 2.42 |
| 1424267_at | 1810043G02Rik | BC010330 | 2.42 |
| 1435755_at | 1110001A16Rik | BB609468 | 2.42 |
| 1460337_at | Sh3kbp1 | BB326929 | 2.42 |
| 1452922_at | Ppp1r3d | AK011539 | 2.42 |
| 1419267_at | Nfyb | AV250496 | 2.42 |
| 1455327_at | Senp2 | BI684973 | 2.42 |
| 1453720_at | Rnf157 | AK011693 | 2.42 |
| 1454695_at | Wdr18 | BQ176396 | 2.42 |
| 1416135_at | Apex1 | NM_009687 | 2.42 |
| 1435237_at | 2310009A05Rik | AV004950 | 2.42 |
| 1455756_at | F730014I05Rik | BB232864 | 2.42 |
| 1454609_x_at | 6430527G18Rik | BB770958 | 2.42 |
| 1423971_at | Thoc3 | BE335845 | 2.41 |
| 1458951_at | Vrk1 | AV341598 | 2.41 |
| 1436380_at | Cdc42bpa | BG518726 | 2.41 |
| 1417542_at | Rps6ka2 | BB737182 | 2.41 |
| 1422718_at | Ap3s2 | NM_009682 | 2.41 |
| 1455546_s_at | Sf3a2 | BI900579 | 2.41 |
| 1451170_s_at | Nomo1 | BC024503 | 2.41 |
| 1429071_at | Me3 | AK006146 | 2.41 |
| 1426843_at | 1810013C15Rik | BG065569 | 2.41 |
| 1453013_at | Zfp740 | AW548228 | 2.41 |
| 1438017_at | Rusc1 | AV327629 | 2.41 |
| 1457979_at | | BM938335 | 2.41 |
| 1423189_at | 6720456B07Rik | BI456243 | 2.41 |
| 1459386_at | Zfp709 | AV319015 | 2.41 |
| 1422919_at | Hrasls | NM_013751 | 2.41 |
| 1424293_s_at | Tmem55a | BC021435 | 2.41 |
| 1455637_x_at | EG245305 | BB465277 | 2.41 |
| 1424510_at | Nudt6 | BC027267 | 2.41 |
| 1434853_x_at | Mkrn1 | AA717142 | 2.41 |
| 1450082_s_at | Etv5 | BG966751 | 2.41 |
| 1460636_at | Map2k2 | AW553456 | 2.40 |
| 1428466_at | Chd3 | AK011183 | 2.40 |
| 1455075_at | Pigv | BB321057 | 2.40 |
| 1417286_at | Ndufa5 | NM_026614 | 2.40 |
| 1454963_at | E430028B21Rik | BQ127172 | 2.40 |
| 1425192_at | Klhl25 | BC027373 | 2.40 |

TABLE 13-continued

Genes differentially translated between medium spiny neurons (MSNs) and the rest of the brain.

| Probe | Symbol | GenBank | FCH |
|---|---|---|---|
| 1430137_at | Map3k13 | AK004850 | 2.40 |
| 1419189_at | Vti1a | BC019386 | 2.40 |
| 1435362_at | Foxj3 | BB026073 | 2.40 |
| 1425071_s_at | Ntrk3 | BE692701 | 2.40 |
| 1429509_at | Lsm12 | BB771548 | 2.40 |
| 1455025_at | Paqr9 | AV103696 | 2.40 |
| 1419138_at | B3galt4 | NM_019420 | 2.40 |
| 1435556_at | Zfp597 | AV270881 | 2.40 |
| 1455362_at | Angel2 | AV275390 | 2.40 |
| 1424520_at | 2010305A19Rik | BC012391 | 2.40 |
| 1450638_at | Pdcd5 | AF161074 | 2.40 |
| 1426727_s_at | Ppp1r10 | BC004771 | 2.40 |
| 1427895_at | 2310004N24Rik | AK009156 | 2.40 |
| 1452797_at | Fastkd3 | AK009264 | 2.40 |
| 1423446_at | Dapk3 | AI642212 | 2.40 |
| 1443948_at | Ttc9c | BB771921 | 2.40 |
| 1429244_at | 1500011B03Rik | AW494389 | 2.40 |
| 1449186_at | Bag4 | NM_026121 | 2.40 |
| 1427413_a_at | Cugbp1 | AK014492 | 2.40 |
| 1449855_s_at | Uchl3 | AB033370 | 2.40 |
| 1452254_at | Mtmr9 | BB292990 | 2.39 |
| 1448483_a_at | Ndufb2 | NM_026612 | 2.39 |
| 1440364_a_at | A230062G08Rik | BB760971 | 2.39 |
| 1451347_at | Ccdc95 | BG065288 | 2.39 |
| 1422798_at | Cntnap2 | AU079588 | 2.39 |
| 1425180_at | Sgip1 | AV344708 | 2.39 |
| 1455671_at | Commd8 | AV365904 | 2.39 |
| 1437239_x_at | Phc2 | BB334118 | 2.39 |
| 1427158_at | Mrps30 | AV095945 | 2.39 |
| 1433867_at | 1810030O07Rik | BG064658 | 2.39 |
| 1451118_a_at | 2410018C17Rik | BC016596 | 2.39 |
| 1429484_at | Kif3c | BB752416 | 2.39 |
| 1457279_at | | BB314393 | 2.39 |
| 1451272_a_at | Ube2f | BC016117 | 2.39 |
| 1450472_s_at | Smad3 | BI150236 | 2.39 |
| 1448664_a_at | Speg | NM_007463 | 2.39 |
| 1434309_at | Fntb | BG063077 | 2.39 |
| 1416537_at | Creld1 | NM_133930 | 2.39 |
| 1437848_x_at | Adpgk | BB490673 | 2.39 |
| 1454637_at | Klhl8 | BM942651 | 2.39 |
| 1422716_a_at | Acp1 | AW554436 | 2.39 |
| 1450054_at | Add1 | BF140063 | 2.39 |
| 1419967_at | Seh1l | AW540070 | 2.39 |
| 1447320_x_at | Rpo1-3 | AU018636 | 2.39 |
| 1425940_a_at | Ssbp3 | AF170906 | 2.39 |
| 1437477_at | Lrrfip1 | AV301584 | 2.39 |
| 1435802_at | ZBTB45 | BE134048 | 2.38 |
| 1441453_at | Dennd2a | BB341122 | 2.38 |
| 1420191_s_at | D16Bwg1494e | N28131 | 2.38 |
| 1454806_at | D12Ertd553e | AV228737 | 2.38 |
| 1455497_at | Leng9 | BB799608 | 2.38 |
| 1418529_at | Osgep | NM_133676 | 2.38 |
| 1435762_at | Pacs1 | BM115617 | 2.38 |
| 1424150_at | Gdpd5 | BC024955 | 2.38 |
| 1417138_s_at | Polr2e | NM_025554 | 2.38 |
| 1450547_x_at | Dub2 | U70369 | 2.38 |
| 1424216_a_at | Papola | U52197 | 2.38 |
| 1453093_at | Rasgef1c | AK018593 | 2.38 |
| 1416774_at | Wee1 | NM_009516 | 2.38 |
| 1435598_at | | BE996371 | 2.38 |
| 1430229_at | 6330416L11Rik | AK018183 | 2.38 |
| 1436077_a_at | Fcho1 | BF730694 | 2.38 |
| 1428127_at | 4921506J03Rik | BG975608 | 2.38 |
| 1423138_at | Wdr4 | BE854862 | 2.38 |
| 1452873_at | 5830415F09Rik | AK017931 | 2.38 |
| 1424554_at | Ppp1r8 | BC025479 | 2.38 |
| 1435683_a_at | Abcc5 | AV150520 | 2.38 |
| 1423408_a_at | 2500003M10Rik | BE692070 | 2.38 |
| 1434423_at | Gulp1 | BB138485 | 2.38 |
| 1443058_at | 2900006F19Rik | AV242558 | 2.38 |
| 1450943_at | 2010012C16Rik | AK006303 | 2.38 |
| 1433462_a_at | Pi4k2a | BB208212 | 2.37 |
| 1417974_at | Kpna4 | BF018653 | 2.37 |
| 1427326_at | 4833439L19Rik | BB489450 | 2.37 |
| 1418032_at | Itfg2 | NM_133927 | 2.37 |
| 1417794_at | Zmym3 | NM_019831 | 2.37 |
| 1424197_s_at | Fance | BC016538 | 2.37 |
| 1436053_at | Tbc1d22b | BB272520 | 2.37 |
| 1418085_at | Prkcz | NM_008860 | 2.37 |
| 1426344_at | Gle1l | AK016671 | 2.37 |
| 1460441_at | Zxdb | BF660409 | 2.37 |
| 1433969_at | AU067824 | AU067824 | 2.37 |
| 1448582_at | Ctnnbl1 | NM_025680 | 2.37 |
| 1452657_at | Ap1s2 | AK005223 | 2.37 |
| 1426811_at | Ppp2r5b | BB080065 | 2.37 |
| 1448202_x_at | 2610524G07Rik | NM_025596 | 2.37 |
| 1417339_a_at | Dynll1 | NM_019682 | 2.37 |
| 1427929_a_at | Pdxk | BG063905 | 2.37 |
| 1447725_at | C030034E14Rik | BE948505 | 2.37 |
| 1448542_at | Bccip | NM_025392 | 2.37 |
| 1435866_s_at | Hist3h2a | AV297651 | 2.37 |
| 1421196_at | Ptpn11 | NM_011202 | 2.36 |
| 1455198_a_at | Ppp2r3a | BB550312 | 2.36 |
| 1418619_at | Icam5 | NM_008319 | 2.36 |
| 1417612_at | Ier5 | BF147705 | 2.36 |
| 1417941_at | Nanp | NM_026086 | 2.36 |
| 1435187_at | Tomm20 | BG064946 | 2.36 |
| 1440229_at | 2310034G01Rik | AI854627 | 2.36 |
| 1448817_at | Otub1 | NM_134150 | 2.36 |
| 1452918_at | D19Ertd737e | AK011404 | 2.36 |
| 1455032_at | Ccnyl1 | BQ176303 | 2.36 |
| 1436129_at | 4930523C11Rik | AV255799 | 2.36 |
| 1428395_at | Smurf1 | BB832916 | 2.36 |
| 1428991_at | Hrasls | BQ176967 | 2.36 |
| 1446957_s_at | BC004022 | C81621 | 2.36 |
| 1460274_at | 4921530G04Rik | NM_027622 | 2.36 |
| 1424052_at | Thap4 | BC013538 | 2.36 |
| 1428937_at | Atp2b1 | BI080417 | 2.36 |
| 1437624_x_at | Nudt16l1 | AV211435 | 2.36 |
| 1454869_at | Wdr40b | BB274776 | 2.35 |
| 1451300_a_at | Chmp7 | BC024115 | 2.35 |
| 1435588_at | Wdfy1 | BQ031098 | 2.35 |
| 1416267_at | Scoc | NM_019708 | 2.35 |
| 1441855_x_at | Cxcl1 | BB554288 | 2.35 |
| 1451726_at | Mtmr6 | BC020019 | 2.35 |
| 1423984_a_at | Mrg2 | BC003762 | 2.35 |
| 1423899_at | Trip12 | BG923744 | 2.35 |
| 1451436_at | Sbno1 | BC023136 | 2.35 |
| 1418319_at | 1810047C23Rik | NM_138668 | 2.35 |
| 1423113_a_at | Ube2d3 | AK009276 | 2.35 |
| 1448946_at | Kif3c | NM_008445 | 2.35 |
| 1427305_at | Piga | AV340508 | 2.35 |
| 1438016_at | BC068171 | BG068512 | 2.35 |
| 1448181_at | Klf15 | BC013486 | 2.35 |
| 1454944_at | Hic2 | BE648070 | 2.35 |
| 1435231_at | Coq4 | BB667890 | 2.35 |
| 1433528_at | Gtf2a2 | BG075741 | 2.35 |
| 1424710_a_at | Gorasp2 | BC016455 | 2.35 |
| 1453200_at | Rai1 | AK013909 | 2.35 |
| 1459657_s_at | Rpo1-3 | AU018636 | 2.35 |
| 1436523_s_at | 1810022K09Rik | AV111033 | 2.35 |
| 1431429_a_at | Arl4a | AK006286 | 2.35 |
| 1454614_at | 1810013D10Rik | C87702 | 2.35 |
| 1444980_at | Onecut2 | BE996518 | 2.34 |
| 1457985_at | Clmn | BE980727 | 2.34 |
| 1456044_at | Nedd4l | BB309512 | 2.34 |
| 1452208_at | Prdm4 | AK013393 | 2.34 |
| 1445342_at | C230004F18Rik | AV338249 | 2.34 |
| 1428742_at | Fbxo45 | AK011438 | 2.34 |
| 1425830_a_at | 2810452K22Rik | BC021867 | 2.34 |
| 1422895_at | Vamp4 | NM_016796 | 2.34 |
| 1437436_s_at | Gprk6 | BB461269 | 2.34 |
| 1416877_a_at | Mrpl51 | AI594880 | 2.34 |
| 1416963_at | Ubadc1 | NM_133835 | 2.34 |
| 1422688_a_at | Nras | BB018528 | 2.34 |
| 1440228_at | Ranbp6 | BB477637 | 2.34 |
| 1435685_x_at | Abcc5 | AV150520 | 2.34 |
| 1420381_a_at | Rpl31 | NM_053257 | 2.34 |
| 1426620_at | Chst10 | BB549997 | 2.34 |
| 1428147_at | Coro7 | BB203098 | 2.34 |

TABLE 13-continued

Genes differentially translated between medium spiny neurons (MSNs) and the rest of the brain.

| Probe | Symbol | GenBank | FCH |
|---|---|---|---|
| 1449181_at | Fech | NM_007998 | 2.34 |
| 1455726_at | Gm71 | BB756522 | 2.34 |
| 1436081_a_at | Zfp414 | BE632205 | 2.34 |
| 1452216_at | Mcat | BB494388 | 2.34 |
| 1425481_at | Cnot6l | BC018506 | 2.33 |
| 1423032_at | Rpl39 | AV107150 | 2.33 |
| 1451214_at | Kbtbd2 | BC022962 | 2.33 |
| 1435883_at | Tmco7 | BM206080 | 2.33 |
| 1436158_at | Eif4ebp2 | BI453292 | 2.33 |
| 1456468_x_at | 1110012N22Rik | BB189996 | 2.33 |
| 1423169_at | Taf7 | AV213552 | 2.33 |
| 1437336_x_at | 1110002E23Rik | AV051733 | 2.33 |
| 1429245_at | 1810009N02Rik | BI202412 | 2.33 |
| 1435426_s_at | Pisd | AV212090 | 2.33 |
| 1433985_at | Abi2 | AV263684 | 2.33 |
| 1416502_at | Preb | NM_016703 | 2.33 |
| 1447754_x_at | Thap4 | BB130418 | 2.33 |
| 1452896_at | Gtl3 | AK011217 | 2.33 |
| 1428527_at | Snx7 | AK011015 | 2.33 |
| 1451398_at | Cbr4 | BC009118 | 2.33 |
| 1416402_at | Abcb10 | AV382118 | 2.33 |
| 1444661_at | Gpr26 | BB247791 | 2.33 |
| 1423658_at | Sppl3 | BC023131 | 2.33 |
| 1455243_at | Brpf3 | BB728354 | 2.33 |
| 1421262_at | Lipg | BC020991 | 2.33 |
| 1424771_at | H2afj | BF661121 | 2.33 |
| 1455430_at | Prr8 | BQ179705 | 2.33 |
| 1437335_x_at | Poldip3 | BB534975 | 2.33 |
| 1440124_at | Ppap2b | BB312387 | 2.33 |
| 1427998_at | Lsm12 | AV015526 | 2.33 |
| 1434970_a_at | | AV216669 | 2.33 |
| 1429718_at | Slitrk5 | BB782729 | 2.33 |
| 1425820_x_at | Gpatc4 | BC019490 | 2.33 |
| 1438402_at | 9630050M13Rik | BB131315 | 2.32 |
| 1423794_at | D2Ertd391e | BM231455 | 2.32 |
| 1423122_at | Avpi1 | BI649826 | 2.32 |
| 1428718_at | Sern1 | AW490544 | 2.32 |
| 1439755_at | Sipa1l1 | BM936013 | 2.32 |
| 1429723_at | 6330409N04Rik | AK018153 | 2.32 |
| 1452100_at | Dullard | AV162210 | 2.32 |
| 1417284_at | Mapkap1 | NM_133841 | 2.32 |
| 1455143_at | Nlgn2 | AU042744 | 2.32 |
| 1417080_a_at | Ecsit | NM_012029 | 2.32 |
| 1452680_at | Snrpd2 | BQ043840 | 2.32 |
| 1427669_a_at | Cit | AF070066 | 2.32 |
| 1448517_at | Timm22 | AK012130 | 2.32 |
| 1429759_at | Rps6ka6 | BB449218 | 2.32 |
| 1448153_at | Cox5a | NM_007747 | 2.32 |
| 1434794_at | Rhof | BM241811 | 2.32 |
| 1456557_at | 1700041C02Rik | BB256666 | 2.32 |
| 1439130_at | Slc44a2 | BB131502 | 2.32 |
| 1444062_at | 2900056L01Rik | AI428930 | 2.32 |
| 1441019_at | Fbxo3 | BB012129 | 2.32 |
| 1450673_at | Col9a2 | NM_007741 | 2.32 |
| 1436078_at | Fcho1 | BF730694 | 2.31 |
| 1426786_s_at | Dhx38 | BM195397 | 2.31 |
| 1448357_at | Snrpg | NM_026506 | 2.31 |
| 1426408_at | Cugbp1 | BI412951 | 2.31 |
| 1458040_at | D7Wsu130e | BM213832 | 2.31 |
| 1440200_at | 9630031F12Rik | BB128528 | 2.31 |
| 1436373_at | Map3k10 | AA789425 | 2.31 |
| 1442789_at | | AW125266 | 2.31 |
| 1418602_at | Cdh15 | NM_007662 | 2.31 |
| 1458295_at | Tmem79 | BE626145 | 2.31 |
| 1449172_a_at | Lin7b | NM_011698 | 2.31 |
| 1433826_at | Tspyl3 | AV325152 | 2.31 |
| 1453705_at | B230110C06Rik | AK020961 | 2.31 |
| 1435061_at | Nudt10 | AI853080 | 2.31 |
| 1449256_a_at | Rab11a | BC010722 | 2.31 |
| 1452899_at | Rian | AK017440 | 2.31 |
| 1416952_at | Atp6v1d | NM_023721 | 2.31 |
| 1459859_x_at | Chrac1 | BB297047 | 2.31 |
| 1420809_a_at | 1500003O03Rik | NM_019769 | 2.31 |
| 1429671_at | 2410018M08Rik | AK010551 | 2.31 |
| 1426222_s_at | Loh11cr2a | BC004727 | 2.31 |
| 1455208_at | Pex19 | AV229364 | 2.31 |
| 1455639_at | Slc25a39 | AV224593 | 2.31 |
| 1431822_a_at | Azi2 | AK004992 | 2.31 |
| 1451267_at | Sharpin | BC016203 | 2.31 |
| 1419787_a_at | Zfp628 | AI608468 | 2.31 |
| 1433971_at | Camta1 | BB558154 | 2.31 |
| 1424331_at | Rab40c | AF422144 | 2.30 |
| 1449017_at | Nutf2 | AA920031 | 2.30 |
| 1452666_a_at | Tmcc2 | AK004359 | 2.30 |
| 1416018_at | Dr1 | NM_026106 | 2.30 |
| 1426240_at | Chmp4b | BC011429 | 2.30 |
| 1437366_at | AI608492 | BB332542 | 2.30 |
| 1415940_at | Zfand2a | NM_133349 | 2.30 |
| 1450243_a_at | Dscr1l1 | NM_030598 | 2.30 |
| 1448968_at | D7Wsu128e | BC011313 | 2.30 |
| 1431419_at | Nsd1 | BI082843 | 2.30 |
| 1425507_at | Arfrp1 | BG695431 | 2.30 |
| 1427427_at | Ryr3 | AV238793 | 2.30 |
| 1428237_at | 2700059D21Rik | BI689227 | 2.30 |
| 1442175_at | C030027H14Rik | BB358264 | 2.30 |
| 1430777_a_at | Golph3 | AK014644 | 2.30 |
| 1438409_at | Cep63 | BG061859 | 2.30 |
| 1453169_a_at | Gtf2h1 | BE688673 | 2.30 |
| 1424296_at | Gclc | BC019374 | 2.30 |
| 1453570_x_at | Bet1l | AV252862 | 2.30 |
| 1423823_at | Mrto4 | BC005734 | 2.30 |
| 1422979_at | Suv39h2 | NM_022724 | 2.30 |
| 1448131_at | Mfn2 | NM_133201 | 2.29 |
| 1428524_at | Cars2 | AK009937 | 2.29 |
| 1417195_at | Wwc2 | NM_133791 | 2.29 |
| 1428025_s_at | Pitpnc1 | BC028271 | 2.29 |
| 1423389_at | Smad7 | BF226166 | 2.29 |
| 1446312_at | | BB273243 | 2.29 |
| 1424539_at | Ubl4 | BI650739 | 2.29 |
| 1438434_at | Arhgap11a | AV349116 | 2.29 |
| 1442763_s_at | Ttll10 | AW324354 | 2.29 |
| 1418835_at | Phlda1 | NM_009344 | 2.29 |
| 1416041_at | Sgk | NM_011361 | 2.29 |
| 1416742_at | Cfdp1 | NM_011801 | 2.29 |
| 1460439_at | BC033915 | AK017789 | 2.29 |
| 1438209_at | 4632404H12Rik | BB216617 | 2.29 |
| 1435799_at | Sfrs14 | BB772209 | 2.29 |
| 1456789_at | Zfp462 | AW491540 | 2.29 |
| 1448293_at | Ebf1 | BB125261 | 2.29 |
| 1423832_at | Prkag2 | BB756794 | 2.29 |
| 1424620_at | D13Wsu177e | AK013251 | 2.29 |
| 1422972_s_at | Gcn5l2 | NM_020004 | 2.29 |
| 1436268_at | Ddn | AI841578 | 2.29 |
| 1433873_s_at | Pcnt | BG069597 | 2.29 |
| 1417571_at | Mpg | BC014754 | 2.29 |
| 1439012_a_at | Dck | BB030204 | 2.29 |
| 1454012_a_at | Parp6 | AK021076 | 2.28 |
| 1438091_a_at | H2afz | AV003424 | 2.28 |
| 1431068_at | Rmnd5a | BI659732 | 2.28 |
| 1456524_at | Nrg1 | AV318914 | 2.28 |
| 1440603_at | | BB073590 | 2.28 |
| 1427279_at | Clip4 | AK017914 | 2.28 |
| 1442099_at | Usp31 | BM227490 | 2.28 |
| 1451021_a_at | Klf5 | BI465857 | 2.28 |
| 1453369_a_at | Fundc1 | AK007686 | 2.28 |
| 1423833_a_at | Brp44 | BC018324 | 2.28 |
| 1423534_at | Pdcd2 | BI526195 | 2.28 |
| 1425929_a_at | Rnf14 | AF249668 | 2.28 |
| 1435695_a_at | A030007L17Rik | AA673177 | 2.28 |
| 1421604_a_at | Klf3 | NM_008453 | 2.28 |
| 1427501_at | BC007180 | BG083894 | 2.28 |
| 1454034_a_at | Usp21 | AK013252 | 2.28 |
| 1455023_at | N28178 | BB171181 | 2.28 |
| 1454749_at | Pcnt | BG069597 | 2.28 |
| 1456795_at | D330027G24Rik | BB449568 | 2.28 |
| 1451724_at | Ankmy2 | BC024959 | 2.28 |
| 1436484_at | C030019I05Rik | BB800286 | 2.28 |
| 1450910_at | Cap2 | AV261931 | 2.28 |
| 1434697_at | 1110001P04Rik | BI692575 | 2.28 |
| 1452800_a_at | 0610008C08Rik | AK002320 | 2.28 |

TABLE 13-continued

Genes differentially translated between medium spiny neurons (MSNs) and the rest of the brain.

| Probe | Symbol | GenBank | FCH |
|---|---|---|---|
| 1460672_at | 2410002F23Rik | BC016099 | 2.28 |
| 1452812_at | Lphn1 | AA987131 | 2.28 |
| 1428941_at | Zmym2 | AK017929 | 2.28 |
| 1435706_at | Btbd9 | AV232817 | 2.28 |
| 1451348_at | Depdc6 | BC004774 | 2.28 |
| 1457267_at | A130010J15Rik | BB667685 | 2.28 |
| 1449048_s_at | Rab4a | NM_009003 | 2.28 |
| 1416583_at | Bad | NM_007522 | 2.28 |
| 1417155_at | Mycn | BC005453 | 2.28 |
| 1443672_at | Lars2 | AI415729 | 2.28 |
| 1423206_s_at | 2310003F16Rik | W45949 | 2.27 |
| 1456766_at | C330001K17Rik | BB036966 | 2.27 |
| 1448711_at | Mcm3ap | NM_019434 | 2.27 |
| 1459897_a_at | Sbsn | AI507307 | 2.27 |
| 1428626_at | Lysmd2 | AK008800 | 2.27 |
| 1424645_at | Tnrc6c | BB795102 | 2.27 |
| 1424997_at | Sfrs8 | BC025219 | 2.27 |
| 1439497_at | 4933415E08Rik | BG065013 | 2.27 |
| 1422647_at | Ring1 | NM_009066 | 2.27 |
| 1460688_s_at | AA407659 | BB390422 | 2.27 |
| 1447632_at | Fancc | BB555719 | 2.27 |
| 1418041_at | Tmem186 | AW488762 | 2.27 |
| 1437742_at | Rab21 | BB767504 | 2.27 |
| 1440285_at | Ppp1r9a | BF472950 | 2.27 |
| 1429874_at | Spata17 | AV265007 | 2.27 |
| 1454931_at | Eid2 | BE225694 | 2.27 |
| 1438232_at | Foxp2 | AV322952 | 2.27 |
| 1429097_at | C030044C12Rik | BB090042 | 2.27 |
| 1433632_at | Irf2bp2 | BB183385 | 2.27 |
| 1452521_a_at | Plaur | X62701 | 2.27 |
| 1417410_s_at | Prkci | NM_008857 | 2.27 |
| 1455046_a_at | Pogz | BI250645 | 2.27 |
| 1460739_at | Zmiz2 | BQ174371 | 2.27 |
| 1432472_a_at | Mccc2 | AK019760 | 2.27 |
| 1419316_s_at | Gnb1l | NM_023120 | 2.27 |
| 1434158_at | Gmds | AI747296 | 2.27 |
| 1415941_s_at | Zfand2a | NM_133349 | 2.27 |
| 1434214_at | 0910001L09Rik | BI525016 | 2.27 |
| 1426678_at | Zfp706 | AK004076 | 2.27 |
| 1419789_at | Centg1 | AI605509 | 2.27 |
| 1431385_a_at | Mbtps1 | AK002809 | 2.27 |
| 1460679_at | Exosc4 | AK005101 | 2.26 |
| 1448875_at | Zhx1 | NM_009572 | 2.26 |
| 1423211_at | Nola3 | AK004120 | 2.26 |
| 1436335_at | Plch2 | BI732150 | 2.26 |
| 1415711_at | Arfgef1 | BC025221 | 2.26 |
| 1418716_at | Mrps25 | AK004037 | 2.26 |
| 1434980_at | Pik3r5 | AV230647 | 2.26 |
| 1431561_a_at | Dhx34 | AK007461 | 2.26 |
| 1450250_at | Otud7a | NM_130880 | 2.26 |
| 1433699_at | Tnfaip3 | BM241351 | 2.26 |
| 1425051_at | Isoc1 | AK010892 | 2.26 |
| 1434254_at | Gna11 | BM235739 | 2.26 |
| 1423239_at | Impdh1 | BB351792 | 2.26 |
| 1433591_at | Ppp3r1 | BF148071 | 2.26 |
| 1434459_at | BC057627 | BF147898 | 2.26 |
| 1426430_at | Jag2 | AV264681 | 2.26 |
| 1451735_at | Arfrp1 | BG695431 | 2.26 |
| 1420825_at | Letm1 | BG060855 | 2.26 |
| 1434456_at | Gm440 | BG075955 | 2.26 |
| 1447899_x_at | Tacstd1 | AV099587 | 2.26 |
| 1428076_s_at | Ndufb4 | BG968046 | 2.26 |
| 1460009_at |  | BB667115 | 2.26 |
| 1451016_at | Ifrd2 | BB540964 | 2.26 |
| 1433572_a_at | BC010304 | AA673192 | 2.26 |
| 1448915_at | Zfp524 | NM_025324 | 2.26 |
| 1420978_at | Nrf1 | NM_010938 | 2.26 |
| 1421903_at | Ixl | AK005112 | 2.26 |
| 1425462_at | Fbxw11 | AY038079 | 2.26 |
| 1426710_at | Calm3 | BB396904 | 2.26 |
| 1449494_at | Rab3c | AY026947 | 2.26 |
| 1449577_x_at | Tpm2 | AK003186 | 2.26 |
| 1448720_at | Lrrc40 | NM_024194 | 2.26 |
| 1429867_at | 4933424C08Rik | AK016884 | 2.26 |
| 1423107_at | Ube2b | AK010432 | 2.25 |
| 1429634_at | Zfp580 | AK005257 | 2.25 |
| 1441773_at | 1700061N14Rik | AV207074 | 2.25 |
| 1417154_at | Slc25a14 | NM_011398 | 2.25 |
| 1450466_at | B230310J22Rik | BI739719 | 2.25 |
| 1458421_at | Kcnq3 | AW494964 | 2.25 |
| 1417096_at | Rrp15 | NM_026041 | 2.25 |
| 1437389_x_at |  | AV117555 | 2.25 |
| 1424610_at | Trub2 | BG064045 | 2.25 |
| 1423335_at | 1110004F10Rik | AW545354 | 2.25 |
| 1425228_a_at | Dguok | AY037862 | 2.25 |
| 1417709_at | Cyp46a1 | NM_010010 | 2.25 |
| 1447757_x_at | 1110007A13Rik | AV033355 | 2.25 |
| 1426760_at | Ipo8 | AW413962 | 2.25 |
| 1428285_at | 8430427H17Rik | AK018446 | 2.25 |
| 1424418_at | Slc25a38 | BC010801 | 2.25 |
| 1440874_at | Slco5a1 | BE686667 | 2.25 |
| 1416714_at | Irf8 | BG069095 | 2.25 |
| 1433902_at | Kbtbd8 | BB469300 | 2.25 |
| 1429457_at | 2310020A21Rik | BB001825 | 2.25 |
| 1456585_x_at | E130309D02Rik | BB546892 | 2.25 |
| 1454680_at | D5Ertd579e | BG073020 | 2.25 |
| 1422767_at | Bys1 | BG079188 | 2.25 |
| 1457276_at | Snf1lk2 | AI315692 | 2.25 |
| 1439934_at | Slc30a10 | BB540543 | 2.25 |
| 1448358_s_at | Snrpg | NM_026506 | 2.25 |
| 1453021_at | Stxbp5 | BM899291 | 2.25 |
| 1423231_at | Nrgn | AK002933 | 2.25 |
| 1424006_at | Aarsd1 | BC005711 | 2.25 |
| 1428512_at | Bhlhb9 | AK012577 | 2.25 |
| 1428266_at | Myl3 | AK002312 | 2.25 |
| 1426624_a_at | Ypel3 | BI660196 | 2.25 |
| 1416228_at | Pin1 | NM_023371 | 2.24 |
| 1434782_at | Usp42 | AW551594 | 2.24 |
| 1437994_x_at | Mier2 | BB531179 | 2.24 |
| 1428825_at | Nr6a1 | AK007201 | 2.24 |
| 1451226_at | Pex6 | BC003424 | 2.24 |
| 1422579_at | Hspe1 | NM_008303 | 2.24 |
| 1433621_at | Wdr41 | BB334979 | 2.24 |
| 1452353_at | Gpr155 | BB762731 | 2.24 |
| 1417527_at | Ap3m2 | BC027301 | 2.24 |
| 1429039_s_at | 1500034J01Rik | BI904336 | 2.24 |
| 1449694_s_at | Commd5 | C77953 | 2.24 |
| 1427033_at | Dnmbp | BC025944 | 2.24 |
| 1425264_s_at | Mbp | BB181247 | 2.24 |
| 1418698_a_at | Fech | NM_007998 | 2.24 |
| 1428826_at | Nr6a1 | AK007201 | 2.24 |
| 1452054_at | Ube2w | BB796558 | 2.24 |
| 1440716_at | 6430604M11Rik | BB188841 | 2.24 |
| 1424629_at | Brca1 | U31625 | 2.24 |
| 1435991_at | Nr3c2 | BQ174990 | 2.24 |
| 1423262_a_at | H3f3a | BI111967 | 2.24 |
| 1434234_at | Zfp341 | BM230261 | 2.24 |
| 1434144_s_at | 2410187C16Rik | BG073505 | 2.24 |
| 1418543_s_at | Ccdc43 | NM_025918 | 2.24 |
| 1451572_a_at | 5230400G24Rik | BC016597 | 2.24 |
| 1447739_x_at | Klhdc4 | AV294746 | 2.24 |
| 1447892_at |  | AV208528 | 2.24 |
| 1453294_at | 1700012B15Rik | AK007702 | 2.24 |
| 1416885_at | 1110038F14Rik | NM_054099 | 2.24 |
| 1424419_at | Lrrc14 | BC022126 | 2.23 |
| 1418899_at | Ufm1 | NM_026435 | 2.23 |
| 1425624_at | Epm2aip1 | BC018474 | 2.23 |
| 1429901_at | Tcba1 | AK018248 | 2.23 |
| 1434116_at | Cbx2 | BI693188 | 2.23 |
| 1441295_at | Lman2l | BB712151 | 2.23 |
| 1423945_a_at | Pkig | BC026550 | 2.23 |
| 1428108_x_at | Tmcc2 | AK004359 | 2.23 |
| 1457696_at | Rilp | AI835553 | 2.23 |
| 1436265_at | 6330405H19 | BB225226 | 2.23 |
| 1419353_at | Dpm1 | NM_010072 | 2.23 |
| 1424211_at | Slc25a33 | BC011293 | 2.23 |
| 1433425_at | 1700101I19Rik | AK007108 | 2.23 |
| 1434509_at | Rapgef6 | BM250883 | 2.23 |
| 1422589_at | Rab3a | NM_009001 | 2.23 |
| 1431050_at | Rps6ka5 | BE291900 | 2.23 |

TABLE 13-continued

Genes differentially translated between medium spiny neurons (MSNs) and the rest of the brain.

| Probe | Symbol | GenBank | FCH |
|---|---|---|---|
| 1450204_a_at | Mynn | AK019238 | 2.23 |
| 1455031_at | Cdc2l6 | AV278072 | 2.23 |
| 1418545_at | Wasf1 | NM_031877 | 2.23 |
| 1439113_at | LOC77114 | BB379753 | 2.23 |
| 1419264_at | 1200014M14Rik | AK012926 | 2.23 |
| 1460391_at | Gtpbp9 | AK013055 | 2.22 |
| 1419717_at | Sema3e | NM_011348 | 2.22 |
| 1424473_at | Polr2h | BC002306 | 2.22 |
| 1444450_at | 9530096D07Rik | BB124025 | 2.22 |
| 1415721_a_at | 1200013P24Rik | AK004750 | 2.22 |
| 1428177_at | Trappc6b | BG066452 | 2.22 |
| 1459813_at | 1700012D01Rik | AV040390 | 2.22 |
| 1417557_at | Ubxd1 | NM_024432 | 2.22 |
| 1448598_at | Mmp17 | NM_011846 | 2.22 |
| 1458511_at | 2410025L10Rik | BE687898 | 2.22 |
| 1452069_a_at | Thap7 | BM210680 | 2.22 |
| 1434139_at | Parp11 | BB026163 | 2.22 |
| 1455504_a_at | Mkrn1 | BE133749 | 2.22 |
| 1460733_at | AA407659 | BB390422 | 2.22 |
| 1429588_at | 2810474O19Rik | AA509870 | 2.22 |
| 1456480_at | Fry | BB527078 | 2.22 |
| 1422969_s_at | Ihpk1 | NM_013785 | 2.22 |
| 1424490_at | Zfp428 | BC024802 | 2.22 |
| 1418717_at | Mrps25 | AK004037 | 2.22 |
| 1420196_s_at | Tbc1d14 | C77429 | 2.22 |
| 1456161_at | 0610040B10Rik | BE198048 | 2.22 |
| 1429140_at | 9830002I17Rik | AK020683 | 2.21 |
| 1417517_at | Plagl2 | NM_018807 | 2.21 |
| 1455286_at | Btbd1 | AV018484 | 2.21 |
| 1423259_at | Id4 | BB121406 | 2.21 |
| 1434176_x_at | Poldip3 | BI963573 | 2.21 |
| 1415936_at | Bcar3 | NM_013867 | 2.21 |
| 1452817_at | Smyd3 | AK010447 | 2.21 |
| 1426248_at | Stk24 | BG060677 | 2.21 |
| 1423378_at | Adam23 | AI838132 | 2.21 |
| 1460333_at | Ddx59 | BB829482 | 2.21 |
| 1451078_at | 2510039O18Rik | BC012878 | 2.21 |
| 1439014_at | 1600021P15Rik | BB703667 | 2.21 |
| 1428367_at | Ndst1 | BI652065 | 2.21 |
| 1421297_a_at | Cacna1c | NM_009781 | 2.21 |
| 1455547_at | Zc3h7b | BM125518 | 2.21 |
| 1424913_at | 2310044G17Rik | AK009800 | 2.21 |
| 1451543_at | Fbxo21 | BC021871 | 2.21 |
| 1434253_s_at | Tmcc3 | BB711990 | 2.21 |
| 1418327_at | 1110058L19Rik | NM_026503 | 2.21 |
| 1443773_at | Ylpm1 | AI851834 | 2.21 |
| 1424300_at | Gemin6 | BC025157 | 2.20 |
| 1422470_at | Bnip3 | NM_009760 | 2.20 |
| 1440932_at |  | BB428585 | 2.20 |
| 1425628_a_at | Gtf2i | AF043220 | 2.20 |
| 1425333_at | Rab43 | BC010248 | 2.20 |
| 1451166_a_at | Ccdc101 | BC026784 | 2.20 |
| 1433936_at | 0610010E21Rik | BG791555 | 2.20 |
| 1455941_s_at | Map2k5 | BB025010 | 2.20 |
| 1416790_a_at | Tdg | NM_011561 | 2.20 |
| 1423649_at | Tmem68 | BC016240 | 2.20 |
| 1453566_at | Prr8 | AK014289 | 2.20 |
| 1416633_a_at | 5730536A07Rik | NM_026635 | 2.20 |
| 1423970_at | Thoc3 | BE335845 | 2.20 |
| 1436976_a_at | Pfkfb2 | BB201861 | 2.20 |
| 1417387_at | Med31 | NM_026068 | 2.20 |
| 1428841_at | Best1 | AK006549 | 2.20 |
| 1455723_at | D1Ertd448e | AV279416 | 2.20 |
| 1420012_at | Xbp1 | C77390 | 2.20 |
| 1455273_at |  | BG064695 | 2.20 |
| 1441173_at | 4930451G09Rik | AV352442 | 2.20 |
| 1436949_a_at | LOC668554 | AV068352 | 2.20 |
| 1430081_at | Phf15 | AK004823 | 2.20 |
| 1433878_at | Mrps26 | AI648866 | 2.20 |
| 1444026_at | AI593442 | BF658761 | 2.20 |
| 1451624_a_at | Phospho2 | BC025612 | 2.20 |
| 1418737_at | Nudt2 | NM_025539 | 2.20 |
| 1450036_at | Sgk3 | BB768208 | 2.20 |
| 1434315_at | Npal3 | BB667103 | 2.20 |
| 1435970_at | Nlk | AU035920 | 2.20 |
| 1458755_at |  | BB125469 | 2.20 |
| 1428468_at | 3110043O21Rik | AK014175 | 2.20 |
| 1455798_at | Galk2 | BB771515 | 2.20 |
| 1430021_a_at | Sae1 | AK011772 | 2.20 |
| 1416910_at | Dnajc15 | NM_025384 | 2.20 |
| 1418929_at | Ift57 | NM_028680 | 2.19 |
| 1451075_s_at | Ctdsp2 | BB294133 | 2.19 |
| 1450520_at | Cacng3 | NM_019430 | 2.19 |
| 1452839_at | Dph5 | AK010475 | 2.19 |
| 1449733_s_at | Siah1a | AA982064 | 2.19 |
| 1416505_at | Nr4a1 | NM_010444 | 2.19 |
| 1433906_at | Asph | BE956483 | 2.19 |
| 1428693_at | 2610044O15Rik | AK011776 | 2.19 |
| 1429367_at | Wipi2 | BB826276 | 2.19 |
| 1423188_a_at | 6720456B07Rik | BI456243 | 2.19 |
| 1415729_at | Pdpk1 | BQ174223 | 2.19 |
| 1417916_a_at | Fxc1 | NM_019502 | 2.19 |
| 1415746_at | Cic | AF363690 | 2.19 |
| 1425679_a_at | Mapk8ip1 | AF109769 | 2.19 |
| 1434196_at | Dnaja4 | BQ176119 | 2.19 |
| 1416379_at | Panx1 | NM_019482 | 2.19 |
| 1457699_at | E330009J07Rik | BB834854 | 2.19 |
| 1428023_at | 3110009E18Rik | AA879840 | 2.19 |
| 1452777_a_at | Nub1 | BG066220 | 2.19 |
| 1451188_at | Wdr26 | BC020044 | 2.19 |
| 1420460_a_at | Pex11b | NM_011069 | 2.19 |
| 1455588_at | Lyrm4 | BE952216 | 2.19 |
| 1457990_at | Anks1b | BB080832 | 2.19 |
| 1459881_at | AI595406 | AI595406 | 2.19 |
| 1419122_at | Mettl1 | NM_010792 | 2.19 |
| 1434076_at | Wdr37 | AV222037 | 2.19 |
| 1424181_at | 5-Sep | BC010489 | 2.19 |
| 1434427_a_at | Rnf157 | BB246182 | 2.19 |
| 1460553_at | 1700025K23Rik | BF466605 | 2.19 |
| 1451568_at | A630054L15Rik | BC025603 | 2.18 |
| 1428071_at | 1110038D17Rik | AK004153 | 2.18 |
| 1429042_at | 2010200O16Rik | AK008415 | 2.18 |
| 1429378_x_at | AY761184 | AK008498 | 2.18 |
| 1418687_at | Arc | NM_018790 | 2.18 |
| 1442120_at |  | AA153229 | 2.18 |
| 1439393_x_at | Ppp2r4 | BB369168 | 2.18 |
| 1448284_a_at | Ndufc1 | NM_025523 | 2.18 |
| 1450042_at | Arx | BB322201 | 2.18 |
| 1455234_at | B3galt1 | BB795733 | 2.18 |
| 1421823_a_at | Ppp2cb | AI323685 | 2.18 |
| 1434155_a_at | 2310061I04Rik | BB174350 | 2.18 |
| 1437918_at | 4930539E08Rik | AV374644 | 2.18 |
| 1460453_at | Tagap | BM220475 | 2.18 |
| 1428317_at | Fundc2 | AI510221 | 2.18 |
| 1434995_s_at | Dedd | BE199280 | 2.18 |
| 1424172_at | Hagh | BC004749 | 2.18 |
| 1452331_s_at | Qser1 | BC021511 | 2.18 |
| 1433700_at | 4933433P14Rik | BB477807 | 2.18 |
| 1436573_at | Scrn3 | BB434447 | 2.18 |
| 1460320_at | Becn1 | NM_019584 | 2.18 |
| 1423737_at | Ndufs3 | BC027270 | 2.18 |
| 1419357_at | Isy1 | NM_133934 | 2.17 |
| 1431804_a_at | Sp3 | AK004607 | 2.17 |
| 1451390_s_at | Zfand2b | BC011495 | 2.17 |
| 1449611_at | Cd82 | AI894122 | 2.17 |
| 1451005_at | Sumo1 | BM209585 | 2.17 |
| 1451574_at | Bcl9 | BC019641 | 2.17 |
| 1453406_a_at | Rab28 | AK012286 | 2.17 |
| 1426939_at | Tsr2 | BG070464 | 2.17 |
| 1424250_a_at | Arhgef3 | BC012262 | 2.17 |
| 1447991_at | Pcsk2 | AI839700 | 2.17 |
| 1436596_at | H2afv | BG092470 | 2.17 |
| 1437082_at | Akap9 | BB246410 | 2.17 |
| 1445194_at | Cnksr2 | BB355006 | 2.17 |
| 1417903_at | Dfna5h | NM_018769 | 2.17 |
| 1423663_at | Flcn | BC025820 | 2.17 |
| 1429213_at | 2310030N02Rik | AK009547 | 2.17 |
| 1459544_at |  | BB180990 | 2.17 |
| 1456320_at | BC049806 | BB701297 | 2.17 |
| 1428600_at | Nin | AK014241 | 2.17 |

TABLE 13-continued

Genes differentially translated between medium spiny neurons (MSNs) and the rest of the brain.

| Probe | Symbol | GenBank | FCH |
|---|---|---|---|
| 1419444_at | Sap18 | NM_009119 | 2.17 |
| 1436405_at | Dock4 | BG068753 | 2.17 |
| 1455991_at | Ccbl2 | BG094881 | 2.17 |
| 1436984_at | Abi2 | BG261647 | 2.17 |
| 1449183_at | Comt | NM_007744 | 2.17 |
| 1435087_at | BC039093 | BI409907 | 2.17 |
| 1415688_at | Ube2g1 | NM_025985 | 2.16 |
| 1434598_at | Larp5 | BM200204 | 2.16 |
| 1450024_at | Sufu | AJ308624 | 2.16 |
| 1460188_at | Ptpn6 | NM_013545 | 2.16 |
| 1452237_at | Hrb | BB130716 | 2.16 |
| 1446775_at |  | C76272 | 2.16 |
| 1417067_s_at | Cabc1 | AK014605 | 2.16 |
| 1434266_at | AI847670 | AI847670 | 2.16 |
| 1415755_a_at | Ube2v1 | BC019372 | 2.16 |
| 1422119_at | Rab5b | NM_011229 | 2.16 |
| 1452776_a_at | Nub1 | BG066220 | 2.16 |
| 1429073_at | 2210015D19Rik | AK005556 | 2.16 |
| 1443733_x_at | Pold3 | C85233 | 2.16 |
| 1433544_at | Als2cr2 | BB277912 | 2.16 |
| 1456089_at | Trim23 | AV276781 | 2.16 |
| 1418048_at | 1110059G10Rik | NM_025419 | 2.16 |
| 1424028_at | 5830457O10Rik | BC023107 | 2.16 |
| 1422516_a_at | Fibp | NM_021438 | 2.16 |
| 1455003_at | AW490810 | BQ032496 | 2.16 |
| 1447994_at | 1700026B20Rik | AV043099 | 2.16 |
| 1429389_at | Setmar | AK017895 | 2.16 |
| 1429151_at | Wdr68 | AK011714 | 2.16 |
| 1452923_at | Ndufal21 | AK007894 | 2.16 |
| 1455042_at | Tbl1x | BF682509 | 2.16 |
| 1456332_at | Tmem17 | AV290482 | 2.16 |
| 1455149_at | Sh3rf1 | BB072090 | 2.16 |
| 1435827_at | 4933404O12Rik | BB501711 | 2.15 |
| 1439253_x_at | 2610524G07Rik | AV111335 | 2.15 |
| 1423313_at | Pde7a | BG070255 | 2.15 |
| 1430361_at | 2610005M20Rik | BC003771 | 2.15 |
| 1452096_s_at | D230025D16Rik | BG065702 | 2.15 |
| 1440427_at | BB124205 | BB127176 | 2.15 |
| 1437617_x_at | 1110034G24Rik | BB387677 | 2.15 |
| 1429296_at | Rab10 | BF465974 | 2.15 |
| 1450103_a_at | Pscd2 | NM_011181 | 2.15 |
| 1455117_at | Mcmdc1 | AV274182 | 2.15 |
| 1417833_at | Zc3h10 | NM_134003 | 2.15 |
| 1417873_at | Pwp1 | BC003199 | 2.15 |
| 1441942_x_at | Snupn | AV331209 | 2.15 |
| 1438009_at | Hist1h2ao | W91024 | 2.15 |
| 1424446_at | Armc7 | BC023126 | 2.15 |
| 1447905_x_at | Nup62 | BB331755 | 2.15 |
| 1431250_at | 9030624G23Rik | BG923645 | 2.15 |
| 1428160_at | Ndufab1 | AK010307 | 2.15 |
| 1453747_at | 2810021J22Rik | BB620330 | 2.15 |
| 1418726_a_at | Tnnt2 | NM_011619 | 2.15 |
| 1427163_at | Ubr2 | AI646734 | 2.15 |
| 1458932_at | Pex2 | BB639093 | 2.15 |
| 1433639_at | 5730593F17Rik | AW548096 | 2.15 |
| 1451305_at | Pgea1 | AF331040 | 2.15 |
| 1431230_a_at | Btbd9 | Z74630 | 2.15 |
| 1456685_at | Nsg2 | BB227199 | 2.15 |
| 1422980_a_at | Bet1l | NM_018742 | 2.15 |
| 1451747_a_at | Atg12 | AK016474 | 2.15 |
| 1460713_at | BC048355 | BE949497 | 2.15 |
| 1452584_at | 1500032L24Rik | BG915672 | 2.15 |
| 1428252_at | Chmp2b | AA881383 | 2.15 |
| 1427471_at | Fbxl3 | BF782863 | 2.15 |
| 1436186_at | E2f8 | BM247465 | 2.15 |
| 1451180_at | Nt5c3l | BC015307 | 2.15 |
| 1420540_a_at | Rit1 | NM_009069 | 2.15 |
| 1418120_at | Rbm8a | NM_025875 | 2.15 |
| 1424837_at | Rnf113a1 | BC024906 | 2.15 |
| 1452888_at | 1110034G24Rik | AK004090 | 2.14 |
| 1423857_at | Mrpl30 | BC004614 | 2.14 |
| 1416755_at | Dnajb1 | AK002290 | 2.14 |
| 1453016_at | 2900042B11Rik | AK013636 | 2.14 |
| 1415714_a_at | 2610209M04Rik | BC027564 | 2.14 |
| 1434341_x_at | 1110020P15Rik | BF681728 | 2.14 |
| 1434250_at | Pak2 | AW537308 | 2.14 |
| 1426828_at | 1300018I17Rik | AK005046 | 2.14 |
| 1418314_a_at | A2bp1 | NM_021477 | 2.14 |
| 1434134_at | Wdr42a | BB123403 | 2.14 |
| 1455139_at | Smarcal1 | BB028226 | 2.14 |
| 1432000_a_at | Dedd | AK006814 | 2.14 |
| 1453048_at | Nhlrc2 | AK002650 | 2.14 |
| 1459021_at |  | BB307071 | 2.14 |
| 1422677_at | Dgat2 | AK002443 | 2.14 |
| 1451955_a_at | Cacna2d2 | AF247140 | 2.14 |
| 1453865_a_at | Otud5 | AK010750 | 2.14 |
| 1419056_at | Rtn2 | AF038538 | 2.14 |
| 1433628_at | Coq10a | BQ044689 | 2.14 |
| 1452601_a_at | Acbd6 | AK002470 | 2.14 |
| 1434042_s_at | Mtmr3 | BF466640 | 2.14 |
| 1452938_at | Anks1b | BQ174247 | 2.14 |
| 1457256_x_at | Ptch2 | BB530125 | 2.14 |
| 1434104_at | Slc35e1 | BB041864 | 2.14 |
| 1434218_at | C330019G07Rik | BB400635 | 2.14 |
| 1452222_at | Utrn | AI788797 | 2.14 |
| 1449290_at | Dpysl5 | NM_023047 | 2.14 |
| 1448853_at | Synj2bp | NM_025292 | 2.14 |
| 1430068_at | C030011L09Rik | BB356045 | 2.14 |
| 1452207_at | Cited2 | Y15163 | 2.14 |
| 1437907_a_at | Tbca | BB559082 | 2.14 |
| 1425710_a_at | Homer1 | AB019479 | 2.14 |
| 1456218_at | Snx22 | AV333851 | 2.14 |
| 1419964_s_at | Hdgf | C80147 | 2.14 |
| 1420008_s_at | Wwc1 | AU017197 | 2.14 |
| 1428971_at | Ccny | AK014507 | 2.14 |
| 1425460_at | Mtmr2 | BB197262 | 2.14 |
| 1426998_at | Zfand3 | BG976649 | 2.14 |
| 1420852_a_at | B3gnt2 | AV306734 | 2.14 |
| 1436309_at | Neto2 | BB125651 | 2.13 |
| 1422859_a_at | Rpl23 | NM_022891 | 2.13 |
| 1418355_at | Nucb2 | NM_016773 | 2.13 |
| 1424922_a_at | Brd4 | BC008532 | 2.13 |
| 1449600_at | Gm1683 | AA682050 | 2.13 |
| 1427341_at | E130103I17Rik | U85993 | 2.13 |
| 1423087_a_at | 1110002E23Rik | BB453951 | 2.13 |
| 1428823_at | Hddc2 | AK009957 | 2.13 |
| 1440655_at |  | BB076281 | 2.13 |
| 1451265_at | Ccdc115 | BC019430 | 2.13 |
| 1426496_at | Wdr55 | AK017695 | 2.13 |
| 1417481_at | Ramp1 | NM_016894 | 2.13 |
| 1419753_at | Nfx1 | AK013866 | 2.13 |
| 1424545_at | BC003965 | W59564 | 2.13 |
| 1457456_at | Ttc9b | AI481735 | 2.13 |
| 1423240_at | Src | BG868120 | 2.13 |
| 1423906_at | Hsbp1 | AK010939 | 2.13 |
| 1459271_at |  | BB036541 | 2.13 |
| 1448196_at | Mat2b | NM_134017 | 2.13 |
| 1441083_at | Clptm1 | BB799287 | 2.13 |
| 1439267_x_at | Cox5a | AV085180 | 2.13 |
| 1437152_at | Rkhd3 | BG072837 | 2.13 |
| 1418256_at | Srf | BI662291 | 2.13 |
| 1433855_at | Abat | BF462185 | 2.13 |
| 1443405_at |  | BB201852 | 2.13 |
| 1454986_at | Zfp668 | BB152304 | 2.13 |
| 1429869_at | 1110020C03Rik | AI561792 | 2.13 |
| 1431198_x_at | 9430038I01Rik | AK020460 | 2.13 |
| 1429380_at | Rgs12 | AK004813 | 2.13 |
| 1455517_at | Rbm4 | BB419586 | 2.13 |
| 1425181_at | Sgip1 | AV344708 | 2.13 |
| 1451570_a_at | 6720467C03Rik | BC020162 | 2.13 |
| 1450675_at | Smap1l | NM_133716 | 2.13 |
| 1435197_at | Pou3f3 | BE993443 | 2.13 |
| 1428989_at | 0710001D07Rik | AK002941 | 2.12 |
| 1451385_at | 2310056P07Rik | BC010826 | 2.12 |
| 1427874_at | Zfp313 | AF502145 | 2.12 |
| 1417105_at | Trappc2l | NM_021502 | 2.12 |
| 1434092_at | Atg9b | AW121498 | 2.12 |
| 1434339_at | Fnbp11 | AW548221 | 2.12 |
| 1433711_s_at | Sesn1 | BG076140 | 2.12 |
| 1436620_at | Ccdc45 | BQ173899 | 2.12 |

TABLE 13-continued

Genes differentially translated between medium spiny neurons (MSNs) and the rest of the brain.

| Probe | Symbol | GenBank | FCH |
|---|---|---|---|
| 1430832_at | 4930426I24Rik | BB055339 | 2.12 |
| 1422155_at | Hist2h3c2 | BC015270 | 2.12 |
| 1419462_s_at | Gtl3 | NM_008187 | 2.12 |
| 1434951_at | Armc8 | BE995635 | 2.12 |
| 1451943_a_at | Ppm1a | AF259673 | 2.12 |
| 1438039_at | Hectd1 | BE630599 | 2.12 |
| 1416775_at | 2310004L02Rik | NM_025504 | 2.12 |
| 1417848_at | Zfp704 | AW413620 | 2.12 |
| 1436449_at | | BB284627 | 2.12 |
| 1446793_at | | BB091198 | 2.12 |
| 1449880_s_at | Bglap1 | NM_007541 | 2.12 |
| 1432431_s_at | 2900006F19Rik | AK004072 | 2.12 |
| 1438692_at | Gtf3c4 | BG069995 | 2.12 |
| 1418593_at | Taf6 | NM_009315 | 2.12 |
| 1440224_at | 9330133O14Rik | BB077224 | 2.12 |
| 1452140_at | Tbc1d20 | BC002196 | 2.12 |
| 1434305_at | U2af1l4 | BF018149 | 2.12 |
| 1415717_at | 4931406I20Rik | BI735988 | 2.12 |
| 1458350_at | | AV290089 | 2.12 |
| 1424075_at | 9430016H08Rik | BC024945 | 2.12 |
| 1459783_s_at | Cno | AV218165 | 2.12 |
| 1424057_at | Gdap2 | BC025070 | 2.12 |
| 1454848_at | Ppp1r12c | BE628628 | 2.12 |
| 1442303_at | | AV139114 | 2.12 |
| 1425531_at | Znhit1 | BC026751 | 2.12 |
| 1428757_at | Aasdhppt | AK013111 | 2.12 |
| 1423635_at | Bmp2 | AV239587 | 2.12 |
| 1448240_at | Mbtps1 | NM_019709 | 2.12 |
| 1451290_at | Map1lc3a | BC010596 | 2.12 |
| 1450926_at | Atp6v1g1 | BI154058 | 2.12 |
| 1436004_at | Usp27x | BB021271 | 2.11 |
| 1443836_x_at | Wdr48 | BB064885 | 2.11 |
| 1456420_at | Arid4a | BB667227 | 2.11 |
| 1427565_a_at | Abcc5 | AF213387 | 2.11 |
| 1434934_at | Atpaf1 | BB771055 | 2.11 |
| 1423675_at | Usp1 | BC018179 | 2.11 |
| 1434483_at | Usp12 | AW539189 | 2.11 |
| 1427131_s_at | Actb | AV234245 | 2.11 |
| 1441764_at | Prdm10 | BF730739 | 2.11 |
| 1451124_at | Sod1 | BC002066 | 2.11 |
| 1428405_at | Hcfc1r1 | BF580567 | 2.11 |
| 1425601_a_at | Rtkn | BC013820 | 2.11 |
| 1454722_at | Pten | BG792618 | 2.11 |
| 1424313_a_at | Ndufs7 | BC013503 | 2.11 |
| 1421315_s_at | Cttn | BI688355 | 2.11 |
| 1429119_at | Iah1 | AK005287 | 2.11 |
| 1437350_at | RP23-143A14.5 | AV290046 | 2.11 |
| 1456109_a_at | Mrps15 | BB314055 | 2.11 |
| 1451303_at | BC002230 | BC025577 | 2.11 |
| 1423736_a_at | Dym | BC018220 | 2.11 |
| 1423245_at | Cops7a | BG974128 | 2.11 |
| 1428717_at | Scrn1 | AW490544 | 2.11 |
| 1424529_s_at | Cgref1 | BC023116 | 2.11 |
| 1433498_at | 2010005J08Rik | BF585125 | 2.11 |
| 1416668_at | Ttc35 | NM_025736 | 2.11 |
| 1418632_at | Ube2h | BI694835 | 2.11 |
| 1428898_at | Mon1a | AK013387 | 2.11 |
| 1430423_s_at | 2610528E23Rik | AK019808 | 2.11 |
| 1441203_at | | BB097040 | 2.11 |
| 1438170_x_at | Adrm1 | AV166873 | 2.11 |
| 1416920_at | Rbm4 | NM_009032 | 2.11 |
| 1448963_at | Nfyc | BC020117 | 2.11 |
| 1419379_x_at | Fxyd2 | NM_052823 | 2.11 |
| 1455659_at | Tmcc1 | AA244468 | 2.11 |
| 1443987_at | Klhl18 | BB283043 | 2.11 |
| 1428106_at | 1300001I01Rik | AK004841 | 2.11 |
| 1432287_a_at | Sntg1 | AK016927 | 2.11 |
| 1435566_s_at | Araf | BG228947 | 2.10 |
| 1433539_at | Commd3 | BB230296 | 2.10 |
| 1448685_at | 2900010M23Rik | NM_026063 | 2.10 |
| 1434071_a_at | Itga1 | AV288264 | 2.10 |
| 1438857_x_at | | BB058253 | 2.10 |
| 1419803_s_at | Ccdc12 | C76605 | 2.10 |
| 1440534_at | | BB177862 | 2.10 |
| 1442994_at | Sod2 | BQ177195 | 2.10 |
| 1433464_at | Ipo13 | BB475675 | 2.10 |
| 1451126_at | Mafl | BC016260 | 2.10 |
| 1452379_at | Auts2 | AK012475 | 2.10 |
| 1431087_at | Spbc24 | BF577722 | 2.10 |
| 1434083_a_at | Elmod1 | BI738305 | 2.10 |
| 1436990_s_at | Ndg2 | AA038464 | 2.10 |
| 1448533_at | Tbcb | NM_025548 | 2.10 |
| 1453364_x_at | 9130019O22Rik | AK020267 | 2.10 |
| 1438769_a_at | Vps26b | BF719766 | 2.10 |
| 1424199_at | Seh1l | AW537349 | 2.10 |
| 1451408_at | Trub2 | BG064045 | 2.10 |
| 1434435_s_at | Cox17 | BM941165 | 2.10 |
| 1434019_at | Pdap1 | BG065186 | 2.10 |
| 1420640_at | Jmy | BF227962 | 2.10 |
| 1457342_at | Ikzf4 | BM114149 | 2.10 |
| 1416477_at | Ube2d2 | NM_019912 | 2.10 |
| 1416550_at | Slc35b4 | BB320416 | 2.10 |
| 1421051_s_at | Vps25 | NM_026776 | 2.10 |
| 1424399_at | Uck1 | BC025146 | 2.10 |
| 1426729_at | 2900046G09Rik | BC003957 | 2.10 |
| 1420367_at | Denr | AK010394 | 2.10 |
| 1455959_s_at | Gclc | AW825835 | 2.10 |
| 1450890_a_at | Abi1 | AW912678 | 2.10 |
| 1431463_at | 1700041C02Rik | AK015391 | 2.10 |
| 1443932_at | Klhdc1 | BQ176961 | 2.09 |
| 1435591_at | AI426330 | AW495162 | 2.09 |
| 1417609_at | Ube2a | BG868960 | 2.09 |
| 1423053_at | Arf4 | BI653265 | 2.09 |
| 1434367_s_at | Nutf2 | AV217767 | 2.09 |
| 1415799_at | Wbp11 | NM_021714 | 2.09 |
| 1424013_at | Etf1 | BC013717 | 2.09 |
| 1449406_at | Cyhr1 | NM_019396 | 2.09 |
| 1456538_at | Sdccag8 | BM233019 | 2.09 |
| 1426219_at | Scp2 | M62361 | 2.09 |
| 1435705_at | LOC232875 | BB305660 | 2.09 |
| 1423990_at | Rab28 | BC004580 | 2.09 |
| 1420846_at | Mrps2 | AV031454 | 2.09 |
| 1418955_at | Zfp93 | NM_009567 | 2.09 |
| 1451811_at | Cacng6 | AV091458 | 2.09 |
| 1424784_at | 6330416L07Rik | AV047635 | 2.09 |
| 1448957_at | Rbpsuh | NM_009035 | 2.09 |
| 1449099_at | Lrba | NM_030695 | 2.09 |
| 1426401_at | Ppp3ca | BQ173889 | 2.09 |
| 1455020_at | Snx25 | AV351081 | 2.09 |
| 1434438_at | Samhd1 | BF148012 | 2.09 |
| 1440947_at | Bat2d | BB481861 | 2.09 |
| 1452690_at | Khsrp | BQ174458 | 2.09 |
| 1427003_at | Ppp2r5c | BG072817 | 2.09 |
| 1442999_at | B930036G03Rik | BB342280 | 2.09 |
| 1453718_at | Bcl2l12 | AK013411 | 2.09 |
| 1448403_at | Lars | NM_134137 | 2.09 |
| 1454866_s_at | Clic6 | BQ176424 | 2.09 |
| 1446624_at | Fcmd | BB518629 | 2.09 |
| 1423632_at | Gpr146 | BI103049 | 2.09 |
| 1452721_a_at | Ccdc53 | BM210204 | 2.09 |
| 1429958_x_at | Haghl | BI790001 | 2.09 |
| 1438196_at | Gpd1l | BB727537 | 2.09 |
| 1421524_at | Cfc1 | NM_007685 | 2.09 |
| 1460363_at | Tnrc6c | BB795102 | 2.09 |
| 1436522_at | Map3k3 | BE948629 | 2.09 |
| 1428578_s_at | Ppfia4 | AK003571 | 2.08 |
| 1455187_at | Zbtb40 | BM231844 | 2.08 |
| 1460691_at | Zfp598 | BF385956 | 2.08 |
| 1455507_s_at | D8Ertd587e | BM223036 | 2.08 |
| 1418996_a_at | Lyrm5 | BC021522 | 2.08 |
| 1449287_at | Srms | NM_011481 | 2.08 |
| 1429683_at | 5830472M02Rik | BG094398 | 2.08 |
| 1426493_a_at | Kifc2 | BB798224 | 2.08 |
| 1436347_a_at | 5530601H04Rik | BB501229 | 2.08 |
| 1417211_at | 1110032A03Rik | NM_023483 | 2.08 |
| 1422844_a_at | Wdr77 | NM_027432 | 2.08 |
| 1452174_at | Srebf2 | BM123132 | 2.08 |
| 1418568_x_at | Srp14 | NM_009273 | 2.08 |
| 1419026_at | Daxx | NM_007829 | 2.08 |
| 1434488_at | Arfrp1 | BQ176611 | 2.08 |

TABLE 13-continued

Genes differentially translated between medium spiny neurons (MSNs) and the rest of the brain.

| Probe | Symbol | GenBank | FCH |
|---|---|---|---|
| 1419912_s_at | Strap | AW557906 | 2.08 |
| 1438360_x_at | Slc25a5 | AV003169 | 2.08 |
| 1441578_at | Ccdc86 | BB142123 | 2.08 |
| 1417825_at | Esd | NM_016903 | 2.08 |
| 1431059_x_at | Htatsf1 | AK012522 | 2.08 |
| 1443401_at | Astn2 | BM941510 | 2.08 |
| 1426643_at | Elp3 | AK012072 | 2.08 |
| 1455073_at | Cdadc1 | BB178837 | 2.08 |
| 1420483_at | Cnnm3 | NM_053186 | 2.08 |
| 1448138_at | Ppp2r4 | NM_138748 | 2.08 |
| 1428806_at | Csnk1g1 | AK018639 | 2.08 |
| 1435153_at | Btbd6 | AV026558 | 2.08 |
| 1431170_at | Efna3 | AA388313 | 2.08 |
| 1431354_a_at | Fars2 | AK020164 | 2.08 |
| 1453106_a_at | Rnmt | AK015403 | 2.08 |
| 1424982_a_at | 2700078E11Rik | BB137173 | 2.08 |
| 1417591_at | Ptges2 | NM_133783 | 2.08 |
| 1420611_at | Prkacb | AV024339 | 2.08 |
| 1417320_at | Grpel1 | NM_024478 | 2.08 |
| 1451412_a_at | Ift20 | AY082613 | 2.08 |
| 1438324_at | 9330182L06Rik | AW550882 | 2.08 |
| 1455583_at | Gne | AV371374 | 2.08 |
| 1419805_s_at | Ggps1 | C79210 | 2.07 |
| 1426980_s_at | E130028A19Rik | BC006054 | 2.07 |
| 1451143_at | 1110006G06Rik | BC023421 | 2.07 |
| 1416506_at | Psma6 | NM_011968 | 2.07 |
| 1421066_at | Jak2 | NM_008413 | 2.07 |
| 1434968_a_at | Actr3 | BB758476 | 2.07 |
| 1460342_s_at | AA536749 | U73200 | 2.07 |
| 1457139_at | Auts2 | AV021813 | 2.07 |
| 1449162_at | Pop7 | NM_028753 | 2.07 |
| 1423777_at | Usp20 | AK006800 | 2.07 |
| 1454855_at | Magi2 | BQ176520 | 2.07 |
| 1428760_at | Snapc3 | AW537061 | 2.07 |
| 1416776_at | Crym | NM_016669 | 2.07 |
| 1420888_at | Bcl2l1 | NM_009743 | 2.07 |
| 1436008_at | Tpd52 | AV336744 | 2.07 |
| 1433505_a_at | Lrrc8d | BB315861 | 2.07 |
| 1419454_x_at | Pias2 | NM_008602 | 2.07 |
| 1423962_at | Wdr26 | BC020044 | 2.07 |
| 1416834_x_at | Ndufb2 | NM_026612 | 2.07 |
| 1426017_a_at | 0610011L14Rik | BC020112 | 2.07 |
| 1426355_a_at | 6330578E17Rik | BB667858 | 2.07 |
| 1421662_a_at | Tusc3 | NM_030254 | 2.07 |
| 1421399_at | Insm1 | NM_016889 | 2.07 |
| 1423303_at | Paxip1 | AW742928 | 2.07 |
| 1421144_at | Rpgrip1 | NM_023879 | 2.07 |
| 1437456_x_at | Ythdf1 | BB332410 | 2.07 |
| 1453342_at | Cdc40 | AK006943 | 2.07 |
| 1425313_at | Carf | AF454947 | 2.07 |
| 1421600_a_at | Trim26 | NM_030698 | 2.07 |
| 1429610_a_at | Zfp511 | AK010407 | 2.06 |
| 1419630_a_at | Trim11 | NM_053168 | 2.06 |
| 1431091_at | Pygo1 | BB595944 | 2.06 |
| 1434994_at | Dedd | BE199280 | 2.06 |
| 1452914_at | 2410024N18Rik | AK010587 | 2.06 |
| 1445763_at | 1700013F07Rik | BG069737 | 2.06 |
| 1428745_at | 2310003L22Rik | AK009123 | 2.06 |
| 1450894_a_at | Ap2m1 | C76671 | 2.06 |
| 1428681_at | 5530400K22Rik | AK017426 | 2.06 |
| 1423668_at | Zdhhc14 | BC021423 | 2.06 |
| 1435092_at | Arl4a | AV328143 | 2.06 |
| 1457171_at | AI854517 | BB334885 | 2.06 |
| 1443528_at | Ttbk1 | BB398560 | 2.06 |
| 1424291_at | Nup93 | BC023140 | 2.06 |
| 1436034_at | Cep68 | AW550283 | 2.06 |
| 1429985_at | 5430439G13Rik | BQ173897 | 2.06 |
| 1452171_at | Grwd1 | BM200151 | 2.06 |
| 1458541_at | Dctn4 | BB125218 | 2.06 |
| 1426467_at | 0610037L13Rik | AK002776 | 2.06 |
| 1430769_s_at | 2900009I07Rik | AW911794 | 2.06 |
| 1452050_at | Camk1d | BG071931 | 2.06 |
| 1416918_at | Dlg3 | NM_016747 | 2.06 |
| 1420660_at | Lrrc6 | NM_019457 | 2.06 |
| 1418975_at | Nckipsd | NM_030729 | 2.06 |
| 1453795_at | Fahd2a | BI872590 | 2.06 |
| 1426427_at | Ttll1 | BB764137 | 2.06 |
| 1443790_x_at | 4930414L22Rik | AV208084 | 2.06 |
| 1453709_at | 3426406O18Rik | AV172660 | 2.06 |
| 1418665_at | Impa2 | NM_053261 | 2.06 |
| 1433707_at | Gabra4 | BB430205 | 2.06 |
| 1425837_a_at | Ccrn4l | AF199491 | 2.06 |
| 1435500_at | Rab26 | BB270778 | 2.06 |
| 1451301_at | Tmod2 | BB633110 | 2.06 |
| 1456769_at | Dusp3 | BQ266434 | 2.06 |
| 1443826_x_at | Men1 | BB269348 | 2.06 |
| 1423460_at | Perq1 | BI688428 | 2.06 |
| 1439900_at | Thtpa | BB308405 | 2.06 |
| 1452056_s_at | Ppp3ca | BQ173889 | 2.06 |
| 1456423_at | Ap2m1 | AV298746 | 2.06 |
| 1449614_s_at | AI314976 | AW558560 | 2.05 |
| 1437293_x_at | Ust | BB561487 | 2.05 |
| 1431985_at | 2210010B09Rik | AK008693 | 2.05 |
| 1459760_at | Ndufs4 | BE852624 | 2.05 |
| 1419070_at | Cys1 | BF466918 | 2.05 |
| 1421945_a_at | Bxdc1 | NM_023323 | 2.05 |
| 1415678_at | Ppm1a | BC008595 | 2.05 |
| 1426909_at | Uck2 | BC004016 | 2.05 |
| 1428345_at | Ppapdc2 | BB229589 | 2.05 |
| 1448455_at | Cln8 | AF125307 | 2.05 |
| 1436354_at | Dzip11 | BE992423 | 2.05 |
| 1460635_at | Fastk | NM_023229 | 2.05 |
| 1458247_s_at | Dctn5 | C78178 | 2.05 |
| 1434383_at | Pja2 | BM114949 | 2.05 |
| 1425410_at | Tprkb | BC027413 | 2.05 |
| 1442003_at |  | BF537922 | 2.05 |
| 1450706_a_at | Arl3 | NM_019718 | 2.05 |
| 1436892_at | Spred2 | BB133520 | 2.05 |
| 1431885_a_at | Mus81 | AK004647 | 2.05 |
| 1424054_at | Btbd2 | BC016566 | 2.05 |
| 1420443_at | Pcdhb19 | NM_053144 | 2.05 |
| 1447926_at | Arl5a | BB811124 | 2.05 |
| 1434451_at |  | AA216953 | 2.05 |
| 1423440_at | 1110001A07Rik | AK003196 | 2.05 |
| 1423453_at | Nol12 | BI408798 | 2.05 |
| 1429383_at | Csnk1g3 | BM195380 | 2.05 |
| 1455421_x_at | 6330503C03Rik | AW490145 | 2.05 |
| 1438649_x_at | Pebp1 | AV207950 | 2.05 |
| 1422885_at | Snrpd3 | NM_026095 | 2.05 |
| 1430588_at | Mro | BI076815 | 2.05 |
| 1440459_at | Setx | BB767941 | 2.05 |
| 1415998_at | Vdac1 | NM_011694 | 2.05 |
| 1416867_at | Bet1 | NM_009748 | 2.05 |
| 1417126_a_at | Rpl22l1 | NM_026517 | 2.04 |
| 1451108_at | Rnf185 | BC014812 | 2.04 |
| 1434652_at | Cdc42bpb | BI154551 | 2.04 |
| 1440238_at | Gltscr1 | BB158599 | 2.04 |
| 1429411_a_at | Eny2 | AI595744 | 2.04 |
| 1422564_at | Actl6b | NM_031404 | 2.04 |
| 1441284_at |  | BB283819 | 2.04 |
| 1430017_at | 1600016N20Rik | AK005476 | 2.04 |
| 1426649_at | Tmeff1 | BM114154 | 2.04 |
| 1417169_at | Usp2 | AI553394 | 2.04 |
| 1456602_at | 4932417I16Rik | AV274211 | 2.04 |
| 1455939_x_at | Srp14 | AV209126 | 2.04 |
| 1457826_a_at | 1810043H04Rik | AV056885 | 2.04 |
| 1418646_at | Gna-rs1 | BF577955 | 2.04 |
| 1434879_at | Cdc34 | BI794243 | 2.04 |
| 1453132_a_at | Gkn2 | AK007451 | 2.04 |
| 1416208_at | Usp14 | BC005571 | 2.04 |
| 1438847_at | Mxd3 | BB836571 | 2.04 |
| 1416852_a_at | Ncdn | BC017126 | 2.04 |
| 1434891_at | Ptgfrn | AV253087 | 2.04 |
| 1418302_at | Ppt2 | BC013462 | 2.04 |
| 1460381_at | BC023179 | BC023179 | 2.04 |
| 1429156_at | 2610036L11Rik | BF453953 | 2.04 |
| 1423976_at | 4930453N24Rik | BC020029 | 2.04 |
| 1420734_at | Ppp1r3f | NM_138605 | 2.04 |
| 1422849_a_at | Pabpn1 | AV028400 | 2.04 |
| 1432003_a_at | Rnf41 | AK016825 | 2.04 |

TABLE 13-continued

Genes differentially translated between medium spiny neurons (MSNs) and the rest of the brain.

| Probe | Symbol | GenBank | FCH |
|---|---|---|---|
| 1422091_at | Pfkfb2 | BC018418 | 2.04 |
| 1434095_at | Unc5a | BM226712 | 2.04 |
| 1455118_at | D9Ertd402e | BM122201 | 2.04 |
| 1419415_a_at | Rarg | NM_011244 | 2.04 |
| 1449018_at | Pfn1 | NM_011072 | 2.04 |
| 1436813_x_at | Khsrp | BB332580 | 2.04 |
| 1449851_at | Per1 | AF022992 | 2.04 |
| 1427908_at | Bnip1 | BG073508 | 2.04 |
| 1432435_s_at | C030004A17Rik | AK012261 | 2.04 |
| 1427025_at | Mtmr7 | AV094609 | 2.04 |
| 1426256_at | Timm17a | AF106620 | 2.04 |
| 1424170_at | Phf5a | BC025161 | 2.04 |
| 1426924_at | Rc3h2 | AA709668 | 2.03 |
| 1448356_at | Ube2d2 | NM_019912 | 2.03 |
| 1417847_at | Ulk2 | NM_013881 | 2.03 |
| 1451442_at | Ccdc104 | BC005731 | 2.03 |
| 1418966_a_at | Dcbld1 | AK014521 | 2.03 |
| 1428246_at | Vps26b | BI081895 | 2.03 |
| 1423757_x_at | Igfbp4 | BC019836 | 2.03 |
| 1429050_at | Chic2 | AK015681 | 2.03 |
| 1450386_at | Kpna3 | BM213828 | 2.03 |
| 1451343_at | Vps36 | BC010811 | 2.03 |
| 1444208_at | Dnahc1 | BE950899 | 2.03 |
| 1428075_at | Ndufb4 | BG968046 | 2.03 |
| 1452635_x_at | Josd3 | AU044383 | 2.03 |
| 1437937_at | Ccbp2 | AV220666 | 2.03 |
| 1438412_at | Phf17 | BM119726 | 2.03 |
| 1441376_at | Gabarapl2 | BB426412 | 2.03 |
| 1423370_a_at | Csnk1g2 | AI326320 | 2.03 |
| 1449702_at | Zfand2a | AU016206 | 2.03 |
| 1457272_at |  | BB284000 | 2.03 |
| 1441782_at | Aak1 | AW121504 | 2.03 |
| 1442046_at | Shroom2 | BM119167 | 2.03 |
| 1451736_a_at | Map2k7 | AW541674 | 2.03 |
| 1460452_at | Mospd3 | BC003880 | 2.03 |
| 1422018_at | Hivep2 | NM_010437 | 2.03 |
| 1452626_at | 1810014F10Rik | AK007494 | 2.03 |
| 1435072_at | Zfyve1 | AV327165 | 2.03 |
| 1416748_a_at | Mre11a | NM_018736 | 2.03 |
| 1418117_at | Ndufs4 | NM_010887 | 2.03 |
| 1433897_at | AI597468 | BQ176744 | 2.03 |
| 1447689_at | Gprasp1 | AV221773 | 2.03 |
| 1451664_x_at | Klra7 | AF283248 | 2.03 |
| 1460209_at | Usp39 | BC026983 | 2.03 |
| 1455841_s_at | Grwd1 | BB251524 | 2.03 |
| 1435645_at | Mmd | AA472735 | 2.03 |
| 1453569_s_at | Mark4 | AK010751 | 2.03 |
| 1427426_at | Kcnq5 | AV362204 | 2.03 |
| 1426692_at | Ccdc97 | AK004762 | 2.02 |
| 1452324_at | Pvt1 | BE956863 | 2.02 |
| 1453002_at | Sox11 | BE825056 | 2.02 |
| 1421520_at | Jph1 | NM_020604 | 2.02 |
| 1430500_s_at | Mtx2 | AK005233 | 2.02 |
| 1449711_at | Atp6v1e1 | C85064 | 2.02 |
| 1420969_at | Btbd14b | NM_025788 | 2.02 |
| 1428756_at | Aasdhppt | AK013111 | 2.02 |
| 1418384_at | Apool | BC024334 | 2.02 |
| 1460697_s_at | 2610209M04Rik | BC027564 | 2.02 |
| 1434165_at | Clic6 | BQ176424 | 2.02 |
| 1433970_at | Bola3 | BB610351 | 2.02 |
| 1416240_at | Psmb7 | NM_011187 | 2.02 |
| 1450908_at | Eif4e | BB406487 | 2.02 |
| 1416192_at | Napa | BC004804 | 2.02 |
| 1435105_at | 1110061N23Rik | BG066986 | 2.02 |
| 1456149_at | D11Bwg0517e | BB386621 | 2.02 |
| 1456125_a_at | EG627788 | AV006937 | 2.02 |
| 1427702_at | Zfp1 | X16493 | 2.02 |
| 1443875_at | Gm603 | BG075083 | 2.02 |
| 1428498_at | 2610206B13Rik | AK011896 | 2.02 |
| 1454236_a_at | C030004A17Rik | AK012261 | 2.02 |
| 1434009_at | Grlf1 | BQ176422 | 2.02 |
| 1448762_at | Rad17 | NM_011233 | 2.02 |
| 1457778_at | Stox2 | BB364290 | 2.02 |
| 1450080_s_at | Cxx1c | NM_028375 | 2.02 |
| 1431510_s_at | 2010110K16Rik | AK008567 | 2.02 |
| 1448247_at | Bcl7b | NM_009745 | 2.02 |
| 1426763_at | Oaz2 | AW214584 | 2.02 |
| 1418905_at | Nubp1 | NM_011955 | 2.02 |
| 1439553_s_at | Nutf2 | AU018817 | 2.02 |
| 1437242_at | Ttll12 | AV121345 | 2.02 |
| 1452753_at | Foxk2 | BM206907 | 2.02 |
| 1423146_at | Hes5 | AV337579 | 2.02 |
| 1456032_x_at | H2afz | AV215230 | 2.02 |
| 1435886_at | Dnajb12 | AW456220 | 2.02 |
| 1456013_x_at | Slc35a4 | BB396486 | 2.01 |
| 1428234_at | Cpsf6 | BB425379 | 2.01 |
| 1428689_at | Tysnd1 | BF466063 | 2.01 |
| 1454769_at | Tatdn2 | BB314680 | 2.01 |
| 1422750_a_at | Zmynd10 | NM_053253 | 2.01 |
| 1435432_at | Centg2 | BE688580 | 2.01 |
| 1429799_at | Zfp606 | BB541617 | 2.01 |
| 1428513_at | Calcoco1 | AK007393 | 2.01 |
| 1416698_a_at | Cks1b | NM_016904 | 2.01 |
| 1416373_at | Nfs1 | NM_010911 | 2.01 |
| 1460562_at | Eftud1 | BB042938 | 2.01 |
| 1445221_at |  | BB451452 | 2.01 |
| 1430675_at | 2900055J20Rik | BM932606 | 2.01 |
| 1419736_a_at | Eif1ay | NM_025437 | 2.01 |
| 1423738_at | Oxa1l | BC027191 | 2.01 |
| 1459846_x_at | Tmem4 | AV100225 | 2.01 |
| 1425621_at | Trim35 | AB060155 | 2.01 |
| 1451207_at | Cbara1 | BC023022 | 2.01 |
| 1429796_at | Kalrn | AK008844 | 2.01 |
| 1430292_a_at | 1810030N24Rik | BG792484 | 2.01 |
| 1426665_at | Katnb1 | AK010364 | 2.01 |
| 1455303_at | Rfxap | BB735651 | 2.01 |
| 1426613_a_at | Snrpb2 | AV066554 | 2.01 |
| 1422560_at | Rsc1a1 | NM_023544 | 2.01 |
| 1437985_a_at | 2310061I04Rik | BB379386 | 2.01 |
| 1421891_at | St3gal2 | BB750118 | 2.01 |
| 1430569_at | Ttc9c | AK008753 | 2.01 |
| 1427915_s_at | Tceb1 | AI019214 | 2.01 |
| 1425780_a_at | Tmem167 | BC024352 | 2.01 |
| 1450394_at | Golph3 | AV174110 | 2.01 |
| 1416499_a_at | Dctn6 | NM_011722 | 2.01 |
| 1434249_s_at | Trim9 | BB083438 | 2.01 |
| 1430030_at | 5330426P16Rik | AK019912 | 2.01 |
| 1423479_at | Nol11 | AK005123 | 2.01 |
| 1459110_at | Myo9b | BB344956 | 2.01 |
| 1416369_at | Hiat1 | NM_133680 | 2.01 |
| 1456444_at | Fbxo41 | BB126849 | 2.01 |
| 1419975_at | Scp2 | C76618 | 2.01 |
| 1447889_x_at | Gm50 | BB172440 | 2.01 |
| 1431505_at | Ppih | AK008394 | 2.01 |
| 1418404_at | Rad9 | NM_011237 | 2.01 |
| 1458103_at | Ncor1 | AV325208 | 2.01 |
| 1428638_at | Efhc2 | BE956904 | 2.01 |
| 1423617_at | Pdf | AA790871 | 2.01 |
| 1419927_s_at | Rabif | AW549708 | 2.01 |
| 1455522_at | Arhgef15 | AW492648 | 2.01 |
| 1417930_at | Nab2 | NM_008668 | 2.01 |
| 1434207_at | 2900057K09Rik | BE570729 | 2.01 |
| 1424121_at | Commd1 | AB076722 | 2.00 |
| 1439874_at | 9330102E08Rik | BB075161 | 2.00 |
| 1434230_at | Polb | BG094331 | 2.00 |
| 1428213_at | Nsmce4a | AK010349 | 2.00 |
| 1450909_at | Eif4e | BB406487 | 2.00 |
| 1423789_at | BC005624 | BC005624 | 2.00 |
| 1428500_at | 2210419D22Rik | AK008985 | 2.00 |
| 1420106_at | Siah1a | AA982064 | 2.00 |
| 1434549_at | Rab11a | BI083615 | 2.00 |
| 1424685_at | Exosc4 | AK005101 | 2.00 |
| 1415864_at | Bpgm | NM_007563 | 2.00 |
| 1428901_at | Dtwd2 | AK004450 | 2.00 |
| 1436438_s_at | Wdr22 | BM234499 | 2.00 |
| 1424703_at | Hemk1 | BC011431 | 2.00 |
| 1419190_at | Vti1a | BC019386 | 2.00 |
| 1419460_at | Rpp14 | BI455861 | 2.00 |
| 1438289_a_at | Sumo1 | AV021595 | 2.00 |
| 1417033_at | Ube2g2 | AF296657 | 2.00 |

TABLE 13-continued

Genes differentially translated between medium spiny neurons (MSNs) and the rest of the brain.

| Probe | Symbol | GenBank | FCH |
|---|---|---|---|
| 1457325_at | Kcns2 | BB442995 | 2.00 |
| 1452605_at | Thnsl1 | AV254642 | 2.00 |
| 1437132_x_at | Nedd9 | BB535494 | 2.00 |
| 1445631_at | Tmem16c | BE865226 | 2.00 |
| 1433774_x_at | Cog1 | AA238341 | 2.00 |
| 1428828_at | Rpain | AK010289 | 2.00 |
| 1419066_at | Ier5l | NM_030244 | 2.00 |

Fold change values (FCH) are given relative to MSN enrichment.
Probe = Affymetrix probe identification; Symbol = official gene symbol.

5) Grouping Enriched Genes According to Biological Function

To group striatonigral- and striatopallidal-enriched genes according to biological function, statistically over-represented Gene Ontology (GO) and Kyoto Encyclopedia of Genes and Genomes (KEGG) pathway terms associated with these genes were searched. GO terms delineate the known molecular function, biological process, as well as the cellular localization (component) for a particular gene (R. Bernardi, P. P. Pandolfi, Nat Rev Mol Cell Biol 8, 1006 (2007), while KEGG pathways summarize known molecular interaction and reaction networks. The most enriched striatonigral KEGG pathways included neuroactive ligand-receptor interaction, long-term depression, and MAPK signaling pathway. The most striatopallidal enriched KEGG pathways included pyrimidine metabolism, purine metabolism, and neuroactive ligand-receptor interaction. Comparison of striatonigral and striatopallidal cell data versus whole brain revealed many striatal-enriched KEGG pathways, including MAPK signaling pathway, long-term potentiation, and insulin signaling pathway. Striatonigral enriched GO molecular function terms included GTPase activity, calcium ion binding, and retinal binding; striatopallidal enriched GO molecular function terms included adrenoceptor activity, calcium channel activity, and rhodopsin-like receptor activity; striatal-enriched GO terms included zinc ion binding, protein serine/threonine kinase activity, and ubiquitin-protein ligase activity.

Example 11

Physiological Differences Between Striatonigral and Striatopallidal Cells

Differentially translated mRNAs discovered in previous examples immediately predict physiological differences between striatonigral and striatopallidal cells. For example, an mRNA selectively enriched in striatopallidal neurons is Gpr6 (S. Gong et al., Nature 425, 917-25 (Oct. 30, 2003).). Gpr6 encodes a G protein-coupled receptor for the lysophospholipid sphingosine 1-phosphate (S1P) (A. Ignatov, J. Lintzel, H. J. Kreienkamp, H. C. Schaller, Biochem Biophys Res Commun 311, 329-36 (Nov. 14, 2003)). In heterologous expression systems, S1P activation of Gpr6 receptors induces the release of Ca2+ from intracellular stores. As intracellular Ca2+ is a crucial regulator of neuronal physiology, whether selective enrichment of Gpr6 in striatopallidal neurons correlated with a differential response to S1P was investigated. To determine whether functional Gpr6 receptors were selectively expressed in striatopallidal neurons, BAC D2 striatopallidal or BAC D1 striatonigral medium spiny neurons (expressing soluble eGFP) were identified in brain slices and patch clamped (FIG. 30) (M. Day et al., Nat Neurosci 9, 251-9 (February, 2006)). Neurons were loaded with Alexa 594 (50 µM) to allow dendrites to be seen and with Fluo-4 (200 µM) to monitor intracellular Ca2+ concentration using 2-photon laser scanning microscopy (2PLSM). After allowing the dyes to equilibrate, neurons were imaged and a second pipette containing SIP (10 µM) was brought into close physical proximity to a dendrite, 60-80 microns from the soma (a and b). With the somatic membrane potential clamped at −70 mV, focal application of SIP consistently and reversibly increased dendritic Ca2+ levels in BAC D2 striatopallidal neurons (Kruskal-Wallis ANOVA, p<0.01, n=6) but not in BAC D1 striatonigral neurons (Kruskal-Wallis ANOVA, p>0.01, n=4). Depletion of intracellular Ca2+ stores with the Ca2+-ATPase inhibitor thapsigargin (10 µM) abolished the response to S1P in BAC D2 striatopallidal neurons (Kruskal-Wallis ANOVA, p>0.01, n=4; c and d), in agreement with previous work showing that Gpr6 receptors mobilize intracellular Ca2+ stores (D. S. Lim et al., Nature 404, 613 (2000). The Gpr6-dependent elevation of cytosolic Ca2+ seen in striatopallidal cells would be predicted to result in a decrease in threonine 34 phosphorylation of the centrally important regulatory protein DARPP-32, due to activation of the Ca2+ and calmodulin-dependent phosphatase calcineurin (A. Nishi, G. L. Snyder, A. C. Nairn, P. Greengard, J Neurochem 72, 2015-21 (May, 1999)) and/or inhibition of adenylyl cyclase type 5 (AC5; Adcy5) (C. E. Glatt, S. H. Snyder, Nature 361, 536-8 (Feb. 11, 1993); Y. Ishikawa et al., J Biol Chem 267, 13553-7 (Jul. 5, 1992)) This demonstrated the physiological consequence of the SIP-induced increase in cytosolic Ca2+ by measurement of the phosphorylation status of DARPP-32. A decrease in threonine 34 DARPP-32 phosphorylation was seen after 5 minutes of SIP treatment of striatal slices (1.04±0.17 normalized units at 0 minutes; 0.58 normalized units±0.24 at 5 minutes after S1P addition, one-tailed Mann-Whitney test, p=0.05, n=12), consistent with cytosolic Ca2+ elevation in D2 cells (which constitute approximately half of the medium-spiny neurons). These data confirm a prediction based on the BACarray translational profiling, demonstrate a strong and cell-type specific response of striatopallidal neurons to sphingosine 1-phosphate, and identify Gpr6 as a novel and important signaling component of striatopallidal, but not striatonigral, medium spiny neurons.

Example 12

Detection of Pharmacologically Induced Transcriptional Changes

1) Overview

In certain embodiments, responses to genetic, pharmacologic or environmental changes can be analyzed effectively in single cell types using translational profiling and molecular Phenotyping methods described herein. To define uncover novel physiological properties of striatal neurons, possible changes in mRNA expression of MSNs upon pharmacological perturbation of dopaminergic signaling was investigated.

Cocaine, a competitive inhibitor of the dopamine transporter, acts as a psychostimulant by elevating synaptic dopamine levels (M. C. Ritz, R. J. Lamb, S. R. Goldberg, M. J. Kuhar, Science 237, 1219-23 (Sep. 4, 1987); G. Di Chiara, A. Imperato, Proc Natl Acad Sci USA 85, 5274-8 (July, 1988)). Adult mice were treated acutely or chronically with cocaine or saline and used for BACarray profiling of striatonigral (D1) and striatopallidal (D2) MSNs.

2) Experimental Design

Quality control steps taken: three biological replicates were performed for each experiment. Arrays were only used if the Spearman correlation between the other arrays for that experiment was >75% but could be adjusted according to biological variation. Quantitative PCR reactions were performed to validate array results using an independent biological source and amplification methodology. The Experiment included 5 comparisons, with each D1 vs. D2 replicates performed on the same day, as described here in Table 14.

TABLE 14

Experimental Design for Effects of Cocaine

| Striatonigral Cells (D1) | Striatopallidal Cells (D2) |
|---|---|
| No treatment | No treatment |
| Acute Saline - Replicate 1 | Acute Saline - Replicate 1 |
| Acute Cocaine - Replicate 1 | Acute Cocaine - Replicate 1 |
| Chronic Saline - Replicate 1 | Chronic Saline - Replicate 1 |
| Chronic Cocaine - Replicate 1 | Chronic Cocaine - Replicate 1 |

3) Animals and Sample Preparation:

Origin of biological sample: seven adult BACarray mice (four female, three male) were pooled for each replicate. Striatal tissue was taken between 7-9 weeks of age. Lines of mice used in each experiment: (Drd1a/eGFP-L10a) and (Drd2/eGFP-L10a).

Manipulation of biological sample: all mice were raised under 12h dark/12h light conditions, housed 5 mice per cage, with food and water ad libitum. All mice used in the study were heterozygous for the eGFP-L10a transgene; mice from each line had been crossed to wild-type Swiss-Webster (Taconic Farms) four times. Four heterozygous adult BAC-array females and three heterozygous adult BACarray males were used for each study. Mice used for the baseline comparison of D1 versus D2 cells were used directly from the home cage. For all cocaine studies, BACarray mice 7-9 weeks of age were singly housed and intraperitoneally injected at the Rockefeller University Laboratory Animal Research Center (LARC) and were moved to the laboratory approximately 16 h before the final injection. For acute cocaine studies, all mice were injected with 100 μl saline (vehicle) once daily for eight days to habituate the mice to handling. On the ninth day mice were injected with a test dose of 20 mg/kg cocaine or 100 μl saline and the striata were harvested 4 h after this test injection. For chronic cocaine studies, mice were injected with 20 mg/kg cocaine or 100 μl saline once daily for fifteen days and the striata were harvested 4 h after the last injection.

Experimental factor values: D1; D2; Acute cocaine D1; Acute saline D1; Acute cocaine D2; Acute saline D2; Chronic cocaine D1; Chronic saline D1; Chronic cocaine D2; Chronic saline D2.

Results:

For the baseline comparison of striatonigral versus striatopallidal cells, a moderated two-tailed paired t-test was performed. The p-value of the moderated t-test was adjusted for multiple hypothesis testing, controlling the false discovery rate (FDR) using the Benjamini-Hochberg procedure. Genes that had an FDR less than 0.1 (10%) and fold change larger than 1.5 were then selected.

For the comparison of striatonigral and striatopallidal BACarray samples versus total brain minus striatum, GeneChip CEL files were imported into Genespring GX 7.3.1, normalized with the GC-RMA algorithm (BACarray samples and whole brain minus striatum samples separately), and expression values on each chip were further normalized to the expression values of several positive control genes and to a constant value of 0.01. A moderated two-tailed paired t-test was then performed. The p-value of the moderated t-test was adjusted for multiple hypothesis testing, controlling the false discovery rate (FDR) using the Benjamini-Hochberg procedure. Genes that had an FDR less than 0.05 (5%) and fold change larger than 2 were selected Upon clustering, all cocaine data exhibited a strong effect of the day the samples were prepared. A more complex model that could take into account and adjust for the day effect was utilized. A linear model was adjusted to each gene with factor Treatment (Saline vs Cocaine), Cell type (D1 vs D2), and Day (three different days for acute and chronic experiments). With this analysis, a large number of genes indeed displayed a Day factor. With this model fitted, all the hypotheses were tested (Cocaine vs Saline and its interaction with Cell type in both Acute and Chronic). For assessing differential expression in the comparisons of interest, the moderated t-statistic was used (G. K. Smyth, Stat Appl Genet Mol Biol 3, Article3 (2004)). In this assessment, an empirical Bayes method is used to moderate the standard errors of the estimated log 2-fold changes. This method was particularly useful for the analysis with only three replicates of each condition, as it delivered more stable inference and improved power. The p-value of the moderated t-test was adjusted for multiple hypothesis testing, controlling the false discovery rate (FDR) using the Benjamini-Hochberg procedure. Genes than have FDR less than 0.1 (10%) and fold change larger than 1.4 were selected.

To translate the gene expression data into functiona profiles, Gene Ontology (GO) analysis and Pathway analysis was utilized to look for enriched GO terms and Pathways in the set of differentially expressed genes. Analysis of GO annotations was performed using the R-packages GOstats and GOtools. To find those GO terms that were overrepresented in the list of genes in question, for each specific term in a given ontology (Biological Process, Molecular Function, Cellular Component), the proportion of genes in the list that falls into the GO term is compared with the proportion in the whole set of genes in the Mouse Genome 430 2.0 array using a conditional hypergeometric test. A conditional instead of the classical hypergeometric test was utilized to address concerns about the hierarchical structure of GO terms (S. Falcon, R. Gentleman, Bioinformatics 23,257-8 (2007); A. Alexa, J. Rahnenfuhrer, T. Lengauer, Bioinformatics 22, 1600-7 (2006)). The conditional test uses the relationship among GO terms to decorrelate results. GO with p-values <0.1 and with more than one gene were considered. To find overrepresented Pathways, a classical hypergeometric test was utilized to compare the proportion of genes among those that are differentially expressed (Up and Down together) that belong to a certain Pathway, using the whole Mouse Genome 430 2.0 array gene set as the universe for the comparison. A Pathways annotation package available at Bioconductor.org (version 1.16.0) was used. The KEGG Pathways terms in that package were obtained from KEGG, file transfer protocol, genome.ad.jp/pub/keg/tarfiles/pathway.tar.gz, build release 41.1, Feb. 1, 2007.

From this analysis hundreds of genes were identified whose expression was increased or decreased in each cell type in response to cocaine.

Table 15 and Table 16). Various genes whose expression has been reported to be affected by cocaine administration were identified, including: Cartpt (J. Douglass, A. A. McKinzie, P. Couceyro, *J Neurosci* 15, 2471-81 (March, 1995) (up in acute D1; Table S12); Fosb (B. Hope, B. Kosofsky, S. E. Hyman, E. J. Nestler, *Proc Natl Acad Sci USA* 89, 5764-8 (Jul. 1, 1992)) (up in acute D1, acute D2, and chronic D1;

Table 15 and Table 16); Homer1 (P. R. Brakeman et al., *Nature* 386, 284-8 (Mar. 20, 1997)) (up in acute D1, acute D2, chronic D1, and chronic D2;

Table 15 and Table 16); Per2 (V. Yuferov et al., *Synapse* 48, 157-69 (Jun. 15, 2003)) (up in acute D2, chronic D1, chronic D2;

Table 15 and Table 16); Vamp2 (C. A. McClung, E. J. Nestler, *Nat Neurosci* 6, 1208-15 (November, 2003)) (up in chronic D1; Table S13); Kcnd2 (C. A. McClung, E. J. Nestler, *Nat Neurosci* 6, 1208-15 (November, 2003)) (up in chronic D1; Table 16); and Zfp64 (C. A. McClung, E. J. Nestler, *Nat Neurosci* 6, 1208-15 (November, 2003)) (up in acute D2, down in chronic D2;

Table 15 and Table 16).

TABLE 15

Gene translation changes upon acute cocaine treatment

| Probe | Symbol | GenBank | FCH D1 | FCH D2 |
|---|---|---|---|---|
| 1459589_at | Cryl1 | C85932 | 6.86 | 0.37 |
| 1459589_at | Vcan | BM251152 | 3.06 | 0.97 |
| 1423287_at | Cbln1 | AA016422 | 2.88 | 1.36 |
| 1428601_at | 1700003E16Rik | AK005628 | 2.69 | 0.76 |
| 1420901_a_at | Hk1 | NM_010438 | 2.38 | 1.03 |
| 1460330_at | Anxa3 | AW702161 | 2.36 | 1.03 |
| 1444137_at | A430108G06Rik | AW120610 | 2.36 | 1.03 |
| 1443699_at | Ptprk | BE957383 | 2.31 | 0.63 |
| 1443998_at |  | BE980823 | 2.28 | 1.02 |
| 1422904_at | Fmo2 | NM_018881 | 2.26 | 0.85 |
| 1456133_x_at | Itgb5 | BB543646 | 2.15 | 1.31 |
| 1452226_at | Rcc2 | AV122997 | 2.11 | 1.28 |
| 1433836_a_at | 8430408G22Rik | AV365503 | 2.11 | 0.72 |
| 1435872_at | Pim1 | BE631223 | 2.11 | 2.83 |
| 1436387_at | Homer1 | BB398124 | 2.10 | 2.41 |
| 1422134_at | Fosb | NM_008036 | 2.09 | 2.49 |
| 1451554_a_at | Aph1a | BC012406 | 2.07 | 0.89 |
| 1431715_a_at | Lig3 | AK010719 | 2.06 | 0.59 |
| 1424393_s_at | Adhfe1 | BC026584 | 1.97 | 1.04 |
| 1437284_at | Fzd1 | BB259670 | 1.97 | 1.19 |
| 1430133_at | Tbc1d8b | AK014817 | 1.96 | 1.31 |
| 1435458_at | Pim1 | AI323550 | 1.96 | 2.90 |
| 1430600_at | Cmtm5 | AK013666 | 1.96 | 1.71 |
| 1440116_at | D630045J12Rik | AW558117 | 1.94 | 1.17 |
| 1458284_at | Ptbp1 | BM195499 | 1.93 | 0.87 |
| 1425585_at | Med12 | AF071310 | 1.92 | 0.99 |
| 1418322_at | Crem | AI467599 | 1.89 | 1.85 |
| 1451411_at | Gprc5b | BC020004 | 1.88 | 1.12 |
| 1430510_at | B130050I23Rik | AK009699 | 1.87 | 1.09 |
| 1436682_at | Tmsb10 | AW259435 | 1.87 | 0.88 |
| 1451440_at | Chodl | AF311699 | 1.87 | 0.91 |
| 1452003_at | Rbm14 | BC010294 | 1.86 | 0.81 |
| 1453787_at | Txndc13 | AK015667 | 1.83 | 0.91 |
| 1432466_a_at | Apoe | AK019319 | 1.82 | 1.58 |
| 1415851_a_at | Impdh2 | M33934 | 1.81 | 0.87 |
| 1460061_at | Adra1a | AV342748 | 1.81 | 1.42 |
| 1427465_at | Atp1a2 | BC025807 | 1.81 | 1.08 |
| 1426225_at | Rbp4 | U63146 | 1.80 | 1.48 |
| 1418520_at | Tgoln1 | NM_009443 | 1.80 | 1.11 |
| 1417782_at | Lass4 | BB006809 | 1.79 | 1.13 |
| 1441334_at |  | BB528600 | 1.78 | 0.94 |
| 1423278_at | Ptprk | AI893646 | 1.77 | 1.21 |
| 1421571_a_at | Ly6c | NM_010741 | 1.77 | 1.19 |
| 1428298_at | 1700029G01Rik | AK006490 | 1.77 | 0.60 |
| 1446147_at |  | BB436856 | 1.77 | 0.80 |
| 1437264_at | BC051142 | AV278321 | 1.77 | 1.22 |
| 1455925_at | Prdm8 | AV349236 | 1.76 | 1.11 |
| 1434110_x_at | Mup1 | BF322785 | 1.76 | 0.72 |
| 1422825_at | Cartpt | NM_013732 | 1.76 | 1.29 |
| 1428054_at | Slc8a2 | AF503502 | 1.76 | 0.92 |
| 1455277_at | Hhip | BB088162 | 1.75 | 0.92 |
| 1457567_at | Nagk | BM938681 | 1.75 | 1.07 |
| 1421276_a_at | Dst | NM_134448 | 1.74 | 1.42 |
| 1434606_at | Erbb3 | BF140685 | 1.74 | 1.60 |
| 1442554_s_at | Kalrn | BG066934 | 1.74 | 0.65 |
| 1435559_at | Myo6 | BB200233 | 1.73 | 1.48 |
| 1425546_a_at | Trf | AF440692 | 1.73 | 1.50 |
| 1422053_at | Inhba | NM_008380 | 1.72 | 2.10 |
| 1428136_at | Sfrp1 | AK008943 | 1.60 | 1.08 |
| 1429256_at | Gtl2 | AU067739 | 1.60 | 0.94 |
| 1418350_at | Hbegf | L07264 | 1.60 | 1.48 |
| 1436785_a_at | Sec14l3 | AV024133 | 1.60 | 0.69 |

TABLE 15-continued

Gene translation changes upon acute cocaine treatment

| Probe | Symbol | GenBank | FCH D1 | FCH D2 |
|---|---|---|---|---|
| 1451289_at | Dcamkl1 | AW105916 | 1.59 | 1.15 |
| 1425725_s_at | Ppp2r5c | BF136532 | 1.59 | 1.30 |
| 1435568_at | AK129128 | AW545855 | 1.59 | 1.12 |
| 1449151_at | Pctk3 | NM_008795 | 1.59 | 1.19 |
| 1436129_at | 4930523C11Rik | AV255799 | 1.58 | 0.84 |
| 1460293_at | Freq | AU079041 | 1.58 | 0.78 |
| 1428488_at | Pigk | BB646655 | 1.58 | 1.24 |
| 1422683_at | Irak1bp1 | NM_022986 | 1.58 | 0.85 |
| 1434856_at | Ankrd44 | AV256780 | 1.58 | 1.17 |
| 1439015_at | Gfra1 | AV221299 | 1.58 | 1.15 |
| 1434987_at | Aldh2 | AI462635 | 1.58 | 0.79 |
| 1436454_x_at | Fen1 | BB393998 | 1.57 | 0.91 |
| 1449799_s_at | Pkp2 | AA516617 | 1.57 | 2.42 |
| 1419557_a_at | Tmem9 | NM_025439 | 1.57 | 1.28 |
| 1423668_at | Zdhhc14 | BC021423 | 1.57 | 1.75 |
| 1427284_a_at | Ttpa | AU019171 | 1.57 | 0.95 |
| 1434270_at | Nptxr | AV221896 | 1.57 | 0.96 |
| 1418318_at | Rnf128 | AK004847 | 1.57 | 1.16 |
| 1434233_at | 2610030H06Rik | BB429625 | 1.57 | 0.72 |
| 1421111_at | Rybp | NM_019743 | 1.57 | 1.00 |
| 1435109_at | Tmem175 | AW123256 | 1.57 | 1.12 |
| 1457956_at | Camta1 | BB777776 | 1.57 | 2.10 |
| 1418149_at | Chga | NM_007693 | 1.57 | 1.66 |
| 1428336_at | Agpat4 | AK005139 | 1.56 | 0.93 |
| 1449972_s_at | Zfp97 | NM_011765 | 1.56 | 0.91 |
| 1451611_at | Hrasls3 | BC024581 | 1.56 | 1.31 |
| 1451961_a_at | Mbp | L07509 | 1.56 | 1.87 |
| 1436094_at | Vgf | BF458396 | 1.56 | 1.41 |
| 1435904_at | Eif2c3 | BB355034 | 1.55 | 1.44 |
| 1450117_at | Tcf3 | NM_009332 | 1.55 | 1.36 |
| 1441127_at |  | BB460036 | 1.54 | 1.23 |
| 1442905_at | Arf4 | BB066458 | 1.54 | 1.14 |
| 1448601_s_at | Msx1 | BC016426 | 1.54 | 1.08 |
| 1436898_at | Sfpq | BI738328 | 1.54 | 1.00 |
| 1424581_at | Stac2 | BC024864 | 1.54 | 1.28 |
| 1451406_a_at | Pcsk5 | BC013068 | 1.54 | 1.16 |
| 1425415_a_at | Slc1a1 | U75214 | 1.54 | 1.26 |
| 1441165_s_at | Clstn2 | AI448973 | 1.54 | 1.04 |
| 1416371_at | Apod | NM_007470 | 1.54 | 1.52 |
| 1429463_at | Prkaa2 | BB612385 | 1.54 | 1.01 |
| 1438118_x_at | Vim | AV147875 | 1.54 | 0.84 |
| 1417502_at | Tspan7 | AF052492 | 1.53 | 1.09 |
| 1435145_at | Cadm2 | BB333386 | 1.53 | 1.30 |
| 1417764_at | Ssr1 | BG077348 | 1.53 | 0.97 |
| 1436805_at | 2810457I06Rik | BG076317 | 1.53 | 1.51 |
| 1452429_s_at | Abcf1 | BF236176 | 1.53 | 1.34 |
| 1423643_at | Ddx39 | BC020134 | 1.53 | 1.44 |
| 1425536_at | Stx3 | D29797 | 1.53 | 0.73 |
| 1451386_at | Blvrb | BC027279 | 1.53 | 1.19 |
| 1456271_at | Gm944 | BB039066 | 1.53 | 0.90 |
| 1434199_at | Gm323 | BM898903 | 1.53 | 1.21 |
| 1455908_a_at | Scpep1 | AV102733 | 1.47 | 0.82 |
| 1418402_at | Adam19 | NM_009616 | 1.46 | 1.03 |
| 1434505_a_at | 6430548M08Rik | BF465109 | 1.46 | 0.87 |
| 1438059_at | 1700011I03Rik | BM116248 | 1.46 | 0.80 |
| 1434235_at | Slc20a2 | BB765719 | 1.46 | 1.37 |
| 1420845_at | Mrps2 | AV031454 | 1.46 | 1.28 |
| 1423566_a_at | Hsp110 | BI499717 | 1.46 | 1.18 |
| 1436919_at | Trp53i11 | BQ175031 | 1.46 | 0.88 |
| 1428403_at | 2410025L10Rik | AV330483 | 1.46 | 1.43 |
| 1430568_at | Zc3h13 | AW539538 | 1.46 | 1.87 |
| 1456620_at | Gnptab | BE944732 | 1.46 | 1.18 |
| 1458384_at |  | AW491514 | 1.46 | 0.85 |
| 1437879_at | Alg10b | BG071776 | 1.45 | 0.97 |
| 1416702_at | Serpini1 | NM_009250 | 1.45 | 1.63 |
| 1451352_s_at | Mta3 | BC022124 | 1.45 | 1.22 |
| 1451369_at | Commd5 | BC025891 | 1.45 | 0.67 |
| 1427994_at | Cd300lf | BM230330 | 1.45 | 0.99 |
| 1460098_at | LOC629517 | BB363968 | 1.45 | 1.46 |
| 1439408_a_at | Pparbp | AV100992 | 1.45 | 1.17 |
| 1449286_at | Ntng1 | NM_030699 | 1.45 | 1.32 |
| 1452624_at | Ctnna2 | BM900077 | 1.45 | 1.78 |
| 1437092_at | Clip4 | AV042829 | 1.45 | 1.03 |
| 1437966_at | Prrt3 | AV329802 | 1.45 | 1.41 |
| 1449164_at | Cd68 | BC021637 | 1.45 | 1.23 |
| 1456727_a_at | Csnk1d | AW413676 | 1.44 | 0.88 |

TABLE 15-continued

Gene translation changes upon acute cocaine treatment

| Probe | Symbol | GenBank | FCH D1 | FCH D2 |
|---|---|---|---|---|
| 1435993_at | 4930470G03Rik | BB027219 | 1.44 | 1.75 |
| 1416588_at | Ptprn | NM_008985 | 1.44 | 1.27 |
| 1419646_a_at | Mbp | NM_010777 | 1.44 | 1.52 |
| 1449730_s_at | Fzd3 | AU020229 | 1.44 | 1.08 |
| 1452203_at | Obfc2a | AV313559 | 1.44 | 1.42 |
| 1426620_at | Chst10 | BB549997 | 1.44 | 1.34 |
| 1427021_s_at | Eif3s5 | AK002778 | 1.44 | 0.98 |
| 1423423_at | Pdia3 | BF319868 | 1.43 | 1.11 |
| 1455009_at | Cpd | AW550842 | 1.43 | 1.35 |
| 1451071_a_at | Atp1a1 | BC025618 | 1.43 | 0.94 |
| 1418331_at | 1110031I02Rik | NM_025402 | 1.43 | 1.05 |
| 1448603_at | Srpk2 | NM_009274 | 1.43 | 1.37 |
| 1421816_at | Gsr | AK019177 | 1.43 | 1.23 |
| 1434102_at | Nfib | BI687652 | 1.43 | 0.86 |
| 1419938_s_at | Arhgef17 | AW558066 | 1.43 | 1.21 |
| 1455917_at | Ntrk3 | BB456963 | 1.43 | 0.93 |
| 1441880_x_at | U2af1l4 | BB009770 | 1.43 | 1.19 |
| 1448397_at | Gjb6 | BC016507 | 1.43 | 1.62 |
| 1457467_at | Pknox1 | BB362579 | 1.43 | 1.03 |
| 1436097_x_at | Arhgap9 | BB327418 | 1.43 | 0.44 |
| 1420419_a_at | Otof | NM_031875 | 1.43 | 0.97 |
| 1438458_a_at | Sfpq | BF224766 | 1.42 | 1.49 |
| 1424781_at | Reep3 | AK005026 | 1.42 | 0.97 |
| 1460205_at | Dcakd | NM_026551 | 1.42 | 1.05 |
| 1421491_a_at | Tmem49 | NM_029478 | 1.42 | 1.60 |
| 1449405_at | Tns1 | NM_027884 | 1.42 | 1.31 |
| 1455122_at | Ptchd2 | AI666776 | 1.42 | 1.01 |
| 1456379_x_at | Dner | BB038556 | 1.42 | 1.27 |
| 1421360_at | Inpp4a | NM_030266 | 1.42 | 1.27 |
| 1450010_at | Hsd17b12 | AK012103 | 1.42 | 1.92 |
| 1442565_at | Pcdh10 | BB174272 | 1.34 | 0.70 |
| 1416271_at | Perp | NM_022032 | 1.34 | 0.70 |
| 1425656_a_at | Baiap2 | AF390178 | 1.34 | 1.41 |
| 1422629_s_at | Shroom3 | NM_015756 | 1.34 | 1.50 |
| 1435158_at | Rbm12b | BB796313 | 1.34 | 1.43 |
| 1434192_at | Zzef1 | BQ175699 | 1.34 | 1.46 |
| 1454608_x_at | Ttr | BG141874 | 1.33 | 0.16 |
| 1425329_a_at | Cyb5r3 | AF332060 | 1.33 | 1.76 |
| 1439406_x_at | Fars2 | BB530332 | 1.33 | 0.71 |
| 1419873_s_at | Csf1r | AI323359 | 1.33 | 1.69 |
| 1454768_at | Kcnf1 | AV337635 | 1.33 | 1.40 |
| 1432000_a_at | Dedd | AK006814 | 1.32 | 1.51 |
| 1436444_at | 6030405A18Rik | AV319257 | 1.32 | 1.53 |
| 1433748_at | Zdhhc18 | BG073303 | 1.32 | 1.45 |
| 1418941_at | Pcdhb22 | NM_053147 | 1.32 | 1.54 |
| 1437472_at | Unc13a | BB429098 | 1.31 | 1.43 |
| 1430193_at | Casc5 | BF021255 | 1.31 | 0.55 |
| 1438619_x_at | Zdhhc14 | BB318221 | 1.31 | 1.44 |
| 1456070_at | 5430405N12Rik | AI507538 | 1.31 | 1.46 |
| 1450905_at | Plxnc1 | BB476707 | 1.31 | 1.54 |
| 1451680_at | Srxn1 | BC011325 | 1.31 | 1.58 |
| 1425517_s_at | Ogt | AF363030 | 1.31 | 1.44 |
| 1427893_a_at | Pmvk | BI713896 | 1.30 | 1.41 |
| 1417279_at | Itpr1 | NM_010585 | 1.30 | 1.49 |
| 1422621_at | Ranbp2 | BM507707 | 1.30 | 1.54 |
| 1436231_at | AU067665 | AU067665 | 1.30 | 1.47 |
| 1448883_at | Lgmn | NM_011175 | 1.30 | 1.46 |
| 1456833_at | Gpr17 | BB353220 | 1.29 | 1.56 |
| 1436611_at | Slc39a12 | AW046938 | 1.29 | 2.04 |
| 1422018_at | Hivep2 | NM_010437 | 1.29 | 1.56 |
| 1437067_at | Phtf2 | BM228625 | 1.29 | 1.43 |
| 1439289_s_at | 0710005I19Rik | BB197516 | 1.29 | 0.62 |
| 1434891_at | Ptgfrn | AV253087 | 1.28 | 1.43 |
| 1416445_at | 2810405J04Rik | NM_133747 | 1.28 | 1.68 |
| 1438078_at |  | BF730550 | 1.28 | 1.48 |
| 1448139_at | Mlc1 | NM_133241 | 1.28 | 2.12 |
| 1416262_at | Tmem19 | AK018383 | 1.28 | 1.53 |
| 1418540_a_at | Ptpre | U35368 | 1.28 | 1.43 |
| 1416178_a_at | Plekhb1 | NM_013746 | 1.28 | 1.47 |
| 1451163_at | Tinf2 | AF214013 | 1.28 | 1.57 |
| 1451499_at | Cadps2 | AF000969 | 1.27 | 0.60 |
| 1416933_at | Por | NM_008898 | 1.27 | 1.48 |
| 1424112_at | Igf2r | BG092290 | 1.27 | 1.59 |
| 1451133_s_at | Tmem168 | BC007160 | 1.27 | 1.45 |
| 1449209_a_at | Rdh11 | AB030503 | 1.27 | 1.54 |
| 1416749_at | Htra1 | NM_019564 | 1.27 | 1.85 |

TABLE 15-continued

Gene translation changes upon acute cocaine treatment

| Probe | Symbol | GenBank | FCH D1 | FCH D2 |
|---|---|---|---|---|
| 1431711_a_at | 9030409G11Rik | AK018497 | 1.27 | 1.67 |
| 1440779_s_at | Slc5a9 | BB502156 | 1.27 | 0.63 |
| 1418007_at | 1810007M14Rik | BM932567 | 1.27 | 1.42 |
| 1428834_at | Dusp4 | AK012530 | 1.27 | 1.55 |
| 1452757_s_at | Hba-a1 | AK011116 | 1.27 | 1.53 |
| 1419063_at | Ugt8a | NM_011674 | 1.27 | 1.47 |
| 1456110_at | Ankrd11 | BB320513 | 1.27 | 1.46 |
| 1418626_a_at | Clu | NM_013492 | 1.27 | 1.70 |
| 1428031_at | Mchr1 | BE647763 | 1.26 | 1.49 |
| 1439333_at | Kcnv1 | BB078927 | 1.20 | 1.60 |
| 1437573_at |  | BF018351 | 1.20 | 0.61 |
| 1455291_s_at | Znrf2 | BG071922 | 1.20 | 1.48 |
| 1418195_at | Galnt10 | BG965198 | 1.20 | 1.61 |
| 1425977_a_at | Slk | AF112855 | 1.20 | 1.85 |
| 1427930_at | Pdxk | BG063905 | 1.20 | 1.82 |
| 1421199_at | Dlg2 | BB622767 | 1.20 | 1.47 |
| 1442400_at | Prickle1 | BF472052 | 1.19 | 0.61 |
| 1427077_a_at | Ap2b1 | AV271093 | 1.19 | 1.52 |
| 1436501_at | Mtus1 | BB747681 | 1.19 | 1.45 |
| 1456388_at | Atp11a | AV378604 | 1.19 | 1.55 |
| 1427304_at | Vps18 | AW541109 | 1.19 | 1.52 |
| 1427889_at | Spna2 | AK011566 | 1.19 | 1.73 |
| 1448353_x_at | Rpn1 | NM_133933 | 1.19 | 1.42 |
| 1450538_s_at | Mcpt9 | AY007568 | 1.19 | 0.56 |
| 1451078_at | 2510039O18Rik | BC012878 | 1.19 | 1.54 |
| 1435947_at | 2810455D13Rik | BQ175669 | 1.18 | 1.44 |
| 1428908_at | 2600011C06Rik | BG228787 | 1.18 | 1.69 |
| 1423553_at | Dnajb3 | AK005688 | 1.18 | 0.71 |
| 1434763_at | Tmem142b | BF457736 | 1.18 | 1.45 |
| 1444509_at |  | AI847347 | 1.18 | 1.49 |
| 1452094_at | P4ha1 | AI314028 | 1.18 | 1.68 |
| 1427308_at | Dab1 | BB644109 | 1.18 | 1.57 |
| 1430700_a_at | Pla2g7 | AK005158 | 1.18 | 2.25 |
| 1436329_at | Egr3 | AV346607 | 1.18 | 1.43 |
| 1438565_at | A830010M20Rik | BB464727 | 1.18 | 1.88 |
| 1430834_at |  | BB359379 | 1.18 | 0.66 |
| 1436811_at | Kctd3 | AV232970 | 1.17 | 1.40 |
| 1426278_at | Ifi27 | AY090098 | 1.17 | 1.52 |
| 1420491_at | Eif2s1 | BC016497 | 1.17 | 1.50 |
| 1426910_at | Pawr | BB398886 | 1.17 | 0.68 |
| 1455110_at | Gabpb2 | AW536205 | 1.17 | 1.61 |
| 1460043_at |  | BB357628 | 1.17 | 2.10 |
| 1424734_at | Rasgrf1 | AF169826 | 1.17 | 1.45 |
| 1453796_a_at | Ergic2 | AK016275 | 1.17 | 1.51 |
| 1434893_at | Atp1a2 | AI845177 | 1.17 | 1.59 |
| 1420402_at | Atp2b2 | NM_009723 | 1.16 | 1.56 |
| 1448154_at | Ndrg2 | NM_013864 | 1.16 | 1.92 |
| 1420022_s_at | Suz12 | AU022339 | 1.16 | 1.48 |
| 1424077_at | Gdpd1 | AK016023 | 1.16 | 1.95 |
| 1424869_at | Dhrs7b | BC003479 | 1.16 | 1.43 |
| 1457456_at | Ttc9b | AI481735 | 1.16 | 0.68 |
| 1460716_a_at | Cbfb | NM_022309 | 1.16 | 0.71 |
| 1427593_at | Trim8 | BB620112 | 1.16 | 1.52 |
| 1426959_at | Bdh1 | BF322712 | 1.16 | 1.88 |
| 1452034_at | Prepl | BB005298 | 1.16 | 1.45 |
| 1426381_at | Pprc1 | BM199989 | 1.15 | 1.54 |
| 1421884_at | Sos1 | BB471450 | 1.15 | 1.43 |
| 1448908_at | Ppap2b | NM_080555 | 1.15 | 1.65 |
| 1455698_at | Tloc1 | BQ175470 | 1.15 | 1.42 |
| 1428168_at | Mpzl1 | AK003513 | 1.15 | 1.51 |
| 1426770_at | Pex5 | AJ416473 | 1.15 | 1.69 |
| 1428540_at | 3321401G04Rik | BE944524 | 1.15 | 1.41 |
| 1455632_at | Gnb5 | BE446953 | 1.15 | 2.01 |
| 1430034_at | Cct4 | BE648588 | 1.10 | 1.66 |
| 1417775_at | Rpo1-4 | BB729239 | 1.10 | 1.43 |
| 1453195_at | Sdccag3 | BF319466 | 1.10 | 1.45 |
| 1455395_at | Oxsm | BB446073 | 1.10 | 0.70 |
| 1442764_at | Suv420h1 | BE456272 | 1.09 | 1.99 |
| 1426542_at | Endod1 | BF168366 | 1.09 | 1.41 |
| 1455023_at | N28178 | BB171181 | 1.09 | 1.43 |
| 1451351_at | Ttc13 | BC017545 | 1.09 | 1.43 |
| 1421100_a_at | Dab1 | NM_010014 | 1.09 | 1.46 |
| 1424036_at | Prpf6 | BC014869 | 1.09 | 1.43 |
| 1440397_at |  | BB464523 | 1.09 | 1.48 |
| 1435717_at | 4833428C12Rik | AV250971 | 1.09 | 1.48 |
| 1451069_at | Pim3 | BC017621 | 1.09 | 1.50 |

TABLE 15-continued

Gene translation changes upon acute cocaine treatment

| Probe | Symbol | GenBank | FCH D1 | FCH D2 |
|---|---|---|---|---|
| 1450135_at | Fzd3 | AU043193 | 1.09 | 1.42 |
| 1420978_at | Nrfl | NM_010938 | 1.09 | 1.45 |
| 1450384_at | Bace1 | AF200346 | 1.09 | 1.92 |
| 1455194_at | Mapk8ip2 | AW536912 | 1.09 | 1.57 |
| 1419283_s_at | Tns1 | NM_027884 | 1.09 | 1.58 |
| 1445415_at | EG328191 | AW048415 | 1.09 | 0.70 |
| 1423449_a_at | Actn4 | BM234779 | 1.09 | 1.46 |
| 1449556_at | H2-T23 | NM_010398 | 1.09 | 1.63 |
| 1442094_at | Ing5 | BB470038 | 1.08 | 0.71 |
| 1426434_at | Tmem43 | AI747289 | 1.08 | 1.68 |
| 1434448_at | Txlna | BG070463 | 1.08 | 1.47 |
| 1438459_x_at | Sfpq | BF224766 | 1.08 | 1.43 |
| 1421342_at | Kcns2 | NM_008436 | 1.08 | 1.45 |
| 1426441_at | Slc11a2 | BG065264 | 1.08 | 1.44 |
| 1447326_s_at | Zmym3 | AW122925 | 1.08 | 1.55 |
| 1450399_at | Psen1 | L42177 | 1.08 | 1.74 |
| 1428352_at | Arrdc2 | AW542672 | 1.08 | 1.41 |
| 1419385_a_at | Ubqln1 | NM_026842 | 1.08 | 1.46 |
| 1436789_at | Ccnjl | BM120177 | 1.08 | 1.56 |
| 1417694_at | Gab1 | NM_021356 | 1.08 | 1.50 |
| 1435390_at | Exod1 | BG067990 | 1.08 | 1.49 |
| 1456570_at | Epb4.1l4b | BB801576 | 1.08 | 1.66 |
| 1452197_at | Smc4 | AV172948 | 1.08 | 1.70 |
| 1444468_at | Paqr8 | AV328983 | 1.07 | 1.66 |
| 1449026_at | Ifnar1 | NM_010508 | 1.07 | 1.57 |
| 1421016_at | Ighmbp2 | AW259474 | 1.07 | 1.41 |
| 1427579_at | Rhbdl3 | BE653576 | 1.07 | 1.58 |
| 1416783_at | Tac1 | NM_009311 | 1.07 | 1.56 |
| 1451446_at | Antxr1 | AF378762 | 1.07 | 1.60 |
| 1436787_x_at | Sec14l3 | AV024133 | 1.07 | 0.53 |
| 1448235_s_at | Hmgb1 | BF166000 | 1.07 | 0.66 |
| 1455763_at | Rnf41 | BB753958 | 1.07 | 0.66 |
| 1452524_a_at | Elavl3 | U29149 | 1.07 | 1.51 |
| 1436353_at | A230046K03Rik | AU018634 | 1.06 | 1.50 |
| 1458584_at | 4832406H04Rik | BE948494 | 1.06 | 1.56 |
| 1423678_at | BC017643 | BC017643 | 1.06 | 1.59 |
| 1432029_a_at | Smap1 | AK006817 | 1.06 | 1.54 |
| 1448591_at | Ctss | NM_021281 | 1.06 | 1.81 |
| 1437864_at | Adipor2 | BE632137 | 1.06 | 1.72 |
| 1426466_s_at | Rps6kl1 | BB311088 | 1.06 | 1.49 |
| 1431422_a_at | Dusp14 | AK009744 | 1.06 | 1.74 |
| 1455913_x_at | Ttr | AV152953 | 1.06 | 0.14 |
| 1417174_at | 1810021J13Rik | NM_025464 | 1.01 | 1.42 |
| 1459544_at | | BB180990 | 1.01 | 1.44 |
| 1438638_x_at | 1700027J05Rik | BB195788 | 1.01 | 0.51 |
| 1438887_a_at | Gmcl1 | BM239632 | 1.01 | 1.64 |
| 1423531_a_at | Hnrpa1 | BI663320 | 1.01 | 1.71 |
| 1434143_at | BC060631 | BQ266886 | 1.01 | 1.42 |
| 1435580_at | C230081A13Rik | AW553275 | 1.01 | 1.46 |
| 1420984_at | Pctp | AF114437 | 1.00 | 0.50 |
| 1431080_at | 1700021K10Rik | BB611374 | 1.00 | 1.51 |
| 1437626_at | Zfp36l2 | BB031791 | 1.00 | 1.43 |
| 1427135_at | Sfrs12 | AV012790 | 1.00 | 0.49 |
| 1454845_x_at | Mchr1 | AW049955 | 1.00 | 1.43 |
| 1424471_at | Rapgef3 | BC020532 | 1.00 | 1.62 |
| 1433776_at | Lhfp | AV149705 | 1.00 | 1.73 |
| 1417566_at | Abhd5 | AK007421 | 1.00 | 1.46 |
| 1432435_s_at | C030004A17Rik | AK012261 | 1.00 | 1.47 |
| 1432161_a_at | Ptar1 | AK006988 | 1.00 | 0.63 |
| 1448954_at | Nrip3 | NM_020610 | 1.00 | 1.53 |
| 1416620_at | Smarcal1 | NM_018817 | 0.99 | 1.43 |
| 1425844_a_at | Rngtt | AF034568 | 0.99 | 1.67 |
| 1437858_at | Dpy19l3 | AV367203 | 0.99 | 1.51 |
| 1451191_at | Crabp2 | BC018397 | 0.99 | 1.58 |
| 1450407_a_at | Anp32a | AF022957 | 0.99 | 0.63 |
| 1416527_at | Rab32 | NM_026405 | 0.99 | 1.44 |
| 1426712_at | Slc6a15 | BB129409 | 0.99 | 1.40 |
| 1415836_at | Aldh18a1 | NM_019698 | 0.99 | 1.56 |
| 1423301_at | Copb1 | BF147382 | 0.99 | 1.46 |
| 1421471_at | Npy1r | NM_010934 | 0.99 | 1.56 |
| 1435171_at | Tbl1xr1 | BB667085 | 0.99 | 1.50 |
| 1417153_at | Btbd14a | NM_026495 | 0.99 | 0.63 |
| 1420922_at | Usp9x | AW107303 | 0.99 | 1.45 |
| 1441300_at | Kcnf1 | BB275623 | 0.98 | 1.52 |
| 1452415_at | Actn1 | BC003232 | 0.98 | 0.67 |
| 1455980_a_at | Gas2l3 | BB770972 | 0.98 | 1.41 |

TABLE 15-continued

Gene translation changes upon acute cocaine treatment

| Probe | Symbol | GenBank | FCH D1 | FCH D2 |
|---|---|---|---|---|
| 1460735_at | Svil | BM203457 | 0.98 | 1.77 |
| 1424290_at | Osgin2 | BB817847 | 0.98 | 1.75 |
| 1443793_x_at | Ints1 | BB444598 | 0.98 | 2.51 |
| 1453264_at | Marveld3 | AK007346 | 0.98 | 0.71 |
| 1416432_at | Pfkfb3 | NM_133232 | 0.98 | 1.54 |
| 1422469_at | Tbk1 | NM_019786 | 0.98 | 1.41 |
| 1423419_at | Lig3 | BM248530 | 0.98 | 1.48 |
| 1424876_s_at | Spg20 | BB040507 | 0.98 | 1.43 |
| 1429684_at | 5830472M02Rik | BG094398 | 0.98 | 2.11 |
| 1439163_at | Zbtb16 | BQ174973 | 0.98 | 1.44 |
| 1451142_at | Exoc1 | BC024678 | 0.97 | 1.43 |
| 1439909_at | Zfp521 | BE133660 | 0.97 | 1.47 |
| 1454944_at | Hic2 | BE648070 | 0.97 | 1.46 |
| 1423569_at | Gatm | AW108522 | 0.97 | 1.52 |
| 1438511_a_at | 1190002H23Rik | BB408123 | 0.97 | 1.56 |
| 1455214_at | Mitf | BB763517 | 0.97 | 1.53 |
| 1425007_at | Zfp566 | BC019790 | 0.97 | 1.50 |
| 1454647_at | Acad11 | BQ031255 | 0.97 | 1.45 |
| 1453527_a_at | Neurl | AK010787 | 0.97 | 0.65 |
| 1421844_at | Il1rap | BE285634 | 0.97 | 1.53 |
| 1443773_at | Ylpm1 | AI851834 | 0.97 | 1.77 |
| 1427998_at | Lsm12 | AV015526 | 0.91 | 1.46 |
| 1428911_at | Ttll4 | AV231607 | 0.91 | 1.49 |
| 1443955_at | 4933434E20Rik | BG074246 | 0.91 | 0.71 |
| 1427208_at | Zfp451 | BC024435 | 0.91 | 1.48 |
| 1424686_at | 2700008B19Rik | BF150550 | 0.90 | 1.55 |
| 1460737_at | Igbp1 | AA960310 | 0.90 | 1.83 |
| 1418726_a_at | Tnnt2 | NM_011619 | 0.90 | 0.67 |
| 1435214_at | Gja12 | BB319817 | 0.90 | 1.54 |
| 1424755_at | Hip1 | BB320674 | 0.90 | 0.68 |
| 1451734_a_at | Dbn1 | AB064321 | 0.90 | 1.41 |
| 1416389_a_at | Rcbtb2 | NM_134083 | 0.90 | 1.59 |
| 1426835_at | Metap1 | BG064851 | 0.90 | 1.41 |
| 1421024_at | Agpat1 | BB524140 | 0.89 | 0.69 |
| 1420287_at |  | R75193 | 0.89 | 1.41 |
| 1418839_at | Glmn | NM_133248 | 0.89 | 1.42 |
| 1421771_a_at | Ipp | NM_008389 | 0.89 | 1.51 |
| 1416348_at | Men1 | AB023401 | 0.89 | 1.73 |
| 1458349_s_at |  | BB278163 | 0.89 | 0.64 |
| 1434815_a_at | Mapkapk3 | AI451985 | 0.89 | 1.57 |
| 1453742_at | Vps33a | BG087455 | 0.89 | 1.55 |
| 1421835_at | Mtap7 | NM_008635 | 0.89 | 1.49 |
| 1435841_s_at | Suclg2 | BB757840 | 0.89 | 1.42 |
| 1427088_at | Ccnt2 | BI872151 | 0.88 | 1.70 |
| 1428750_at | Cdc42ep2 | BF453885 | 0.88 | 1.82 |
| 1431939_a_at | Mina | AK014426 | 0.88 | 1.40 |
| 1452699_at | Mett11d1 | AK009576 | 0.88 | 1.65 |
| 1429249_at | 4833424O15Rik | BB346520 | 0.88 | 1.71 |
| 1428757_at | Aasdhppt | AK013111 | 0.88 | 1.52 |
| 1433618_at | C330006A16Rik | BB397899 | 0.88 | 0.69 |
| 1438114_x_at | Efs | BB168690 | 0.88 | 1.50 |
| 1419400_at | Mttp | AW553649 | 0.87 | 1.42 |
| 1424842_a_at | Arhgap24 | BC025502 | 0.87 | 1.43 |
| 1433820_a_at | 1110012D08Rik | BB489180 | 0.87 | 1.53 |
| 1438115_a_at | Slc9a3r1 | BB805362 | 0.87 | 1.65 |
| 1424894_at | Rab13 | BC027214 | 0.87 | 0.66 |
| 1421235_s_at | Recql5 | NM_130454 | 0.86 | 1.47 |
| 1439623_at | Otud1 | BE687142 | 0.86 | 0.71 |
| 1426563_at | Zfp553 | BB770954 | 0.86 | 1.47 |
| 1451136_a_at | Eif2b2 | BC003326 | 0.86 | 1.42 |
| 1421895_at | Eif2s3x | NM_012010 | 0.86 | 1.83 |
| 1435076_at | 2310047D13Rik | AV291303 | 0.85 | 1.53 |
| 1418145_at | Tfip11 | NM_018783 | 0.85 | 1.50 |
| 1448346_at | Cfl1 | NM_007687 | 0.85 | 0.71 |
| 1441867_x_at | 4930534B04Rik | AI480494 | 0.85 | 0.65 |
| 1445763_at | 1700013F07Rik | BG069737 | 0.85 | 0.63 |
| 1445824_at | Zfp458 | AV276001 | 0.84 | 1.43 |
| 1423560_at | Nell2 | AI838010 | 0.84 | 1.68 |
| 1436185_at | AI314180 | BG076313 | 0.84 | 1.50 |
| 1452324_at | Pvt1 | BE956863 | 0.84 | 0.70 |
| 1435005_at | Cenpe | BG916502 | 0.84 | 2.25 |
| 1435937_at | Sptlc2 | BB794710 | 0.84 | 1.55 |
| 1444020_at | Ncan | BM939365 | 0.84 | 2.00 |
| 1448614_at | Nt5c2 | BI202534 | 0.84 | 1.51 |
| 1444874_at | Atp5g1 | BG074583 | 0.84 | 1.52 |
| 1460602_at | Dlc1 | BB768194 | 0.84 | 0.61 |

TABLE 15-continued

Gene translation changes upon acute cocaine treatment

| Probe | Symbol | GenBank | FCH D1 | FCH D2 |
|---|---|---|---|---|
| 1439884_at | Nudt16 | AI851783 | 0.75 | 0.70 |
| 1442707_at | Camk2a | BI134616 | 0.75 | 0.68 |
| 1427982_s_at | Syne2 | BF582734 | 0.74 | 1.59 |
| 1429758_at | 1700017B05Rik | BB046208 | 0.73 | 0.69 |
| 1435119_at | | BE956710 | 0.73 | 1.59 |
| 1445421_at | | AV238942 | 0.73 | 1.84 |
| 1432187_at | Nup43 | AK011422 | 0.73 | 1.44 |
| 1453105_at | Zfp263 | BG069835 | 0.72 | 1.48 |
| 1459472_at | AU022583 | AU022583 | 0.72 | 1.83 |
| 1457426_at | 1700048O20Rik | BE980678 | 0.72 | 0.69 |
| 1422557_s_at | Mt1 | NM_013602 | 0.71 | 0.88 |
| 1423732_at | Tram1 | BC012401 | 0.71 | 0.90 |
| 1428281_at | Trub1 | AK011362 | 0.71 | 0.97 |
| 1440795_x_at | Rabep2 | BB259371 | 0.71 | 1.12 |
| 1417886_at | Ints5 | BE307471 | 0.71 | 0.91 |
| 1429232_at | 2610528B01Rik | AK012160 | 0.71 | 1.09 |
| 1436393_a_at | Trim37 | BG065227 | 0.71 | 1.03 |
| 1438278_a_at | BC003993 | BB532946 | 0.71 | 1.07 |
| 1440161_at | Mmp16 | BB378819 | 0.71 | 1.37 |
| 1442408_at | 2010305B15Rik | BE981170 | 0.71 | 1.05 |
| 1453783_at | Pura | BE864772 | 0.71 | 0.93 |
| 1421375_a_at | S100a6 | NM_011313 | 0.71 | 0.96 |
| 1424942_a_at | Myc | BC006728 | 0.71 | 0.88 |
| 1426265_x_at | Dlat | AV336908 | 0.71 | 0.94 |
| 1426583_at | Atf2 | BM119623 | 0.71 | 1.15 |
| 1427104_at | Zfp612 | BG076162 | 0.71 | 0.99 |
| 1429790_at | Brunol6 | AK018246 | 0.71 | 0.93 |
| 1438684_at | Nuak1 | BF021001 | 0.71 | 1.57 |
| 1452127_a_at | Ptpn13 | BM236743 | 0.71 | 1.01 |
| 1420767_at | 1700019G17Rik | NM_029331 | 0.71 | 0.88 |
| 1433628_at | Coq10a | BQ044689 | 0.71 | 1.03 |
| 1440512_at | AW048066 | BF471100 | 0.71 | 0.91 |
| 1444139_at | Ddit41 | BG797099 | 0.71 | 0.80 |
| 1446244_at | Zyg11b | BB077439 | 0.71 | 0.94 |
| 1452609_at | Cox4nb | BI133691 | 0.71 | 0.80 |
| 1423757_x_at | Igfbp4 | BC019836 | 0.71 | 0.83 |
| 1424430_at | Mterfd2 | BC002280 | 0.71 | 1.22 |
| 1426289_at | Qrich1 | BC006738 | 0.71 | 0.93 |
| 1434301_at | D330050I23Rik | BE303700 | 0.71 | 0.82 |
| 1460362_at | 2410001C21Rik | BC004803 | 0.71 | 0.98 |
| AFFX-BioC-5_at | | AFFX-BIOC-5 | 0.71 | 0.86 |
| 1419101_at | Sin3a | NM_011378 | 0.71 | 1.39 |
| 1419606_a_at | Tnnt1 | NM_011618 | 0.71 | 0.96 |
| 1429601_x_at | 1110019K23Rik | AK003824 | 0.71 | 1.37 |
| 1433500_at | Dennd2a | AV260555 | 0.71 | 1.17 |
| 1458163_at | BC066028 | AV328953 | 0.71 | 0.93 |
| 1437623_x_at | Xrcc3 | BB251723 | 0.71 | 0.77 |
| 1449307_at | Dbndd1 | NM_028146 | 0.71 | 0.88 |
| 1450448_at | Stc1 | BQ032752 | 0.71 | 1.02 |
| 1459804_at | Crebbp | BB475090 | 0.71 | 1.27 |
| 1435077_at | Asxl1 | BE956516 | 0.71 | 0.87 |
| 1445461_at | | BB096245 | 0.71 | 1.08 |
| 1448495_at | Tsta3 | NM_031201 | 0.71 | 1.01 |
| 1448923_at | Prkra | NM_011871 | 0.71 | 0.79 |
| 1428285_at | 8430427H17Rik | AK018446 | 0.70 | 1.05 |
| 1443870_at | Abcc4 | BB291885 | 0.70 | 1.17 |
| 1452445_at | Slc41a2 | BC026874 | 0.70 | 1.02 |
| 1460434_at | Fundc2 | AI510221 | 0.70 | 0.88 |
| 1423363_at | Sort1 | AV247637 | 0.69 | 0.80 |
| 1436373_at | Map3k10 | AA789425 | 0.69 | 0.97 |
| 1437606_at | | BB829614 | 0.69 | 0.89 |
| 1448222_x_at | Cox8a | NM_007750 | 0.69 | 0.97 |
| 1449999_a_at | Cacna2d1 | NM_009784 | 0.69 | 1.01 |
| 1460639_a_at | Atox1 | NM_009720 | 0.69 | 0.96 |
| 1419046_at | Brp16 | NM_021555 | 0.69 | 1.25 |
| 1421204_a_at | Nudt16 | NM_029385 | 0.69 | 0.94 |
| 1422622_at | Nos3 | NM_008713 | 0.69 | 1.16 |
| 1439332_at | Ddit4l | AV251625 | 0.69 | 0.92 |
| 1455661_at | | BB211563 | 0.69 | 0.94 |
| 1429229_s_at | 4930534B04Rik | BE980134 | 0.69 | 0.77 |
| 1450849_at | Hnrpu | BF228203 | 0.69 | 2.02 |
| 1430999_a_at | Scoc | BM932452 | 0.69 | 0.96 |
| 1433969_at | AU067824 | AU067824 | 0.69 | 1.01 |
| 1460005_at | AF013969 | BB542960 | 0.69 | 0.95 |
| 1435027_at | Golga1 | AW552851 | 0.69 | 1.09 |
| 1439341_at | AK220484 | BB203252 | 0.69 | 1.12 |

TABLE 15-continued

Gene translation changes upon acute cocaine treatment

| Probe | Symbol | GenBank | FCH D1 | FCH D2 |
|---|---|---|---|---|
| 1450881_s_at | Gpr137b | AK010724 | 0.69 | 1.02 |
| 1417065_at | Egr1 | NM_007913 | 0.69 | 0.99 |
| 1424922_a_at | Brd4 | BC008532 | 0.69 | 0.99 |
| 1427390_at | Bloc1s3 | BC025913 | 0.69 | 0.94 |
| 1450083_at | Cnot4 | AI448404 | 0.69 | 0.97 |
| 1458464_at | Hecw2 | BB445169 | 0.69 | 1.22 |
| 1453381_at | C030033M12Rik | BB771017 | 0.69 | 1.04 |
| 1427992_a_at | Rab12 | BF729629 | 0.69 | 1.01 |
| 1419130_at | Deadc1 | NM_025748 | 0.69 | 1.94 |
| 1428600_at | Nin | AK014241 | 0.69 | 0.99 |
| 1431820_at | 4632404H12Rik | AK014549 | 0.69 | 0.83 |
| 1447827_x_at | Spop | AV353779 | 0.69 | 1.15 |
| 1420579_s_at | Cftr | NM_021050 | 0.68 | 2.52 |
| 1429058_at | 1110004B13Rik | AK003403 | 0.68 | 0.84 |
| 1435237_at | 2310009A05Rik | AV004950 | 0.68 | 0.81 |
| 1453684_s_at | Zc3h15 | AK005661 | 0.68 | 1.03 |
| 1454968_at | 1110034A24Rik | AV011961 | 0.68 | 1.00 |
| 1418135_at | Affl | NM_133919 | 0.68 | 1.10 |
| 1418971_x_at | Bcl10 | AF100339 | 0.68 | 0.99 |
| 1437003_at | | BB323930 | 0.68 | 0.71 |
| 1448306_at | Nfkbia | NM_010907 | 0.68 | 1.13 |
| 1416607_at | 4931406C07Rik | AI461712 | 0.68 | 1.13 |
| 1431120_a_at | Golga1 | BC024637 | 0.68 | 0.97 |
| 1435544_at | Exosc6 | BB446614 | 0.68 | 1.10 |
| 1439888_at | | BB271581 | 0.68 | 1.17 |
| 1444150_at | Epb4.1 | BB462549 | 0.68 | 0.88 |
| 1448218_s_at | Ywhaz | AV027921 | 0.68 | 0.86 |
| 1457825_x_at | Tcn2 | BB515151 | 0.68 | 1.25 |
| AFFX-r2-Ec-bioC-5_at | | "AFFX-R2-EC-BIOC-5" | 0.68 | 0.89 |
| 1418432_at | Cab39 | AK005226 | 0.68 | 1.39 |
| 1444001_at | Strbp | AW488249 | 0.67 | 1.51 |
| 1457669_x_at | Rfc2 | AV096765 | 0.67 | 0.96 |
| 1432378_at | C030004G16Rik | AK021043 | 0.66 | 1.03 |
| 1451132_at | Pbxip1 | AV220340 | 0.66 | 1.01 |
| 1417107_at | Tpd52l2 | NM_025482 | 0.66 | 0.94 |
| 1421997_s_at | Itga3 | NM_013565 | 0.66 | 1.11 |
| 1448851_a_at | Dnajc5 | AK012029 | 0.66 | 1.11 |
| 1451213_at | Pex11b | BB010355 | 0.66 | 1.07 |
| 1456645_at | Wdr25 | BB352668 | 0.66 | 0.72 |
| 1422842_at | Xrn2 | NM_011917 | 0.66 | 1.04 |
| 1452517_at | Plekhh1 | BC006045 | 0.66 | 1.25 |
| 1424169_at | Tax1bp3 | BC008166 | 0.66 | 0.73 |
| 1424207_at | Smarca5 | BI661719 | 0.66 | 1.36 |
| 1428841_at | Best1 | AK006549 | 0.66 | 0.99 |
| 1425528_at | Prrx1 | L06502 | 0.66 | 1.16 |
| 1451020_at | Gsk3b | BB831420 | 0.66 | 0.90 |
| 1452228_at | Tbc1d23 | AV209678 | 0.66 | 0.94 |
| 1419144_at | Cd163 | NM_053094 | 0.66 | 0.96 |
| 1441742_at | Kcnh5 | AW048994 | 0.66 | 1.08 |
| 1448553_at | Myh7 | NM_080728 | 0.66 | 0.86 |
| 1416622_at | Wbscr16 | NM_033572 | 0.66 | 1.37 |
| 1423834_s_at | Gga1 | BC026802 | 0.66 | 0.92 |
| 1449470_at | Dlx1 | NM_010053 | 0.66 | 0.87 |
| 1426360_at | Zc3h11a | AV328883 | 0.66 | 1.33 |
| 1419266_at | Nfyb | AV250496 | 0.65 | 1.22 |
| 1432391_at | Ccdc21 | AK010621 | 0.65 | 0.84 |
| 1441453_at | Dennd2a | BB341122 | 0.65 | 0.94 |
| 1455801_x_at | Tbcd | BB392080 | 0.65 | 1.03 |
| 1429125_at | Zbtb9 | AV283825 | 0.65 | 0.93 |
| 1426584_a_at | Sord | BI143942 | 0.65 | 0.85 |
| AFFX-BioDn-3_at | | "AFFX-BIODN-3" | 0.65 | 0.90 |
| 1416112_at | Cox8a | NM_007750 | 0.65 | 0.96 |
| 1418172_at | Hebp1 | AF117613 | 0.65 | 1.21 |
| 1427334_s_at | 2810474O19Rik | BE196832 | 0.65 | 0.95 |
| 1429362_a_at | Sf3b2 | BF022081 | 0.65 | 1.01 |
| 1453006_at | Fgfbp3 | AI506568 | 0.65 | 1.00 |
| 1424899_at | Nmnat3 | BC005737 | 0.65 | 0.95 |
| 1437018_at | Pnma2 | BG072348 | 0.65 | 1.16 |
| 1422164_at | Pou3f4 | X66603 | 0.65 | 0.99 |
| 1452817_at | Smyd3 | AK010447 | 0.65 | 0.99 |
| 1437118_at | Usp7 | C77542 | 0.65 | 1.76 |
| 1460021_at | EG626231 | BB825323 | 0.65 | 1.28 |
| 1422662_at | Lgals8 | AI987967 | 0.64 | 0.94 |
| 1428198_at | Adal | AK016299 | 0.64 | 1.10 |

TABLE 15-continued

Gene translation changes upon acute cocaine treatment

| Probe | Symbol | GenBank | FCH D1 | FCH D2 |
|---|---|---|---|---|
| 1423184_at | Itsn2 | AI326108 | 0.64 | 0.76 |
| 1426631_at | Pus7 | BM199125 | 0.64 | 1.11 |
| 1437694_at | Zfp809 | AW536892 | 0.64 | 0.92 |
| 1455586_at | Rnf168 | BB275228 | 0.64 | 0.49 |
| 1447494_at | D7Bwg0826e | R74675 | 0.64 | 1.01 |
| 1430242_at | Rwdd1 | AV356665 | 0.64 | 1.14 |
| 1430745_at | 5930409G06Rik | AK020028 | 0.64 | 0.71 |
| 1458685_at | Garnl1 | BB552367 | 0.64 | 1.03 |
| 1438477_a_at | Mcee | AA960125 | 0.64 | 0.86 |
| 1447344_at |  | AI447264 | 0.60 | 1.04 |
| 1450759_at | Bmp6 | NM_007556 | 0.60 | 1.22 |
| 1422230_s_at | Cyp2a5 | NM_007812 | 0.60 | 0.81 |
| 1428047_s_at | Zfx | BC028506 | 0.60 | 1.07 |
| 1432269_a_at | Sh3kbp1 | AK018032 | 0.59 | 1.49 |
| 1440215_at | "OTTMUSG 00000004461" | BG068916 | 0.59 | 0.93 |
| 1453083_at | 6430701C03Rik | AK018294 | 0.59 | 0.99 |
| 1455998_at | Zc3h11a | BM232738 | 0.59 | 0.96 |
| 1427924_at | Stx17 | BE943517 | 0.59 | 0.72 |
| 1449357_at | 2310030G06Rik | NM_025865 | 0.59 | 0.82 |
| 1438032_at | Lrch1 | BB755336 | 0.59 | 0.74 |
| 1417938_at | Rad51ap1 | BC003738 | 0.59 | 1.02 |
| 1453320_at | 1700027A23Rik | AK006407 | 0.59 | 1.02 |
| 1449109_at | Socs2 | NM_007706 | 0.58 | 1.03 |
| 1449677_s_at | Tmem38b | C77858 | 0.58 | 1.11 |
| 1452748_at | Xrcc3 | AW537713 | 0.58 | 1.06 |
| 1457693_a_at | 6430537H07Rik | AV343405 | 0.58 | 0.85 |
| 1441306_at | 6820408C15Rik | AW048149 | 0.57 | 0.97 |
| 1439783_at | C330018D20Rik | BB809870 | 0.57 | 0.79 |
| 1428826_at | Nr6a1 | AK007201 | 0.57 | 0.94 |
| 1456067_at | Gli3 | AW546010 | 0.57 | 0.87 |
| 1430520_at | Cpne8 | AW548480 | 0.57 | 1.29 |
| 1441161_at | B230216G23Rik | BB307791 | 0.57 | 2.63 |
| 1430240_a_at | Clgn | AK019534 | 0.56 | 1.04 |
| 1439555_at | Rlf | BB704706 | 0.56 | 1.30 |
| 1426534_a_at | Arfgap3 | BG067878 | 0.56 | 0.78 |
| 1445564_at |  | BE688513 | 0.56 | 1.32 |
| 1456674_at | E130016E03Rik | BB772877 | 0.55 | 1.05 |
| 1434950_a_at | Armc8 | BE995635 | 2.87 | 0.78 |
| 1422533_at | Cyp51 | NM_020010 | 2.84 | 0.92 |
| 1438752_at | A230058F20Rik | AV327739 | 2.80 | 1.67 |
| 1420158_s_at | Abcf1 | AA408356 | 1.72 | 0.83 |
| 1427692_a_at | Cask | Y17137 | 1.72 | 1.08 |
| 1423700_at | Rfc3 | BC026795 | 1.72 | 1.12 |
| 1424805_a_at | 1110039B18Rik | BC027046 | 1.72 | 1.02 |
| 1429628_at | 6330407J23Rik | AK012378 | 1.71 | 0.93 |
| 1437920_at | Epha5 | AI854630 | 1.70 | 1.29 |
| 1417509_at | Rnf19 | AF120206 | 1.70 | 1.26 |
| 1456384_at | Nlgn3 | BB308872 | 1.70 | 1.03 |
| 1440862_at | Tmem181 | BB629079 | 1.70 | 1.24 |
| 1455492_at | B330016D10Rik | BB313577 | 1.69 | 1.40 |
| 1448502_at | Slc16a7 | NM_011391 | 1.68 | 1.10 |
| 1453583_at | Zzef1 | AI466222 | 1.68 | 0.80 |
| 1420652_at | Ate1 | BE309332 | 1.68 | 0.71 |
| 1420720_at | Nptx2 | NM_016789 | 1.68 | 1.43 |
| 1437147_at | Gabrg2 | AV348821 | 1.67 | 1.23 |
| 1435749_at | Gda | AW911807 | 1.67 | 1.11 |
| 1437308_s_at | F2r | AV024285 | 1.67 | 0.90 |
| 1416589_at | Sparc | NM_009242 | 1.66 | 1.58 |
| 1450708_at | Scg2 | NM_009129 | 1.66 | 1.59 |
| 1425227_a_at | Atp6v0a1 | BC001995 | 1.66 | 1.19 |
| 1433607_at | Cbln4 | AV343573 | 1.66 | 1.56 |
| 1450976_at | Ndrg1 | AI987929 | 1.66 | 1.25 |
| 1429475_at | 2810457I06Rik | AK013361 | 1.66 | 1.83 |
| 1447005_at |  | BE991564 | 1.65 | 0.83 |
| 1452754_at | Creld2 | AK017880 | 1.65 | 1.42 |
| 1449411_at | Dscam | NM_031174 | 1.65 | 0.99 |
| 1428922_at | 1200009O22Rik | AK004681 | 1.65 | 1.56 |
| 1421959_s_at | Adcy3 | AF458089 | 1.64 | 1.13 |
| 1453056_at | Slc16a13 | AK005699 | 1.64 | 1.08 |
| 1455061_a_at | Acaa2 | BB718075 | 1.64 | 1.66 |
| 1439764_s_at | Igf2bp2 | BB098431 | 1.64 | 1.10 |
| 1451699_at | EG668468 | BC024416 | 1.64 | 0.78 |
| 1456825_at | Wdr33 | BB482118 | 1.63 | 0.98 |
| 1438725_at | Thrap1 | BB212816 | 1.63 | 1.17 |
| 1448384_at | Pofut2 | BC018194 | 1.63 | 1.59 |

TABLE 15-continued

Gene translation changes upon acute cocaine treatment

| Probe | Symbol | GenBank | FCH D1 | FCH D2 |
|---|---|---|---|---|
| 1444690_at | Epha5 | BE951744 | 1.63 | 1.29 |
| 1415885_at | Chgb | NM_007694 | 1.63 | 1.54 |
| 1442788_at | 2600003E23Rik | BB698513 | 1.63 | 0.98 |
| 1449289_a_at | B2m | BF715219 | 1.63 | 1.17 |
| 1418132_a_at | D7Wsu128e | BC011313 | 1.62 | 0.79 |
| 1427539_a_at | Zwint | BC013559 | 1.62 | 1.42 |
| 1450193_at | Hcn1 | NM_010408 | 1.62 | 1.45 |
| 1457536_at | Gpc5 | BB171986 | 1.62 | 1.11 |
| 1420564_at | Insrr | NM_011832 | 1.62 | 0.81 |
| 1460583_at | Golt1b | AV349681 | 1.62 | 1.08 |
| 1425110_at | Sorcs3 | AK018111 | 1.62 | 1.19 |
| 1421535_a_at | Pde4a | NM_019798 | 1.62 | 0.75 |
| 1452768_at | Tex261 | AK013971 | 1.62 | 0.97 |
| 1438750_at | Atrx | BB425841 | 1.61 | 1.05 |
| 1443898_at | Bcl7c | BB826733 | 1.61 | 1.08 |
| 1453531_at | Zfp248 | AK012874 | 1.61 | 1.01 |
| 1418260_at | Hunk | NM_015755 | 1.61 | 0.72 |
| 1438151_x_at | Zdhhc14 | BB544336 | 1.60 | 1.26 |
| 1425899_a_at | Itsn1 | AF132478 | 1.60 | 0.89 |
| 1418253_a_at | Hspa4l | NM_011020 | 1.60 | 1.12 |
| 1450983_at | Akap8 | BG069776 | 1.52 | 1.11 |
| 1452905_at | Gtl2 | AV015833 | 1.52 | 0.67 |
| 1449381_a_at | Pacsin1 | BI731319 | 1.52 | 1.08 |
| 1445268_at |  | AW550459 | 1.52 | 1.09 |
| 1425568_a_at | Tmem33 | BC005562 | 1.51 | 1.05 |
| 1450699_at | Selenbp1 | NM_009150 | 1.51 | 1.35 |
| 1418104_at | Nrip3 | NM_020610 | 1.51 | 1.90 |
| 1448050_s_at | Map4k4 | BF450398 | 1.51 | 2.05 |
| 1452835_a_at | Polrmt | AK003792 | 1.51 | 1.44 |
| 1423070_at | Rpl21 | BG922742 | 1.51 | 1.13 |
| 1430798_x_at | Mrpl15 | AV306676 | 1.51 | 1.76 |
| 1439380_x_at | Gtl2 | BB093563 | 1.51 | 0.91 |
| 1460170_at | Ext2 | NM_010163 | 1.51 | 1.17 |
| 1450965_at | Tex261 | BF181445 | 1.51 | 1.24 |
| 1456389_at | Zeb2 | BB244754 | 1.51 | 0.90 |
| 1421374_a_at | Fxyd1 | NM_019503 | 1.51 | 0.92 |
| 1450351_a_at | Clip1 | NM_019765 | 1.51 | 1.10 |
| 1424133_at | Tmem98 | BC011208 | 1.50 | 1.24 |
| 1434585_at | Tulp4 | BB667130 | 1.50 | 1.45 |
| 1429591_at | Tacc1 | BE862546 | 1.50 | 1.45 |
| 1418816_at | Chmp1b | BG073376 | 1.50 | 1.42 |
| 1424950_at | Sox9 | BC024958 | 1.50 | 0.97 |
| 1460743_at | Tigd5 | BB553398 | 1.49 | 1.22 |
| 1439559_at | 1700040D17Rik | AV260432 | 1.49 | 1.08 |
| 1460331_at | Tm9sf2 | BB747462 | 1.49 | 1.40 |
| 1435703_at |  | AW045947 | 1.49 | 1.64 |
| 1436325_at | Rora | BB306272 | 1.49 | 0.76 |
| 1453334_at | B230216N24Rik | AK021003 | 1.49 | 1.60 |
| 1423859_a_at | Ptgds | AB006361 | 1.49 | 1.06 |
| 1438706_at | 6430517E21Rik | BB309608 | 1.49 | 1.27 |
| 1415806_at | Plat | NM_008872 | 1.49 | 1.56 |
| 1429055_at | 4930506M07Rik | BB559293 | 1.48 | 1.10 |
| 1431755_a_at | Ccdc49 | BC021478 | 1.48 | 1.05 |
| 1437495_at | Mbtps2 | AV272026 | 1.48 | 1.16 |
| 1421487_a_at | Nck1 | NM_010878 | 1.48 | 1.40 |
| 1426781_at | Tyw1 | BF021045 | 1.48 | 1.05 |
| 1426852_x_at | Nov | X96585 | 1.48 | 1.53 |
| 1436137_at | Slc6a17 | AV340147 | 1.48 | 1.17 |
| 1447759_x_at | Ccdc22 | BB345575 | 1.48 | 0.73 |
| 1418045_at | Inpp1 | NM_008384 | 1.48 | 1.52 |
| 1448242_at | Sec61a1 | BC003707 | 1.48 | 1.20 |
| 1424861_at | Zbtb24 | BM200153 | 1.48 | 0.86 |
| 1437142_a_at | Pigo | BB546713 | 1.48 | 1.14 |
| 1423796_at | Sfpq | AY034062 | 1.47 | 1.40 |
| 1458622_at | Ntrk2 | AW121243 | 1.47 | 1.29 |
| 1416032_at | Tmem109 | AW494906 | 1.47 | 0.95 |
| 1455476_a_at | Gse1 | BE686504 | 1.47 | 1.55 |
| 1426311_s_at | Zdhhc5 | AV241525 | 1.47 | 1.51 |
| 1418456_a_at | Cxcl14 | AF252873 | 1.47 | 0.92 |
| 1455965_at | Adamts4 | BG064671 | 1.47 | 1.26 |
| 1455993_at | Odz4 | BG071076 | 1.47 | 1.25 |
| 1431385_a_at | Mbtps1 | AK002809 | 1.47 | 1.09 |
| 1450172_at | Pknox1 | AA409923 | 1.47 | 1.77 |
| 1415901_at | Plod3 | NM_011962 | 1.47 | 1.16 |
| 1420838_at | Ntrk2 | AK018789 | 1.47 | 1.61 |
| 1436057_at | Gtl2 | BM117428 | 1.42 | 1.23 |

TABLE 15-continued

Gene translation changes upon acute cocaine treatment

| Probe | Symbol | GenBank | FCH D1 | FCH D2 |
|---|---|---|---|---|
| 1449885_at | Tmem47 | NM_138751 | 1.42 | 2.12 |
| 1426280_at | AV249152 | AF424701 | 1.42 | 1.13 |
| 1438165_x_at | Vat1 | BB559097 | 1.42 | 0.88 |
| 1440258_at | Kcnq2 | BE951512 | 1.41 | 1.35 |
| 1448113_at | Stmn1 | BC010581 | 1.41 | 0.93 |
| 1428793_at | Slc36a1 | AK017918 | 1.41 | 1.43 |
| 1438957_x_at | Cds2 | BB027654 | 1.41 | 1.19 |
| 1438975_x_at | Zdhhc14 | AV361868 | 1.41 | 1.49 |
| 1448957_at | Rbpsuh | NM_009035 | 1.41 | 1.14 |
| 1429257_at | Gtl2 | AU067739 | 1.41 | 0.81 |
| 1447774_x_at | 5730469M10Rik | AV332575 | 1.41 | 1.14 |
| 1426767_at | 3230401M21Rik | AK014328 | 1.41 | 1.87 |
| 1428586_at | Tmem41b | BB823331 | 1.41 | 1.00 |
| 1441737_s_at | Rassf1 | BB757103 | 1.41 | 0.90 |
| 1450872_s_at | Lipa | AI596237 | 1.41 | 1.18 |
| 1417946_at | Abhd3 | NM_134130 | 1.41 | 1.26 |
| 1439776_at | Ogfod1 | BE956398 | 1.41 | 1.31 |
| 1453581_at | Cep170 | BB361436 | 1.41 | 1.30 |
| 1452232_at | Galnt7 | AV302406 | 1.41 | 1.55 |
| 1440143_at | Pigz | AI413722 | 1.41 | 0.94 |
| 1460327_at | Gpr88 | BE947345 | 1.40 | 1.40 |
| 1423294_at | Mest | AW555393 | 1.40 | 1.79 |
| 1445605_s_at | 4921533L14Rik | AI835491 | 1.40 | 1.06 |
| 1450268_at | Fign | NM_021716 | 1.40 | 1.68 |
| 1417605_s_at | Camk1 | NM_133926 | 1.40 | 0.94 |
| 1423950_at | Kcnab3 | BC017518 | 1.40 | 1.38 |
| 1425301_at | Ncam2 | AF001287 | 1.40 | 0.87 |
| 1417149_at | P4ha2 | NM_011031 | 1.40 | 1.53 |
| 1420969_at | Btbd14b | NM_025788 | 1.39 | 0.69 |
| 1448673_at | Pvrl3 | NM_021495 | 1.39 | 0.67 |
| 1451718_at | Plp1 | BB768495 | 1.38 | 1.44 |
| 1423826_at | Noc4l | BC024616 | 1.38 | 1.45 |
| 1437614_x_at | Zdhhc14 | AV223474 | 1.38 | 1.46 |
| 1425474_a_at | Vps39 | BC007479 | 1.38 | 1.61 |
| 1430294_at | Ssbp1 | AK013425 | 1.38 | 1.43 |
| 1448216_at | Syngr3 | NM_011522 | 1.38 | 1.45 |
| 1423192_at | Pspc1 | BB590675 | 1.37 | 1.84 |
| 1456783_at | 9330107J05Rik | BB075402 | 1.37 | 1.44 |
| 1426449_a_at | Pja1 | BM199789 | 1.37 | 1.45 |
| 1437857_at | Dpy19l3 | AV367203 | 1.37 | 1.45 |
| 1418349_at | Hbegf | L07264 | 1.37 | 1.62 |
| 1444327_at | Edd1 | BF224640 | 1.37 | 1.63 |
| 1431802_a_at | D5Wsu178e | AK014530 | 1.36 | 1.47 |
| 1435553_at | Pdzd2 | AV376136 | 1.36 | 1.83 |
| 1436201_x_at | Mbp | BB761376 | 1.36 | 1.51 |
| 1426837_at | Metap1 | BG064851 | 1.36 | 1.77 |
| 1417110_at | Man1a | BB070019 | 1.35 | 1.45 |
| 1444661_at | Gpr26 | BB247791 | 1.35 | 1.96 |
| 1447672_x_at | Pskh1 | BB102342 | 1.35 | 1.64 |
| 1417954_at | Sst | NM_009215 | 1.35 | 1.41 |
| 1444614_x_at | 6430537H07Rik | AV258949 | 1.35 | 1.33 |
| 1435456_at | Ttc28 | AW552254 | 1.35 | 1.44 |
| 1451726_at | Mtmr6 | BC020019 | 1.34 | 1.66 |
| 1421201_a_at | Tro | AF241244 | 1.34 | 1.50 |
| 1454654_at | Dirc2 | BG069395 | 1.26 | 1.47 |
| 1423574_s_at | Srd5a2l | BB206480 | 1.26 | 1.49 |
| 1450971_at | Gadd45b | AK010420 | 1.26 | 1.98 |
| 1452377_at | Mll1 | AK017541 | 1.26 | 1.57 |
| 1458979_at |  | BB332816 | 1.26 | 1.54 |
| 1444307_at |  | AW491448 | 1.26 | 2.53 |
| 1420502_at | Sat1 | NM_009121 | 1.26 | 1.47 |
| 1439041_at | Slc39a10 | BM239325 | 1.26 | 1.56 |
| 1428387_at | Acsl3 | AK012088 | 1.25 | 1.55 |
| 1458842_at |  | AV340888 | 1.25 | 1.40 |
| 1424482_at | Arhgef7 | AF343877 | 1.25 | 1.46 |
| 1418169_at | Zcchc14 | BB223737 | 1.25 | 1.45 |
| 1427931_s_at | Pdxk | BG063905 | 1.25 | 1.60 |
| 1429183_at | Pkp2 | AK005020 | 1.25 | 1.57 |
| 1434510_at | Papss2 | BF780807 | 1.25 | 1.68 |
| 1424098_at | Elovl7 | BC005602 | 1.25 | 1.41 |
| 1415857_at | Emb | BG064842 | 1.25 | 1.61 |
| 1418539_a_at | Ptpre | U35368 | 1.24 | 1.45 |
| 1417988_at | Resp18 | NM_009049 | 1.24 | 1.60 |
| 1444226_at | Foxo3a | W07885 | 1.24 | 1.81 |
| 1450326_at | Shc3 | NM_009167 | 1.24 | 1.44 |
| 1438402_at | 9630050M13Rik | BB131315 | 1.24 | 1.51 |

TABLE 15-continued

Gene translation changes upon acute cocaine treatment

| Probe | Symbol | GenBank | FCH D1 | FCH D2 |
|---|---|---|---|---|
| 1439279_at | 3110007F17Rik | AV339304 | 1.24 | 1.45 |
| 1415743_at | Hdac5 | NM_010412 | 1.24 | 1.42 |
| 1417947_at | Pcna | BC010343 | 1.24 | 1.53 |
| 1423795_at | Sfpq | AY034062 | 1.24 | 1.53 |
| 1428112_at | Armet | AK014338 | 1.24 | 1.46 |
| 1437159_at | Eif2c5 | AW553762 | 1.24 | 1.55 |
| 1429517_at | Zfyve20 | BC017622 | 1.23 | 2.63 |
| 1448460_at | Acvr1 | NM_007394 | 1.23 | 1.44 |
| 1453109_at | Arsk | AK013194 | 1.23 | 0.67 |
| 1421010_at | Mobp | NM_008614 | 1.23 | 1.78 |
| 1434761_at | Lrrtm3 | BM224801 | 1.23 | 1.85 |
| 1449773_s_at | Gadd45b | AI323528 | 1.23 | 1.55 |
| 1437633_at | Ankrd11 | BB320513 | 1.23 | 1.46 |
| 1421190_at | Gabrb3 | BB367779 | 1.23 | 1.55 |
| 1434595_at | Trim9 | BQ174474 | 1.23 | 1.69 |
| 1459737_s_at | Ttr | AA408768 | 1.23 | 0.18 |
| 1428350_at | 2310061F22Rik | AV091287 | 1.23 | 1.70 |
| 1429683_at | 5830472M02Rik | BG094398 | 1.22 | 1.51 |
| 1457125_at | | AV266261 | 1.22 | 1.86 |
| 1425351_at | Srxn1 | BC011325 | 1.22 | 1.46 |
| 1435245_at | Gls2 | AI195532 | 1.22 | 1.43 |
| 1431645_a_at | Gdi2 | AK013104 | 1.22 | 1.52 |
| 1434759_at | Lrrtm3 | BM224801 | 1.22 | 1.52 |
| 1460206_at | Grasp | NM_019518 | 1.22 | 1.67 |
| 1437880_at | Lbxcor1 | AV273001 | 1.22 | 0.67 |
| 1428765_at | Gtl2 | AV015833 | 1.21 | 0.66 |
| 1451895_a_at | Dhcr24 | BC004738 | 1.21 | 1.44 |
| 1428781_at | Dmkn | BI452905 | 1.21 | 1.80 |
| 1417238_at | Ewsr1 | NM_007968 | 1.21 | 1.85 |
| 1425396_a_at | Lck | BC011474 | 1.21 | 0.62 |
| 1438116_x_at | Slc9a3r1 | BB805362 | 1.21 | 1.70 |
| 1421948_a_at | Ccdc123 | BB042564 | 1.20 | 1.50 |
| 1438194_at | 2900019G14Rik | AW488243 | 1.20 | 1.42 |
| 1424684_at | Rab5c | BC023027 | 1.15 | 0.69 |
| 1452829_at | Cad | AK010453 | 1.15 | 1.41 |
| 1455628_at | Epb4.1l4b | BB317849 | 1.14 | 1.46 |
| 1430990_s_at | Mrpl44 | AK019986 | 1.14 | 1.50 |
| 1430066_at | 4930589M24Rik | AK014044 | 1.14 | 1.49 |
| 1434360_s_at | Ptprg | AI596632 | 1.14 | 1.58 |
| 1415964_at | Scd1 | NM_009127 | 1.14 | 1.55 |
| 1439254_at | Akap13 | BE981392 | 1.14 | 0.64 |
| 1425617_at | Dhx9 | U91922 | 1.14 | 1.67 |
| 1450777_at | Xrn2 | NM_011917 | 1.14 | 1.46 |
| 1417170_at | Lztfl1 | NM_033322 | 1.14 | 1.52 |
| 1439324_at | D230004J03Rik | BB282778 | 1.14 | 0.66 |
| 1454915_at | Rab3gap2 | BB032142 | 1.14 | 1.71 |
| 1424146_at | Gpr37l1 | AB016602 | 1.14 | 1.58 |
| 1416562_at | Gad1 | AF326547 | 1.14 | 1.56 |
| 1422779_at | Smpd3 | NM_021491 | 1.14 | 1.63 |
| 1455468_at | | BB768758 | 1.14 | 1.43 |
| 1427016_at | 4932438A13Rik | BC027125 | 1.14 | 1.41 |
| 1427138_at | 0610010D24Rik | AW556861 | 1.14 | 1.41 |
| 1423475_at | Cnnm2 | BB278418 | 1.13 | 1.57 |
| 1423479_at | Nol11 | AK005123 | 1.13 | 1.53 |
| 1451285_at | Fus | AF224264 | 1.13 | 2.12 |
| 1456312_x_at | Gsn | AV224521 | 1.13 | 2.63 |
| 1436515_at | E030004N02Rik | BB529913 | 1.13 | 1.44 |
| 1442714_at | D130037M23Rik | BB322545 | 1.13 | 1.93 |
| 1454811_a_at | Serinc1 | AV026664 | 1.13 | 1.55 |
| 1420262_at | | AV291437 | 1.13 | 0.67 |
| 1454890_at | Amot | BG067039 | 1.13 | 1.40 |
| 1454784_at | Hs3st2 | AV340742 | 1.13 | 1.44 |
| 1426809_at | C430004E15Rik | BF582414 | 1.12 | 1.83 |
| 1453122_at | 4921533L14Rik | AK019549 | 1.12 | 1.44 |
| 1416794_at | Arl6ip2 | NM_019717 | 1.12 | 1.61 |
| 1458417_at | Jmjd1b | BB712040 | 1.12 | 1.56 |
| 1437295_at | Pkn2 | AI507382 | 1.12 | 1.57 |
| 1417475_at | Atp13a1 | NM_133224 | 1.12 | 1.48 |
| 1455459_at | Prdm15 | BB213846 | 1.12 | 1.44 |
| 1417602_at | Per2 | AF035830 | 1.12 | 1.88 |
| 1426991_at | 1810048J11Rik | AV273819 | 1.12 | 1.40 |
| 1441921_x_at | Esrrb | BB386239 | 1.12 | 0.62 |
| 1450480_a_at | Gprk6 | AF040749 | 1.12 | 1.42 |
| 1457791_at | B830008H07Rik | BB333194 | 1.12 | 1.62 |
| 1426897_at | Rcc2 | AV122997 | 1.11 | 1.42 |
| 1424161_at | Ddx27 | BC011321 | 1.11 | 1.54 |

TABLE 15-continued

Gene translation changes upon acute cocaine treatment

| Probe | Symbol | GenBank | FCH D1 | FCH D2 |
|---|---|---|---|---|
| 1429514_at | Ppap2b | AW111876 | 1.11 | 1.60 |
| 1453851_a_at | Gadd45g | AK007410 | 1.11 | 1.41 |
| 1424373_at | Armcx3 | AK004598 | 1.11 | 1.52 |
| 1435890_at | AW228836 | BB795103 | 1.11 | 1.54 |
| 1457664_x_at | C2 | AV227574 | 1.11 | 1.45 |
| 1427888_a_at | Spna2 | AK011566 | 1.11 | 1.45 |
| 1425713_a_at | Rnf146 | BC019182 | 1.11 | 1.45 |
| 1423269_a_at | Nedd4l | BB663717 | 1.10 | 1.66 |
| 1451308_at | Elovl4 | BB829575 | 1.10 | 1.44 |
| 1426600_at | Slc2a1 | BM209618 | 1.10 | 2.23 |
| 1421845_at | Golph3 | AV174110 | 1.10 | 1.49 |
| 1442823_at |  | BB536648 | 1.05 | 1.79 |
| 1424613_at | Gprc5b | BC020004 | 1.05 | 1.59 |
| 1442073_at |  | BQ266693 | 1.05 | 1.67 |
| 1452441_at | Phf3 | AW910425 | 1.05 | 0.68 |
| 1422902_s_at | Mgea5 | NM_023799 | 1.05 | 1.47 |
| 1450748_at | Smpd3 | NM_021491 | 1.05 | 1.42 |
| 1426590_at | Gfm2 | BB497484 | 1.05 | 1.48 |
| 1442257_at | Cdh6 | BI134319 | 1.05 | 1.70 |
| 1431056_a_at | Lpl | AK017272 | 1.04 | 1.43 |
| 1417749_a_at | Tjp1 | NM_009386 | 1.04 | 1.53 |
| 1460694_s_at | Svil | BM203457 | 1.04 | 1.76 |
| 1426368_at | Rin2 | AK014548 | 1.04 | 1.47 |
| 1450875_at | Gpr37 | BQ175510 | 1.04 | 1.68 |
| 1419115_at | Alg14 | AA198774 | 1.04 | 0.61 |
| 1427189_at | Arih1 | BB362210 | 1.04 | 1.46 |
| 1435621_at | Mlstd1 | BQ175346 | 1.04 | 1.45 |
| 1437105_at | Jarid1a | BM246184 | 1.04 | 1.45 |
| 1450108_at | Kif1a | NM_008440 | 1.04 | 1.51 |
| 1454844_at | Mchr1 | AW049955 | 1.04 | 1.47 |
| 1418754_at | Adcy8 | NM_009623 | 1.04 | 1.41 |
| 1451115_at | Pias3 | BC023128 | 1.04 | 0.61 |
| 1419058_at | Polr1e | NM_022811 | 1.04 | 1.56 |
| 1432452_at | 1700054O19Rik | AK006789 | 1.04 | 0.70 |
| 1435444_at | Atf6 | AV270913 | 1.04 | 1.42 |
| 1431717_at | 3526401B18Rik | AK014386 | 1.03 | 1.63 |
| 1452295_at | Tmepai | AV291712 | 1.03 | 1.46 |
| 1431035_at | Daam1 | AW988556 | 1.03 | 1.67 |
| 1434791_at | Atp6v0a2 | BM229554 | 1.03 | 1.50 |
| 1459703_at | D7Ertd443e | BG067408 | 1.03 | 0.55 |
| 1422688_a_at | Nras | BB018528 | 1.03 | 1.61 |
| 1424532_at | Ylpm1 | AB033168 | 1.03 | 1.60 |
| 1448439_at | D17Wsu104e | NM_080837 | 1.03 | 1.59 |
| 1416541_at | Clpb | NM_009191 | 1.03 | 1.43 |
| 1434548_at | Serinc3 | BM244064 | 1.03 | 1.44 |
| 1435590_at | D430047L21Rik | AV325177 | 1.03 | 1.47 |
| 1425803_a_at | Mbd2 | AF072245 | 1.03 | 1.41 |
| 1437788_at | Sp6 | BB473680 | 1.03 | 0.55 |
| 1455945_at | Zfp87 | AV282347 | 1.03 | 1.87 |
| 1441323_at | Qpctl | AV370587 | 1.03 | 1.61 |
| 1417356_at | Peg3 | AB003040 | 1.02 | 1.44 |
| 1424111_at | Igf2r | BG092290 | 1.02 | 1.66 |
| 1433599_at | Baz1a | BM239162 | 1.02 | 3.59 |
| 1416550_at | Slc35b4 | BB320416 | 1.02 | 1.70 |
| 1434506_at | Arid2 | AV273623 | 1.02 | 1.43 |
| 1450850_at | Vil2 | BM119387 | 1.02 | 1.64 |
| 1428623_at | Plxna1 | AK011193 | 1.02 | 1.43 |
| 1450213_at | Pde7b | NM_013875 | 1.02 | 1.46 |
| 1454995_at | Ddah1 | AW556888 | 1.02 | 1.57 |
| 1420011_s_at | Xbp1 | C77390 | 1.02 | 1.48 |
| 1435295_at | Dopey1 | BG075614 | 1.01 | 1.42 |
| 1437467_at | Alcam | AV315205 | 1.01 | 0.71 |
| 1454680_at | D5Ertd579e | BG073020 | 1.01 | 1.41 |
| 1420619_a_at | Aes | NM_010347 | 1.01 | 0.70 |
| 1452690_at | Khsrp | BQ174458 | 1.01 | 0.58 |
| 1460733_at | AA407659 | BB390422 | 1.01 | 1.41 |
| 1433649_at | Aof1 | BM243793 | 0.96 | 1.41 |
| 1428560_at | Xpo5 | AK012248 | 0.96 | 1.67 |
| 1431066_at | Fut11 | BB626220 | 0.96 | 1.61 |
| 1423311_s_at | Tpbg | BQ177165 | 0.96 | 1.56 |
| 1440251_s_at | Zfp64 | BE947768 | 0.96 | 1.45 |
| 1437244_at | Gas2l3 | BB770972 | 0.96 | 1.79 |
| 1437745_at | Chd7 | BB127276 | 0.96 | 1.45 |
| 1418937_at | Dio2 | AF177196 | 0.96 | 1.53 |
| 1437247_at | Fosl2 | BM245170 | 0.96 | 1.43 |
| 1456233_at |  | BB080923 | 0.96 | 1.46 |

TABLE 15-continued

Gene translation changes upon acute cocaine treatment

| Probe | Symbol | GenBank | FCH D1 | FCH D2 |
|---|---|---|---|---|
| 1426733_at | Itpk1 | AW552407 | 0.96 | 1.56 |
| 1452312_at | 2810002D19Rik | BC022909 | 0.96 | 1.75 |
| 1454070_a_at | Ddhd1 | AK014975 | 0.96 | 1.71 |
| 1422502_at | Parp1 | AF126717 | 0.96 | 1.50 |
| 1425987_a_at | Kcnma1 | L16912 | 0.96 | 1.43 |
| 1434737_at | Obfc1 | AV000765 | 0.95 | 1.44 |
| 1425529_s_at | D19Wsu162e | BC026369 | 0.95 | 1.48 |
| 1415685_at | Mtif2 | NM_133767 | 0.95 | 1.52 |
| 1420669_at | Arnt2 | AI428888 | 0.95 | 1.49 |
| 1452292_at | Ap2b1 | AV271093 | 0.95 | 1.44 |
| 1442754_at | C030013G03Rik | BE692283 | 0.95 | 2.35 |
| 1420003_at | Nsun5 | C80273 | 0.95 | 1.48 |
| 1426979_at | Mlxip | AF265663 | 0.95 | 1.42 |
| 1423247_at | Txndc4 | BI100077 | 0.94 | 1.52 |
| 1419669_at | Prtn3 | U97073 | 0.94 | 0.64 |
| 1420886_a_at | Xbp1 | NM_013842 | 0.94 | 1.48 |
| 1416505_at | Nr4a1 | NM_010444 | 0.94 | 0.65 |
| 1426606_at | Crtac1 | BB426194 | 0.94 | 1.78 |
| 1434537_at | Slco3a1 | BM237089 | 0.94 | 1.43 |
| 1428273_at | Abhd13 | BE573480 | 0.93 | 1.53 |
| 1427071_at | Fbxo42 | BC003960 | 0.93 | 1.44 |
| 1435309_at | Rbm13 | AV030795 | 0.93 | 1.80 |
| 1420852_a_at | B3gnt2 | AV306734 | 0.93 | 1.49 |
| 1438236_at | Nfia | BB485864 | 0.93 | 0.64 |
| 1437818_at | 9430016H08Rik | AV228487 | 0.93 | 1.43 |
| 1452963_at | 9530077C05Rik | AK003384 | 0.92 | 1.62 |
| 1455735_at | Ap1s3 | AW259574 | 0.92 | 1.45 |
| 1427510_at | Gnai1 | U38501 | 0.92 | 1.56 |
| 1417878_at | E2f1 | NM_007891 | 0.92 | 0.65 |
| 1428174_x_at | Khsrp | BQ174458 | 0.92 | 0.62 |
| 1426677_at | Flna | BM233746 | 0.92 | 1.45 |
| 1428803_at | Acot6 | AK014558 | 0.92 | 1.43 |
| 1418786_at | Mapk8ip2 | AF220195 | 0.92 | 1.52 |
| 1434023_at | Ccdc100 | BG065282 | 0.92 | 1.41 |
| 1437183_at | Lrrc4b | AW491122 | 0.92 | 1.49 |
| 1454730_at | Tapt1 | AV273867 | 0.92 | 1.41 |
| 1425287_at | Zfp189 | BC021326 | 0.92 | 1.40 |
| 1419224_at | Cecr6 | NM_033567 | 0.91 | 1.40 |
| 1425111_at | Sorcs3 | AK018111 | 0.91 | 1.69 |
| 1451833_a_at | Setdb1 | BC007176 | 0.91 | 1.56 |
| 1418969_at | Skp2 | AV259620 | 0.91 | 2.19 |
| 1453727_at | Esf1 | BB612598 | 0.91 | 1.89 |
| 1454989_at | Cspp1 | AW553463 | 0.91 | 1.68 |
| 1450679_at | 5730470L24Rik | BC004090 | 0.91 | 1.50 |
| 1451033_a_at | Trpc4 | BB271442 | 0.91 | 1.41 |
| 1416521_at | Sepw1 | NM_009156 | 0.84 | 0.56 |
| 1418526_at | Fusip1 | NM_010178 | 0.83 | 1.48 |
| 1454745_at | Arhgap29 | BG074320 | 0.83 | 0.70 |
| 1417528_at | Spag6 | NM_015773 | 0.83 | 1.43 |
| 1459896_at | Pogk | AW911766 | 0.83 | 1.49 |
| 1426546_at | Tesk2 | BQ179435 | 0.83 | 1.66 |
| 1431469_a_at | Cxxc5 | AK015150 | 0.83 | 0.71 |
| 1449365_at | Edg8 | NM_053190 | 0.83 | 1.90 |
| 1426217_at | 2810441K11Rik | AF332866 | 0.82 | 1.74 |
| 1431131_s_at | A630007B06Rik | BI106826 | 0.82 | 1.41 |
| 1439844_at | 8430426J06Rik | BE628126 | 0.82 | 0.70 |
| 1437122_at | Bcl2 | BM119782 | 0.82 | 1.52 |
| 1456026_at | 8030451K01Rik | AV303159 | 0.82 | 1.83 |
| 1418107_at | Tcea2 | NM_009326 | 0.82 | 1.46 |
| 1421137_a_at | Pkib | AV047342 | 0.82 | 2.01 |
| 1419621_at | Ankrd2 | NM_020033 | 0.82 | 2.02 |
| 1454727_at | Afap1l1 | BB106834 | 0.82 | 1.69 |
| 1444395_at | Dixdc1 | AW455436 | 0.82 | 1.77 |
| 1448942_at | Gng11 | NM_025331 | 0.82 | 1.54 |
| 1417400_at | Rai14 | NM_030690 | 0.81 | 1.74 |
| 1416714_at | Irf8 | BG069095 | 0.81 | 1.82 |
| 1430135_at | Dnase2a | AK018651 | 0.81 | 0.70 |
| 1427148_at | Pja2 | BF160731 | 0.81 | 1.44 |
| 1438517_at | Wwox | BB818997 | 0.81 | 1.54 |
| 1428919_at | Fgfr1op | BB667817 | 0.81 | 1.47 |
| 1460623_at | Skap2 | BB753881 | 0.81 | 0.70 |
| 1417384_at | Entpd5 | NM_007647 | 0.81 | 1.61 |
| 1422910_s_at | Smc6 | AU022584 | 0.80 | 1.58 |
| 1460136_at | AW047481 | AI462839 | 0.80 | 1.42 |
| 1423447_at | Clpx | BF020441 | 0.80 | 1.57 |
| 1441055_at | Akap2 | BB431157 | 0.80 | 0.60 |

TABLE 15-continued

Gene translation changes upon acute cocaine treatment

| Probe | Symbol | GenBank | FCH D1 | FCH D2 |
|---|---|---|---|---|
| 1434981_at | E130303B06Rik | AA116393 | 0.80 | 1.57 |
| 1431592_a_at | Sh3kbp1 | AK007283 | 0.79 | 1.56 |
| 1421017_at | Nrg3 | NM_008734 | 0.79 | 1.53 |
| 1460390_at | Sorl1 | BI648081 | 0.79 | 1.53 |
| 1423339_s_at | Ccdc16 | AI530149 | 0.79 | 1.49 |
| 1457816_at | Casp9 | BB781510 | 0.79 | 0.63 |
| 1447359_at | Zfp575 | AI326876 | 0.78 | 0.71 |
| 1417637_a_at | Hmg20b | NM_010440 | 0.78 | 0.61 |
| 1422472_at | Pex13 | BB045429 | 0.78 | 1.45 |
| 1449214_a_at | Opa1 | BC025160 | 0.78 | 1.70 |
| 1443863_at | Fndc3a | AA770704 | 0.78 | 0.64 |
| 1418417_at | Msc | NM_010827 | 0.78 | 1.60 |
| 1429162_at | 1500015A07Rik | AK005240 | 0.78 | 2.31 |
| 1452884_at | Sfrs2ip | AK012092 | 0.78 | 1.64 |
| 1436020_at | D8Ertd457e | AV099356 | 0.77 | 1.59 |
| 1458249_at |  | BB771227 | 0.77 | 1.41 |
| 1424687_at | 2700008B19Rik | BF150550 | 0.77 | 1.47 |
| 1447228_at | 1110051M20Rik | BM248411 | 0.77 | 1.41 |
| 1456859_at | Lnp | BI133590 | 0.77 | 1.65 |
| 1428328_at | Nup50 | AK006556 | 0.76 | 1.41 |
| 1434089_at | Synpo | BB426294 | 0.76 | 1.72 |
| 1458103_at | Ncor1 | AV325208 | 0.76 | 0.69 |
| 1436326_at | Rora | BB306272 | 0.75 | 0.65 |
| 1419309_at | Pdpn | NM_010329 | 0.75 | 1.50 |
| 1456061_at | Gimap8 | BM243674 | 0.71 | 0.91 |
| 1457262_at | 2610207I05Rik | BB024162 | 0.71 | 1.32 |
| 1417204_at | Kdelr2 | AJ278133 | 0.71 | 1.12 |
| 1419789_at | Centg1 | AI605509 | 0.71 | 2.20 |
| 1428903_at | 3110037I16Rik | AK014134 | 0.71 | 0.95 |
| 1449935_a_at | Dnaja3 | AK004575 | 0.71 | 1.13 |
| 1433639_at | 5730593F17Rik | AW548096 | 0.70 | 0.72 |
| 1436388_a_at | 3830406C13Rik | BB763097 | 0.70 | 0.93 |
| 1436581_at | Ccdc39 | BQ174391 | 0.70 | 1.18 |
| 1436875_at | Dnm3 | BB130476 | 0.70 | 1.12 |
| 1453343_s_at | Vrk2 | AK012664 | 0.70 | 1.08 |
| 1424228_at | Polr3h | AK019868 | 0.70 | 0.93 |
| 1426138_a_at | Ube2j2 | AF296656 | 0.70 | 1.13 |
| 1432972_at | 4921518B13Rik | AK014916 | 0.70 | 1.51 |
| 1436833_x_at | Ttll1 | BB251824 | 0.70 | 0.94 |
| 1452721_a_at | Ccdc53 | BM210204 | 0.70 | 0.96 |
| 1418236_s_at | Atg5 | AV168389 | 0.70 | 1.15 |
| 1427098_at | Wwp1 | BI102531 | 0.70 | 0.85 |
| 1429243_at | 1110054O05Rik | BG076073 | 0.70 | 0.95 |
| 1431059_x_at | Htatsf1 | AK012522 | 0.70 | 1.01 |
| 1436099_at | AI836003 | AV294537 | 0.70 | 0.90 |
| 1437591_a_at | Wdr1 | AW542545 | 0.70 | 0.99 |
| 1452880_at | Znhit3 | AK003721 | 0.70 | 0.96 |
| 1425580_a_at | Pik3c3 | BC024675 | 0.70 | 1.24 |
| 1426624_a_at | Ypel3 | BI660196 | 0.70 | 0.89 |
| 1429710_at | Styx | BB812465 | 0.70 | 1.24 |
| 1436456_at | 9130023D20Rik | BQ031896 | 0.70 | 1.34 |
| 1438028_at | 4930535B03Rik | BB817800 | 0.70 | 1.13 |
| 1460609_at | Ints8 | BB224305 | 0.70 | 0.78 |
| 1426078_a_at | Gpr108 | AF376726 | 0.70 | 1.02 |
| 1440895_at | LOC665193 | BB122340 | 0.70 | 0.98 |
| AFFX-r2-Ec-bioC-3_at | "AFFX-R2-EC-BIOC-3" | 0.70 | 0.96 | |
| 1418970_a_at | Bcl10 | AF100339 | 0.70 | 1.02 |
| 1419257_at | Tcea1 | BC006022 | 0.70 | 0.87 |
| 1422857_at | Trip4 | AV350958 | 0.70 | 1.02 |
| 1423191_at | Fnbp4 | AK013152 | 0.70 | 1.18 |
| 1435864_a_at | 1810063B05Rik | BG975168 | 0.70 | 0.89 |
| 1438269_at | Zbtb38 | BB278987 | 0.70 | 0.73 |
| 1456366_at | 1700015F17Rik | BB833901 | 0.70 | 0.82 |
| 1460670_at | Riok3 | NM_024182 | 0.70 | 1.00 |
| 1425203_at | Ddx19b | BE553267 | 0.70 | 0.79 |
| 1428172_at | Prpf39 | BB460975 | 0.70 | 1.21 |
| 1431429_a_at | Arl4a | AK006286 | 0.70 | 1.11 |
| 1436617_at | Cetn4 | AV211098 | 0.70 | 0.92 |
| 1437449_at | Rsad1 | BB818348 | 0.70 | 0.95 |
| 1456884_at | LOC67660 | AI854003 | 0.70 | 0.95 |
| 1419655_at | Tle3 | NM_009389 | 0.70 | 1.40 |
| 1430694_at | Star | BE630656 | 0.70 | 0.94 |
| 1435744_at | 6720401G13Rik | BG075556 | 0.70 | 0.94 |
| 1437202_at | Mysm1 | BB494594 | 0.70 | 1.00 |
| 1449746_s_at | Krr1 | AU020154 | 0.70 | 0.90 |

TABLE 15-continued

Gene translation changes upon acute cocaine treatment

| Probe | Symbol | GenBank | FCH D1 | FCH D2 |
|---|---|---|---|---|
| 1423144_at | Pik3ca | AI528567 | 0.70 | 1.13 |
| 1426879_at | 1190005F20Rik | AK004493 | 0.70 | 1.17 |
| 1426230_at | Sphk2 | AK016616 | 0.68 | 0.81 |
| 1433743_at | Dach1 | BG075820 | 0.68 | 0.82 |
| 1437203_at | Cbll1 | BB460904 | 0.68 | 1.17 |
| 1458951_at | Vrk1 | AV341598 | 0.68 | 1.07 |
| 1421087_at | Per3 | NM_011067 | 0.68 | 0.95 |
| 1455074_at | Efcab1 | AV307860 | 0.68 | 1.31 |
| AFFX-r2-Ec-bioB-3_at | | "AFFX-R2-EC-BIOB-3" | 0.68 | 0.86 |
| 1420053_at | Psmb1 | C81484 | 0.68 | 0.93 |
| 1421097_at | Endog | NM_007931 | 0.68 | 0.97 |
| 1426326_at | Zfp91 | U05343 | 0.68 | 0.99 |
| 1434423_at | Gulp1 | BB138485 | 0.68 | 0.83 |
| 1437866_at | Dusp18 | AV276425 | 0.68 | 1.26 |
| 1418024_at | Narg1 | BG067031 | 0.68 | 1.14 |
| 1430168_at | Cstad | AK020589 | 0.68 | 0.99 |
| 1433720_s_at | Ndg2 | AI647775 | 0.68 | 0.95 |
| 1440060_at | EG331480 | AV306340 | 0.68 | 1.03 |
| 1453754_at | S100pbp | AK015229 | 0.68 | 0.76 |
| 1457232_at | Fbxl21 | BE946365 | 0.68 | 0.93 |
| 1436104_a_at | 2310015A05Rik | BG068839 | 0.68 | 0.93 |
| 1439780_at | Rpl7l1 | BG071958 | 0.67 | 0.56 |
| 1451270_at | Dusp18 | BC020036 | 0.67 | 1.11 |
| 1453993_a_at | Bnip2 | AK014659 | 0.67 | 0.88 |
| 1428635_at | Comtd1 | AK007659 | 0.67 | 0.97 |
| 1433793_s_at | Nrip2 | AW491344 | 0.67 | 0.97 |
| 1439497_at | 4933415E08Rik | BG065013 | 0.67 | 0.68 |
| 1455463_at | Phyhip | BB427286 | 0.67 | 0.76 |
| 1419193_a_at | Gmfg | NM_022024 | 0.67 | 1.00 |
| 1447641_at | Dmwd | AV354897 | 0.67 | 0.91 |
| 1457354_at | Krt222 | AI845957 | 0.67 | 0.83 |
| 1458425_at | Myl6b | BM945176 | 0.67 | 1.04 |
| 1420530_at | Neud4 | AW553317 | 0.67 | 0.80 |
| 1423456_at | Bzw2 | BM932775 | 0.67 | 1.04 |
| 1423477_at | Zic1 | BB361162 | 0.67 | 1.10 |
| 1429914_at | Epc1 | AK017858 | 0.67 | 1.03 |
| 1439699_at | Pgr | BB525237 | 0.67 | 0.84 |
| 1443579_s_at | Depdc6 | AI957118 | 0.67 | 0.96 |
| 1430222_at | 9130007G19Rik | BB538672 | 0.67 | 0.86 |
| 1454086_a_at | Lmo2 | AK013416 | 0.67 | 1.01 |
| 1428659_at | Phf7 | AK005852 | 0.67 | 0.67 |
| 1440202_at | 5930412I24Rik | BB036159 | 0.67 | 1.60 |
| 1440338_at | E430028B21Rik | BM933532 | 0.67 | 0.98 |
| 1417387_at | Med31 | NM_026068 | 0.67 | 0.98 |
| 1423630_at | Cygb | BM899392 | 0.67 | 0.92 |
| 1424486_a_at | Txnrd1 | BB284199 | 0.67 | 0.84 |
| 1434145_s_at | Serhl | C80355 | 0.67 | 1.12 |
| 1435365_at | 4732415M23Rik | BB614874 | 0.67 | 1.07 |
| 1429842_at | Mdh1b | AK007262 | 0.67 | 1.04 |
| 1436796_at | 1110061A14Rik | BB237072 | 0.67 | 1.15 |
| 1451751_at | Ddit4l | AF335325 | 0.67 | 0.95 |
| 1452849_at | Sin3b | AK013202 | 0.67 | 0.87 |
| 1418408_at | Zfand1 | NM_025512 | 0.67 | 1.04 |
| 1430286_s_at | 4930402H24Rik | AK013448 | 0.67 | 0.93 |
| 1437840_s_at | LOC673662 | BB222646 | 0.67 | 1.05 |
| 1446357_at | BC020402 | BB029175 | 0.64 | 1.47 |
| 1447097_at | 8430426H19Rik | BG068083 | 0.64 | 0.88 |
| 1438491_x_at | A530054K11Rik | BF227108 | 0.63 | 1.22 |
| 1448547_at | Rassf3 | BB703307 | 0.63 | 0.85 |
| 1450543_at | Kctd10 | NM_026145 | 0.63 | 0.93 |
| 1423284_at | Mansc1 | AK002644 | 0.63 | 0.99 |
| 1441316_at | LOC677060 | BB234335 | 0.63 | 0.59 |
| 1452594_at | Dusp11 | BB004080 | 0.63 | 1.19 |
| 1428943_at | Nudt13 | BE134119 | 0.63 | 1.05 |
| 1438732_at | 6430511F03 | BE947483 | 0.63 | 1.04 |
| 1453771_at | Gulp1 | BF144687 | 0.63 | 0.92 |
| 1417219_s_at | Tmsb10 | NM_025284 | 0.63 | 0.67 |
| 1424487_x_at | Txnrd1 | BB284199 | 0.63 | 1.09 |
| 1426458_at | Slmap | BB473571 | 0.63 | 0.92 |
| 1448417_at | Ninj1 | NM_013610 | 0.63 | 0.90 |
| 1452161_at | Tiparp | BB707122 | 0.63 | 0.67 |
| 1427030_at | Ccdc52 | BG067674 | 0.63 | 0.83 |
| 1442281_at | D4Ertd796e | BG069783 | 0.63 | 0.86 |
| 1451677_at | Narf | BI452475 | 0.63 | 1.02 |

TABLE 15-continued

Gene translation changes upon acute cocaine treatment

| Probe | Symbol | GenBank | FCH D1 | FCH D2 |
|---|---|---|---|---|
| 1429040_at | 6820431F20Rik | BE692399 | 0.63 | 1.33 |
| 1416661_at | Eif3s10 | AW701127 | 0.63 | 1.18 |
| 1421479_at | Zfp318 | NM_021346 | 0.62 | 0.78 |
| 1452187_at | Rbm5 | BB541007 | 0.62 | 1.32 |
| 1456120_at | 3110001I20Rik | BB427489 | 0.62 | 0.95 |
| 1428863_at | Ankrd39 | AK018681 | 0.62 | 1.00 |
| 1457038_at | Frem2 | BM201912 | 0.62 | 1.71 |
| 1457072_at | Bcl11a | BF731393 | 0.62 | 1.04 |
| 1419924_at | Fnip1 | AW557298 | 0.62 | 1.60 |
| 1425927_a_at | Atf5 | AF375476 | 0.62 | 1.00 |
| 1426832_at | Ddx26b | BB460424 | 0.62 | 1.08 |
| 1454777_at | Slco2b1 | BB553107 | 0.62 | 0.92 |
| 1418323_at | Fem1b | BM232562 | 0.61 | 1.13 |
| 1425309_at | Catsper2 | AF411816 | 0.61 | 0.98 |
| 1456517_at | Tmem44 | BB035891 | 0.61 | 0.92 |
| 1429260_at | 1810014B01Rik | AW985991 | 0.61 | 1.07 |
| 1445099_at | | BB383493 | 0.61 | 1.01 |
| 1452474_a_at | Art3 | AJ311773 | 0.61 | 1.07 |
| 1439073_at | Mllt4 | BB821719 | 0.61 | 1.20 |
| 1438481_at | AW047464 | AI854375 | 0.61 | 0.88 |
| 1442024_at | Ppp1r3e | BB328892 | 0.61 | 0.98 |
| 1453591_at | 5730437N04Rik | AK017626 | 0.61 | 1.06 |
| 1418894_s_at | Pbx2 | NM_017463 | 0.61 | 0.97 |
| 1440756_at | | BB712642 | 0.61 | 0.82 |
| 1456419_at | 5730455P16Rik | BI108098 | 0.61 | 0.87 |
| 1437305_at | Zfp770 | AV296864 | 0.60 | 0.98 |
| 1438928_x_at | Ninj1 | BB252065 | 0.60 | 0.82 |
| 1424117_at | BC056474 | BC024937 | 0.60 | 0.99 |
| 1454830_at | Fbn2 | AV010392 | 0.60 | 1.05 |
| 1458353_at | Nwd1 | BB173301 | 0.60 | 0.93 |
| 1427456_at | Wdfy3 | BF150771 | 0.60 | 1.09 |
| 1426421_s_at | Rbm26 | AK005802 | 0.60 | 1.39 |
| 1454174_a_at | C330007P06Rik | AK021190 | 0.60 | 2.16 |
| 1423353_at | Crispld1 | BE693025 | 0.60 | 0.90 |
| 1437108_at | Lsm6 | BE949068 | 0.60 | 0.88 |
| 1437884_at | Arl5b | BB545273 | 0.60 | 0.85 |
| 1435351_at | 2310026E23Rik | AA189197 | 0.55 | 1.25 |
| 1429984_at | 5730455O13Rik | AK017666 | 0.55 | 1.14 |
| 1447476_at | Abcc10 | BB079952 | 0.55 | 0.56 |
| 1419390_at | Pde10a | BQ180352 | 0.55 | 0.87 |
| 1442927_at | Ptk2b | BB548690 | 0.55 | 1.40 |
| 1418707_at | Bag4 | NM_026121 | 0.55 | 1.58 |
| 1457625_s_at | Cdkl2 | BE979937 | 0.55 | 1.12 |
| 1456333_a_at | Arhgap6 | BB367529 | 0.54 | 0.93 |
| 1442588_at | EG329217 | BB117375 | 0.53 | 0.80 |
| 1458438_at | Ccdc122 | AW554226 | 0.53 | 0.94 |
| 1441106_at | Zfand5 | BB320444 | 0.52 | 1.11 |
| 1447809_x_at | | BB080932 | 0.52 | 1.41 |
| 1452473_at | Prr15 | AJ132433 | 0.51 | 0.58 |
| 1453309_at | 9330179D12Rik | BB749938 | 0.51 | 0.70 |
| 1426478_at | Rasa1 | AA124924 | 0.51 | 1.36 |
| 1449669_at | Rabif | AW549708 | 0.51 | 0.91 |
| 1458397_at | Dnaja1 | BB260315 | 0.50 | 0.93 |
| 1449141_at | Fblim1 | BG070068 | 0.49 | 0.80 |
| 1444141_at | Snx13 | BB828008 | 0.49 | 1.95 |
| 1420533_at | Gucy1a3 | AK004815 | 0.49 | 0.92 |
| 1445165_at | 1200003I07Rik | BM194850 | 0.48 | 0.91 |
| 1460285_at | Itga9 | NM_133721 | 0.46 | 1.44 |
| 1426612_at | Tipin | AK011357 | 0.45 | 0.84 |
| 1441871_at | 1810044D09Rik | AV057045 | 0.45 | 1.12 |
| 1419230_at | A830036E02Rik | NM_010661 | 0.43 | 1.03 |
| 1441123_at | ORF34 | BB023801 | 0.43 | 1.41 |
| 1449388_at | Thbs4 | NM_011582 | 0.41 | 2.16 |

Probe = Affymetrix probe identification; Symbol = official gene symbol; FCH D1 = fold change in striatonigral (D1) cells; FCH D2 = fold change in striatopallidal (D2) cells.

TABLE 16

Gene translation changes upon chronic cocaine treatment

| Probe | Symbol | GenBank | FCH D1 | FCH D2 |
|---|---|---|---|---|
| 1430648_at | Scn2b | AK013326 | 12.83 | 0.60 |
| 1455799_at | Rorb | BB751387 | 3.11 | 1.93 |
| 1445081_at | A930041I02Rik | BB335888 | 3.02 | 1.23 |
| 1452906_at | Gtl2 | BE990468 | 2.92 | 0.51 |
| 1448606_at | Edg2 | U70622 | 2.86 | 1.04 |
| 1442061_at | Btbd7 | BB199960 | 2.60 | 1.60 |
| 1421978_at | Gad2 | AF326550 | 2.56 | 0.76 |
| 1426458_at | Slmap | BB473571 | 2.50 | 0.79 |
| 1432558_a_at | Mal | AK019046 | 2.50 | 0.82 |
| 1433599_at | Baz1a | BM239162 | 2.48 | 2.03 |
| 1417029_a_at | Trim2 | BB283676 | 2.45 | 1.80 |
| 1438388_at | Nxph1 | BB078029 | 2.45 | 0.77 |
| 1418189_s_at | Ramp2 | AF146523 | 2.42 | 0.99 |
| 1429769_at | Pggt1b | BI107300 | 2.39 | 0.83 |
| 1457077_at |  | BB306048 | 2.37 | 1.49 |
| 1438702_at | Flrt2 | BG075699 | 2.35 | 1.05 |
| 1418188_a_at | Ramp2 | AF146523 | 2.34 | 1.16 |
| 1425693_at | Braf | M64429 | 2.32 | 1.10 |
| 1418937_at | Dio2 | AF177196 | 2.30 | 0.88 |
| 1446981_at | A830010M20Rik | BB127813 | 2.30 | 0.99 |
| 1435635_at | Pcmtd1 | BB549335 | 2.29 | 0.63 |
| 1424708_at | Tmed10 | BI409239 | 2.27 | 1.20 |
| 1448944_at | Nrp1 | AK011144 | 2.26 | 1.91 |
| 1434393_at | Usp34 | BM235696 | 2.23 | 1.35 |
| 1421090_at | Epb4.1l1 | NM_013510 | 2.21 | 1.10 |
| 1460330_at | Anxa3 | AW702161 | 2.19 | 1.43 |
| 1429256_at | Gtl2 | AU067739 | 2.17 | 0.88 |
| 1427464_s_at | Hspa5 | AJ002387 | 2.16 | 1.44 |
| 1436898_at | Sfpq | BI738328 | 2.14 | 1.33 |
| 1455607_at | Rspo3 | BG072958 | 2.12 | 0.97 |
| 1428306_at | Ddit4 | AK017926 | 2.10 | 0.26 |
| 1440282_at | Tulp4 | BB268998 | 2.10 | 1.78 |
| 1454950_at | B930006L02Rik | BB699417 | 2.10 | 0.94 |
| 1417602_at | Per2 | AF035830 | 2.07 | 2.79 |
| 1421970_a_at | Gria2 | NM_013540 | 2.07 | 0.79 |
| 1454655_at | Dgkd | BB094429 | 2.07 | 1.58 |
| 1452507_at | Dlx6 | AF022078 | 2.04 | 0.57 |
| 1419029_at | Ero1l | BM234652 | 2.04 | 1.07 |
| 1455182_at | Kif1b | AV104668 | 2.02 | 1.10 |
| 1450760_a_at | Ing3 | BB020556 | 2.01 | 0.61 |
| 1417604_at | Camk1 | NM_133926 | 2.00 | 1.33 |
| 1418350_at | Hbegf | L07264 | 1.99 | 1.32 |
| 1449372_at | Dnajc3 | BE624323 | 1.99 | 0.88 |
| 1446147_at |  | BB436856 | 1.98 | 0.69 |
| 1429095_at | Cenpp | AK006234 | 1.97 | 0.84 |
| 1428157_at | Gng2 | AV021455 | 1.97 | 1.02 |
| 1455831_at | Fus | BE985138 | 1.97 | 0.70 |
| 1424186_at | Ccdc80 | BG074158 | 1.95 | 1.24 |
| 1428112_at | Armet | AK014338 | 1.95 | 1.53 |
| 1417110_at | Man1a | BB070019 | 1.95 | 1.64 |
| 1448545_at | Sdc2 | AU021035 | 1.94 | 0.98 |
| 1452089_at | Cacnb4 | AW106929 | 1.94 | 0.88 |
| 1450708_at | Scg2 | NM_009129 | 1.94 | 1.24 |
| 1426340_at | Slc1a3 | BB357585 | 1.94 | 1.42 |
| 1448115_at | Htf9c | NM_008307 | 1.93 | 0.97 |
| 1424486_a_at | Txnrd1 | BB284199 | 1.92 | 1.10 |
| 1442695_at | C030007I01Rik | AW494399 | 1.91 | 1.41 |
| 1418322_at | Crem | AI467599 | 1.91 | 1.84 |
| 1453796_a_at | Ergic2 | AK016275 | 1.90 | 0.69 |
| 1437122_at | Bcl2 | BM119782 | 1.90 | 1.66 |
| 1420886_a_at | Xbp1 | NM_013842 | 1.90 | 1.27 |
| 1420011_s_at | Xbp1 | C77390 | 1.89 | 1.19 |
| 1421354_at | Prkg2 | NM_008926 | 1.89 | 0.59 |
| 1443846_x_at | Pank2 | BB402666 | 1.88 | 0.39 |
| 1428600_at | Nin | AK014241 | 1.88 | 1.04 |
| 1422134_at | Fosb | NM_008036 | 1.88 | 1.16 |
| 1449870_a_at | Atp6v0a2 | NM_011596 | 1.88 | 1.08 |
| 1420720_at | Nptx2 | NM_016789 | 1.86 | 1.73 |
| 1449552_at | Zfr | NM_011767 | 1.86 | 0.60 |
| 1452754_at | Creld2 | AK017880 | 1.86 | 1.41 |
| 1443579_s_at | Depdc6 | AI957118 | 1.84 | 0.61 |
| 1434674_at | Lyst | BB463428 | 1.84 | 1.23 |
| 1439780_at | Rpl7l1 | BG071958 | 1.84 | 0.81 |
| 1418380_at | Terf1 | NM_009352 | 1.84 | 0.92 |
| 1448943_at | Nrp1 | AK011144 | 1.83 | 1.16 |
| 1455403_at | Manea | BB035197 | 1.83 | 0.97 |
| 1440371_at |  | BQ176223 | 1.82 | 1.07 |
| 1436387_at | Homer1 | BB398124 | 1.82 | 1.91 |
| 1438458_a_at | Sfpq | BF224766 | 1.82 | 1.21 |
| 1428130_at | Lman1 | BG071597 | 1.82 | 1.42 |
| 1449289_a_at | B2m | BF715219 | 1.82 | 1.50 |
| 1433595_at | Slc35d1 | BB409668 | 1.82 | 1.34 |
| 1417011_at | Man1a | BB070019 | 1.82 | 1.31 |
| 1437433_at | B3galt2 | BB254922 | 1.82 | 0.97 |
| 1434913_at | Hmgcll1 | BF471959 | 1.81 | 0.72 |
| 1435770_at | Txndc13 | BB215068 | 1.81 | 1.03 |
| 1425942_a_at | Gpm6b | AF254879 | 1.81 | 0.99 |
| 1416447_at | Tmem30a | BE986812 | 1.80 | 0.97 |
| 1454158_at | Mpp7 | AK012883 | 1.80 | 1.19 |
| 1416064_a_at | Hspa5 | NM_022310 | 1.80 | 1.54 |
| 1417812_at | Lamb3 | NM_008484 | 1.80 | 0.95 |
| 1450029_s_at | Itga9 | NM_133721 | 1.79 | 1.14 |
| 1429718_at | Slitrk5 | BB782729 | 1.79 | 1.11 |
| 1437002_at | C030011O14Rik | BB303443 | 1.79 | 1.18 |
| 1421189_at | Gabrb3 | BB367779 | 1.79 | 0.99 |
| 1420502_at | Sat1 | NM_009121 | 1.78 | 1.07 |
| 1433582_at | 1190002N15Rik | AV309085 | 1.78 | 1.29 |
| 1423363_at | Sort1 | AV247637 | 1.78 | 1.17 |
| 1417875_at | Ddx50 | NM_053183 | 1.78 | 0.93 |
| 1434673_at | Gpr22 | BB429977 | 1.78 | 0.53 |
| 1424028_at | 5830457O10Rik | BC023107 | 1.78 | 0.49 |
| 1421116_a_at | Rtn4 | NM_024226 | 1.77 | 0.78 |
| 1428484_at | Osbpl3 | AK004768 | 1.77 | 1.73 |
| 1426951_at | Crim1 | AK018666 | 1.77 | 1.15 |
| 1437857_at | Dpy19l3 | AV367203 | 1.77 | 1.51 |
| 1420850_at | Crnkl1 | AV143435 | 1.76 | 0.80 |
| 1423066_at | Dnmt3a | BB795491 | 1.76 | 1.38 |
| 1448008_at | Ankhd1 | BG081523 | 1.76 | 1.31 |
| 1421961_a_at | Dnajb5 | AI664344 | 1.76 | 1.31 |
| 1460705_at | Rps6kb1 | AI451506 | 1.76 | 0.85 |
| 1428361_x_at | Hba-a1 | AK011116 | 1.76 | 1.22 |
| 1423720_a_at | Sar1a | BC005549 | 1.75 | 0.96 |
| 1425130_a_at | Ptpn5 | U28216 | 1.75 | 0.87 |
| 1450208_a_at | Elmo1 | NM_080288 | 1.74 | 1.34 |
| 1438578_a_at | Btbd10 | BG064119 | 1.74 | 1.17 |
| 1436661_at | Dpp10 | BQ174532 | 1.74 | 1.28 |
| 1435471_at | Zfp708 | BE994129 | 1.74 | 0.57 |
| 1453238_s_at | A130040M12Rik | AU018141 | 1.74 | 1.68 |
| 1428946_at | Ube1l2 | BB417360 | 1.74 | 0.76 |
| 1452377_at | Mll1 | AK017541 | 1.73 | 1.16 |
| 1439434_x_at | Pcmt1 | BB317673 | 1.73 | 1.04 |
| 1438796_at | Nr4a3 | BE692107 | 1.73 | 1.85 |
| 1426326_at | Zfp91 | U05343 | 1.73 | 1.14 |
| 1419228_at | Elac1 | NM_028983 | 1.72 | 1.48 |
| 1419647_a_at | Ier3 | NM_133662 | 1.72 | 1.08 |
| 1442887_at | Gpr39 | BQ175060 | 1.71 | 1.05 |
| 1456137_at | Nrxn3 | BB132137 | 1.71 | 0.68 |
| 1428834_at | Dusp4 | AK012530 | 1.71 | 1.84 |
| 1435520_at | Msi2 | BQ174527 | 1.71 | 1.58 |
| 1449164_at | Cd68 | BC021637 | 1.71 | 1.69 |
| 1459750_s_at | Gpr123 | AU015577 | 1.71 | 1.25 |
| 1436343_at | Chd4 | BM502696 | 1.70 | 1.37 |
| 1420048_at | C78859 | C78859 | 1.70 | 0.94 |
| 1456769_at | Dusp3 | BQ266434 | 1.70 | 1.37 |
| 1451311_a_at | Adipor1 | BC014875 | 1.70 | 0.97 |
| 1455085_at | 1700086L19Rik | BI526033 | 1.69 | 1.19 |
| 1430869_at | Habp4 | BF460630 | 1.69 | 0.96 |
| 1427256_at | Vcan | BM251152 | 1.69 | 1.32 |
| 1437667_a_at | Bach2 | AW553304 | 1.68 | 2.26 |
| 1454920_at | Uhrf2 | BQ266387 | 1.68 | 1.28 |
| 1426736_at | Gspt1 | AB003502 | 1.68 | 1.10 |
| 1415986_at | Clcn4-2 | NM_011334 | 1.68 | 1.04 |
| 1437339_s_at | Pcsk5 | BB241731 | 1.68 | 1.48 |
| 1428967_at | Igf1r | BB446952 | 1.67 | 1.38 |
| 1457142_at | Efcbp1 | BB667731 | 1.67 | 1.20 |
| 1422886_a_at | Clk4 | NM_007714 | 1.67 | 0.66 |
| 1422579_at | Hspe1 | NM_008303 | 1.66 | 0.98 |
| 1439333_at | Kcnv1 | BB078927 | 1.66 | 0.80 |
| 1448701_a_at | Krit1 | AF310134 | 1.66 | 1.12 |
| 1421900_at | Eif2ak1 | BB077436 | 1.66 | 0.85 |

TABLE 16-continued

Gene translation changes upon chronic cocaine treatment

| Probe | Symbol | GenBank | FCH D1 | FCH D2 |
|---|---|---|---|---|
| 1452237_at | Hrb | BB130716 | 1.65 | 1.18 |
| 1429159_at | Itih5 | AK018605 | 1.65 | 0.95 |
| 1416714_at | Irf8 | BG069095 | 1.64 | 1.32 |
| 1428142_at | Etv5 | AK003461 | 1.64 | 1.63 |
| 1436094_at | Vgf | BF458396 | 1.64 | 1.57 |
| 1452168_x_at | Gspt1 | AB003502 | 1.64 | 1.29 |
| 1456964_at | Rbm12 | BB104271 | 1.63 | 0.76 |
| 1424686_at | 2700008B19Rik | BF150550 | 1.63 | 0.96 |
| 1449342_at | Ptplb | NM_023587 | 1.63 | 0.94 |
| 1423314_s_at | Pde7a | BG070255 | 1.63 | 1.47 |
| 1430520_at | Cpne8 | AW548480 | 1.63 | 0.47 |
| 1439293_at | BC031353 | BB369212 | 1.63 | 0.87 |
| 1426934_at | Nhsl1 | BC013565 | 1.63 | 1.44 |
| 1429249_at | 4833424O15Rik | BB346520 | 1.63 | 1.19 |
| 1436645_a_at | Cnot4 | BB066603 | 1.62 | 1.04 |
| 1459858_x_at | Crtac1 | AV354465 | 1.62 | 1.11 |
| 1437114_at | A930001N09Rik | AV230892 | 1.62 | 1.10 |
| 1441197_at | 9530059O14Rik | AW494454 | 1.62 | 1.47 |
| 1442212_at | Cpd | BB519218 | 1.62 | 1.36 |
| 1449799_s_at | Pkp2 | AA516617 | 1.62 | 1.53 |
| 1420947_at | Atrx | BB825830 | 1.62 | 0.51 |
| 1434228_at | Ppm2c | AV255921 | 1.62 | 1.09 |
| 1427470_s_at | Napb | AU067119 | 1.62 | 0.88 |
| 1430511_at | 1500037O19Rik | AK005367 | 1.62 | 1.15 |
| 1443017_at | Cpeb2 | BB235708 | 1.61 | 1.11 |
| 1417404_at | Elovl6 | NM_130450 | 1.61 | 1.30 |
| 1419211_s_at | 4933424B01Rik | NM_138757 | 1.61 | 1.03 |
| 1423162_s_at | Spred1 | BQ044290 | 1.61 | 1.39 |
| 1448669_at | Dkk3 | AK004853 | 1.61 | 1.42 |
| 1428999_at | Phf3 | AK010013 | 1.61 | 0.79 |
| 1440891_at | Gria4 | AV336506 | 1.61 | 1.49 |
| 1434883_at | Mtdh | AV083741 | 1.61 | 0.82 |
| 1421815_at | Epdr1 | AF353717 | 1.60 | 1.63 |
| 1417416_at | Kcna1 | NM_010595 | 1.60 | 1.12 |
| 1433887_at | Dnajc3 | AV024539 | 1.60 | 1.24 |
| 1420580_at | 4930429B21Rik | NM_026249 | 1.60 | 0.91 |
| 1435250_at | Ints8 | BB206299 | 1.60 | 1.39 |
| 1421768_a_at | Homer1 | NM_011982 | 1.60 | 0.96 |
| 1417977_at | Eif4e3 | BC027014 | 1.60 | 0.83 |
| 1419988_at | Map3k7 | C87327 | 1.60 | 1.12 |
| 1421346_at | Slc6a6 | NM_009320 | 1.60 | 1.04 |
| 1428344_at | Ppapdc2 | BB229589 | 1.60 | 1.25 |
| 1439661_at | Slc16a14 | BB426676 | 1.59 | 0.86 |
| 1419110_at | Riok1 | BM228482 | 1.59 | 0.78 |
| 1415957_a_at | Nnp1 | AV297071 | 1.59 | 0.83 |
| 1416479_a_at | Tmem14c | NM_025387 | 1.59 | 0.68 |
| 1430274_a_at | Stard3nl | AK018331 | 1.59 | 1.01 |
| 1450213_at | Pde7b | NM_013875 | 1.59 | 1.52 |
| 1419650_at | Zfr | NM_011767 | 1.59 | 0.88 |
| 1420838_at | Ntrk2 | AK018789 | 1.59 | 1.58 |
| 1428461_at | Ppp2r5e | BB535888 | 1.59 | 1.12 |
| 1436763_a_at | Klf9 | AI267126 | 1.59 | 0.84 |
| 1417818_at | Wwtr1 | BC014727 | 1.58 | 0.97 |
| 1436051_at | Myo5a | BQ174518 | 1.58 | 0.95 |
| 1434421_at | Islr2 | BB344549 | 1.58 | 0.51 |
| 1430667_at | Pcdh10 | BB077413 | 1.58 | 1.16 |
| 1435158_at | Rbm12b | BB796313 | 1.58 | 1.80 |
| 1418104_at | Nrip3 | NM_020610 | 1.58 | 0.58 |
| 1416093_a_at | Mrpl20 | NM_025570 | 1.58 | 1.17 |
| 1426187_a_at | Hax1 | AF465243 | 1.58 | 1.16 |
| 1439605_at |  | BB464198 | 1.58 | 0.69 |
| 1425660_at | Btbd3 | BC018174 | 1.57 | 2.19 |
| 1423294_at | Mest | AW555393 | 1.57 | 1.22 |
| 1416085_s_at | Zfand5 | AA124553 | 1.57 | 1.11 |
| 1421280_at | Gabra1 | Z36357 | 1.57 | 0.66 |
| 1424405_at | Mbip | BC002277 | 1.57 | 0.90 |
| 1453020_at | 1810048J11Rik | AK007829 | 1.57 | 1.05 |
| 1428920_at | Hmg20a | AI987819 | 1.57 | 1.13 |
| 1450247_a_at | Scamp5 | NM_020270 | 1.57 | 0.89 |
| 1456796_at | Snai3 | BB238756 | 1.57 | 1.13 |
| 1438682_at | Pik3r1 | BB426164 | 1.56 | 1.00 |
| 1439900_at | Thtpa | BB308405 | 1.56 | 1.55 |
| 1423648_at | Pdia6 | BC006865 | 1.55 | 1.07 |
| 1434246_at | L3mbtl3 | BB022070 | 1.55 | 1.08 |
| 1427358_a_at | Dapk1 | BC026671 | 1.55 | 0.80 |
| 1435357_at | D4Wsu53e | BE652553 | 1.55 | 1.13 |
| 1460440_at | Lphn3 | BE945410 | 1.55 | 1.04 |
| 1424342_at | Fyttd1 | BC010204 | 1.55 | 1.08 |
| 1425608_at | Dusp3 | BC016269 | 1.55 | 1.18 |
| 1426824_at | Psme4 | BM195254 | 1.55 | 1.10 |
| 1424532_at | Ylpm1 | AB033168 | 1.55 | 1.14 |
| 1426490_at | Bfar | AK013874 | 1.55 | 0.69 |
| 1424350_s_at | Lpgat1 | BE987427 | 1.55 | 1.20 |
| 1457277_at | BC038925 | AI314927 | 1.55 | 1.14 |
| 1435641_at | 9530018I07Rik | BB109391 | 1.55 | 1.27 |
| 1422553_at | Pten | AA214868 | 1.55 | 1.10 |
| 1455009_at | Cpd | AW550842 | 1.55 | 1.19 |
| 1433581_at | 1190002N15Rik | AV309085 | 1.54 | 1.21 |
| 1419256_at | Spnb2 | BM213516 | 1.54 | 1.22 |
| 1428793_at | Slc36a1 | AK017918 | 1.54 | 1.20 |
| 1418772_at | BC016423 | NM_134063 | 1.54 | 0.75 |
| 1423247_at | Txndc4 | BI100077 | 1.54 | 0.95 |
| 1434283_at | Arid5b | BB079486 | 1.54 | 1.60 |
| 1424089_a_at | Tcf4 | U16321 | 1.53 | 1.13 |
| 1426023_a_at | Rabep1 | AF248489 | 1.53 | 1.04 |
| 1441603_at | Sstr3 | BQ174132 | 1.53 | 1.86 |
| 1443969_at | Irs2 | BE199054 | 1.53 | 1.20 |
| 1450011_at | Hsd17b12 | AK012103 | 1.53 | 1.03 |
| 1454816_at | Rp2h | BB431808 | 1.53 | 0.48 |
| 1424244_at | Rwdd4a | AK005797 | 1.53 | 1.30 |
| 1425014_at | Nr2c2 | AU066920 | 1.53 | 1.11 |
| 1425713_a_at | Rnf146 | BC019182 | 1.53 | 1.30 |
| 1450184_s_at | Tef | NM_017376 | 1.53 | 1.00 |
| 1439764_s_at | Igf2bp2 | BB098431 | 1.53 | 1.20 |
| 1438473_at | Arl15 | BB445175 | 1.53 | 0.97 |
| 1440886_at | Cdc37l1 | BE949427 | 1.53 | 1.65 |
| 1451622_at | Lmbrd1 | BM206793 | 1.53 | 1.21 |
| 1429265_a_at | Rnf130 | AK011088 | 1.53 | 0.93 |
| 1420514_at | Tmem47 | NM_138751 | 1.52 | 1.12 |
| 1419444_at | Sap18 | NM_009119 | 1.52 | 1.11 |
| 1421867_at | Nr3c1 | NM_008173 | 1.52 | 0.94 |
| 1455020_at | Snx25 | AV351081 | 1.52 | 1.14 |
| 1427311_at | Bptf | BB380312 | 1.52 | 1.07 |
| 1451018_at | Leprotl1 | BF658789 | 1.52 | 1.15 |
| 1420833_at | Vamp2 | BG871810 | 1.52 | 1.26 |
| 1450174_at | Ptprt | NM_021464 | 1.52 | 1.25 |
| 1425563_s_at | Pcdh10 | AF334801 | 1.51 | 1.48 |
| 1428523_at | Lphn3 | BE945410 | 1.51 | 0.98 |
| 1450907_at | Spcs2 | BI078449 | 1.51 | 0.86 |
| 1437318_at | Pak3 | BB468082 | 1.51 | 0.99 |
| 1448896_at | Pigf | NM_008838 | 1.51 | 1.08 |
| 1422607_at | Etv1 | NM_007960 | 1.51 | 1.36 |
| 1452757_s_at | Hba-a1 | AK011116 | 1.51 | 1.16 |
| 1423060_at | Pa2g4 | BM232515 | 1.51 | 0.79 |
| 1438407_at | Dsel | AV336691 | 1.51 | 0.95 |
| 1426301_at | Alcam | U95030 | 1.51 | 0.58 |
| 1450668_s_at | Hspe1 | NM_008303 | 1.50 | 1.07 |
| 1418318_at | Rnf128 | AK004847 | 1.50 | 0.88 |
| 1429857_at | Pou3f3 | BB807002 | 1.50 | 1.22 |
| 1453380_a_at | Xrcc6bp1 | AK010471 | 1.50 | 1.57 |
| 1426258_at | Sorl1 | BI648081 | 1.50 | 1.13 |
| 1432287_a_at | Sntg1 | AK016927 | 1.50 | 0.92 |
| 1419035_s_at | Csnk2a1 | BB283759 | 1.50 | 1.08 |
| 1425929_a_at | Rnf14 | AF249668 | 1.50 | 1.06 |
| 1447771_at |  | AW050081 | 1.50 | 0.49 |
| 1450120_at | Scn1a | AV336781 | 1.50 | 1.12 |
| 1460061_at | Adra1a | AV342748 | 1.50 | 1.06 |
| 1421353_at | Pde7b | NM_013875 | 1.50 | 1.29 |
| 1431094_at | 1110006E14Rik | AK003491 | 1.50 | 0.81 |
| 1434937_at | Phr1 | AW546647 | 1.50 | 0.96 |
| 1429330_at | Gabra4 | AK013727 | 1.50 | 0.95 |
| 1450051_at | Atrx | BB825830 | 1.50 | 0.86 |
| 1452714_at | Tanc1 | AK004560 | 1.49 | 1.07 |
| 1427988_s_at | Safb2 | BM239918 | 1.49 | 1.30 |
| 1452335_at | 2810423E13Rik | AV024565 | 1.49 | 0.72 |
| 1429045_at | Smurf2 | BI697997 | 1.49 | 1.09 |
| 1436451_a_at | Tmed2 | AW824211 | 1.49 | 1.06 |
| 1425132_at | Neto1 | AF448840 | 1.49 | 1.15 |
| 1435226_at | Ibrdc3 | BG064140 | 1.49 | 1.23 |
| 1430780_a_at | Pmm1 | BI739353 | 1.49 | 0.80 |

TABLE 16-continued

Gene translation changes upon chronic cocaine treatment

| Probe | Symbol | GenBank | FCH D1 | FCH D2 |
|---|---|---|---|---|
| 1434736_at | Hlf | BB744589 | 1.49 | 1.21 |
| 1437481_at | 1110039F03Rik | AV032349 | 1.49 | 0.93 |
| 1426300_at | Alcam | U95030 | 1.49 | 0.84 |
| 1434386_at | Atp2c1 | BM225269 | 1.49 | 1.11 |
| 1434206_s_at | Ppp2r5c | BM247370 | 1.48 | 1.34 |
| 1437560_at | Ntrk2 | BQ174783 | 1.48 | 1.26 |
| 1450569_a_at | Rbm14 | NM_019869 | 1.48 | 1.22 |
| 1448346_at | Cfl1 | NM_007687 | 1.48 | 0.97 |
| 1455365_at | Cdh8 | BB426483 | 1.48 | 1.04 |
| 1426455_at | Sdccag10 | AK014025 | 1.48 | 0.84 |
| 1426397_at | Tgfbr2 | BG793483 | 1.48 | 1.37 |
| 1433772_at | Stch | BE650268 | 1.48 | 1.23 |
| 1451147_x_at | Csdc2 | BC016109 | 1.48 | 1.38 |
| 1450744_at | Ell2 | NM_138953 | 1.48 | 0.92 |
| 1423503_at | Jam3 | AK017692 | 1.47 | 1.32 |
| 1448376_at | Wrnip1 | NM_030215 | 1.47 | 1.11 |
| 1419580_at | Dlg4 | AI646416 | 1.47 | 0.58 |
| 1424749_at | Wdfy1 | BC025226 | 1.47 | 1.32 |
| 1427427_at | Ryr3 | AV238793 | 1.47 | 1.13 |
| 1431020_a_at | Fgfr1op2 | AK008983 | 1.47 | 0.95 |
| 1416123_at | Ccnd2 | NM_009829 | 1.47 | 1.55 |
| 1422621_at | Ranbp2 | BM507707 | 1.47 | 1.53 |
| 1434877_at | Nptx1 | AI152800 | 1.47 | 1.19 |
| 1420849_at | Crnkl1 | AV143435 | 1.47 | 1.06 |
| 1420661_a_at | 4933439F18Rik | NM_025757 | 1.47 | 1.64 |
| 1426491_at | Herc2 | AW701798 | 1.47 | 1.43 |
| 1428998_at | Phf3 | AK010013 | 1.47 | 0.93 |
| 1444015_at | Papola | AV307016 | 1.47 | 0.76 |
| 1434353_at | Sfmbt2 | BM200222 | 1.46 | 0.55 |
| 1417538_at | Slc35a1 | NM_011895 | 1.46 | 0.84 |
| 1445843_at |  | BE199465 | 1.46 | 0.82 |
| 1419914_s_at | D10Ertd438e | AW538011 | 1.46 | 1.25 |
| 1436788_at | Acp2 | AI131584 | 1.46 | 1.04 |
| 1419392_at | Pclo | NM_011995 | 1.46 | 1.14 |
| 1421990_at | Syt1 | NM_009306 | 1.46 | 1.30 |
| 1416133_at | C920006C10Rik | BB188557 | 1.46 | 1.18 |
| 1416726_s_at | Ube2s | NM_133777 | 1.46 | 0.97 |
| 1417924_at | Pak3 | BQ174935 | 1.46 | 1.12 |
| 1420165_s_at | Dnajc17 | N28111 | 1.46 | 0.90 |
| 1418084_at | Nrp1 | AK011144 | 1.46 | 1.60 |
| 1423753_at | Bambi | AF153440 | 1.46 | 0.94 |
| 1430134_a_at | Yars2 | AK008774 | 1.46 | 1.19 |
| 1425060_s_at | Clip1 | BG969810 | 1.45 | 1.15 |
| 1425855_a_at | Crk | AF239673 | 1.45 | 1.05 |
| 1428620_at | Ensa | BF584204 | 1.45 | 1.24 |
| 1417878_at | E2f1 | NM_007891 | 1.45 | 1.33 |
| 1429336_at | Tmem87b | BB161454 | 1.45 | 0.97 |
| 1423211_at | Nola3 | AK004120 | 1.45 | 1.09 |
| 1460336_at | Ppargc1a | BB745167 | 1.45 | 0.95 |
| 1416266_at | Pdyn | AF026537 | 1.45 | 1.76 |
| 1437366_at | AI608492 | BB332542 | 1.45 | 1.02 |
| 1438452_at | Nebl | BM121794 | 1.45 | 0.86 |
| 1452894_at | Elavl4 | AK013588 | 1.45 | 0.54 |
| 1426885_a_at | Cdk2ap1 | AK004852 | 1.45 | 1.06 |
| 1424886_at | Ptprd | BC025145 | 1.45 | 0.94 |
| 1434956_at | AI481227 | AV145226 | 1.45 | 0.85 |
| 1452813_a_at | 5033428A16Rik | AK017198 | 1.45 | 1.33 |
| 1455309_at | Tmem16f | BG074632 | 1.45 | 1.15 |
| 1419398_a_at | Reep5 | NM_007874 | 1.45 | 0.96 |
| 1429475_at | 2810457I06Rik | AK013361 | 1.45 | 2.15 |
| 1428237_at | 2700059D21Rik | BI689227 | 1.44 | 1.15 |
| 1452271_at | Xpr1 | AV337591 | 1.44 | 1.10 |
| 1457293_at |  | BF714580 | 1.44 | 1.01 |
| 1426613_a_at | Snrpb2 | AV066554 | 1.44 | 1.12 |
| 1426310_at | Zdhhc5 | AV241525 | 1.44 | 1.68 |
| 1455215_at | C530028O21Rik | AU067746 | 1.44 | 1.04 |
| 1427308_at | Dab1 | BB644109 | 1.44 | 1.04 |
| 1434306_at | Rab3ip | BF319015 | 1.44 | 1.33 |
| 1436473_at | Zfp248 | AV300441 | 1.44 | 0.48 |
| 1420922_at | Usp9x | AW107303 | 1.44 | 0.93 |
| 1432435_s_at | C030004A17Rik | AK012261 | 1.44 | 1.35 |
| 1438975_x_at | Zdhhc14 | AV361868 | 1.44 | 1.44 |
| 1416328_a_at | Atp6v0e | NM_025272 | 1.44 | 1.15 |
| 1419397_at | Pola1 | NM_008892 | 1.44 | 1.03 |
| 1416288_at | Dnaja1 | BF141076 | 1.44 | 1.06 |
| 1429564_at | Pcgf5 | AK002387 | 1.44 | 1.35 |
| 1439573_at | Rtn4rl2 | BE992565 | 1.44 | 2.15 |
| 1438258_at | Vldlr | BE647363 | 1.43 | 1.21 |
| 1460441_at | Zxdb | BF660409 | 1.43 | 0.98 |
| 1417106_at | Tpd52l2 | NM_025482 | 1.43 | 1.22 |
| 1425480_at | Cnot6l | BC018506 | 1.43 | 1.00 |
| 1428184_at | 3110035E14Rik | BB348639 | 1.43 | 1.21 |
| 1436985_at | Zfp644 | BM115349 | 1.43 | 0.69 |
| 1439847_s_at | Klf12 | BM249597 | 1.43 | 1.12 |
| 1450773_at | Kcnd2 | BB051684 | 1.43 | 0.86 |
| 1451270_at | Dusp18 | BC020036 | 1.43 | 1.00 |
| 1450949_at | Katna1 | AK012319 | 1.43 | 0.80 |
| 1419169_at | Mapk6 | BC024684 | 1.43 | 1.11 |
| 1437021_at | Arl13b | AV225959 | 1.43 | 0.91 |
| 1448882_at | Tmem93 | NM_025318 | 1.43 | 1.08 |
| 1429488_at | Zdhhc21 | AK017682 | 1.43 | 1.07 |
| 1436169_at | C730029A08Rik | BB428892 | 1.43 | 1.21 |
| 1455944_at | Zfp516 | BB467812 | 1.43 | 0.78 |
| 1436796_at | 1110061A14Rik | BB237072 | 1.43 | 0.83 |
| 1419280_at | Pip5k2a | AK012196 | 1.43 | 0.70 |
| 1420537_at | Kctd4 | NM_026214 | 1.43 | 0.86 |
| 1418927_a_at | Habp4 | NM_019986 | 1.43 | 1.05 |
| 1434791_at | Atp6v0a2 | BM229554 | 1.43 | 1.45 |
| 1454987_a_at | H2-Ke6 | AI323545 | 1.43 | 1.10 |
| 1441371_at | Plxna4 | BQ174019 | 1.43 | 0.93 |
| 1442051_at | Hist2h3c1 | BE691662 | 1.43 | 1.19 |
| 1427683_at | Egr2 | X06746 | 1.43 | 1.27 |
| 1433532_a_at | Mbp | AI323506 | 1.43 | 1.20 |
| 1436868_at | Rtn4rl1 | BM508396 | 1.43 | 1.14 |
| 1442027_at | Nbeal1 | BB223743 | 1.43 | 1.56 |
| 1423316_at | Tmem39a | AK017817 | 1.42 | 0.91 |
| 1426743_at | Appl2 | BC002232 | 1.42 | 1.21 |
| 1431024_a_at | Arid4b | AK020165 | 1.42 | 0.54 |
| 1453787_at | Txndc13 | AK015667 | 1.42 | 1.10 |
| 1431711_a_at | 9030409G11Rik | AK018497 | 1.42 | 1.88 |
| 1422968_at | Ihpk1 | NM_013785 | 1.42 | 0.91 |
| 1421193_a_at | Pbx3 | NM_016768 | 1.42 | 1.01 |
| 1423198_a_at | Smek2 | AV305633 | 1.42 | 0.88 |
| 1422517_a_at | Znrd1 | NM_023162 | 1.42 | 0.88 |
| 1423501_at | Max | AA617392 | 1.42 | 0.95 |
| 1451486_at | 1200006F02Rik | BC006902 | 1.42 | 0.86 |
| 1419954_s_at | Zfand3 | AW539211 | 1.42 | 1.02 |
| 1435244_at | Vav2 | BF535947 | 1.42 | 0.92 |
| 1437614_x_at | Zdhhc14 | AV223474 | 1.42 | 1.43 |
| 1437858_at | Dpy19l3 | AV367203 | 1.42 | 1.05 |
| 1455076_a_at | 4933424B01Rik | AV255808 | 1.42 | 0.80 |
| 1455113_at | Armc8 | BM232782 | 1.42 | 1.01 |
| 1435451_at | Hel308 | BG068026 | 1.42 | 1.54 |
| 1416711_at | Tbr1 | NM_009322 | 1.41 | 1.19 |
| 1453264_at | Marveld3 | AK007346 | 1.41 | 0.58 |
| 1454771_at |  | AW060701 | 1.41 | 1.21 |
| 1416510_at | Mrpl4 | NM_023167 | 1.41 | 1.13 |
| 1448344_at | Rps12 | NM_011295 | 1.41 | 0.93 |
| 1451572_a_at | 5230400G24Rik | BC016597 | 1.41 | 1.00 |
| 1418367_x_at | Hist2h2aa1 | BC010564 | 1.41 | 1.08 |
| 1425780_a_at | Tmem167 | BC024352 | 1.41 | 0.98 |
| 1455632_at | Gnb5 | BE446953 | 1.41 | 1.75 |
| 1416675_s_at | Atp5e | NM_025983 | 1.41 | 1.20 |
| 1418469_at | Nrip1 | NM_008735 | 1.41 | 1.40 |
| 1418386_at | N6amt2 | NM_026526 | 1.41 | 1.15 |
| 1453077_a_at | Snapc3 | AK016168 | 1.41 | 0.97 |
| 1433868_at | Btbd3 | AV028445 | 1.41 | 1.09 |
| 1434604_at | Eif5b | BM236870 | 1.41 | 1.16 |
| 1437118_at | Usp7 | C77542 | 1.41 | 1.04 |
| 1453406_a_at | Rab28 | AK012286 | 1.41 | 1.12 |
| 1435553_at | Pdzd2 | AV376136 | 1.40 | 1.47 |
| 1416214_at | Mcm4 | BC013094 | 1.40 | 0.82 |
| 1449507_a_at | Cd47 | NM_010581 | 1.40 | 1.01 |
| 1457587_at | Ga17 | BB196645 | 1.40 | 0.97 |
| 1416566_at | Strap | NM_011499 | 1.40 | 1.02 |
| 1417612_at | Ier5 | BF147705 | 1.40 | 1.18 |
| 1460174_at | Dexi | NM_021428 | 1.40 | 1.23 |
| 1423172_at | Napb | BB147418 | 1.40 | 0.89 |
| 1449324_at | Ero1l | BM234652 | 1.40 | 1.21 |
| 1423477_at | Zic1 | BB361162 | 1.40 | 0.79 |

TABLE 16-continued

Gene translation changes upon chronic cocaine treatment

| Probe | Symbol | GenBank | FCH D1 | FCH D2 |
|---|---|---|---|---|
| 1452905_at | Gtl2 | AV015833 | 1.40 | 0.68 |
| 1442257_at | Cdh6 | BI134319 | 1.40 | 1.56 |
| 1417933_at | Igfbp6 | NM_008344 | 1.39 | 1.65 |
| 1453286_at | Plxna2 | BB085537 | 1.39 | 1.64 |
| 1429779_at | Eif2c4 | AI481660 | 1.39 | 1.47 |
| 1419127_at | Npy | NM_023456 | 1.38 | 1.65 |
| 1435891_x_at | 2610021A01Rik | BQ175465 | 1.38 | 0.53 |
| 1441961_at | Mtap9 | BB698742 | 1.37 | 0.68 |
| 1452370_s_at | B230208H17Rik | BB449608 | 1.37 | 0.59 |
| 1454701_at | 4930503L19Rik | AI450962 | 1.37 | 0.59 |
| 1424373_at | Armcx3 | AK004598 | 1.37 | 1.45 |
| 1418003_at | 1190002H23Rik | NM_025427 | 1.36 | 1.78 |
| 1433733_a_at | Cry1 | BG069864 | 1.36 | 1.57 |
| 1434202_a_at | BC055107 | BF682848 | 1.35 | 1.42 |
| 1416316_at | Slc27a2 | BC013442 | 1.35 | 0.58 |
| 1423278_at | Ptprk | AI893646 | 1.35 | 1.73 |
| 1456685_at | Nsg2 | BB227199 | 1.34 | 1.75 |
| 1445669_at | Spry4 | BB080456 | 1.34 | 2.12 |
| 1440437_at | Herc1 | BM247513 | 1.34 | 0.51 |
| 1458358_at | Pank2 | BB402666 | 1.34 | 0.41 |
| 1449885_at | Tmem47 | NM_138751 | 1.34 | 1.69 |
| 1433864_at | Lrp12 | AV254798 | 1.34 | 1.51 |
| 1456388_at | Atp11a | AV378604 | 1.34 | 1.72 |
| 1416630_at | Id3 | NM_008321 | 1.33 | 1.61 |
| 1427134_at | Sfrs12 | AV012790 | 1.33 | 1.41 |
| 1429150_at | Jarid1a | BM224226 | 1.33 | 1.52 |
| 1452868_at | Usp24 | AK012842 | 1.33 | 1.66 |
| 1447275_at | Bbs12 | AI449447 | 1.33 | 1.65 |
| 1435616_at | Cyp20a1 | BE686557 | 1.33 | 1.51 |
| 1457670_s_at | Lmna | AV238225 | 1.33 | 0.61 |
| 1446090_at |  | BB521597 | 1.32 | 1.50 |
| 1416432_at | Pfkfb3 | NM_133232 | 1.32 | 1.56 |
| 1453172_at | Stch | BE533039 | 1.32 | 1.41 |
| 1435156_at | BC046331 | BF730275 | 1.32 | 1.55 |
| 1419182_at | Svep1 | NM_022814 | 1.31 | 1.90 |
| 1456946_at | Sh3md4 | BE949337 | 1.31 | 1.55 |
| 1423104_at | Irs1 | BB345784 | 1.30 | 1.45 |
| 1419453_at | Uchl5 | AV313813 | 1.30 | 0.50 |
| 1423337_at | Orc4l | BB775020 | 1.29 | 0.71 |
| 1428083_at | 2310043N10Rik | AK018202 | 1.29 | 1.44 |
| 1449913_at | Zfp2 | NM_009550 | 1.29 | 0.67 |
| 1455876_at | Slc4a7 | BM237826 | 1.29 | 0.55 |
| 1436103_at | Rab3ip | AV235634 | 1.29 | 1.44 |
| 1436758_at | Hdac4 | AI661423 | 1.29 | 1.43 |
| 1422320_x_at | Phxr5 | NM_008836 | 1.28 | 3.21 |
| 1436137_at | Slc6a17 | AV340147 | 1.28 | 1.65 |
| 1426852_x_at | Nov | X96585 | 1.28 | 1.77 |
| 1456753_at |  | AW209075 | 1.28 | 1.41 |
| 1457693_a_at | 6430537H07Rik | AV343405 | 1.28 | 2.14 |
| 1418966_a_at | Dcbld1 | AK014521 | 1.28 | 1.64 |
| 1455164_at | Cdgap | AV308092 | 1.28 | 1.42 |
| 1455518_at |  | BB324402 | 1.27 | 1.45 |
| 1454014_a_at | Mkks | AK004987 | 1.26 | 1.57 |
| 1418587_at | Traf3 | U21050 | 1.26 | 1.53 |
| 1448569_at | Cd8b1 | BF682469 | 1.26 | 1.47 |
| 1422533_at | Cyp51 | NM_020010 | 1.26 | 1.48 |
| 1435229_at | Gramd1b | BI729743 | 1.26 | 1.42 |
| 1439019_at | Fras1 | BB541392 | 1.26 | 1.73 |
| 1420807_a_at | Egfl9 | NM_134120 | 1.25 | 1.48 |
| 1457694_at | 6430537H07Rik | AV343405 | 1.25 | 1.71 |
| 1417219_s_at | Tmsb10 | NM_025284 | 1.25 | 1.52 |
| 1440308_at | Cmpk | AV347071 | 1.25 | 0.67 |
| 1460426_at | Pde4dip | AI639670 | 1.25 | 1.47 |
| 1422165_at | Pou3f4 | X66603 | 1.24 | 1.44 |
| 1436588_at | Rttn | BB700837 | 1.24 | 1.53 |
| 1427035_at | Slc39a14 | BB399837 | 1.24 | 1.46 |
| 1432431_s_at | 2900006F19Rik | AK004072 | 1.24 | 1.61 |
| 1451753_at | Plxna2 | D86949 | 1.24 | 1.69 |
| 1452123_s_at | Frmd4b | BG067753 | 1.24 | 1.48 |
| 1420579_s_at | Cftr | NM_021050 | 1.23 | 1.89 |
| 1437291_at | 2700081O15Rik | AV131166 | 1.23 | 0.55 |
| 1424590_at | Ddx19b | BC002300 | 1.23 | 1.55 |
| 1427902_at | Srrm2 | BQ176063 | 1.23 | 0.63 |
| 1431541_at | Stt3b | AK016943 | 1.23 | 1.89 |
| 1420530_at | Neud4 | AW553317 | 1.23 | 0.57 |
| 1438007_at | AI851790 | BB432758 | 1.22 | 0.58 |
| 1427343_at | Rasd2 | BC026377 | 1.22 | 1.82 |
| 1457440_at | Sstr4 | BB451927 | 1.22 | 1.40 |
| 1441396_at | B3galt1 | AV328619 | 1.22 | 1.76 |
| 1450684_at | Etv1 | NM_007960 | 1.22 | 1.53 |
| 1437049_at |  | BE627361 | 1.21 | 0.51 |
| 1448918_at | Slco3a1 | NM_023908 | 1.21 | 1.69 |
| 1423137_at | Rala | BG073338 | 1.21 | 0.64 |
| 1424169_at | Tax1bp3 | BC008166 | 1.21 | 0.50 |
| 1426373_at | Ski | AK019148 | 1.21 | 1.42 |
| 1415840_at | Elovl5 | NM_134255 | 1.21 | 1.43 |
| 1426047_a_at | Ptprr | AF129509 | 1.21 | 0.71 |
| 1453166_at | Ccdc109a | AK008216 | 1.20 | 0.64 |
| 1421148_a_at | Tial1 | NM_009383 | 1.20 | 0.68 |
| 1427064_a_at | Scrib | BC006859 | 1.20 | 1.41 |
| 1426434_at | Tmem43 | AI747289 | 1.20 | 0.47 |
| 1440504_at | AI844750 | BB397002 | 1.20 | 0.50 |
| 1451525_at | Arhgap12 | BG064038 | 1.19 | 0.69 |
| 1417675_a_at | Mdn1 | NM_133874 | 1.19 | 1.53 |
| 1420845_at | Mrps2 | AV031454 | 1.19 | 1.43 |
| 1422675_at | Smarce1 | AK018493 | 1.19 | 0.69 |
| 1420485_at | Nol7 | AW060738 | 1.19 | 0.66 |
| 1460300_a_at | Ltk | NM_008523 | 1.19 | 1.54 |
| 1418595_at | S3-12 | NM_020568 | 1.19 | 2.42 |
| 1459917_at | Ggnbp2 | BG078867 | 1.19 | 0.64 |
| 1428340_s_at | Atp13a2 | BM944122 | 1.19 | 1.45 |
| 1454962_at | Spire1 | AU067702 | 1.18 | 1.46 |
| 1423475_at | Cnnm2 | BB278418 | 1.18 | 1.46 |
| 1438724_at | Osbpl3 | AI875442 | 1.18 | 1.41 |
| 1438838_at | B230206F22Rik | BG141977 | 1.18 | 0.49 |
| 1440688_at | Arhgap26 | BM244666 | 1.18 | 1.60 |
| 1435304_at | Sod1 | BM240246 | 1.18 | 0.71 |
| 1424160_at | Alg5 | BC027160 | 1.18 | 0.59 |
| 1426886_at | Cln5 | AV315220 | 1.18 | 1.48 |
| 1439615_at | Gan | BB187898 | 1.18 | 1.49 |
| 1454693_at | Hdac4 | BQ176116 | 1.18 | 1.48 |
| 1455260_at | Lcorl | BE650208 | 1.17 | 0.63 |
| 1422910_s_at | Smc6 | AU022584 | 1.17 | 0.57 |
| 1449351_s_at | Pdgfc | NM_019971 | 1.17 | 1.48 |
| 1423269_a_at | Nedd4l | BB663717 | 1.17 | 1.40 |
| 1435402_at | Gramd1b | BB066186 | 1.17 | 1.51 |
| 1444359_at | Zfp777 | BB354954 | 1.17 | 0.51 |
| 1451227_a_at | Slc10a3 | BC027440 | 1.17 | 1.47 |
| 1427004_at | Fbxo2 | BB311718 | 1.17 | 1.61 |
| 1430986_at | Farslb | AK012154 | 1.17 | 2.67 |
| 1453556_x_at | Cd99 | AK002762 | 1.17 | 1.43 |
| 1457948_at |  | BF456094 | 1.16 | 0.54 |
| 1427287_s_at | Itpr2 | BB216794 | 1.16 | 1.62 |
| 1419672_at | Spock1 | BB308491 | 1.16 | 0.59 |
| 1437252_at | Gats | BB768012 | 1.16 | 1.43 |
| 1455086_at | Uchl5 | AV312620 | 1.16 | 0.47 |
| 1427261_at | Wwc1 | BQ176786 | 1.16 | 1.44 |
| 1456256_at | Eif5 | BM242785 | 1.16 | 1.66 |
| 1419380_at | Zfp423 | NM_033327 | 1.16 | 1.56 |
| 1435642_at | Sft2d1 | BB081437 | 1.16 | 1.51 |
| 1446357_at | BC020402 | BB029175 | 1.16 | 0.71 |
| 1455150_at |  | BB038506 | 1.16 | 0.63 |
| 1455601_at |  | BB507994 | 1.16 | 0.69 |
| 1421819_a_at | Set | BF134272 | 1.15 | 0.68 |
| 1427785_x_at | Solh | BC022685 | 1.15 | 1.41 |
| 1428166_at | Cdan1 | AK005239 | 1.15 | 1.51 |
| 1416246_a_at | Coro1a | BC002136 | 1.15 | 1.65 |
| 1427542_at | 5330439J01Rik | BC027318 | 1.15 | 1.74 |
| 1454824_s_at | Pdgfrl | BB699957 | 1.15 | 1.44 |
| 1417379_at | Iqgap1 | NM_016721 | 1.15 | 1.46 |
| 1425731_at | Ankrd24 | BC017633 | 1.15 | 0.55 |
| 1415772_at | Ncl | BF118393 | 1.15 | 0.58 |
| 1423213_at | Plxnc1 | BB476707 | 1.15 | 1.46 |
| 1438011_at | Pcyt1a | BB280291 | 1.15 | 1.50 |
| 1434505_a_at | 6430548M08Rik | BF465109 | 1.14 | 2.11 |
| 1451474_a_at | Parp8 | BC022679 | 1.14 | 2.13 |
| 1454878_at | 2310047C04Rik | BM936291 | 1.14 | 0.57 |
| 1439380_x_at | Gtl2 | BB093563 | 1.14 | 0.66 |
| 1419757_at | Pitpnm2 | NM_011256 | 1.14 | 1.77 |
| 1448655_at | Lrp1 | NM_008512 | 1.14 | 1.47 |

TABLE 16-continued

Gene translation changes upon chronic cocaine treatment

| Probe | Symbol | GenBank | FCH D1 | FCH D2 |
|---|---|---|---|---|
| 1434215_at | B230308N11Rik | AW554529 | 1.14 | 1.54 |
| 1441636_at | | BB133117 | 1.14 | 1.43 |
| 1452199_at | 2700094F01Rik | BB667255 | 1.14 | 0.68 |
| 1416803_at | Fkbp7 | NM_010222 | 1.13 | 0.56 |
| 1425732_a_at | Mxi1 | D31824 | 1.13 | 1.50 |
| 1436515_at | E030004N02Rik | BB529913 | 1.13 | 1.98 |
| 1426577_a_at | 1810054G18Rik | BM570079 | 1.13 | 1.45 |
| 1437813_at | Aim1l | BE948330 | 1.13 | 0.66 |
| 1432156_a_at | Rnf32 | AK012288 | 1.13 | 1.56 |
| 1417312_at | Dkk3 | AK004853 | 1.13 | 1.71 |
| 1427978_at | 4732418C07Rik | BB318254 | 1.13 | 1.50 |
| 1436630_at | Aqp11 | AI550443 | 1.13 | 1.49 |
| 1428301_at | LOC554327 | BM195235 | 1.12 | 1.50 |
| 1456316_a_at | Acbd3 | BI965035 | 1.12 | 0.30 |
| 1440930_a_at | Scrt2 | BG807042 | 1.12 | 0.68 |
| 1429984_at | 5730455O13Rik | AK017666 | 1.12 | 0.49 |
| 1424523_at | Elmo1 | BC024727 | 1.12 | 1.59 |
| 1454720_at | Hs3st5 | AV328620 | 1.12 | 1.64 |
| 1418025_at | Bhlhb2 | NM_011498 | 1.12 | 1.66 |
| 1439561_at | 2010012O05Rik | BB322051 | 1.12 | 0.51 |
| 1418045_at | Inpp1 | NM_008384 | 1.12 | 1.44 |
| 1427209_at | Baz2a | AW910654 | 1.12 | 0.66 |
| 1443493_at | Dhx37 | BB766805 | 1.12 | 0.46 |
| 1417567_at | Ctnnbip1 | BF457754 | 1.11 | 1.45 |
| 1420934_a_at | Srrm1 | NM_016799 | 1.11 | 0.58 |
| 1426594_at | Frmd4b | BG067753 | 1.11 | 1.47 |
| 1450661_x_at | Nfic | NM_008688 | 1.11 | 1.64 |
| 1452306_at | Zfyve26 | BC006654 | 1.11 | 1.45 |
| 1415692_s_at | Canx | BI653492 | 1.11 | 0.70 |
| 1416049_at | Gldc | NM_138595 | 1.11 | 1.51 |
| 1435952_at | Tsc22d1 | AV118079 | 1.11 | 1.93 |
| 1425492_at | Bmpr1a | BM939768 | 1.11 | 1.43 |
| 1429489_at | Rexo1 | AK012127 | 1.11 | 1.74 |
| 1420925_at | Tub | NM_021885 | 1.11 | 1.45 |
| 1448396_at | Tmem131 | NM_018872 | 1.11 | 1.48 |
| 1455153_at | Zfp236 | BQ177220 | 1.11 | 1.53 |
| 1419362_at | Mrpl35 | BF787384 | 1.11 | 0.53 |
| 1450135_at | Fzd3 | AU043193 | 1.10 | 0.62 |
| 1429224_at | Pnma1 | AK017476 | 1.10 | 0.70 |
| 1451362_at | Rab7l1 | BC016133 | 1.10 | 1.49 |
| 1455520_at | LOC629605 | AV327200 | 1.10 | 2.74 |
| 1436302_at | Slc10a7 | BB770006 | 1.10 | 1.55 |
| 1435488_at | | BB427289 | 1.10 | 1.68 |
| 1455622_at | Podxl2 | BB461988 | 1.10 | 1.90 |
| 1416444_at | Elovl2 | NM_019423 | 1.10 | 1.76 |
| 1435031_at | 2010310D06Rik | AV069499 | 1.10 | 1.53 |
| 1453434_at | 1110019D14Rik | AK003812 | 1.10 | 1.86 |
| 1416683_at | Plxnb2 | NM_138749 | 1.10 | 1.52 |
| 1437983_at | Sall1 | BB739342 | 1.10 | 1.76 |
| 1455014_at | AV009015 | BM213104 | 1.10 | 0.66 |
| 1449476_at | Rage | NM_011973 | 1.10 | 0.71 |
| 1453500_at | Cyp2u1 | AK018458 | 1.10 | 1.58 |
| 1434826_at | Rfesd | AW124912 | 1.09 | 0.63 |
| 1417216_at | Pim2 | NM_138606 | 1.09 | 0.71 |
| 1425067_at | Celsr3 | AF427498 | 1.09 | 1.73 |
| 1436030_at | Cachd1 | BB730977 | 1.09 | 1.82 |
| 1426979_at | Mlxip | AF265663 | 1.09 | 1.56 |
| 1454136_a_at | 4921524J17Rik | AK013123 | 1.09 | 0.62 |
| 1456697_x_at | Dmtf1 | BB248138 | 1.09 | 2.03 |
| 1451156_s_at | Vldlr | BB628702 | 1.09 | 0.70 |
| 1422742_at | Hivep1 | NM_007772 | 1.09 | 1.74 |
| 1455448_at | Nt5dc3 | BG804066 | 1.08 | 1.41 |
| 1423560_at | Nell2 | AI838010 | 1.08 | 1.93 |
| 1454036_a_at | Usp15 | AK014891 | 1.08 | 1.49 |
| 1453246_at | Rab39b | AK020665 | 1.08 | 0.65 |
| 1454606_at | 4933426M11Rik | BF144564 | 1.08 | 1.42 |
| 1421191_s_at | Gopc | NM_053187 | 1.08 | 1.50 |
| 1451332_at | Zfp521 | BC021376 | 1.08 | 1.47 |
| 1442739_at | BC031441 | BF225404 | 1.07 | 0.55 |
| 1449390_at | Gpatc4 | NM_025663 | 1.07 | 1.63 |
| 1454756_at | Lrch3 | BB763476 | 1.07 | 2.17 |
| 1417303_at | Mvd | NM_138656 | 1.07 | 0.69 |
| 1417551_at | Cln3 | NM_009907 | 1.07 | 1.52 |
| 1437020_at | Ep400 | BM236717 | 1.07 | 0.43 |
| 1416589_at | Sparc | NM_009242 | 1.07 | 1.71 |
| 1440972_at | Nsd1 | AI413236 | 1.07 | 0.64 |
| 1442220_at | | BB313387 | 1.07 | 1.53 |
| 1418313_at | Zfp276 | BB667131 | 1.07 | 1.50 |
| 1415874_at | Spry1 | NM_011896 | 1.06 | 1.52 |
| 1415758_at | Fryl | BM118442 | 1.06 | 1.48 |
| 1433682_at | Arhgef17 | BE287052 | 1.06 | 1.42 |
| 1442917_at | | BM1953841 | 1.06 | 1.63 |
| 1438363_at | EG434128 | BB332375 | 1.06 | 1.57 |
| 1440215_at | "OTTMUS G00000004461" | BG068916 | 1.06 | 0.62 |
| 1435737_a_at | Nde1 | BQ032232 | 1.05 | 1.45 |
| 1437891_at | Frs2 | AV331887 | 1.05 | 1.55 |
| 1444072_at | | AW123332 | 1.05 | 0.59 |
| 1429440_at | 1810041L15Rik | BI734299 | 1.05 | 1.74 |
| 1435527_at | Nfic | BB533448 | 1.05 | 1.42 |
| 1440291_at | | BE954335 | 1.05 | 0.62 |
| 1416187_s_at | Pnrc2 | NM_026383 | 1.05 | 0.68 |
| 1442754_at | C030013G03Rik | BE692283 | 1.05 | 1.99 |
| 1443770_x_at | Auts2 | BB026407 | 1.05 | 1.99 |
| 1428466_at | Chd3 | AK011183 | 1.05 | 1.50 |
| 1448733_at | Bmi1 | M64279 | 1.05 | 0.63 |
| 1460001_at | Pgpep1 | AI642171 | 1.05 | 0.66 |
| 1430814_at | 1300013D18Rik | AK004984 | 1.05 | 1.43 |
| 1447550_at | Zfp644 | BB545511 | 1.05 | 0.62 |
| 1449349_at | Nudt1 | NM_008637 | 1.04 | 0.61 |
| 1421252_a_at | Mef2a | NM_013597 | 1.04 | 0.63 |
| 1434654_at | Cog3 | BE570422 | 1.04 | 1.50 |
| 1439783_at | C330018D20Rik | BB809870 | 1.04 | 0.68 |
| 1422635_at | Ache | NM_009599 | 1.04 | 2.16 |
| 1425423_at | Glis1 | AF220434 | 1.04 | 0.61 |
| 1435719_at | AI448984 | BM935216 | 1.04 | 0.62 |
| 1424042_at | Tmem5 | BC020100 | 1.04 | 0.67 |
| 1454198_a_at | Efcab1 | AK015866 | 1.04 | 0.58 |
| 1439817_at | 2900064A13Rik | AI451465 | 1.04 | 0.70 |
| 1428403_at | 2410025L10Rik | AV330483 | 1.04 | 1.95 |
| 1455333_at | Tns3 | AI315031 | 1.03 | 1.43 |
| 1435700_at | Mterfd3 | BB359043 | 1.03 | 0.65 |
| 1427172_at | Ofd1 | AJ278702 | 1.03 | 0.49 |
| 1428431_at | 2310047A01Rik | BB813478 | 1.03 | 1.57 |
| 1460394_a_at | Inppl1 | BB769433 | 1.03 | 1.47 |
| 1455275_at | E530001K10Rik | AW046441 | 1.03 | 0.45 |
| 1456520_at | Zfp652 | BF147545 | 1.03 | 1.57 |
| 1435295_at | Dopey1 | BG075614 | 1.03 | 1.45 |
| 1422324_a_at | Pthlh | NM_008970 | 1.03 | 1.63 |
| 1435783_at | B230112C05Rik | BB476773 | 1.03 | 0.69 |
| 1458307_at | B230334C09Rik | BE992834 | 1.03 | 0.51 |
| 1426405_at | Rnf11 | BI150320 | 1.02 | 0.69 |
| 1455758_at | Prkcc | BM215011 | 1.02 | 1.62 |
| 1425118_at | Spire2 | BC026502 | 1.02 | 1.68 |
| 1452267_at | Flywch1 | BB477613 | 1.02 | 0.49 |
| 1429684_at | 5830472M02Rik | BG094398 | 1.02 | 2.23 |
| 1421830_at | Ak3l1 | NM_009647 | 1.02 | 1.48 |
| 1450937_at | Lin7c | BQ176612 | 1.02 | 0.65 |
| 1442415_at | 5830454E08Rik | BQ180241 | 1.02 | 0.64 |
| 1417577_at | Trpc3 | NM_019510 | 1.02 | 0.56 |
| 1421586_a_at | Cd46 | NM_010778 | 1.02 | 0.62 |
| 1434691_at | Sfrs2ip | BB154529 | 1.02 | 0.71 |
| 1448554_s_at | Myh7 | NM_080728 | 1.02 | 0.69 |
| 1457544_at | Ube2w | BB442807 | 1.01 | 0.59 |
| 1429783_at | Pdlim5 | AK009464 | 1.01 | 0.48 |
| 1423738_at | Oxa1l | BC027191 | 1.01 | 1.40 |
| 1425405_a_at | Adar | AF291876 | 1.01 | 0.71 |
| 1449248_at | Clcn2 | NM_009900 | 1.01 | 0.70 |
| 1429836_at | Ugcgl2 | BM218963 | 1.01 | 1.93 |
| 1428352_at | Arrdc2 | AW542672 | 1.01 | 0.49 |
| 1451625_a_at | C8g | BC019967 | 1.00 | 1.41 |
| 1444001_at | Strbp | AW488249 | 1.00 | 0.52 |
| 1452661_at | Tfrc | AK011596 | 1.00 | 0.71 |
| 1458492_x_at | Hnt | BB081359 | 1.00 | 0.67 |
| 1440884_s_at | A530047J11Rik | BB218047 | 1.00 | 0.55 |
| 1419047_at | Pcnx | BG073499 | 1.00 | 1.43 |
| 1423097_s_at | Capn7 | BQ257745 | 1.00 | 0.71 |
| 1455497_at | Leng9 | BB799608 | 1.00 | 0.67 |
| 1436165_at | Luc7l2 | BI076494 | 1.00 | 0.63 |
| 1458337_at | Tcfl2 | BB476667 | 0.99 | 0.60 |

TABLE 16-continued

Gene translation changes upon chronic cocaine treatment

| Probe | Symbol | GenBank | FCH D1 | FCH D2 |
|---|---|---|---|---|
| 1456858_at | Gpr149 | BB075339 | 0.99 | 0.60 |
| 1438469_at | Bcorl1 | BG071122 | 0.99 | 1.42 |
| 1452029_a_at | Purg | AF479673 | 0.99 | 1.54 |
| 1429185_at | 4631416L12Rik | BB774721 | 0.99 | 1.81 |
| 1420375_at | Kif3a | NM_008443 | 0.99 | 0.59 |
| 1435810_at | 5730455O13Rik | AV297833 | 0.99 | 0.71 |
| 1444736_at | Cdh7 | BB129525 | 0.99 | 1.48 |
| 1421392_a_at | Birc3 | NM_007464 | 0.98 | 1.72 |
| 1424138_at | Rhbdf1 | BC027346 | 0.98 | 1.42 |
| 1452347_at | Mef2a | AV255689 | 0.98 | 0.68 |
| 1417870_x_at | Ctsz | NM_022325 | 0.98 | 1.50 |
| 1435335_a_at | Gnptab | BG144467 | 0.98 | 1.42 |
| 1439506_at | Gm98 | BB193557 | 0.98 | 1.49 |
| 1447230_at | AI553587 | BE954466 | 0.98 | 0.63 |
| 1455293_at | Leo1 | BG065311 | 0.98 | 0.63 |
| 1416806_at | Fdxr | NM_007997 | 0.97 | 0.70 |
| 1430776_s_at | Ankrd24 | AK017778 | 0.97 | 0.66 |
| 1436200_at | Lonrf3 | BE956940 | 0.97 | 1.52 |
| 1428794_at | Specc1 | BQ175052 | 0.97 | 1.55 |
| 1434600_at | Tjp2 | BB758095 | 0.97 | 1.49 |
| 1428732_at | 1700008J07Rik | AK005774 | 0.97 | 0.61 |
| 1426865_a_at | Ncam1 | BB698413 | 0.97 | 0.56 |
| 1422612_at | Hk2 | NM_013820 | 0.97 | 1.52 |
| 1436032_at |  | BB201888 | 0.97 | 1.96 |
| 1426848_at | Sec24b | BE947982 | 0.97 | 1.49 |
| 1431072_a_at | Ccdc50 | BB865814 | 0.97 | 1.59 |
| 1455906_at | 6030446N20Rik | AV222909 | 0.97 | 0.59 |
| 1439558_at | Zfp75 | BM729399 | 0.97 | 0.68 |
| 1443528_at | Ttbk1 | BB398560 | 0.97 | 1.55 |
| 1425968_s_at | Speg | AF215896 | 0.96 | 1.52 |
| 1452604_at | Stard13 | BB667840 | 0.96 | 1.47 |
| 1426316_at | 6330416G13Rik | AV326978 | 0.96 | 0.71 |
| 1427269_at | Sfrs11 | AW261583 | 0.96 | 0.61 |
| 1434952_at | Cox4nb | BI734783 | 0.96 | 1.45 |
| 1444208_at | Dnahc1 | BE950899 | 0.96 | 0.57 |
| 1436707_x_at | Ncaph | BB725358 | 0.96 | 0.70 |
| 1428223_at | Mfsd2 | AK006096 | 0.96 | 1.82 |
| 1438476_a_at | Chd4 | BB201828 | 0.96 | 1.49 |
| 1417384_at | Entpd5 | NM_007647 | 0.96 | 1.97 |
| 1416953_at | Ctgf | NM_010217 | 0.96 | 1.62 |
| 1438478_a_at | Ppp3ca | AI313926 | 0.96 | 0.48 |
| 1428198_at | Adal | AK016299 | 0.95 | 0.67 |
| 1420402_at | Atp2b2 | NM_009723 | 0.95 | 1.97 |
| 1452055_at | Ctdsp1 | BB770944 | 0.95 | 1.51 |
| 1439516_at | 2610201A13Rik | AW488471 | 0.95 | 0.66 |
| 1433890_a_at | Bat3 | AW545877 | 0.95 | 1.46 |
| 1417937_at | Dact1 | NM_021532 | 0.95 | 1.61 |
| 1418924_at | Rassf7 | NM_025886 | 0.95 | 0.68 |
| 1452831_s_at | Ppat | AV305746 | 0.95 | 0.67 |
| 1419905_s_at | Hpgd | AV026552 | 0.94 | 0.45 |
| 1424125_at | Kcnk13 | BC023443 | 0.94 | 1.49 |
| 1429499_at | Fbxo5 | AK011820 | 0.94 | 0.70 |
| 1442434_at | D8Ertd82e | BM195829 | 0.94 | 1.40 |
| 1435324_x_at | Hmgb1 | AI648759 | 0.94 | 1.50 |
| 1448546_at | Rassf3 | BB703307 | 0.94 | 0.63 |
| 1439869_at | 2900054J07Rik | BB326106 | 0.94 | 0.51 |
| 1435617_at | 1700106N22Rik | BQ175501 | 0.94 | 0.40 |
| 1452338_s_at | Itsn1 | AA172344 | 0.94 | 2.52 |
| 1428870_at | Nolc1 | BM213850 | 0.94 | 0.68 |
| 1439463_x_at | EG666836 | AV127023 | 0.94 | 1.48 |
| 1439909_at | Zfp521 | BE133660 | 0.94 | 1.51 |
| 1425094_at | Lhx6 | AB031040 | 0.94 | 2.01 |
| 1430435_at | Aff3 | AK014322 | 0.94 | 1.96 |
| 1439684_at | 4930570G19Rik | BB428007 | 0.94 | 0.63 |
| 1455463_at | Phyhip | BB427286 | 0.94 | 0.60 |
| 1422725_at | Mak | BG069426 | 0.94 | 1.48 |
| 1457536_at | Gpc5 | BB171986 | 0.94 | 2.03 |
| 1421892_at | St3gal2 | BB750118 | 0.93 | 1.42 |
| 1422881_s_at | Sypl | BE333485 | 0.93 | 0.69 |
| 1431820_at | 4632404H12Rik | AK014549 | 0.93 | 0.66 |
| 1449857_at | 1200011I18Rik | NM_026177 | 0.93 | 0.66 |
| 1434610_at | Plec1 | BM210485 | 0.93 | 1.74 |
| 1426292_at | 6330581L23Rik | BG068796 | 0.93 | 1.42 |
| 1424400_a_at | Aldh1l1 | AK007822 | 0.93 | 0.71 |
| 1425391_a_at | Osbpl5 | AB074008 | 0.93 | 1.46 |
| 1420487_at | Nol7 | AW060738 | 0.93 | 0.63 |
| 1427186_a_at | Mef2a | AV255689 | 0.93 | 0.66 |
| 1435555_at | Cd247 | AW552088 | 0.93 | 1.42 |
| 1427138_at | 0610010D24Rik | AW556861 | 0.92 | 1.56 |
| 1429087_at | 1110054O05Rik | AK005245 | 0.92 | 0.67 |
| 1418252_at | Padi2 | NM_008812 | 0.92 | 0.57 |
| 1435110_at | Unc5b | BG065285 | 0.92 | 1.57 |
| 1419313_at | Cent1 | NM_009833 | 0.92 | 1.41 |
| 1433979_at | Rbms2 | BQ176636 | 0.92 | 1.45 |
| 1439239_at | Lin7b | BB806633 | 0.92 | 1.44 |
| 1429517_at | Zfyve20 | BC017622 | 0.92 | 1.54 |
| 1448726_s_at | Sptlc1 | BB470898 | 0.92 | 0.69 |
| 1452127_a_at | Ptpn13 | BM236743 | 0.92 | 1.70 |
| 1421112_at | Nkx2-2 | NM_010919 | 0.92 | 1.60 |
| 1433873_s_at | Pcnt | BG069597 | 0.91 | 1.46 |
| 1439485_at | Zfp608 | AV222442 | 0.91 | 1.43 |
| 1449536_at | Kcnn1 | NM_032397 | 0.91 | 0.58 |
| 1450097_s_at | Gna12 | BF302166 | 0.91 | 1.56 |
| 1460121_at | 9630010G10Rik | BI076710 | 0.91 | 0.64 |
| 1424638_at | Cdkn1a | AK007630 | 0.91 | 0.57 |
| 1434085_at | Zfp523 | AV136654 | 0.91 | 1.41 |
| 1441173_at | 4930451G09Rik | AV352442 | 0.91 | 0.69 |
| 1437554_at | Plec1 | BM232239 | 0.91 | 1.62 |
| 1455991_at | Cbl2 | BG094881 | 0.91 | 0.67 |
| 1459882_at | Asf1a | AV312905 | 0.91 | 0.65 |
| 1416199_at | Kifc3 | NM_010631 | 0.91 | 1.47 |
| 1458839_at | Exoc8 | BB032637 | 0.90 | 1.57 |
| 1439038_at | 9130227C08Rik | BF455240 | 0.90 | 0.59 |
| 1420928_at | St6gal1 | BG075800 | 0.90 | 1.56 |
| 1423130_a_at | Sfrs5 | AW212917 | 0.90 | 0.59 |
| 1421478_a_at | Zfp318 | NM_021346 | 0.90 | 0.63 |
| 1436524_at | 4833438C02Rik | AV252102 | 0.90 | 0.63 |
| 1416536_at | Mum1 | NM_023431 | 0.90 | 0.63 |
| 1435108_at | Arhgap22 | BG295243 | 0.90 | 1.42 |
| 1436278_at |  | BM934468 | 0.90 | 0.64 |
| 1426597_s_at | C79267 | BG066466 | 0.90 | 1.53 |
| 1418534_at | Fzd2 | BB371406 | 0.89 | 1.45 |
| 1460520_at | Mocs1 | AK014178 | 0.89 | 0.67 |
| 1427544_a_at | Papola | U58135 | 0.89 | 0.68 |
| 1448145_at | Wwp2 | AK004087 | 0.89 | 0.70 |
| 1428773_s_at | Bcor | AK018370 | 0.89 | 1.41 |
| 1424687_at | 2700008B19Rik | BF150550 | 0.89 | 1.79 |
| 1419292_at | Htra3 | NM_030127 | 0.89 | 0.68 |
| 1417194_at | Sod2 | NM_013671 | 0.89 | 0.59 |
| 1429573_at | Dmrtc1a | AK014934 | 0.89 | 0.70 |
| 1457811_at |  | BM217632 | 0.89 | 1.52 |
| 1415680_at | Anapc1 | NM_008569 | 0.89 | 1.45 |
| 1443210_at |  | BB354985 | 0.88 | 0.62 |
| 1434762_at | Tmem142b | BF457736 | 0.88 | 0.66 |
| 1424571_at | Ddx46 | BF023426 | 0.88 | 0.50 |
| 1438210_at | Gpr149 | BB126999 | 0.88 | 0.55 |
| 1420391_at | Pard3 | NM_033620 | 0.88 | 1.70 |
| 1437571_x_at | Clcc1 | BB100861 | 0.88 | 0.69 |
| 1434950_a_at | Armc8 | BE995635 | 0.87 | 0.63 |
| 1440997_at | Tnrc6c | AV236734 | 0.87 | 0.58 |
| 1452618_at | Cdk5rap2 | BM230774 | 0.87 | 1.59 |
| 1441534_at | C86753 | BG067565 | 0.87 | 1.81 |
| 1456781_at |  | AW121365 | 0.87 | 0.66 |
| 1425489_at | Slu7 | BC025870 | 0.87 | 0.71 |
| 1427911_at | 2610307O08Rik | AK012006 | 0.87 | 1.67 |
| 1448417_at | Ninj1 | NM_013610 | 0.87 | 0.69 |
| 1435438_at | Sox8 | AV345303 | 0.87 | 0.67 |
| 1435456_at | Ttc28 | AW552254 | 0.86 | 1.46 |
| 1448384_at | Pofut2 | BC018194 | 0.86 | 1.52 |
| 1454969_at | Lypd6 | AV299725 | 0.86 | 1.49 |
| 1440709_at | C130081A10Rik | BB375586 | 0.86 | 0.58 |
| 1417489_at | Npy2r | NM_008731 | 0.86 | 1.55 |
| 1440251_s_at | Zfp64 | BE947768 | 0.86 | 0.61 |
| 1435279_at | BC059842 | AV338182 | 0.85 | 1.80 |
| 1438081_at | Mcc | BB794635 | 0.85 | 1.53 |
| 1438951_x_at | Nup54 | BB168451 | 0.85 | 0.70 |
| 1429556_at | 2610024B07Rik | BM214769 | 0.85 | 1.59 |
| 1437498_at | Klf9 | BB327336 | 0.85 | 0.51 |
| 1460333_at | Ddx59 | BB829482 | 0.85 | 0.63 |
| 1443246_at | Fastkd2 | BB476363 | 0.85 | 0.68 |

TABLE 16-continued

Gene translation changes upon chronic cocaine treatment

| Probe | Symbol | GenBank | FCH D1 | FCH D2 |
|---|---|---|---|---|
| 1457512_at | | BB167650 | 0.85 | 0.63 |
| 1434596_at | | BB194318 | 0.85 | 1.56 |
| 1419606_a_at | Tnnt1 | NM_011618 | 0.84 | 0.41 |
| 1430019_a_at | Hnrpa1 | AK007802 | 0.84 | 0.70 |
| 1422615_at | Map4k4 | NM_008696 | 0.84 | 1.58 |
| 1447344_at | | AI447264 | 0.84 | 0.71 |
| 1440965_at | Pigl | AW018348 | 0.84 | 0.59 |
| 1419048_at | Pcnx | BG073499 | 0.84 | 1.70 |
| 1418983_at | Inadl | AV287690 | 0.84 | 1.46 |
| 1439060_s_at | Wipi1 | BI251603 | 0.84 | 0.69 |
| 1450779_at | Fabp7 | NM_021272 | 0.84 | 0.68 |
| 1419310_s_at | Rfxank | L43164 | 0.84 | 0.71 |
| 1429634_at | Zfp580 | AK005257 | 0.84 | 0.48 |
| 1435753_a_at | Nucks1 | BM209748 | 0.84 | 0.63 |
| 1418369_at | Prim1 | J04620 | 0.84 | 0.67 |
| 1452600_at | Taf6l | AV280284 | 0.84 | 0.50 |
| 1455694_at | Nbeal2 | C77476 | 0.83 | 1.59 |
| 1437140_at | Serf2 | BB667186 | 0.83 | 0.64 |
| 1441429_at | Irs4 | BB295945 | 0.83 | 2.12 |
| 1454671_at | Insig1 | BB005488 | 0.83 | 0.69 |
| 1451042_a_at | Mina | AK013451 | 0.83 | 0.62 |
| 1448602_at | Pygm | NM_011224 | 0.83 | 1.45 |
| 1426015_s_at | Asph | AF302653 | 0.82 | 0.71 |
| 1430135_at | Dnase2a | AK018651 | 0.81 | 0.67 |
| 1454765_at | Gtf3c3 | AW549348 | 0.81 | 1.48 |
| 1422793_at | Pafah1b2 | BB539054 | 0.81 | 0.69 |
| 1438189_s_at | Rai16 | BB492312 | 0.80 | 2.01 |
| 1422036_at | Strn | NM_011500 | 0.80 | 0.68 |
| 1415728_at | Pabpn1 | BG806432 | 0.80 | 0.65 |
| 1433446_at | Hmgcs1 | BB705380 | 0.80 | 0.69 |
| 1443928_at | Pscdbp | AI462064 | 0.79 | 0.56 |
| 1434347_s_at | Rufy2 | BB827830 | 0.79 | 0.71 |
| 1426589_at | Gab3 | BB037935 | 0.79 | 0.60 |
| 1424721_at | Mfap3 | BI661422 | 0.78 | 1.45 |
| 1420146_at | Tfb1m | AI429207 | 0.78 | 0.70 |
| 1453518_at | Pdzd11 | AI429425 | 0.78 | 0.52 |
| 1434749_at | | BC067068 | 0.77 | 0.67 |
| 1439774_at | Prrx1 | BB051738 | 0.77 | 2.18 |
| 1452121_at | Fbxo22 | BB756840 | 0.77 | 0.63 |
| 1444461_at | Zmynd11 | BB346871 | 0.77 | 0.52 |
| 1452228_at | Tbc1d23 | AV209678 | 0.77 | 0.54 |
| 1427149_at | Plekha6 | BB486127 | 0.77 | 1.52 |
| 1453163_at | Ppp1r12a | BI653999 | 0.77 | 0.48 |
| 1435448_at | Bcl2l11 | BM120925 | 0.77 | 1.66 |
| 1426226_at | Dyrk1a | U58497 | 0.76 | 0.54 |
| 1441993_at | Ap3s2 | BB762985 | 0.76 | 1.42 |
| 1445564_at | | BE688513 | 0.75 | 1.45 |
| 1434166_at | 9330151L19Rik | BM935724 | 0.75 | 0.62 |
| 1457195_at | Plekhm1 | BB206527 | 0.74 | 0.67 |
| 1451809_s_at | Rwdd3 | AF439556 | 0.74 | 0.52 |
| 1434423_at | Gulp1 | BB138485 | 0.74 | 0.62 |
| 1442046_at | Shroom2 | BM119167 | 0.74 | 0.67 |
| 1434695_at | Dtl | AV270035 | 0.74 | 1.86 |
| 1448700_at | G0s2 | NM_008059 | 0.74 | 1.57 |
| 1428684_at | 1500001M20Rik | BG065846 | 0.74 | 0.71 |
| 1428825_at | Nr6a1 | AK007201 | 0.73 | 1.43 |
| 1435079_at | 5730406M06Rik | BB767442 | 0.73 | 0.45 |
| 1424839_a_at | Nsun4 | BC024628 | 0.73 | 0.70 |
| 1429796_at | Kalrn | AK008844 | 0.72 | 0.67 |
| 1434730_at | AI854517 | BB346879 | 0.72 | 0.70 |
| 1449800_x_at | Phf7 | AI427892 | 0.71 | 0.66 |
| 1418984_at | Inadl | AV287690 | 0.71 | 1.81 |
| 1428481_s_at | Cdca8 | AV307110 | 0.71 | 0.77 |
| 1443710_s_at | Spats1 | AW045373 | 0.71 | 1.04 |
| 1452805_at | D11Wsu47e | AK017508 | 0.71 | 1.21 |
| 1423854_at | Rasl11b | BC008101 | 0.71 | 0.86 |
| 1428115_a_at | Rab2b | AK005230 | 0.71 | 0.75 |
| 1439645_at | Adra2b | BQ031032 | 0.71 | 0.91 |
| 1420059_at | 2410166I05Rik | AI480750 | 0.71 | 0.85 |
| 1424742_at | Creb3 | BG070002 | 0.71 | 0.88 |
| 1420287_at | | R75193 | 0.71 | 0.74 |
| 1454614_at | 1810013D10Rik | C87702 | 0.71 | 0.90 |
| 1436245_at | Usp20 | AV272484 | 0.71 | 1.10 |
| 1455124_at | Trim68 | AW493298 | 0.71 | 0.99 |
| 1455563_at | Ddx49 | BM210028 | 0.71 | 0.94 |
| 1457378_at | Mrpl54 | AW123022 | 0.71 | 1.23 |
| 1419967_at | Seh1l | AW540070 | 0.70 | 0.82 |
| 1441000_at | EG237749 | BB076832 | 0.70 | 0.75 |
| 1435152_at | Leng8 | AV024387 | 0.70 | 0.81 |
| 1431322_at | Igsf3 | AK019524 | 0.70 | 0.70 |
| 1418070_at | Cdyl | AF081260 | 0.70 | 1.27 |
| 1443372_at | | BB417900 | 0.70 | 0.97 |
| 1445161_at | Usp6nl | BE952061 | 0.70 | 0.82 |
| 1449062_at | Khk | BC013464 | 0.70 | 0.87 |
| 1439867_at | Ubox5 | BB079377 | 0.70 | 0.83 |
| 1422622_at | Nos3 | NM_008713 | 0.70 | 1.04 |
| 1429229_s_at | 4930534B04Rik | BE980134 | 0.70 | 0.90 |
| 1443966_at | C030046E11Rik | BF466594 | 0.70 | 0.82 |
| 1429895_at | 2310010G23Rik | AK009271 | 0.70 | 0.88 |
| 1446041_at | | BB343268 | 0.70 | 0.75 |
| 1424336_at | Ppcdc | BB329391 | 0.70 | 0.91 |
| 1454727_at | Afap1l1 | BB106834 | 0.70 | 1.47 |
| 1458667_at | 4930519N13Rik | AV266695 | 0.70 | 0.64 |
| 1425891_a_at | Grtp1 | AF329833 | 0.70 | 1.08 |
| 1429671_at | 2410018M08Rik | AK010551 | 0.70 | 1.00 |
| 1433023_at | 2310068G24Rik | AK010109 | 0.70 | 0.98 |
| 1439047_s_at | Recql | BB258011 | 0.70 | 0.90 |
| 1445308_at | Tssc1 | BB082634 | 0.70 | 0.81 |
| 1436787_x_at | Sec14l3 | AV024133 | 0.69 | 0.65 |
| 1438573_at | Rmi1 | AV339477 | 0.69 | 0.93 |
| 1453320_at | 1700027A23Rik | AK006407 | 0.69 | 0.69 |
| 1441106_at | Zfand5 | BB320444 | 0.69 | 1.09 |
| 1423747_a_at | Pdk1 | BC027196 | 0.69 | 1.01 |
| 1451692_at | Tmco6 | BC005637 | 0.69 | 0.95 |
| 1424597_at | ORF19 | W34605 | 0.69 | 0.75 |
| 1441867_x_at | 4930534B04Rik | AI480494 | 0.69 | 0.71 |
| 1420044_at | Nrd1 | AI875733 | 0.69 | 0.81 |
| 1426230_at | Sphk2 | AK016616 | 0.69 | 0.71 |
| 1438852_x_at | Mcm6 | BB099487 | 0.69 | 0.88 |
| 1424955_at | Ccdc5 | BC024400 | 0.68 | 0.75 |
| 1433954_at | 4632419I22Rik | AV227569 | 0.68 | 1.17 |
| 1434326_x_at | Coro2b | BB317923 | 0.68 | 0.87 |
| 1417920_at | Amn | NM_033603 | 0.68 | 0.57 |
| 1418717_at | Mrps25 | AK004037 | 0.68 | 1.17 |
| 1427838_at | Tubb2a | M28739 | 0.68 | 0.94 |
| 1428704_at | Zfp661 | BB065039 | 0.68 | 1.03 |
| 1434591_at | 4732460K03Rik | BB004441 | 0.68 | 1.18 |
| 1445285_at | Hrh3 | AV381093 | 0.68 | 1.22 |
| 1418739_at | Sgk2 | NM_013731 | 0.68 | 1.05 |
| 1455114_at | Ccnu | BB547482 | 0.68 | 0.69 |
| 1416429_a_at | Cat | NM_009804 | 0.68 | 0.87 |
| 1433600_at | Adra2a | BB262415 | 0.68 | 1.01 |
| 1454840_at | Mccc2 | BB548059 | 0.68 | 0.65 |
| 1444395_at | Dixdc1 | AW455436 | 0.68 | 1.04 |
| 1435691_at | C630028N24Rik | BB209207 | 0.68 | 0.80 |
| 1436573_at | Scrn3 | BB434447 | 0.68 | 0.63 |
| 1415877_at | Dpysl3 | NM_009468 | 0.68 | 0.97 |
| 1458281_at | Arsb | BF018283 | 0.67 | 0.58 |
| 1431279_s_at | Ttll5 | AK016145 | 0.67 | 0.97 |
| 1421209_s_at | Ikbkg | NM_010547 | 0.67 | 0.95 |
| 1417325_at | Btrc | NM_009771 | 0.67 | 0.76 |
| 1417752_at | Coro1c | NM_011779 | 0.67 | 1.03 |
| 1423829_s_at | Gpsm1 | BC026486 | 0.67 | 0.76 |
| 1431341_at | Ppp2cb | BF143676 | 0.67 | 1.14 |
| 1453061_at | 2610018O07Rik | AK011449 | 0.67 | 0.71 |
| 1455048_at | Igsf3 | BB484576 | 0.67 | 0.91 |
| 1428547_at | Nt5e | AV273591 | 0.67 | 0.88 |
| 1432391_at | Ccdc21 | AK010621 | 0.67 | 1.14 |
| 1438606_a_at | Clic4 | BB814844 | 0.67 | 0.97 |
| 1438733_at | Zfp689 | BF461546 | 0.67 | 1.01 |
| 1447278_at | Cep164 | BB822306 | 0.67 | 1.08 |
| 1441919_x_at | Crat | BB515871 | 0.66 | 1.06 |
| 1423762_at | Adck1 | BC010539 | 0.66 | 0.81 |
| 1459703_at | D7Ertd443e | BG067408 | 0.66 | 0.59 |
| 1419069_at | Rabgef1 | BB280137 | 0.66 | 1.55 |
| 1434987_at | Aldh2 | AI462635 | 0.66 | 0.85 |
| 1448246_at | Hdac1 | NM_008228 | 0.66 | 0.67 |
| 1460665_a_at | Cnot7 | NM_011135 | 0.66 | 0.52 |
| 1421786_at | Ppp3r1 | NM_024459 | 0.65 | 1.23 |
| 1427491_at | Nsun6 | BI108529 | 0.65 | 0.93 |

TABLE 16-continued

Gene translation changes upon chronic cocaine treatment

| Probe | Symbol | GenBank | FCH D1 | FCH D2 |
|---|---|---|---|---|
| 1429012_at | Arhgef6 | BM246754 | 0.65 | 0.67 |
| 1440084_at | AI663975 | AV380966 | 0.65 | 0.60 |
| 1440742_at | Epc1 | BF019417 | 0.65 | 0.91 |
| 1434844_at | Hexdc | BF582632 | 0.65 | 1.34 |
| 1443719_x_at | Ddx42 | AW763628 | 0.65 | 0.97 |
| 1447851_x_at | Atp10a | BB487289 | 0.65 | 0.89 |
| 1421986_at | Eif4e2 | AI449084 | 0.65 | 0.87 |
| 1429295_s_at | Trip13 | AK010336 | 0.65 | 0.58 |
| 1420192_at | D16Bwg1494e | N28171 | 0.65 | 0.83 |
| 1424451_at | Acaa1b | BC019882 | 0.64 | 0.53 |
| 1443918_at | 2700050L05Rik | BG068962 | 0.64 | 0.86 |
| 1426313_at | Bre | BE984258 | 0.64 | 0.49 |
| 1439391_at | 2810002I04Rik | BB559552 | 0.64 | 0.78 |
| 1446769_at | 2810439F02Rik | AV028075 | 0.64 | 1.01 |
| 1438979_s_at | 1700029I15Rik | AV043667 | 0.64 | 1.20 |
| 1451434_s_at | Gpatch8 | BC019948 | 0.64 | 0.88 |
| 1420130_s_at | D10Wsu52e | AA409545 | 0.64 | 0.86 |
| 1445221_at | | BB451452 | 0.64 | 0.96 |
| 1441380_at | 2810439F02Rik | BB044461 | 0.63 | 0.81 |
| 1455805_x_at | Ccdc22 | BB165451 | 0.63 | 0.82 |
| 1456674_at | E130016E03Rik | BB772877 | 0.63 | 0.77 |
| 1429698_at | LOC208595 | AK016498 | 0.63 | 0.82 |
| 1448818_at | Wnt5a | BC018425 | 0.63 | 1.04 |
| 1429819_at | Nmnat1 | AK017631 | 0.63 | 1.06 |
| 1451602_at | Snx6 | BC025911 | 0.63 | 0.81 |
| 1421141_a_at | Foxp1 | BG962849 | 0.63 | 1.05 |
| 1428665_at | Pfn4 | BQ174081 | 0.63 | 0.73 |
| 1455075_at | Pigv | BB321057 | 0.62 | 1.10 |
| 1432589_at | Plcg1 | BF166706 | 0.62 | 0.83 |
| 1447870_x_at | 1110002E22Rik | BB099116 | 0.62 | 0.61 |
| 1422307_at | | NM_031400 | 0.62 | 0.77 |
| 1431578_at | Wbp2nl | AK015863 | 0.62 | 1.00 |
| 1430997_at | Cd47 | AI882525 | 0.62 | 0.76 |
| 1441208_at | Hdhd2 | AW546142 | 0.62 | 1.10 |
| 1453607_at | Mfap3l | AV280494 | 0.61 | 1.54 |
| 1452328_s_at | Pja2 | BF160731 | 0.61 | 0.80 |
| 1447292_at | Actr1b | BB815306 | 0.61 | 1.01 |
| 1458870_x_at | Phrl | BG083658 | 0.61 | 1.48 |
| 1456760_at | Centg3 | BB342676 | 0.61 | 0.94 |
| 1436332_at | Hspb6 | BB755506 | 0.60 | 0.90 |
| 1436867_at | Srl | BG795043 | 0.60 | 0.72 |
| 1416164_at | Fbln5 | NM_011812 | 0.60 | 0.63 |
| 1447544_at | | BB486335 | 0.60 | 1.06 |
| 1421144_at | Rpgrip1 | NM_023879 | 0.60 | 0.50 |
| 1439609_at | | BB536410 | 0.59 | 0.86 |
| 1456641_at | 1190007F08Rik | AV225851 | 0.59 | 0.84 |
| 1443813_x_at | Bckdk | AV373435 | 0.59 | 0.78 |
| 1443542_at | | BB767151 | 0.59 | 0.79 |
| 1420864_at | Zfp161 | NM_009547 | 0.59 | 0.86 |
| 1418128_at | Adcy6 | NM_007405 | 0.58 | 1.65 |
| 1433923_at | Krt77 | AV230775 | 0.58 | 0.78 |
| 1420913_at | Slco2a1 | NM_033314 | 0.58 | 0.98 |
| 1437785_at | Adamts9 | AV364944 | 0.57 | 1.07 |
| 1431206_at | 5730601F06Rik | BI110339 | 0.57 | 0.83 |
| 1426658_x_at | Phgdh | L21027 | 0.57 | 0.81 |
| 1417420_at | Ccnd1 | NM_007631 | 0.57 | 0.92 |
| 1421036_at | Npas2 | BG070037 | 0.57 | 0.79 |
| 1430222_at | 9130007G19Rik | BB538672 | 0.55 | 0.63 |
| 1445536_at | AW061096 | AW061096 | 0.55 | 0.86 |
| 1449915_at | Zfp202 | NM_030713 | 0.55 | 0.79 |
| 1456784_at | "OTTMUSG 00000015762" | BB011034 | 0.55 | 0.73 |
| 1444304_at | A330102K23Rik | BE980520 | 0.54 | 0.89 |
| 1438679_at | Trim8 | AI843272 | 0.54 | 0.70 |
| 1456515_s_at | Tcfl5 | AV044715 | 0.54 | 0.96 |
| 1455255_at | 4833420G11Rik | AV250006 | 0.54 | 1.12 |
| 1430582_at | Shprh | BB496854 | 0.54 | 0.76 |
| 1452473_at | Prr15 | AJ132433 | 0.53 | 0.60 |
| 1447580_at | | AI835197 | 0.53 | 1.41 |
| 1427148_at | Pja2 | BF160731 | 0.52 | 0.75 |
| 1418019_at | Cpd | NM_007754 | 0.51 | 0.25 |
| 1454429_at | 5830462O15Rik | AK018030 | 0.51 | 0.56 |
| 1456799_at | E130110O22Rik | BB540910 | 0.51 | 0.85 |
| 1417479_at | Ppp2r3c | AV367559 | 0.51 | 0.82 |
| 1427963_s_at | Rdh9 | BE979765 | 0.50 | 0.69 |

TABLE 16-continued

Gene translation changes upon chronic cocaine treatment

| Probe | Symbol | GenBank | FCH D1 | FCH D2 |
|---|---|---|---|---|
| 1420889_at | Hccs | BB129992 | 0.49 | 1.12 |
| 1459766_x_at | Sf1 | BB055869 | 0.47 | 0.93 |
| 1431216_s_at | Dnajc6 | BI730538 | 0.41 | 0.79 |
| 1447773_x_at | 6330409D20Rik | BB308792 | 0.41 | 1.22 |

Probe = Affymetrix probe identification; Symbol = official gene symbol; FCH D1 = fold change in striatonigral (D1) cells; FCH D2 = fold change in striatopallidal (D2) cells.

Statistically over-represented Gene Ontology (GO) and Kyoto Encyclopedia of Genes and Genomes (KEGG) pathway terms associated with genes whose expression was changed upon acute or chronic cocaine administration were searched (tables below). Amongst the most GO biological processes altered in D1-expressing striatonigral neurons upon chronic cocaine administration was the gamma-aminobutyric acid (GABA) signaling pathway (Gabrb3, Gabra1, Cacnb4, and Gabra4). This finding is relevant in light of positron emission tomography (PET) studies that have documented an enhanced sensitivity to the benzodiazepine lorazepam (binds GABA receptors) among chronic cocaine abusers (N. D. Volkow et al., *Am J Psychiatry* 155, 200-6 (February, 1998)).

TABLE 17

Top 1,000 striatonigral (D1) cell translated mRNAs enriched when compared to a reference sample

| ProbeSymbol | FEN | Genbank | GeneSymbol |
|---|---|---|---|
| 1452217_at | 112.5 | BE570050 | Ahnak |
| 1426814_at | 100.6 | BM248309 | AU024582 |
| 1418357_at | 71.38 | NM_008241 | Foxg1 |
| 1419231_s_at | 70.83 | NM_010661 | Krt1-12 |
| 1427017_at | 70.71 | BB104560 | Satb2 |
| 1435564_at | 68.33 | BB547893 | C230078M08Rik |
| 1457132_at | 57.88 | BF456117 | |
| 1458499_at | 47.5 | AW123977 | Pde10a |
| 1443287_at | 47.05 | BB555669 | Gm1337 |
| 1422079_at | 45.93 | NM_008856 | Prkch |
| 1438022_at | 45.81 | BQ266518 | Rab11fip3 |
| 1457424_at | 44.35 | BB760085 | Eya1 |
| 1426815_s_at | 44.33 | BM248309 | AU024582 |
| 1436268_at | 40.01 | AI841578 | Ddn |
| 1456051_at | 38.14 | BB282271 | Drd1a |
| 1416711_at | 36.16 | NM_009322 | Tbr1 |
| 1420437_at | 34.39 | NM_008324 | Indo |
| 1455629_at | 33.34 | BE957273 | Drd1a |
| 1454867_at | 32.24 | BB234631 | Mn1 |
| 1434917_at | 31.38 | BQ173923 | Cobl |
| 1428642_at | 31.19 | AK018094 | Slc35d3 |
| 1423117_at | 30.07 | BB837171 | Pum1 |
| 1460325_at | 29.16 | BB837171 | Pum1 |
| 1416776_at | 24.48 | NM_016669 | Crym |
| 1424606_at | 23.37 | BC024854 | Cplx3 |
| 1450339_a_at | 22.89 | NM_021399 | Bcl11b |
| 1449425_at | 22.68 | BC026373 | Wnt2 |
| 1423802_at | 22.57 | BC017634 | Camkv |
| 1437698_at | 22.46 | AV370579 | Myo5b |
| 1427807_at | 22.23 | BC017159 | 4930448N21Rik |
| 1422720_at | 21.52 | BQ176915 | Isl1 |
| 1435083_at | 21.47 | BI155559 | Ctxn1 |
| 1439854_at | 21.22 | BQ175572 | AI838259 |
| 1450042_at | 21.2 | BB322201 | Arx |
| 1425756_at | 21.04 | AF425643 | Rab40b |
| 1436650_at | 20.92 | AV241894 | Filip1 |
| 1436275_at | 20.82 | AW490636 | Kcnip2 |
| 1427975_at | 20.66 | AK008807 | 2210403B10Rik |
| 1436566_at | 20.43 | AV364488 | Rab40b |
| 1435749_at | 19.85 | AW911807 | Gda |
| 1423530_at | 19.32 | BB320288 | Stk32c |

TABLE 17-continued

Top 1,000 striatonigral (D1) cell translated mRNAs enriched when compared to a reference sample

| ProbeSymbol | FEN | Genbank | GeneSymbol |
|---|---|---|---|
| 1417356_at | 19.31 | AB003040 | Peg3 |
| 1425870_a_at | 19.26 | AF439339 | Kcnip2 |
| 1427358_a_at | 18.94 | BC026671 | Dapk1 |
| 1435615_at | 18.72 | BB277790 | Zfp365 |
| 1455034_at | 18.64 | BB703394 | Nr4a2 |
| 1444681_at | 18.62 | BB749686 | D14Ertd171e |
| 1434248_at | 18.36 | BM243756 | Prkch |
| 1427343_at | 18.15 | BC026377 | Rasd2 |
| 1450071_at | 18.15 | BG694892 | Ash1l |
| 1451280_at | 17.94 | BB159263 | MGI: 107562 |
| 1436329_at | 17.56 | AV346607 | Egr3 |
| 1434653_at | 17.09 | AV026976 | Ptk2b |
| 1434115_at | 16.95 | BQ176681 | |
| 1424507_at | 16.92 | BC011277 | Rin1 |
| 1452176_at | 16.72 | BB292874 | Nup153 |
| 1453129_a_at | 16.55 | AK004813 | Rgs12 |
| 1427683_at | 16.48 | X06746 | Egr2 |
| 1418782_at | 16.46 | NM_009107 | Rxrg |
| 1452966_at | 16.43 | AK020296 | 9130430L19Rik |
| 1457341_at | 16.07 | BE991676 | |
| 1425503_at | 16.07 | AB037596 | Gcnt2 |
| 1423171_at | 15.52 | BE947345 | Gpr88 |
| 1430306_a_at | 15.47 | AK004157 | Atp6v1c2 |
| 1456283_at | 15.47 | AV346431 | Neto1 |
| 1427682_at | 15.33 | X06746 | Egr2 |
| 1422034_a_at | 15.24 | NM_023128 | Palm |
| 1449420_at | 15.22 | NM_008800 | Pde1b |
| 1450072_at | 14.84 | BG694892 | Ash1l |
| 1435227_at | 14.76 | BM117007 | |
| 1455200_at | 14.73 | BB818370 | Pak6 |
| 1433566_at | 14.65 | BB381618 | Rasl10b |
| 1456054_a_at | 14.47 | BB314559 | Pum1 |
| 1435366_at | 14.24 | BB486367 | D430042O09Rik |
| 1426980_s_at | 14.23 | BC006054 | E130012A19Rik |
| 1424248_at | 14.1 | BB159263 | MGI: 107562 |
| 1416953_at | 13.95 | NM_010217 | Ctgf |
| 1433701_at | 13.94 | BB371430 | Mpped1 |
| 1448364_at | 13.87 | U95826 | Ccng2 |
| 1418619_at | 13.83 | NM_008319 | Icam5 |
| 1450750_a_at | 13.58 | NM_013613 | Nr4a2 |
| 1450061_at | 13.55 | BM120053 | Enc1 |
| 1454043_a_at | 13.52 | AK015412 | Kcnab1 |
| 1450723_at | 13.4 | BQ176915 | Isl1 |
| 1435748_at | 13.37 | AW911807 | Gda |
| 1425479_at | 13.34 | BF160451 | Smyd5 |
| 1452202_at | 13.28 | BG069616 | Pde2a |
| 1432646_a_at | 13.21 | BE859789 | 2900097C17Rik |
| 1452974_at | 13.21 | AK017551 | Nol8 |
| 1460038_at | 13.11 | BG065255 | Pou3f1 |
| 1425130_a_at | 13.06 | U28216 | Ptpn5 |
| 1458342_at | 13.01 | BB313069 | |
| 1455190_at | 12.97 | BM114283 | Gng7 |
| 1436066_at | 12.96 | BI965477 | Kalrn |
| 1428951_at | 12.89 | AK017551 | Nol8 |
| 1436408_at | 12.84 | BE946298 | |
| 1454906_at | 12.83 | BB266455 | Rarb |
| 1417560_at | 12.81 | BB478992 | Sfxn1 |
| 1440204_at | 12.8 | AW494150 | 3110039M20Rik |
| 1424037_at | 12.77 | BC027291 | Itpka |
| 1422230_s_at | 12.67 | NM_007812 | Cyp2a4; Cyp2a5 |
| 1429422_at | 12.57 | AK016788 | 4933412E12Rik |
| 1436532_at | 12.51 | BB326709 | Dcamkl3 |
| 1431936_a_at | 12.33 | AK009828 | Neu2 |
| 1452298_at | 12.18 | AW546331 | Myo5b |
| 1422153_a_at | 12.11 | NM_026853 | Asb11 |
| 1427931_s_at | 12.09 | BG063905 | Pdxk |
| 1433627_at | 12.04 | AW546839 | Sec23ip |
| 1417279_at | 11.94 | NM_010585 | Itpr1 |
| 1428139_at | 11.9 | AK015988 | 4930538D17Rik |
| 1450213_at | 11.85 | NM_013875 | Pde7b |
| 1439552_at | 11.83 | BE985618 | Trio |
| 1449634_a_at | 11.74 | AW046296 | C030032C09Rik |
| 1438355_at | 11.68 | AI414870 | |
| 1417355_at | 11.64 | AB003040 | Peg3 |
| 1456640_at | 11.46 | AW910872 | Sh3rf2 |
| 1454721_at | 11.44 | AV257687 | 1110018G07Rik |
| 1435780_at | 11.44 | BG966595 | Psd |
| 1418047_at | 11.42 | NM_009717 | Neurod6 |
| 1421176_at | 11.39 | BB354696 | Rasgrp1 |
| 1450026_a_at | 11.37 | AV306734 | B3gnt1 |
| 1457311_at | 11.36 | AW490258 | Camk2a |
| 1451604_a_at | 11.23 | BC014291 | Acvrl1 |
| 1416437_a_at | 11.21 | AF262046 | Mapk8ip3 |
| 1451726_at | 11.18 | BC020019 | Mtmr6 |
| 1440534_at | 11.16 | BB177862 | |
| 1451808_at | 11.16 | U11075 | Kcnj4 |
| 1434295_at | 11.16 | BE691356 | Rasgrp1 |
| 1457143_at | 11.12 | BB322292 | Gli3 |
| 1416456_a_at | 11.11 | BC011134 | Chia |
| 1442166_at | 11.08 | BB273427 | Cpne5 |
| 1448366_at | 11.05 | NM_016801 | Stx1a |
| 1421739_a_at | 11.05 | NM_010768 | Matk |
| 1427045_at | 11.03 | AI849322 | Synpo |
| 1435296_at | 10.95 | AV349563 | Adra2c |
| 1434521_at | 10.89 | BB148972 | Rfxdc2 |
| 1438665_at | 10.88 | BF456582 | Smpd3 |
| 1444978_at | 10.86 | BM223267 | |
| 1451331_at | 10.75 | BC026568 | Ppp1r1b |
| 1422710_a_at | 10.73 | NM_021415 | Cacna1h |
| 1430013_at | 10.7 | BE993118 | 2210008F06Rik |
| 1422902_s_at | 10.63 | NM_023799 | Mgea5 |
| 1422779_at | 10.57 | NM_021491 | Smpd3 |
| 1428781_at | 10.54 | BI452905 | 1110014F24Rik |
| 1460136_at | 10.52 | AI462839 | |
| 1416691_at | 10.51 | NM_019581 | Gtpbp2 |
| 1450143_at | 10.51 | BB354696 | Rasgrp1 |
| 1435741_at | 10.46 | BB312125 | Pde8b |
| 1420656_at | 10.35 | BM117900 | Doc2b |
| 1437125_at | 10.24 | BB476448 | Camk2a |
| 1454768_at | 10.24 | AV337635 | Kcnf1 |
| 1420978_at | 10.23 | NM_010938 | Nrf1 |
| 1450227_at | 10.22 | BM199504 | Ankrd6 |
| 1447359_at | 10.22 | AI326876 | LOC381955 |
| 1436092_at | 10.21 | BB336256 | |
| 1448327_at | 10.11 | NM_033268 | Actn2 |
| 1420545_a_at | 10.1 | NM_029716 | Chn1 |
| 1418691_at | 10.03 | NM_011268 | Rgs9 |
| 1423756_s_at | 10.02 | BC019836 | Igfbp4 |
| 1460343_at | 10.02 | AF401228 | Neurl |
| 1421028_a_at | 10.01 | AI595932 | Mef2c |
| 1429089_s_at | 9.93 | BG063749 | 2900026A02Rik |
| 1418015_at | 9.916 | BI689507 | Pum2 |
| 1428950_s_at | 9.758 | AK017551 | Nol8 |
| 1419033_at | 9.756 | AW556821 | 2610018G03Rik |
| 1452879_at | 9.72 | AI848603 | Synpo2 |
| 1441368_at | 9.671 | BB102769 | |
| 1447326_s_at | 9.625 | AW122925 | Zfp261 |
| 1455564_at | 9.621 | BQ176236 | Bcr |
| 1455620_at | 9.572 | BQ177219 | |
| 1452507_at | 9.568 | AF022078 | Dlx6 |
| 1415904_at | 9.554 | BC003305 | Lpl |
| 1451507_at | 9.554 | BB280300 | Mef2c |
| 1428338_at | 9.553 | AK019166 | 2610039E05Rik |
| 1421353_at | 9.538 | NM_013875 | Pde7b |
| 1419470_at | 9.495 | BI713933 | Gnb4 |
| 1417114_at | 9.466 | AF163665 | Gcl |
| 1448990_s_at | 9.433 | AI255256 | Myo1b |
| 1458406_at | 9.404 | BG144063 | |
| 1430521_s_at | 9.38 | AW548480 | Cpne8 |
| 1434025_at | 9.365 | BG069607 | |
| 1422621_at | 9.363 | BM507707 | Ranbp2 |
| 1423202_a_at | 9.355 | U22016 | Ncor1 |
| 1422165_at | 9.336 | X66603 | Pou3f4 |
| 1433815_at | 9.334 | AV290082 | MGI: 1923321 |
| 1423489_at | 9.324 | BC021914 | Mmd |
| 1460567_at | 9.318 | BB148972 | Rfxdc2 |
| 1446492_at | 9.312 | BB396896 | C630028F04Rik |
| 1420580_at | 9.273 | NM_026249 | 4930429B21Rik |
| 1417804_at | 9.21 | NM_011242 | LOC381240 |
| 1457052_at | 9.179 | BG064867 | AW536275 |

TABLE 17-continued

Top 1,000 striatonigral (D1) cell translated mRNAs enriched when compared to a reference sample

| ProbeSymbol | FEN | Genbank | GeneSymbol |
|---|---|---|---|
| 1460555_at | 9.176 | BM242294 | 6330500D04Rik |
| 1417680_at | 9.153 | NM_008419 | Kcna5 |
| 1454656_at | 9.123 | AV271736 | Spata13 |
| 1458407_s_at | 9.093 | BG144063 | |
| 1454752_at | 9.081 | AV307961 | AI606861 |
| 1452368_at | 9.043 | AI853148 | Bcr |
| 1453273_at | 9.038 | AV142265 | Kcnv1 |
| 1455701_at | 9.019 | BI965517 | Snx26 |
| 1452476_at | 8.997 | W41214 | Cacnb2 |
| 1418169_at | 8.988 | BB223737 | Zcchc14 |
| 1423285_at | 8.971 | BB731671 | Coch |
| 1455447_at | 8.93 | BM116882 | D430019H16Rik |
| 1436998_at | 8.924 | BB428991 | Ankrd43 |
| 1455220_at | 8.9 | BB353860 | Frat2 |
| 1419224_at | 8.894 | NM_033567 | Cecr6 |
| 1442234_at | 8.872 | BB770422 | Chst2 |
| 1439557_s_at | 8.849 | BB097063 | Ldb2 |
| 1457729_at | 8.819 | AW492805 | |
| 1448978_at | 8.804 | NM_019867 | Ngef |
| 1419221_a_at | 8.803 | NM_016758 | Rgs14 |
| 1456515_s_at | 8.774 | AV044715 | Tcfl5 |
| 1455272_at | 8.747 | BB429139 | Grm5 |
| 1418373_at | 8.673 | NM_018870 | Pgam2 |
| 1422787_at | 8.672 | NM_019873 | Fkbpl |
| 1437091_at | 8.631 | AV323885 | Accn4 |
| 1451517_at | 8.627 | AF420001 | Rhobtb2 |
| 1417462_at | 8.62 | NM_007598 | Cap1 |
| 1455361_at | 8.612 | AW493391 | Dgkb |
| 1416783_at | 8.595 | NM_009311 | Tac1 |
| 1428872_at | 8.573 | AW495537 | 4121402D02Rik |
| 1418881_at | 8.568 | NM_054095 | Efcbp2 |
| 1431164_at | 8.563 | AK017818 | Rragd |
| 1455754_at | 8.54 | BQ043839 | Lmo3 |
| 1439767_at | 8.526 | BB130159 | Dlgap2 |
| 1432378_at | 8.526 | AK021043 | C030004G16Rik |
| 1422018_at | 8.509 | NM_010437 | Hivep2 |
| 1441894_s_at | 8.487 | BB071890 | Grasp |
| 1421142_s_at | 8.473 | BG962849 | Foxp1 |
| 1423551_at | 8.43 | BB776961 | Cdh13 |
| 1420961_a_at | 8.428 | NM_028582 | Ivns1abp |
| 1455683_at | 8.423 | BB451404 | Tbc1d8 |
| 1434077_at | 8.407 | AV222037 | Wdr37 |
| 1436312_at | 8.405 | AV317621 | Zfpn1a1 |
| 1445539_at | 8.395 | BE687857 | Pde7b |
| 1435221_at | 8.388 | BM220880 | Foxp1 |
| 1441733_s_at | 8.387 | C88147 | Nup153 |
| 1426915_at | 8.387 | BC021490 | Dapk1 |
| 1416286_at | 8.354 | NM_009062 | Rgs4 |
| 1418714_at | 8.352 | NM_008748 | Dusp8 |
| 1427005_at | 8.339 | BM234765 | Plk2 |
| 1453782_at | 8.33 | BI737125 | 3021401C12Rik |
| 1421101_a_at | 8.319 | NM_010698 | Ldb2 |
| 1416266_at | 8.283 | AF026537 | Pdyn |
| 1423376_a_at | 8.251 | AV341904 | Dok4 |
| 1429617_at | 8.246 | BM119209 | Cyld |
| 1427344_s_at | 8.237 | BC026377 | Rasd2 |
| 1437929_at | 8.236 | AV306847 | Dact2 |
| 1421817_at | 8.23 | AK019177 | Gsr |
| 1443612_at | 8.216 | AW123199 | |
| 1428852_at | 8.213 | AK018140 | Dock3 |
| 1423561_at | 8.172 | AI838010 | Nell2 |
| 1417440_at | 8.166 | NM_033566 | Arid1a |
| 1440849_at | 8.044 | AV327187 | 6330417G04Rik |
| 1437918_at | 8.028 | AV374644 | 4930539E08Rik |
| 1433583_at | 8.025 | AV327248 | Zfp365 |
| 1429285_at | 8.014 | AK009343 | Serpina9 |
| 1436734_at | 8.003 | BB523550 | E130309F12Rik |
| 1438985_x_at | 8 | BB158937 | Otud5 |
| 1418017_at | 7.974 | BI689507 | Pum2 |
| 1435435_at | 7.965 | BB357580 | Cttnbp2 |
| 1455885_at | 7.965 | AV238106 | 6530401C20Rik |
| 1423544_at | 7.964 | BB188812 | Ptpn5 |
| 1421446_at | 7.962 | NM_011102 | Prkcc |
| 1454742_at | 7.942 | BB003229 | Rasgef1b |
| 1419389_at | 7.941 | BQ180352 | Pde10a |
| 1426518_at | 7.939 | AV333951 | Tubgcp5 |
| 1423636_at | 7.931 | AK017259 | Wdr31 |
| 1433767_at | 7.931 | AV257687 | 1110018G07Rik |
| 1416562_at | 7.91 | AF326547 | Gad1 |
| 1427450_x_at | 7.907 | BI080370 | Myo1b |
| 1454845_x_at | 7.905 | AW049955 | Gpr24 |
| 1420388_at | 7.905 | NM_008939 | Prss12 |
| 1422901_at | 7.896 | NM_023799 | Mgea5 |
| 1416804_at | 7.845 | NM_053252 | LOC114601 |
| 1416350_at | 7.826 | NM_078477 | Klf16 |
| 1440148_at | 7.825 | AI852874 | Gpr6 |
| 1424796_at | 7.809 | BC024705 | 1700054N08Rik |
| 1457440_at | 7.808 | BB451927 | Sstr4 |
| 1427618_at | 7.801 | BQ176417 | Cdh9 |
| 1447863_s_at | 7.794 | BB322941 | Nr4a2 |
| 1428535_at | 7.775 | AK004276 | 9430020K01Rik |
| 1431394_a_at | 7.754 | AK014938 | Lrrk2 |
| 1430675_at | 7.733 | BM932606 | 2900055J20Rik |
| 1460206_at | 7.728 | NM_019518 | Grasp |
| 1423186_at | 7.703 | BM228957 | Tiam2 |
| 1448807_at | 7.7 | NM_133849 | Hrh3 |
| 1456401_at | 7.693 | BB078175 | Cacnb2 |
| 1450690_at | 7.69 | BM507707 | Ranbp2 |
| 1434494_at | 7.684 | AV348245 | Syt16 |
| 1451506_at | 7.667 | BB280300 | Mef2c |
| 1427426_at | 7.619 | AV362204 | Kcnq5 |
| 1445691_at | 7.613 | AW121426 | Chn1 |
| 1434695_at | 7.594 | AV270035 | Dtl |
| 1425833_a_at | 7.582 | AF326551 | Hpca |
| 1456336_at | 7.561 | BB182912 | A330102K23Rik |
| 1437865_at | 7.55 | AW546433 | Spata13 |
| 1435605_at | 7.538 | BB125424 | Actr3b |
| 1422678_at | 7.531 | AK002443 | Dgat2 |
| 1449472_at | 7.521 | NM_008151 | Gpr12 |
| 1456786_at | 7.493 | BB097063 | Ldb2 |
| 1429741_at | 7.479 | AV142265 | Kcnv1 |
| 1442434_at | 7.465 | BM195829 | D8Ertd82e |
| 1442113_at | 7.463 | BB183350 | 5330417C22Rik |
| 1448656_at | 7.462 | NM_007581 | Cacnb3 |
| 1423012_at | 7.457 | NM_018801 | Syt7 |
| 1446698_at | 7.409 | BB551879 | E230031K19 |
| 1422068_at | 7.389 | NM_011141 | Pou3f1 |
| 1417129_a_at | 7.369 | U68384 | Mrg1 |
| 1423344_at | 7.368 | AK010968 | Epor |
| 1454877_at | 7.333 | BQ174721 | Sertad4 |
| 1426585_s_at | 7.326 | BM209765 | Mapk1 |
| 1426901_s_at | 7.32 | BB657856 | Camta2 |
| 1423240_at | 7.31 | BG868120 | Src |
| 1420981_a_at | 7.304 | NM_010723 | Lmo4 |
| 1431074_a_at | 7.298 | BI654600 | Pitpnc1 |
| 1438889_at | 7.294 | BB183456 | |
| 1418847_at | 7.268 | NM_009705 | Arg2 |
| 1436733_at | 7.257 | BB523550 | E130309F12Rik |
| 1424201_a_at | 7.248 | AW537349 | Sehl1 |
| 1457979_at | 7.244 | BM938335 | |
| 1421141_a_at | 7.232 | BG962849 | Foxp1 |
| 1450655_at | 7.231 | AA214868 | Herc1 |
| 1437586_at | 7.22 | BB756908 | Cnot4 |
| 1434008_at | 7.201 | BE993937 | Scn4b |
| 1419696_at | 7.198 | NM_013488 | Cd4 |
| 1417341_a_at | 7.194 | NM_025800 | Ppp1r2 |
| 1434458_at | 7.182 | BB444134 | Fst |
| 1438784_at | 7.162 | BB329234 | |
| 1421789_s_at | 7.149 | NM_007478 | Arf3 |
| 1452624_at | 7.147 | BM900077 | Lrrtm1 |
| 1450835_a_at | 7.147 | NM_020014 | Gfra4 |
| 1419390_at | 7.143 | BQ180352 | Pde10a |
| 1429316_at | 7.138 | AK018120 | Rasgef1a |
| 1436381_at | 7.133 | BQ175774 | Dlgap3 |
| 1433969_at | 7.121 | AU067824 | AU067824 |
| 1426009_a_at | 7.119 | BC003763 | Pip5k1b |
| 1434090_at | 7.098 | BB037094 | 4930429A22Rik |
| 1437018_at | 7.083 | BG072348 | Pnma2 |
| 1430127_a_at | 7.067 | AK007904 | Ccnd2 |
| 1415743_at | 7.065 | NM_010412 | Hdac5 |

TABLE 17-continued

Top 1,000 striatonigral (D1) cell translated mRNAs
enriched when compared to a reference sample

| ProbeSymbol | FEN | Genbank | GeneSymbol |
|---|---|---|---|
| 1452940_x_at | 7.049 | AI595920 | Pitpnc1 |
| 1456280_at | 7.049 | BG067086 | Clspn |
| 1416398_at | 7.036 | BB474887 | Mesdc1 |
| 1423231_at | 7.034 | AK002933 | Nrgn |
| 1451270_at | 7.031 | BC020036 | Dusp18 |
| 1452467_at | 7.029 | BQ042988 | Mmab |
| 1438799_at | 7.028 | AV338180 | Dlx6os1 |
| 1429637_at | 7.024 | AK008987 | 2210419I08Rik |
| 1432073_at | 7.021 | AK007198 | 1700113I22Rik |
| 1435558_at | 7.019 | BB351248 | Bai2 |
| 1436738_at | 6.98 | AV094878 | AI449441 |
| 1456785_at | 6.96 | BQ175889 | Crsp2 |
| 1435808_at | 6.954 | BB174377 | A230051G13Rik |
| 1439855_at | 6.931 | AV341449 | BC023818 |
| 1417524_at | 6.918 | NM_009920 | Cnih2 |
| 1435553_at | 6.896 | AV376183 | Pdzk3 |
| 1431920_a_at | 6.896 | AK008082 | 2010004A03Rik |
| 1441963_at | 6.895 | BB427703 | MGI: 2656976 |
| 1448989_a_at | 6.888 | AI255256 | Myo1b |
| 1421027_a_at | 6.878 | AI595932 | Mef2c |
| 1455296_at | 6.854 | BE952286 | Adcy5 |
| 1435666_at | 6.846 | AW553439 | |
| 1435071_at | 6.829 | AV327165 | Zfyve1 |
| 1439548_at | 6.82 | BB390705 | Rap2b |
| 1429104_at | 6.817 | AK012581 | 0610025L06Rik |
| 1437460_x_at | 6.805 | BB264363 | Rin1 |
| 1455758_at | 6.804 | BM215011 | |
| 1425929_a_at | 6.804 | AF249668 | Rnf14 |
| 1457919_at | 6.801 | BB446049 | D030054H15Rik |
| 1443694_at | 6.8 | BB794177 | Rgs20 |
| 1417090_at | 6.799 | NM_009037 | Rcn1 |
| 1452964_at | 6.774 | AK016577 | 4932702F08Rik |
| 1431230_a_at | 6.748 | Z74630 | Btbd9 |
| 1439569_at | 6.734 | AV291031 | Gpr83 |
| 1439866_at | 6.733 | BQ173950 | Parc |
| 1447728_x_at | 6.677 | BB718260 | Hspa9a |
| 1435210_s_at | 6.675 | BQ174936 | Snph |
| 1419542_at | 6.653 | NM_010021 | Dazl |
| 1430617_at | 6.632 | BB238604 | Oip5 |
| 1419137_at | 6.631 | NM_021423 | Shank3 |
| 1420530_at | 6.63 | AW553317 | Neud4 |
| 1447301_at | 6.625 | BG228875 | Gm258 |
| 1418144_a_at | 6.621 | NM_008847 | Pip5k1b |
| 1422683_at | 6.62 | NM_022986 | Irak1bp1 |
| 1455056_at | 6.612 | BM231903 | Lmo7 |
| 1421346_a_at | 6.608 | NM_009320 | Slc6a6 |
| 1434359_at | 6.607 | AV329070 | 6330500D04Rik |
| 1423640_at | 6.584 | BC026512 | Synpr |
| 1418080_at | 6.581 | AW125856 | B4galt2 |
| 1421140_a_at | 6.58 | BG962849 | Foxp1 |
| 1451285_at | 6.58 | AF224264 | Fus |
| 1451236_at | 6.57 | BC026463 | Rerg |
| 1435043_at | 6.569 | BB794833 | Plcb1 |
| 1434029_at | 6.567 | AW545676 | LOC545794 |
| 1443888_at | 6.535 | BB426608 | |
| 1430037_at | 6.531 | AK017836 | Snx27 |
| 1447178_at | 6.529 | BB173057 | |
| 1420857_at | 6.525 | NM_133737 | Lancl2 |
| 1460447_at | 6.52 | AK019372 | 3000003F02Rik |
| 1420146_at | 6.514 | AI429207 | Tiam2 |
| 1419216_at | 6.506 | NM_009734 | Azi1 |
| 1460262_a_at | 6.492 | NM_026401 | 1700037H04Rik |
| 1421340_at | 6.483 | NM_008580 | Map3k5 |
| 1415976_a_at | 6.468 | AU080787 | Carhsp1 |
| 1419066_at | 6.46 | NM_030244 | Ier5l |
| 1422706_at | 6.45 | AV370981 | Tmepai |
| 1459679_s_at | 6.45 | AA406997 | Myo1b |
| 1438751_at | 6.44 | BB736474 | Slc30a10 |
| 1454960_at | 6.43 | BI646741 | Smad3 |
| 1425510_at | 6.43 | BM213936 | Mark1 |
| 1429224_at | 6.419 | AK017476 | Pnma1 |
| 1449468_at | 6.412 | NM_012028 | St6galnac5 |
| 1450748_at | 6.41 | NM_021491 | Smpd3 |
| 1431422_a_at | 6.399 | AK009744 | Dusp14 |
| 1423532_at | 6.374 | AI850285 | Rnf44 |

TABLE 17-continued

Top 1,000 striatonigral (D1) cell translated mRNAs
enriched when compared to a reference sample

| ProbeSymbol | FEN | Genbank | GeneSymbol |
|---|---|---|---|
| 1422335_at | 6.373 | NM_007418 | Adra2c |
| 1422527_at | 6.373 | NM_010386 | H2-DMa |
| 1421191_s_at | 6.372 | NM_053187 | Gopc |
| 1434762_at | 6.358 | BF457736 | A730041O15Rik |
| 1420377_at | 6.336 | BG071333 | St8sia2 |
| 1437001_at | 6.333 | BQ173949 | Gsk3b |
| 1435763_at | 6.322 | BI218684 | Tbc1d16 |
| 1434153_at | 6.316 | BI408715 | Shb |
| 1427565_a_at | 6.309 | AF213387 | Abcc5 |
| 1427468_at | 6.307 | M81483 | Ppp3cb |
| 1440940_at | 6.305 | BE949510 | Cacnb1 |
| 1449956_at | 6.301 | NM_011104 | Prkce |
| 1436100_at | 6.298 | AV347995 | Sh2d5 |
| 1420871_at | 6.293 | BF472806 | Gucy1b3 |
| 1455225_at | 6.293 | AV237615 | Syne1 |
| 1448709_at | 6.292 | NM_033566 | Arid1a |
| 1438224_at | 6.287 | BE572265 | Zswim5 |
| 1448023_at | 6.278 | BB662566 | Kalrn |
| 1426024_a_at | 6.278 | AF187147 | Dbn1 |
| 1435500_at | 6.266 | BB270778 | Rab26 |
| 1451751_at | 6.258 | AF335325 | Ddit4l |
| 1453836_a_at | 6.25 | AK006949 | Mgll |
| 1417559_at | 6.244 | BB478992 | Sfxn1 |
| 1456509_at | 6.236 | BB382807 | 1110032F04Rik |
| 1440361_at | 6.23 | BB272510 | |
| 1425465_a_at | 6.225 | AV317107 | Senp2 |
| 1460279_a_at | 6.222 | AF043219 | Gtf2i |
| 1440207_at | 6.219 | BI155142 | AI505034 |
| 1444139_at | 6.189 | BG797099 | Ddit4l |
| 1421860_at | 6.171 | BG065300 | Clstn1 |
| 1458443_at | 6.17 | BE986758 | Mect1 |
| 1448374_at | 6.167 | AK005130 | Med28 |
| 1454762_at | 6.164 | BM932447 | Xkrx |
| 1451908_a_at | 6.154 | BC005766 | Sec14l1 |
| 1429718_at | 6.15 | BB782729 | Slitrk5 |
| 1451696_at | 6.146 | BC004695 | Zfp64 |
| 1449957_at | 6.14 | NM_007955 | Ptprv |
| 1439041_at | 6.128 | BM239325 | Slc39a10 |
| 1433471_at | 6.127 | AI323642 | Tcf7 |
| 1430640_a_at | 6.126 | BI695530 | Prkar2b |
| 1429111_at | 6.102 | AV270892 | Tln2 |
| 1421768_a_at | 6.092 | NM_011982 | Homer1 |
| 1421000_at | 6.085 | AI448404 | Cnot4 |
| 1460718_s_at | 6.076 | AF192558 | Mtch1 |
| 1434776_at | 6.06 | AW543460 | Pard3 |
| 1435218_at | 6.058 | BI134758 | Rasgef1a |
| 1452861_at | 6.049 | AK008485 | 2010300C02Rik |
| 1454609_x_at | 6.047 | BB770958 | 6430527G18Rik |
| 1457651_x_at | 6.046 | BB270375 | Rem2 |
| 1438068_at | 6.042 | BB251859 | |
| 1452380_at | 6.026 | BB075797 | Epha7 |
| 1428184_at | 6.025 | BB348639 | 3110035E14Rik |
| 1425249_a_at | 6.025 | AV317107 | Senp2 |
| 1426012_a_at | 6.024 | BC010499 | 2610301G19Rik |
| 1418535_at | 6.023 | NM_016846 | Rgl1 |
| 1425249_a_at | 6.007 | AB000828 | Tyro3 |
| 1453886_a_at | 6.005 | AK017037 | Slc25a26 |
| 1421897_at | 6 | AI385733 | Elk1 |
| 1455178_at | 6 | BB496468 | Rutbc1 |
| 1436403_at | 5.998 | BB452429 | BC025575 |
| 1420610_at | 5.979 | AV024339 | Prkacb |
| 1416996_at | 5.979 | BC005421 | Tbc1d8 |
| 1433451_at | 5.967 | BB177836 | Cdk5r1 |
| 1438664_at | 5.966 | BB216074 | Prkar2b |
| 1417461_at | 5.957 | NM_007598 | Cap1 |
| 1459051_at | 5.956 | BB781615 | 6530418L21Rik |
| 1426450_at | 5.955 | BM207017 | Plcl2 |
| 1455301_at | 5.95 | BG064092 | BQ952480 |
| 1423973_a_at | 5.949 | BC024935 | Arf3 |
| 1417612_at | 5.948 | NM_008484 | Lamb3 |
| 1423694_at | 5.934 | BC006935 | Kctd10 |
| 1417612_at | 5.933 | BF147705 | Ier5 |
| 1425680_a_at | 5.92 | AF110396 | Btrc |
| 1448063_at | 5.918 | AW226526 | Iqsec2 |
| 1448414_at | 5.911 | NM_011232 | Rad1 |

TABLE 17-continued

Top 1,000 striatonigral (D1) cell translated mRNAs enriched when compared to a reference sample

| ProbeSymbol | FEN | Genbank | GeneSymbol |
|---|---|---|---|
| 1423478_at | 5.909 | BF660388 | Prkcb1 |
| 1449921_s_at | 5.903 | NM_009947 | Cpne6 |
| 1429438_at | 5.888 | AV318805 | Bcor |
| 1457077_at | 5.875 | BB306048 | |
| 1427299_at | 5.87 | BE376079 | Rps6ka3 |
| 1428892_at | 5.869 | AK004331 | Ppil1 |
| 1449164_at | 5.866 | BC021637 | Cd68 |
| 1434763_at | 5.864 | BF457736 | A730041O15Rik |
| 1435265_at | 5.861 | BF466929 | |
| 1436754_at | 5.86 | BB360523 | AI839735 |
| 1433642_at | 5.857 | BB384173 | Arfrp2 |
| 1434154_at | 5.83 | BQ177107 | Kctd13 |
| 1449158_at | 5.824 | NM_010607 | Kcnk2 |
| 1441867_x_at | 5.82 | AI480494 | 4930534B04Rik |
| 1429228_at | 5.818 | BE980134 | 4930534B04Rik |
| 1421116_a_at | 5.811 | NM_024226 | Rtn4 |
| 1426416_a_at | 5.809 | AV216410 | Yipf4 |
| 1449241_at | 5.803 | NM_053105 | Klhl1 |
| 1453093_at | 5.801 | AK018593 | Rasgef1c |
| 1417305_at | 5.798 | NM_007463 | Apeg1 |
| 1441065_at | 5.787 | BB305753 | |
| 1442754_at | 5.778 | BE692283 | C030013G03Rik |
| 1440711_at | 5.777 | BB426320 | C630001G18Rik |
| 1418263_at | 5.774 | BC024852 | Ddx25 |
| 1421175_at | 5.771 | NM_008666 | Myt1l |
| 1431056_a_at | 5.77 | AK017272 | Lpl |
| 1457702_at | 5.766 | BB284435 | Gpr12 |
| 1422407_s_at | 5.761 | NM_008284 | Hras1 |
| 1422208_a_at | 5.761 | BC016135 | Gnb5 |
| 1455387_at | 5.76 | AV112972 | 1110001M19Rik |
| 1455191_x_at | 5.747 | BB822856 | Pip5k1b |
| 1440918_at | 5.735 | AW495511 | Rasgrf2 |
| 1418982_at | 5.731 | BC011118 | Cebpa |
| 1433988_s_at | 5.729 | BG075755 | C230098O21Rik |
| 1435392_at | 5.726 | BB277182 | Wdr17 |
| 1448842_at | 5.714 | NM_033037 | Cdo1 |
| 1426339_at | 5.713 | AB060081 | Ak5 |
| 1452917_at | 5.709 | AK011489 | Rfc5 |
| 1427063_at | 5.709 | AK017241 | 5330417C22Rik |
| 1436005_at | 5.689 | BQ174136 | Sfrs14 |
| 1447017_at | 5.687 | BE956696 | |
| 1426108_s_at | 5.685 | AY094172 | Cacnb1 |
| 1451008_at | 5.683 | BB360510 | St8sia3 |
| 1424899_at | 5.68 | BC005737 | Nmnat3 |
| 1428527_at | 5.679 | AK011526 | Snx7 |
| 1415985_at | 5.679 | NM_133953 | Sf3b3 |
| 1448468_a_at | 5.676 | AF033003 | Kcnab1 |
| 1418592_at | 5.675 | NM_021422 | Dnaja4 |
| 1416982_at | 5.671 | AI462296 | Foxo1 |
| 1433460_at | 5.669 | BB329157 | Ttc7b |
| 1420496_at | 5.666 | NM_021489 | F12 |
| 1444661_at | 5.663 | BB247791 | Gpr26 |
| 1448546_at | 5.651 | BB703307 | Rassf3 |
| 1447707_s_at | 5.649 | BB367174 | Pde2a |
| 1418743_a_at | 5.647 | NM_021344 | MGI: 1930803 |
| 1415834_at | 5.646 | NM_026268 | Dusp6 |
| 1448747_at | 5.636 | AF441120 | Fbxo32 |
| 1417192_at | 5.631 | NM_138599 | Tomm70a |
| 1416754_at | 5.63 | NM_008923 | Prkar1b |
| 1425617_at | 5.626 | U91922 | Dhx9 |
| 1417522_at | 5.606 | AF441120 | Fbxo32 |
| 1416770_at | 5.604 | NM_021537 | Stk25 |
| 1421498_a_at | 5.595 | NM_023450 | 2010204K13Rik |
| 1441363_at | 5.594 | BQ174855 | LOC546381 |
| 1421037_at | 5.594 | BG070037 | Npas2 |
| 1452278_a_at | 5.59 | BG922449 | Hace1 |
| 1421048_a_at | 5.583 | NM_023249 | Ypel1 |
| 1422977_at | 5.577 | NM_010327 | Gp1bb |
| 1430168_at | 5.57 | AK020589 | Cstad |
| 1418789_at | 5.563 | NM_133742 | Sntg2 |
| 1438213_at | 5.563 | BB128962 | A830018L16Rik |
| 1420965_a_at | 5.546 | BM120053 | Enc1 |
| 1451630_at | 5.544 | BC018513 | Ttl |
| 1426852_x_at | 5.539 | X96585 | Nov |
| 1456946_at | 5.531 | BE949337 | 4831416G18Rik |
| 1426354_at | 5.53 | AK009033 | Bap1 |
| 1422293_a_at | 5.527 | NM_134112 | Kctd1 |
| 1433724_at | 5.519 | BM235412 | D15Ertd621e |
| 1449125_at | 5.518 | NM_025566 | Tnfaip8l1 |
| 1421622_a_at | 5.518 | NM_019688 | Rapgef4 |
| 1436216_s_at | 5.516 | BM234799 | 2610204M08Rik |
| 1422705_at | 5.515 | AV370981 | Tmepai |
| 1444723_at | 5.506 | BB049759 | 6530418L21Rik |
| 1441350_at | 5.505 | AV302620 | Fgf3 |
| 1435204_at | 5.501 | BG065273 | Hrmt1l4 |
| 1422799_at | 5.501 | AK019427 | Bat2 |
| 1427067_at | 5.498 | AJ404329 | 4933439F18Rik |
| 1437580_s_at | 5.492 | C77054 | Nek2 |
| 1452057_at | 5.49 | BG801851 | Actr1b |
| 1437405_a_at | 5.489 | BB787243 | Igfbp4 |
| 1439618_at | 5.476 | AI448308 | Pde10a |
| 1431749_a_at | 5.467 | AK013548 | Rasgrp1 |
| 1434902_at | 5.456 | BB163668 | Rnf157 |
| 1423488_at | 5.453 | BC021914 | Mmd |
| 1452718_at | 5.452 | BG073486 | Edd1 |
| 1448598_at | 5.449 | NM_011846 | Mmp17 |
| 1436142_at | 5.446 | BM218877 | 3526401B18Rik |
| 1424047_at | 5.427 | BC016218 | Dera |
| 1451483_s_at | 5.421 | BC024705 | 1700054N08Rik |
| 1424132_at | 5.42 | BC011083 | Hras1 |
| 1454784_at | 5.419 | AV340742 | Hs3st2 |
| 1454835_at | 5.413 | AV340515 | Epm2aip1 |
| 1448724_at | 5.409 | NM_009895 | Cish |
| 1451098_at | 5.406 | BC010524 | Pcoln3 |
| 1418784_at | 5.39 | NM_008168 | Grik5 |
| 1449470_at | 5.388 | NM_010053 | Dlx1 |
| 1427082_at | 5.383 | AK014586 | 4632417N05Rik |
| 1455085_at | 5.379 | BI526033 | 1700086L19Rik |
| 1455033_at | 5.363 | BB325849 | B430201A12Rik |
| 1426241_a_at | 5.356 | AB030906 | Scmh1 |
| 1456755_at | 5.353 | AI467545 | 2310001H13Rik |
| 1420718_at | 5.352 | NM_011856 | Odz2 |
| 1457632_s_at | 5.35 | BB207647 | Mrg1 |
| 1427579_at | 5.348 | BE653576 | Rhbdl4 |
| 1423228_at | 5.347 | BG066773 | B4galt6 |
| 1451254_at | 5.344 | AF367244 | Ikbkap |
| 1416242_at | 5.343 | NM_026167 | Klhl13 |
| 1425679_a_at | 5.34 | AF109769 | Mapk8ip1 |
| 1439611_at | 5.307 | BE947522 | Chrm1 |
| 1425059_at | 5.306 | BC022899 | Hrmt1l6 |
| 1454985_at | 5.303 | BI872009 | D030051N19Rik |
| 1435128_at | 5.301 | BB429313 | Baiap2 |
| 1434800_at | 5.301 | BQ175909 | Sv2b |
| 1421959_s_at | 5.298 | AF458089 | Adcy3 |
| 1434819_at | 5.297 | BB709312 | St6gal2 |
| 1448687_at | 5.291 | NM_026125 | C1qdc2 |
| 1455279_at | 5.284 | BG070552 | Gm1060 |
| 1454824_at | 5.275 | BG228702 | Phactr1 |
| 1418181_at | 5.273 | AK014601 | Ptp4a3 |
| 1420872_at | 5.27 | BF472806 | Gucy1b3 |
| 1423658_at | 5.267 | BC023131 | Sppl3 |
| 1455242_at | 5.267 | BM220880 | Foxp1 |
| 1456444_at | 5.265 | BB126849 | Fbxo41 |
| 1456930_at | 5.264 | BE989461 | Camsap1 |
| 1450520_at | 5.261 | NM_019430 | Cacng3 |
| 1438417_at | 5.256 | BB809239 | Pwwp2 |
| 1434594_at | 5.255 | BB497449 | Dnahc1 |
| 1424175_at | 5.249 | BC017689 | Tef |
| 1424028_at | 5.249 | BC023107 | 5830457O10Rik |
| 1435367_at | 5.244 | BQ177154 | Mapk4 |
| 1437485_at | 5.236 | BB098161 | Nos1ap |
| 1452506_a_at | 5.231 | BC011427 | Ilkap |
| 1448553_at | 5.228 | NM_080728 | Myh7 |
| 1424389_at | 5.228 | BC026743 | Nupl1 |
| 1451273_x_at | 5.223 | BC025546 | BC025546 |
| 1441928_x_at | 5.223 | BB139475 | Ell |
| 1431717_at | 5.222 | AK014386 | 3526401B18Rik |
| 1450910_at | 5.213 | AV261931 | Cap2 |
| 1419581_at | 5.212 | AI646416 | Dlgh4 |
| 1423395_at | 5.202 | BM021706 | Tsnax |

TABLE 17-continued

Top 1,000 striatonigral (D1) cell translated mRNAs enriched when compared to a reference sample

| ProbeSymbol | FEN | Genbank | GeneSymbol |
|---|---|---|---|
| 1456818_at | 5.201 | BB279083 | Stk32a |
| 1448554_s_at | 5.199 | NM_080728 | Myh6 |
| 1441369_at | 5.193 | BB329116 | |
| 1448805_at | 5.192 | NM_009480 | Usf1 |
| 1435844_at | 5.19 | BB164247 | A330009N23Rik |
| 1443129_at | 5.19 | BB363699 | |
| 1421312_a_at | 5.19 | NM_010630 | Kifc2 |
| 1428676_at | 5.187 | AK004939 | Tmprss6 |
| 1454759_at | 5.183 | AV230461 | Git1 |
| 1455080_at | 5.182 | BB375209 | Ppp1r16b |
| 1454092_a_at | 5.182 | AK017176 | Gtf2h3 |
| 1438663_at | 5.18 | BF730196 | Bat2d |
| 1416050_a_at | 5.176 | NM_016741 | Scarb1 |
| 1435618_at | 5.174 | BB473446 | Pnma2 |
| 1427523_at | 5.168 | AI509029 | Six3 |
| 1450930_at | 5.167 | AK002992 | Hpca |
| 1433987_at | 5.163 | AV153557 | Hpcal4 |
| 1419742_at | 5.16 | NM_026091 | 1700037H04Rik |
| 1440371_at | 5.151 | BQ176223 | |
| 1434825_at | 5.151 | BQ175203 | LOC381742 |
| 1423420_at | 5.148 | AK018378 | Adrb1 |
| 1434415_at | 5.141 | BB797871 | |
| 1417716_at | 5.139 | U82470 | Got2 |
| 1449188_at | 5.139 | NM_021565 | Midn |
| 1417032_at | 5.138 | AF296657 | Ube2g2 |
| 1441815_at | 5.136 | AI851453 | AI851453 |
| 1435767_at | 5.132 | BE951842 | Scn3b |
| 1426430_at | 5.131 | AV264261 | Jag2 |
| 1438913_x_at | 5.127 | AW322533 | Hdgfrp2 |
| 1449007_at | 5.127 | NM_009770 | Btg3 |
| 1434805_at | 5.127 | BG063049 | Mllt1 |
| 1423049_a_at | 5.126 | AK002271 | Tpm1 |
| 1423352_at | 5.123 | BE693025 | Crispld1 |
| 1424475_at | 5.121 | BI157430 | Camkk2 |
| 1452783_at | 5.118 | AK005500 | Fndc3b |
| 1425363_at | 5.113 | BC022180 | Galgt1 |
| 1455313_at | 5.104 | BB336693 | Ablim2 |
| 1455703_at | 5.102 | BG074736 | Akt2 |
| 1434832_at | 5.099 | BB364488 | Foxo3a |
| 1439888_at | 5.096 | BB271581 | |
| 1433747_at | 5.093 | BQ176475 | Lnpep |
| 1435206_at | 5.092 | BB767169 | Slc24a4 |
| 1428173_at | 5.088 | AK005562 | Eml2 |
| 1416586_at | 5.084 | NM_008616 | Zfp239 |
| 1442370_at | 5.082 | BB267006 | |
| 1417311_at | 5.075 | NM_024223 | Crip2 |
| 1440166_x_at | 5.066 | BB378627 | Htr1d |
| 1416402_at | 5.066 | AV382118 | Abcb10 |
| 1422807_at | 5.065 | NM_007480 | Arf5 |
| 1455771_at | 5.062 | BB847799 | Bzrap1 |
| 1418417_at | 5.058 | NM_010827 | Msc |
| 1448411_at | 5.055 | NM_011716 | Wfs1 |
| 1435598_at | 5.043 | BE996871 | Shc2 |
| 1424481_s_at | 5.042 | BC027106 | MGC38735 |
| 1422751_at | 5.039 | NM_011599 | Tle1 |
| 1423699_at | 5.036 | BC003900 | D15Ertd785e |
| 1433805_at | 5.034 | BQ032637 | Jak1 |
| 1416087_at | 5.03 | NM_007457 | Ap1s1 |
| 1419522_at | 5.027 | NM_026021 | Zmynd19 |
| 1449494_at | 5.026 | AY026947 | Rab3c |
| 1425132_at | 5.026 | AF448840 | Neto1 |
| 1436648_at | 5.025 | BB251623 | Nanos1 |
| 1443676_at | 5.023 | AV339935 | Slc4a4 |
| 1451475_at | 5.023 | BC019530 | Plxnd1 |
| 1421225_a_at | 5.022 | NM_018760 | Slc4a4 |
| 1420999_at | 5.022 | AI448404 | Cnot4 |
| 1441967_at | 5.021 | BB467791 | BC023835 |
| 1439662_at | 5.018 | BM124609 | Homer1 |
| 1437750_at | 5.015 | BI133257 | 2310037P21Rik |
| 1426897_at | 5.011 | AV122997 | Rcc2 |
| 1424759_at | 5.006 | BC017528 | Arrdc4 |
| 1417393_a_at | 4.997 | NM_026125 | C1qdc2 |
| 1435588_at | 4.996 | BQ031098 | |
| 1450486_a_at | 4.991 | X91813 | Oprl1 |
| 1455108_at | 4.989 | BM119888 | Eif4e2 |
| 1459920_at | 4.988 | AA163908 | 4933415E08Rik |
| 1417216_at | 4.986 | NM_138606 | Pim2; LOC229005 |
| 1457696_at | 4.982 | AI835553 | Rilp |
| 1452938_at | 4.979 | BQ174247 | C030032C09Rik |
| 1433450_at | 4.978 | BB177836 | Cdk5r1 |
| 1418172_at | 4.974 | AF117613 | Hebp1 |
| 1422552_at | 4.965 | NM_023396 | Rprm |
| 1422255_at | 4.964 | NM_021275 | Kcna4 |
| 1423442_a_at | 4.962 | BE854125 | Fbxw2 |
| 1460285_at | 4.947 | NM_133721 | Itga9 |
| 1452911_at | 4.943 | AK017680 | Spred1 |
| 1452851_at | 4.937 | AK019578 | Tnrc4 |
| 1422609_at | 4.936 | BE648432 | Arpp19 |
| 1429174_at | 4.936 | AK014304 | Wdr34 |
| 1448922_at | 4.934 | NM_024438 | Dusp19 |
| 1425711_a_at | 4.932 | M94335 | Akt1 |
| 1454844_at | 4.929 | AW049955 | Gpr24 |
| 1416155_at | 4.928 | NM_008253 | Hmgb3 |
| 1423311_s_at | 4.927 | BQ177165 | Tpbg |
| 1418497_at | 4.922 | AF020737 | Fgf13 |
| 1418463_at | 4.915 | NM_008841 | Pik3r2 |
| 1416448_at | 4.914 | NM_025922 | Itpa |
| 1428357_at | 4.912 | AK011462 | 2610019F03Rik |
| 1450269_a_at | 4.907 | NM_008826 | Pfkl |
| 1424199_at | 4.905 | AW537349 | Seh1l |
| 1433833_at | 4.902 | BG064539 | Fndc3b |
| 1426383_at | 4.898 | BF303057 | Cry2 |
| 1417626_at | 4.898 | NM_031401 | Usmg4 |
| 1415998_at | 4.891 | NM_011694 | Vdac1 |
| 1424208_at | 4.891 | BC011193 | Ptger4 |
| 1454086_a_at | 4.889 | AK013416 | Lmo2 |
| 1424503_at | 4.886 | BC006596 | Rab22a |
| 1456766_at | 4.883 | BB036966 | C330001K17Rik |
| 1423415_at | 4.883 | BB110067 | Gpr83 |
| 1434082_at | 4.882 | BM243464 | Pctk2 |
| 1433707_at | 4.881 | BB430205 | Gabra4 |
| 1426710_at | 4.878 | BB396904 | Calm3 |
| 1417897_at | 4.878 | NM_134155 | Brms1 |
| 1437292_at | 4.874 | BB431052 | A330019N05Rik |
| 1416605_at | 4.874 | BC024944 | Nola2 |
| 1425051_at | 4.872 | AK010892 | Isoc1 |
| 1426539_at | 4.872 | AI117611 | Usp11 |
| 1427006_at | 4.87 | BB339051 | Rapgef1 |
| 1434563_at | 4.87 | BM207149 | Rps6kc1 |
| 1452292_at | 4.869 | AV271093 | Ap2b1 |
| 1421975_a_at | 4.868 | AF189769 | Add2 |
| 1455024_at | 4.868 | AV269836 | Tlk1 |
| 1423519_at | 4.855 | BE457744 | 2210412D01Rik |
| 1442180_at | 4.855 | BB382040 | Dleu7 |
| 1435974_at | 4.855 | BB271482 | Arhgef9 |
| 1428839_at | 4.854 | AK005105 | Wdr53 |
| 1431751_a_at | 4.85 | AK012553 | Mpped2 |
| 1426069_s_at | 4.849 | BC016100 | Slc7a4 |
| 1448285_at | 4.848 | NM_009062 | Rgs4 |
| 1452092_at | 4.848 | AK019474 | 4631426J05Rik |
| 1456144_at | 4.842 | AW537064 | Nav3 |
| 1454797_at | 4.838 | AW556098 | Tmem55b |
| 1426465_at | 4.838 | BG066219 | Dlgap4 |
| 1427954_at | 4.837 | BC028785 | BC048403 |
| 1451914_a_at | 4.834 | AF100423 | Add2 |
| 1442562_at | 4.83 | BB346556 | D630040G17Rik |
| 1450710_at | 4.825 | NM_021878 | Jarid2 |
| 1449147_at | 4.821 | NM_023850 | Chst1 |
| 1435285_at | 4.816 | BB731805 | Mpped2 |
| 1425031_at | 4.81 | AB077383 | Fcmd |
| 1433714_at | 4.808 | AV338618 | Sult4a1 |
| 1421606_a_at | 4.794 | NM_013873 | Sult4a1 |
| 1450008_a_at | 4.783 | NM_007614 | Ctnnb1 |
| 1421107_at | 4.778 | NM_021420 | Stk4 |
| 1437579_at | 4.773 | C77054 | Nek2 |
| 1434058_at | 4.772 | BB667459 | Mtmr12 |
| 1432295_a_at | 4.77 | AK009634 | 2310035K24Rik |
| 1419737_a_at | 4.769 | NM_010699 | Ldh1 |
| 1423200_at | 4.765 | U22016 | Ncor1 |

TABLE 17-continued

Top 1,000 striatonigral (D1) cell translated mRNAs enriched when compared to a reference sample

| ProbeSymbol | FEN | Genbank | GeneSymbol |
|---|---|---|---|
| 1449770_x_at | 4.753 | N28171 | D16Bwg1494e |
| 1416683_at | 4.75 | NM_138749 | Plxnb2 |
| 1425718_a_at | 4.747 | BC004092 | Ivns1abp |
| 1422590_at | 4.745 | NM_007668 | Cdk5 |
| 1438196_at | 4.739 | BB727537 | Gpd1l |
| 1417794_at | 4.738 | NM_019831 | Zfp261 |
| 1434693_at | 4.737 | BE952823 | |
| 1442099_at | 4.733 | BM227490 | Usp31 |
| 1442220_at | 4.733 | BB313387 | Ube3a |
| 1435547_at | 4.728 | BQ175722 | Mkl2 |
| 1426051_a_at | 4.725 | BC006628 | Cenpb |
| 1434476_at | 4.713 | BM119896 | Mect1 |
| 1440108_at | 4.711 | BM964154 | Foxp2 |
| 1423330_at | 4.708 | AK006149 | Ensa |
| 1429443_at | 4.706 | AK014396 | Cpne4 |
| 1427912_at | 4.699 | AK003232 | Cbr3 |
| 1458351_s_at | 4.697 | BB428573 | Klhl2 |
| 1422762_at | 4.697 | AB008867 | Kif17 |
| 1433962_at | 4.693 | BB131965 | 6720458F09Rik |
| 1458518_at | 4.692 | BM935843 | Cpeb2 |
| 1426792_s_at | 4.691 | BC024790 | Rusc2 |
| 1422718_at | 4.688 | NM_009682 | Ap3s2 |
| 1440258_at | 4.685 | BE951512 | Kcnq2 |
| 1443225_at | 4.684 | BB396526 | Acvr1c |
| 1416409_at | 4.68 | AB034914 | Acox1 |
| 1416215_at | 4.68 | NM_016810 | Gosr1 |
| 1417003_at | 4.679 | BC021536 | 0610012G03Rik |
| 1434904_at | 4.678 | AW321967 | Hivep2 |
| 1428434_at | 4.677 | AK012833 | Zcchc12 |
| 1436225_at | 4.676 | BB082386 | Trpm2 |
| 1439867_at | 4.676 | BB079377 | Ubox5 |
| 1429229_s_at | 4.674 | BE980134 | 4930534B04Rik |
| 1421046_a_at | 4.673 | NM_130881 | Pabpc4; LOC432881 |
| 1453323_at | 4.664 | AK013806 | 2900079G21Rik |
| 1429392_at | 4.656 | BI558553 | Wdr40a |
| 1428718_at | 4.656 | AW490544 | Scrn1 |
| 1424225_at | 4.649 | AF398969 | Asb8 |
| 1435942_at | 4.647 | BE993301 | Kcnq2 |
| 1447711_x_at | 4.646 | BB265147 | 4933412E12Rik |
| 1439497_at | 4.637 | BG065013 | 4933415E08Rik |
| 1453734_at | 4.633 | BF165715 | Atrx |
| 1419056_at | 4.632 | AF038538 | Rtn2 |
| 1447124_at | 4.631 | BE634581 | |
| 1447861_x_at | 4.629 | AV329643 | Mrg1 |
| 1425844_a_at | 4.622 | AF034568 | Rngtt |
| 1449063_at | 4.614 | BC009024 | Sec22l1 |
| 1451722_s_at | 4.611 | BF160651 | Smyd5 |
| 1417349_at | 4.611 | NM_019788 | Pldn |
| 1429367_at | 4.611 | BB826276 | 2510001I10Rik |
| 1420901_a_at | 4.609 | NM_010438 | Hk1 |
| 1437017_at | 4.606 | BB046727 | AI480653 |
| 1420985_at | 4.606 | BG694892 | Ash1l |
| 1428878_a_at | 4.602 | AI595920 | Pitpnc1 |
| 1436387_at | 4.601 | BB398124 | C330006P03Rik |
| 1427232_at | 4.601 | AV291373 | Sdccag33 |
| 1426978_at | 4.6 | AW682368 | Klhl2 |
| 1416550_at | 4.6 | BB320416 | Slc35b4 |
| 1428903_at | 4.599 | AK014134 | 3110037I16Rik |
| 1440376_at | 4.597 | AI747062 | Fbxo41 |
| 1434228_at | 4.594 | AV255921 | Ppm2c |
| 1460030_at | 4.594 | BB355843 | Hecw1 |
| 1450484_a_at | 4.594 | AK004595 | Tyk1 |
| 1455140_at | 4.593 | AV376568 | A330068P14Rik |
| 1451998_at | 4.592 | BC024597 | 4930485D02Rik |
| 1460116_s_at | 4.59 | AI450584 | Spred1 |
| 1427286_at | 4.587 | BB130195 | D11Bwg0517e |
| 1437861_s_at | 4.584 | BB335101 | Prkce |
| 1445605_s_at | 4.581 | AI835491 | 4921533L14Rik |
| 1415803_at | 4.578 | AF010586 | Cx3cl1 |
| 1449511_a_at | 4.577 | NM_133772 | Ssbp4 |
| 1419420_at | 4.577 | NM_012028 | St6galnac5 |
| 1425656_a_at | 4.575 | AF390178 | Baiap2 |
| 1435222_at | 4.575 | BM220880 | Foxp1 |
| 1428864_at | 4.575 | AK017419 | 5530400B01Rik |
| 1423831_at | 4.575 | BB756794 | Prkag2 |
| 1439148_a_at | 4.574 | BE914497 | Pfkl |
| 1428540_at | 4.566 | BE944524 | 3321401G04Rik |
| 1426742_at | 4.562 | AK019459 | Atp5f1 |
| 1455026_at | 4.56 | BE947961 | Sbno1 |
| 1452234_s_at | 4.555 | BF457957 | D16Bwg1494e |
| 1425760_a_at | 4.554 | AF006467 | Pitpnm1 |
| 1434682_at | 4.554 | AV347367 | 6430601A21Rik |
| 1428095_a_at | 4.552 | AK004920 | Tmem24 |
| 1447696_x_at | 4.552 | BB091427 | Adcy5 |
| 1415710_at | 4.55 | BM123013 | BC038311 |
| 1455462_at | 4.54 | BQ175609 | Ap2a2 |
| 1435425_at | 4.539 | AV212090 | 4933439C20Rik; Pisd |
| 1438841_s_at | 4.539 | AV002218 | Arg2 |
| 1423785_at | 4.538 | BE995700 | Egln1 |
| 1453000_at | 4.538 | AK005444 | Camsap1l1 |
| 1429623_at | 4.534 | AV261187 | Zfp644 |
| 1418110_a_at | 4.533 | U39203 | Inpp5d |
| 1460223_a_at | 4.531 | NM_013514 | Epb4.9 |
| 1418168_at | 4.53 | BB223737 | Zcchc14 |
| 1437366_at | 4.525 | BB332542 | AI608492 |
| 1455074_at | 4.521 | AV307860 | |
| 1453077_a_at | 4.521 | AK016168 | Snapc3 |
| 1434032_at | 4.519 | BQ175381 | |
| 1417709_at | 4.519 | NM_010010 | Cyp46a1 |
| 1428924_at | 4.514 | AU016306 | Mocs3 |
| 1453428_at | 4.514 | AK012380 | 2700045P11Rik |
| 1423195_at | 4.512 | BM208582 | Hiat1 |
| 1450918_s_at | 4.503 | BG868120 | Src |
| 1457695_at | 4.502 | C76297 | Ap1gbp1 |
| 1451028_at | 4.501 | AA796998 | Baiap2 |
| 1442558_at | 4.501 | BB180191 | |
| 1438067_at | 4.497 | BB526552 | Nf1 |
| 1459107_at | 4.496 | BG069378 | Kcnh3 |
| 1438039_at | 4.493 | BE630599 | Hectd1 |
| 1433526_at | 4.493 | BM942651 | Klhl8 |
| 1460191_at | 4.49 | NM_019661 | 0610042I15Rik |
| 1447771_at | 4.49 | AW050081 | |
| 1442883_s_at | 4.488 | BI413749 | D10Bwg1364e |
| 1455023_at | 4.487 | BB171181 | N28178 |
| 1428550_at | 4.486 | AK007503 | 1810015A11Rik |
| 1426643_at | 4.485 | AK012072 | Elp3 |
| 1453317_a_at | 4.484 | AK014353 | Khdrbs3 |
| 1460436_at | 4.479 | BI652065 | Ndst1 |
| 1429124_s_at | 4.477 | BQ178367 | Rexo1 |
| 1418235_at | 4.477 | AV168389 | Atg5 |
| 1427058_at | 4.475 | AK010644 | Eif4a1 |
| 1453412_a_at | 4.475 | BI652727 | Sec14l1 |
| 1425104_at | 4.473 | BC022615 | Kctd1 |
| 1430612_at | 4.471 | BB533148 | 1810033B17Rik |
| 1426972_at | 4.471 | AK009425 | Sec24d |
| 1416853_at | 4.47 | BC017126 | Ncdn |
| 1426644_at | 4.464 | BC002196 | Tbc1d20 |
| 1434339_at | 4.461 | AW548221 | Fnbp1l |
| 1428327_at | 4.46 | BB010301 | 2310001H13Rik |
| 1451138_x_at | 4.459 | BC005748 | 2700087H15Rik |
| 1449863_a_at | 4.459 | NM_010056 | Dlx5 |
| 1417178_at | 4.458 | NM_016867 | Gipc2 |
| 1423269_a_at | 4.456 | BB663717 | Nedd4l |
| 1416292_at | 4.454 | NM_007452 | Prdx3 |
| 1435698_at | 4.452 | BQ176694 | 4921505C17Rik |
| 1419838_s_at | 4.45 | AI385771 | Plk4 |
| 1452063_at | 4.448 | AK010736 | 2410081M15Rik |
| 1423038_at | 4.446 | BQ174465 | Stx6 |
| 1424645_at | 4.446 | BB795102 | Tnrc6c |
| 1434102_at | 4.441 | BI687652 | Nfib |
| 1422431_at | 4.439 | NM_053201 | Magee1 |
| 1459994_x_at | 4.435 | AV027486 | Trfr2 |
| 1418467_at | 4.433 | NM_025891 | Smarcd3 |
| 1428941_at | 4.429 | AK017929 | Zfp198 |
| 1439422_a_at | 4.429 | AV048291 | C1qdc2 |
| 1424480_s_at | 4.428 | BC026151 | Akt2 |
| 1419358_at | 4.425 | NM_030889 | Sorcs2 |
| 1451746_a_at | 4.424 | AK016474 | Atg12 |

TABLE 17-continued

Top 1,000 striatonigral (D1) cell translated mRNAs enriched when compared to a reference sample

| ProbeSymbol | FEN | Genbank | GeneSymbol |
|---|---|---|---|
| 1454741_s_at | 4.421 | BG064061 | AW547186 |
| 1455247_at | 4.419 | BB767281 | Amotl1 |
| 1430614_at | 4.412 | BG962576 | 4632415K11Rik |
| 1435078_at | 4.411 | BQ173895 | 3526402J09Rik |
| 1452269_at | 4.411 | AF026489 | Spnb3 |
| 1427930_at | 4.405 | BG063905 | Pdxk |
| 1420810_at | 4.403 | NM_019769 | 1500003O03Rik |
| 1417829_a_at | 4.401 | NM_134050 | Rab15 |
| 1416287_at | 4.401 | NM_009062 | Rgs4 |
| 1422473_at | 4.398 | BM246564 | Pde4b |
| 1455961_at | 4.397 | AV174022 | Mme |
| 1436513_at | 4.396 | BM208226 | 3526402J09Rik |
| 1431711_a_at | 4.393 | AK018497 | 9030409G11Rik |
| 1425452_s_at | 4.388 | BC002154 | Ptprj; AW125753 |
| 1432184_a_at | 4.387 | AK011884 | 2610204M08Rik |
| 1433699_at | 4.387 | BM241351 | Tnfaip3 |
| 1417225_at | 4.386 | NM_022992 | Arl6ip5 |
| 1436013_at | 4.384 | AI852434 | C230098I05Rik |
| 1455156_at | 4.382 | BG519214 | Strn |
| 1448378_at | 4.382 | NM_007984 | Fscn1 |
| 1437390_x_at | 4.378 | AV339210 | Stx1a |
| 1455883_a_at | 4.375 | BB269910 | Lrrtm1 |
| 1431875_a_at | 4.374 | AK017841 | E2f1 |
| 1455888_at | 4.369 | BB125202 | Lrrn6c |
| 1457046_s_at | 4.369 | BB545241 | C77370 |
| 1454977_at | 4.365 | AW551191 | AU020772 |
| 1432271_a_at | 4.364 | AK012764 | Dcun1d5 |
| 1423606_at | 4.36 | BI110565 | Postn |
| 1455548_at | 4.357 | BB314358 | Dlgap4 |
| 1436081_a_at | 4.354 | BE632205 | Zfp414 |
| 1425710_a_at | 4.352 | AB019479 | Homer1 |
| 1416528_at | 4.349 | NM_080559 | Sh3bgrl3 |
| 1450038_s_at | 4.346 | AW107303 | Usp9x |
| 1453021_at | 4.345 | BM899291 | Stxbp5 |
| 1454675_at | 4.344 | BI076689 | Thra |
| 1440455_at | 4.341 | AI848599 | AI848599 |
| 1433499_at | 4.333 | BF585125 | 2010005J08Rik |
| 1432478_a_at | 4.333 | AK015966 | Ibrdc3 |
| 1429678_at | 4.325 | AK017758 | 5730508B09Rik |
| 1460563_at | 4.317 | BE949414 | |
| 1424418_at | 4.316 | BC010801 | BC010801 |
| 1452925_a_at | 4.314 | AK009364 | 5-Mar |
| 1428354_at | 4.312 | BM206907 | Foxk2 |
| 1417481_at | 4.311 | NM_016894 | Ramp1 |
| 1422677_at | 4.311 | AK002443 | Dgat2 |
| 1415975_at | 4.31 | AU080787 | Carhsp1 |
| 1456601_x_at | 4.309 | AV002675 | Fxyd2 |
| 1441917_s_at | 4.307 | BB468188 | Tmem40 |
| 1432091_a_at | 4.307 | AK007455 | Rutbc3 |
| 1448196_at | 4.305 | NM_134017 | Mat2b |
| 1431811_a_at | 4.303 | AK020018 | Fbxo34 |
| 1458133_at | 4.302 | BB360008 | |
| 1457080_at | 4.302 | BB046159 | |
| 1449932_at | 4.3 | NM_027874 | Csnk1d |
| 1433937_at | 4.298 | BB814564 | Trp53bp2 |
| 1455772_at | 4.296 | BB428874 | Pgr |
| 1453069_at | 4.292 | BF018155 | Pik3cb |
| 1416983_s_at | 4.289 | AI462296 | Foxo1 |
| 1432813_at | 4.289 | AK013749 | 2900064F13Rik |
| 1436786_at | 4.289 | AV024133 | 1110069O07Rik |
| 1458967_at | 4.289 | BM939341 | |
| 1425327_at | 4.288 | AU067643 | BC008163 |

ProbeSymbol = Affymetrix probe identification corresponding to gene symbol; FEN = fold enrichment when compared to reference sample; Genbank = Genbank identification; GeneSymbol = official gene symbol.

TABLE 18

Top 1,000 striatopallidal (D2) cell translated mRNAs enriched when compared to a reference sample

| ProbeSymbol | FEN | Genbank | GeneSymbol |
|---|---|---|---|
| 1435211_at | 183.2 | BB554351 | Ttc12 |
| 1426814_at | 104.8 | BM248309 | AU024582 |
| 1452217_at | 88.94 | BE570050 | Ahnak |
| 1440148_at | 80.24 | AI852874 | Gpr6 |
| 1418950_at | 72.42 | NM_010077 | Drd2 |
| 1419231_s_at | 65.33 | NM_010661 | Krt1-12 |
| 1418357_at | 52.9 | NM_008241 | Foxg1 |
| 1426815_s_at | 44.02 | BM248309 | AU024582 |
| 1457132_at | 43.55 | BF456117 | |
| 1443287_at | 42.58 | BB555669 | Gm1337 |
| 1438022_at | 40.99 | BQ266518 | Rab11fip3 |
| 1435564_at | 40.44 | BB547893 | C230078M08Rik |
| 1436268_at | 37.26 | AI841578 | Ddn |
| 1458499_at | 36.61 | AW123977 | Pde10a |
| 1421365_at | 32.61 | NM_008046 | Fst |
| 1454867_at | 32.18 | BB234631 | Mn1 |
| 1420437_at | 31.55 | NM_008324 | Indo |
| 1460710_at | 28.67 | BB748999 | |
| 1423171_at | 27.79 | BE947345 | Gpr88 |
| 1423117_at | 24.88 | BB837171 | Pum1 |
| 1434458_at | 23.89 | BB444134 | Fst |
| 1450142_a_at | 21.46 | NM_130886 | Card14 |
| 1434917_at | 20.15 | BQ173923 | Cob1 |
| 1450339_a_at | 19.88 | NM_021399 | Bcl11b |
| 1435366_at | 19.68 | BB486367 | D430042O09Rik |
| 1427017_at | 19.47 | BB104560 | Satb2 |
| 1460325_at | 19.42 | BB837171 | Pum1 |
| 1439854_at | 18.58 | BQ175572 | AI838259 |
| 1423802_at | 18.24 | BC017634 | Camkv |
| 1450071_at | 17.88 | BG694892 | Ash1l |
| 1418782_at | 17.83 | NM_009107 | Rxrg |
| 1436275_at | 17.8 | AW490636 | Kcnip2 |
| 1457143_at | 17.66 | BB322292 | Gli3 |
| 1449425_at | 16.64 | BC026373 | Wnt2 |
| 1422079_at | 16.52 | NM_008856 | Prkch |
| 1437698_at | 15.91 | AV370579 | Myo5b |
| 1424567_at | 15.72 | BC011277 | Rin1 |
| 1454581_at | 15.58 | AK019908 | 5330425B07Rik |
| 1433566_at | 15.41 | BB381618 | Rasl10b |
| 1441368_at | 15.29 | BB102769 | |
| 1452966_at | 15.02 | AK020296 | 9130430L19Rik |
| 1450072_at | 14.94 | BG694892 | Ash1l |
| 1455190_at | 14.83 | BM114283 | Gng7 |
| 1419230_at | 14.66 | NM_010661 | Krt1-12 |
| 1449420_at | 14.07 | NM_008800 | Pde1b |
| 1427807_at | 14.06 | BC017159 | 4930448N21Rik |
| 1452879_at | 13.95 | AI848603 | Synpo2 |
| 1452176_at | 13.95 | BB292874 | Nup153 |
| 1425870_a_at | 13.88 | AF439339 | Kcnip2 |
| 1434653_at | 13.48 | AV026976 | Ptk2b |
| 1418619_at | 13.42 | NM_008319 | Icam5 |
| 1458342_at | 13.38 | BB313069 | |
| 1436566_at | 13.32 | AV364488 | Rab40b |
| 1435227_at | 12.96 | BM117007 | |
| 1451280_at | 12.87 | BB159263 | MGI: 107562 |
| 1425503_at | 12.63 | AB037596 | Gcnt2 |
| 1454043_a_at | 12.44 | AK015412 | Kcnab1 |
| 1436650_at | 12.37 | AV241894 | Filip1 |
| 1449241_at | 12.35 | NM_053105 | Klhl1 |
| 1456054_a_at | 12.32 | BB314559 | Pum1 |
| 1423530_at | 12.24 | BB320288 | Stk32c |
| 1452202_at | 12.21 | BG069616 | Pde2a |
| 1444734_at | 12.08 | BB183877 | A330001L22Rik |
| 1417356_at | 12.04 | AB003040 | Peg3 |
| 1433627_at | 11.96 | AW546839 | Sec23ip |
| 1418847_at | 11.93 | NM_009705 | Arg2 |
| 1456283_at | 11.85 | AV346211 | Neto1 |
| 1450026_a_at | 11.85 | AV306734 | B3gnt1 |
| 1435615_at | 11.83 | BB277790 | Zfp365 |
| 1455683_at | 11.73 | BB451404 | Tbc1d8 |
| 1436329_at | 11.4 | AV346607 | Egr3 |
| 1428338_at | 11.3 | AK019166 | 2610039E05Rik |
| 1424248_at | 11.23 | BB159263 | MGI: 107562 |
| 1434521_at | 11.2 | BB148972 | Rfxdc2 |
| 1427358_a_at | 11.19 | BC026671 | Dapk1 |

TABLE 18-continued

Top 1,000 striatopallidal (D2) cell translated mRNAs enriched when compared to a reference sample

| ProbeSymbol | FEN | Genbank | GeneSymbol |
|---|---|---|---|
| 1435083_at | 11.09 | BI155559 | Ctxn1 |
| 1451331_at | 11.09 | BC026568 | Ppp1r1b |
| 1417090_at | 10.95 | NM_009037 | Rcn1 |
| 1457311_at | 10.92 | AW490258 | Camk2a |
| 1460038_at | 10.84 | BG065255 | Pou3f1 |
| 1451236_at | 10.81 | BC026463 | Rerg |
| 1448807_at | 10.78 | NM_133849 | Hrh3 |
| 1417804_at | 10.75 | NM_011242 | LOC381240 |
| 1452476_at | 10.64 | W41214 | Cacnb2 |
| 1438355_at | 10.63 | AI414870 | |
| 1418015_at | 10.61 | BI689507 | Pum2 |
| 1458406_at | 10.6 | BG144063 | |
| 1427005_at | 10.53 | BM234765 | Plk2 |
| 1426980_s_at | 10.29 | BC006054 | E130012A19Rik |
| 1450213_at | 10.17 | NM_013875 | Pde7b |
| 1442166_at | 10.03 | BB273427 | Cpne5 |
| 1435749_at | 9.907 | AW911807 | Gda |
| 1423561_at | 9.752 | AI838010 | Nell2 |
| 1456640_at | 9.723 | AW910872 | Sh3rf2 |
| 1455754_at | 9.708 | BQ043839 | Lmo3 |
| 1428150_at | 9.671 | BB203098 | Coro7 |
| 1423186_at | 9.628 | BM228957 | Tiam2 |
| 1444681_at | 9.613 | BB749686 | D14Ertd171e |
| 1454906_at | 9.596 | BB266455 | Rarb |
| 1425833_a_at | 9.537 | AF326551 | Hpca |
| 1418169_at | 9.532 | BB223737 | Zcchc14 |
| 1418714_at | 9.511 | NM_008748 | Dusp8 |
| 1425756_at | 9.479 | AF425643 | Rab40b |
| 1433701_at | 9.466 | BB371430 | Mpped1 |
| 1448327_at | 9.366 | NM_033268 | Actn2 |
| 1419517_at | 9.345 | NM_028408 | Cnih3 |
| 1441000_at | 9.343 | BB076832 | |
| 1451604_a_at | 9.334 | BC014291 | Acvrl1 |
| 1422710_a_at | 9.333 | NM_021415 | Cacna1h |
| 1440204_at | 9.247 | AW494150 | 3110039M20Rik |
| 1417680_at | 9.208 | NM_008419 | Kcna5 |
| 1438799_at | 9.154 | AV338180 | Dlx6os1 |
| 1433815_at | 9.13 | AV290082 | MGI: 1923321 |
| 1418373_at | 9.111 | NM_018870 | Pgam2 |
| 1458407_s_at | 9.046 | BG144063 | |
| 1434115_at | 9.043 | BQ176681 | |
| 1449158_at | 8.965 | NM_010607 | Kcnk2 |
| 1435334_at | 8.945 | BG866904 | Ttc7 |
| 1438665_at | 8.935 | BF456582 | Smpd3 |
| 1437125_at | 8.93 | BB476463 | Camk2a |
| 1460567_at | 8.928 | BB148972 | Rfxdc2 |
| 1435780_at | 8.914 | BG966595 | Psd |
| 1452298_a_at | 8.862 | AW546331 | Myo5b |
| 1451917_a_at | 8.818 | AF155820 | Dcamkl1 |
| 1424037_at | 8.796 | BC027291 | Itpka |
| 1422621_at | 8.772 | BM507707 | Ranbp2 |
| 1443334_at | 8.709 | BB487579 | D430042O09Rik |
| 1422153_a_at | 8.653 | NM_026853 | Asb11 |
| 1415904_at | 8.636 | BC003305 | Lpl |
| 1439552_at | 8.633 | BE985618 | Trio |
| 1437460_x_at | 8.63 | BB264363 | Rin1 |
| 1427683_at | 8.629 | X06746 | Egr2 |
| 1460136_at | 8.61 | AI462839 | |
| 1448990_a_at | 8.524 | AI255256 | Myo1b |
| 1427931_s_at | 8.518 | BG063905 | Pdxk |
| 1429089_s_at | 8.504 | BG063749 | 2900026A02Rik |
| 1427673_a_at | 8.502 | Z93948 | Sema3e |
| 1419224_at | 8.47 | NM_033567 | Cecr6 |
| 1422068_at | 8.454 | NM_011141 | Pou3f1 |
| 1429285_at | 8.419 | AK009343 | Serpina9 |
| 1460244_at | 8.419 | NM_133995 | Upb1 |
| 1434295_at | 8.405 | BE691356 | Rasgrp1 |
| 1438985_x_at | 8.393 | BB158937 | Otud5 |
| 1438889_at | 8.391 | BB183456 | |
| 1434248_at | 8.328 | BM243786 | Prkch |
| 1456401_at | 8.318 | BB078175 | Cacnb2 |
| 1419696_at | 8.287 | NM_013488 | Cd4 |
| 1441733_s_at | 8.245 | C88147 | Nup153 |
| 1421141_a_at | 8.234 | BG962849 | Foxp1 |
| 1430127_a_at | 8.229 | AK007904 | Ccnd2 |
| 1454721_at | 8.185 | AV257687 | 1110018G07Rik |
| 1454768_at | 8.147 | AV337635 | Kcnf1 |
| 1421140_a_at | 8.143 | BG962849 | Foxp1 |
| 1437586_at | 8.123 | BB756908 | Cnot4 |
| 1455629_at | 8.11 | BE957273 | Drd1a |
| 1460343_at | 8.092 | AF401228 | Neurl |
| 1418881_at | 8.09 | NM_054095 | Efcbp2 |
| 1435741_at | 8.074 | BB312125 | Pde8b |
| 1455701_at | 8.033 | BI965517 | Snx26 |
| 1434008_at | 8.029 | BE993937 | Scn4b |
| 1435748_at | 8.028 | AW911807 | Gda |
| 1460555_at | 8.026 | BM242294 | 6330500D04Rik |
| 1435221_at | 7.968 | BM220880 | Foxp1 |
| 1436532_at | 7.932 | BB326709 | Dcamkl3 |
| 1450061_at | 7.921 | BM120053 | Enc1 |
| 1454845_x_at | 7.898 | AW049955 | Gpr24 |
| 1423544_at | 7.878 | BB188812 | Ptpn5 |
| 1457341_at | 7.864 | BE991676 | |
| 1427343_at | 7.862 | BC026377 | Rasd2 |
| 1416996_at | 7.811 | BC005421 | Tbc1d8 |
| 1417355_at | 7.81 | AB003040 | Peg3 |
| 1452135_at | 7.783 | AV001252 | Gpx6 |
| 1451517_at | 7.723 | AF420001 | Rhobtb2 |
| 1428547_at | 7.718 | AV273591 | Nt5e |
| 1436738_at | 7.707 | AV094878 | AI449441 |
| 1418691_at | 7.696 | NM_011268 | Rgs9 |
| 1455361_at | 7.674 | AW493391 | Dgkb |
| 1452507_at | 7.668 | AF022078 | Dlx6 |
| 1422706_at | 7.638 | AV370981 | Tmepai |
| 1456858_at | 7.624 | BB075339 | Gpr149 |
| 1427519_at | 7.603 | BG311385 | Adora2a |
| 1450748_at | 7.6 | NM_021491 | Smpd3 |
| 1420146_at | 7.544 | AI429207 | Tiam2 |
| 1421739_a_at | 7.531 | NM_010768 | Matk |
| 1438841_s_at | 7.492 | AV002218 | Arg2 |
| 1427015_at | 7.466 | BI732921 | LOC380969 |
| 1418908_at | 7.398 | NM_013626 | Pam |
| 1419221_a_at | 7.395 | NM_016758 | Rgs14 |
| 1459299_at | 7.39 | AV381193 | A430065P19Rik |
| 1425479_at | 7.377 | BF160651 | Smyd5 |
| 1422165_at | 7.374 | X66603 | Pou3f4 |
| 1416804_at | 7.373 | NM_053252 | LOC114601 |
| 1454762_at | 7.368 | BM932447 | Xkrx |
| 1427344_s_at | 7.364 | BC026377 | Rasd2 |
| 1420852_a_at | 7.355 | AV306734 | B3gnt1 |
| 1433767_at | 7.344 | AV257687 | 1110018G07Rik |
| 1452368_at | 7.313 | AI853148 | Bcr |
| 1416691_at | 7.294 | NM_019581 | Gtpbp2 |
| 1426919_at | 7.292 | BC021490 | Dapk1 |
| 1454752_at | 7.276 | AV307961 | AI606861 |
| 1417279_at | 7.259 | NM_010585 | Itpr1 |
| 1456336_at | 7.245 | BB182912 | A330102K23Rik |
| 1419389_at | 7.231 | BQ180352 | Pde10a |
| 1455447_at | 7.218 | BM116882 | D430019H16Rik |
| 1450690_at | 7.212 | BM507707 | Ranbp2 |
| 1422705_at | 7.205 | AV370981 | Tmepai |
| 1455200_at | 7.202 | BB818370 | Pak6 |
| 1422678_at | 7.198 | AK002443 | Dgat2 |
| 1436066_at | 7.162 | BI965477 | Kalrn |
| 1447359_at | 7.13 | AI326876 | LOC381955 |
| 1423231_at | 7.123 | AK002933 | Nrgn |
| 1436408_at | 7.113 | BE946298 | |
| 1420978_at | 7.112 | NM_010938 | Nrf1 |
| 1436216_s_at | 7.097 | BM234799 | 2610204M08Rik |
| 1451726_at | 7.091 | BC020019 | Mtmr6 |
| 1442434_at | 7.087 | BM195829 | D8Ertd82e |
| 1453782_at | 7.086 | BI737125 | 3021401C12Rik |
| 1448364_at | 7.072 | U95826 | Ccng2 |
| 1435296_at | 7.051 | AV349563 | Adra2c |
| 1438210_at | 7.049 | BB126999 | Gpr149 |
| 1416776_at | 7.04 | NM_016669 | Crym |
| 1432073_at | 7.007 | AK007198 | 1700113I22Rik |
| 1432972_at | 7.004 | AK014916 | 4921518B13Rik |
| 1426518_at | 6.977 | AV333951 | Tubgcp5 |
| 1427045_at | 6.977 | AI849322 | Synpo |

TABLE 18-continued

Top 1,000 striatopallidal (D2) cell translated mRNAs enriched when compared to a reference sample

| ProbeSymbol | FEN | Genbank | GeneSymbol |
|---|---|---|---|
| 1429156_at | 6.97 | BF453953 | 2610036L11Rik |
| 1417129_a_at | 6.954 | U68384 | Mrg1 |
| 1429422_at | 6.945 | AK016788 | 4933412E12Rik |
| 1425130_a_at | 6.941 | U28216 | Ptpn5 |
| 1421353_at | 6.94 | NM_013875 | Pde7b |
| 1439569_at | 6.925 | AV291031 | Gpr83 |
| 1430675_at | 6.915 | BM932606 | 2900055J20Rik |
| 1452618_at | 6.887 | BM230774 | Cdk5rap2 |
| 1439566_at | 6.882 | BB245373 | C030038J10Rik |
| 1452452_at | 6.863 | M73818 | |
| 1420580_at | 6.861 | NM_026249 | 4930429B21Rik |
| 1416350_at | 6.855 | NM_078477 | Klf16 |
| 1424409_at | 6.851 | BC019534 | Cldn23 |
| 1455272_at | 6.83 | BB429139 | Grm5 |
| 1416456_a_at | 6.824 | BC011134 | Chia |
| 1457052_at | 6.783 | BG064867 | AW536275 |
| 1428951_at | 6.765 | AK017551 | Nol8 |
| 1431936_a_at | 6.749 | AK009828 | Neu2 |
| 1439767_at | 6.715 | BB130159 | Dlgap2 |
| 1419216_at | 6.709 | NM_009734 | Azi1 |
| 1455564_at | 6.703 | BQ176236 | Bcr |
| 1429617_at | 6.702 | BM119209 | Cyld |
| 1447178_at | 6.679 | BB173057 | |
| 1444441_at | 6.676 | AW490909 | |
| 1421101_a_at | 6.671 | NM_010698 | Ldb2 |
| 1427975_at | 6.648 | AK008807 | 2210403B10Rik |
| 1421000_at | 6.647 | AI448404 | Cnot4 |
| 1420545_a_at | 6.634 | NM_029716 | Chn1 |
| 1445539_at | 6.63 | BE687857 | Pde7b |
| 1419542_at | 6.615 | NM_010021 | Dazl |
| 1439557_s_at | 6.585 | BB097063 | Ldb2 |
| 1436998_at | 6.578 | BB428991 | Ankrd43 |
| 1424796_at | 6.575 | BC024705 | 1700054N08Rik |
| 1456468_x_at | 6.555 | BB189996 | 1110012N22Rik |
| 1455301_at | 6.535 | BG064092 | BQ952480 |
| 1422718_at | 6.531 | NM_009682 | Ap3s2 |
| 1456051_at | 6.527 | BB282271 | Drd1a |
| 1456818_at | 6.464 | BB279083 | Stk32a |
| 1427523_at | 6.461 | AI509029 | Six3 |
| 1423240_at | 6.423 | BG868120 | Src |
| 1449634_a_at | 6.416 | AW046274 | C030032C09Rik |
| 1426901_s_at | 6.376 | BB657856 | Camta2 |
| 1440534_at | 6.373 | BB177862 | |
| 1438417_at | 6.362 | BB809239 | Pwwp2 |
| 1426572_at | 6.359 | BM235734 | Me2 |
| 1452380_at | 6.348 | BB075797 | Epha7 |
| 1422208_a_at | 6.347 | BC016135 | Gnb5 |
| 1435435_at | 6.333 | BB357580 | Cttnbp2 |
| 1454877_at | 6.319 | BQ174721 | Sertad4 |
| 1419754_at | 6.298 | NM_010864 | Myo5a |
| 1420666_at | 6.296 | BM117900 | Doc2b |
| 1424028_at | 6.292 | BC023107 | 5830457O10Rik |
| 1417440_at | 6.266 | NM_033566 | Arid1a |
| 1453886_a_at | 6.265 | AK017037 | Slc25a26 |
| 1456946_at | 6.262 | BE949337 | 4831416G18Rik |
| 1420377_at | 6.23 | BG071333 | St8sia2 |
| 1443365_at | 6.216 | BB431008 | Htr4 |
| 1416437_a_at | 6.213 | AF262046 | Mapk8ip3 |
| 1427682_a_at | 6.21 | X06746 | Egr2 |
| 1448978_at | 6.205 | NM_019867 | Ngef |
| 1454656_at | 6.19 | AV271736 | Spata13 |
| 1428535_at | 6.16 | AK004274 | 9430020K01Rik |
| 1455178_at | 6.142 | BB496468 | Rutbc1 |
| 1416562_at | 6.137 | AF326547 | Gad1 |
| 1448709_at | 6.131 | NM_033566 | Arid1a |
| 1457979_at | 6.128 | BM938335 | |
| 1435666_at | 6.098 | AW553439 | |
| 1433583_at | 6.093 | AV327248 | Zfp365 |
| 1422018_at | 6.075 | NM_010437 | Hivep2 |
| 1455056_at | 6.068 | BM231903 | Lmo7 |
| 1436092_at | 6.045 | BB336256 | |
| 1455296_at | 6.031 | BE952286 | Adcy5 |
| 1420534_at | 6.016 | AK004815 | Gucy1a3 |
| 1421142_s_at | 6.012 | BG962849 | Foxp1 |
| 1427450_x_at | 6.007 | BI080370 | Myo1b |
| 1434429_at | 6.002 | AV348245 | Syt16 |
| 1423420_at | 5.998 | AK018378 | Adrb1 |
| 1416627_at | 5.974 | NM_016907 | Spint1 |
| 1435808_at | 5.95 | BB174377 | A230051G13Rik |
| 1440711_at | 5.93 | BB426320 | C630001G18Rik |
| 1435763_at | 5.899 | BI218684 | Tbc1d16 |
| 1417114_at | 5.894 | AF163665 | Gcl |
| 1453129_a_at | 5.892 | AK004813 | Rgs12 |
| 1417709_at | 5.881 | NM_010010 | Cyp46a1 |
| 1453264_at | 5.87 | AK007346 | Marveld3 |
| 1455703_at | 5.867 | BG074736 | Akt2 |
| 1427912_at | 5.858 | AK003232 | Cbr3 |
| 1419137_at | 5.825 | NM_021423 | Shank3 |
| 1455620_at | 5.814 | BQ177219 | |
| 1429111_at | 5.808 | AV270892 | Tln2 |
| 1433988_s_at | 5.808 | BG075755 | C230098O21Rik |
| 1435210_s_at | 5.785 | BQ174936 | Snph |
| 1434090_at | 5.771 | BB037094 | 4930429A22Rik |
| 1450143_at | 5.766 | BB354696 | Rasgrp1 |
| 1435265_at | 5.763 | BF466929 | |
| 1441963_at | 5.744 | BB427703 | MGI: 2656976 |
| 1448023_at | 5.741 | BB662566 | Kalrn |
| 1447771_at | 5.706 | AW050081 | |
| 1416286_at | 5.696 | NM_009062 | Rgs4 |
| 1460206_at | 5.688 | NM_019518 | Grasp |
| 1423376_a_at | 5.685 | AV341904 | Dok4 |
| 1435558_at | 5.683 | BB351248 | Bai2 |
| 1455961_at | 5.675 | AV174022 | Mme |
| 1447017_at | 5.661 | BE956696 | |
| 1460285_at | 5.647 | NM_133721 | Itga9 |
| 1432184_a_at | 5.611 | AK011884 | 2610204M08Rik |
| 1431751_a_at | 5.605 | AK012553 | Mpped2 |
| 1422902_s_at | 5.594 | NM_023799 | Mgea5 |
| 1431394_at | 5.59 | AK014938 | Lrrk2 |
| 1434359_at | 5.589 | AV329070 | 6330500D04Rik |
| 1445691_at | 5.588 | AW121426 | Chn1 |
| 1435071_at | 5.583 | AV327165 | Zfyve1 |
| 1425510_at | 5.578 | BM213279 | Mark1 |
| 1427038_at | 5.577 | M13227 | Penk1 |
| 1417462_at | 5.576 | NM_007598 | Cap1 |
| 1433937_at | 5.559 | BB814564 | Trp53bp2 |
| 1415743_at | 5.537 | NM_010412 | Hdac5 |
| 1452861_at | 5.534 | AK008485 | 2010300C02Rik |
| 1453273_at | 5.533 | AV142265 | Kcnv1 |
| 1419358_at | 5.53 | NM_030889 | Sorcs2 |
| 1460352_s_at | 5.526 | BC017537 | Pik3r4 |
| 1453836_a_at | 5.523 | AK006949 | Mgll |
| 1416050_a_at | 5.505 | NM_016741 | Scarb1 |
| 1420985_at | 5.46 | BG694892 | Ash1l |
| 1450655_at | 5.455 | AA214868 | Herc1 |
| 1450042_at | 5.44 | BB322201 | Arx |
| 1417626_at | 5.435 | NM_031401 | Usmg4 |
| 1421116_a_at | 5.427 | NM_024226 | Rtn4 |
| 1438784_at | 5.42 | BB329234 | |
| 1434775_at | 5.419 | AW543460 | Pard3 |
| 1419390_at | 5.411 | BQ180352 | Pde10a |
| 1418017_at | 5.398 | BI689507 | Pum2 |
| 1418535_at | 5.387 | NM_016846 | Rgl1 |
| 1438068_at | 5.378 | BB251859 | |
| 1435825_at | 5.364 | BG969012 | Acvrl1 |
| 1431056_a_at | 5.359 | AK017272 | Lpl |
| 1417612_at | 5.347 | BF147705 | Ier5 |
| 1420871_at | 5.339 | BF472806 | Gucy1b3 |
| 1423532_at | 5.337 | AI850285 | Rnf44 |
| 1438664_at | 5.337 | BB216074 | Prkar2b |
| 1417812_a_at | 5.325 | NM_008484 | Lamb3 |
| 1447861_x_at | 5.322 | AV329643 | Mrg1 |
| 1419033_at | 5.32 | AW556821 | 2610018G03Rik |
| 1455220_at | 5.317 | BB353860 | Frat2 |
| 1435767_at | 5.314 | BE951842 | Scn3b |
| 1435285_at | 5.312 | BB731805 | Mpped2 |
| 1439611_at | 5.305 | BE947522 | Chrm1 |
| 1448063_at | 5.302 | AW226526 | Iqsec2 |
| 1427426_at | 5.295 | AV362204 | Kcnq5 |
| 1421028_a_at | 5.291 | AI595932 | Mef2c |

TABLE 18-continued

Top 1,000 striatopallidal (D2) cell translated mRNAs enriched when compared to a reference sample

| ProbeSymbol | FEN | Genbank | GeneSymbol |
|---|---|---|---|
| 1421346_a_at | 5.268 | NM_009320 | Slc6a6 |
| 1430013_at | 5.263 | BE993118 | 2210008F06Rik |
| 1452964_at | 5.26 | AK016577 | 4932702F08Rik |
| 1422787_at | 5.259 | NM_019873 | Fkbp1 |
| 1450227_at | 5.254 | BM199504 | Ankrd6 |
| 1426450_at | 5.25 | BM207017 | Plcl2 |
| 1441468_at | 5.242 | BB326028 | |
| 1436733_at | 5.239 | BB523550 | E130309F12Rik |
| 1429316_at | 5.234 | AK018120 | Rasgef1a |
| 1440166_x_at | 5.232 | BB378627 | Htr1d |
| 1455225_at | 5.217 | AV237615 | Syne1 |
| 1435043_at | 5.214 | BB794831 | Plcb1 |
| 1417522_at | 5.211 | AF441120 | Fbxo32 |
| 1448468_a_at | 5.207 | AF033003 | Kcnab1 |
| 1452295_at | 5.207 | AV291712 | Tmepai |
| 1426037_a_at | 5.192 | U94828 | Rgs16 |
| 1434745_at | 5.186 | BQ175880 | Ccnd2 |
| 1447728_x_at | 5.183 | BB718260 | Hspa9a |
| 1426024_a_at | 5.177 | AF187147 | Dbn1 |
| 1448989_a_at | 5.176 | AI255256 | Myo1b |
| 1416398_at | 5.172 | BB474887 | Mesdc1 |
| 1429637_at | 5.163 | AK008987 | 2210419I08Rik |
| 1450930_at | 5.161 | AK002992 | Hpca |
| 1442558_at | 5.16 | BB180191 | |
| 1433962_at | 5.153 | BB131965 | 6720458F09Rik |
| 1441894_s_at | 5.148 | BB071890 | Grasp |
| 1447707_s_at | 5.127 | BB367174 | Pde2a |
| 1433451_at | 5.109 | BB177836 | Cdk5r1 |
| 1422609_at | 5.084 | BE648432 | Arpp19 |
| 1420530_at | 5.083 | AW553317 | Neud4 |
| 1432646_a_at | 5.076 | BE859789 | 2900097C17Rik |
| 1423285_at | 5.065 | BB731671 | Coch |
| 1435605_at | 5.039 | BB125424 | Actr3b |
| 1451483_s_at | 5.039 | BC024705 | 1700054N08Rik |
| 1428321_at | 5.027 | AK003593 | Eml1 |
| 1448842_at | 5.02 | NM_033037 | Cdo1 |
| 1420496_at | 4.998 | NM_021489 | F12 |
| 1442113_at | 4.991 | BB183350 | 5330417C22Rik |
| 1451078_at | 4.988 | BC012878 | 2510039O18Rik |
| 1459679_s_at | 4.975 | AA406997 | Myo1b |
| 1425363_at | 4.931 | BC022186 | Galgt1 |
| 1434141_at | 4.928 | BG072799 | Gucy1a3 |
| 1454832_at | 4.917 | BG228702 | Phactr1 |
| 1449863_a_at | 4.911 | NM_010056 | Dlx5 |
| 1434077_at | 4.896 | AV222031 | Wdr37 |
| 1423358_at | 4.89 | AK007407 | 1810009K13Rik |
| 1424379_at | 4.877 | BC019393 | Car11 |
| 1431320_a_at | 4.872 | AK002362 | Myo5a |
| 1435222_at | 4.872 | BM220681 | Foxp1 |
| 1456786_at | 4.87 | BB097063 | Ldb2 |
| 1454742_at | 4.87 | BB003229 | Rasgef1b |
| 1424201_a_at | 4.864 | AW537349 | Seh1l |
| 1423658_at | 4.86 | BC023091 | Sppl3 |
| 1441884_x_at | 4.854 | BB278992 | Cx3cl1 |
| 1422901_at | 4.85 | NM_023799 | Mgea5 |
| 1440940_at | 4.845 | BE949510 | Cacnb1 |
| 1448724_at | 4.841 | NM_009895 | Cish |
| 1436645_a_at | 4.84 | BB066603 | Cnot4 |
| 1429438_at | 4.838 | AV318805 | Bcor |
| 1420872_at | 4.79 | BF472806 | Gucy1b3 |
| 1458133_at | 4.784 | BB360008 | |
| 1418172_at | 4.778 | AF117613 | Hebp1 |
| 1415803_at | 4.775 | AF010586 | Cx3cl1 |
| 1423551_at | 4.771 | BB776961 | Cdh13 |
| 1419225_at | 4.768 | NM_009785 | Cacna2d3 |
| 1423489_at | 4.764 | BC021914 | Mmd |
| 1435500_at | 4.756 | BB270778 | Rab26 |
| 1449472_at | 4.747 | NM_008151 | Gpr12 |
| 1457651_x_at | 4.737 | BB270375 | Rem2 |
| 1424899_at | 4.734 | BC005737 | Nmnat3 |
| 1416982_at | 4.725 | AI462296 | Foxo1 |
| 1423640_at | 4.718 | BC026512 | Synpr |
| 1441065_at | 4.717 | BB305753 | |
| 1427006_at | 4.717 | BB339051 | Rapgef1 |
| 1455313_at | 4.716 | BB336053 | Ablim2 |
| 1450448_at | 4.714 | BQ032752 | Stc1 |
| 1452974_at | 4.706 | AK017551 | Nol8 |
| 1452411_at | 4.692 | BG966295 | Lrrc1 |
| 1425680_a_at | 4.692 | AF110396 | Btrc |
| 1417341_a_at | 4.692 | NM_025800 | Ppp1r2 |
| 1430617_at | 4.68 | BB238604 | Oip5 |
| 1434594_at | 4.679 | BB497449 | Dnahc1 |
| 1428095_a_at | 4.663 | AK004920 | Tmem24 |
| 1438224_at | 4.663 | BE572265 | Zswim5 |
| 1448598_at | 4.662 | NM_011846 | Mmp17 |
| 1415834_at | 4.658 | NM_026268 | Dusp6 |
| 1435218_at | 4.656 | BI134758 | Rasgef1a |
| 1416683_at | 4.647 | NM_138749 | Plxnb2 |
| 1416983_s_at | 4.643 | AI462296 | Foxo1 |
| 1437929_at | 4.642 | AV306847 | Dact2 |
| 1452092_at | 4.641 | AK019474 | 4631426J05Rik |
| 1433450_at | 4.634 | BB177836 | Cdk5r1 |
| 1435392_at | 4.631 | BB277182 | Wdr17 |
| 1451475_at | 4.628 | BC019530 | Plxnd1 |
| 1420981_a_at | 4.628 | NM_010723 | Lmo4 |
| 1418144_a_at | 4.62 | NM_008847 | Pip5k1b |
| 1452917_at | 4.614 | AK011489 | Rfc5 |
| 1425466_at | 4.611 | AV317107 | Senp2 |
| 1421622_a_at | 4.611 | NM_019684 | Rapgef4 |
| 1434153_at | 4.603 | BI408715 | Shb |
| 1422977_at | 4.594 | NM_010327 | Gp1bb |
| 1455463_at | 4.594 | BB427286 | Phyhip |
| 1422473_at | 4.59 | BM246564 | Pde4b |
| 1426553_at | 4.579 | AK017830 | Dnajc14 |
| 1436002_at | 4.579 | BB484128 | C230013L11Rik |
| 1435482_at | 4.575 | BB318003 | Fibcd1 |
| 1452851_at | 4.573 | AK019578 | Tnrc4 |
| 1426354_at | 4.57 | AK009033 | Bap1 |
| 1441764_at | 4.562 | BF730739 | Prdm10 |
| 1454759_at | 4.56 | AV230461 | Git1 |
| 1434825_at | 4.556 | BQ175287 | LOC381742 |
| 1437017_at | 4.556 | BB046727 | AI480653 |
| 1435128_at | 4.546 | BB429313 | Baiap2 |
| 1419066_at | 4.546 | NM_030244 | Ier5l |
| 1448805_at | 4.545 | NM_009480 | Usf1 |
| 1437018_at | 4.536 | BG072348 | Pnma2 |
| 1439618_at | 4.531 | AI448308 | Pde10a |
| 1437001_at | 4.527 | BQ173949 | Gsk3b |
| 1421048_a_at | 4.521 | NM_023249 | Ypel1 |
| 1455881_at | 4.52 | BB078200 | Ier5l |
| 1449188_at | 4.52 | NM_021565 | Midn |
| 1428540_at | 4.509 | BE944524 | 3321401G04Rik |
| 1426454_at | 4.507 | AK002516 | Arhgdib |
| 1429124_s_at | 4.502 | BQ178367 | Rexo1 |
| 1425617_at | 4.501 | U91922 | Dhx9 |
| 1417207_at | 4.497 | BF466091 | Dvl2 |
| 1422762_at | 4.489 | AB008867 | Kif17 |
| 1451610_at | 4.486 | BC018513 | Ttl |
| 1457632_s_at | 4.485 | BB207647 | Mrg1 |
| 1443036_at | 4.477 | BG073535 | C630007C17Rik |
| 1446840_at | 4.475 | BQ032894 | |
| 1449468_at | 4.468 | NM_012028 | St6galnac5 |
| 1423415_at | 4.461 | BB110067 | Gpr83 |
| 1441928_x_at | 4.461 | BB139475 | Ell |
| 1428950_s_at | 4.461 | AK017551 | Nol8 |
| 1431230_a_at | 4.461 | Z74630 | Btbd9 |
| 1424475_at | 4.459 | BI157430 | Camkk2 |
| 1448687_at | 4.457 | NM_026125 | C1qdc2 |
| 1428864_at | 4.456 | AK017419 | 5530400B01Rik |
| 1437378_x_at | 4.45 | BB224405 | Scarb1 |
| 1423785_at | 4.448 | BE995700 | Egln1 |
| 1442370_at | 4.436 | BB267006 | |
| 1424175_at | 4.433 | BC017689 | Tef |
| 1460718_s_at | 4.433 | AF192558 | Mtch1 |
| 1436100_at | 4.431 | AV347995 | Sh2d5 |
| 1440479_at | 4.431 | BB821623 | Cbx4 |
| 1451696_at | 4.43 | BC004695 | Zfp64 |
| 1426585_s_at | 4.429 | BM209765 | Mapk1 |
| 1439548_at | 4.428 | BB390705 | Rap2b |
| 1436754_at | 4.42 | BB360523 | AI839735 |

TABLE 18-continued

Top 1,000 striatopallidal (D2) cell translated mRNAs enriched when compared to a reference sample

| ProbeSymbol | FEN | Genbank | GeneSymbol |
|---|---|---|---|
| 1433707_at | 4.419 | BB430205 | Gabra4 |
| 1451285_at | 4.416 | AF224264 | Fus |
| 1439422_a_at | 4.414 | AV048291 | C1qdc2 |
| 1456755_at | 4.388 | AI467545 | 2310001H13Rik |
| 1416537_at | 4.386 | NM_133930 | Creld1 |
| 1423478_at | 4.377 | BF660388 | Prkcb1 |
| 1424480_s_at | 4.374 | BC026151 | Akt2 |
| 1422751_at | 4.374 | NM_011599 | Tle1 |
| 1417456_at | 4.372 | NM_010322 | Gnpat |
| 1418168_at | 4.371 | BB223737 | Zcchc14 |
| 1448656_at | 4.365 | NM_007581 | Cacnb3 |
| 1426241_a_at | 4.358 | AB030906 | Scmh1 |
| 1423049_a_at | 4.352 | AK002271 | Tpm1 |
| 1426900_at | 4.35 | AV293164 | Jmjd1c |
| 1458443_at | 4.345 | BE986758 | Mect1 |
| 1426822_at | 4.344 | BM201133 | Rhot2 |
| 1417461_at | 4.335 | NM_007598 | Cap1 |
| 1427674_a_at | 4.33 | D29763 | Sez6 |
| 1450835_a_at | 4.329 | NM_020014 | Gfra4 |
| 1454844_at | 4.325 | AW049955 | Gpr24 |
| 1421962_at | 4.324 | AI664344 | Dnajb5 |
| 1424645_at | 4.32 | BB795102 | Tnrc6c |
| 1455080_at | 4.317 | BB375209 | Ppp1r16b |
| 1423228_at | 4.317 | BG066773 | B4galt6 |
| 1423200_at | 4.317 | U22016 | Ncor1 |
| 1417393_a_at | 4.314 | NM_026125 | C1qdc2 |
| 1418467_at | 4.305 | NM_025891 | Smarcd3 |
| 1420427_a_at | 4.296 | NM_133941 | Dhx32 |
| 1422407_s_at | 4.294 | NM_008284 | Hras1 |
| 1425929_a_at | 4.289 | AF249668 | Rnf14 |
| 1451908_a_at | 4.287 | BC005766 | Sec14l1 |
| 1415998_at | 4.284 | NM_011694 | Vdac1 |
| 1428937_at | 4.281 | BI080417 | Atp2b1 |
| 1417062_at | 4.279 | NM_026034 | 2810037C14Rik |
| 1428148_s_at | 4.271 | BB203098 | Coro7 |
| 1441369_at | 4.27 | BB329116 | |
| 1431074_a_at | 4.268 | BI654602 | Pitpnc1 |
| 1441815_at | 4.266 | AI851453 | AI851453 |
| 1442562_at | 4.263 | BB346556 | D630040G17Rik |
| 1459920_at | 4.262 | AA163908 | 4933415E08Rik |
| 1458399_at | 4.261 | AI413999 | Lrrc3 |
| 1448877_at | 4.26 | NM_010054 | Dlx2 |
| 1439866_at | 4.255 | BQ173950 | Parc |
| 1423522_at | 4.254 | BB811478 | Npm3 |
| 1449214_a_at | 4.252 | BC025160 | Opa1 |
| 1460717_at | 4.252 | AF042180 | Tspyl1 |
| 1437579_at | 4.246 | C77054 | Nek2 |
| 1431920_a_at | 4.234 | AK008082 | 2010004A03Rik |
| 1442708_at | 4.225 | BB504418 | |
| 1424759_at | 4.224 | BC017528 | Arrdc4 |
| 1441786_at | 4.217 | AW048005 | |
| 1430037_at | 4.216 | AK017836 | Snx27 |
| 1426978_at | 4.213 | AW682368 | Klhl2 |
| 1455555_at | 4.212 | BF224468 | AV071699 |
| 1443888_at | 4.206 | BB426608 | |
| 1451507_at | 4.205 | BB280300 | Mef2c |
| 1435441_at | 4.204 | BB336053 | Ablim2 |
| 1435845_at | 4.2 | BB764479 | 2900006N09Rik |
| 1415985_at | 4.199 | NM_133953 | Sf3b3 |
| 1448747_at | 4.194 | AF441120 | Fbxo32 |
| 1421897_at | 4.194 | AI385733 | Elk1 |
| 1416402_at | 4.184 | AV382118 | Abcb10 |
| 1426465_at | 4.175 | BG066219 | Dlgap4 |
| 1455771_at | 4.174 | BB467799 | Bzrap1 |
| 1430128_a_at | 4.169 | AK002562 | Dp1l1 |
| 1437865_at | 4.168 | AW546433 | Spata13 |
| 1427300_at | 4.167 | D49658 | Lhx8 |
| 1440258_at | 4.165 | BE951512 | Kcnq2 |
| 1426012_a_at | 4.147 | BC010499 | 2610301G19Rik |
| 1434805_at | 4.147 | BG063049 | Mllt1 |
| 1417524_at | 4.144 | NM_009920 | Cnih2 |
| 1455772_at | 4.141 | BB428874 | Pgr |
| 1424384_a_at | 4.14 | BC006765 | Znrf1 |
| 1416448_at | 4.137 | NM_025922 | Itpa |
| 1435204_at | 4.129 | BG065273 | Hrmt1l4 |
| 1422527_at | 4.123 | NM_010386 | H2-DMa |
| 1455548_at | 4.122 | BB314358 | Dlgap4 |
| 1423694_at | 4.121 | BC006935 | Kctd10 |
| 1428872_at | 4.117 | AW495537 | 4121402D02Rik |
| 1421175_at | 4.116 | NM_008666 | Myt1l |
| 1426897_at | 4.115 | AV122997 | Rcc2 |
| 1434762_at | 4.114 | BF457736 | A730041O15Rik |
| 1436005_at | 4.111 | BQ174136 | Sfrs14 |
| 1420738_at | 4.109 | NM_016793 | Zfp98 |
| 1423699_at | 4.107 | BC003900 | D15Ertd785e |
| 1438663_at | 4.106 | BF730196 | Bat2d |
| 1435674_at | 4.101 | BB351953 | Rhobtb2 |
| 1420718_at | 4.093 | NM_011856 | Odz2 |
| 1454960_at | 4.09 | BI646741 | Smad3 |
| 1447947_at | 4.089 | BM220786 | Zfyve16 |
| 1435598_at | 4.089 | BE996371 | Shc2 |
| 1416397_at | 4.077 | BB474887 | Mesdc1 |
| 1433526_at | 4.076 | BM942651 | Klhl8 |
| 1460279_a_at | 4.074 | AF043219 | Gtf2i |
| 1453952_x_at | 4.072 | AK005207 | Pparbp |
| 1425679_at | 4.066 | AF109769 | Mapk8ip1 |
| 1448553_at | 4.063 | NM_080728 | Myh7 |
| 1429738_at | 4.057 | AK013847 | Myt1l |
| 1439497_at | 4.056 | BG065013 | 4933415E08Rik |
| 1428443_a_at | 4.048 | AK005063 | Rap1ga1 |
| 1443694_at | 4.045 | BB794177 | Rgs20 |
| 1421340_at | 4.043 | NM_008580 | Map3k5 |
| 1430604_a_at | 4.039 | BI695530 | Prkar2b |
| 1416605_at | 4.036 | BC024944 | Nola2 |
| 1435206_at | 4.036 | BB767169 | Slc24a4 |
| 1428147_at | 4.035 | BB203098 | Coro7 |
| 1446312_at | 4.034 | BB273243 | |
| 1429174_at | 4.032 | AK014304 | Wdr34 |
| 1428508_at | 4.029 | AK004526 | 1810061M12Rik |
| 1456280_at | 4.022 | BG067086 | Clspn |
| 1434563_at | 4.021 | BM207149 | Rps6kc1 |
| 1440870_at | 4.018 | BB356786 | Prdm16 |
| 1454835_at | 4.014 | AV340515 | Epm2aip1 |
| 1422293_a_at | 4.008 | NM_134112 | Kctd1 |
| 1452063_at | 4.007 | AK010736 | 2410081M15Rik |
| 1425600_a_at | 4.007 | AW049748 | Plcb1 |
| 1455242_at | 3.999 | BM220880 | Foxp1 |
| 1456930_at | 3.999 | BE989461 | Camsap1 |
| 1433499_at | 3.998 | BF585125 | 2010005J08Rik |
| 1417216_at | 3.997 | NM_138606 | Pim2; LOC229005 |
| 1440487_at | 3.995 | BE824778 | Dcc |
| 1437400_at | 3.992 | BB309512 | Nedd4l |
| 1434904_at | 3.991 | AW321867 | Hivep2 |
| 1439867_at | 3.987 | BB079377 | Ubox5 |
| 1420961_a_at | 3.983 | NM_028582 | Ivns1abp |
| 1421498_a_at | 3.982 | NM_023450 | 2010204K13Rik |
| 1451008_at | 3.982 | BB360510 | St8sia3 |
| 1429718_at | 3.981 | BB782729 | Slitrk5 |
| 1451098_at | 3.98 | BC010524 | Pcoln3 |
| 1433642_at | 3.974 | BB384173 | Arfrp2 |
| 1456785_at | 3.973 | BQ175889 | Crsp2 |
| 1422255_at | 3.97 | NM_021275 | Kcna4 |
| 1429104_at | 3.964 | AK012581 | 0610025L06Rik |
| 1447642_x_at | 3.96 | AV354897 | Dmwd |
| 1420999_at | 3.958 | AI448404 | Cnot4 |
| 1459994_x_at | 3.955 | AV027486 | Trfr2 |
| 1455820_x_at | 3.955 | BB138434 | Scarb1 |
| 1456606_a_at | 3.949 | AV259240 | Chst11; Phactr1 |
| 1455365_at | 3.948 | BB426483 | Cdh8 |
| 1455191_x_at | 3.948 | BB822856 | Pip5k1b |
| 1440177_at | 3.948 | BM899529 | 9.63E+17 |
| 1443073_at | 3.945 | BB355954 | LOC545681 |
| 1422335_at | 3.942 | NM_007418 | Adra2c |
| 1460223_a_at | 3.942 | NM_013514 | Epb4.9 |
| 1433743_at | 3.937 | BG075820 | Dach1 |
| 1426785_s_at | 3.931 | BI411560 | Mgll |
| 1415976_a_at | 3.93 | AU080787 | Carhsp1 |
| 1452938_at | 3.924 | BQ174247 | C030032C09Rik |
| 1418323_at | 3.921 | BM232562 | Fem1b |

TABLE 18-continued

Top 1,000 striatopallidal (D2) cell translated mRNAs enriched when compared to a reference sample

| ProbeSymbol | FEN | Genbank | GeneSymbol |
|---|---|---|---|
| 1424132_at | 3.92 | BC011083 | Hras1 |
| 1426487_a_at | 3.918 | BB092954 | Rbbp6 |
| 1426108_s_at | 3.917 | AY094172 | Cacnb1 |
| 1426383_at | 3.917 | BF303057 | Cry2 |
| 1428914_at | 3.917 | AK009333 | 2310014D11Rik |
| 1455279_at | 3.911 | BG070552 | Gm1060 |
| 1460610_at | 3.91 | BG143491 | 9430057O19Rik |
| 1428259_at | 3.91 | AK010185 | 2310075M15Rik |
| 1440207_at | 3.907 | BI155142 | AI505034 |
| 1450853_at | 3.904 | AU045006 | Tle4 |
| 1427579_at | 3.904 | BE653576 | Rhbdl4 |
| 1426973_at | 3.903 | AK004377 | Gpr153 |
| 1439888_at | 3.902 | BB271581 | |
| 1427618_at | 3.901 | BQ176417 | Cdh9 |
| 1435844_at | 3.896 | BB164247 | A330009N23Rik |
| 1426644_at | 3.886 | BC002196 | Tbc1d20 |
| 1436563_at | 3.882 | AV277283 | 4932441J04Rik |
| 1436381_at | 3.88 | BQ175774 | Dlgap3 |
| 1460552_at | 3.878 | AI327392 | Ascc3l1 |
| 1454609_x_at | 3.878 | BB770958 | 6430527G18Rik |
| 1429715_at | 3.878 | AK010380 | Ppp2r2a |
| 1452911_at | 3.872 | AK017680 | Spred1 |
| 1455956_x_at | 3.864 | AV310588 | Ccnd2 |
| 1416981_at | 3.864 | AI462296 | Foxo1 |
| 1456838_at | 3.863 | BE995608 | LOC237403 |
| 1417749_a_at | 3.862 | NM_009386 | Tjp1 |
| 1434969_at | 3.859 | BB381558 | |
| 1421107_at | 3.859 | NM_021420 | Stk4 |
| 1454875_a_at | 3.857 | BF011461 | Rbbp4 |
| 1422807_at | 3.856 | NM_007480 | Arf5 |
| 1460436_at | 3.856 | BI652065 | Ndst1 |
| 1434082_at | 3.851 | BM243464 | Pctk2 |
| 1436513_at | 3.85 | BM208226 | 3526402J09Rik |
| 1452844_at | 3.844 | AK009674 | Pou6f1 |
| 1422590_at | 3.844 | NM_007668 | Cdk5 |
| 1453915_a_at | 3.841 | AK012071 | Slc37a3 |
| 1443612_at | 3.84 | AW123199 | |
| 1419080_at | 3.831 | NM_010275 | Gdnf |
| 1460568_at | 3.819 | BI156583 | Trim46 |
| 1426643_at | 3.815 | AK012072 | Elp3 |
| 1435618_at | 3.814 | BB473446 | Pnma2 |
| 1422485_at | 3.814 | AK004804 | Smad4 |
| 1452057_at | 3.807 | BG801851 | Actr1b |
| 1435125_at | 3.804 | BB303627 | BB120497 |
| 1416122_at | 3.801 | NM_009829 | Ccnd2 |
| 1428839_at | 3.8 | AK005105 | Wdr53 |
| 1426770_at | 3.799 | AJ416473 | Pex5 |
| 1452940_x_at | 3.798 | AI595920 | Pitpnc1 |
| 1441867_x_at | 3.796 | AI480494 | 4930534B04Rik |
| 1423195_at | 3.796 | BM208582 | Hiat1 |
| 1456444_at | 3.795 | BB126849 | Fbxo41 |
| 1433811_at | 3.794 | BG245272 | Mllt6 |
| 1433747_at | 3.793 | BQ176475 | Lnpep |
| 1417305_at | 3.793 | NM_007463 | Apeg1 |
| 1457077_at | 3.791 | BB306048 | |
| 1428853_at | 3.79 | BG071079 | Ptch1 |
| 1428852_at | 3.788 | AK018140 | Dock3 |
| 1424150_at | 3.788 | BC024955 | Gdpd5 |
| 1421191_s_at | 3.786 | NM_053187 | Gopc |
| 1427468_at | 3.782 | M81483 | Ppp3cb |
| 1418080_at | 3.782 | AW125856 | B4galt2 |
| 1453689_at | 3.781 | AK013325 | Fance |
| 1419234_at | 3.781 | BG070273 | Helb |
| 1460210_at | 3.78 | NM_013630 | Pkd1 |
| 1428173_at | 3.777 | AK005562 | Eml2 |
| 1435547_at | 3.776 | BQ175722 | Mkl2 |
| 1428892_at | 3.773 | AK004331 | Ppil1 |
| 1456766_at | 3.773 | BB036966 | C330001K17Rik |
| 1439662_at | 3.771 | BM124609 | Homer1 |
| 1428786_at | 3.77 | BM238996 | Nckap1l |
| 1445194_at | 3.77 | BB355006 | Cnksr2 |
| 1438266_at | 3.77 | BB764453 | Thsd6 |
| 1428926_at | 3.769 | AK003388 | 1110003O08Rik |
| 1427071_at | 3.767 | BC003960 | Fbxo42 |
| 1452149_at | 3.766 | AU067784 | Ube3b |
| 1422737_at | 3.765 | NM_008679 | Ncoa3 |
| 1423842_a_at | 3.764 | AF305730 | Rnf41 |
| 1426972_at | 3.763 | AK009425 | Sec24d |
| 1454659_at | 3.762 | BG069699 | Dctd |
| 1423519_at | 3.759 | BE457744 | 2210412D01Rik |
| 1445359_at | 3.756 | BE993830 | Adcy1 |
| 1447696_x_at | 3.754 | BB091427 | Adcy5 |
| 1429228_at | 3.754 | BE980134 | 4930534B04Rik |
| 1421817_at | 3.754 | AK019177 | Gsr |
| 1440741_at | 3.751 | BB829587 | Htr1d |
| 1457919_at | 3.739 | BB446049 | D030054H15Rik |
| 1456601_x_at | 3.738 | AV002675 | Fxyd2 |
| 1452718_at | 3.736 | BG073486 | Edd1 |
| 1442883_s_at | 3.734 | BI413749 | D10Bwg1364e |
| 1417844_at | 3.734 | NM_026119 | Med4 |
| 1420965_a_at | 3.732 | BM120053 | Enc1 |
| 1455023_at | 3.728 | BB171181 | N28178 |
| 1452913_at | 3.725 | AV337888 | Pcp4l1 |
| 1453428_at | 3.72 | AK012380 | 2700045P11Rik |
| 1432813_at | 3.718 | AK013749 | 2900064F13Rik |
| 1433924_at | 3.709 | BM200248 | Peg3 |
| 1438913_x_at | 3.707 | AW322533 | Hdgfrp2 |
| 1438213_at | 3.705 | BB128962 | A830018L16Rik |
| 1429201_at | 3.705 | AK013508 | Cyld |
| 1416125_at | 3.699 | U16959 | Fkbp5 |
| 1457213_a_at | 3.698 | AV276089 | Dgkh |
| 1416106_at | 3.695 | NM_029571 | Kti12 |
| 1442099_at | 3.695 | BM227490 | Usp31 |
| 1421860_at | 3.689 | BG065300 | Clstn1 |
| 1450366_at | 3.689 | NM_007545 | Hrk |
| 1433777_at | 3.688 | BB152370 | L3mbtl2 |
| 1416953_at | 3.685 | NM_010217 | Ctgf |
| 1426009_a_at | 3.685 | BC003763 | Pip5k1b |
| 1422453_at | 3.674 | NM_138659 | Prpf8 |
| 1445854_at | 3.674 | BB380166 | C230004F18Rik |
| 1452438_s_at | 3.672 | BE632382 | Taf4a |
| 1426069_s_at | 3.671 | BC016100 | Slc7a4 |
| 1424047_at | 3.67 | BC016218 | Dera |
| 1433987_at | 3.666 | AV153557 | Hpcal4 |
| 1454700_at | 3.665 | BB093349 | Lrfn4 |
| 1448498_at | 3.663 | NM_019924 | Rps6ka4 |
| 1416863_at | 3.663 | NM_022419 | Abhd8 |
| 1428222_at | 3.66 | AK018179 | Dcamkl2 |
| 1430413_at | 3.66 | AK018228 | 6330540D07Rik |
| 1428716_at | 3.656 | BG076082 | Pex1 |
| 1451998_at | 3.653 | BC024597 | 4930485D02Rik |
| 1431717_at | 3.653 | AK014386 | 3526401B18Rik |
| 1454685_at | 3.649 | BQ177047 | |
| 1423629_a_at | 3.649 | BB663717 | Nedd4l |
| 1450910_at | 3.647 | AV261931 | Cap2 |
| 1416535_at | 3.644 | BC003746 | Mcrs1; LOC433780 |
| 1417032_at | 3.644 | AF296657 | Ube2g2 |
| 1421312_a_at | 3.643 | NM_010630 | Kifc2 |
| 1460009_at | 3.639 | BB667115 | Ier5 |
| 1416550_at | 3.639 | BB320416 | Slc35b4 |
| 1449168_a_at | 3.638 | BC003735 | Akap2 |
| 1418639_at | 3.631 | NM_011359 | Sftpc |
| 1435504_at | 3.63 | BM217861 | Rsnl2 |
| 1435019_at | 3.629 | BB532141 | Atxn7l3 |
| 1423673_at | 3.628 | BC023053 | Ldoc1l |
| 1437842_at | 3.626 | BB311508 | Plcxd1 |
| 1433787_at | 3.623 | AI841091 | B230343H07Rik |
| 1451568_at | 3.62 | BC025603 | A630054L15Rik |
| 1452624_at | 3.618 | BM900077 | Lrrtm1 |
| 1450520_at | 3.617 | NM_019430 | Cacng3 |
| 1433699_at | 3.617 | BM241351 | Tnfaip3 |
| 1433468_at | 3.614 | BB770958 | 6430527G18Rik |
| 1418016_at | 3.614 | BI689507 | Pum2 |
| 1419248_at | 3.612 | AF215668 | Rgs2 |
| 1429021_at | 3.608 | AK013481 | Epha4 |
| 1427954_at | 3.606 | BC028785 | BC048403 |
| 1449932_at | 3.605 | NM_027874 | Csnk1d |
| 1454985_at | 3.604 | BI872009 | D030051N19Rik |
| 1451722_s_at | 3.602 | BF160651 | Smyd5 |

TABLE 18-continued

Top 1,000 striatopallidal (D2) cell translated mRNAs enriched when compared to a reference sample

| ProbeSymbol | FEN | Genbank | GeneSymbol |
|---|---|---|---|
| 1429122_a_at | 3.6 | AK006658 | 1700040I03Rik |
| 1424317_at | 3.6 | BC018167 | Slc25a19 |
| 1447124_at | 3.599 | BE634581 | |
| 1437989_at | 3.598 | BB357157 | Pde8b |
| 1448374_at | 3.595 | AK005130 | Med28 |
| 1424044_at | 3.594 | BC007145 | Jmjd2b |
| 1434832_at | 3.59 | BB364488 | Foxo3a |
| 1436483_at | 3.589 | BM116113 | Myt1l |
| 1453324_at | 3.588 | BF459399 | 6330509M23Rik |
| 1437750_at | 3.586 | BI133257 | 2310037P21Rik |
| 1443542_at | 3.582 | BB767151 | |
| 1429392_at | 3.58 | BI558553 | Wdr40a |
| 1456144_at | 3.58 | AW537064 | Nav3 |
| 1457456_at | 3.577 | AI481735 | Map3k10 |
| 1419056_at | 3.577 | AF038538 | Rtn2 |
| 1429832_at | 3.575 | AK014665 | Ppih |
| 1458351_s_at | 3.572 | BB428573 | Klhl2 |
| 1428936_at | 3.572 | BI080417 | Atp2b1 |
| 1418173_at | 3.571 | NM_133730 | 4631426H08Rik |
| 1454728_s_at | 3.569 | AW610650 | Atp8a1 |
| 1422474_at | 3.568 | BM246564 | Pde4b |
| 1451106_at | 3.565 | BC025499 | Rbm21 |
| 1422677_at | 3.564 | AK002443 | Dgat2 |
| 1423973_a_at | 3.562 | BC024935 | Arf3 |
| 1422799_at | 3.562 | AK019427 | Bat2 |
| 1446681_at | 3.562 | AV327329 | BB086117 |
| 1451506_at | 3.557 | BB280300 | Mef2c |
| 1429678_at | 3.557 | AK017708 | 5730508B09Rik |
| 1457361_at | 3.555 | BB628626 | C630007C17Rik |
| 1424117_at | 3.552 | BC024937 | BC056474 |
| 1436142_at | 3.55 | BM218877 | 3526401B18Rik |
| 1452467_at | 3.549 | BQ042988 | Mmab |
| 1434830_at | 3.547 | AV228517 | Mxd1 |
| 1428327_at | 3.547 | BB010301 | 2310001H13Rik |
| 1423442_a_at | 3.545 | BE854125 | Fbxw2 |
| 1423330_at | 3.543 | AK006149 | Ensa |
| 1433621_at | 3.536 | BB334979 | Wdr41 |
| 1455395_at | 3.536 | BB446073 | 4933425A18Rik |
| 1425180_at | 3.535 | AV344708 | Sgip1 |
| 1427091_at | 3.532 | BC025488 | AI481105 |
| 1423395_at | 3.53 | BM021706 | Tsnax |
| 1437921_x_at | 3.53 | AW744723 | Zfp516 |
| 1419577_at | 3.524 | NM_133999 | A530089I17Rik |
| 1434154_at | 3.523 | BQ177107 | Kctd13 |
| 1416292_at | 3.521 | NM_007457 | Prdx3 |
| 1438478_a_at | 3.52 | AI313926 | Ppp3ca |
| 1434415_at | 3.519 | BB797871 | |
| 1449494_at | 3.514 | AY026947 | Rab3c |
| 1424503_at | 3.511 | BC006596 | Rab22a |
| 1455247_at | 3.508 | BB767281 | Amotl1 |
| 1417349_at | 3.507 | NM_019788 | Pldn |
| 1452269_at | 3.506 | AF026489 | Spnb3 |
| 1460623_at | 3.506 | BB753881 | Scap1 |
| 1429330_at | 3.504 | AK013727 | Gabra4 |
| 1425580_a_at | 3.504 | BC024675 | Pik3c3 |
| 1418895_at | 3.502 | NM_018773 | Scap2 |
| 1428642_at | 3.497 | AK018094 | Slc35d3 |
| 1428550_at | 3.496 | AK007503 | 1810015A11Rik |
| 1452234_s_at | 3.493 | BF457957 | D16Bwg1494e |
| 1428600_at | 3.49 | AK014241 | 3110068G20Rik |
| 1448745_s_at | 3.487 | NM_008508 | Lor |
| 1434603_at | 3.485 | BG074645 | Thrap2 |
| 1419522_at | 3.484 | NM_026021 | Zmynd19 |
| 1444363_at | 3.477 | BB269445 | |
| 1423978_at | 3.476 | BC025837 | Sbk1 |
| 1436013_at | 3.476 | AI852434 | C230098I05Rik |
| 1433558_at | 3.476 | BM231046 | Dab2ip |
| 1424320_a_at | 3.474 | BC008598 | Traf7 |
| 1434025_at | 3.469 | BG069607 | |
| 1438421_at | 3.469 | BI134275 | Pvrl1 |
| 1429588_at | 3.468 | AA509870 | 2810474O19Rik |
| 1450436_s_at | 3.466 | AI664344 | Dnajb5 |
| 1416918_at | 3.465 | NM_016747 | Dlgh3 |
| 1429618_at | 3.465 | BM119209 | Cyld |
| 1449843_at | 3.465 | BG071333 | St8sia2 |
| 1455265_a_at | 3.464 | BB100249 | Rgs16 |
| 1450863_a_at | 3.462 | BQ174703 | Dcamkl1 |
| 1417794_at | 3.461 | NM_019831 | Zfp261 |
| 1423583_at | 3.46 | AK005041 | Fem1a |
| 1457729_at | 3.458 | AW492805 | |
| 1428585_at | 3.456 | BE853286 | Actn1 |
| 1437580_s_at | 3.453 | C77054 | Nek2 |
| 1460262_a_at | 3.451 | NM_026091 | 1700037H04Rik |
| 1434339_at | 3.45 | AW548221 | Fnbp1l |
| 1428777_at | 3.447 | AK017680 | Spred1 |
| 1418743_a_at | 3.447 | NM_021344 | MGI: 1930803 |
| 1450040_at | 3.444 | M93954 | Timp2 |
| 1455033_at | 3.444 | BB325849 | B430201A12Rik |
| 1427930_at | 3.444 | BG063905 | Pdxk |
| 1457256_x_at | 3.441 | BB530125 | Ptch2 |
| 1454092_a_at | 3.441 | AK017176 | Gtf2h3 |
| 1427993_at | 3.434 | AI852705 | Rufy2 |
| 1448554_s_at | 3.432 | NM_080728 | Myh6 |
| 1448445_at | 3.431 | AB030038 | Acp6 |
| 1426786_s_at | 3.431 | BM195397 | Dhx38 |
| 1455401_at | 3.428 | AW061083 | Camkk2 |
| 1420694_a_at | 3.425 | BB522228 | Dach1 |
| 1416087_at | 3.419 | NM_007457 | Ap1s1 |
| 1449502_at | 3.418 | NM_010021 | Dazl |
| 1419583_at | 3.416 | NM_007625 | Cbx4 |
| 1425415_a_at | 3.414 | U75214 | Slc1a1 |
| 1434902_at | 3.413 | BB163668 | Rnf157 |
| 1454827_at | 3.41 | BG070415 | Pogz |
| 1435169_at | 3.409 | BB431047 | A930001N09Rik |
| 1420533_at | 3.409 | AK004815 | Gucy1a3 |
| 1422431_at | 3.408 | NM_053201 | Magee1 |
| 1437214_at | 3.408 | BB667279 | Lrrtm4 |
| 1417829_a_at | 3.406 | NM_134050 | Rab15 |
| 1455865_at | 3.404 | BB468410 | Insm1 |
| 1437980_at | 3.404 | BB814947 | 9130230N09Rik |
| 1451273_x_at | 3.404 | BC025546 | BC025546 |
| 1434720_at | 3.403 | BF320240 | 9530033F24Rik |
| 1419834_x_at | 3.4 | AW491150 | Mark1 |
| 1434531_at | 3.397 | BB400317 | GnT-IX |
| 1435233_at | 3.396 | BM234716 | Ncoa2 |
| 1424199_at | 3.396 | AW537349 | Seh1l |
| 1438039_at | 3.396 | BE630599 | Hectd1 |
| 1455102_at | 3.393 | BB213860 | D330037H05Rik |
| 1435549_at | 3.392 | BI685685 | Trpm4 |
| 1416013_at | 3.392 | NM_011116 | Pld3 |
| 1438272_at | 3.391 | BB315073 | Csmd3 |
| 1453485_s_at | 3.391 | AK016897 | 1110005A03Rik |
| 1428924_at | 3.39 | AU016306 | Mocs3 |
| 1436260_at | 3.387 | BB131085 | |
| 1436354_at | 3.386 | BE992423 | Dzip1l |
| 1436763_a_at | 3.386 | AI267126 | Klf9 |
| 1421662_a_at | 3.384 | NM_030254 | Tusc3 |
| 1421037_at | 3.384 | BG070037 | Npas2 |
| 1438662_at | 3.382 | AW123234 | LOC433810 |
| 1431076_at | 3.382 | BG976853 | Add2 |
| 1456863_at | 3.381 | AI385584 | Epha4 |
| 1421399_at | 3.38 | NM_016889 | Insm1 |
| 1452292_at | 3.379 | AV271093 | Ap2b1 |
| 1425132_at | 3.377 | AF448840 | Neto1 |
| 1437231_at | 3.374 | AV246497 | Slitrk6 |
| 1423777_at | 3.374 | AK006800 | Usp20 |
| 1451751_at | 3.372 | AF335325 | Ddit4l |
| 1439106_at | 3.371 | AV320128 | Zfp462 |
| 1421027_a_at | 3.37 | AI595932 | Mef2c |
| 1436085_at | 3.37 | BB361974 | Zbtb34 |
| 1434819_at | 3.369 | BB709312 | St6gal2 |
| 1441572_at | 3.369 | BB264612 | C030036D22Rik |
| 1453200_at | 3.368 | AK013909 | Rai1 |
| 1418181_at | 3.366 | AK014601 | Ptp4a3 |
| 1448141_at | 3.364 | NM_029101 | 1110014J01Rik |
| 1452647_a_at | 3.361 | AK011199 | Dph2 |
| 1455670_at | 3.36 | BQ175884 | Rbms3 |
| 1423367_at | 3.36 | AK004683 | Wnt7a |
| 1423832_at | 3.359 | BB756794 | Prkag2 |
| 1453260_a_at | 3.355 | AK010380 | Ppp2r2a |

TABLE 18-continued

Top 1,000 striatopallidal (D2) cell translated mRNAs enriched when compared to a reference sample

| ProbeSymbol | FEN | Genbank | GeneSymbol |
|---|---|---|---|
| 1436396_at | 3.355 | AV291191 | D430033N04Rik |
| 1419879_s_at | 3.354 | AA960166 | Trim25 |
| 1421943_at | 3.351 | M92420 | Tgfa |
| 1415753_at | 3.35 | BC005632 | D10Bwg1364e |
| 1434476_at | 3.349 | BM119896 | Mect1 |
| 1418174_at | 3.347 | BC018323 | Dbp |
| 1451888_a_at | 3.341 | AB025413 | Odz4 |
| 1447301_at | 3.338 | BG228875 | Gm258 |
| 1417890_at | 3.336 | NM_020271 | Pdxp |
| 1437918_at | 3.335 | AV374644 | 4930539E08Rik |
| 1434228_at | 3.334 | AV255921 | Ppm2c |
| 1432091_a_at | 3.333 | AK007455 | Rutbc3 |
| 1417375_at | 3.332 | AW491660 | Tuba4 |
| 1442093_at | 3.331 | AU040368 | |
| 1451533_at | 3.328 | BC022687 | BC022687 |
| 1427212_at | 3.328 | BC027377 | Mapkap1 |
| 1458967_at | 3.326 | BM939341 | |
| 1449063_at | 3.326 | BC009024 | Sec22l1 |
| 1455029_at | 3.325 | BB342219 | Kif21a |
| 1453268_at | 3.322 | AV224102 | 5730409G07Rik |
| 1422594_at | 3.318 | BC004090 | 5730470L24Rik |
| 1455289_at | 3.317 | BQ174304 | Ankrd13b |
| 1423344_at | 3.316 | AK010968 | Epor |
| 1426416_a_at | 3.316 | AV216410 | Yipf4 |
| 1438434_at | 3.313 | AV349116 | Arhgap11a |
| 1456760_at | 3.311 | BB342676 | |
| 1451207_at | 3.31 | BC023022 | Cbara1 |

ProbeSymbol = Affymetrix probe identification corresponding to gene symbol; FEN = fold enrichment when compared to reference sample; Genbank = Genbank identification; GeneSymbol = official gene symbol.

TABLE 19

Top 1,000 brain stem cholinergic motor neuron (Chat) translated mRNAs enriched when compared to a reference sample

| ProbeSymbol | FEN | Genbank | GeneSymbol |
|---|---|---|---|
| 1422203_at | 1618.00 | NM_021712 | Slc18a3 |
| 1422639_at | 1463.00 | NM_054084 | Calcb |
| 1422530_at | 385.40 | NM_013639 | Prph1 |
| 1452004_at | 363.20 | AF330212 | Calca |
| 1417788_at | 192.50 | NM_011430 | Sncg |
| 1452243_at | 190.40 | BB282273 | Kcnj14 |
| 1438042_at | 177.90 | AV332957 | Shox2 |
| 1426511_at | 149.60 | AK004703 | Susd2 |
| 1455907_x_at | 124.40 | BB059017 | Phox2b |
| 1438967_x_at | 120.00 | AV259665 | Amhr2 |
| 1436461_at | 115.40 | BQ175922 | G3bp |
| 1416034_at | 108.50 | NM_009846 | Cd24a |
| 1433578_at | 103.50 | BE824538 | E130304D01 |
| 1422644_at | 98.31 | NM_015825 | Sh3bgr |
| 1451440_at | 90.54 | AF311699 | Chodl |
| 1420388_at | 86.56 | NM_008939 | Prss12 |
| 1439609_at | 85.66 | BB536410 | |
| 1425964_x_at | 85.58 | U03561 | Hspb1 |
| 1449254_at | 83.13 | NM_009263 | Spp1 |
| 1443372_at | 80.13 | BB417900 | Chat |
| 1455893_at | 78.48 | BG067392 | Rspo2 |
| 1419200_at | 74.53 | NM_022007 | Fxyd7 |
| 1421799_at | 69.66 | NM_011910 | Uts2 |
| 1460668_at | 62.98 | NM_010253 | Gal |
| 1422943_a_at | 61.77 | NM_013560 | Hspb1 |
| 1454660_at | 59.01 | BB367590 | 1100001E04Rik |
| 1419573_a_at | 58.02 | NM_008495 | Lgals1 |
| 1418917_at | 52.82 | NM_019487 | Hebp2 |
| 1416762_at | 52.76 | NM_009112 | S100a10 |
| 1448182_a_at | 51.25 | NM_009846 | Cd24a |
| 1436520_at | 50.88 | BB378317 | AI450948 |
| 1417013_at | 50.33 | AF250139 | Hspb8 |
| 1455439_a_at | 48.08 | AI642438 | Lgals1 |
| 1427357_at | 46.95 | AK008793 | Cda |
| 1418787_at | 45.08 | NM_010776 | Mbl2 |

TABLE 19-continued

Top 1,000 brain stem cholinergic motor neuron (Chat) translated mRNAs enriched when compared to a reference sample

| ProbeSymbol | FEN | Genbank | GeneSymbol |
|---|---|---|---|
| 1453351_at | 44.45 | AK020409 | Tbx20 |
| 1427351_s_at | 43.40 | BB226392 | Igh-6 |
| 1421359_at | 41.03 | NM_009050 | Ret |
| "AFFX-r2-Bs-dap-3_at" | 40.73 | AFFX-r2-Bs-dap-3 | |
| 1457021_x_at | 39.81 | AV209206 | Amhr2 |
| 1449106_at | 39.51 | NM_008161 | Gpx3 |
| 1453127_at | 38.86 | AK009235 | Ppm1j |
| 1423856_at | 38.80 | BC003896 | Popdc3 |
| 1443906_at | 38.28 | BE686894 | Daf1 |
| 1449271_a_at | 38.26 | NM_019487 | Hebp2 |
| 1436239_at | 37.11 | BB328706 | Slc5a5 |
| 1448816_at | 35.41 | NM_008968 | Ptgis |
| 1427989_at | 35.01 | AF503863 | Amhr2 |
| 1423557_at | 34.83 | BF537076 | Ifngr2 |
| 1436359_at | 34.72 | BF471533 | Ret |
| 1423693_at | 34.64 | BC011218 | Ela1 |
| 1419091_a_at | 34.50 | NM_007585 | Anxa2 |
| 1415983_at | 34.34 | NM_008879 | Lcp1 |
| 1418517_at | 34.07 | NM_008393 | Irx3 |
| 1437137_at | 33.87 | AV280875 | 6430550H21Rik |
| "AFFX-DapX-3_at" | 31.89 | AFFX-DapX-3 | |
| 1437502_x_at | 31.73 | BB560574 | Cd24a |
| 1454171_x_at | 31.57 | AK020608 | 9530053H05Rik |
| 1421428_at | 31.11 | NM_022025 | Slc5a7 |
| 1418762_at | 30.97 | NM_010016 | Daf1 |
| 1448291_at | 30.74 | NM_013599 | Mmp9 |
| 1446681_at | 30.58 | AV327329 | BB086117 |
| 1436503_at | 30.52 | BF302511 | BC048546 |
| 1448160_at | 30.41 | NM_008879 | Lcp1 |
| 1453855_at | 30.02 | BG295762 | 1810057P16Rik |
| 1423947_at | 29.93 | BC024615 | 1110008P14Rik |
| 1428536_at | 29.46 | AK015001 | Kcng4 |
| 1422586_at | 28.71 | NM_021306 | Ecel1 |
| 1456532_at | 28.49 | BB428671 | Pdgfd |
| 1418352_at | 28.42 | BC012682 | Hsd17b2 |
| 1421862_a_at | 28.31 | AK018783 | Vamp1 |
| 1416357_a_at | 28.06 | NM_023061 | Mcam |
| 1418415_at | 27.45 | NM_008268 | Hoxb5 |
| 1423560_at | 27.34 | AI838010 | Nell2 |
| 1422860_at | 26.84 | NM_024435 | Nts |
| 1452913_at | 26.70 | AV337888 | Pcp4l1 |
| 1450610_at | 26.27 | NM_021290 | Ucn |
| 1434442_at | 25.66 | BB667844 | D5Ertd593e |
| "AFFX-r2-Bs-dap-M_at" | 24.43 | AFFX-r2-Bs-dap-M | |
| 1455919_at | 24.09 | AV330588 | |
| 1441778_at | 23.92 | BB171354 | Adcyap1 |
| 1444165_at | 23.75 | BB530994 | E030012M19Rik |
| 1452010_at | 23.39 | AF472588 | Chrna3 |
| 1451515_s_at | 23.24 | BC010799 | Glyat |
| 1424900_at | 22.65 | BC025599 | Slc29a4 |
| "AFFX-DapX-M_at" | 22.56 | AFFX-DapX-M | |
| 1422635_at | 22.40 | NM_009599 | Ache |
| 1435184_at | 22.18 | BG066982 | B430320C24Rik |
| 1445281_a_at | 21.58 | BB309504 | B230311B06Rik |
| 1417312_at | 21.31 | AK004853 | Dkk3 |
| 1436141_at | 21.14 | BM934616 | 2610510L01Rik |
| 1436332_at | 20.96 | BB755506 | Hspb6 |
| "AFFX-r2-Bs-thr-3_s_at" | 20.94 | AFFX-r2-Bs-thr-3 | |
| 1460299_at | 20.73 | NM_019944 | Hlxb9 |
| 1449899_at | 20.42 | NM_130455 | Grin3b |
| 1420385_at | 20.25 | NM_008137 | Gna14 |
| 1427747_a_at | 20.23 | X14607 | Lcn2 |
| 1442608_at | 20.21 | AV071586 | E030012M19Rik |
| "AFFX-ThrX-3_at" | 20.17 | AFFX-ThrX-3 | |
| 1417228_at | 20.11 | AF084459 | Capn1 |
| 1422825_at | 20.10 | NM_013732 | MGI: 1351330 |

TABLE 19-continued

Top 1,000 brain stem cholinergic motor neuron (Chat) translated mRNAs enriched when compared to a reference sample

| ProbeSymbol | FEN | Genbank | GeneSymbol |
|---|---|---|---|
| 1421223_a_at | 20.05 | NM_013471 | Anxa4 |
| 1420984_at | 19.96 | AF114437 | Pctp |
| 1439015_at | 19.88 | AV221299 | Gfra1 |
| 1428664_at | 19.81 | AK018599 | Vip |
| 1439086_at | 19.60 | BB278168 | A930009L07Rik |
| 1439885_at | 19.35 | AA051236 | Hoxc5 |
| 1424531_a_at | 19.22 | BC010807 | Tcea3 |
| 1424176_a_at | 19.16 | BE628614 | Anxa4 |
| 1438444_at | 18.99 | AV381832 | A230091H23Rik |
| 1418176_at | 18.97 | AV290079 | Vdr |
| 1423427_at | 18.96 | AI323434 | Adcyap1 |
| 1450869_at | 18.84 | AI649186 | Fgf1 |
| 1452968_at | 18.50 | AK003674 | Cthrc1 |
| 1434779_at | 18.48 | BQ175551 | Cbln2 |
| 1432198_at | 18.14 | AK018172 | |
| 1427975_at | 18.09 | AK008807 | 2210403B10Rik |
| 1416298_at | 17.83 | NM_013599 | Mmp9 |
| 1423281_at | 17.70 | BM115022 | Stmn2 |
| 1453638_at | 17.69 | AK018520 | 9030420J04Rik |
| 1449545_at | 17.67 | NM_008005 | Fgf18 |
| 1451814_a_at | 17.61 | AF061972 | Htatip2 |
| 1453593_at | 17.42 | BG066866 | 1700110N18Rik |
| 1447791_s_at | 17.37 | AV230778 | Gna14 |
| 1429154_at | 17.30 | BG069340 | Slc35f2 |
| 1437762_at | 17.18 | BB130995 | Rab39 |
| 1430596_s_at | 17.13 | BG066866 | 1700110N18Rik |
| 1426063_a_at | 17.06 | U10551 | Gem |
| 1422452_at | 16.97 | NM_013863 | Bag3 |
| 1435790_at | 16.91 | BG864960 | Olfm2 |
| 1450723_at | 16.81 | BQ176915 | Isl1 |
| 1417960_at | 16.61 | NM_007755 | Cpeb1 |
| 1457048_at | 16.38 | BB526932 | Gpr103 |
| 1440677_at | 16.34 | BB308744 | LOC245305 |
| 1416713_at | 16.34 | NM_026481 | 2700055K07Rik |
| 1460255_at | 16.17 | NM_033622 | Tnfsf13b |
| 1422852_at | 16.02 | NM_019686 | Cib2 |
| 1420256_x_at | 15.90 | AV354142 | |
| 1439578_at | 15.80 | BB713457 | Lsm11 |
| 1455642_a_at | 15.79 | AI844703 | Tspan17 |
| 1418901_at | 15.77 | NM_009883 | Cebpb |
| 1428544_at | 15.64 | BE689422 | 0610007L01Rik |
| 1456247_x_at | 15.57 | AV166926 | Plp2 |
| 1424249_a_at | 15.48 | BC024535 | Arhgap9 |
| 1459750_s_at | 15.27 | AU015577 | Gpr123 |
| 1452246_at | 15.22 | U58888 | Ostf1 |
| 1424927_at | 15.10 | BC025083 | Glipr1 |
| 1436622_at | 15.02 | AW492241 | Iqsec2 |
| 1426937_at | 15.01 | AK018128 | 6330406I15Rik |
| 1459890_s_at | 14.98 | C79326 | 1110008P14Rik |
| 1422118_at | 14.92 | NM_023485 | Sync |
| 1417956_at | 14.86 | NM_007702 | Cidea |
| 1425245_a_at | 14.81 | BC019741 | Rgs11 |
| 1429696_at | 14.81 | BE946247 | Gpr123 |
| 1422720_at | 14.68 | BQ176915 | Isl1 |
| 1427900_at | 14.53 | BC028795 | Pip5k1l |
| 1424443_at | 14.46 | AV378394 | Tm6sf1 |
| 1449155_at | 14.40 | NM_026190 | Polr3g |
| 1449571_at | 14.38 | M59811 | Trhr |
| 1451232_at | 14.34 | U89772 | Cd151 |
| 1416935_at | 14.31 | NM_011706 | Trpv2 |
| 1456925_at | 14.22 | AW490413 | P2rxl1 |
| 1450791_at | 14.19 | NM_008726 | Nppb |
| 1433626_at | 14.17 | BB826296 | Plscr4 |
| 1429385_at | 14.17 | BI082535 | Wdr68 |
| 1459300_at | 14.14 | BB226459 | |
| 1448259_at | 14.02 | BI452727 | Fstl1 |
| 1459921_at | 13.98 | BQ042959 | Nxph1 |
| 1427853_a_at | 13.97 | AF047377 | Hspb1 |
| 1424692_at | 13.85 | BC004753 | 2810055F11Rik |
| 1449161_at | 13.83 | NM_007902 | Edn2 |
| 1444060_at | 13.80 | BB497990 | Bcas3 |
| 1451346_at | 13.74 | BG075139 | Mtap |
| 1457779_at | 13.64 | AV013305 | 1110046J04Rik |
| 1449368_at | 13.64 | NM_007833 | Dcn |
| 1453111_a_at | 13.61 | AK019396 | D11Ertd333e |
| 1455239_at | 13.57 | BM116861 | 6330512M04Rik |
| 1447493_at | 13.55 | AI413840 | A530088H08Rik |
| 1415832_at | 13.54 | NM_007429 | Agtr2 |
| 1452451_at | 13.53 | AF240460 | MGI: 1929597 |
| 1424680_at | 13.50 | BC025893 | BB146404 |
| 1419810_x_at | 13.50 | AU043488 | Arhgap9 |
| 1449130_at | 13.50 | NM_007639 | Cd1d1 |
| 1449832_at | 13.48 | NM_028570 | 1700091H14Rik |
| 1418610_at | 13.47 | NM_080853 | Slc17a6 |
| 1425051_at | 13.46 | AK010892 | Isoc1 |
| 1421973_at | 13.44 | BE534815 | Gfra1 |
| 1416080_at | 13.41 | NM_009614 | Adam15 |
| 1427512_a_at | 13.32 | X84014 | Lama3 |
| 1451636_at | 13.31 | BC022726 | Ankrd33 |
| 1422545_at | 13.28 | NM_009324 | Tbx2 |
| 1434340_at | 13.26 | BF681728 | |
| 1426540_at | 13.21 | BF168366 | 2310067E08Rik |
| 1417291_at | 13.20 | L26349 | Tnfrsf1a |
| 1428384_at | 13.18 | AK003950 | D4Bwg0951e |
| 1456596_at | 13.13 | BB093996 | 6430550H21Rik |
| 1456746_a_at | 13.05 | BB334959 | Cd9912 |
| 1444790_at | 13.04 | AV048499 | 1810005K13Rik |
| 1424246_a_at | 12.98 | BC003808 | Tes |
| 1419555_at | 12.97 | BC012424 | Elf5 |
| 1439905_at | 12.93 | BE948639 | |
| 1422245_a_at | 12.91 | U63408 | Mrvi1 |
| 1417014_at | 12.91 | AF250139 | Hspb8 |
| 1424093_x_at | 12.86 | U89772 | Cd151 |
| 1452103_at | 12.77 | BI456906 | 2600005N12Rik |
| 1422870_at | 12.60 | NM_013553 | Hoxc4 |
| 1418471_at | 12.54 | NM_008827 | Pgf |
| 1442865_at | 12.50 | BB361845 | MGI: 3580254 |
| 1435813_at | 12.44 | BM212838 | Mypn |
| 1438948_x_at | 12.43 | AV101079 | Bzrp |
| 1429007_at | 12.43 | AK003377 | Slc35b2 |
| 1455931_at | 12.42 | BB460687 | Chrna3 |
| 1453591_at | 12.38 | AK017626 | 5730437N04Rik |
| 1457008_at | 12.36 | AW456706 | Chrnb4 |
| 1434493_at | 12.35 | BG092222 | 1810022K09Rik |
| 1449429_at | 12.31 | NM_016863 | Fkbp1b |
| 1429732_at | 12.24 | AK016334 | Ppp1r1c |
| 1437914_at | 12.20 | BB104097 | E2f6 |
| 1423426_at | 12.19 | BB018522 | 1300012G16Rik |
| 1450885_at | 12.12 | BB446076 | Dffa |
| 1415978_at | 12.09 | NM_023279 | Tubb3 |
| 1423136_at | 12.04 | AI649186 | Fgf1 |
| 1427854_x_at | 12.02 | AF047377 | Hspb1 |
| 1456468_x_at | 12.00 | BB189996 | 1110012N22Rik |
| 1416656_at | 11.95 | NM_033444 | Clic1 |
| 1428751_at | 11.95 | AK005771 | Pacrg |
| 1448669_at | 11.94 | AK004853 | Dkk3 |
| 1418571_at | 11.94 | NM_013749 | Tnfrsf12a |
| 1424487_x_at | 11.93 | BB284199 | Txnrd1 |
| 1426606_at | 11.88 | BB426194 | Crtac1 |
| 1429953_at | 11.85 | AK008705 | 2210011C24Rik |
| 1429934_at | 11.81 | AK015678 | 4930502E18Rik |
| 1416431_at | 11.67 | NM_026473 | Tubb6 |
| 1438763_at | 11.64 | BB016771 | |
| 1448660_at | 11.58 | NM_008113 | Arhgdig |
| 1418780_at | 11.52 | NM_018887 | Cyp39a1 |
| 1441957_x_at | 11.51 | AV216663 | 2410076I21Rik |
| 1452508_x_at | 11.50 | BC021465 | A230083G16Rik |
| 1442180_at | 11.49 | BB382040 | Dleu7 |
| 1443684_at | 11.48 | BE956557 | |
| 1418649_at | 11.39 | BB284358 | Egln3 |
| 1453755_at | 11.38 | BM951302 | Lsm11 |
| 1426221_at | 11.37 | BC004727 | Loh11cr2a |
| 1442631_at | 11.34 | BM935306 | |
| 1451322_at | 11.27 | BC024580 | 2310016A09Rik |
| 1436238_at | 11.23 | AI841179 | Lgi3 |
| 1434341_x_at | 11.20 | BF681728 | 1110020P15Rik |
| 1429231_at | 11.18 | AK015078 | |
| 1451956_a_at | 11.15 | AF226605 | Oprs1 |
| 1450230_at | 11.10 | NM_138582 | D17H6S56E-3 |
| 1456251_x_at | 11.08 | BB132602 | Bzrp |

TABLE 19-continued

Top 1,000 brain stem cholinergic motor neuron (Chat) translated mRNAs enriched when compared to a reference sample

| ProbeSymbol | FEN | Genbank | GeneSymbol |
|---|---|---|---|
| 1417943_at | 11.06 | NM_010317 | Gng4 |
| 1451413_at | 11.03 | AB026997 | Cast |
| 1427004_at | 10.98 | BB311718 | Fbxo2 |
| 1418268_at | 10.98 | NM_013561 | Htr3a |
| 1456642_x_at | 10.94 | AV295650 | S100a10 |
| 1421483_at | 10.91 | NM_010712 | Lhx4 |
| 1430539_at | 10.91 | BB469133 | 1810057P16Rik |
| 1443505_at | 10.87 | BE651535 | A630076J17Rik |
| 1437139_at | 10.84 | AV344554 | Glra1 |
| 1425341_at | 10.81 | BF467278 | Kcnk3 |
| 1426255_at | 10.77 | M20480 | Nefl |
| 1425326_at | 10.70 | BI456232 | Acly |
| 1454891_at | 10.69 | BM214378 | Cds2 |
| 1427375_at | 10.68 | BB198308 | Rg9mtd2 |
| 1426926_at | 10.66 | AW546508 | Plcg2 |
| 1420559_a_at | 10.64 | NM_013665 | Shox2 |
| 1422185_a_at | 10.62 | NM_029787 | Cyb5r3 |
| 1436528_at | 10.60 | AI842353 | Kazald1 |
| 1417389_at | 10.56 | NM_016696 | Gpc1 |
| 1445475_at | 10.56 | BB003750 | Pak6 |
| 1445124_at | 10.54 | BB193580 | A930009L07Rik |
| 1418916_a_at | 10.54 | NM_029269 | Spp2 |
| 1448883_at | 10.53 | NM_011175 | Lgmn |
| 1452806_at | 10.51 | AK005271 | 1500016O10Rik |
| 1427539_a_at | 10.50 | BC013559 | Zwint |
| 1455162_at | 10.50 | BI147002 | 4922503N01Rik |
| 1434976_x_at | 10.49 | AV216412 | Eif4ebp1 |
| 1424847_at | 10.46 | M35131 | Nefh |
| 1450389_s_at | 10.45 | NM_008846 | Pip5k1a |
| 1456524_at | 10.44 | AV318914 | Nrg1 |
| 1421391_at | 10.44 | NM_009511 | Vipr2 |
| 1449397_at | 10.43 | NM_134032 | Hoxb2 |
| 1417988_at | 10.42 | NM_009049 | Resp18 |
| 1457281_at | 10.41 | BB224547 | 4930461P20Rik |
| 1451680_at | 10.36 | BC011325 | Srxn1 |
| 1417473_a_at | 10.35 | NM_026494 | Ppcs |
| 1456187_at | 10.33 | BB278836 | Slc7a14 |
| 1436035_at | 10.31 | AV225683 | 3830431G21Rik |
| 1424048_a_at | 10.31 | BC024618 | Cyb5r1 |
| 1421781_at | 10.29 | NM_009476 | Upk2 |
| 1416695_at | 10.28 | BC002055 | Bzrp |
| 1416750_at | 10.27 | NM_011014 | Oprs1 |
| 1429348_at | 10.27 | AK004119 | Sema3c |
| 1448781_at | 10.23 | NM_008667 | Nab1 |
| 1418403_at | 10.22 | NM_009616 | Adam19 |
| 1441280_at | 10.19 | BF322939 | Kcnk12 |
| 1431597_a_at | 10.16 | AK020731 | Nrip3 |
| 1425963_at | 10.16 | AF419324 | Cabp7 |
| 1416111_at | 10.16 | NM_009856 | Cd83 |
| 1427940_s_at | 10.13 | BB046347 | Mycbp |
| 1451345_at | 10.12 | BG075139 | Mtap |
| 1452449_at | 10.10 | AI006067 | F830020C16Rik |
| 1456747_x_at | 10.05 | BB334959 | Cd99l2 |
| 1435815_at | 10.03 | AW541598 | Ldoc1 |
| 1427951_s_at | 10.02 | BG141739 | Ccdc28a |
| 1432224_at | 10.02 | AK019510 | 4831407H17Rik |
| 1432211_a_at | 9.97 | AK018482 | Fbxo9 |
| 1455736_at | 9.97 | AI326984 | Mybpc2 |
| 1436295_at | 9.95 | BB803143 | Hcrtr1 |
| 1449079_s_at | 9.90 | NM_018784 | St3gal6 |
| 1434055_at | 9.83 | BB048942 | Galnt9 |
| 1455947_at | 9.83 | BB667208 | 9630025C22 |
| 1423966_at | 9.78 | BB038546 | Cd99l2 |
| 1419100_at | 9.78 | NM_009252 | Serpina3n |
| 1416871_at | 9.77 | NM_007403 | Adam8 |
| 1456229_at | 9.70 | BG073383 | Hoxb3 |
| 1426595_at | 9.69 | BB011871 | Slc18a1 |
| 1421195_at | 9.69 | BC020534 | Cckar |
| 1430521_s_at | 9.65 | AW548480 | Cpne8 |
| 1430114_at | 9.62 | AK017323 | 5430420C16Rik |
| 1457429_s_at | 9.61 | BB549174 | Gm106 |
| 1459665_s_at | 9.57 | BB800078 | Mrvi1 |
| 1418713_at | 9.57 | NM_025273 | Pcbd1 |
| 1426444_at | 9.49 | BB233055 | Rhbdl7 |
| AFFX-r2-Bs- | 9.47 | | AFFX-r2-Bs- |
| thr-M_s_at | 9.47 | | thr-M |
| 1422481_at | 9.47 | NM_008473 | Krt2-1 |
| 1424976_at | 9.43 | BC021307 | Rhov |
| 1450001_a_at | 9.40 | NM_023649 | Ush1c |
| 1460378_a_at | 9.40 | BC010465 | Tes |
| 1441481_at | 9.39 | AV262974 | Mfap31 |
| 1428190_at | 9.37 | AK005070 | Slc25a1 |
| 1457696_at | 9.36 | AI835553 | Rilp |
| 1439186_at | 9.34 | BB022463 | E130319B15Rik |
| 1429775_a_at | 9.33 | AK009736 | Tm7sf1 |
| 1424580_at | 9.33 | AW822833 | Slc35a3 |
| 1447263_at | 9.32 | BB138441 | A730089K16Rik |
| 1459888_at | 9.31 | AI429562 | LOC545261 |
| 1460351_at | 9.24 | BC021916 | S100a11 |
| 1453341_a_at | 9.22 | AK008510 | 4930425N13Rik |
| 1425050_at | 9.20 | AK010892 | Isoc1 |
| 1419455_at | 9.18 | NM_008349 | Il10rb |
| 1423720_a_at | 9.18 | BC005549 | Sara1 |
| 1450444_a_at | 9.16 | NM_013839 | Nr1h3 |
| 1434092_at | 9.14 | AW121498 | Nos3as |
| 1437670_x_at | 9.13 | BB113673 | Cd151 |
| 1452936_at | 9.08 | AV341285 | Crtac1 |
| 1417133_at | 9.06 | NM_008885 | Pmp22 |
| 1423425_at | 9.03 | BB018522 | 1300012G16Rik |
| 1447773_x_at | 9.02 | BB308792 | 6330409D20Rik |
| 1449426_a_at | 8.98 | NM_011922 | Anxa10 |
| 1429684_at | 8.97 | BG094398 | 5830472M02Rik |
| 1423561_at | 8.94 | AI838010 | Nell2 |
| 1418710_at | 8.94 | NM_007652 | Cd59a |
| 1460174_at | 8.92 | NM_021428 | Dexi |
| 1449848_at | 8.91 | NM_008137 | Gna14 |
| 1460191_at | 8.91 | NM_019661 | 0610042I15Rik |
| 1439006_x_at | 8.89 | BB093996 | 6430550H21Rik |
| 1449619_s_at | 8.88 | AU043488 | Arhgap9 |
| 1416592_at | 8.88 | AF276917 | Glrx1 |
| 1451099_at | 8.86 | BC011482 | Mbc2 |
| 1420664_s_at | 8.85 | NM_011171 | Procr |
| 1460242_at | 8.85 | NM_010016 | Daf1 |
| 1416168_at | 8.83 | NM_011340 | Serpinf1 |
| 1460379_at | 8.82 | AV307188 | Hoxb4 |
| 1415919_at | 8.82 | NM_008721 | Npdc1 |
| 1446729_at | 8.81 | BB179083 | Disp2 |
| 1448722_s_at | 8.81 | NM_026494 | Ppcs |
| 1434528_at | 8.79 | AV256613 | Aard |
| 1431160_x_at | 8.78 | AW543121 | 6030426L16Rik |
| 1418345_at | 8.77 | NM_023517 | "Tnfsf13; Tnfsf12-tnfsf13" |
| 1421834_at | 8.76 | NM_008846 | Pip5k1a |
| 1425052_at | 8.74 | AK010892 | 2610034N03Rik |
| 1430577_at | 8.68 | BE686390 | 2410007P03Rik |
| 1441363_at | 8.67 | BQ174855 | LOC546381 |
| 1416435_at | 8.66 | NM_010736 | Ltbr |
| 1416148_at | 8.66 | BC019120 | Laptm4b |
| 1451210_at | 8.65 | BC010332 | Ppap2c |
| 1449928_at | 8.65 | NM_025975 | Tcte11 |
| 1422520_at | 8.64 | NM_008691 | Nef3 |
| 1436948_a_at | 8.62 | BB520013 | 6430550H21Rik |
| 1434046_at | 8.58 | BG961961 | AA467197 |
| 1435972_at | 8.57 | BB148748 | Cast |
| 1460702_at | 8.56 | AK007514 | 1810015M01Rik |
| 1456085_x_at | 8.55 | AV169215 | Cd151 |
| 1427340_at | 8.50 | BB274058 | Rgs6 |
| 1420566_at | 8.46 | NM_025367 | |
| 1429246_a_at | 8.45 | AK013026 | Anxa6 |
| 1426319_at | 8.44 | AF335583 | Pdgfd |
| 1438055_at | 8.43 | BB035017 | Rarres1 |
| 1439807_at | 8.43 | BB816169 | Tmem74 |
| 1453067_at | 8.43 | AU043467 | 2610040C18Rik |
| 1424129_at | 8.41 | BC024891 | Mfsd1 |
| 1425828_at | 8.40 | AF357883 | Nkx6-1 |
| 1448429_at | 8.38 | NM_013755 | Gyg1 |
| 1456778_at | 8.34 | BB409477 | Nrp2 |
| 1430648_at | 8.32 | AK013326 | Scn2b |

TABLE 19-continued

Top 1,000 brain stem cholinergic motor neuron (Chat) translated mRNAs enriched when compared to a reference sample

| ProbeSymbol | FEN | Genbank | GeneSymbol |
|---|---|---|---|
| AFFX-ThrX-M_at | 8.31 | AFFX-ThrX-M | |
| 1452399_at | 8.29 | BB274058 | Rgs6 |
| 1458932_at | 8.24 | BB639093 | Pex2 |
| 1446838_at | 8.20 | BB292625 | Atad1 |
| 1460377_a_at | 8.18 | BC005722 | Tmem8 |
| 1423345_at | 8.18 | AV286991 | Degs1 |
| 1448693_at | 8.17 | NM_024472 | BC002216 |
| 1430999_a_at | 8.15 | BM932452 | Scoc |
| 1430778_a_at | 8.15 | AK020876 | Nubp1 |
| AFFX-LysX-3_at | 8.14 | AFFX-LysX-3 | |
| 1435134_at | 8.12 | AV369935 | Aadacl1 |
| 1451666_at | 8.12 | BI456232 | Acly |
| 1449961_at | 8.10 | NM_011286 | Rph3a |
| 1436509_at | 8.09 | BB000110 | 2410014A08Rik |
| 1438717_a_at | 8.07 | BG070848 | Osbpl6 |
| 1432319_at | 8.07 | AK007004 | 1700085C21Rik |
| 1427708_a_at | 8.06 | L22989 | Nf2 |
| 1453523_at | 8.03 | AK020698 | A030006P16Rik |
| 1428400_at | 8.03 | BB066985 | 2200002K05Rik |
| 1429204_at | 8.03 | AK013788 | 2900075A18Rik |
| 1429203_at | 7.99 | AK010725 | 2410076I21Rik |
| 1460239_at | 7.97 | BB807707 | Tspan13 |
| 1453232_at | 7.97 | AK006582 | Calr3 |
| 1442600_at | 7.97 | BB456595 | |
| 1437107_at | 7.95 | AV220161 | Rab6b |
| 1429266_at | 7.95 | AK020670 | Tmhs |
| 1452362_at | 7.94 | BB834440 | Trim16 |
| 1419473_a_at | 7.94 | NM_031161 | Cck |
| 1444204_at | 7.93 | BE687976 | Hoxb2 |
| 1429087_at | 7.91 | AK005245 | 1110054O05Rik |
| 1424050_s_at | 7.91 | M33760 | Fgfr1 |
| 1424518_at | 7.90 | BC020489 | "2310016F22Rik; LOC223672" |
| 1415818_at | 7.88 | NM_013472 | Anxa6 |
| 1437040_at | 7.85 | AV280878 | Etnk2 |
| 1418107_at | 7.84 | NM_009326 | Tcea2 |
| 1437648_at | 7.84 | BB541022 | Pcyt1b |
| 1433600_at | 7.83 | BB262415 | |
| 1426542_at | 7.82 | BF168366 | 2310067E08Rik |
| 1441049_at | 7.81 | AV328356 | Kcna6 |
| 1418686_at | 7.80 | NM_033541 | Oas1c |
| 1449921_s_at | 7.80 | NM_009947 | Cpne6 |
| 1440531_at | 7.80 | BB333100 | Rbm11 |
| 1416221_at | 7.80 | BI452727 | Fstl1 |
| 1421606_a_at | 7.79 | NM_013873 | Sult4a1 |
| 1418572_x_at | 7.79 | NM_013749 | Tnfrsf12a |
| 1452450_at | 7.79 | BG277213 | Atp8b2 |
| 1439959_at | 7.77 | AW488620 | Fgf11 |
| 1431105_a_at | 7.77 | AK012413 | Tmem33 |
| 1445424_at | 7.76 | BB082380 | |
| 1415856_at | 7.75 | BG064842 | Emb |
| 1427182_s_at | 7.73 | BQ032363 | D18Ertd653e |
| 1441902_x_at | 7.73 | BB264298 | |
| 1441284_at | 7.72 | BB283819 | |
| 1451707_s_at | 7.72 | BC011108 | Slc41a3 |
| 1439603_at | 7.72 | AW125555 | |
| 1443198_at | 7.68 | BB107751 | |
| 1434494_at | 7.68 | BG071693 | Zar1 |
| 1426672_at | 7.64 | BB327301 | Tmem16k |
| 1420654_at | 7.64 | NM_028803 | Gbe1 |
| 1448260_at | 7.64 | NM_011670 | Uchl1 |
| "AFFX-r2-Bs-phe-5_at" | 7.63 | AFFX-r2-Bs-phe-5 | |
| 1417038_at | 7.63 | NM_017380 | |
| 1434665_at | 7.63 | AV052058 | Aga |
| 1417430_at | 7.62 | NM_007672 | Cdr2 |
| 1441551_at | 7.60 | BB196537 | Mypn |
| 1420731_a_at | 7.60 | NM_007792 | Csrp2 |
| 1423087_a_at | 7.60 | BB453951 | 1110002E23Rik |
| 1430780_a_at | 7.60 | BI739353 | Pmm1 |
| 1431086_s_at | 7.60 | AA389937 | Pcmt1 |
| 1417780_at | 7.59 | BB006809 | Lass4 |
| 1455783_at | 7.58 | AV361804 | |
| 1426622_a_at | 7.57 | BB150720 | Qpct |
| "AFFX-r2-Bs-dap-5_at" | 7.56 | AFFX-r2-Bs-dap-5 | |
| 1443745_s_at | 7.55 | AV020965 | Dmp1 |
| 1449139_at | 7.54 | NM_025509 | 2310008M10Rik |
| 1430514_a_at | 7.52 | AK002762 | 2410026K10Rik |
| 1440071_at | 7.52 | BB367260 | Baiap1 |
| 1418173_at | 7.50 | NM_133730 | 4631426H08Rik |
| 1437217_at | 7.50 | BM225135 | Ankrd6 |
| 1425573_at | 7.48 | BE943736 | Ddef1 |
| 1449491_at | 7.47 | NM_130859 | Card10 |
| 1421321_a_at | 7.47 | NM_019671 | Net1 |
| 1451828_a_at | 7.47 | AB033886 | Acsl4 |
| 1420693_at | 7.47 | NM_010867 | Myom1 |
| 1440413_at | 7.46 | BB800596 | A830006F12Rik |
| 1449189_at | 7.45 | NM_030252 | BC003266 |
| 1418175_at | 7.44 | AV290079 | Vdr |
| 1417507_at | 7.43 | BC006732 | Cyb561 |
| 1417969_at | 7.42 | NM_133765 | Fbxo31 |
| 1425329_a_at | 7.42 | AF332060 | Cyb5r3 |
| 1450731_s_at | 7.39 | BG972377 | Tnfrsf21 |
| 1416046_a_at | 7.39 | BM054266 | Fuca2 |
| 1422583_at | 7.37 | NM_023537 | Rab3b |
| 1417902_at | 7.37 | NM_054087 | Slc19a2 |
| 1426543_x_at | 7.36 | BF168366 | 2310067E08Rik |
| 1449983_a_at | 7.35 | NM_020282 | Nqo2 |
| 1424560_at | 7.35 | U87814 | Pstpip1 |
| 1431255_at | 7.34 | AI324734 | Calr3 |
| 1417539_at | 7.34 | NM_011895 | Slc35a1 |
| 1424882_a_at | 7.34 | BC011230 | 2510015F01Rik |
| 1418206_at | 7.34 | NM_022324 | Sdf2l1 |
| 1436339_at | 7.32 | BE627374 | 1810058I24Rik |
| 1418248_at | 7.27 | NM_013463 | Gla |
| 1449012_s_at | 7.25 | BC027164 | Fndc4 |
| 1455523_s_at | 7.25 | BB779140 | 2700089E24Rik |
| 1431946_a_at | 7.24 | AK013520 | Apba2bp |
| 1435575_at | 7.21 | AW536884 | Kntc1 |
| 1427919_at | 7.19 | BC028307 | Srpx2 |
| 1419728_at | 7.18 | NM_009141 | Cxcl5 |
| 1418129_at | 7.18 | BG295389 | Dhcr24 |
| 1455025_at | 7.14 | AV103696 | Paqr9 |
| 1450500_at | 7.13 | AW012751 | Uhmk1 |
| 1418478_at | 7.13 | NM_057173 | Lmo1 |
| 1434256_s_at | 7.13 | BM214378 | Cds2 |
| 1448549_a_at | 7.12 | NM_007875 | Dpagt1 |
| 1455775_at | 7.12 | AW988196 | |
| 1429712_at | 7.12 | AK005093 | Etohi1 |
| 1445564_at | 7.11 | BE688513 | |
| 1421127_at | 7.10 | NM_025339 | Tmem42 |
| 1430631_at | 7.10 | AK016942 | Ppm1f |
| 1416914_s_at | 7.10 | NM_023166 | Mtvr2 |
| 1429300_at | 7.09 | AK010867 | Ankrd9 |
| 1425440_x_at | 7.09 | BC011108 | Slc41a3 |
| 1422158_at | 7.08 | NM_022319 | Clstn2 |
| 1418371_at | 7.07 | AY029255 | 6720463E02Rik |
| 1454893_at | 7.06 | BB765852 | 1110013L07Rik |
| 1418187_at | 7.04 | AF146523 | Ramp2 |
| 1417807_at | 7.04 | NM_027356 | 2700038N03Rik |
| 1424486_a_at | 7.03 | BB284199 | Txnrd1 |
| 1424109_a_at | 7.02 | BC024663 | Glo1 |
| 1452807_s_at | 7.02 | AK005271 | 1500016O10Rik |
| 1433787_at | 7.01 | AI841091 | B230343H07Rik |
| 1433793_s_at | 7.01 | AW491344 | Nrip2 |
| 1445437_at | 7.00 | BE948587 | 2310015A05Rik |
| 1456857_at | 6.99 | BB782615 | |
| 1451427_a_at | 6.99 | BC024610 | Egfl7 |
| 1418890_a_at | 6.98 | BB349707 | Rab3d |
| 1440248_at | 6.97 | BB238478 | Casc4 |
| 1460466_at | 6.97 | BB824055 | 1700047I17Rik |
| 1439407_x_at | 6.96 | AV212626 | Tagln2 |
| 1448944_at | 6.96 | AK011144 | Nrp1 |
| 1424178_at | 6.94 | BC014728 | Tmem38a |
| 1454604_s_at | 6.93 | BB072896 | Tspan12 |

TABLE 19-continued

Top 1,000 brain stem cholinergic motor neuron (Chat) translated mRNAs enriched when compared to a reference sample

| ProbeSymbol | FEN | Genbank | GeneSymbol |
|---|---|---|---|
| 1420386_at | 6.93 | NM_028112 | Seh1l |
| 1455622_at | 6.89 | BB461988 | Podxl2 |
| 1418752_at | 6.89 | NM_007436 | Aldh3a1 |
| 1443812_x_at | 6.89 | BB319311 | Prkg1 |
| "AFFX-DapX-5_at" | 6.88 | AFFX-DapX-5 | |
| 1443746_x_at | 6.86 | AV020965 | Dmp1 |
| 1418084_at | 6.85 | AK011144 | Nrp1 |
| 1443664_s_at | 6.85 | AW123724 | Cd164l2 |
| 1451386_at | 6.84 | BC027279 | Blvrb |
| 1429783_at | 6.83 | AK009464 | Pdlim5 |
| 1452545_a_at | 6.80 | U37029 | Itgb1 |
| 1450440_at | 6.79 | BE534815 | Gfra1 |
| 1460409_at | 6.79 | AI987925 | Cpt1a |
| 1418474_at | 6.79 | NM_033146 | 1500005A01Rik |
| 1430726_at | 6.78 | AV331288 | Rassf8 |
| 1438623_x_at | 6.78 | AV038578 | Rbx1 |
| 1433796_at | 6.77 | BI734389 | 2310067E08Rik |
| 1455085_at | 6.76 | BI526033 | 1700086L19Rik |
| 1427548_a_at | 6.75 | U53455 | Clns1a |
| 1442015_at | 6.75 | BG070940 | |
| 1422854_at | 6.74 | BB753533 | Shc1 |
| 1416593_at | 6.72 | AF276917 | Glrx1 |
| 1436902_x_at | 6.70 | BB096368 | Tmsb10 |
| 1459717_at | 6.70 | AW045505 | |
| 1436861_at | 6.68 | BG069762 | Il7 |
| 1418451_at | 6.68 | BB522409 | Gng2 |
| 1427196_at | 6.68 | BG074348 | Wnk4 |
| 1450138_a_at | 6.67 | NM_009254 | Serpinb6a |
| 1448772_at | 6.65 | BG868960 | Ube2a |
| 1418452_at | 6.65 | BB522409 | Gng2 |
| 1444178_at | 6.64 | BB609792 | LOC433237 |
| 1455427_at | 6.64 | AV269710 | Angpt4 |
| 1423954_at | 6.64 | K02782 | C3 |
| 1423280_at | 6.64 | BM115022 | Stmn2 |
| 1460375_at | 6.62 | BC019418 | 0610038D11Rik |
| 1419398_a_at | 6.61 | NM_007874 | Dp1 |
| 1419383_at | 6.61 | NM_009115 | |
| 1454227_at | 6.61 | AK015389 | Htatip2 |
| 1438007_at | 6.60 | BB432758 | AI851790 |
| 1419518_at | 6.59 | NM_017379 | Tuba8 |
| 1431446_at | 6.57 | AK002366 | 0610009B14Rik |
| 1428139_at | 6.56 | AK015988 | 4930538D17Rik |
| 1436150_at | 6.54 | BB391675 | 2310028H24Rik |
| 1450486_a_at | 6.54 | X91813 | Oprl1 |
| 1416673_at | 6.53 | NM_019517 | Bace2 |
| 1419550_a_at | 6.52 | BG919998 | Stk39 |
| 1437043_a_at | 6.52 | AV012400 | 1110012M11Rik |
| 1450787_at | 6.48 | NM_016691 | Clcn5 |
| 1420772_a_at | 6.47 | NM_010286 | Tsc22d3 |
| "AFFX-PheX-M_at" | 6.46 | AFFX-PheX-M | |
| 1441281_s_at | 6.45 | AU024536 | Ninj1 |
| 1446218_at | 6.42 | BB306329 | Ppfia2 |
| 1449433_at | 6.42 | NM_033321 | P2rx5 |
| 1422597_at | 6.41 | NM_008609 | Mmp15 |
| 1417290_at | 6.41 | NM_029796 | Lrg1 |
| 1444291_at | 6.41 | BB184872 | 4930506D23Rik |
| 1441456_at | 6.40 | BB335489 | Mmp24 |
| 1448300_at | 6.40 | NM_025569 | Mgst3 |
| 1452825_at | 6.40 | AK005155 | 5330410G16Rik |
| 1427956_at | 6.40 | BG068910 | Pcgf1 |
| 1417399_at | 6.38 | NM_019521 | Gas6 |
| 1438635_x_at | 6.38 | BB258476 | B930041F14Rik |
| 1449460_at | 6.38 | AF403041 | Asb13 |
| 1426858_at | 6.37 | BB253137 | Inhbb |
| 1428495_at | 6.35 | BF300229 | 2410003K15Rik |
| 1423951_at | 6.35 | BC024620 | Tm2d3 |
| 1415993_at | 6.35 | NM_009270 | Sqle |
| 1451426_at | 6.34 | AF316999 | D11Lgp2e |
| 1417022_at | 6.34 | NM_007515 | Slc7a3 |
| 1422620_s_at | 6.33 | NM_008903 | Ppap2a |
| 1423840_at | 6.33 | BC026206 | D11Ertd99e |
| 1429840_at | 6.33 | AW491495 | 4933439G12Rik |
| 1424356_a_at | 6.32 | BC024445 | Metrnl |
| 1452244_at | 6.31 | AK018128 | 6330406I15Rik |
| 1442011_at | 6.31 | BB177150 | A230065H16Rik |
| 1416710_at | 6.30 | NM_026239 | Tmem35 |
| 1416410_at | 6.30 | NM_008776 | Pafah1b3 |
| 1437501_at | 6.30 | BB125794 | AF529169 |
| 1431359_a_at | 6.29 | AK003526 | 1110007C09Rik |
| 1450738_at | 6.29 | NM_016705 | Kif21a |
| 1433462_a_at | 6.29 | BB208212 | Pi4k2a |
| 1454811_at | 6.28 | AV026664 | Tde2 |
| 1424426_at | 6.28 | BG075139 | Mtap |
| 1444687_at | 6.27 | BB804635 | C1ql2 |
| 1458438_at | 6.27 | AW554226 | 4933415L06Rik |
| 1426376_at | 6.25 | BI249075 | Dp1 |
| 1430520_at | 6.25 | AW548480 | Cpne8 |
| 1427202_at | 6.24 | AV002340 | 4833442J19Rik |
| 1416979_at | 6.24 | NM_025624 | 2510048O06Rik |
| 1433835_at | 6.23 | BE825122 | Ppp3cb |
| 1431226_a_at | 6.21 | AK013203 | Fndc4 |
| 1458413_at | 6.20 | BB357976 | Fbxw8 |
| 1418359_at | 6.20 | NM_024479 | Wbscr27 |
| 1452608_at | 6.20 | BB046347 | Mycbp |
| 1422637_at | 6.20 | NM_018750 | Rassf5 |
| 1432271_a_at | 6.19 | AK012764 | Dcun1d5 |
| "AFFX-r2-Bs-phe-M_at" | 6.16 | AFFX-r2-Bs-phe-M | |
| 1417458_s_at | 6.16 | NM_025415 | Cks2 |
| 1417026_at | 6.15 | BC024693 | Pfdn1 |
| 1417979_at | 6.15 | AF291655 | Tnmd |
| 1417203_at | 6.15 | BC010592 | Ethe1 |
| 1423101_at | 6.14 | BB279185 | Paqr4 |
| 1430098_at | 6.14 | AK018150 | 6330409D20Rik |
| 1429273_at | 6.11 | AK014221 | Bmper |
| 1418104_at | 6.09 | NM_020610 | Nrip3 |
| 1421034_a_at | 6.09 | NM_010557 | Il4ra |
| 1431241_at | 6.08 | AA692147 | Chchd3 |
| 1429522_at | 6.07 | BB796723 | Ankrd42 |
| 1429753_at | 6.07 | AK004130 | Nxph4 |
| 1427773_a_at | 6.07 | L40934 | Rabac1 |
| 1440308_at | 6.06 | AV347071 | 0610011D08Rik |
| 1424732_s_at | 6.06 | BC020157 | 3110005G23Rik |
| 1455197_at | 6.05 | BE852181 | Rnd1 |
| 1431684_at | 6.05 | AK016622 | 4933402J24Rik |
| 1424773_at | 6.03 | BC020119 | 1110012M11Rik |
| 1417040_a_at | 6.03 | NM_016778 | Bok |
| 1418934_at | 6.02 | NM_011839 | Mab21l2 |
| 1425053_at | 6.02 | AK010892 | Isoc1 |
| 1423321_at | 6.01 | BI078799 | Myadm |
| 1429756_at | 6.01 | AK016481 | 4931428F04Rik |
| "AFFX-r2-Bs-lys-M_at" | 6.01 | AFFX-r2-Bs-lys-M | |
| 1451428_x_at | 6.00 | BC024610 | Egfl7 |
| 1460059_at | 6.00 | BB272732 | Upp2 |
| 1420712_a_at | 6.00 | NM_008281 | Hpn |
| 1436408_at | 5.99 | BE946298 | |
| 1422645_at | 5.98 | AJ306425 | Hfe |
| 1423948_at | 5.98 | BC016230 | Bag2 |
| 1429830_a_at | 5.97 | AK005507 | Cd59a |
| 1435332_at | 5.96 | BQ175864 | Htr7 |
| 1421015_s_at | 5.96 | NM_021498 | Pole3 |
| "AFFX-LysX-M_at" | 5.94 | AFFX-LysX-M | |
| 1451501_a_at | 5.94 | BC024375 | Ghr |
| 1454219_at | 5.94 | AK013295 | Dnajc2 |
| 1459669_at | 5.94 | AW913782 | D930010J01Rik |
| 1457076_at | 5.93 | BQ175967 | Gm693 |
| 1448477_at | 5.93 | NM_021528 | Chst12 |
| 1436127_at | 5.93 | AI854101 | Crhbp |
| 1428823_at | 5.93 | AK009957 | |
| 1449473_s_at | 5.91 | NM_011611 | Cd40 |
| 1436718_at | 5.91 | BB274960 | Nxph1 |
| "AFFX-PheX-3_at" | 5.91 | AFFX-PheX-3 | |
| 1450040_at | 5.90 | M93954 | Timp2 |

TABLE 19-continued

Top 1,000 brain stem cholinergic motor neuron (Chat) translated mRNAs enriched when compared to a reference sample

| ProbeSymbol | FEN | Genbank | GeneSymbol |
|---|---|---|---|
| 1436416_x_at | 5.88 | BB609429 | Fxc1 |
| 1458395_at | 5.84 | BB811756 | B930054O08 |
| 1426220_at | 5.84 | BC019457 | 4930471M23Rik |
| 1449347_a_at | 5.83 | NM_021365 | Xlr4b; Xlr4a |
| 1427246_at | 5.83 | BB702366 | Magi1 |
| 1448699_at | 5.82 | NM_025317 | Mrpl54 |
| 1448852_at | 5.82 | NM_009060 | Rgn |
| 1453605_s_at | 5.82 | AK007017 | 1810060J02Rik |
| 1449283_a_at | 5.82 | BC021640 | Mapk12 |
| 1437292_at | 5.81 | BB431052 | A330019N05Rik |
| 1432349_a_at | 5.81 | AK004279 | Sync |
| 1460150_at | 5.81 | BE979371 | Sh2d3c |
| 1438568_at | 5.81 | BB373312 | Mrgpre |
| 1417149_at | 5.80 | NM_011031 | P4ha2 |
| 1451683_x_at | 5.80 | M34962 | H2-D1 |
| 1455346_at | 5.80 | BB477214 | Masp1 |
| 1450661_x_at | 5.79 | NM_008688 | Nfic |
| 1444009_at | 5.78 | AV217868 | Rassf4 |
| 1437637_at | 5.77 | BE852433 | Phtf2 |
| 1458299_s_at | 5.76 | BB820441 | Nfkbie |
| 1454771_at | 5.76 | AW060701 | |
| 1454800_at | 5.76 | BF319573 | MGI: 2674071 |
| 1424767_at | 5.76 | AB019618 | Cdh22 |
| 1459552_at | 5.75 | BB404047 | |
| 1453607_at | 5.75 | AV280494 | Mfap31 |
| 1418344_at | 5.75 | NM_021793 | Tmem8 |
| 1423211_at | 5.75 | AK004120 | Nola3 |
| 1416994_at | 5.74 | NM_133795 | Ttc1 |
| 1428377_at | 5.74 | AK018115 | Btbd11 |
| 1419399_at | 5.73 | AW553649 | Mttp |
| 1416028_a_at | 5.73 | NM_008258 | Hn1 |
| 1427329_a_at | 5.73 | AI326478 | Igh-6 |
| 1424278_a_at | 5.72 | BC004702 | Birc5 |
| 1454613_at | 5.72 | AV162270 | 9430041P20Rik |
| 1438378_at | 5.72 | AV208934 | 1700013G23Rik |
| 1429743_at | 5.72 | BG068031 | 6720468P15Rik |
| 1451690_a_at | 5.71 | BC024948 | Pvrl4 |
| 1427937_at | 5.70 | BB410125 | "2610030H06Rik; LOC434793; LOC545620" |
| 1452579_at | 5.70 | AK009021 | Nifun |
| 1417457_at | 5.69 | NM_025415 | Cks2 |
| 1423552_at | 5.69 | BF658789 | Leprotl1 |
| 1416749_at | 5.69 | NM_019564 | Htra1 |
| 1455378_at | 5.68 | BI735497 | BC057371 |
| 1432287_a_at | 5.67 | AK016927 | Sntg1 |
| 1436869_at | 5.67 | AV304616 | Shh |
| 1423653_at | 5.67 | BC025618 | Atp1a1 |
| 1424842_a_at | 5.67 | BC025502 | Arhgap24 |
| 1436124_at | 5.66 | BE996519 | Pcyt1b |
| 1416230_at | 5.66 | NM_019437 | Rfk |
| 1457232_at | 5.66 | BE946365 | Fbxl21 |
| 1428988_at | 5.65 | AK006128 | Abcc3 |
| 1450010_at | 5.65 | AK012103 | Hsd17b12 |
| 1449078_at | 5.65 | NM_018784 | St3gal6 |
| 1453752_at | 5.65 | BF453369 | Rpl17 |
| 1455147_at | 5.64 | BB177828 | |
| 1427481_a_at | 5.64 | BC027114 | Atp1a3 |
| 1426918_at | 5.64 | BM120341 | Itgb1 |
| 1435551_at | 5.63 | BG066491 | FHOS2 |
| 1425351_at | 5.62 | BC011325 | Srxn1 |
| 1455812_x_at | 5.62 | BB530515 | Slitl2 |
| 1416781_at | 5.61 | NM_138602 | Praf2 |
| 1447975_a_at | 5.60 | AI429562 | LOC545261 |
| 1459927_at | 5.60 | AA867818 | 4833445I07Rik |
| 1449471_at | 5.60 | NM_021452 | Kcnmb4 |
| 1418888_a_at | 5.60 | NM_013759 | Sepx1 |
| 1456231_at | 5.59 | BB315153 | Pla2g3 |
| 1428357_at | 5.59 | AK011462 | 2610019F03Rik |
| 1419118_at | 5.57 | NM_021387 | 2900093B09Rik |
| 1428804_at | 5.57 | AK017269 | Mfap31 |
| 1429110_a_at | 5.56 | AW701004 | 2810405F18Rik |
| 1416022_at | 5.55 | BC002008 | Fabp5 |
| 1422965_at | 5.55 | NM_009642 | Agtrap |
| 1443811_at | 5.55 | BB319311 | Prkg1 |
| 1430332_a_at | 5.55 | AK002832 | Gusb |
| 1453281_at | 5.54 | BB700084 | Pik3cd |
| 1448987_at | 5.54 | BB728073 | Acadl |
| 1439221_s_at | 5.54 | BB220422 | Cd40 |
| 1435404_at | 5.54 | BB023743 | Disp2 |
| 1453461_at | 5.53 | AK002949 | Fxc1 |
| 1427373_at | 5.53 | BC010598 | Amigo1 |
| 1434049_at | 5.53 | BB547934 | Entpd3 |
| 1452717_at | 5.53 | BM230959 | Slc25a24 |
| 1428663_at | 5.53 | AK017223 | 5133401H06Rik |
| 1423158_at | 5.52 | AK008566 | Gnpnat1 |
| 1423686_a_at | 5.52 | BC016234 | 1110020C13Rik |
| 1437462_x_at | 5.52 | BB484002 | |
| 1424699_at | 5.51 | BC006583 | 4921511K06Rik |
| 1457124_at | 5.50 | AV328224 | |
| 1426298_at | 5.50 | AF295369 | Irx2 |
| 1420554_a_at | 5.49 | NM_133223 | Rac3 |
| 1433667_at | 5.48 | BB187947 | Lgi3 |
| 1430111_a_at | 5.48 | AK012821 | Bcat1 |
| 1416637_at | 5.46 | NM_009207 | Slc4a2 |
| 1452770_at | 5.46 | AK003237 | Vkorc1 |
| 1439152_at | 5.46 | BE985292 | BC052066 |
| 1437936_at | 5.45 | AI428240 | 6330534C20Rik |
| 1428379_at | 5.45 | BQ180367 | Slc17a6 |
| 1425780_a_at | 5.45 | BC024352 | 0610041E09Rik |
| 1416953_at | 5.45 | NM_010217 | Ctgf |
| 1448592_at | 5.45 | NM_019922 | Crtap |
| 1451817_at | 5.44 | BC011214 | Suv420h1 |
| 1418482_at | 5.44 | NM_019720 | Cyb561d2 |
| 1438388_at | 5.44 | BB078029 | |
| 1420113_s_at | 5.43 | AA409325 | 2410022L05Rik |
| 1420548_a_at | 5.43 | NM_023197 | 2310008H09Rik |
| 1423286_at | 5.41 | AA016422 | Cbln1 |
| 1455793_at | 5.41 | BB766438 | BC035537 |
| 1435244_at | 5.40 | BF535947 | Vav2 |
| 1453715_at | 5.39 | AK015921 | Sv2c |
| 1446260_at | 5.39 | BB282393 | Six6os1 |
| 1421863_at | 5.38 | AK018783 | Vamp1 |
| 1419740_at | 5.37 | NM_008806 | Pde6b |
| 1428734_at | 5.37 | AK018169 | 3200002M19Rik |
| 1427181_at | 5.37 | BQ032363 | D18Ertd653e |
| 1435109_at | 5.37 | AW123256 | "0710007G10Rik; 3010001K23Rik" |
| 1449267_at | 5.36 | BC006876 | 3110023E09Rik |
| 1437943_s_at | 5.36 | AA764430 | Mea1 |
| 1448140_at | 5.36 | NM_134141 | Ciapin1 |
| 1449021_at | 5.36 | NM_026308 | Rpp21 |
| 1429212_a_at | 5.36 | AK005758 | Lrrc51 |
| 1422717_at | 5.35 | AW554436 | Acp1 |
| 1456663_x_at | 5.35 | BB718785 | Tm2d2 |
| 1448472_at | 5.35 | AF087680 | Vars2 |
| 1438746_at | 5.35 | BB253959 | A530058N18Rik |
| 1425155_x_at | 5.35 | M21149 | Csf1 |
| 1417240_at | 5.34 | NM_011777 | Zyx |
| 1453558_at | 5.33 | AK015697 | 4930504H06Rik |
| 1422952_at | 5.32 | NM_023893 | MGI: 2388100 |
| 1437950_at | 5.32 | BB818275 | BC035537 |
| 1430219_at | 5.32 | AK017861 | Fts |
| 1420614_at | 5.31 | NM_025975 | Tcte1l |
| 1436978_at | 5.30 | AV273409 | Wnt9a |
| 1416366_at | 5.30 | NM_024220 | Ndufc2 |
| 1460030_at | 5.29 | BB355811 | Hecw1 |
| 1436433_at | 5.28 | AV264828 | BC049762 |
| 1440772_x_at | 5.28 | BB257157 | 9530077C05Rik |
| 1425784_a_at | 5.28 | D78264 | Olfm1 |
| 1451409_at | 5.27 | BC025858 | 2210021J22Rik |
| 1436800_at | 5.27 | AV376318 | Fstl5 |
| 1416940_at | 5.27 | NM_134084 | Ppif |
| 1451493_at | 5.27 | BC026372 | Ndfip1 |
| 1451395_at | 5.26 | BC021492 | D5Bwg0834e |
| 1426254_at | 5.26 | AF353993 | Tm2d1 |
| 1436517_at | 5.26 | BI416101 | H1fx |
| 1453304_s_at | 5.25 | BM245572 | Ly6e |
| 1423034_at | 5.25 | AK004219 | Txnl5 |
| 1432415_at | 5.25 | AK014050 | Rab3c |

TABLE 19-continued

Top 1,000 brain stem cholinergic motor neuron (Chat) translated mRNAs enriched when compared to a reference sample

| ProbeSymbol | FEN | Genbank | GeneSymbol |
|---|---|---|---|
| 1426621_a_at | 5.25 | BB560759 | Ppp2r2b |
| 1432591_at | 5.25 | BB635017 | Pappa |
| 1416245_at | 5.24 | NM_025338 | Aurkaip1 |
| 1434980_at | 5.24 | AV230647 | Pik3r5 |
| 1452923_at | 5.24 | AK007894 | 1810058I14Rik |
| 1419445_s_at | 5.23 | NM_009119 | Sap18 |
| 1430869_a_at | 5.23 | BF460630 | Habp4 |
| 1430866_at | 5.23 | BB432681 | 4921537D05Rik |
| 1442143_at | 5.22 | AI463477 | Tmem16d |
| 1417619_at | 5.22 | BE368753 | Gadd45gip1 |
| 1431694_a_at | 5.21 | AK003595 | Ctnnbip1 |
| 1417627_a_at | 5.21 | NM_010717 | Limk1 |
| 1435297_at | 5.21 | BI737842 | Gja9 |
| 1428753_a_at | 5.21 | AK019346 | Dgcr6 |
| 1452427_s_at | 5.19 | BM950003 | AW742319 |
| 1442542_at | 5.18 | BB363812 | Eya4 |
| 1425090_s_at | 5.16 | BC024837 | Kcnc4 |
| 1415857_at | 5.15 | BG064842 | Emb |
| 1430777_a_at | 5.14 | AK014644 | Golph3 |
| 1451128_s_at | 5.14 | BC003427 | Kif22 |
| 1431507_a_at | 5.14 | AK008254 | Synj2bp |
| 1431510_s_at | 5.12 | AK008567 | 2010110K16Rik |
| 1453358_s_at | 5.11 | BB238321 | "5830467E07Rik; C730024G19Rik" |
| 1426400_a_at | 5.11 | BI159030 | Capns1 |
| 1437249_at | 5.10 | BG075562 | Scap1 |
| 1419254_at | 5.09 | BG076333 | Mthfd2 |
| 1424528_at | 5.09 | BC023116 | Cgref1 |
| 1423608_at | 5.09 | BI966443 | Itm2a |
| 1422559_at | 5.09 | AY039837 | Ube2n |
| 1435017_at | 5.09 | AV000569 | Mel13 |
| 1418736_at | 5.08 | BC003835 | B3galt3 |
| 1436250_at | 5.08 | BM946369 | 5430455G05Rik |
| 1447683_x_at | 5.08 | AV118676 | Mettl1 |
| 1449850_at | 5.08 | NM_022723 | Scube1 |
| 1424403_a_at | 5.07 | AW494299 | D5Bwg0860e |
| 1432181_s_at | 5.07 | AK013765 | Ecgf1 |
| 1429602_at | 5.06 | AK009888 | Cd164l2 |
| 1450506_a_at | 5.06 | NM_026531 | Isg20l1 |
| 1450925_a_at | 5.06 | BB836796 | Rps27l |
| 1460483_at | 5.05 | AV115271 | 2610034E01Rik |
| 1430040_at | 5.05 | AK006867 | Hspa12a |
| 1460628_at | 5.05 | AV245208 | Nme3 |
| 1442466_a_at | 5.04 | BG071019 | B430315C20Rik |
| 1436377_at | 5.04 | BI410102 | AI428855 |
| 1429274_at | 5.04 | AK009282 | 2310010M24Rik |
| 1437055_x_at | 5.04 | BB143944 | 1200003O06Rik |
| 1417832_at | 5.03 | BB156359 | Smc1l1 |
| 1435130_at | 5.03 | AI131918 | LOC383103 |
| 1418746_at | 5.03 | NM_019999 | MGI: 1930773 |
| 1460674_at | 5.03 | BC022922 | Paqr7 |
| 1454006_a_at | 5.03 | AK016964 | Ubxd6 |
| 1429088_at | 5.03 | AK007400 | MGI: 1925139 |
| 1430889_a_at | 5.01 | AK002335 | Tpmt |
| 1430053_a_at | 5.00 | AK019142 | 2810409H07Rik |
| 1447728_x_at | 5.00 | BB718260 | Hspa9a |
| "AFFX-r2-Bs-phe-3_at" | 5.00 | | AFFX-r2-Bs-phe-3 |
| 1424579_at | 5.00 | AW822833 | Slc35a3 |
| 1449256_a_at | 4.99 | BC010722 | Rab11a |
| 1423423_at | 4.99 | BF319868 | Pdia3 |
| 1434549_at | 4.99 | BI083615 | Rab11a |
| 1449517_at | 4.99 | BB119571 | Qpctl |
| 1422034_a_at | 4.99 | NM_023128 | Palm |
| "AFFX-r2-Bs-lys-3_at" | 4.99 | | AFFX-r2-Bs-lys-3 |
| 1438251_x_at | 4.98 | BB559067 | Htra1 |
| 1454572_at | 4.98 | AK013093 | 2810414N06Rik |
| 1449107_at | 4.97 | NM_027722 | Nudt4 |
| 1416167_at | 4.97 | NM_016764 | Prdx4 |
| 1428650_at | 4.97 | AK003780 | Tns1 |
| 1458997_at | 4.97 | BB183491 | A230106M20Rik |
| 1426528_at | 4.97 | BQ176723 | Nrp2 |
| 1438957_x_at | 4.96 | BB027654 | Cds2 |
| 1436512_at | 4.96 | BI964400 | Arl7 |
| 1449083_at | 4.96 | AA067702 | 1810060J02Rik |
| 1436094_at | 4.95 | BF458396 | |
| 1457558_at | 4.95 | AV325555 | A330050F15Rik |
| 1417916_a_at | 4.95 | NM_019502 | Fxc1; 8030491N06Rik |
| 1430134_a_at | 4.94 | AK008774 | Yars2 |
| 1428447_at | 4.93 | AK017734 | Tmem14a |
| 1417219_s_at | 4.93 | NM_025284 | Tmsb10 |
| 1418281_at | 4.93 | NM_011234 | Rad51 |
| 1423035_s_at | 4.93 | AK004219 | Txnl5 |
| 1434362_at | 4.92 | BM249454 | AW550831 |
| 1435429_x_at | 4.92 | AV111399 | Rps27l |
| 1451931_x_at | 4.92 | M69068 | H2-D1 |
| 1457230_at | 4.92 | BB458901 | Gnpda2 |
| 1436105_at | 4.91 | BG068839 | 2310015A05Rik |
| 1420873_at | 4.91 | BI662615 | Ptk9 |
| 1451609_at | 4.91 | BC024685 | Tspan33 |
| 1424334_at | 4.90 | BC010334 | Tspan17 |
| 1423082_at | 4.90 | AW545361 | Derl1 |
| 1418795_at | 4.90 | BB487604 | Cds2 |
| 1427894_at | 4.90 | AK012169 | Slitl2 |
| 1451353_at | 4.89 | AV378394 | Tm6sf1 |
| 1438928_x_at | 4.88 | BB252065 | Ninj1 |
| 1448887_x_at | 4.88 | NM_019502 | Fxc1 |
| 1453317_a_at | 4.87 | AK014353 | Khdrbs3 |
| 1435755_at | 4.87 | BB609468 | 1110001A16Rik |
| 1418927_a_at | 4.87 | NM_019986 | Habp4 |
| 1425118_at | 4.87 | BC026502 | Spire2 |
| 1428605_at | 4.86 | AI227096 | 1810023B24Rik |
| 1429984_at | 4.86 | AK017666 | 5730455O13Rik |
| 1435750_at | 4.85 | BB610454 | Gchfr |
| 1417959_at | 4.85 | NM_026131 | Pdlim7 |
| 1415681_at | 4.85 | NM_053164 | Mrpl43 |
| 1429600_at | 4.85 | AK003824 | 1110019K23Rik |
| 1422379_at | 4.85 | BB020678 | MGC99845 |
| 1434342_at | 4.84 | BB316114 | |
| 1452272_a_at | 4.84 | BI901126 | Gfer |
| 1426416_a_at | 4.84 | AV216410 | Yipf4 |
| 1431611_a_at | 4.84 | AK013775 | Igsf4a |
| 1438210_at | 4.84 | BB126999 | Gpr149 |
| 1427921_s_at | 4.83 | AW045976 | 2310061C15Rik |
| 1444908_at | 4.83 | BM228113 | Habp4 |
| 1417103_at | 4.83 | NM_010027 | Ddt |
| 1428157_at | 4.83 | AV021455 | Gng2 |
| 1415910_s_at | 4.82 | NM_134141 | Ciapin1 |
| 1416379_at | 4.81 | NM_019482 | Panx1 |
| 1424441_at | 4.81 | BC023114 | Slc27a4 |
| 1449536_at | 4.80 | NM_032397 | Kcnn1 |
| 1457052_at | 4.80 | BG064867 | AW536275 |
| 1449448_at | 4.80 | BC019367 | Med9 |
| 1429213_at | 4.80 | AK009547 | 2310030N02Rik |
| 1438713_at | 4.79 | BB391868 | Rassf8 |
| 1450397_at | 4.79 | BB731480 | Mtap1b |
| 1459858_x_at | 4.79 | AV354465 | Crtac1 |
| 1456233_at | 4.78 | BB080923 | |
| 1435650_at | 4.78 | BB082407 | Hapln4 |
| 1418184_at | 4.78 | NM_025639 | 2610019I03Rik |
| 1436671_at | 4.77 | BB151200 | A030011M19 |
| 1420124_s_at | 4.77 | C85065 | Tcta |
| 1455825_s_at | 4.77 | BB131619 | Lnx1 |
| 1428699_at | 4.77 | AW744143 | Sms |
| 1419124_at | 4.77 | NM_133829 | 2210010L05Rik |
| 1437360_at | 4.76 | BB053591 | Pcdh19 |
| 1451643_a_at | 4.76 | BC007147 | Rab4b |
| 1434826_at | 4.76 | AW124912 | AI256775 |
| 1429520_a_at | 4.75 | BE573407 | Phca |
| 1436341_at | 4.75 | BM125569 | F830020C16Rik |
| 1426187_a_at | 4.75 | AF465243 | Hax1 |
| 1416849_at | 4.75 | NM_134007 | D10Ertd214e |
| 1440815_x_at | 4.74 | BB099075 | LOC545039 |
| 1416503_at | 4.74 | NM_016753 | Lxn |
| 1417593_at | 4.74 | NM_019742 | Tusc2 |
| 1439963_x_at | 4.73 | BB660640 | 1700129I04Rik |

TABLE 19-continued

Top 1,000 brain stem cholinergic motor neuron (Chat) translated mRNAs enriched when compared to a reference sample

| ProbeSymbol | FEN | Genbank | GeneSymbol |
|---|---|---|---|
| 1458396_at | 4.73 | BB452660 | Ssrp1 |
| 1429916_at | 4.73 | AK021129 | 9530077C05Rik |
| 1450868_at | 4.73 | BF468249 | D8Ertd354e |
| 1423170_at | 4.73 | AV213552 | Taf7 |
| 1427230_at | 4.73 | BB322737 | B930041F14Rik |
| 1448619_at | 4.73 | NM_007856 | Dhcr7 |
| 1417541_at | 4.73 | NM_008234 | Hells |
| 1430574_at | 4.72 | AK010426 | Cdkn3 |
| 1415947_at | 4.72 | BC027426 | Creg1 |
| 1426541_a_at | 4.71 | BF168366 | 2310067E08Rik |
| 1416965_at | 4.71 | AF181560 | Pcsk1n |
| 1418743_a_at | 4.71 | NM_021344 | MGI: 1930803 |
| 1419056_at | 4.71 | AF038538 | Rtn2 |
| 1460639_a_at | 4.71 | NM_009720 | Atox1 |
| 1424496_at | 4.71 | BC026742 | 5133401N09Rik |
| 1460711_at | 4.70 | BG071611 | 4930461P20Rik |
| 1452976_a_at | 4.70 | AK004710 | Slc9a3r2 |
| 1433950_at | 4.70 | BB769866 | Igsf21 |
| 1423759_a_at | 4.70 | BC020098 | Tmco1 |
| 1430274_a_at | 4.70 | AK018331 | Stard3nl |
| 1416696_at | 4.70 | NM_080837 | D17Wsu104e |
| 1427943_at | 4.70 | BI730288 | Acyp2 |
| 1424197_s_at | 4.69 | BC016538 | Fance |
| 1448950_at | 4.69 | NM_008362 | Il1rl |
| 1447541_s_at | 4.69 | AV210813 | Itgae |
| 1433635_at | 4.68 | BG073188 | Wdr18 |
| 1448700_at | 4.68 | NM_008059 | G0s2 |

ProbeSymbol = Affymetrix probe identification corresponding to gene symbol; FEN = fold enrichment when compared to reference sample; Genbank = Genbank identification; GeneSymbol = official gene symbol.

TABLE 20

Top 1,000 cerebellar Purkinje (Pcp2) cell translated mRNAs enriched when compared to a reference sample

| ProbeSymbol | FEN | Genbank | GeneSymbol |
|---|---|---|---|
| 1438405_at | 520.4 | BB791906 | Fgf7 |
| 1450079_at | 441.1 | AK012873 | Nrk |
| 1440436_at | 353.6 | BQ176471 | A730030A06 |
| 1449240_at | 333.9 | BC026822 | MGI: 1333876 |
| 1427624_s_at | 304.2 | AJ249492 | Il22; Iltifb |
| 1420994_at | 301 | BM214359 | B3gnt5 |
| 1432515_at | 298.4 | AK010774 | 2410124H12Rik |
| 1419084_a_at | 289.1 | NM_008790 | Pcp2 |
| 1436410_at | 254.9 | BB346846 | AI449023 |
| 1418095_at | 223.9 | NM_025357 | Smpx |
| 1427291_at | 180.5 | AV275615 | Sycp1 |
| 1435750_at | 168.7 | BB610454 | Gchfr |
| 1424958_at | 168.2 | BC010773 | Car8 |
| 1424859_at | 155.8 | BC005773 | Homer3 |
| 1457904_at | 144.2 | BB125515 | |
| 1455970_at | 134.4 | BE370618 | |
| 1458341_x_at | 130.3 | BB397841 | |
| 1443699_at | 119.9 | BE957383 | Ptprk |
| 1419518_at | 109.9 | NM_017379 | Tuba8 |
| 1458284_at | 108.9 | BM195499 | Ptbp1; LOC236294 |
| 1450428_at | 106.6 | AV335209 | Lhx1 |
| 1457523_at | 98.38 | BB125017 | 9530056K15Rik |
| 1448509_at | 96.98 | BC021353 | 3110001A13Rik |
| 1439232_at | 93.96 | BB781460 | |
| 1437209_at | 89.42 | AV324566 | 6230425F05Rik |
| 1435275_at | 84.82 | AV013496 | Cox6b2 |
| 1438340_at | 80.48 | BB277600 | A930006D11 |
| 1447742_at | 79.1 | BB216290 | Laptm5 |
| 1429346_a_at | 78.36 | BB733638 | 4933440J22Rik |
| 1419057_at | 77.86 | AF208031 | Slc5a1 |
| 1450078_at | 77.37 | AK012873 | Nrk |
| 1425179_at | 75.87 | AF237702 | Shmt1 |
| 1455512_at | 75.01 | AI852151 | |
| 1418173_at | 69.35 | NM_133730 | 4631426H08Rik |

TABLE 20-continued

Top 1,000 cerebellar Purkinje (Pcp2) cell translated mRNAs enriched when compared to a reference sample

| ProbeSymbol | FEN | Genbank | GeneSymbol |
|---|---|---|---|
| 1441776_at | 68.9 | BB732603 | Tspan11 |
| 1434973_at | 68.36 | BE650380 | Car7 |
| 1440944_at | 66.97 | BF463236 | LOC544718 |
| 1450997_at | 66.54 | AV173139 | Stk17b |
| 1460118_at | 63.38 | BF455409 | |
| 1418494_at | 61.18 | U71189 | Ebf2 |
| 1436035_at | 57.75 | AV225683 | 3830431G21Rik |
| 1427707_a_at | 57.14 | BC004585 | Sil |
| 1434588_x_at | 52.98 | AI181686 | Tbca |
| 1452484_at | 52.2 | AF291660 | Car7 |
| 1459995_at | 51.58 | AV047656 | 1700015G11Rik |
| 1437558_at | 51.52 | AV325555 | A330050F15Rik |
| 1437580_s_at | 51.44 | C77054 | Nek2 |
| 1423366_at | 50.63 | BE133651 | Scd3 |
| 1422243_at | 49.69 | NM_008008 | Fgf7 |
| 1417833_s_at | 47.32 | NM_133191 | Eps8l2 |
| 1441166_at | 46.97 | AW123460 | A330050F15Rik |
| 1433639_at | 46.62 | AW548096 | 5730593F17Rik |
| 1422481_at | 46.07 | NM_008473 | Krt2-1 |
| 1418933_at | 45.46 | NM_009200 | Slc1a6 |
| 1428536_at | 44.48 | AK015001 | Kcng4 |
| 1446771_at | 44.34 | BB047533 | |
| 1457011_at | 44.01 | BB797251 | |
| 1424443_at | 43.15 | AV378394 | Tm6sf1 |
| 1417552_at | 42.43 | NM_007986 | Fap |
| 1447405_at | 42.03 | BB479096 | |
| 1442751_at | 41.29 | AI587721 | D430034N21 |
| 1449102_at | 40.59 | U71189 | Ebf2 |
| 1437836_x_at | 38.92 | BB357560 | 0610011L14Rik |
| 1453127_at | 38.89 | AK009235 | Ppm1j |
| 1433579_at | 38.28 | BG068678 | Tmem30b |
| 1437254_at | 38.26 | BB315525 | 6230425F05Rik |
| 1416892_s_at | 37.97 | BC021353 | 3110001A13Rik |
| 1459589_at | 37.6 | C85932 | Cryl1 |
| 1438708_x_at | 37.14 | BI465579 | Ywhab |
| 1423452_at | 37.03 | AV173139 | Stk17b |
| 1445913_at | 36.44 | AV251751 | A730090H04Rik |
| 1433553_at | 36.26 | BB131106 | Garnl3 |
| 1427760_s_at | 35.5 | X75557 | Plf; Plf2; Mrpplf3 |
| 1419061_at | 35.41 | D89821 | Rhod |
| 1455431_at | 33.78 | AV371434 | Slc5a1 |
| 1458434_at | 33.56 | BB245484 | A730009L09Rik |
| 1456798_at | 32.78 | BB317517 | 9330118A15Rik |
| 1455758_at | 32.74 | BM215011 | |
| 1425469_a_at | 32.47 | BC003855 | |
| 1454884_at | 32.03 | BG073185 | Btbd4 |
| 1430310_at | 32.02 | BB535262 | Tspan11 |
| 1457337_at | 31.88 | AV028487 | |
| 1453223_s_at | 31.6 | AK010743 | Dppa2 |
| 1421951_at | 31.31 | AV335209 | Lhx1 |
| 1431197_at | 31.19 | BB641782 | Arl6ip2 |
| 1443824_s_at | 31.1 | BB193643 | Car7 |
| 1445576_at | 30.75 | AI413817 | 4930526H21Rik |
| 1417597_at | 30.24 | NM_007642 | Cd28 |
| 1429719_at | 30.19 | AK009204 | Foxp4 |
| 1440727_at | 30.1 | BF472124 | |
| 1424046_at | 29.81 | AF002823 | Bub1 |
| 1447439_at | 29.67 | AI848394 | 1700023E05Rik |
| 1419326_at | 29.63 | NM_026188 | 1700028P14Rik |
| 1427676_a_at | 29.62 | X66118 | Grik1 |
| 1420348_at | 29.14 | NM_008499 | Lhx5 |
| 1438773_at | 28.87 | BB817972 | Steap2 |
| 1416893_at | 28.74 | BC021353 | 3110001A13Rik |
| 1439745_at | 28.58 | AV338037 | Cacng7 |
| 1448738_at | 28.2 | BB246032 | Calb1 |
| 1460482_at | 27.39 | AW123948 | 3110047P20Rik |
| 1437025_at | 27.27 | AV313615 | Cd28 |
| 1455607_at | 26.98 | BG072958 | Rspo3 |
| 1417299_at | 26.87 | NM_010892 | Nek2 |
| 1458667_at | 26.77 | AV266695 | 4930519N13Rik |
| 1443999_at | 26.77 | BB203873 | Nek2 |
| 1421129_a_at | 26.42 | NM_016745 | Atp2a3 |
| 1456834_at | 26.03 | BB277828 | Ibrdc2 |
| 1452404_at | 25.64 | BB321846 | Phactr2 |

TABLE 20-continued

Top 1,000 cerebellar Purkinje (Pcp2) cell translated mRNAs enriched when compared to a reference sample

| ProbeSymbol | FEN | Genbank | GeneSymbol |
|---|---|---|---|
| 1453904_at | 25.52 | AK015926 | 4930528G09Rik |
| 1441785_at | 25.37 | AW120650 | |
| 1423978_at | 25.35 | BC025837 | Sbk1 |
| 1441236_at | 25.32 | AV373598 | Slc9a3 |
| 1452986_at | 25.31 | AK002584 | Hgd |
| 1446612_at | 25.06 | BB169371 | 9330118A15Rik |
| 1426015_s_at | 24.98 | AF302653 | Asph |
| 1416794_at | 24.9 | NM_019717 | Arl6ip2 |
| 1428349_s_at | 24.75 | AK014058 | Ebf3 |
| 1429262_at | 24.27 | AK005472 | Rassf6 |
| 1438558_x_at | 24.07 | AV009267 | Foxq1 |
| 1426047_a_at | 23.71 | AF129509 | Ptprr |
| 1440815_x_at | 23.69 | BB099075 | LOC545039 |
| 1446894_at | 23.56 | BB117494 | Arnt2 |
| 1442209_at | 23.42 | BB251707 | 2400009B08Rik |
| 1456729_x_at | 23.29 | BB218661 | Rtel1 |
| 1418957_at | 23.25 | NM_016853 | Stac |
| 1429712_at | 23.19 | AK005093 | Etohi1 |
| 1421309_at | 22.81 | NM_008598 | Mgmt |
| 1447828_x_at | 22.69 | BB226589 | 2310005P05Rik |
| 1439181_at | 22.67 | AV020760 | BC043301 |
| 1443939_at | 22.58 | BF021397 | LOC230628 |
| 1443591_at | 22.42 | BB827848 | Dlx4 |
| 1420052_x_at | 22.4 | C81484 | Psmb1 |
| 1433605_at | 22.29 | BB307136 | Inpp5a |
| 1450956_at | 21.88 | BE133651 | Scd3 |
| 1436627_at | 21.84 | BB368203 | D17Ertd663e |
| 1440688_at | 21.83 | BM244666 | Arhgap26 |
| 1439834_at | 21.73 | AA261399 | 2400009B08Rik |
| 1454171_x_at | 21.52 | AK020608 | 9530053H05Rik |
| 1433588_at | 21.11 | BM238232 | D6Wsu116e |
| 1460666_a_at | 20.9 | NM_010096 | Ebf3 |
| 1437250_at | 20.87 | AV298358 | MGI: 2151839 |
| 1416698_a_at | 20.85 | NM_016904 | Cks1b |
| 1447178_at | 20.83 | BB173057 | |
| 1459801_at | 20.67 | BB189298 | B3galt5 |
| 1448117_at | 20.66 | BB815530 | Kitl |
| "AFFX-r2-Bs-dap-3_at" | 20.63 | AFFX-r2-Bs-dap-3 | |
| 1451683_x_at | 20.56 | M34962 | H2-D1 |
| 1424904_at | 20.35 | BC019143 | 1300010F03Rik |
| 1417178_at | 20.32 | NM_016867 | Gipc2 |
| 1420993_at | 20.27 | BM214359 | B3gnt5 |
| 1446071_at | 20.07 | BB529332 | Steap2 |
| 1454653_at | 19.99 | BB274531 | A730016F12Rik |
| 1454079_at | 19.88 | AK016591 | 4933400F03Rik |
| 1451112_s_at | 19.86 | BC024876 | Dap |
| 1419473_a_at | 19.72 | NM_031161 | Cck |
| 1425198_at | 19.7 | BG076152 | Ptpn2 |
| 1441836_x_at | 19.66 | AV045004 | 1700006H03Rik |
| 1447004_at | 19.26 | BB128185 | |
| 1433893_s_at | 19.24 | BM208112 | Spag5 |
| 1415855_at | 18.97 | BB815530 | Kitl |
| 1426738_at | 18.96 | BC014860 | Dgkz |
| 1420664_s_at | 18.94 | NM_011171 | Procr |
| 1417577_at | 18.9 | NM_019510 | Trpc3 |
| 1443560_at | 18.77 | BB283805 | Pofut2 |
| 1422752_at | 18.77 | BG070121 | Polr3k |
| 1433582_at | 18.76 | AV309085 | 1190002N15Rik |
| 1455952_at | 18.69 | AI503324 | Adprhl1 |
| 1449874_at | 18.66 | NM_016923 | Ly96 |
| 1435959_at | 18.4 | BM246535 | Arhgap15 |
| 1436326_at | 18.27 | BB306272 | Rora |
| 1437880_at | 18.02 | AV273001 | Lbxcor1 |
| 1433892_at | 18.02 | BM208112 | Spag5 |
| 1418237_s_at | 17.9 | NM_009929 | Col18a1 |
| 1421392_a_at | 17.78 | NM_007464 | Birc3 |
| 1452889_at | 17.75 | AK009207 | 2310007H09Rik |
| 1437444_at | 17.74 | BB479976 | Pcdhgc3 |
| 1448355_at | 17.71 | NM_019429 | Prss16 |
| 1426955_at | 17.58 | D17546 | Col18a1 |
| 1420334_at | 17.54 | NM_134251 | Slc12a8 |
| 1418733_at | 17.53 | NM_011658 | Twist1 |
| 1451931_x_at | 17.43 | M69068 | H2-D1 |
| 1419985_s_at | 17.41 | C87579 | D11Ertd461e |
| 1436716_at | 17.3 | BM941586 | Ppp1r14b |
| 1445173_at | 17.28 | BF472675 | AK129341 |
| 1452704_at | 17.28 | AK004786 | 1200015F23Rik |
| 1422529_s_at | 17.26 | NM_009814 | Casq2 |
| 1455977_x_at | 17.2 | AV053098 | Klk6; Klk5 |
| 1437101_at | 17.18 | AV271979 | Lats2 |
| 1439146_s_at | 16.94 | AA867167 | Lck |
| 1439729_at | 16.77 | BB463084 | A930038B10Rik |
| 1439377_x_at | 16.68 | BB041150 | Cdc20 |
| 1448459_at | 16.6 | NM_027398 | Kcnip1 |
| 1422537_a_at | 16.52 | NM_010496 | Id2 |
| 1429166_s_at | 16.42 | AW494443 | Clmn |
| "AFFX-DapX-3_at" | 16.41 | AFFX-DapX-3 | |
| 1435487_at | 16.38 | BB049642 | Grid2 |
| 1417088_at | 16.37 | AW493043 | Zfp346 |
| 1428977_at | 16.23 | AK005217 | Chst8 |
| 1439266_a_at | 16.18 | AV260647 | Polr3k |
| 1423790_at | 16.14 | BC024876 | Dap |
| 1455101_at | 16.12 | BE631955 | |
| 1459660_at | 16.05 | BE944772 | |
| 1457441_at | 16.04 | AI385540 | Ebf1 |
| 1431446_at | 16 | AK002366 | 0610009B14Rik |
| 1428196_a_at | 15.96 | AK004786 | 1200015F23Rik |
| 1415947_at | 15.95 | BC027426 | Creg1 |
| 1450389_s_at | 15.78 | NM_008846 | Pip5k1a |
| 1420453_at | 15.73 | NM_009967 | Crygs |
| 1418709_at | 15.68 | AF037370 | Cox7a1 |
| 1424826_s_at | 15.5 | BC024131 | Mtss1 |
| 1454713_s_at | 15.43 | BG072171 | Hdc |
| 1420583_a_at | 15.35 | NM_013646 | Rora |
| 1451707_s_at | 15.31 | BC011108 | Slc41a3 |
| 1434201_at | 15.21 | AV144145 | Chrdl1 |
| 1417164_at | 15.19 | NM_022019 | Dusp10 |
| 1421446_at | 15.12 | NM_011102 | Prkcc |
| 1434790_at | 15.08 | AV048499 | 1810005K13Rik |
| 1420522_at | 15.06 | NM_026202 | 2610529H08Rik |
| 1450276_a_at | 15.03 | NM_009132 | Scin |
| 1427178_at | 14.89 | BB667469 | Tmc4 |
| 1444582_at | 14.68 | AV032530 | 4833420K19Rik |
| 1435226_at | 14.46 | BG064140 | Ibrdc3 |
| 1423365_at | 14.4 | AW494038 | Cacna1g |
| 1423652_at | 14.39 | AV209097 | Hbld2 |
| 1443798_at | 14.38 | BB207248 | Pik3cd |
| 1434950_a_at | 14.35 | BE995635 | Armc8 |
| 1434034_at | 14.27 | BI905090 | Cerk |
| 1417279_at | 14.26 | NM_010585 | Itpr1 |
| 1450896_at | 14.19 | BM248774 | Arhgap5 |
| 1425545_x_at | 14.14 | M86502 | H2-D1; H2-L |
| 1419017_at | 14.14 | NM_016869 | Corin |
| 1449577_x_at | 14.02 | AK003186 | Tpm2 |
| 1426923_at | 14.02 | BB130716 | Hrb |
| 1426500_at | 13.95 | BF462080 | Icmt |
| 1415948_at | 13.89 | BC027426 | Creg1 |
| 1458129_at | 13.86 | BB559501 | Rora |
| 1416302_at | 13.81 | BB125261 | Ebf1 |
| 1420595_at | 13.79 | NM_007867 | Dlx4 |
| 1421996_at | 13.77 | NM_011547 | Tcfap2a |
| 1437987_at | 13.73 | BB389497 | |
| 1441786_at | 13.7 | AW048005 | |
| 1452890_at | 13.66 | AK009255 | Ttll5 |
| 1436690_at | 13.55 | BB494139 | Lrba |
| 1418758_a_at | 13.43 | NM_011182 | Pscd3 |
| 1419999_at | 13.4 | C81413 | Igbp1 |
| 1439799_at | 13.31 | AW488620 | Fgfl1 |
| 1438036_x_at | 13.29 | BB748934 | AW061290 |
| 1447625_at | 13.25 | BB286270 | E2f5 |
| 1439447_x_at | 13.19 | AV056887 | Rpl37a |
| 1421436_at | 13.13 | NM_008167 | Grid2 |
| 1456934_at | 13.11 | BB177770 | |
| 1416160_at | 13.1 | AI463873 | Nr2f2 |
| 1418831_at | 13.06 | AW475993 | Pkp3 |
| 1436867_at | 13 | BG795043 | Srl |
| 1432478_a_at | 12.96 | AK015966 | Ibrdc3 |

TABLE 20-continued

Top 1,000 cerebellar Purkinje (Pcp2) cell translated mRNAs enriched when compared to a reference sample

| ProbeSymbol | FEN | Genbank | GeneSymbol |
|---|---|---|---|
| 1416301_a_at | 12.96 | BB125261 | Ebf1 |
| 1452362_at | 12.89 | BB834440 | Trim16 |
| 1442502_at | 12.89 | BB011593 | Lrch1 |
| 1426981_at | 12.86 | BI157485 | Pcsk6 |
| 1421435_at | 12.86 | NM_008167 | Grid2 |
| 1439789_at | 12.85 | BQ177189 | |
| 1423536_at | 12.67 | BF148627 | Strn3 |
| 1438073_at | 12.66 | AW047633 | |
| 1439699_at | 12.66 | BB525237 | Pgr |
| 1451784_x_at | 12.65 | L36068 | H2-D1; H2-K1; H2-L; LOC56628 |
| 1428636_at | 12.62 | AK015015 | Steap2 |
| 1460084_at | 12.62 | BB473929 | |
| 1433764_at | 12.6 | BB026221 | Clec21 |
| 1453936_at | 12.6 | BQ032796 | |
| 1455775_at | 12.55 | AW988196 | |
| 1431241_at | 12.29 | AA692147 | Chchd3 |
| 1422426_at | 12.29 | NM_020612 | Cmar |
| 1434006_at | 12.27 | BQ030992 | BC051227 |
| 1436948_a_at | 12.14 | BB520013 | 6430550H21Rik |
| 1439254_at | 12 | BE981392 | Akap13 |
| 1452751_at | 11.99 | AK014058 | Ebf3 |
| 1424037_at | 11.97 | BC027291 | Itpka |
| 1451776_s_at | 11.96 | BC024546 | MGI: 1916782 |
| 1421834_at | 11.96 | NM_008846 | Pip5k1a |
| 1428268_at | 11.86 | AK018116 | Psd2 |
| 1433589_at | 11.85 | BM238232 | D6Wsu116e |
| 1422409_at | 11.84 | NM_008237 | Hes3 |
| 1423062_at | 11.76 | AV175389 | Igfbp3 |
| 1438035_at | 11.73 | BB748934 | AW061290 |
| 1456631_at | 11.65 | AV272901 | LOC381279 |
| 1425440_x_at | 11.61 | BC011108 | Slc41a3 |
| 1446441_at | 11.55 | BB126659 | Slc20a1 |
| 1458918_at | 11.52 | BB552741 | Slc12a8 |
| 1451602_at | 11.5 | BC025911 | Snx6 |
| 1452462_a_at | 11.45 | BC013339 | Banp |
| 1418254_at | 11.43 | NM_019735 | Apip |
| 1452478_at | 11.42 | AY044451 | Alpk2 |
| 1428064_at | 11.41 | BI248650 | Centd2 |
| 1455455_at | 11.39 | BB008997 | Glt28d2 |
| 1450914_at | 11.37 | BE986849 | Ppp1r14b |
| 1455343_at | 11.37 | BF159528 | Plekha7 |
| 1447282_at | 11.36 | BE979542 | Chtf18 |
| 1416785_at | 11.34 | NM_027398 | Kcnip1 |
| 1448799_s_at | 11.24 | NM_011885 | Mrps12 |
| 1457232_at | 11.22 | BE946365 | Fbxl21 |
| 1438812_x_at | 11.2 | BB771589 | Usp19 |
| 1434273_at | 11.18 | BG073439 | A830073O21Rik |
| 1438987_at | 11.17 | AV044525 | 4921509E07Rik |
| 1416645_a_at | 11.16 | NM_007423 | Afp |
| 1426324_at | 11.01 | M33151 | H2-D1 |
| 1416664_at | 10.97 | NM_023223 | Cdc20 |
| 1428345_at | 10.96 | BB229589 | 4932443D16Rik |
| 1450852_s_at | 10.9 | BQ173958 | F2r |
| 1443187_at | 10.89 | AV235077 | Rspo3 |
| 1420653_at | 10.89 | NM_011577 | Tgfb1 |
| 1453829_at | 10.89 | BE948719 | 2310007J06Rik |
| 1434036_at | 10.72 | AV024771 | Mtss1 |
| 1450310_at | 10.69 | NM_133355 | Grid2ip |
| 1456596_at | 10.63 | BB093996 | 6430550H21Rik |
| 1453409_at | 10.62 | AK004156 | Cgrrf1 |
| 1433581_at | 10.62 | AV309085 | 1190002N15Rik |
| 1457118_at | 10.61 | AV353605 | 6230417E10Rik |
| 1421078_at | 10.56 | NM_053085 | Tcf23 |
| 1438151_x_at | 10.55 | BB544336 | Zdhhc14 |
| 1424709_at | 10.52 | AB016248 | Sc5d |
| 1436399_s_at | 10.52 | BI901194 | Nrk |
| 1442015_at | 10.49 | BG070940 | |
| 1455165_at | 10.45 | BE335227 | Rora |
| 1457942_at | 10.42 | BI467159 | Pdcl |
| 1452095_a_at | 10.37 | AK005204 | H47 |
| 1439849_at | 10.33 | BB215381 | |
| 1433919_at | 10.31 | AV302111 | Asb4 |
| 1455637_x_at | 10.29 | BB465277 | |
| 1442823_at | 10.24 | BB536648 | |
| 1451426_at | 10.23 | AF316999 | D11Lgp2e |
| 1431167_at | 10.16 | AI646503 | Dgkg |
| 1440827_x_at | 10.15 | BB018032 | Sox5 |
| 1449872_at | 10.14 | NM_019960 | Hspb3 |
| 1415887_at | 10.12 | NM_019678 | Tfg |
| 1441622_at | 10.05 | AV374024 | LOC433023 |
| "AFFX-r2-Bs-phe-3_at" | 10.02 | AFFX-r2-Bs-phe-3 | |
| 1416158_at | 10.02 | AI463873 | Nr2f2 |
| 1458753_at | 9.948 | BB548169 | Gm941 |
| 1422753_a_at | 9.868 | BG070121 | Polr3k |
| 1441025_at | 9.865 | BB333919 | 3110047P20Rik |
| 1422157_a_at | 9.816 | NM_008403 | Itgb1bp1 |
| 1432355_at | 9.808 | AK008780 | 2210039B01Rik |
| 1453060_at | 9.804 | AK018337 | Rgs8 |
| 1423422_at | 9.794 | AV113827 | Asb4 |
| 1424541_at | 9.785 | BC011320 | Tmem70 |
| 1450897_at | 9.748 | BM248774 | Arhgap5 |
| 1416131_s_at | 9.717 | BB188557 | C920006C10Rik |
| 1458395_at | 9.717 | BB811756 | B930054O08 |
| 1458595_at | 9.712 | AW907704 | Pdzk6 |
| 1449876_at | 9.684 | NM_011160 | Prkg1 |
| 1443733_x_at | 9.655 | C85233 | Pold3 |
| 1458677_at | 9.609 | BB517186 | Entpd5 |
| 1428601_at | 9.415 | AK005628 | 1700003E16Rik |
| 1449202_at | 9.38 | NM_011976 | Sema4g |
| 1434110_x_at | 9.284 | BF322785 | Mup1 |
| 1430780_a_at | 9.284 | BI739353 | Pmm1 |
| 1434014_at | 9.27 | BB291836 | Atg4c |
| 1427594_at | 9.263 | BC002224 | Zfp697 |
| 1455164_at | 9.239 | AV308092 | Cdgap |
| 1429884_at | 9.16 | AK005172 | Srgap2 |
| 1441161_at | 9.152 | BB307791 | B230216G23Rik |
| 1442042_at | 9.113 | BG092211 | |
| 1419660_at | 9.097 | NM_025904 | 1600012F09Rik |
| 1441536_at | 9.105 | AK009195 | Mtfr1 |
| 1425017_at | 9.095 | BB314809 | Pcdhac1 |
| 1451147_x_at | 9.037 | BC016109 | Csdc2 |
| 1435735_x_at | 9.034 | BB285733 | H47 |
| 1449307_at | 9.014 | NM_028146 | 2810427I04Rik |
| 1429156_at | 8.998 | BF453953 | 2610036L11Rik |
| 1430125_s_at | 8.981 | AK009256 | Pqlc1 |
| 1449403_at | 8.978 | NM_008804 | Pde9a |
| 1450702_at | 8.907 | AJ306425 | Hfe |
| 1448704_s_at | 8.889 | NM_024439 | H47 |
| 1440725_at | 8.882 | BB131092 | Gpr63 |
| 1450837_at | 8.853 | NM_031499 | Prh1 |
| 1439006_x_at | 8.849 | BB093996 | 6430550H21Rik |
| 1444363_at | 8.848 | BB269445 | |
| 1428760_at | 8.831 | AW537061 | Snapc3 |
| 142005_s_at | 8.83 | AI480750 | 2410166I05Rik |
| 1459300_at | 8.784 | BB226459 | |
| 1447296_at | 8.755 | AW490725 | Fbxo27 |
| 1459592_a_at | 8.755 | BB752796 | LOC547217 |
| 1420667_at | 8.751 | BM117900 | Doc2b |
| 1418423_a_at | 8.719 | AV226526 | Trappc5 |
| 1451163_at | 8.717 | AF214013 | Tinf2 |
| 1449461_at | 8.67 | NM_023462 | Rbp7 |
| 1445218_at | 8.661 | BE955408 | Vax2 |
| 1436281_at | 8.642 | BB465277 | |
| 1437841_x_at | 8.624 | BB248249 | Csdc2 |
| 1438502_x_at | 8.618 | AA030209 | Rps17; LOC383032 |
| 1443197_at | 8.608 | BB501165 | Wnt9b |
| 1431073_at | 8.594 | AK015225 | 4930428J16Rik |
| 1425028_a_at | 8.571 | BC024358 | Tpm2 |
| 1436112_at | 8.555 | BB128317 | AI118078 |
| 1425891_a_at | 8.555 | AF329833 | Grtp1 |
| 1417147_at | 8.535 | NM_019833 | B230317C12Rik |
| 1452244_at | 8.517 | AK018128 | 6330406I15Rik |
| 1439441_x_at | 8.505 | BB134767 | Lats2 |
| 1417430_at | 8.503 | NM_007672 | Cdr2 |
| 1425779_a_at | 8.469 | AF326960 | Tbx1 |

TABLE 20-continued

Top 1,000 cerebellar Purkinje (Pcp2) cell translated mRNAs enriched when compared to a reference sample

| ProbeSymbol | FEN | Genbank | GeneSymbol |
|---|---|---|---|
| 1444730_at | 8.421 | BB297867 | Tlk1 |
| 1435517_x_at | 8.385 | BB465250 | Ralb |
| 1434881_s_at | 8.365 | BM220945 | Kctd12 |
| 1436895_at | 8.353 | BB182934 | Centd1 |
| 1437392_at | 8.352 | AW123113 | LOC433485 |
| 1416398_at | 8.346 | BB474887 | Mesdc1 |
| 1426374_at | 8.34 | AK010825 | 2410166I05Rik |
| 1444112_at | 8.331 | BQ174086 | |
| 1459107_at | 8.323 | BG069378 | Kcnh3 |
| 1448160_at | 8.305 | NM_008879 | Lcp1 |
| 1416121_at | 8.303 | M65143 | Lox |
| 1416793_at | 8.293 | NM_019717 | Arl6ip2 |
| "AFFX-r2-Bs-dap-M_at" | 8.268 | AFFX-r2-Bs-dap-M | |
| 1424350_s_at | 8.259 | BE987427 | Lpgat1 |
| 1436728_s_at | 8.218 | BG071028 | Rtel1 |
| 1447864_s_at | 8.212 | AV377712 | Pogk |
| "AFFX-DapX-M_at" | 8.187 | AFFX-DapX-M | |
| 1460735_at | 8.169 | BM203457 | Svil |
| 1423194_at | 8.139 | BM248774 | Arhgap5 |
| 1452642_at | 8.115 | BE372017 | Tmem16f |
| 1460647_at | 8.106 | NM_010150 | Nr2f6 |
| 1419647_a_at | 8.096 | NM_133662 | Ier3 |
| 1427940_s_at | 8.082 | BB046347 | Mycbp |
| 1448812_at | 8.055 | NM_016677 | Hpcal1 |
| 1419614_at | 8.039 | BC021592 | Pla2g12b |
| 1434064_at | 8.026 | BQ175677 | BC061259 |
| 1437683_x_at | 8.004 | AV047585 | Serf2 |
| 1453528_at | 7.985 | AK005161 | Lta4h |
| 1435208_at | 7.966 | AV327407 | Dtx31 |
| 1423535_at | 7.959 | BF148627 | Strn3 |
| 1420566_at | 7.945 | NM_025367 | |
| 1435671_at | 7.945 | BB526605 | Mipol1 |
| 1456731_x_at | 7.932 | AV169424 | Polr3k |
| 1437914_at | 7.923 | BB104097 | E2f6 |
| 1450500_at | 7.916 | AW012751 | Uhmk1 |
| 1420666_at | 7.908 | BM117900 | Doc2b |
| 1443766_x_at | 7.895 | BB311234 | Rab11fip4 |
| 1454842_x_at | 7.884 | AI853240 | B3galnt2 |
| 1426048_s_at | 7.883 | BC021623 | Tcfap2a |
| 1445728_at | 7.88 | BB667663 | |
| 1416159_at | 7.878 | AI463873 | Nr2f2 |
| 1430489_at | 7.83 | BB086802 | 5430416G10Rik |
| 1416542_at | 7.826 | NM_009343 | Phf1 |
| 1425197_at | 7.813 | BG076152 | Ptpn2 |
| 1440735_at | 7.812 | BB283168 | Polr3k |
| 1425177_at | 7.809 | AF237702 | Shmt1 |
| 1454161_s_at | 7.733 | AK002308 | 0610007P14Rik |
| 1439425_x_at | 7.729 | AV100801 | BC024814 |
| 1418909_at | 7.722 | NM_013848 | |
| 1450235_at | 7.718 | NM_015759 | Fgd3 |
| 1420304_x_at | 7.709 | AV128236 | |
| 1456722_at | 7.685 | BI966456 | Chrdl1 |
| 1452827_at | 7.657 | AK005178 | 1500009C09Rik |
| 1449176_a_at | 7.637 | NM_007832 | Dck |
| 1457341_at | 7.636 | BE991676 | |
| 1417960_at | 7.623 | NM_007755 | Cpeb1 |
| 1449584_at | 7.562 | NM_138650 | Dgkg |
| 1438698_at | 7.547 | AV305379 | 4632425D07Rik |
| 1433623_at | 7.546 | BE629588 | Zfp367 |
| 1424902_at | 7.481 | AF378760 | Plxdc1 |
| 1451796_s_at | 7.479 | AF109137 | Hdc |
| 1443846_x_at | 7.477 | BB402666 | Pank2 |
| 1421833_at | 7.473 | NM_008846 | Pip5k1a |
| 1458536_at | 7.455 | BB097972 | Ccni |
| 1422941_at | 7.449 | NM_053116 | Wnt16 |
| 1455448_at | 7.415 | BG804066 | MGI: 2677061 |
| 1436322_a_at | 7.391 | BE952576 | 2810001A02Rik |
| 1426937_at | 7.383 | AK018128 | 6330406I15Rik |
| 1441271_at | 7.371 | C78231 | Idh3b |
| 1458328_x_at | 7.36 | BE993003 | 3110007P09Rik |
| 1424692_at | 7.351 | BC004753 | 2810055F11Rik |
| 1416632_at | 7.335 | BC011081 | Mod1 |
| 1425737_at | 7.324 | BC002195 | 2510016G02Rik |
| 1454866_s_at | 7.313 | BQ176424 | Clic6 |
| 1417876_at | 7.307 | AF143181 | Fcgr1 |
| 1419422_at | 7.301 | BB706784 | Pkd212 |
| 1428948_at | 7.297 | BE952741 | 5730414M22Rik |
| 1438967_x_at | 7.297 | AV259665 | Amhr2 |
| 1442614_at | 7.297 | BE945253 | Il1rap |
| 1424034_at | 7.297 | BI660199 | Rora |
| 1430827_a_at | 7.271 | AV301702 | Ptk2 |
| 1428197_at | 7.263 | AK020159 | Tspan9 |
| 1431226_a_at | 7.26 | AK013203 | Fndc4 |
| 1459875_x_at | 7.25 | AV333371 | |
| 1432271_a_at | 7.247 | AK012764 | Dcun1d5 |
| 1436528_at | 7.222 | AI842353 | Kazald1 |
| 1426922_s_at | 7.212 | BB130716 | Hrb |
| 1430490_at | 7.21 | AK017409 | |
| 1423845_at | 7.202 | BC016109 | Csdc2 |
| 1446786_at | 7.197 | BG073077 | Aplp2 |
| 1449347_a_at | 7.19 | NM_021365 | Xlr4b; Xlr4a |
| 1455056_at | 7.188 | BM231903 | Lmo7 |
| 1419406_a_at | 7.177 | NM_016707 | Bcl11a |
| 1451353_at | 7.171 | AV378394 | Tm6sf1 |
| 1452451_at | 7.168 | AF240460 | MGI: 1929597 |
| 1435491_at | 7.167 | BI076615 | AI875089 |
| 1438501_at | 7.166 | AA030209 | |
| 1455710_x_at | 7.16 | AI528732 | Mtcp1 |
| 1449079_s_at | 7.154 | NM_018784 | St3gal6 |
| 1417653_at | 7.141 | NM_013645 | Pvalb |
| 1419836_at | 7.105 | AU040583 | |
| 1435594_at | 7.1 | AV334690 | Arl6ip2 |
| 1456251_x_at | 7.095 | BB132602 | Bzrp |
| 1451190_a_at | 7.063 | BC025837 | Sbk1 |
| 1417344_at | 7.009 | BE915256 | 2900064A13Rik |
| 1455850_at | 7.006 | BG073353 | 2310003H01Rik |
| 1437308_s_at | 7 | AV024285 | F2r |
| 1458358_at | 6.994 | BB402666 | Pank2 |
| 1417121_at | 6.991 | NM_008068 | Gabra4 |
| 1447753_at | 6.987 | BB391093 | Cdc37l1 |
| 1431172_at | 6.987 | BB620704 | Orc4l |
| 1431299_a_at | 6.979 | AK009340 | 2310014H01Rik |
| 1420059_at | 6.964 | AI480750 | 2410166I05Rik |
| 1418932_at | 6.936 | AY061760 | Nfil3 |
| 1443714_at | 6.935 | AI451920 | |
| 1423055_at | 6.917 | NM_010942 | Nsg1 |
| 1429204_at | 6.905 | AK013788 | 2900075A18Rik |
| 1426032_at | 6.897 | AF289078 | Nfatc2 |
| 1456337_at | 6.896 | AV291818 | Centd1 |
| 1440700_a_at | 6.895 | BB227996 | Arhgef18 |
| 1419880_x_at | 6.893 | AA204020 | |
| 1449621_at | 6.892 | AW121720 | Thsd1 |
| 1426189_at | 6.89 | AF357887 | Dusp15 |
| 1455160_at | 6.882 | BM220421 | 2610203C20Rik |
| 1460462_at | 6.871 | AK012903 | Med18 |
| 1427556_at | 6.869 | BC019408 | Mylk2 |
| 1419742_at | 6.862 | NM_026091 | 1700037H04Rik |
| 1437935_at | 6.85 | BB821151 | 4930486G11Rik |
| 1454276_x_at | 6.844 | BB722680 | |
| 1437942_at | 6.843 | AV100095 | Tube1 |
| 1424216_a_at | 6.831 | U52197 | Papola |
| 1436829_at | 6.82 | BB667112 | Trim67 |
| 1428452_at | 6.813 | AK012812 | 2810025M15Rik |
| 1432059_x_at | 6.775 | AK017143 | 5031425E22Rik |
| 1453554_a_at | 6.771 | AK009297 | Wdr33 |
| 1452016_at | 6.759 | BC026209 | Alox5ap |
| 1434877_at | 6.746 | AI152800 | Nptx1 |
| 1449836_x_at | 6.743 | NM_007546 | Biklk |
| 1428604_at | 6.739 | AK011986 | 2610305D13Rik |
| 1418028_at | 6.735 | NM_010024 | Dct |
| 1425178_s_at | 6.732 | AF237702 | Shmt1 |
| 1438948_x_at | 6.73 | AV101079 | Bzrp |
| 1442376_at | 6.717 | BB560441 | Ablim1 |
| 1424784_at | 6.709 | AV047635 | 1700029I01Rik; LOC433791; LOC545705 |
| 1427878_at | 6.695 | AK002512 | 0610010O12Rik |

TABLE 20-continued

Top 1,000 cerebellar Purkinje (Pcp2) cell translated mRNAs enriched when compared to a reference sample

| ProbeSymbol | FEN | Genbank | GeneSymbol |
|---|---|---|---|
| 1457330_at | 6.682 | BB014986 | Semcap2 |
| 1436141_at | 6.681 | BM934616 | 2610510L01Rik |
| 1442099_at | 6.681 | BM227490 | Usp31 |
| 1437642_at | 6.674 | BB243375 | Hrbl |
| 1450168_at | 6.666 | NM_025971 | Ankrd12 |
| 1436536_at | 6.665 | AW108488 | C730015A04Rik |
| 1425701_a_at | 6.662 | AF350047 | Rgs3 |
| 1442791_x_at | 6.657 | BF459282 | 6720407P12Rik |
| 1454939_at | 6.643 | BB268102 | Phf20l1 |
| 1421360_at | 6.636 | NM_030266 | Inpp4a |
| AFFX-ThrX-3_at | 6.611 | AFFX-ThrX-3 | |
| 1450537_at | 6.601 | AF196480 | Mid2 |
| 1457894_at | 6.601 | BB284616 | |
| 1433792_at | 6.597 | AW491344 | Nrip2 |
| 1416846_a_at | 6.59 | NM_018884 | Pdzrn3 |
| 1459842_x_at | 6.588 | AV035368 | Nubp2 |
| 1433429_at | 6.584 | BB309245 | Pigs |
| 1431279_s_at | 6.569 | AK016145 | Ttll5 |
| 1420020_at | 6.559 | AU022339 | Suz12 |
| 1431421_x_at | 6.55 | BI082843 | 2610524G07Rik |
| 1454219_at | 6.543 | AK013295 | Dnajc2 |
| 1431088_at | 6.536 | BQ286886 | Foxp4 |
| 1451840_at | 6.535 | BG261945 | Kcnip4 |
| 1431293_a_at | 6.519 | AK012260 | 1110019C08Rik |
| 1439078_at | 6.513 | BB037068 | Klh14 |
| 1435621_at | 6.513 | BQ175346 | Mlstd1 |
| 1457290_at | 6.49 | BB127590 | Mab21l1 |
| 1436347_a_at | 6.485 | BB501229 | 5530601H04Rik |
| 1458320_at | 6.47 | BB012140 | |
| 1454638_a_at | 6.464 | AW106920 | Pah |
| 1457256_x_at | 6.463 | BB530125 | Ptch2 |
| 1429583_at | 6.46 | BE865033 | LOC554362 |
| 1433836_a_at | 6.447 | AV365503 | 8430408G22Rik |
| 1427174_at | 6.433 | BM235840 | 3100002L24Rik; LOC329575; LOC433520; LOC433523; LOC433531; LOC545489; LOC545490; LOC545491; LOC545492 |
| 1423371_at | 6.417 | BF577544 | Pole4 |
| 1419399_at | 6.416 | AW553649 | Mttp |
| 1456926_at | 6.4 | BB049544 | Rims4 |
| 1442160_at | 6.4 | AV360034 | 7530404M11Rik |
| 1451601_a_at | 6.399 | BC025823 | BC011467 |
| 1436661_at | 6.394 | BQ174532 | Dpp10 |
| 1430803_at | 6.391 | BB074761 | 2810403D23Rik |
| 1455080_at | 6.376 | BB375209 | Ppp1r16b |
| 1431642_at | 6.373 | AV122850 | Eif2s3y |
| 1452237_at | 6.361 | BB130716 | Hrb |
| 1424191_a_at | 6.354 | BC019770 | Tmem41a |
| 1419756_at | 6.348 | NM_138650 | Dgkg |
| 1416848_at | 6.343 | NM_025401 | Ubl5 |
| 1420774_a_at | 6.34 | NM_026358 | 4930583H14Rik |
| 1417222_a_at | 6.34 | NM_133739 | 2310075C12Rik |
| 1430866_at | 6.339 | BB432681 | 4921537D05Rik |
| 1436087_at | 6.328 | BQ176414 | Dpp10 |
| 1439117_at | 6.328 | AU067755 | Clmn |
| 1415854_at | 6.321 | BB815530 | Kitl |
| 1431229_at | 6.286 | AK019361 | C030032C09Rik |
| 1431356_at | 6.282 | AK019889 | 6430710C18Rik |
| 1460262_a_at | 6.274 | NM_026091 | 1700037H04Rik |
| 1450115_at | 6.267 | NM_008139 | Gnaq |
| 1418247_s_at | 6.246 | BG277926 | Rbm9 |
| 1439837_at | 6.242 | BE136147 | Tnrc15 |
| 1430519_a_at | 6.228 | AK007767 | Cnot7 |
| 1422313_at | 6.222 | NM_010518 | Igfbp5 |
| 1439825_at | 6.209 | BB705351 | Dtx31 |
| 1448613_at | 6.205 | NM_007899 | Ecm1 |
| 1460479_at | 6.201 | AK020726 | A330094K24Rik |
| 1423020_at | 6.188 | NM_053120 | |
| 1424604_s_at | 6.18 | BC026981 | Sumf1 |
| 1453301_a_at | 6.178 | AK008083 | 2010004B12Rik |
| 1450622_at | 6.176 | NM_009954 | Bcar1 |
| 1418760_at | 6.168 | AB030503 | Rdh11 |
| 1439479_at | 6.16 | C78577 | Lct |
| 1424846_at | 6.159 | BC027174 | BC027174 |
| 1458268_s_at | 6.133 | AI649005 | Igfbp3 |
| 1418007_at | 6.125 | BM932567 | 1810007M14Rik |
| 1435092_at | 6.125 | AV328143 | Arl4 |
| 1448487_at | 6.124 | NM_008515 | Lrrfip1 |
| 1415791_at | 6.122 | NM_030564 | Rnf34 |
| 1427593_at | 6.114 | BB620112 | Trim8 |
| 1437762_at | 6.106 | BB130995 | Rab39 |
| 1453024_at | 6.105 | AK014128 | Wdr37 |
| 1428344_at | 6.093 | BB229589 | 4932443D16Rik |
| 1448441_at | 6.086 | NM_016904 | Cks1b |
| 1423854_a_at | 6.085 | BC008101 | Rasl11b |
| 1449310_at | 6.079 | BC005440 | Ptger2 |
| 1449896_at | 6.07 | NM_053015 | Mlph |
| 1435947_at | 6.069 | BQ175669 | |
| 1425439_a_at | 6.06 | BC011108 | Slc41a3 |
| 1460382_at | 6.06 | BC020535 | BC020535 |
| 1437631_at | 6.038 | BB188374 | Kcnip4 |
| 1418202_a_at | 6.031 | NM_011717 | Wiz |
| 1435238_x_at | 6.028 | AV004950 | 2310009A05Rik |
| 1444601_at | 6.02 | AI463033 | |
| 1459468_at | 5.999 | C79743 | C79743 |
| 1453591_at | 5.98 | AK017626 | 5730437N04Rik |
| 1431707_at | 5.976 | AK016645 | Pscd3 |
| 1451085_at | 5.974 | BC019462 | C030006K11Rik |
| 1426544_a_at | 5.974 | BB118847 | Ttc14 |
| 1456210_at | 5.967 | AV222628 | |
| 1450506_a_at | 5.914 | NM_026531 | Isg20l1 |
| 1437262_x_at | 5.902 | AA940256 | Bcas2 |
| 1430763_at | 5.9 | BB016642 | 4930563E22Rik |
| 1449259_at | 5.896 | BB349707 | Rab3d |
| 1419305_a_at | 5.879 | NM_025386 | Fbxo36 |
| 1424092_at | 5.871 | BC017137 | Epb4.1 |
| 1417933_at | 5.857 | NM_008344 | Igfbp6 |
| 1421281_at | 5.851 | Z36357 | Gabra1 |
| 1437594_x_at | 5.835 | BB376188 | Pigt |
| 1423229_at | 5.835 | BM217803 | Inpp5e |
| 1435204_at | 5.83 | BG065273 | Hrmt1l4 |
| 1449072_a_at | 5.828 | NM_026526 | 2510005D08Rik |
| 1433134_at | 5.826 | AK017998 | 5830448L01Rik |
| 1430879_at | 5.825 | BB283753 | C030008P14Rik |
| 1440708_at | 5.803 | BM121854 | Myh9 |
| 1427981_a_at | 5.79 | AY033912 | Csad |
| 1449509_at | 5.788 | NM_011353 | Serf1 |
| 1437371_at | 5.785 | BB008528 | 9930021J17Rik |
| 1451975_at | 5.783 | BC005638 | 2810453I06Rik |
| 1439152_at | 5.78 | BE985292 | BC052066 |
| 1455755_at | 5.776 | BB026554 | Gm88 |
| 1437595_at | 5.762 | BB531414 | E030010A14Rik |
| 1424229_at | 5.748 | BC006704 | Dyrk3 |
| 1456313_x_at | 5.744 | BB257397 | Mrpl28 |
| 1429971_at | 5.731 | BE948556 | Txnrd2 |
| 1435270_x_at | 5.72 | BF730076 | 2510005D08Rik |
| 1444141_at | 5.711 | BB828008 | Snx13 |
| 1449287_at | 5.695 | NM_011481 | Srms |
| 1451363_a_at | 5.686 | BC008266 | Dennd2d |
| 1457433_x_at | 5.685 | BB187816 | Zfp120 |
| 1420150_at | 5.685 | AI596360 | Spsb1 |
| 1447771_at | 5.679 | AW050081 | |
| 1418890_a_at | 5.678 | BB349707 | Rab3d |
| 1448986_x_at | 5.675 | NM_010062 | Dnase2a |
| 1422847_a_at | 5.674 | AF251036 | Prkcd |
| 1439035_at | 5.673 | BG075830 | Zfp322a |
| 1457961_at | 5.667 | BB713538 | |
| 1449897_a_at | 5.664 | NM_010839 | Mtcp1 |
| 1437820_at | 5.654 | BB040642 | Fkhl18 |
| 1440242_at | 5.647 | BB356428 | C030014K22Rik |
| 1428216_s_at | 5.645 | BB609428 | Tomm7 |
| 1449362_a_at | 5.642 | NM_016713 | Mink1 |
| 1458347_s_at | 5.635 | BB414224 | Tmprss2 |
| 1423384_s_at | 5.633 | BF181445 | Tex261 |

TABLE 20-continued

Top 1,000 cerebellar Purkinje (Pcp2) cell translated mRNAs enriched when compared to a reference sample

| ProbeSymbol | FEN | Genbank | GeneSymbol |
|---|---|---|---|
| 1430590_at | 5.628 | BG228878 | D3Ertd751e |
| 1428447_at | 5.611 | AK017734 | Tmem14a |
| 1419421_at | 5.609 | NM_031158 | Ank1 |
| 1424969_s_at | 5.604 | BC027189 | Upp2 |
| 1438793_x_at | 5.601 | BB222127 | 1200007D18Rik |
| 1458132_at | 5.592 | BB429249 | Cnnm2 |
| 1435970_at | 5.588 | AU035920 | Nlk |
| 1418389_at | 5.585 | NM_133703 | 2810453I06Rik |
| 1455281_at | 5.581 | BB520667 | Wdr33 |
| 1422645_at | 5.576 | AJ306425 | Hfe |
| 1420887_a_at | 5.569 | NM_009743 | Bcl2l1 |
| 1436906_at | 5.56 | BF781579 | Rnf166 |
| 1434382_at | 5.547 | AV083936 | Tde21 |
| 1436879_x_at | 5.544 | AV124668 | Afp |
| 1437711_x_at | 5.541 | BB519474 | Odc1; LOC545783; LOC546355 |
| 1423668_at | 5.537 | BC021423 | Zdhhc14 |
| 1434165_at | 5.523 | BQ176424 | Clic6 |
| 1427170_at | 5.521 | BF318721 | Psma8 |
| 1436160_at | 5.516 | BB150142 | 4732407F15Rik |
| 1423671_at | 5.515 | AF370126 | Dner |
| 1457652_x_at | 5.509 | BB477203 | |
| 1438992_x_at | 5.507 | AV314773 | Atf4 |
| 1433787_at | 5.491 | AI841091 | B230343H07Rik |
| 1435138_at | 5.456 | AV016797 | Tmem28 |
| 1418796_at | 5.446 | NM_009131 | Clec11a |
| 1451365_at | 5.445 | BC025619 | Rbm19 |
| 1456563_at | 5.443 | BB769119 | |
| 1451418_a_at | 5.428 | BC023083 | Spsb4 |
| 1421799_at | 5.423 | NM_011910 | Uts2 |
| 1422093_at | 5.421 | NM_009522 | Wnt3a |
| 1444380_at | 5.412 | AI844869 | AI844869 |
| 1426552_a_at | 5.412 | BB772866 | Bcl11a |
| 1457472_at | 5.407 | BB782031 | Tnrc15 |
| 1418386_at | 5.384 | NM_026526 | 2510005D08Rik |
| 1435277_x_at | 5.377 | AV156640 | Nme1 |
| 1436454_x_at | 5.372 | BB393998 | Fen1 |
| 1421746_a_at | 5.366 | NM_015796 | Fbxo17 |
| 1432161_a_at | 5.363 | AK006988 | 4930428J16Rik |
| 1430156_at | 5.351 | AK015855 | 4930520O04Rik |
| 1449910_at | 5.345 | NM_029813 | 2210418O10Rik |
| 1419739_at | 5.342 | AK003186 | Tpm2 |
| 1419913_at | 5.339 | AW557906 | Strap |
| 1460652_at | 5.338 | NM_007953 | Esrra |
| 1438014_at | 5.337 | BE984852 | Mrpl34 |
| 1418583_at | 5.337 | NM_025798 | Hint3 |
| 1423286_at | 5.331 | AA016422 | Cbln1 |
| 1449209_at | 5.323 | AB030503 | Rdh11 |
| 1459941_at | 5.323 | BB096900 | 4933402J24Rik |
| 1426901_s_at | 5.313 | BB657856 | Camta2 |
| 1419851_at | 5.305 | W13854 | Slc4a8 |
| 1427997_at | 5.305 | BG064890 | 1110007M04Rik |
| 1427318_s_at | 5.302 | BI555209 | Dysf; Fer1l3 |
| 1429726_at | 5.301 | AK004684 | Slc16a9 |
| 1426856_at | 5.293 | BM200015 | Hsdl2 |
| 1453968_at | 5.282 | AK019523 | 4833439F03Rik |
| 1448999_at | 5.281 | AV226526 | Trappc5 |
| "AFFX-r2-Bs-thr-3_s_at" | 5.276 | | AFFX-r2-Bs-thr-3 |
| 1441883_at | 5.266 | AV092359 | 0610010O12Rik |
| 1455599_at | 5.264 | AV220135 | AI850995 |
| 1450965_at | 5.263 | BF181445 | Tex261 |
| 1423048_a_at | 5.263 | BB400304 | Tollip |
| 1444703_at | 5.242 | BB525928 | 2810403D21Rik |
| 1459871_x_at | 5.241 | AV349132 | 2-Mar |
| 1423686_a_at | 5.241 | BC016234 | 1110020C13Rik |
| 1437857_at | 5.234 | AV367203 | Dpy19l3 |
| 1428472_at | 5.232 | AK003707 | Spsb1 |
| 1449762_at | 5.231 | AV047896 | |
| 1436897_at | 5.227 | BE225764 | Mfhas1 |
| 1419351_a_at | 5.226 | BC003916 | 0610007P06Rik |
| 1425330_a_at | 5.226 | AJ271836 | Ppm1b; LOC433336 |
| 1416521_at | 5.225 | NM_009156 | Sepw1 |
| 1442711_at | 5.222 | BB129490 | A530065E19Rik |
| 1452169_a_at | 5.221 | BC014860 | Dgkz |
| 1429881_at | 5.221 | AK018058 | Arhgap15 |
| 1429092_at | 5.212 | AK009497 | Vkorc1l1 |
| 1436189_at | 5.207 | AV380561 | |
| 1435516_x_at | 5.204 | BB752007 | Rtel1 |
| 1418234_s_at | 5.202 | NM_026602 | Bcas2 |
| 1434177_at | 5.199 | AI551117 | Ece1 |
| 1437137_at | 5.197 | AV280875 | 6430550H21Rik |
| 1448344_at | 5.189 | NM_011295 | Rps12; LOC432865; LOC546370; LOC546371; LOC546372; LOC546373 |
| 1451881_at | 5.186 | BC027044 | |
| 1437489_x_at | 5.184 | BB497590 | Sdhd |
| 1429972_s_at | 5.183 | BE948556 | Txnrd2 |
| 1432579_at | 5.177 | AA544511 | Rshl2 |
| 1439150_x_at | 5.166 | BB480256 | Grtp1 |
| 1451596_a_at | 5.161 | AF068749 | Sphk1 |
| 1447397_at | 5.158 | BB733030 | 1700129I04Rik |
| 1434664_at | 5.151 | BI153133 | 2410129H14Rik |
| 1452274_at | 5.13 | BG976649 | Tex27 |
| 1422627_a_at | 5.121 | BF581250 | Mkks |
| 1422490_at | 5.116 | AV144704 | Bnip2 |
| 1418259_a_at | 5.112 | NM_009849 | Entpd2 |
| 1432343_at | 5.111 | AK015168 | 4930419G24Rik |
| 1426880_at | 5.106 | BM250266 | BC026657 |
| 1438769_a_at | 5.105 | BF719766 | MGI: 1925112 |
| 1452640_at | 5.104 | AK014019 | 3110007F17Rik; LOC546367; LOC546368 |
| 1436475_at | 5.103 | AI527205 | Nr2f2 |
| 1435237_at | 5.098 | AV004950 | 2310009A05Rik |
| 1419738_a_at | 5.094 | AK003186 | Tpm2 |
| 1428296_at | 5.085 | AV102258 | Polr2l |
| 1418008_at | 5.085 | BM932567 | 1810007M14Rik |
| 1436042_at | 5.084 | BI648366 | Tln1 |
| 1445074_at | 5.078 | BB519491 | |
| 1455601_at | 5.072 | BB507994 | |
| 1454898_s_at | 5.072 | AU016407 | 4833421E05Rik |
| 1417946_at | 5.058 | NM_134130 | Abhd3 |
| 1452768_at | 5.058 | AK013971 | Tex261 |
| 1434291_a_at | 5.054 | AA709993 | Serf1 |
| 1437677_at | 5.053 | BG063913 | AI449595 |
| 1428822_a_at | 5.053 | BB815011 | Snx24 |
| 1421083_x_at | 5.042 | NM_011793 | Banf1 |
| 1426382_at | 5.042 | AJ271833 | Ppm1b |
| 1437980_at | 5.041 | BB814947 | 9130230N09Rik |
| 1449471_at | 5.04 | NM_021452 | Kcnmb4 |
| 1438408_at | 5.039 | BB131927 | 5730467H21Rik |
| 1417677_at | 5.037 | NM_010098 | Opn3 |
| 1459896_at | 5.036 | AW911766 | Pogk |
| 1439574_at | 5.029 | BI737205 | 1110020A21Rik |
| 1438549_a_at | 5.007 | BB020681 | Srr |
| 1456467_s_at | 5.006 | BB389081 | Nlk |
| 1458662_at | 4.999 | BB546123 | Daam1 |
| 1455052_a_at | 4.998 | BI153133 | 2410129H14Rik |
| 1454225_s_at | 4.984 | AK012700 | D3Ertd751e |
| 1421330_at | 4.979 | NM_019933 | Ptpn4 |
| 1448740_at | 4.975 | NM_021329 | 2400006H24Rik |
| 1451395_at | 4.972 | BC021492 | D5Bwg0834e |
| 1447097_at | 4.966 | BG068083 | |
| 1420010_at | 4.966 | C80083 | LOC574418 |
| 1456056_a_at | 4.963 | AV338866 | D6Wsu116e |
| AFFX-LysX-3_at | 4.957 | | AFFX-LysX-3 |
| 1460203_at | 4.95 | NM_010585 | Itpr1 |
| 1429620_at | 4.949 | BB040330 | 8430406I07Rik |
| 1442218_at | 4.945 | BM201230 | Map3k9 |
| 1417335_at | 4.94 | NM_017465 | Sult2b1 |
| 1435875_at | 4.934 | AV223660 | Prkab2 |
| 1442073_at | 4.931 | BQ266693 | |

TABLE 20-continued

Top 1,000 cerebellar Purkinje (Pcp2) cell translated mRNAs enriched when compared to a reference sample

| ProbeSymbol | FEN | Genbank | GeneSymbol |
|---|---|---|---|
| 1459696_at | 4.928 | AI844428 | 9330186A19Rik |
| 1420148_at | 4.923 | AA589629 | Slc6a6 |
| 1448661_at | 4.922 | NM_008874 | Plcb3 |
| 1429005_at | 4.919 | BB107412 | Mfhas1 |
| 1429664_at | 4.917 | AI464135 | Cdkl1 |
| 1424848_at | 4.915 | U09383 | Kcnma1 |
| 1447552_s_at | 4.913 | AV169798 | Catnd2 |
| 1455885_at | 4.902 | AV238106 | 6530401C20Rik |
| 1451387_s_at | 4.894 | BC021463 | 0610039D01Rik |
| 1453993_a_at | 4.883 | AK014659 | Bnip2 |
| 1453077_a_at | 4.882 | AK016168 | Snapc3 |
| 1451525_at | 4.877 | BG064038 | Arhgap12 |
| 1454824_s_at | 4.865 | BB699957 | Mtus1 |
| 1438623_x_at | 4.86 | AV038578 | Rbx1 |
| 1436681_x_at | 4.857 | BE199670 | 0610009D07Rik |
| 1440882_at | 4.852 | BB750940 | Lrp8 |
| 1435755_at | 4.85 | BB609468 | 1110001A16Rik |
| 1438656_x_at | 4.831 | AV157500 | Timm17b |
| 1450648_s_at | 4.83 | NM_010379 | H2-Ab1 |
| 1439509_at | 4.826 | BE985592 | 2900008C10Rik |
| 1449012_s_at | 4.818 | BC027164 | Fndc4 |
| 1436869_at | 4.817 | AV304616 | Shh |
| 1439388_s_at | 4.813 | BB251739 | Bcar1 |
| 1428662_a_at | 4.809 | AK009007 | MGI: 1916782 |
| 1429988_at | 4.804 | AK002713 | Zfp235 |
| 1436614_at | 4.804 | AI843639 | AI843639 |
| 1419112_at | 4.803 | NM_008702 | Nlk |
| 1449983_a_at | 4.799 | NM_020282 | Nqo2 |
| 1441481_at | 4.799 | AV262974 | Mfap31 |
| 1460030_at | 4.796 | BB355811 | Hecw1 |
| 1457644_s_at | 4.785 | BB554288 | Cxcl1 |
| 1440886_at | 4.781 | BE949427 | Cdc37l1 |
| 1428309_s_at | 4.78 | AK003410 | Pdrg1 |
| 1456036_x_at | 4.777 | AV003026 | Gsto1 |
| 1425149_a_at | 4.775 | BC006578 | Pdcl |
| 1419400_at | 4.761 | AW553649 | Mttp |
| 1418996_a_at | 4.759 | BC021522 | 4930469P12Rik |
| 1428607_at | 4.754 | AK010060 | |
| 1423318_at | 4.75 | AK012795 | Rad18 |
| 1421295_at | 4.749 | NM_031258 | Chrdl1 |
| 1449027_at | 4.747 | AF378088 | Rhou |
| "AFFX-PheX-3_at" | 4.746 | AFFX-PheX-3 | |
| 1430203_at | 4.746 | BG067256 | Usp16 |
| 1434732_x_at | 4.745 | AV044898 | Tomm7 |
| 1420655_at | 4.729 | NM_054088 | Adpn |
| 1417095_a_at | 4.729 | NM_015765 | Hspa14 |
| 1420556_at | 4.728 | NM_011025 | Oxt |
| 1458466_at | 4.726 | AV338634 | Ppgb |
| 1444475_at | 4.721 | BE983052 | 1810009N02Rik |
| 1440226_at | 4.717 | BB088782 | BC029103 |
| 1440995_at | 4.709 | BE946005 | 6430531B16Rik |
| 1430686_at | 4.705 | AK014719 | 4833418N02Rik |
| 1429114_at | 4.699 | AV276619 | Sestd1 |
| 1454663_at | 4.698 | BQ176989 | Eif5 |
| 1417590_at | 4.693 | NM_024264 | Cyp27a1 |
| 1460648_at | 4.684 | NM_010150 | Nr2f6 |
| 1439012_a_at | 4.683 | BB030204 | Dck |
| 1420888_at | 4.673 | NM_009743 | Bcl2l1 |
| 1415956_a_at | 4.668 | NM_011049 | Pctk1 |
| 1433700_at | 4.667 | BB477807 | 4933433P14Rik |
| 1449534_at | 4.661 | NM_011517 | Sycp3 |
| 1435523_s_at | 4.656 | BB779140 | 2700089E24Rik |
| 1456097_a_at | 4.653 | BB830191 | Itgb3bp |
| 1434763_at | 4.646 | BF457736 | A730041O15Rik |
| 1426035_at | 4.646 | BC026459 | LOC574418 |
| 1440663_at | 4.634 | BB322506 | Xpo4 |
| 1460553_at | 4.623 | BF466605 | 1700025K23Rik |
| 1449021_at | 4.618 | NM_026308 | Rpp21 |
| 1437213_at | 4.618 | BG070110 | Nudt21 |
| 1431072_a_at | 4.614 | BB865814 | 2610529H08Rik |
| 1438947_x_at | 4.613 | BB459744 | Sema3f |
| 1441839_s_at | 4.61 | BB250824 | BC024814 |
| 1436294_at | 4.608 | AV337707 | Ankrd29 |
| 1450752_at | 4.604 | NM_009989 | Cyct |
| 1434135_at | 4.602 | BB107552 | B3galnt2 |
| 1423005_a_at | 4.597 | NM_019585 | Espn |
| 1434777_at | 4.596 | BG064871 | Lmyc1 |
| 1423833_a_at | 4.592 | BC018324 | Brp44 |
| 1456782_at | 4.589 | BB525604 | D1Ertd251e |
| 1422293_a_at | 4.587 | NM_134112 | Kctd1 |
| 1454119_at | 4.587 | AK010697 | Mknk1 |
| 1455890_x_at | 4.586 | BB709603 | Snrpn; LOC545062 |
| 1451377_a_at | 4.583 | BC025501 | Aaas |
| 1435966_x_at | 4.579 | BE953095 | Mrpl13 |
| 1418891_a_at | 4.577 | BB349707 | Rab3d |
| 1454102_at | 4.57 | AK017143 | 5031425E22Rik |
| 1433462_a_at | 4.564 | BB208212 | Pi4k2a |
| 1436889_at | 4.564 | BQ268470 | Gabra1 |
| 1453782_at | 4.562 | BI737125 | 3021401C12Rik |
| 1440603_at | 4.555 | BB073590 | |
| 1451370_at | 4.549 | BC027414 | |
| 1451607_at | 4.544 | AB039276 | Klk21 |
| 1443073_at | 4.543 | BB355954 | LOC545681 |
| 1459890_s_at | 4.539 | C79326 | 1110008P14Rik |
| 1417912_at | 4.536 | NM_025318 | 0610009E20Rik |
| 1438619_x_at | 4.533 | BB318221 | Zdhhc14 |
| 1436698_x_at | 4.529 | AV167328 | BC054438 |
| 1421640_a_at | 4.528 | NM_011529 | Tank |
| 1453386_at | 4.528 | AK008612 | Tusc1 |
| 1424944_at | 4.526 | BC024853 | Pcp2 |
| 1448954_at | 4.523 | NM_020610 | Nrip3 |
| 1422153_a_at | 4.522 | NM_026853 | Asb11 |
| 1451477_at | 4.518 | AV047635 | LOC545705; LOC545706 |
| 1437067_at | 4.517 | BM228625 | Phtf2 |
| 1430616_at | 4.513 | BB185833 | 4930528A17Rik |
| 1434032_at | 4.511 | BQ175381 | |
| 1419808_at | 4.506 | AU022131 | Cog4 |
| 1428488_at | 4.498 | BB646655 | Pigk |
| 1436926_at | 4.491 | AV333667 | Esrrb |
| 1423219_a_at | 4.49 | BM951442 | Mrpl49 |
| 1421280_at | 4.485 | Z36357 | Gabra1 |
| 1417163_at | 4.473 | NM_022019 | Dusp10 |
| 1416132_at | 4.467 | BB188557 | C920006C10Rik |
| 1450770_at | 4.465 | BC023359 | 3632451O06Rik |
| 1456500_at | 4.465 | AV232784 | Aph1b |
| 1448586_at | 4.461 | NM_015765 | Hspa14 |
| 1422897_at | 4.457 | NM_009203 | Slc22a12 |
| 1451272_a_at | 4.455 | BC016117 | 2510010F15Rik |
| 1458638_at | 4.451 | AI852796 | Mtdh |
| 1426496_at | 4.447 | AK017695 | Wdr55 |
| 1449752_at | 4.445 | AI596360 | 4930422J18Rik |
| 1428996_at | 4.443 | AK014774 | Gm1705 |
| 1440883_at | 4.439 | BM125576 | Usp6nl |
| 1422683_at | 4.428 | NM_022986 | Irak1bp1 |
| 1452291_at | 4.426 | AV375176 | Centd1 |
| 1441960_x_at | 4.423 | AV267590 | 5730494M16Rik |
| 1421230_a_at | 4.416 | BI696168 | Msi2h |
| 1433847_at | 4.415 | BB098407 | D330017J20Rik |
| 1430521_s_at | 4.412 | AW548480 | Cpne8 |
| 1456727_a_at | 4.41 | AW413676 | Csnk1d |
| 1433927_at | 4.408 | AW552571 | E430026A01Rik |
| 1453567_s_at | 4.404 | AK014997 | 2810441K11Rik |
| 1424847_at | 4.403 | M35131 | Nefh |
| 1419380_at | 4.403 | NM_033327 | Zfp423 |
| 1437810_a_at | 4.4 | AV311770 | Hbb-bh1 |
| 1451432_x_at | 4.399 | BC022729 | 2010004B12Rik |
| 1446566_at | 4.397 | BB461266 | Ap2b1 |
| 1417740_at | 4.394 | BB756370 | Cdc37l1 |
| 1425780_a_at | 4.393 | BC024352 | 0610041E09Rik |
| 1451998_at | 4.391 | BC024597 | 4930485D02Rik |
| 1417035_at | 4.391 | BI134670 | Sac3d1 |
| 1432096_at | 4.39 | AK010671 | Snrpn |
| 1447927_at | 4.388 | BG092512 | Mpa2l |
| 1457395_at | 4.381 | AW553048 | 5330421F07Rik |
| 1428308_at | 4.373 | AK003410 | Pdrg1 |
| 1434249_s_at | 4.371 | BB083438 | |
| 1423874_at | 4.368 | BC019463 | Wdr33 |

TABLE 20-continued

Top 1,000 cerebellar Purkinje (Pcp2) cell translated mRNAs enriched when compared to a reference sample

| ProbeSymbol | FEN | Genbank | GeneSymbol |
|---|---|---|---|
| 1424262_at | 4.364 | BC024599 | 2810003C17Rik |
| 1428568_at | 4.363 | BB376573 | B230217C12Rik |
| 1435510_at | 4.363 | BB283101 | Ppm1h |
| 1454572_at | 4.352 | AK013093 | 2810414N06Rik |
| 1423869_s_at | 4.352 | AF349659 | Txnrd3 |
| 1451548_at | 4.35 | BC027189 | Upp2 |
| 1418716_at | 4.347 | AK004037 | Mrps25 |
| 1426558_x_at | 4.334 | BB283527 | 3100002L24Rik |
| 1420596_at | 4.332 | NM_007583 | Cacng2 |
| 1441453_at | 4.328 | BB341122 | B930096L08Rik |
| 1454086_a_at | 4.324 | AK013416 | Lmo2 |
| 1429087_at | 4.323 | AK005245 | 1110054O05Rik |
| 1456163_at | 4.323 | AV127670 | 2700049P18Rik |
| 1457545_at | 4.321 | BB110572 | Shh |
| 1435956_at | 4.317 | BB277380 | A930004K21Rik |
| 1460133_at | 4.315 | BF607205 | Efna5 |
| 1437637_at | 4.315 | BE852433 | Phtf2 |
| 1452238_at | 4.311 | BB130716 | Hrb |
| 1436060_at | 4.31 | BB480659 | 0710005M24Rik |
| 1452374_at | 4.309 | BB315154 | Zfp322a |
| 1451385_at | 4.308 | BC010826 | 2310056P07Rik |
| 1421468_at | 4.29 | NM_008426 | Kcnj3 |
| 1449557_at | 4.289 | NM_025904 | 1600012F09Rik |
| 1421985_a_at | 4.288 | AI449084 | Eif4e2 |
| 1448699_at | 4.286 | NM_025317 | Mrpl54 |
| 1450095_a_at | 4.283 | NM_025421 | Acyp1 |
| 1423495_at | 4.272 | BE952632 | Decr2 |
| 1427039_at | 4.271 | AF057285 | Epn1 |
| 1416407_at | 4.269 | AI323543 | Pea15 |
| 1436349_at | 4.267 | BI408855 | 2700094K13Rik |

ProbeSymbol = Affymetrix probe identification corresponding to gene symbol; FEN = fold enrichment when compared to reference sample; Genbank = Genbank identification; GeneSymbol = official gene symbol.

TABLE 21

Probesets used as negative controls in the comparison of BACarray samples with the reference sample.

| Gene Symbol | Probe Symbol | Gene Symbol | Probe Symbol | Gene Symbol | Probe Symbol | Gene Symbol | Probe Symbol |
|---|---|---|---|---|---|---|---|
| Cnp1 | 1418980_a_at | Glul | 1426235_a_at | Apoe | 1432466_a_at | Slc1a3 | 1426340_at |
| Cnp1 | 1437341_x_at | Glul | 1426236_a_at | Apoe | 1444108_at | Slc1a3 | 1426341_at |
| Cnp1 | 1449296_a_at | Mbp | 1419646_a_at | Laptm5 | 1417721_s_at | Slc1a3 | 1439072_at |
| Cnp1 | 1460032_at | Mbp | 1433532_a_at | Laptm5 | 1426025_s_at | Slc1a3 | 1440491_at |
| Fthfd | 1424400_a_at | Mbp | 1436201_x_at | Laptm5 | 1436905_x_at | Slc1a3 | 1443749_x_at |
| Fthfd | 1424401_at | Mbp | 1451961_a_at | Laptm5 | 1447742_at | Slc1a3 | 1452031_at |
| Galc | 1420547_at | Mbp | 1454651_x_at | Laptm5 | 1459841_x_at | Vim | 1438118_x_at |
| Galc | 1449900_at | Mbp | 1456228_x_at | Slc1a2 | 1439940_at | Vim | 1450641_at |
| Galc | 1452907_at | Mog | 1448768_at | Slc1a2 | 1451627_a_at | Vim | 1456292_a_at |
| Gfap | 1426508_at | Plp | 1425467_a_at | Slc1a2 | 1457800_at | | |
| Gfap | 1426509_s_at | Plp | 1425468_at | Slc1a2 | 1458314_at | | |
| Gfap | 1440142_s_at | Plp | 1451718_at | Slc1a2 | 1459014_at | | |

GeneSymbol = official gene symbol; ProbeSymbol = Affymetrix probe identification corresponding to gene symbol.
Probesets with an average expression over 100 in the reference sample were plotted.

Example 13

Physiological Evaluation of TRAP Methodology Results

1) Overview

In order to evaluate the physiological significance of differential expression of genes associated with $GABA_A$ receptors in D1 striatonigral of mice treated with cocaine, mice were chronically treated with cocaine or vehicle (saline) and then $GABA_A$ receptor function was assayed electrophysiologically.

2) Brain Slice Preparation for Optical/Electrophysiological Study

Slices were obtained from 32- to 37-day-old BAC D1 or BAC D2 soluble eGFP-expressing transgenic mice (S. Falcon, R. Gentleman, Bioinformatics 23, 257-8 (2007)). All animals were handled in accord with Northwestern University ACUC and NIH guidelines. For chronic cocaine studies, mice were injected with 20 mg/kg cocaine or 100 µl saline once daily for fifteen days and brain slices were prepared 4 h after the last injection, as in the mRNA studies. Coronal slices containing the striatum were prepared at a thickness of 250 µm. The mice were deeply anesthetized with ketamine and Xylazine, transcardially perfused with oxygenated, ice cold, artificial cerebral spinal fluid (ACSF), and decapitated. Brains were rapidly removed and sectioned in oxygenated, ice-cold, ACSF using a Leica VT1000S vibratome (Leica Microsystems, Germany). The ACSF contained the following (in mM): 126 NaCl, 3 KCl, 2 $CaCl_2$, 1 $MgCl_2$, 25 $NaHCO_3$, 1.25 $NaH_2PO_4$, and 15.6 D-(+)-glucose. Unless otherwise noted, all chemicals and reagents were obtained from Sigma (St. Louis, Mo.). The slices were transferred to a holding chamber in which they were completely submerged in ACSF at 35° C. for 1 h, after which they were stored at room temperature (22° C.-23° C.) until whole-cell recording. All ACSF solutions were bubbled continuously with 95% $O_2$ and 5% $CO_2$ to maintain oxygenation and a pH≈7.4, and periodically checked to ensure≈300 mOsm/l.

3) Electrophysiological Analysis of GABAergic Synaptic Events

Whole-cell voltage-clamp recordings were performed using standard techniques. Individual slices were transferred to a submersion-style recording chamber on Olympus Optical (Melville, N.Y.) BX50WI microscope and continuously superfused with ACSF at a rate of 2-3 ml/min at 22° C.-23° C. Whole-cell voltage-clamp recordings were performed on striatal medium spiny neurons detected in the slice with the help of an infrared-differential interference contrast (IR-DIC) video microscope with an Olympus OLY-150 camera/controller system (Olympus, Japan). The following were added to the superfusion medium for all experiments to isolate mIPSCs: 50 µM 2-amino-5-phosphonopentanoic acid (AP-5, Tocris Cookson, Ellisville, Mo.) to block NMDA glutamate receptors, 5 µM 1,2,3,4-Tetrahydro-6-nitro2,3-dioxo-benzo[2] quinoxaline-7-sulfonamide (NBQX) to block AMPA/kainite glutamate receptors, and 1 µM tetrodotoxin (TTX, Alomone Labs, Jerusalem, Israel) to block sodium channels. Patch electrodes were made by pulling Sutter BF150-86-10 glass on a P-97 Flaming/Brown micropipette puller (Sutter Instrument, Novato, Calif.) and fire polished before recording. Pipette resistance was typically 2.5-4 Mf after filling with an internal solution containing the following (in mM): 140 CsCl, 1.5 MgCl2, 10 HEPES, 0.1 BAPTA-Cs, 5 QX-314, 2 ATP-Na2, 0.4 GTP-Na2, pH 7.25-7.3 adjusted with CsOH, 270-280 mOsm/L. Miniature IPSCs were recorded with a Multiclamp 700A amplifier, a Digidata 1322A 16-bit data acquisition system, and pClamp software version 8.2 (Molecular Devices, Union City, Calif.) in gap free mode. Neurons were voltage-clamped at −80 mV and allowed to reach a stable baseline (≈5 min) before mIPSCs were recorded for 7 min. Mini Analysis (Synaptosoft Inc., Fort Lee, N.J.) was used to analyze mIPSC amplitude, frequency, 10-90% rise time, decay time, and non-stationary noise analysis. A threshold of 5 times the root mean square baseline noise level (commonly≈20-25 pA) was set for event detection. Records were then visually inspected and all events triggered by noise were discarded. Frequency analysis was carried out on all mIPSCs that met threshold criteria. Events were then selected for amplitude, 10-90% rise time, and decay time analysis on the following criteria: 1) Events with 10-90% rise times faster than 1 ms were selected to minimize space clamp errors and electronic filtering; 2) Events with decay times faster than 50 ms were selected to minimize events in which multiple events precluded accurate decay time measurement. For non-stationary noise analysis, the same criteria for amplitude and mIPSCs kinetics were used followed by these additional criteria: 3) No multiple events in which the decay did not return to baseline; 4) Events had to have a stable baseline before the rise and after the end of the decay. Mean values of mIPSC measures were compared between groups with a t-test or Mann-Whitney rank sum test using Sigma Stat 3.0 (Systat Software Inc., Richmond, Calif.). Pooled data are presented as means±SE and box plots using IGOR 5.00 (WaveMetrics, Lake Oswego, Oreg.).

4) 2-photon Laser Scanning Microscopy (2PLSM)

Striatonigral (BAC D1) or striatopallidal (BAC D2) neurons expressing soluble eGFP (S. Falcon, R. Gentleman, Bioinformatics 23, 257-8 (2007)) in 275 m thick corticostriatal slices were identified by somatic eGFP fluorescence. eGFP 2PLSM green signals (500-550 nm) were acquired from eGFP+BAC Drd2 neurons using 810 nm excitation, while eGFP+BAC Drd1 neurons required 900 nm excitation. eGFP+MSNs were then patched using infrared-differential interference contrast (IR-DIC) video microscopy with a Hamamatsu C2400 Newvicon camera/controller system (Hamamatsu, Japan) and a 60×/0.9NA water-dipping lens. Patch electrodes were made by pulling BF150-86-10 glass on a P-97 Flaming/Brown micropipette puller (both from Sutter Instrument Co., Novato, Calif.). The pipette solution contained the following (in mM): 135 KMeSO4 (ICN Biomedicals Inc., Aurora, Ohio), 5 KCl, 10 HEPES, 2 MgATP, 0.2 Na2GTP, and 0.1 spermine, pH=7.25-7.3 with KOH, 270 mOsm/1. As measured in the bath, the pipette resistance was ~4 MΩ. Seals were formed in voltage-clamp mode on the cell somas with series resistance>1GΩ. After seal rupture in whole-cell configuration the series-resistance decreased to 10-15MΩ. Alexa 594 (50 μM, $Ca^{2+}$-insensitive red dye), for visualization of the dendrites, and Fluo-4 (200 M, $Ca^{2+}$-sensitive green dye), for measuring changes in intracellular dendritic $Ca^{2+}$, was dissolved in the internal pipette solution. eGFP fluorescence was below the threshold for detection in the dendrites and did not contribute background signal during calcium imaging. Thapsigargin was also added to the internal solution in some experiments to block ER-mediated $Ca^{2+}$ release. The thapsigargin was initially dissolved in DMSO at a concentration of 10 mM. This stock was then diluted 1000× in the internal recording solution. Following break in, the internal solution was allowed to approach diffusional equilibrium for at least 15 min prior to imaging. The cells were voltage clamped at −70 mV and monitored for somatic depolarization.

For the duration of the recordings, 2PLSM green and red signals (570-620 nm) were acquired using 810 nm excitation with 90 MHz pulse repetition frequency and ~250 fs pulse duration at the sample plane. A second puffer pipette containing sphingosine 1-phosphate (SIP, 10 μM) was positioned for focal dendritic application. The S1P was initially dissolved in DMSO at a concentration of 10 mM. This stock was then diluted 1000× into HEPES-buffered ACSF containing 4 mg/ml BSA, pH=7.4. Changes in dendritic $Ca^{2+}$ were measured by acquiring high magnification maximum projection images of dendrite segments 50-100 μm from the soma. These images were acquired with 0.17 μm² pixels and 2.2 μs dwell time and consisted of 10-20 images taken at 0.5 μm focal steps. The change in $Ca^{2+}$ was determined by calculating the percent change in fluorescence of the green dye normalized to the red dye (ΔG/R). Following $Ca^{2+}$ imaging, maximum projection images of the soma and dendritic field were acquired with 0.27 μm² pixels and 2.6 μs pixel dwell time and consisted of ~80 images taken at 0.7 μm focal steps.

The two-photon excitation source was a Chameleon-XR tunable laser system (705 nm to 980 nm, Coherent Laser Group, Santa Clara, Calif.). Laser average power attenuation was achieved with two Pockels cell electro-optic modulators (models 350-80 and 350-50, Con Optics, Danbury, Conn.). The two cells are aligned in series to provide enhanced modulation range for fine control of the excitation dose (0.1% steps over four decades). The laser-scanned images were acquired with a Bio-Rad Radiance MPD system (Hemel Hempstead, England, UK). The fluorescence emission was collected by external or non-de-scanned photomultiplier tubes (PMTs). The green fluorescence (500 to 550 nm) was detected by a bialkali-cathode PMT and the red fluorescence (570 nm to 620 nm) was collected by a multi-alkali-cathode (S20) PMT. The fluorescence was acquired in 16 bit photon counting mode. The laser light transmitted through the sample was collected by the condenser lens and sent to another PMT to provide a bright-field transmission image in registration with the fluorescent images. The stimulation, display, and analysis software was a custom-written shareware package, WinFluor and PicViewer (John Dempster, Strathclyde University, Glasgow, Scotland; UK).

5) Evaluation of Differential $GABA_A$ Receptor Function in D1 and D2 Following Chronic Cocaine Treatment Cocaine treatment increased the frequency of $GABA_A$ receptor miniature inhibitory postsynaptic currents (mIPSCs) in striatonigral neurons as presented in the following figures.

FIG. 31 showed that cocaine treatment increased the frequency of small amplitude GABAergic mIPSCs in BAC D1 striatonigral neurons. (a) Representative spontaneous mIPSCs traces from BAC D1 striatonigral neurons (expressing soluble eGFP under the D1 promoter) taken from mice treated for 15 days with saline or (b) cocaine (20 mg/kg/day). (c) Bar graph summary of mean mIPSC frequency showing a increase in BAC D1 striatonigral neuron mIPSCs frequency following cocaine treatment (Mann-Whitney Rank Sum Test, p<0.05, saline median=0.82 Hz, n=22; cocaine median=1.03 Hz, n=26). (d) Bar graph summary showing that the number of small amplitude mIPSCs (<75 pA) in equal length records (7 min) increased in BAC D1 striatonigral neurons following cocaine treatment (t-test, $p<0.05$, saline=79.4±18.2, n=22; cocaine=104.2±6.3, n=26). (e) Representative variance-mean current plots from saline treated and cocaine treated BAC D1 neurons suggesting that the cocaine-induced small amplitude events arise from synapses that have fewer GABAA receptors (N) per synapse but receptors with an unchanged unitary receptor conductance (g) (saline N=33, g=31 pS; cocaine N=27, g=30 pS). (f) Representative spontaneous mIPSCs traces from BAC D2 striatopallidal neurons following saline treatment for 15 days and (g) following cocaine treatment for 15 days. (h) Bar graph summary of mean mIPSC frequency in saline and cocaine treated neurons, showing no effect of treatment condition (t-test, $p>0.05$, saline=0.72±0.05 Hz, n=12; cocaine=0.78±0.07 Hz, n=16). (i) Bar graph summary showing that the number of small amplitude mIPSCs (<75 pA) in equal length records (7 min) was not altered by treatment condition in BAC D2 neurons (t-test, $p>0.05$, saline=68.1±9.7, n=12; cocaine=71.7±7.5, n=16). (j) Representative variance-mean current plots showing that cocaine treatment did not change in the number of receptors per synapse or the unitary receptor conductance in BAC D2 neurons (saline N=29, g=33 pS; cocaine N=31, g=29 pS).

In summary, FIG. 32 showed that cocaine treatment decreased the number of GABAA channels per synapse in BAC D1 striatonigral neurons. Box plot summaries showing mean mIPSCs kinetics and non-stationary noise analysis measures of individual striatonigral neurons taken from saline-treated control and 15-day treated cocaine BAC D1 mice. (a) Neither mean 10-90% rise times (t-test, $p>0.05$, Saline=0.64-0.008, n=22; Cocaine=0.65±0.006, n=26) nor (b) mean decay times (ttest, $p>0.05$, Saline=17.3±0.5, n=22; Cocaine=17.0±0.5, n=26) were different between groups. Non-stationary noise analysis of mIPSCs demonstrated no change between groups in the (c) mean unitary conductance (g) of GABAA receptors of striatonigral neurons (t-test, $p>0.05$, Saline g=31.1±1.6, n=22; Cocaine g=30.8±1.2, n=26), and a decrease in the (d) mean number of channels per synapse in striatonigral neurons taken from cocaine treated BAC D1 mice (t-test, $p<0.05$, Saline N=33.1±1.4, n=22; Cocaine N=29.3±1.0, n=26).

In summary, FIG. 33 showed that cocaine treatment did not alter GABAergic mIPSCs kinetics or GABAA receptor number per synapse or unitary receptor conductance in BAC D2 striatopallidal neurons. Box plot summaries showing mean mIPSCs kinetics and non-stationary noise analysis measures of individual striatopallidal neurons taken from saline-treated control and 15-day treated cocaine BAC D2. (a) Neither mean 10-90% rise times (t-test, $p>0.05$, Saline=0.65±0.007, n=12; Cocaine=0.64±0.010, n=16) nor (b) mean decay times (t-test, $p>0.05$, Saline=18.0±1.0, n=12; Cocaine=18.0±0.5, n=16) were different between groups. Non-stationary noise analysis of mIPSCs demonstrated no change between groups in the (c) mean unitary conductance (g) of GABAA receptors of striatopallidal neurons (t-test, $p>0.05$, Saline g=30.7±1.5, n=12; Cocaine g=30.3±1.2, n=16) or in the (d) mean number of channels per synapse in striatopallidal neurons taken from cocaine treated BAC D2 mice (t-test, $p>0.05$, Saline N=33.8±2.7, n=12; Cocaine N=33.0±1.6, n=16).

Example 14

Molecular Phenotyping and Translational Profiling of Cerebellar Cells

1) Overview

The cerebellum is a region of the brain that plays a role in the integration of sensory perception and motor control. In order to coordinate motor control, there are several neural pathways linking the cerebellum with the cerebral motor cortex (which sends information to the muscles causing them to move) and the spinocerebellar tract (which provides proprioceptive feedback on the position of the body in space). The cerebellum integrates these pathways using constant feedback on body position to fine-tune motor movements (Fine E J, Ionita C C, Lohr L (2002). "The history of the development of the cerebellar examination". Semin Neurol 22 (4): 375-84. doi:10.1055/s-2002-36759). Studies show that the cerebellum also serves other functions, such as cognitive functions, including attention and the processing of language, music, and other sensory temporal stimuli (Rapp, Brenda (2001). The Handbook of Cognitive Neuropsychology: What Deficits Reveal about the Human Mind. Psychology Press, 481).

Damage to the cerebellum typically is not so debilitating as to cause paralysis, but rather presents as feedback deficits resulting in disorders in fine movement, equilibrium, posture, and motor learning. Ataxia is a complex of symptoms, generally involving a lack of coordination, that is often found in disease processes affecting the cerebellum. To identify cerebellar problems, the neurological examination includes assessment of gait (a broad-based gait being indicative of ataxia), finger-pointing tests and assessment of posture. Structural abnormalities of the cerebellum (hemorrhage, infarction, neoplasm, degeneration) may be identified on cross-sectional imaging. Magnetic resonance imaging is the modality of choice, as computed tomography is insufficiently sensitive for detecting structural abnormalities of the cerebellum (Gilman S (1998). "Imaging the brain. Second of two parts". N. Engl. J. Med. 338 (13): 889-96).

2) BACarray Mice Expressing eGFP in Individual Cerebellar Cell Types

There are multiple cell layers and several cerebellar cell types. The innermost granular layer contains the cell bodies three types of cells: the numerous and tiny granule cells, the larger Golgi cells and the medium sized neuronal unipolar brush cells. The middle Purkinje layer contains only one type neuron, the Purkinje cell. Purkinje cells are the primary integrative neurons of the cerebellar cortex and provide its sole output. Bergmann glia, a type of glia also known as radial epithelial cells are astrocytes in the cerebellum that have their cell bodies in the Purkinje cell layer and processes that extend into the molecular layer, terminating with bulbous endfeet at the pial surface (Eccles J. C Ito, M and Szentagothai J. (1967). "The cerebellum as a neuronal machine". Springer Verlag; Llinds, R., Baker, R. and Sotelo, C. (1974). "Electrotonic coupling between neurons in cat inferior olive". J. Neurophysiol 37:.560-571). The outermost layer of the cerebellar cortex contains two types of inhibitory interneurons: the stellate and basket cells. It also contains the dendritic arbors of Purkinje neurons and parallel fiber tracts from the granule cells. BACarray mice with specific expression patterns in specific cerebellar cell types can be created: expression of tagged ribosomal protein under the control of a regulatory region from the Neurod1 loci to label cerebellar granule cells; expression of tagged ribosomal protein under the control of a regulatory region from the Grm2 loci to label cerebellar inner golgi neurons; expression of tagged ribosomal protein under the control of a regulatory region from the Grp loci to label unipolar brush cells; expression of tagged ribosomal protein under the control of a regulatory region from the Pttg3 loci to label cerebellar astrocytes; and expression of tagged ribosomal protein under the control of a regulatory region from the Lypd6 loci to label stellate, basked cells.

3) Translational Profiling and Molecular Phenotyping of Cells from AT Mice

Ataxia telangiectasia (AT) is a disease whose principle features includes ataxia, development of lymphocytic tumors and cerebellar degeneration (P. J. McKinnon, *EMBO Rep* 5, 772 (2004); F. Gumy-Pause, P. Wacker, A. P. Sappino, *Leukemia* 18, 238 (2004); L. Farina et al., *J Comput Assist Tomogr* 18, 724 (1994); F. Tavani et al., *Neuroradiology* 45, 315 (2003)). AT is caused by recessive loss of function mutations in the gene encoding ataxia telangiectasia mutated (ATM), a ubiquitously expressed nuclear protein kinase involved in the DNA damage response and cell cycle control (K. Savitsky et al., *Science* 268, 1749 (1995); R. T. Abraham, *Genes Dev* 15, 2177 (2001); Y. Shiloh, *Nat Rev Cancer* 3, 155 (2003); M. F. Lavin, S. Kozlov, Cell Cycle 6, 931 (2007); S. Matsuoka et al., *Science* 316, 1160 (2007)). Atm knockout mice display many of the characteristics of the human disorder, including sensitivity to irradiation and lymphocytic tumor formation (C. Barlow, K. D. Brown, C. X. Deng, D. A. Tagle, A. Wynshaw-Boris, *Nat Genet* 17, 453 (1997); K. H. Herzog, M. J. Chong, M. Kapsetaki, J. I. Morgan, P. J. McKinnon, *Science* 280, 1089 (1998); A. Elson et al., *Proc Natl Acad Sci USA* 93, 13084 (1996); Y. Xu et al., *Genes Dev* 10, 2411 (1996); P. R. Borghesani et al., *Proc Natl Acad Sci USA* 97, 3336 (2000)). However, one of the distinguishing features of AT, the degeneration of cerebellar Purkinje cells, does not occur in the mouse model of the disease. Since clinical evidence of substantial Purkinje cell loss in AT patients is not seen until affected children reach several years of age (R. A. Gatti et al., *Clin Rev Allergy Immunol* 20, 87 (2001)), and since the average lifespan of a mouse is less than two years, it is possible that the pathogenic process simply does not have enough time to result in Purkinje cell degeneration in the AT mouse model. In one embodiment, ribosomes in specific cerebellar cell types in a mouse model of AT can be molecularly labeled (Doyle et al., submitted).

Molecular phenotyping and translational profiling of Purkinje cells in Atm knockout mice, hereafter Atm −/− mice, could reveal changes in response to the mutation. This enables the identification of genes that are differentially regulated in a cell-type specific manner, by employing the BACarray strategy and TRAP methods. Changes in response to the Atm mutation were analyzed in Purkinje cells and Bergmann glia, a specialized glial cell population with similar abundance and anatomical distribution as Purkinje cells.

Transgenic BACarray mice expressing the eGFP-L10a fusion protein were prepared using the Purkinje cell protein 2 (Pcp2) and Septin 4 (Sept4) BAC vectors described by the GENSAT project (found on the world wide web at gensat.org; S. Gong et al., *Nature* 425, 917 (2003)) (FIG. 34). BAC transgenic animals were generated using modified BAC constructs as previously described (J. Zahringer, B.S. Baliga, H. N. Munro, Proc Natl Acad Sci US A 73, 857-61 1976)) using either the Pcp2 gene or the Septin 4 gene as drivers for the ribosomal protein L10 enhanced green fluorescent protein (eGFP L 10a) construct in the Purkinje cells, and Bergmann glia, respectively. In other embodiments, other drivers of cell-type specific gene expression could be used, and is in no means meant to be limiting. Transgenic lines were generated and genotyping confirmed using conventional techniques. Pcp2 and Sept4 BACarray transgenic animals were then crossed with Atm+/ animals. After two generations, the Pcp2 and Sept4 BACarray constructs could be recovered in Atm +/+or Atm −/− animals. Heterozygote Atm +/ littermates were bred to generate wildtype +/+and knockout animals lmmunohistochemical and double immunofluorescence staining of sections from the BACarray mice is presented in FIG. 35. Panel A demonstrated the expression of the eGFP-L10a fusion specifically in the soma and primary dendrites of cerebellar Purkinje cells in the Pcp2 line, and panel B demonstrated its expression in Bergmann glia in the Sept4 line.

To ensure that Purkinje cell and Bergmann glial cell mRNAs could be enriched from the Pcp2 and Sept4 BACarray transgenic lines, microarray data were collected from each of the BACarray lines in triplicate by affinity purification of eGFP-L10a containing polysomes. In each case, the levels of expression of immuno-precipitated (IP) mRNAs were compared to their expression levels in the unbound fraction to determine their enrichment in Purkinje cells or Bergmann glia. Scatter plots (FIG. 36) of these data revealed that thousands of mRNAs could be enriched by affinity purification of polysomes from either the Pcp2 or Sept 4 BACarray cerebella. As expected, known Purkinje cell specific mRNAs were specifically enriched in IP samples from the Pcp2 BACarray mice ( Table 22), and known Bergmann glial enriched mRNAs were specifically enriched in the IP samples from the Sept4 BACarray mice (Table 23). The data establish translational profiles and molecular phenotypes of these two cerebellar cell types.

Microarray data were imported into Genespring GX 7.3.1 (Agilent Technologies, Santa Clara, Calif.) as GeneChip CEL files. For each experiment, Atm+/+ and Atm −/− data sets were imported together and normalized using GC RMA. For total cerebellum experiments, four replicates for each condition (Atm+/+ or Atm −/−) were used, for the Septin4 experiments, five replicates for each condition were used, and for the Pcp2 experiments, six replicates were used for each condition. Once imported, experiments were viewed as scatter plots for further analysis. For PCP2 and Septin 4 experiments, Atm+/+ and Atm −/− data were further normalized per chip using the Affymetrix hybridization controls as positive control genes and divided by the constant value of 0.001. In order to generate lists of regulated genes, data were filtered on expression with a cutoff of 25 and filtered on fold change with a cutoff of 1.5. One-way ANOVA analysis was used to determine statistical significance with a p value of ≤0.05.

TABLE 22

Purkinje Cell Positive Control Genes.
Genes known to be specifically expressed in Purkinje cells were analyzed by scatter plot analyses with data from both Pcp2 and Septin4 lines. These genes are enriched in the Pcp2 IP data relative to total cerebellum (Unb), whereas they are underrepresented in the Septin4 IP data relative to total cerebellum (Unb).

| Gene Symbol | GenBank Accession | Affymetrix ID | Fold Change, PCP2 IP vs. Unb | Fold Change, Septin4 IP vs. Unb |
| --- | --- | --- | --- | --- |
| Slc1a6 | NM_009200 | 1418933_at | 14.76 | 0.126 |
| Kcnip1 | NM_027398 | 1416785_at | 12.26 | 0.627 |
| Pcp4l1 | AV337888 | 1452913_at | 11.59 | 0.959 |
| Car8 | BC010773 | 1424958_at | 11.37 | 0.0251 |
| Cdr2 | NM_007672 | 1417430_at | 10.23 | 0.0651 |
| Trpc3 | NM_019510 | 1417577_at | 9.951 | 0.0976 |
| Kcnip1 | NM_027398 | 1448459_at | 9.694 | 0.456 |
| Pcp2 | NM_008790 | 1419084_a_at | 9.553 | 0.173 |
| Kitl | BB815530 | 1448117_at | 9.02 | 0.599 |
| Kitl | M64262 | 1426152_a_at | 7.551 | 1.116 |
| Plxdc1 | AF378760 | 1424902_at | 6.91 | 0.0552 |
| Kitl | BB815530 | 1415855_at | 6.547 | 1.077 |
| Pcp2 | NM_008790 | 1419085_at | 6.21 | 0.287 |
| Grid2ip | NM_133355 | 1450310_at | 5.514 | 0.414 |
| Calb1 | BB246032 | 1448738_at | 4.769 | 0.0384 |
| Thy1 | AV028402 | 1423135_at | 4.488 | 0.167 |
| Kitl | AW551461 | 1440621_at | 3.836 | 0.985 |
| Dab1 | NM_010014 | 1421100_a_at | 3.085 | 0.346 |
| Car8 | X61397 | 1427482_a_at | 2.984 | 0.0834 |
| Pcp4 | NM_008791 | 1460214_at | 2.434 | 0.642 |
| Dab1 | BB644109 | 1427308_at | 2.388 | 0.151 |
| Calb1 | BB246032 | 1417504_at | 1.824 | 0.0755 |
| Grid2 | BG075811 | 1459245_s_at | 1.816 | 1.032 |
| Kcnip1 | AK013657 | 1454504_at | 1.752 | 1.223 |
| Dab1 | BB429377 | 1435577_at | 1.659 | 0.122 |
| Slc1a6 | NM_009200 | 1418933_at | 14.76 | 0.126 |
| Dab1 | BB644109 | 1427307_a_at | 1.529 | 0.774 |

TABLE 23

Bergmann Glial Cell Positive Control Genes
Genes known to be expressed in Bergmann glial cells were analyzed by scatter plot analyses with data from both Septin4 and Pcp2 lines. These genes are robustly enriched in the Septin4 IP data relative to data from total cerebellum (Unb). Conversely, these genes are underrepresented in data from Pcp2 IP relative to total cerebellum (Unb).

| Gene Symbol | GenBank Accession | Affymetrix ID | Fold Change, Septin4 IPvsUnb | Fold Change, PCP2 IPvsUnb |
| --- | --- | --- | --- | --- |
| Vim | AV147875 | 1456292_a_at | 20.41 | 0.0313 |
| Vim | M24849 | 1450641_at | 13.29 | 0.053 |
| Mlc1 | NM_133241 | 1448139_at | 13.07 | 0.0218 |
| Slc1a3 | BB357585 | 1426340_at | 12.85 | 0.0635 |
| Phgdh | L21027 | 1426657_s_at | 12.32 | 0.106 |
| Vim | AV147875 | 1438118_x_at | 12.31 | 0.0556 |
| Slc1a3 | BB357585 | 1426341_at | 11.79 | 0.268 |
|  | NM_009115 | 1419383_at | 10.77 | 0.039 |
| 4-Sep | AW208509 | 1455422_x_at | 10.48 | 0.415 |
| Slc1a3 | BB357585 | 1452031_at | 9.359 | 0.0409 |
| Fabp7 | NM_021272 | 1450779_at | 8.724 | 0.0966 |
| Phgdh | AV216768 | 1437621_x_at | 8.696 | 0.0343 |
| 4-Sep | NM_011129 | 1448729_a_at | 8.277 | 0.474 |
| Ednrb | BF100813 | 1437347_at | 7.807 | 0.103 |
| Slc1a3 | BB308757 | 1439072_at | 7.424 | 0.537 |
| Slc1a3 | BB085413 | 1443749_x_at | 6.165 | 0.102 |
| Gfap | BB183081 | 1426508_at | 6.075 | 1.031 |
| Gsta4 | NM_010357 | 1416368_at | 5.171 | 0.0499 |
| Ednrb | BB451714 | 1423594_a_at | 5.026 | 0.153 |
| Gfap | BB183081 | 1426509_s_at | 4.77 | 0.408 |
| Gfap | BB750040 | 1440142_s_at | 4.311 | 0.0098 |
| Ednrb | BB770914 | 1426314_at | 3.959 | 0.651 |
| Phgdh | BB495884 | 1456584_x_at | 3.039 | 0.105 |
| Phgdh | L21027 | 1426658_x_at | 2.927 | 0.997 |
| Mthfd1 | AV215673 | 1436704_x_at | 2.072 | 0.663 |
| Phgdhl1 | BC024467 | 1423928_at | 2.006 | 0.576 |
| Phgdhl1 | BC024467 | 1423929_at | 1.844 | 1.363 |
| Nes | AI413223 | 1449022_at | 1.794 | 0.732 |

TABLE 23-continued

Bergmann Glial Cell Positive Control Genes
Genes known to be expressed in Bergmann glial cells were analyzed by scatter plot
analyses with data from both Septin4 and Pcp2 lines. These genes are robustly enriched
in the Septin4 IP data relative to data from total cerebellum (Unb). Conversely, these
genes are underrepresented in data from Pcp2 IP relative to total cerebellum (Unb).

| Gene Symbol | GenBank Accession | Affymetrix ID | Fold Change, Septin4 IPvsUnb | Fold Change, PCP2 IPvsUnb |
|---|---|---|---|---|
| Mthfd1 | NM_138745 | 1415917_at | 1.786 | 0.759 |
| Mthfd1 | NM_138745 | 1415916_a_at | 1.773 | 0.32 |

4) Loss of ATM Function

Pcp2 and Sept4 BACarray transgenic animals were then crossed with Atm+/− animals. After two generations, the Pcp2 and Sept4 BACarray constructs could be recovered in Atm+/+ or Atm −/− animals. To determine whether Purkinje cells respond differently than do Bergmann glia to loss of ATM function, microarray data were collected from total cerebellum, from Purkinje cells and from Bergmann glial cells using 6-8 week old Pcp2 and Sept4 wt and Atm −/− BACarray mice. Lists of genes regulated in Atm −/− animals were generated by identifying all genes with expression values greater than 25 and at least a 1.5 fold difference in expression between wt and Atm −/− animals. One-way ANOVA analysis with p-value cutoff of 0.05 was used to select for significance. Scatter plot and Venn diagram analyses were used to identify genes whose expression changed in response to the Atm mutation in whole cerebellum, Purkinje cells or Bergmann glia (FIG. 37). Data for individual genes are presented in Table 24-Table 29.

The majority of genes whose expression is altered in Purkinje cells of Atm −/− mice (65/89) can not be detected by microarray analysis of total cerebellar mRNA. Moreover, only 17 of the 89 mRNAs whose expression changes in Purkinje cells in Atm −/− animals are also changed in Bergmann glial cells. Finally, the levels of expression of 94 genes are altered specifically in Atm −/− Bergmann glia versus Purkinje cells. The responses of specific cell types to the Atm mutation are largely distinct, and that translational profiling and molecular phenotyping of specific cell types using the BACarray strategy can reveal responses that can not be observed by analysis of histologically complex tissues.

TABLE 24

Genes Upregulated in Atm −/− Total Cerebellum Data
Genes which are upregulated in Atm −/− cerebellum relative to
Atm +/+ cerebellum. Microarray data from Atm +/+ and
Atm −/− cerebellum were compared in scatter plots, and filtered
on expression of at least 25 and on fold change of at least 1.5, with
Atm −/− values greater than Atm +/+. Enriched genes were
selected based on one-way ANOVA analysis with a p-value of ≤0.05.

| Gene Symbol | GenBank Accession | Affymetrix ID | Fold Change |
|---|---|---|---|
| AI451250 | AI451250 | 1447436_at | 21.3 |
| Scn2b | AK013326 | 1430648_at | 16.86 |
| Nedd4 | NM_010890 | 1421955_a_at | 6.112 |
| 2010007H06Rik | BB483585 | 1446748_at | 5.587 |
| MGI: 2136405 | BB272589 | 1440386_at | 3.752 |
| C920006O11Rik | BB552195 | 1435704_at | 3.486 |
| Ddx6 | BC021452 | 1424598_at | 3.371 |
| Opcml | BB383296 | 1457446_at | 2.273 |
| Cyp11a1 | C87524 | 1439947_at | 2.113 |
| Btbd15 | BC027138 | 1427271_at | 2.048 |
| Mod1 | BC011081 | 1416632_at | 2.032 |
| Cgnl1 | BB409331 | 1452309_at | 1.941 |
| Loh11cr2a | BC004727 | 1426221_at | 1.914 |
| Arcn1 | BB757123 | 1436062_at | 1.829 |
| AI835735 | AI835735 | 1459716_at | 1.817 |
| Map2k6 | BB261602 | 1426850_a_at | 1.783 |
| Nedd4 | BG073415 | 1451109_a_at | 1.757 |
| Grid2 | NM_008167 | 1421435_at | 1.749 |
| Hif3a | AF416641 | 1425428_at | 1.747 |
| Arid5b | BB699910 | 1420973_at | 1.747 |
| LOC546041 | AI585679 | 1436740_at | 1.744 |
| Thy1 | AV028402 | 1423135_at | 1.727 |
| AI593442 | BF658761 | 1444026_at | 1.697 |
| Usp2 | AI553394 | 1417168_a_at | 1.697 |
| Enpp3 | BB039510 | 1439260_a_at | 1.693 |
| Cdkn1a | AK007630 | 1424638_at | 1.688 |
| Tspan18 | AK011742 | 1429856_at | 1.665 |
| Mecr | NM_025297 | 1417097_at | 1.656 |
| D13Ertd787e | AU020421 | 1420098_s_at | 1.645 |
| Bcl6 | U41465 | 1421818_at | 1.644 |
| Arid5b | BB079486 | 1434283_at | 1.64 |
| A730090H04Rik | AV251751 | 1445913_at | 1.63 |
| Sgk | NM_011361 | 1416041_at | 1.628 |
| 1500041N16Rik | NM_026399 | 1418732_s_at | 1.602 |
| Dlat | AV336908 | 1426265_x_at | 1.589 |
| A430108E01Rik | AW541326 | 1438049_at | 1.584 |
| Hif3a | BB486740 | 1446708_at | 1.573 |
| Syt13 | BE648447 | 1451045_at | 1.564 |
| Mtap6 | BM233608 | 1457316_at | 1.555 |
| Cald1 | AK014755 | 1433147_at | 1.549 |
| Elmo1 | BC024727 | 1424523_at | 1.547 |
| Arf2 | AV023312 | 1438661_a_at | 1.544 |
| 2610005L07Rik | BB471300 | 1437717_x_at | 1.534 |
| AI449310 | AW552116 | 1455451_at | 1.523 |
| Scn2b | BQ175340 | 1436134_at | 1.522 |
| Mvp | NM_080638 | 1448618_at | 1.521 |
| Pcdha11 | BB265776 | 1451769_s_at | 1.518 |
| Txnrd3 | AI196535 | 1449623_at | 1.516 |
| Frmd6 | BC019939 | 1451264_at | 1.513 |
| 4732464A07Rik | BB004948 | 1459951_at | 1.51 |
|  | BB627097 | 1442019_at | 1.509 |
| 8430436O14Rik | AK018466 | 1452761_a_at | 1.508 |

TABLE 25

Genes Downregulated in Atm −/− Total Cerebellum Data
Genes which are downregulated in Atm −/− cerebellum relative to
Atm +/+ cerebellum. Microarray data from Atm +/+ and Atm −/−
cerebellum were compared in scatter plots, and filtered on
expression values of at least 25 and selected for genes with wt
values at least 1.5 fold greater than Atm −/− values.
Differential genes were selected based on one-way ANOVA
analysis with a p-value of ≤0.05.

| Gene Symbol | GenBank Accession | Affymetrix ID | Fold Change |
|---|---|---|---|
| Tmod3 | AK017725 | 1423088_at | 0.66 |
| Leo1 | BG065311 | 1455293_at | 0.658 |
| Sirt4 | AK016400 | 1426847_at | 0.656 |
| Kcna6 | AV328356 | 1441049_at | 0.656 |
|  | BG066504 | 1435998_at | 0.655 |
| Osbpl6 | AI851164 | 1449627_at | 0.654 |
| Cryab | AV016515 | 1434369_a_at | 0.653 |
| Malat1 | AW012617 | 1427285_s_at | 0.646 |
| Ddx42 | AW763628 | 1443719_x_at | 0.642 |
|  | AV372127 | 1438754_at | 0.639 |
| 6430514L14Rik | BC025646 | 1425213_at | 0.637 |
| Smarce1 | AK018493 | 1422675_at | 0.632 |
| Dnaja4 | BQ176119 | 1434196_at | 0.63 |
| 1700047I17Rik | BB516625 | 1445334_at | 0.629 |
| 2010309E21Rik | BF017486 | 1441796_at | 0.629 |
| Htr2c | BQ174268 | 1435513_at | 0.625 |
| Dpy19l1 | BE949451 | 1433759_at | 0.615 |
| Gpr153 | AK004377 | 1426973_at | 0.613 |
| Ncam2 | AF001287 | 1425301_at | 0.602 |
| 2310004I03Rik | BM939621 | 1428698_at | 0.598 |
| Ier2 | NM_010499 | 1416442_at | 0.597 |
| Cd80 | BQ175573 | 1440592_at | 0.591 |
| Vps11 | BB322416 | 1441922_x_at | 0.591 |
| 1110037N09Rik | BG143502 | 1438216_at | 0.588 |
| Gcl | BM239632 | 1438888_at | 0.586 |
| Nrip1 | BB041915 | 1454295_at | 0.586 |
| Tmod2 | AK018223 | 1430153_at | 0.582 |
| Rfxdc2 | BB148972 | 1460567_at | 0.577 |
| A130022J15Rik | BI149851 | 1433671_at | 0.577 |
| Pou3f2 | BE991235 | 1457734_at | 0.567 |
| Tmem25 | BB245618 | 1436644_x_at | 0.562 |
| Phf20l1 | BB268102 | 1454939_at | 0.556 |
| Mcam | NM_023061 | 1416357_a_at | 0.552 |
| Aph1c; Aph1b | AK002310 | 1429466_s_at | 0.543 |
| Cryab | NM_009964 | 1416455_a_at | 0.541 |
| Fmr1 | AF170530 | 1452550_a_at | 0.531 |
| B3galt1 | AV328619 | 1441396_at | 0.516 |
| 4833427G06Rik | AK014780 | 1430762_at | 0.496 |
| Pts | NM_011220 | 1450660_at | 0.467 |
| BC027092 | BB445523 | 1435676_at | 0.43 |
| BC034204 | BB830346 | 1433661_at | 0.425 |
| BC038167 | BB211614 | 1458104_a_at | 0.422 |
| Ptch2 | BB530125 | 1457256_x_at | 0.415 |
| Dixdc1 | BC024834 | 1425256_a_at | 0.415 |
| Fxyd6 | AB032010 | 1417343_at | 0.369 |
| Bace1 | AF200346 | 1421825_at | 0.356 |
| Pdgfd | BB428671 | 1456532_at | 0.34 |
| Lrrc49 | BB484412 | 1447954_at | 0.327 |
| Tipin | BB796715 | 1459720_x_at | 0.277 |
| C030014I23Rik | AK021081 | 1453044_at | 0.265 |
| 2310030G06Rik | NM_025865 | 1449357_at | 0.238 |
| Rps25 | BM729504 | 1430978_at | 0.129 |
| Ppcdc | BB329391 | 1424336_at | 0.103 |

TABLE 26

Genes Upregulated in Atm −/− Septin4 IP Data
Genes which are upregulated in Atm −/− relative to Atm +/+
in the Septin4 experiments. Microarray data from Atm +/+ and
Atm −/− Septin4 IPs were compared in scatter plots, and filtered
on expression values of at least 25 and with Atm −/− values at least 1.5
fold greater than Atm +/+. Enriched genes were selected based on
one-way ANOVA analysis with a p-value of ≤0.05.

| Gene Symbol | GenBank Accession | Affymetrix ID | Fold Change |
|---|---|---|---|
| 2010007H06Rik | BB483585 | 1446748_at | 14.16 |
| Nedd4 | NM_010890 | 1421955_a_at | 4.926 |
| Bmp5 | AV032115 | 1455851_at | 4.228 |
| C920006O11Rik | BB552195 | 1435704_at | 3.964 |
| Scn2b | AK013326 | 1430648_at | 3.629 |
| AI451250 | AI451250 | 1447436_at | 3.451 |
| Ddx6 | BC021452 | 1424598_at | 2.672 |
| Bmp5 | NM_007555 | 1421282_at | 2.57 |
| Bmp5 | NM_007555 | 1421283_at | 2.44 |
| Ccl27 | NM_011336 | 1419188_s_at | 2.179 |
|  | BB520860 | 1458145_at | 2.178 |
| Tle1 | NM_011599 | 1422751_at | 1.973 |
| Loh11cr2a | BC004727 | 1426221_at | 1.957 |
| Kcna4 | BB131475 | 1438613_at | 1.955 |
| Mod1 | BC011081 | 1416632_at | 1.942 |
| MGI: 2136405 | BB272589 | 1440386_at | 1.866 |
|  | AI467657 | 1442025_a_at | 1.864 |
| Cebpd | BB831146 | 1423233_at | 1.846 |
| Btbd15 | BC027138 | 1427271_at | 1.777 |
| Tpm1 | BM232388 | 1456623_at | 1.767 |
| Wee1 | NM_009516 | 1416773_at | 1.621 |
| D15Ertd366e | AV114522 | 1450629_at | 1.579 |
| 4832420M10 | BB012037 | 1440990_at | 1.57 |
| Hhip | NM_020259 | 1421426_at | 1.547 |
| 4930466F19Rik | AV044111 | 1432648_at | 1.541 |
| Il11ra1; Il11ra2 | BC004619 | 1417505_s_at | 1.52 |
| MGI: 1921571 | AK011357 | 1426612_at | 1.512 |

TABLE 27

Genes Downregulated in Atm −/− Septin4 Data
Genes which are downregulated in Atm −/− relative to Atm +/+
in the Septin4 experiments. Microarray data from Atm +/+ and
Atm −/− Septin4 IPs were compared in scatter plots, and filtered on
expression values of at least 25 and selected for genes with Atm +/+
values at least 1.5 fold greater than Atm −/− values. Differential
genes were selected based on one-way ANOVA analysis with a
p-value of ≤0.05.

| Gene Symbol | GenBank Accession | Affymetrix ID | Fold Change |
|---|---|---|---|
| Aak1 | AW121504 | 1441782_at | 0.667 |
|  | AI503515 | 1437979_at | 0.666 |
| Nmnat1 | AF260924 | 1425773_s_at | 0.663 |
|  | BM940493 | 1445699_at | 0.663 |
| Dpy19l1 | BE949451 | 1433759_at | 0.663 |
| Jmjd3 | BB494168 | 1447612_x_at | 0.662 |
| Zfyve20 | BC017622 | 1429517_at | 0.662 |
| 2410076I21Rik | AV216663 | 1441957_x_at | 0.66 |
| Tln2 | AV270892 | 1429111_at | 0.657 |
| Hdlbp | C77256 | 1449615_s_at | 0.657 |
| Fbxo5 | AK011820 | 1429499_at | 0.657 |
| Ddc | AF071068 | 1426215_at | 0.656 |
| Hmg20a | AI987819 | 1428920_at | 0.649 |
| Pcdhb12 | NM_053137 | 1422877_at | 0.649 |
| Zcchc3 | AV140894 | 1428401_at | 0.647 |
| Vps11 | AK004695 | 1428110_x_at | 0.647 |
| Itsn1 | AA172344 | 1452338_s_at | 0.646 |
| LOC545039 | BB099075 | 1440815_x_at | 0.646 |
| 2810452K22Rik | AK007812 | 1454253_at | 0.644 |
| Zdhhc24 | BB271151 | 1428278_at | 0.644 |
|  | BB354954 | 1444359_at | 0.644 |
| Sstr3 | BQ174132 | 1441603_at | 0.641 |
| 4933427G17Rik | AK016951 | 1431905_s_at | 0.638 |
| Calml4 | AY061807 | 1424713_at | 0.637 |
| Tbl3 | BC019504 | 1415750_at | 0.636 |
| A830053O21Rik | BB271275 | 1446501_at | 0.635 |

TABLE 27-continued

Genes Downregulated in Atm −/− Septin4 Data
Genes which are downregulated in Atm −/− relative to Atm +/+ in the Septin4 experiments. Microarray data from Atm +/+ and Atm −/− Septin4 IPs were compared in scatter plots, and filtered on expression values of at least 25 and selected for genes with Atm +/+ values at least 1.5 fold greater than Atm −/− values. Differential genes were selected based on one-way ANOVA analysis with a p-value of ≤0.05.

| Gene Symbol | GenBank Accession | Affymetrix ID | Fold Change |
|---|---|---|---|
| Car7 | BB193643 | 1443824_s_at | 0.634 |
| Zfp316 | AV367169 | 1444528_at | 0.63 |
| 4833424O15Rik | BB346520 | 1429249_at | 0.629 |
| 2310076O21Rik | BC017618 | 1451304_at | 0.627 |
| Dusp16 | BB121278 | 1440615_at | 0.627 |
| Tgoln1 | AI314055 | 1423308_at | 0.625 |
| Sv2a | BC026494 | 1423406_at | 0.625 |
| Map3k10 | BG070411 | 1440500_at | 0.624 |
| Foxp1 | BM220880 | 1435221_at | 0.623 |
| Bace1 | AF200346 | 1421825_at | 0.623 |
| Nr2f2 | AI527205 | 1436475_at | 0.619 |
|  | AV028487 | 1457337_at | 0.617 |
| 1110025F24Rik | AK012340 | 1453562_a_at | 0.617 |
|  | AV023306 | 1438395_at | 0.617 |
| 8430427H17Rik | AK018446 | 1428284_at | 0.616 |
| Cops3 | BB283617 | 1443570_at | 0.616 |
| 4930506M07Rik | BB559293 | 1429055_at | 0.614 |
| Larp6 | NM_026235 | 1418400_at | 0.609 |
| Lzp-s | AV058500 | 1439426_x_at | 0.609 |
|  | BQ175164 | 1441091_at | 0.607 |
| C230004F18Rik | BB380166 | 1445854_at | 0.607 |
| Doc2b | BM117900 | 1420667_at | 0.606 |
| Atm | AK021102 | 1428830_at | 0.605 |
| A930001A20Rik | BB280276 | 1431522_at | 0.603 |
| Pim1 | AI323550 | 1435458_at | 0.602 |
| Susd4 | BF455403 | 1460593_at | 0.598 |
|  | BB384728 | 1447012_at | 0.598 |
| 4930538K18Rik | BB548441 | 1453632_at | 0.596 |
| Csf1r | AI323359 | 1419872_at | 0.594 |
| Fhad1 | AW537651 | 1439190_at | 0.59 |
| MGI: 1925112 | BF719766 | 1438769_a_at | 0.583 |
| Cd276 | NM_133983 | 1417599_at | 0.578 |
| Cpm | AK004327 | 1453009_at | 0.574 |
| 1110059F07Rik | BE956260 | 1447533_at | 0.573 |
| Pts | NM_011220 | 1450660_at | 0.567 |
| Prss18 | NM_011177 | 1448982_at | 0.559 |
| BC027092 | BB445523 | 1435676_at | 0.556 |
| Cryab | NM_009964 | 1416455_a_at | 0.536 |
| H2-DMb1 | NM_010387 | 1418638_at | 0.534 |
| Tmem25 | BB245618 | 1436644_x_at | 0.533 |
| Dixdc1 | BB758432 | 1435207_at | 0.532 |
| D630044F24Rik | AV285979 | 1454839_a_at | 0.528 |
| Sox10 | BC018551 | 1451689_a_at | 0.525 |
| Dnaja4 | BQ176119 | 1434196_at | 0.518 |
| Rfxdc2 | BB148972 | 1460567_at | 0.506 |
| 3110005L24Rik | AA611589 | 1431381_at | 0.504 |
| Lzp-s | AV066625 | 1436996_x_at | 0.498 |
| Islr | NM_012043 | 1418450_at | 0.486 |
| Pex2 | AV327933 | 1451062_a_at | 0.475 |
| Lemd1 | AV156411 | 1445642_at | 0.472 |
| Nrp2 | BB752129 | 1435349_at | 0.451 |
| B230220N19Rik | BB539872 | 1442585_at | 0.445 |
| Fos | AV026617 | 1423100_at | 0.42 |
|  | BB047533 | 1446771_at | 0.412 |
|  | AI836671 | 1459747_at | 0.394 |
| Mcam | NM_023061 | 1416357_a_at | 0.384 |
| Rab27a | BB025283 | 1429123_at | 0.326 |
| 4921517L17Rik | BC027204 | 1425047_at | 0.31 |
| Rps25 | BM729504 | 1430978_at | 0.308 |
| Dixdc1 | BC024834 | 1425256_a_at | 0.289 |
| C030014I23Rik | AK021081 | 1453044_at | 0.287 |
| Ppcdc | BB329391 | 1424336_at | 0.244 |
| Tipin | BB796715 | 1459720_x_at | 0.199 |

TABLE 28

Genes Upregulated in Atm −/− Pcp2 Data
Genes which are upregulated in Atm −/− relative to Atm +/+ in the Pcp2 experiments. Data from Atm +/+ and Atm −/− Pcp2 IPs were compared in scatter plots, and filtered on expression of at least 25 and with Atm −/− values at least 1.5 fold greater than Atm +/+ values. Enriched genes were selected based on one-way ANOVA analysis with a p-value of ≤0.05.

| Gene Symbol | GenBank Accession | Affymetrix ID | Fold Change |
|---|---|---|---|
| Nedd4 | NM_010890 | 1421955_a_at | 4.614 |
| MGI: 2136405 | BB272589 | 1440386_at | 4.155 |
| AI451250 | AI451250 | 1447436_at | 4.04 |
| Eva1 | BC015076 | 1416236_a_at | 3.992 |
| Tex12 | AF285582 | 1421183_at | 3.409 |
| C920006O11Rik | BB552195 | 1435704_at | 2.684 |
| AI593442 | AV327193 | 1434052_at | 2.584 |
| Opcml | BB383296 | 1457446_at | 2.538 |
| Ddx6 | BC021452 | 1424598_at | 2.372 |
| 2900052N01Rik | AU067665 | 1436231_at | 2.167 |
| Cyp11a1 | C87524 | 1439947_at | 1.983 |
| 9330159M07Rik | BB214614 | 1441092_at | 1.973 |
|  | U58494 | 1451626_x_at | 1.962 |
| Btbd15 | BC027138 | 1427271_at | 1.948 |
| Mod1 | BC011081 | 1416632_at | 1.891 |
| Anln | BI690018 | 1433543_at | 1.882 |
| Nedd4 | BG073415 | 1451109_a_at | 1.869 |
| E430024C06Rik | AU018141 | 1453238_s_at | 1.853 |
| AI593442 | BF658761 | 1444026_at | 1.834 |
| Pml | BB667149 | 1456103_at | 1.824 |
| Pml | NM_008884 | 1448757_at | 1.777 |
| Ccrn4l | NM_010490 | 1448715_x_at | 1.721 |
| AI835735 | AI835735 | 1459716_at | 1.703 |
| Pvrl3 | NM_021495 | 1448673_at | 1.698 |
| C330006P03Rik | BB398124 | 1436387_at | 1.681 |
| 5730601F06Rik | BI110339 | 1431206_at | 1.671 |
| Zfp191 | BB579760 | 1426896_at | 1.648 |
| Rora | BB306272 | 1436326_at | 1.644 |
| Ccrn4l | AI987693 | 1455316_x_at | 1.571 |
| Zfp451 | BI714076 | 1456350_at | 1.556 |
| Tpm1 | AK002271 | 1423049_a_at | 1.542 |
| Peg3 | AB003040 | 1417355_at | 1.523 |
| Chst2 | BB770422 | 1442234_at | 1.519 |
| C230082I21Rik | AV317838 | 1455146_at | 1.519 |
| Ddx26 | BB381966 | 1423275_at | 1.509 |
| Mjd | BQ176512 | 1434408_at | 1.508 |
| C79468 | BQ086025 | 1459900_at | 1.508 |
| Mtf2 | BG066919 | 1449115_at | 1.507 |

TABLE 29

Genes Downregulated in Atm −/− Pcp2 Data
Genes which are downregulated in Atm −/− relative to Atm +/+ in the Pcp2 experiments. Microarray data from Atm +/+ and Atm −/− Pcp2 IPs were compared in scatter plots, and filtered on expression values of at least 25 and selected for genes with Atm +/+ values at least 1.5 fold greater than Atm −/− values. Differential genes were selected based on one-way ANOVA analysis with a p-value of ≤0.05.

| Gene Symbol | GenBank Accession | Affymetrix ID | Fold Change |
|---|---|---|---|
| Nlgn3 | BB308872 | 1456384_at | 0.662 |
| Ptbp1; LOC236294 | BM195499 | 1458284_at | 0.661 |
| Fth1; Dpep2 | AK002778 | 1427021_s_at | 0.66 |
| Zfyve21 | BC019521 | 1424669_at | 0.656 |
| Gtf2f1 | AV325174 | 1417699_at | 0.655 |
| 1700027J05Rik | BB195788 | 1438638_x_at | 0.653 |
| MGI: 1925112 | BF719766 | 1438769_a_at | 0.653 |
| Tm2d1 | AF353993 | 1451996_at | 0.64 |
|  | BB174864 | 1435126_at | 0.64 |
| Sh2d3c | AB043953 | 1415886_at | 0.64 |
| Ddx46 | BG243238 | 1457744_at | 0.639 |
| Spa17 | NM_011449 | 1417635_at | 0.633 |
| Boc | BB005556 | 1426869_at | 0.626 |
| 4930549C01Rik | NM_026300 | 1421367_at | 0.625 |
|  | BQ175377 | 1443960_at | 0.624 |

TABLE 29-continued

Genes Downregulated in Atm −/− Pcp2 Data
Genes which are downregulated in Atm −/− relative to Atm +/+ in the Pcp2 experiments. Microarray data from Atm +/+ and Atm −/− Pcp2 IPs were compared in scatter plots, and filtered on expression values of at least 25 and selected for genes with Atm +/+ values at least 1.5 fold greater than Atm −/− values. Differential genes were selected based on one-way ANOVA analysis with a p-value of ≤0.05.

| Gene Symbol | GenBank Accession | Affymetrix ID | Fold Change |
| --- | --- | --- | --- |
| Adamts4 | BB443585 | 1452595_at | 0.62 |
| Cryab | AV016515 | 1434369_a_at | 0.619 |
| BC027092 | BB445523 | 1435676_at | 0.617 |
| D730049H07Rik | BQ173909 | 1424989_at | 0.616 |
| Fbf1 | AF241249 | 1425979_a_at | 0.615 |
| AA589481 | BE200208 | 1437276_at | 0.615 |
| Pts | NM_011220 | 1450660_at | 0.614 |
| Cyp4f13 | NM_130882 | 1418767_at | 0.613 |
| BC020025 | BC020025 | 1451298_at | 0.607 |
| AV340375 | AV273541 | 1437737_at | 0.604 |
| Mmp17 | NM_011846 | 1448598_at | 0.596 |
| Pcdh8 | BB076893 | 1447825_x_at | 0.588 |
| Tcrb-V13 | X14388 | 1427656_at | 0.579 |
| Cd4 | U75219 | 1427779_a_at | 0.575 |
| Atm | AK021102 | 1428830_at | 0.57 |
| Decr2 | BE952632 | 1423495_at | 0.567 |
| Tmod2 | AK018223 | 1430153_at | 0.566 |
| Dusp7 | BE136125 | 1452097_a_at | 0.558 |
| 1200003M09Rik | BC011077 | 1423887_a_at | 0.551 |
| Dap | BC024876 | 1423790_at | 0.546 |
| 2310004I03Rik | BM939621 | 1428698_at | 0.543 |
| Rps25 | BM729504 | 1430978_at | 0.513 |
|  | BG066504 | 1435998_at | 0.512 |
| Rab3il1 | AK004767 | 1428391_at | 0.507 |
| Tmem25 | BB245618 | 1436644_x_at | 0.481 |
| C330003B14Rik | AU019881 | 1419958_at | 0.469 |
| Fmo2 | NM_018881 | 1422904_at | 0.436 |
|  | BB393620 | 1443754_x_at | 0.423 |
| Dixdc1 | BC024834 | 1425256_a_at | 0.392 |
| 4930523C11Rik; Adam6 | AV255799 | 1436129_at | 0.387 |
| Bace1 | AF200346 | 1421825_at | 0.379 |
| Lrrc49 | BB484412 | 1447954_at | 0.314 |
|  | BC003855 | 1425469_a_at | 0.313 |
| 2310030G06Rik | NM_025865 | 1449357_at | 0.274 |
| Tipin | BB796715 | 1459720_x_at | 0.227 |
| Ppcdc | BB329391 | 1424336_at | 0.0711 |

Identification of Functional Groups of Genes

To identify functional groups of genes which are enriched in the knockout cerebellum and each cell type, Gene Ontology (GO) analysis was performed using both DAVID (G. Dennis, Jr. et al., Genome Biol 4, P3 (2003)) and Genespring, each program essentially giving the same results. It was also essential to compare the gene lists and pertinent literature in order to completely analyze data as the GO database is incomplete. Genes enriched in total cerebellum of Atm −/− animals include those involved in cell cycle control (Tacc1, Cdkn1a (p21)) and apoptosis (Cdkn1a (p21)). Bergmann glial cells from Atm −/− animals are enriched in genes related to development and cellular differentiation, including BMP5. Purkinje cells from Atm −/− animals are enriched in genes involved in chromatin organization, nucleotide metabolism, and transcription regulation. These include transcription factors such as Tex12, Zfp191, Rora, Mtf2, and Mjd and genes involved in mRNA metabolism such as Ccm41 and Ddx6. Several of these differentially regulated genes are either directly or indirectly associated with ataxia. Rora is an orphan retinoic acid receptor which is mutated in the staggerer mouse mutant (B. A. Hamilton et al., Nature 379, 736 (1996)). Mjd (Atxn3, Sca3) is the gene responsible for Machado-Joseph disease (Y. Kawaguchi et al., Nat Genet 8, 221 (1994)). Ddx6 is known to associate with Ataxin-2 in P-bodies, multiprotein complexes involved in mRNA degradation (U. Nonhoff et al., Mol Biol Cell 18, 1385 (2007); N. Cougot, S. Babajko, B. Seraphin, J Cell Biol 165, 31 (2004)). Ccrn41 is a deadenylase which is also found in P-bodies (N. Cougot, S. Babajko, B. Seraphin, J Cell Biol 165, 31 (2004)); deadenylation is a critical first step in the degradation of mRNA by P-bodies. Over-expression of these genes could potentially either enhance neurodegeneration of Purkinje cells, or protect against it.

Example 15

Screening Methods for Parkinson's Disease

1) Translational Profiles of VTA and SNc Neurons

Dopamine producing (dopaminergic) neurons are present primarily in the ventral tegmental area (VTA) of the midbrain, substantia nigra pars compacta (SNc), and the arcuate nucleus of the hypothalamus. Dopaminergic neurons of the SNc are particularly susceptible to neurodegeneration in Parkinson's disease (PD) and in pharmacologically-induced models of PD. The selective degeneration of the dopaminergic neurons in the substantia nigra pars compacta leads to PD but the exact cause for this nigral cell loss is still unknown. The ventral tegmental area dopaminergic neurons are relatively spared in comparison. The tremor, bradykinesia and rigidity seen in PD patients are in a large part caused by the loss of striatal dopamine innervation. Expression of a ribosomal protein (e.g. L10a) fused to a detectable tag, whose expression is regulated by SNc and VTA-specific gene regulatory regions can be used to explore the differential vulnerability of SNc cells and VTA cells in animal models of PD or subjects diagnosed with PD or Parkinsonian-like symptoms. By utilizing the BACarray and TRAP methods described herein, mice with molecularly tagged ribosomal proteins are produced. These are driven by regulatory sequences for cell-type specific expression in either the SNc or VTA (FIG. 38). It is expected that differentially expressed mRNAs in SNc cells will be identified as potential therapeutic targets for the amelioration of PD.

2) Translational Profiles of VTA and SNc Neurons in PD

Dopaminergic cell loss mimicking what is seen in PD is induced with intracerebral injections of the neurotoxins 6-hydroxydopamine (6-OHDA) or 1-methyl 4-phenyl 1,2,3,6-tetrahydropyridine (MPTP) either bilaterally or unilaterally in rodents (either mice or rats). By utilizing the BACarray and TRAP methods described herein, mice with molecularly tagged ribosomal proteins are produced. These are driven by regulatory sequences for cell-type specific expression in either the SNc or VTA (FIG. 39). Three weeks following a 6-OHDA treatment (bilateral or unilateral treatment), gene translational profiles from the SNc and VTA neurons are obtained. These translational profiles are compared to reference profiles from mice treated with saline vehicle. It is expected that therapeutic targets relevant to PD will be obtained (FIG. 40).

3) Screening for Therapeutic Targets in the Striatopallidal Cells for Antagonism or Stimulation High-frequency stimulation of the subthalamic nucleus (STN) is one neurosurgical procedure currently available for the alleviation of motor symptoms of PD and the debilitating medication-induced dyskinesias that often accompany the disease. Stimulation of the STN is achieved by implanting deep brain stimulation (DBS) electrodes precisely in the nucleus. The striatopallidal cells of the striatum tonically inhibit the Globus Pallidus External segment (GPe) and the Sub-thalamic nucleus (STN) (FIG. 41). By inhibiting activity in striatopallidal cells with a small molecule or other non-electrical, non-surgery requiring method, it will be possible to alleviate the tonically inhibited STN neurons and alleviate PD symptoms, much in the way of deep brain stimulation. By utilizing the methods described herein and exemplified, using D2 BACarray mice one mRNA was found to be selectively enriched in striatopallidal neurons of the striatum is Gpr6 (Table 12). Gpr6 represents a target for which antagonists can be screened for and developed as a therapeutic for PD. In a similar manner, any mRNA found to be downregulated in striatopallidal cells represents a target for agonism as a therapeutic for PD.

Example 16

Screening Methods for Obesity

The hypothalamus plays a central role in several regulatory and homeostatic processes including blood pressure, body temperature, sleep, fluid and electrolyte balance, and body weight. The lateral hypothalamus in particular is implicated as a feeding and satiety center. Food intake is regulated by hypothalamic neuropeptides which respond to peripheral signals. Homeostasis disrupted can lead to feeding and metabolic disorders leading to such diseases as obesity. Orexin, also named Hypocretin, is a excitatory neuropeptide hormone released by the lateral hypothalamus. Orexin release modulates feeding behavior, wakefulness, and energy expenditure. A hypothalamic Hcrt (orexin) BAC-array line has expression in the lateral hypothalamus.

By utilizing the BACarray and TRAP methods described herein, mice with molecularly tagged ribosomal proteins are produced. These are driven by regulatory sequences for lateral hypothalamic cell-type specific expression under the control of regulatory sequences from the Hcrt (orexin) locus. By obtaining translational profiles from these animals, it is expected that targets relevant to obesity will be identified, in particular for feeding regulation.

While some embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A nucleic acid molecule comprising a nucleotide sequence encoding a ribosomal fusion protein comprising mouse ribosomal protein L10a having the amino acid sequence of SEQ ID NO: 30 fused to an optically detectable protein, wherein the nucleotide sequence is operably linked to a mouse endogenous regulatory sequence that causes expression of the fusion protein in a chosen cell type, and wherein the ribosomal fusion protein is incorporated in an intact ribosome that translates and/or binds mRNA.

2. The nucleic acid molecule of claim 1, wherein the optically detectable protein is a fluorescent protein.

3. The nucleic acid molecule of claim 2, wherein the fluorescent protein has greater than approximately 200 amino acids.

4. The nucleic acid molecule of claim 3, wherein the fluorescent protein is an enhanced green fluorescent protein (eGFP).

5. The nucleic acid molecule of claim 1, wherein the cell type is neuronal.

6. The nucleic acid molecule of claim 1, wherein the cell type is located in the central nervous system.

7. The nucleic acid molecule of claim 6, wherein the cell type is an astrocyte.

8. The nucleic acid molecule of claim 6, wherein the cell type is a cholinergic neuron.

9. The nucleic acid molecule of claim 6, wherein the location of the cell type is selected from the group consisting of spinal cord, cerebellum, hypothalamus, substantia nigra, ventral tegmental area, and striatum.

10. A mouse comprising a nucleic acid molecule comprising:
    a nucleotide sequence encoding a ribosomal fusion protein comprising mouse ribosomal protein L10a having the amino acid sequence of SEQ ID NO: 30 fused to an optically detectable protein, wherein the nucleotide sequence is operably linked to an endogenous mouse regulatory sequence that causes expression of the fusion protein in a chosen cell type, and wherein the ribosomal fusion protein is incorporated in an intact ribosome that translates and/or binds mRNA.

11. The mouse of claim 10, wherein the optically detectable protein is a fluorescent protein.

12. The mouse of claim 11, wherein the fluorescent protein has greater than approximately 200 amino acids.

13. The mouse of claim 12, wherein the fluorescent protein is an enhanced green fluorescent protein (eGFP).

14. The mouse of claim 10, wherein the cell type is neuronal.

15. The mouse of claim 10, wherein the cell type is located in the central nervous system.

16. The mouse of claim 15, wherein the cell type is an astrocyte.

17. The mouse of claim 15, wherein the cell type is a cholinergic neuron.

18. The mouse of claim 15, wherein the location of the cell type is selected from the group consisting of spinal cord, cerebellum, hypothalamus, substantia nigra, ventral tegmental area, and striatum.

* * * * *

SEQUENCE LISTING

```
<160> NUMBER OF SEQ ID NOS: 30

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: misc_feature
<222> LOCATION: (25)..(25)
<223> OTHER INFORMATION: n is a, c, g, or t

<400> SEQUENCE: 1 ttttttttt tttttttttt tttvn                                          25

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agagggaaat cgtgcgtgac                                               20

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```

```
gtaaagactg tggagatgcg ggatggtgag g                                31
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
ccattgtgaa gcggtttggg                                             20
```

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
gtgaagatag gcgtgctatt tgc                                         23
```

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
tgcttgatga taccaaccac g                                           21
```

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
tgcagggcga tcggatggag gag                                         23
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
ctgatgcggc aacctcagat                                             20
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
tgactgaaca cccactctgc                                             20
```

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgaaaagcg taaacggctc a                                          21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaattggagg tgttcgtccc a                                          21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gctctggtcc ggtcttttag c                                          21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aagtcgctga tagcctcaga g                                          21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagacttccg ctcgtaccta a                                          21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cttggctctc cacttgagtt c                                          21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 16
caatagtgat gacctggccg t                                              21

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 17
gtgctggtgt gggtgggaac tgag                                           24

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 18
gccaggcggt tgtttagata ca                                             22

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 19
gactgtggag gcgaacatga c                                              21

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 20
gctgggcaca gtctagtcg                                                 19

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 21 tgagggggtga gcaggggttg agg                                           23

```
<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttgagcaaga acacgttggc t                                              21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
actgccaccc ataaaaccta ct                                             22

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cagagcaaaa gagcagagtg a                                              21

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tccccgtctg agcctaagg                                                 19

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtactgggag gtcattgtcg g                                              21

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtctggtgt atctccacgt tc                                             22

<210> SEQ ID NO 28
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tcgccctggg gtaagatgt                                                19

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggagcgatgc gtgtatttct g                                             21

<210> SEQ ID NO 30
<211> LENGTH: 217
<212> TYPE: PRT
<213> ORGANISM: Mus musculus

<400> SEQUENCE: 30

Met Ser Ser Lys Val Ser Arg Asp Thr Leu Tyr Glu Ala Val Arg Glu
1               5                   10                  15

Val Leu His Gly Asn Gln Arg Lys Arg Arg Lys Phe Leu Glu Thr Val
            20                  25                  30

Glu Leu Gln Ile Ser Leu Lys Asn Tyr Asp Pro Gln Lys Asp Lys Arg
        35                  40                  45

Phe Ser Gly Thr Val Arg Leu Lys Ser Thr Pro Arg Pro Lys Phe Ser
    50                  55                  60

Val Cys Val Leu Gly Asp Gln Gln His Cys Asp Glu Arg Lys Ala Val
65                  70                  75                  80

Asp Ile Pro His Met Asp Ile Glu Ala Leu Lys Lys Leu Asn Lys Asn
                85                  90                  95

Lys Lys Leu Val Lys Lys Leu Ala Lys Lys Tyr Asp Ala Phe Leu Ala
            100                 105                 110

Ser Glu Ser Leu Ile Lys Gln Ile Pro Arg Ile Leu Gly Pro Gly Leu
        115                 120                 125

Asn Lys Ala Gly Lys Phe Pro Ser Leu Leu Thr His Asn Glu Asn Met
    130                 135                 140

Val Ala Lys Val Asp Glu Val Lys Ser Thr Ile Lys Phe Gln Met Lys
145                 150                 155                 160

Lys Val Leu Cys Leu Ala Val Ala Val Gly His Val Lys Met Thr Asp
                165                 170                 175

Asp Glu Leu Val Tyr Asn Ile His Leu Ala Val Asn Phe Leu Val Ser
            180                 185                 190

Leu Leu Lys Lys Asn Trp Gln Asn Val Arg Ala Leu Tyr Ile Lys Ser
        195                 200                 205

Thr Met Gly Lys Pro Gln Arg Leu Tyr
    210                 215
```